United States Patent [19]

White et al.

[11] Patent Number: 5,646,139

[45] Date of Patent: Jul. 8, 1997

[54] ANTIMICROBIAL CARBAPENEM QUINOLONES

[75] Inventors: Ronald Eugene White, South Plymouth; Thomas Prosser Demuth, Jr., Norwich, both of N.Y.

[73] Assignee: The Procter & Gamble Company, Cincinnati, Ohio

[21] Appl. No.: 477,968

[22] Filed: Jun. 7, 1995

Related U.S. Application Data

[62] Division of Ser. No. 692,821, Apr. 26, 1991, which is a continuation of Ser. No. 416,645, Oct. 10, 1989, abandoned, which is a continuation-in-part of Ser. No. 261,948, Oct. 24, 1988, abandoned.

[51] Int. Cl.$^6$ .......... C07D 477/06; C07D 463/00; A61K 31/435; A61K 31/40
[52] U.S. Cl. .......... 514/210; 540/302; 514/222.8
[58] Field of Search .......... 540/302; 514/210

[56] References Cited

U.S. PATENT DOCUMENTS

| | | | |
|---|---|---|---|
| 4,146,719 | 3/1979 | Irikura | 544/363 |
| 4,584,132 | 4/1986 | Albrecht et al. | 260/239 |
| 4,599,443 | 7/1986 | Chan et al. | 560/219 |
| 4,605,744 | 8/1986 | Wei et al. | 546/210 |
| 4,620,007 | 10/1986 | Grohe et al. | 546/156 |
| 4,631,150 | 12/1986 | Battistini et al. | 540/310 |
| 4,642,364 | 2/1987 | Chan et al. | 556/438 |
| 4,663,469 | 5/1987 | Wei et al. | 549/449 |
| 4,670,444 | 6/1987 | Grohe et al. | 514/300 |
| 4,692,450 | 9/1987 | Cassal et al. | 514/256 |
| 4,742,053 | 5/1988 | Nakagawa et al. | 514/202 |
| 4,801,704 | 1/1989 | Keith et al. | 540/312 |
| 4,806,541 | 2/1989 | Jolidon et al. | 514/254 |
| 4,831,130 | 5/1989 | Albrecht et al. | 540/363 |
| 4,845,087 | 7/1989 | Lattrell et al. | 514/202 |
| 4,845,105 | 7/1989 | Clemence et al. | 514/312 |
| 4,874,764 | 10/1989 | Ueda et al. | 514/254 |
| 4,900,476 | 2/1990 | Chan et al. | 552/309 |
| 4,904,468 | 2/1990 | Walsdorf et al. | 424/468 |
| 4,904,647 | 2/1990 | Kulcsar et al. | 514/154 |
| 4,912,214 | 3/1990 | Albrecht et al. | 540/363 |
| 4,927,926 | 5/1990 | Corominas et al. | 544/101 |
| 4,954,507 | 9/1990 | Weber et al. | 514/300 |
| 5,008,259 | 4/1991 | Siret et al. | 514/202 |
| 5,013,730 | 5/1991 | Arnould et al. | 514/202 |
| 5,013,731 | 5/1991 | Arnould et al. | 514/202 |
| 5,039,683 | 8/1991 | Nakanishi | 514/312 |
| 5,147,871 | 9/1992 | Albrecht et al. | 514/202 |
| 5,159,077 | 10/1992 | Keith et al. | 540/222 |
| 5,162,523 | 11/1992 | Keith et al. | 540/227 |
| 5,180,719 | 1/1993 | White et al. | 514/190 |
| 5,189,157 | 2/1993 | Wei et al. | 540/222 |
| 5,273,973 | 12/1993 | White et al. | 514/210 |
| 5,328,908 | 7/1994 | Demuth et al. | 544/363 |
| 5,336,768 | 8/1994 | Albrecht | 540/222 |

FOREIGN PATENT DOCUMENTS

| | | | |
|---|---|---|---|
| 87/75009 | 1/1988 | Australia | C07D 501/26 |
| 88/27554 | 6/1989 | Australia | A61K 031/545 |
| 053816 | 6/1982 | European Pat. Off. | C07D 205/08 |
| 062328 | 10/1982 | European Pat. Off. | C07D 501/24 |
| 0124081 | 11/1984 | European Pat. Off. | C07D 501/00 |
| 0191185 | 8/1986 | European Pat. Off. | C07D 215/56 |
| 0203559 | 12/1986 | European Pat. Off. | C07D 519/00 |
| 0224178 | 6/1987 | European Pat. Off. | C07D 215/56 |
| 0235676 | 9/1987 | European Pat. Off. | C07D 401/04 |
| 0235762 | 9/1987 | European Pat. Off. | C07D 215/56 |
| 0237955 | 9/1987 | European Pat. Off. | C07D 215/56 |
| 0295630 | 5/1988 | European Pat. Off. | C07D 501/36 |
| 0266576 | 5/1988 | European Pat. Off. | C07D 215/56 |
| 0286144 | 10/1988 | European Pat. Off. | C07D 501/36 |
| 030487 B1 | 2/1989 | European Pat. Off. | C07D 401/04 |
| 0303172 | 2/1989 | European Pat. Off. | C07D 501/20 |

(List continued on next page.)

OTHER PUBLICATIONS

Albrecht et al., "Dual–Action Cephalosporins: An Idea Whose Time Has Come", Program and Abstracts of the Twenty–Eighth Interscience Conference on Antimicrobial Agents and Chemotherapy 186 (American Society for Microbiology, no month identified 1988).

Albrecht et al., "Dual–Action Cephalosporins: An Idea Whose Time Has Come", Poster Session: 28th Interscience Conference on Antimicrobial Agents and Chemotherapy (Oct. 24, 1988).

(List continued on next page.)

*Primary Examiner*—Matthew V. Grumbling
*Attorney, Agent, or Firm*—David L. Suter; Karen F. Clark; Richard A. Hake

[57] ABSTRACT

Compounds of Structure:

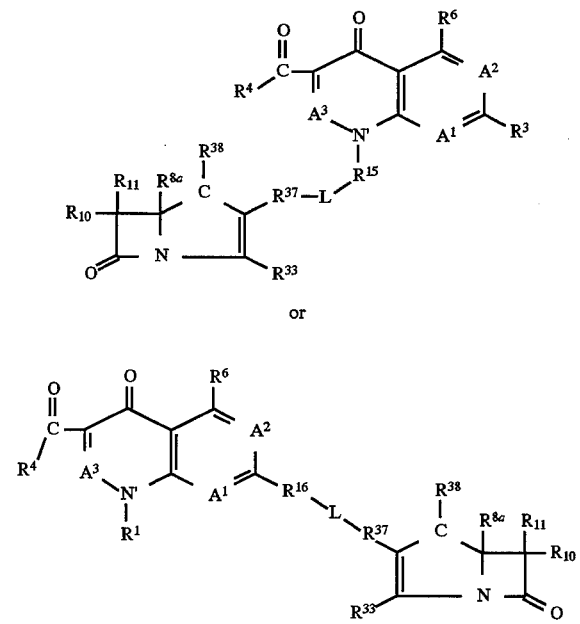

as well as their pharmaceutically-acceptable salts and biohydrolyzable esters, and hydrates thereof, are effective antiinfective agents, useful in treating and preventing infection.

45 Claims, No Drawings

FOREIGN PATENT DOCUMENTS

| | | | |
|---|---|---|---|
| 0304158 | 2/1989 | European Pat. Off. | C07D 501/46 |
| 0335297 | 10/1989 | European Pat. Off. | C07D 501/26 |
| 0341649 | 11/1989 | European Pat. Off. | C12P 17/18 |
| 0341990 | 11/1989 | European Pat. Off. | C07D 501/46 |
| 0348088 | 12/1989 | European Pat. Off. | C07D 215/56 |
| 0366193 | 5/1990 | European Pat. Off. | C07D 499/88 |
| 0366640 | 5/1990 | European Pat. Off. | C07D 501/26 |
| 0366641 | 5/1990 | European Pat. Off. | C07D 499/88 |
| 0366643 | 5/1990 | European Pat. Off. | C07D 215/56 |
| 0393400 | 10/1990 | European Pat. Off. | C07D 471/04 |
| 0409081 | 1/1991 | European Pat. Off. | C07D 499/02 |
| 0451764 | 10/1991 | European Pat. Off. | C07D 519/00 |
| 0453924 | 10/1991 | European Pat. Off. | C07D 501/26 |
| 0453952 | 10/1991 | European Pat. Off. | C07D 501/26 |
| 2191556 | 3/1974 | France | C07D 99/00 |
| 2243940 | 4/1975 | France | C07D 501/20 |
| 1940511 | 3/1970 | Germany | C07D 99/16 |
| 2322750 | 11/1972 | Germany | C07D 99/16 |
| 2448966 | 4/1975 | Germany | C07D 499/68 |
| 2514322 | 10/1975 | Germany | C07D 501/36 |
| 2947948 | 6/1980 | Germany | C07D 499/70 |
| 3345093 | 6/1984 | Germany | C07D 501/46 |
| 3913245 | 11/1989 | Germany | C07D 498/06 |
| 47-11237 | 4/1972 | Japan . | |
| 49-35392 | 4/1974 | Japan . | |
| 50-23036 | 8/1975 | Japan | A61K 31/43 |
| 50-23037 | 8/1975 | Japan | A61K 31/43 |
| 57-32290 | 2/1982 | Japan | C07D 471/04 |
| 57-46988 | 3/1982 | Japan | A61K 31/43 |
| 57-46990 | 3/1982 | Japan | A61K 31/54 |
| 60-06617 | 1/1985 | Japan | A61K 31/54 |
| 1-93573 | 4/1989 | Japan | C07D 215/56 |
| 1-106886 | 4/1989 | Japan | C07D 471/04 |
| 1-258684 | 10/1989 | Japan | A61K 31/54 |
| 1-290683 | 11/1989 | Japan | C07D 519/00 |
| 87/05297 | 9/1987 | WIPO | C07D 501/28 |
| 91/16310 | 10/1991 | WIPO | C07D 501/28 |
| 91/16327 | 10/1991 | WIPO | C07D 215/00 |

OTHER PUBLICATIONS

Albrecht et al., "Dual–Action Cephalosporins: Cephalosporin–3'–Quaternary Quinolones", Program and Abstracts of the Twenty–Ninth Interscience Conference on Antimicrobial Agents and Chemotherapy (American Society for Microbiology, (no month identified 1989).

Albrecht, H.A., "Dual–Acton Cephalosporins Incorporating 3'–Tertiary Amine–Linked Quinolones", 31st Interscience Conference on Antibacterial Agents and Chemotherapy, Chicago, Illinois; Poster Session: Oct. 2, 1991 (Abs. & Poster).

Alpegiani, M. et al., "2–(Heteroatom–substituted)methyl Penems. IV. Oxygen Derivatives", Heterocycles, vol. 30, No. 2, pp. 799–812 (no month identified 1990).

Aries, R., "Acylated Aminopenicillins", Abstract #25655c, Heterocycles, vol. 81, p. 433 (no month identified 1974).

Aries, R., "Nalidixamido Cephems", Abstract #164210h, Heterocycles, vol. 83, p. 558 (no month identified 1975).

Bartkovitz, D. et al., "The Synthesis and Biological Properties of 2a–Methyl Substituted Penicillins", Abstract #824, 31st Interscience Conference on Antibacterial Agents and Chemotherapy (Chicago, Illinois), Oct. 1, 1991 (Abstract & Poster).

Beskid et al., "In Vitro Antibacterial Activity of Dual–Action Cephalosporin Ro 23–9424 and Comparative Agents", Program and Abstracts of the Twenty–Eighth Interscience Conference on Antimicrobial Agents and Chemotherapy 187 (American Society for Microbiology, (no month identified 1988).

Beskid et al., "In Vivo Antibacterial Activity of Dual–Action Cephalosporin Ro 23–9424 Compared to Cefotaxime and Fleroxacin", Program and Abstracts of the Twenty–Eighth Interscience Conference on Antimicrobial Agents and Chemotherapy 187 (American Society for Microbiology, (no month identified) 1988.

Beskid et al., "In Vitro Antibacterial Activity of Dual–Action Cephalosporin Ro 23–9424 and Comparative Agents", Poster Session: 28th Interscience Conference on Antimicrobial Agents and Chemotherapy (Oct. 24, 1988).

Beskid et al., "In Vivo Antibacterial Activity of Dual–Action Cephalosporin Ro 23–9424 Compared to Cefotaxime and Fleroxacin", Poster Session: 28th Interscience Conference on Antimicrobial Agents and Chemotherapy (Oct. 24, 1988).

Christenson et al., "Mode of Action of Ro 23–9424, a Dual–Action Cephalosporin", Poster Session: 28th Interscience Conference on Antimicrobial Agents and Chemotherapy (Oct. 24, 1988).

Christenson et al., "Hydrolysis of Ro 23–9424 by β–Lactamases", Poster Session: 28th Interscience Conference on Antimicrobial Agents and Chemotherapy (Oct. 24, 1988).

Christenson et al., "Pharmakinetics of Ro 23–9424, a Dua-1–Action Cephalosporin, in Animals", Poster Session: 28th Interscience Conference on Antimicrobial Agents and Chemotherapy (Oct. 24, 1988).

Christensen et al., "Pharmacokinetics of Ro 23–9424, a Dual–Action Cephalosporin In Animals", Program and Abstracts of the Twenty–Eighth Interscience Conference on Antimicrobial Agents and Chemotherapy 188 (American Society for Microbiology, (no month indentified) 1988).

Christensen et al., "Hydrolysis of Ro 23–9424 by β–Lactamases", Program and Abstracts of the Twenty–Eighth Interscience Conference on Antimicrobial Agents and Chemotherapy 187 (American Society for Microbiology, (no month identified) 1988).

Christensen et al., "Mode of Action of Ro 23–9424, a Dual–Action Cephalosporin", Program and Abstracts of the Twenty–Eighth Interscience Conference on Antimicrobial Agents and Chemotherapy 187 (American Society for Microbiology, (no month identified) 1988).

Christensen et al., "Mode of Action of Ro 23–5068, a Dual–Action Cephalosporin", Program and Abstracts of the Twenty–Eighth Interscience Conference on Antimicrobial Agents and Chemotherapy, 188 (American Society for Microbiology, (no month identified) 1988).

Christensen et al., "Mode of Action of Ro 23–5068, a Dual–Action Cephalosporin", Poster Session: 28th Interscience Conference on Antimicrobial Agents and Chemotherapy (Oct. 24, 1988).

Cimarusti et al., "Monocyclic β–Lactam Antibiotics", Medicinal Research Reviews, vol. 4, No. 1, pp. 1–24 (no month identified 1984).

Cleeland et al., "Dual–Action Antibacterials: A Concept Newly Recognized for Antibacterial Chemotherapy", Antimicrobic Newsletter, vol. 6, No. 8, pp. 61–68 (no month identified 1989).

Corraz, A.J. et al., "Dual-Action Penems and Carbapenems", Abstract #826, Poster #73, 31st Interscience Conference on Antibacterial Agents and Chemotherapy (Chicago, Illinois) Oct. 1, 1991 (Abstract & Poster).

Demuth, T.P., et al., "Synthesis and Antibacterial Activity of New C-10 Quinolonyl-Cephem Esters", The Journal of Antibiotics, vol. 44, No. 2, pp. 200-209 (Feb. 1991).

Dürckheimer et al., "Recent Developments In The Field of β-Lactam Antibiotics", Angew. Chem. Int. Ed. Engl., vol. 24, pp. 180-202 (no month identified 1985).

Fujimoto Pharmaceutical C., Ltd., "Penicillin Derivaties", Abstract #217590j, Chemical Abstracts, vol. 96, p. 718 (no month identified 1982).

Fujimoto Pharmaceutical C., Ltd., "Penicillin Derivaties", Abstract #55572w, Chemical Abstracts, vol. 97, p. 626 (no month identified 1982).

Fujimoto Pharmaceutical C., Ltd., "Cephalexin Derivaties", Abstract #72183n, Chemical Abstracts, vol. 96, p. 616 (no month identified 1982).

Georgopapadakou et al., "Cephalosporin-Quinolone Esters: Biological Properties", Program and Abstracts of the Twenty-Eighth Interscience Conference on Antimicrobial Agents and Chemotherapy 186 (American Society for Microbiology, (no month identified) 1988).

Georgopapadakou et al., "Mode of Action of the Dual-Action Cephalosporin Ro 23-9424", Program and Abstracts of the Twenty-Eighth Interscience Conference on Antimicrobial Agents and Chemotherapy 187 (American Society for Microbiology, (no month identified) 1988).

Georgopapadakou et al., "Cephalosporin-Quinolone Esters: Biological Properties", Poster Session: 28th Interscience Conference on Antimicrobial Agents and Chemotherapy (Oct. 24, 1988).

Georgopapadakou et al., "Mode of Action of the Dual-Action Cephalosporin Ro 23-9424", Poster Session: 28th Interscience Conference on Antimicrobial Agents and Chemotherapy (Oct. 24, 1988).

Georgopapadakou et al., "Mode of Action of the Dual-Action Cephalosporin Ro 23-9424, 33" Antimicrobial Agents and Chemotherapy 1067 (no month identified 1989).

Greenwood et al., "Dual-Action Cephalosporin Utilizing A Novel Therapeutic Principle", Antimicrobial Agents and Chemotherapy, vol. 10, p. 249 (no month identified 1976).

Hirose et al., "Desulfurization of 7-Aminodeacetoxycephalosporanic Acid", Yakugaku Zasshi, vol. 104, No. 3, pp. 302-307 (no month identified 1984) (Chemical Abstract 101:110596).

Isaka, I. et al., "α-(Oxodihydropyridylcarbonylamino)-a-phenylacetylaminocephalosporin Derivatives", Abstract #120651g, Heterocycles, vol. 81, p. 541 (no month identified 1974).

Jones et al., "Antimicrobial Activity of Ro 23-9424, a Novel Ester Fusion of Fleroxin and Desacetyl-Cefotaxime", Program and Abstracts of the Twenty-Eighth Interscience Conference on Antimicrobial Agents and Chemotherapy 187 (American Society for Microbiology, (no month identified) 1988).

Jones, R.N., "In Vitro Activity of Ro 24-6392, a Novel Ester-Linked Co-Drug Combining Ciprofloxacin and Desacetylcefotaxime", Eur. J. Clin. Microb. Infect. Dis., vol. 9, No. 6, pp. 435-438 (Jun. 1990).

Kishimoto, S. et al., "1-Sulfo-2-oxoazetidine Derivatives and Their Use", Abstract #143181u, Chemical Abstracts, vol. 98, p. 556 (no month identified 1983).

Kyorin Pharmaceutical Co., Ltd., "Synergistic Antimicrobial Preparations", Abstract #19770t, Chemical Abstracts, vol. 103, p. 332 (no month identified 1985).

Le Noc et al., "Activite Antibacterienee in vitro du Cefpirome en Association Avec Quatre Aminoglycosides et Deux Fluoroquinolones", Path. Biol., vol. 36, No. 5, pp. 762-767 (Jun. 1988).

Machida, Y. et al., "Pencillin and Cephalosporin Compounds and Antibacterial Composition Containing the Compounds", Abstract #125757g, Biomolecules, vol. 98, p. 609 (no month identified 1983).

Machida, Y. et al., "7-Carboxymethoxyphenylacetamido-3-cephem Derivatives and Antibacterial Drugs Containing Them", Abstract #230234n, Biomolecules, vol. 101, p. 743 (no month identified 1984).

Matsubara, A. et al., "Penicillins", Abstract #204633p, Heterocycles, vol. 93, p. 689 (no month identified 1980).

McCombie et al., "Synthesis and In Vitro Activity of the Penem Antibiotics", Medicinal Research Reviews, vol. 8, No. 3, pp. 393-440 (no month identified 1988).

Mobashery et al., "Inactivation Of Alanine Racemase By β-Chloro-L-alanine Released Enzymatically From Amino Acid and Peptide $C_{10}$ Esters of Deacetylcephalothin", Biochemistry, vol. 26, pp. 5878-5884 (no month identified 1987).

Mobashery et al., "Conscripting β-Lactamase For Use In Drug Delivery, Synthesis and Biological Activity of A Cephalosporin $C_{10}$-Ester of An Antibiotic Dipeptide", J. American Chemical Society, vol. 108, pp. 1685-1686 (no month identified 1986).

Mobashery et al., "Reactions of *Escherichia coli* TEM β-Lactamase With Cephalothin And With $C_{10}$-Dipeptidyl Cephalosoporin Esters", J. Biological Chemistry, vol. 261, No. 17, pp. 7879-7887 (Jun. 1986).

Murakami, M. et al., "Ampiicillanin Derivatives Substituted with Heterocyclic Acyl Groups", Abstract #70803q, Heterocycles, vol. 80, p. 346 (no month identified 1974).

Murakami, M. et al., "Pharmaceutical Amoxicillins and Epicillins", Abstract #79236b, Heterocycles, vol. 83, p. 665 (no month identified 1975).

Murakami, M. et al., "Cephalosporin Derivatives", Abstract #31104a, Heterocycles, vol. 84, p. 471 (no month identified 1976).

O'Callaghan, et al., "A New Cephalosporin With A Dual Mode of Action", Antimicrobial Agents and Chemotherapy, vol. 10, No. 2, pp. 245-248 (Aug. 1976).

Perrone, E. et al., "Dual Action Penems", Abstract #825; Abstracts of the 1991 ICAAC (Abstract Only).

Ravagnan, G., "Pencillin Derivative Containing Naphthyridine", Abstract #119552d, Chemical Abstracts, vol. 106, p. 612 (no month identified 1987).

Rolinson, "β-Lactam Antibiotics", J. Antimicrobial Chemotherapy, vol. 17, pp. 5-36 (Sep. 1986).

Schaefer, F.F. et al., "The Role of AMPC β-Lactamase in the Mechanism of Action of Ester-Linked Dual-Action Cephalosporins", Abstract #953, 31st Interscience Conference on Antibacterial Agents and Chemotherapy, Poster Session: Oct. 1, 1991 (Abstract & Poster).

Thabaut et al., "Beta-lactam Antibiotic—New Quinolone Combinations", Presse Med., vol. 16, pp. 2167, (no month identified 1987) (Chemical Abstracts 108:147028).

Tobiki, H. et al., "Penicillins", Abstract #135637t, Heterocycles, vol. 84, p. 499 (no month identified 1976).

Tobiki, H. et al., "Penicillins", Abstract #164760h, Heterocycles, vol. 84, p. 467 (no month identified 1976).

Uglesic et al., "New Semisynthetic Penicillins", Advan. Atimicrob. Antineoplastic Chemother., Proc. Int. Congr. Chemother., 7th, Meeting Date 1971, vol. 1, Pt. 2, 997 (no month identified 1972) (Chemical Abstracts 79:61968).

Uglesic et al., "6–(Nalidixamido)penicillanic acid", Abstract #111464k, Heterocyclic Compounds, vol. 72, p. 409 (no month identified 1970).

Walker, D.G., "Use of Bistrimethylsilylated Intermediates in the Preparation of Semisynthetic 7–Amino–3–substituted–cephems. Expedient Synthesis of a New 3–[1–Methyl–1–pyrrolidinio)methyl]cephalosporin", J. Org. Chem., No. 53, No. 5, pp. 983–991, (no month identified 1988).

Wise, "Minireview—In Vitro and Pharmocokinetic Properties of The Carbapenems", Antimicrobial Agents and Chemotherapy, vol. 30, No. 3, pp. 343–349 (Sep. 1986).

Wolfson et al., "Minireview—The Fluoroquinolones: Structures, Mechanisms of Action and Resistance, and Spectra of Activity In Vitro", Antimicrobial Agents and Chemotherapy, vol. 28, No. 4, pp. 581–586 (Oct. 1985).

Yamada et al., "New Broad–Spectrum Cephalosporins With Antipseudomonal Activity", J. Antibiotics, vol. 36, No. 5, pp. 532–542 (no month identified 1983) (Chemical Abstracts 99:87869).

Yamada, H. et al., "6–Aminopenicillanic Acid Derivatives", Abstract #19636y, Heterocycles, vol. 77, p. 511 (no month identified 1972).

ANTIMICROBIAL CARBAPENEM QUINOLONES

This is a divisional of application Ser. No. 07/692,821, filed on Apr. 26, 1991, which is a continuation of application Ser. No. 07/416,645, filed Oct. 10, 1989, (now abandoned), which was a continuation-in-part of application Ser. No. 07/261,948, filed Oct. 24, 1988 (now abandoned).

BACKGROUND OF THE INVENTION

This invention relates to novel antimicrobial compounds and compositions. The compounds of this invention contain, as integral substituents, a quinolone moiety and a lactam-containing moiety.

The chemical and medical literature describes a myriad of compounds that are said to be antimicrobial, i.e., capable of destroying or suppressing the growth or reproduction of microorganisms, such as bacteria. In particular, antibacterials include a large variety of naturally-occurring (antibiotic), synthetic, or semi-synthetic compounds. They may be classified (for example) as the aminoglycosides, ansamacrolides, beta-lactams (including penicillins and cephalosporins), lincos-aminides, macrolides, nitrofurans, nucleosides, oligosaccharides, peptides and polypeptides, phenazines, polyenes, polyethers, quinolones, tetracyclines, and sulfonamides. Such antibacterials and other antimicrobials are described in *Antibiotics, Chemotherapeutics, and Antibacterial Agents for Disease Control* (M. Grayson, editor, 1982), and E. Gale et al., *The Molecular Basis of Antibiotic Action* 2d edition (1981), both incorporated by reference herein.

The mechanism of action of these antibacterials vary. However, each can be generally classified as functioning in one or more of four ways: by inhibiting cell wall synthesis or repair; by altering cell wall permeability; by inhibiting protein synthesis; or by inhibiting synthesis of nucleic acids. For example, beta-lactam antibacterials act through inhibiting the essential penicillin binding proteins (PBPs) in bacteria, which are responsible for cell wall synthesis. On the other hand, quinolones act by inhibiting synthesis of bacterial DNA, thus preventing the bacteria from replicating.

Not surprisingly, the pharmacological characteristics of antibacterials and other antimicrobials, and their suitability for any given clinical use, also vary considerably. For example, the classes of antimicrobials (and members within a class) may vary in their relative efficacy against different types of microorganisms, and their susceptibility to development of microbial resistance. These antimicrobials may also differ in their pharmacological characteristics, such as their bioavailability, and biodistribution. Accordingly, selection of an appropriate antibacterial (or other antimicrobial) in any given clinical situation can be a complicated analysis of many factors, including the type of organism involved, the desired method of administration, and the location of the infection to be treated.

The development of microbial resistance is one factor in the selection of an appropriate antimicrobial (particularly anti-bacterials), which is of increasing concern in medical science. This "resistance" can be defined as existence of organisms, within a population of a given microbial species, that are less susceptible to the action of a given antimicrobial agent. Such resistant strains may subvert the mechanism of action of a particular antimicrobial, or chemically degrade the antimicrobial before it can act. For example, bacterial resistance to beta-lactam antibacterials has arisen through development of bacterial strains that produce beta-lactamase enzymes, which degrade the antibacterial.

In part as a result of the intense use of antibacterials over extended periods of time, many highly resistant strains of bacteria have evolved. This is of particular concern in environments such as hospitals and nursing homes, which are characterized by relatively high rates of infection and intense use of antibacterials. See, e.g., W. Sanders, Jr. et al., "Inductible Beta-lactamases: Clinical and Epidemiologic Implications for Use of Newer Cephalosporins", 10 *Reviews of Infectious Diseases* 830 (1988). Indeed, the development of resistant bacterial strains has led to a concern that pathogenic bacteria may be produced that are essentially resistant to even the newest developed antibacterial agents.

The literature describes many attempts to enhance the efficacy of antimicrobials, and to overcome the development of microbial resistance. Many such attempts involve the combination of antimicrobials. For example, Thabaut et al., 16 *Presse Med.* 2167 (1987) describes combinations of pefloxacin (a quinolone) with the beta-lactams cefotaxime and cefsulodin. Lenoc et al., 36 *Path. Biol.* 762 (1988), describes combined use of cephems with aminoglycosides, and with quinolones. Japanese Patent Publication 60/06,617, published Jan. 14, 1985, also describes compositions containing beta-lactams and quinolones. O'Callaghan et al., 10 *Antimicrobial Agents and Chemotherapy* 245 (1976), describes a mercapto pyridine-substituted cephem, which is said to liberate an active antimicrobial agent when the cephalosporin is hydrolyzed by beta-lactamase. Mobashery et al., 108 *J. American Chemical Society* 1684 (1986), presents a theory of employing bacterial beta-lactamase in situ to release an antibacterially-active leaving group from the 10-position of a cephem.

However, many such attempts to produce improved antimicrobials yield equivocal results. Indeed, few antimicrobials are produced that are truly clinically-acceptable in terms of their spectrum of antimicrobial activity, avoidance of microbial resistance, and pharmacology.

SUMMARY OF THE INVENTION

The present invention provides compounds of the general structure wherein Q, L and B are defined as follows:

(I) Q is a structure according to Formula (I)

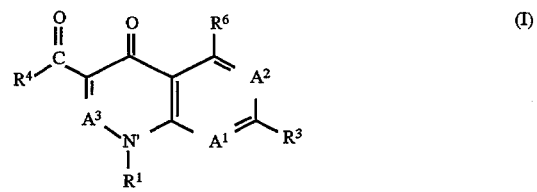

wherein
(A)
(1) $A^1$ is N or $C(R^7)$; where
  (i) $R^7$ is hydrogen, hydroxy, alkoxy, nitro, cyano, halogen, alkyl, or $N(R^8)(R^9)$, and
  (ii) $R^8$ and $R^9$ are, independently, $R^{8a}$ where $R^{8a}$ is hydrogen, alkyl, alkenyl, carbocyclic ring, or heterocyclic ring; or $R^8$ and $R^9$ together comprise a heterocyclic ring including the nitrogen to which they are bonded;
(2) $A^2$ is N or $C(R^2)$; where $R^2$ is hydrogen or halogen;
(3) $A^3$ is N or $C(R^5)$; where $R^5$ is hydrogen;
(4) $R^1$ is hydrogen or $R^{15}$, where $R^{15}$ is alkyl, a carbocyclic ring, a heterocyclic ring, alkoxy, hydroxy, alkenyl, arylalkyl, or $N(R^8)(R^9)$;

(5) $R^3$ is hydrogen, halogen, or $R^{16}$, where $R^{16}$ is alkyl, a carbocyclic ring, or a heterocyclic ring;

(6) $R^4$ is hydroxy; and (7) $R^6$ is hydrogen, halogen, nitro, or $N(R^8)(R^9)$;

(B) except that (1) when $A^1$ is $C(R^7)$, $R^1$ and $R^7$ may together comprise a heterocyclic ring including N' and $A^1$;

(2) when $A^2$ is $C(R^2)$, $R^2$ and $R^3$ may together comprise —O—$(CH_2)_n$—O—, where n is an integer from 1 to 4;

(3) when $A^3$ is $C(R^5)$, $R^4$ and $R^5$ may together comprise a heterocyclic ring including the carbon atoms to which $R^4$ and $R^5$ are bonded and the carbon atom of Formula (I) to which said carbon atoms are bonded; and (4) when $A^3$ is $C(R^5)$, $R^1$ and $R^5$ may together comprise a heterocyclic ring including N' and the adjacent carbon to which $R^5$ is bonded;

(C) and either (1) $R^1$ is $R^{15}$ and is a substituent moiety of L; or (2) $R^3$ is $R^{16}$ and is a substituent moiety of L;

(II) B is a structure according to Formula (II), where L is bonded to $R^{14}$:

$$R^{10}\underset{O}{\overset{R^{11}}{\underset{|}{\biggm|}}}\underset{N''R^{13}}{\overset{R^{12}}{\diagdown}}\overset{a}{\underset{b}{\diagdown}}R^{14}-L \qquad (II)$$

wherein (A) $R^{10}$ is hydrogen, halogen, alkyl, alkenyl, heteroalkyl, a carbocyclic ring, a heterocyclic ring, $R^{8a}$—O—, $R^{8a}$CH=N—, $(R^8)(R^9)$N—, $R^{17}$—C(=CHR$^{20}$)—C(=O)NH—, $R^{17}$—C(=NO—R$^{19}$)—C(=O)NH—, or $R^{18}$—$(CH_2)_m$—C(=O)NH—; where (1) m is an integer from 0 to 9;

(2) $R^{17}$ is hydrogen, alkyl, alkenyl, heteroalkyl, heteroalkenyl, a carbocyclic ring, or a heterocyclic ring;

(3) $R^{18}$ is $R^{17}$, —$Y^1$, or —CH($Y^2$)($R^{17}$);

(4) $R^{19}$ is $R^{17}$, arylalkyl, heteroarylalkyl, —C($R^{22}$)($R^{23}$)COOH, —C(=O)O—$R^{17}$, or —C(=O)NH—$R^{17}$, where $R^{22}$ and $R^{23}$ are, independently, $R^{17}$ or together comprise a carbocyclic ring or a heterocyclic ring including the carbon atom to which $R^{22}$ and $R^{23}$ are bonded;

(5) $R^{20}$ is $R^{19}$, halogen, —$Y^1$, or —CH($Y^2$)($R^{17}$);

(6) $Y^1$ is —C(=O)O$R^{21}$, —C(=O)$R^{21}$, —N($R^{24}$)$R^{21}$, —S(O)$_p$$R^{29}$, or —O$R^{29}$; and $Y^2$ is $Y^1$ or —OH, —SH, or —SO$_3$H;

(a) p is an integer from 0 to 2;

(b) $R^{24}$ is hydrogen; alkyl; alkenyl; heteroalkyl; heteroalkenyl; a carbocyclic ring; a heterocyclic ring; —SO$_3$H; —C(=O)$R^{25}$; or, when $R^{18}$ is —CH(N($R^{24}$)$R^{21}$)($R^{17}$), $R^{24}$ may comprise a moiety bonded to $R^{21}$ to form a heterocyclic ring; and (c) $R^{25}$ is $R^{17}$, NH($R^{17}$), N($R^{17}$)($R^{26}$), O($R^{26}$), or S($R^{26}$); where $R^{26}$ is alkyl, alkenyl, a carbocyclic ring, a heterocyclic ring, or when $R^{25}$ is N($R^{17}$)($R^{26}$), $R^{26}$ may be a moiety bonded to $R^{17}$ to form a heterocyclic ring; and (7) $R^{21}$ is $R^{29}$ or hydrogen; where $R^{29}$ is alkyl; alkenyl; arylalkyl; heteroalkyl; heteroalkenyl; heteroarylalkyl; a carbocyclic ring; a heterocyclic ring; or, when $Y^1$ is N($R^{24}$)$R^{21}$ and $R^{21}$ is $R^{29}$, $R^{21}$ and $R^{24}$ may together comprise a heterocyclic ring including the nitrogen atom to which $R^{24}$ is bonded;

(B) $R^{11}$ is hydrogen, halogen, alkoxy, or $R^{27}$C(=O)NH—, where $R^{27}$ is hydrogen or alkyl;

(C) bond "a" is a single bond or is nil; and bond "b" is a single bond, a double bond, or is nil; except bond "a" and bond "b" are not both nil;

(D) $R^{12}$ is —C($R^{8a}$)—, or —CH$_2$—$R^{28}$—; where $R^{28}$ is —C($R^{8a}$), —O—, or —N—, and $R^{28}$ is directly bonded to N" in Formula (II) to form a 5-membered ring; except, if bond "a" is nil, then $R^{12}$ is (1) —C($R^{8a}$)($X^1$)—, where (i) $X^1$ is —$R^{21}$; —O$R^{30}$; —S(O)$_r$$R^{30}$, where r is an integer from 0 to 2; —O(C=O)$R^{30}$; or N($R^{30}$)$R^{31}$; and (ii) $R^{30}$ and $R^{31}$ are, independently, alkyl, alkenyl, carbocyclic ring or heterocyclic ring substituents; or $R^{30}$ and $R^{31}$ together comprise a heterocyclic ring including the nitrogen atom to which $R^{30}$ and $R^{31}$ are bonded; or (2) —CH$_2$—$R^{32}$—; where $R^{32}$ is —C($R^{8a}$)($R^{21}$), —O—, or —NR$^{8a}$, and $R^{32}$ is directly bonded to N" in Formula (II) to form a 5-membered ring;

(E) (1) if bond "b" is a single bond, $R^{13}$ is —CH($R^{33}$)—; or, —C(O)NHSO$_2$—, if bond "a" is nil; or —C*($R^{33}$)— if $R^{14}$ contains a $R^{36}$ moiety; where $R^{33}$ is hydrogen or COOH, and C* is linked to $R^{36}$ to form a 3-membered ring;

(2) if bond "b" is a double bond, $R^{13}$ is —C($R^{33}$)=; or (3) if bond "b" is nil, $R^{13}$ is hydrogen, —SO$_3$H, —PO(O$R^{34}$)OH, —C(O)NHSO$_2$N($R^{34}$)($R^{35}$), —OSO$_3$H, —CH($R^{35}$)COOH, or —OCH($R^{34}$)COOH; where $R^{34}$ is hydrogen, alkyl, alkenyl, a carbocyclic ring, or a heterocyclic ring; and $R^{35}$ is hydrogen, alkyl, alkenyl, or —NHR$^{8a}$; or, if $R^{13}$ is —C(O)NHSO$_2$N($R^{34}$)($R^{35}$), $R^{34}$ and $R^{35}$ may together comprise a heterocyclic ring including the nitrogen to which $R^{34}$ and $R^{35}$ are bonded; and (F) (1) if bond "a" or bond "b" is nil, then $R^{14}$ is nil and L is bonded directly to $R^{12}$ or $R^{13}$;

(2) if bond "a" and "b" are single bonds, $R^{14}$ is —W—C'''=C($R^{8a}$)—$R^{37}$—, or —W—C'''($R^{36}$)—$R^{37}$—; or (3) if bond "a" is a single bond and bond "b" is a double bond, $R^{14}$ is —C($R^{8a}$) ($R^{38}$)—W—C'''—$R^{37}$—; —W—C($R^{8a}$) ($R^{38}$)—C'''—$R^{37}$—; or —W—C'''—$R^{37}$—; where (a) W is O; S(O)$_s$, where s is an integer from 0 to 2; or C($R^{38}$), where $R^{38}$ is hydrogen, alkyl or alkoxy;

(b) $R^{36}$ hydrogen; alkyl; alkenyl; —COOH; or, if $R^{13}$ is —C*($R^{33}$), $R^{36}$ may be linked to C* to form a 3-membered carbocyclic ring;

(c) $R^{37}$ is nil, alkyl, alkenyl, a carbocyclic ring, or a heterocyclic ring; and (d) C''' is directly bonded to $R^{13}$ to form a 5- or 6-membered ring, and (III) L links Q to B; and L is L', —$X^2_t$—$R^{39}$—L', or —$X^3_t$—$R^{39}$—L', where L' is Q', —$X^2$—Q'', —$X^3$—Q'', —$X^4_t$—C(=$Y^3_u$)—Z—Q'', —$X^5_t$—PO($Y^4_u$ $R^{8a}$)—Z'—Q'', or $X^5_t$—SO$_2$—Z'—Q'';

(1) t and u are, independently, 0 or 1;

(2) $R^{39}$ is alkyl, alkenyl, heteroalkyl, heteroalkenyl, a carbocyclic ring, or a heterocyclic ring;

(3) $X^2$ is oxygen, or S(O)$_v$, where v is an integer from 0 to 2;

(4) $X^3$ is nitrogen; N($R^{40}$); N$^+$($R^{41}$)($R^{42}$); or $R^{43}$—N($R^{41}$); and is linked to $R^{14}$ by a single or double bond; or, if $R^{14}$ is nil, $X^3$ is linked to B by a single or double bond; where (a) $R^{40}$ is $R^{8a}$; —$OR^{8a}$; or —$C(=O)R^{8a}$;
(b) $R^{41}$ and $R^{42}$ are, independently, hydrogen; alkyl; alkenyl; carbocyclic rings; heterocyclic rings; or, together with Q", comprise a heterocyclic ring as $R^{15}$ or $R^{16}$;
(c) $R^{43}$ is $N(R^{41})$, oxygen or sulfur;
(5) $X^4$ is oxygen, sulfur, $NR^{40}$, or $R^{43}$—$NR^{41}$;
(6) $X^5$ is oxygen or $NR^{41}$;
(7) $Y^3$ is oxygen, sulfur, $NR^{40}$ or $N^+(R^{41})(R^{42})$;
(8) $Y^4$ is oxygen or $NR^{41}$;
(9) Z is nil, oxygen, sulfur, nitrogen, $NR^{40}$, or $N(R^{41})$—$R^{43}$;
(10) Z' is nil, oxygen, nitrogen, or $NR^{41}$;
(11) Q' is $R^{15}$ or $R^{16}$; and
(12) Q" is Q'; or together with $X^2$, $X^3$, Z or Z', is an $R^{15}$ or $R^{16}$ group;

and pharmaceutically-acceptable salts and biohydrolyzable esters thereof, and hydrates thereof.

It has been found that the compounds of this invention, and compositions containing these compounds, are effective antimicrobial agents against a broad range of pathogenic microorganisms. These compounds provide advantages versus antimicrobial agents among those known in the art, including (for example) the spectrum of antimicrobial activity, potency, the avoidance of microbial resistance, reduced toxicity, and improved pharmacology.

DESCRIPTION OF THE INVENTION

The present invention encompasses certain novel lactam-quinolones, methods for their manufacture, dosage forms, and methods of administering the lactam-quinolones to a human or other animal subject. Specific compounds and compositions to be used in the invention must, accordingly, be pharmaceutically acceptable. As used herein, such a "pharmaceutically-acceptable" component is one that is suitable for use with humans and/or animals without undue adverse side effects (such as toxicity, irritation, and allergic response) commensurate with a reasonable benefit/risk ratio.

Lactam-Quinolones

The compounds of this invention, herein referred to as "lactam-quinolones", encompass any of a variety of lactam moieties linked, by a linking moiety, to a quinolone moiety at positions other than the 3-carboxy position. These compounds include those having the general formula

Q—L—B wherein Q, L and B are defined as follows:
(I) Q is a structure according to Formula (I)

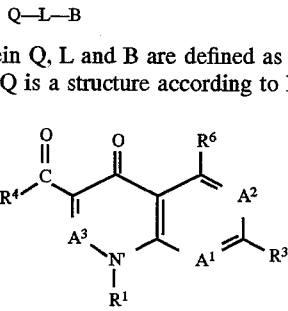

wherein
(A)
(1) $A^1$ is N or $C(R^7)$; where
(i) $R^7$ is hydrogen, hydroxy, alkoxy, nitro, cyano, halogen, alkyl, or $N(R^8)(R^9)$ (preferably hydrogen or halogen), and (ii) $R^8$ and $R^9$ are, independently, $R^{8a}$, where $R^{8a}$ is hydrogen, alkyl, alkenyl, carbocyclic ring, or heterocyclic ring substituents; or $R^8$ and $R^9$ together comprise a heterocyclic ring including the nitrogen to which they are bonded;
(2) $A^2$ is N or $C(R^2)$ (preferably $C(R^2)$); where $R^2$ is hydrogen or halogen;
(3) $A^3$ is N or (preferably) $C(R^5)$; where $R^5$ is hydrogen;
(4) $R^1$ is hydrogen or $R^{15}$, where $R^{15}$ is alkyl, a carbocyclic ring, a heterocyclic ring, alkoxy, hydroxy, alkenyl, arylalkyl, or $N(R^8)(R^9)$ (preferably alkyl or a carbocyclic ring);
(5) $R^3$ is hydrogen, halogen, or $R^{16}$, where $R^{16}$ is alkyl, a carbocyclic ring, or a heterocyclic ring (preferably a heterocyclic ring);
(6) $R^4$ is hydroxy; and
(7) $R^6$ is hydrogen, halogen, nitro, or $N(R^8)(R^9)$ (preferably hydrogen);
(B) except that
(1) when $A^1$ is $C(R^7)$, $R^1$ and $R^7$ may together comprise a heterocyclic ring including N' and $A^1$;
(2) when $A^2$ is $C(R^2)$, $R^2$ and $R^3$ may together comprise —O—$(CH_2)_n$—O—, where n is an integer from 1 to 4;
(3) when $A^3$ is $C(R^5)$, $R^4$ and $R^5$ may together comprise a heterocyclic ring including the carbon atoms to which $R^4$ and $R^5$ are bonded and the carbon atom of Formula (I) to which said carbon atoms are bonded; and
(4) when $A^3$ is $C(R^5)$, $R^1$ and $R^5$ may together comprise a heterocyclic ring including N' and the adjacent carbon to which $R^5$ is bonded;
(C) and either
(1) $R^1$ is $R^{15}$ and is a substituent moiety of L; or
(2) $R^3$ is $R^{16}$ and is a substituent moiety of L;
(II) B is a structure according to Formula (II), where L is bonded to $R^{14}$:

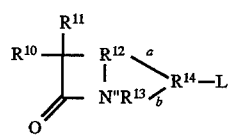

wherein
(A) $R^{10}$ is hydrogen, halogen, heteroalkyl, a carbocyclic ring, a heterocyclic ring, $R^{8a}$—O—, $R^{8a}CH=N$—, $(R^8)(R^9)N$—, $R^{17}$—$C(=CHR^{20})$—$C(=O)NH$—, or (preferably) alkyl, alkenyl, $R^{17}$—$C(=NO—R^{19})$—$C(=O)NH$—, or $R^{18}$—$(CH_2)_m$—$C(=O)NH$—; where
(1) m is an integer from 0 to 9 (preferably from 0 to 3);
(2) $R^{17}$ is hydrogen, alkyl, alkenyl, heteroalkyl, heteroalkenyl, a carbocyclic ring, or a heterocyclic ring (preferably alkyl, a carbocyclic ring, or a heterocyclic ring);
(3) $R^{18}$ is $R^{17}$, —$Y^1$, or —$CH(Y^2)(R^{17})$;
(4) $R^{19}$ is $R^{17}$, arylalkyl, heteroarylalkyl, —$C(R^{22})(R^{23})$ COOH, —$C(=O)O$—$R^{17}$, or —$C(=O)NH$—$R^{17}$, where $R^{22}$ and $R^{23}$ are, independently, $R^{17}$ or together comprise a carbocyclic ring or a heterocyclic ring including the carbon atom to which $R^{22}$ and $R^{23}$ are bonded (preferably $R^{17}$ or —$C(R^{22})(R^{23})COOH$)
(5) $R^{20}$ is $R^{19}$, halogen, —$Y^1$, or —$CH(Y^2)(R^{17})$ (preferably $R^{19}$ or halogen);
(6) $Y^1$ is —$C(=O)OR^{21}$, —$C(=O)R^{21}$, —$N(R^{24})R^{21}$, or —$S(O)_pR^{29}$ or —$OR^{29}$; and $Y^2$ is $Y^1$ or —OH, —SH, or —$SO_3H$;

(a) p is an integer from 0 to 2 (preferably 0);

(b) $R^{24}$ is hydrogen; alkyl; alkenyl; heteroalkyl; heteroalkenyl; a carbocyclic ring; a heterocyclic ring; —$SO_3H$; —$C(=O)R^{25}$; or, when $R^{18}$ is —$CH(N(R^{24})R^{21})(R^{17})$, $R^{24}$ may comprise a moiety bonded to $R^{21}$ to form a heterocyclic ring; and (c) $R^{25}$ is $R^{17}$, $NH(R^{17})$, $N(R^{17})(R^{26})$, $O(R^{26})$, or $S(R^{26})$ (preferably $R^{17}$, $NH(R^{17})$ or $N(R^{17})(R^{26})$); where $R^{26}$ is alkyl, alkenyl, a carbocyclic ring, a heterocyclic ring or (preferably) when $R^{25}$ is $N(R^{17})(R^{26})$, $R^{26}$ may comprise a moiety bonded to $R^{17}$ to form a heterocyclic ring; and (7) $R^{21}$ is $R^{29}$ or hydrogen; where $R^{29}$ is alkyl; alkenyl; arylalkyl; heteroalkyl; heteroalkenyl; heteroarylalkyl; a carbocyclic ring; a heterocyclic ring; or, when $Y^1$ is $N(R^{24})R^{21}$ and $R^{21}$ is $R^{29}$, $R^{21}$ and $R^{24}$ may together comprise a heterocyclic ring including the nitrogen atom to which $R^{24}$ is bonded (preferably hydrogen, alkyl, a carbocyclic ring or a heterocyclic ring);

(B) $R^{11}$ is hydrogen, halogen, alkoxy, or $R^{27}C(=O)NH$— (preferably hydrogen or alkoxy), where $R^{27}$ is hydrogen or alkyl (preferably hydrogen);

(C) bond "a" is a single bond or is nil; and bond "b" is a single bond, a double bond, or is nil; except bond "a" and bond "b" are not both nil;

(D) $R^{12}$ is —$C(R^{8a})$—, or —$CH_2$—$R^{28}$— (preferably —$C(R^{8a})$—); where $R^{28}$ is —$C(R^{8a})$, —O—, or —N—, and $R^{28}$ is directly bonded to N" in Formula (II) to form a 5-membered ring; except, if bond "a" is nil, then $R^{12}$ is (1) (preferably) —$C(R^{8a})(X^1)$—, where (i) $X^1$ is —$R^{21}$; —$OR^{30}$; —$S(O)_r^{30}$, where r is an integer from 0 to 2 (preferably 0); —$O(C=O)R^{30}$; or $N(R^{30})R^{31}$; and (ii) $R^{30}$ and $R^{31}$ are, independently, alkyl, alkenyl, carbocyclic ring or heterocyclic ring substituents; or $R^{30}$ and $R^{31}$ together comprise a heterocyclic ring including the nitrogen atom to which $R^{30}$ and $R^{31}$ are bonded; or (2) —$CH_2$—$R^{32}$—; where $R^{32}$ is —$C(R^{8a})(R^{21})$, —O—, or —$NR^{8a}$, and $R^{32}$ is directly bonded to N" in Formula (II) to form a 5-membered ring;

(E) (1) if bond "b" is a single bond, $R^{13}$ is preferably —$CH(R^{33})$—; or, —$C(O)NHSO_2$—, if bond "a" is nil; or —$C^*(R^{33})$—, if $R^{14}$ contains a $R^{36}$ moiety; where $R^{33}$ is hydrogen or COOH (preferably COOH), and $C^*$ is linked to $R^{36}$ to form a 3-membered ring;

(2) if bond "b" is a double bond, $R^{13}$ is —$C(R^{33})=$; or (3) if bond "b" is nil, $R^{13}$ is hydrogen, —$SO_3H$, —$PO(OR^{34})OH$, —$C(O)NHSO_2N(R^{34})(R^{35})$, —$OSO_3H$, —$CH(R^{35})COOH$, or —$OCH(R^{34})COOH$ (preferably —$SO_3H$, or —$C(O)NHSO_2N(R^{34})(R^{35})$); where $R^{34}$ is hydrogen, alkyl, alkenyl, a carbocyclic ring, or a heterocyclic ring; and $R^{35}$ is hydrogen, alkyl, alkenyl, or —$NHR^{8a}$; or (preferably), if $R^{13}$ is —$C(O)NHSO_2N(R^{34})(R^{35})$, $R^{34}$ and $R^{35}$ may together comprise a heterocyclic ring including the nitrogen to which $R^{34}$ and $R^{35}$ are bonded; and (F) (1) if bond "a" or bond "b" is nil, then $R^{14}$ is nil and L is bonded directly to $R^{12}$ or $R^{13}$;

(2) if bond "a" and "b" are single bonds, $R^{14}$ is —W—C'''=$C(R^{8a})$—$R^{37}$—, or —W—C'''($R^{36}$)—$R^{37}$—; or (3) (preferably) if bond "a" is a single bond and bond "b" is a double bond, $R^{14}$ is —$C(R^{8a})(R^{38})$—W—C'''—$R^{37}$—; or (preferably) —W—$C(R^{8a})(R^{38})$—C'''—$R^{37}$, or —W—C'''—$R^{37}$—; where (a) W is O; $S(O)_s$, where s is an integer from 0 to 2 (preferably 0); or $C(R^{38})$, where $R^{38}$ is hydrogen, alkyl or alkoxy;

(b) $R^{36}$ hydrogen; alkyl; alkenyl; —COOH; or, if $R^{13}$ is —$C^*(R^{33})$, $R^{36}$ may be linked to $C^*$ to form a 3-membered carbocyclic ring;

(c) $R^{37}$ is nil, alkyl, alkenyl, a carbocyclic ring, or a heterocyclic ring; and (d) C''' is directly bonded to $R^{13}$ to form a 5- or 6-membered ring, and (III) L links Q to B; and L is L', —$X^2_t$—$R^{39}$—L', or —$X^3_t$—$R^{39}$—L', where L' is Q', —$X^2$—$_{Q''}$, —$X^3$—$_{Q''}$, —$X^4_t$—$C(=Y^3_u)$—Z—Q", —$X^5_t$—$PO(Y^4_u R^{8a})$—Z'—Q", or $X^5_t$—$SO_2$—Z'—Q" (preferably —$X^2$—Q", —$X^3$—$_{Q''}$, —$X^4_t$—$C(=Y^3_u)$—Z—Q");

(1) t and u are, independently, 0 or 1;

(2) $R^{39}$ is alkyl, alkenyl, heteroalkyl, heteroalkenyl, a carbocyclic ring, or a heterocyclic ring (preferably alkyl or alkenyl);

(3) $X^2$ is oxygen, or $S(O)_v$, where v is an integer from 0 to 2 (preferably 0);

(4) $X^3$ is nitrogen; $N(R^{40})$; $N^+(R^{41})(R^{42})$; or $R^{43}$—$N(R^{41})$; and is linked to $R^{14}$ by a single or double bond; or, if $R^{14}$ is nil, $X^3$ is linked to B by a single or double bond (preferably $X^3$ is nitrogen, $N(R^{40})$ or $N^+(R^{41})(R^{42})$); where (a) $R^{40}$ is $R^{8a}$; —$OR^{8a}$; or —$C(=O)R^{8a}$; (preferably $R^{8a}$);

(b) $R^{41}$ and $R^{42}$ are, independently, hydrogen; alkyl; alkenyl; carbocyclic rings; heterocyclic rings; or, (preferably) together with Q", comprise a heterocyclic ring as $R^{15}$ or $R^{16}$;

(c) $R^{43}$ is $N(R^{41})$, oxygen or sulfur;

(5) $X^4$ is oxygen, sulfur, $NR^{40}$, or $R^{43}$—$NR^{41}$ (preferably oxygen, sulfur or $NR^{40}$);

(6) $X^5$ is oxygen or $NR^{41}$ (preferably oxygen);

(7) $Y^3$ is oxygen, sulfur, $NR^{40}$ or $N^+(R^{41})(R^{42})$;

(8) $Y^4$ is oxygen or $NR^{41}$ (preferably oxygen);

(9) Z is nil, oxygen, sulfur, nitrogen, $NR^{40}$, or $N(R^{41})$—$R^{43}$ (preferably oxygen, sulfur, nitrogen or $NR^{40}$);

(10) Z' is nil, oxygen, nitrogen, or $NR^{41}$ (preferably oxygen);

(11) Q' is $R^{15}$ or $R^{16}$; and

(12) Q" is Q'; or together with $X^2$, $X^3$, Z or Z', is an $R^{15}$ or $R^{16}$ group;

and pharmaceutically-acceptable salts and biohydrolyzable esters thereof, and hydrates thereof.

Definitions and Usage of Terms

The following is a list of definitions for terms used herein.

"Heteroatom" is a nitrogen, sulfur or oxygen atom. Groups containing one or more heteroatoms may contain different heteroatoms.

"Alkyl" is an unsubstituted or substituted saturated hydrocarbon chain radical having from 1 to 8 carbon atoms, preferably from 1 to 4 carbon atoms. Preferred alkyl groups include (for example) methyl, ethyl, propyl, isopropyl, and butyl.

"Heteroalkyl" is an unsubstituted or substituted saturated chain radical having from 3 to 8 members comprising carbon atoms and one or two heteroatoms.

"Alkenyl" is an unsubstituted or substituted hydrocarbon chain radical having from 2 to 8 carbon atoms, preferably from 2 to 4 carbon atoms, and having at least one olefinic double bond.

"Carbocyclic ring" is an unsubstituted or substituted, saturated, unsaturated or aromatic, hydrocarbon ring radical. Carbocyclic rings are monocyclic or are fused, bridged or spiro polycyclic ring systems. Monocyclic rings contain from 3 to 9 atoms, preferably 3 to 6 atoms. Polycyclic rings contain from 7 to 17 atoms, preferably from 7 to 13 atoms.

"Cycloalkyl" is a saturated carbocyclic ring radical. Preferred cycloalkyl groups include (for example) cyclopropyl, cyclobutyl and cyclohexyl.

"Heterocyclic ring" is an unsubstituted or substituted, saturated, unsaturated or aromatic ring radical comprised of carbon atoms and one or more heteroatoms in the ring. Heterocyclic rings are monocyclic or are fused, bridged or spiro polycyclic ring systems. Monocyclic rings contain from 3 to 9 atoms, preferably 3 to 6 atoms. Polycyclic rings contain from 7 to 17 atoms, preferably from 7 to 13 atoms.

"Aryl" is an aromatic carbocyclic ring radical. Preferred aryl groups include (for example) phenyl, tolyl, xylyl, cumenyl and naphthyl.

"Heteroaryl" is an aromatic heterocyclic ring radical. Preferred heteroaryl groups include (for example) thienyl, furyl, pyrrolyl, pyridinyl, pyrazinyl, thiazolyl, quinolinyl, pyrimidinyl and tetrazolyl.

"Alkoxy" is an oxygen radical having a hydrocarbon chain substituent, where the hydrocarbon chain is an alkyl or alkenyl (i.e., —O-alkyl or —O-alkenyl). Preferred alkoxy groups include (for example) methoxy, ethoxy, propoxy and allyloxy.

"Alkylamino" is an amino radical having one or two alkyl substituents (i.e., —N-alkyl).

"Arylalkyl" is an alkyl radical substituted with an aryl group. Preferred arylalkyl groups include benzyl and phenylethyl.

"Arylamino" is an amine radical substituted with an aryl group (i.e., —NH—aryl).

"Aryloxy" is an oxygen radical having a aryl substituent (i.e., —O-aryl).

"Acyl" or "carbonyl" is a radical formed by removal of the hydroxy from a carboxylic acid (i.e., R—C(=O)—). Preferred alkylacyl groups include (for example) acetyl, formyl, and propionyl.

"Acyloxy" is an oxygen radical having an acyl substituent (i.e., —O-acyl); for example, —O—C(=O)-alkyl.

"Acylamino" is an amino radical having an acyl substituent (i.e., —N-acyl); for example, —NH—C(=O)-alkyl.

"Halo", "halogen", or "halide" is a chloro, bromo, fluoro or iodo atom radical. Chloro and fluoro are preferred halides. Also, as referred to herein, a "lower" hydrocarbon moiety (e.g., "lower" alkyl) is a hydrocarbon chain comprised of from 1 to 6, preferably from 1 to 4, carbon atoms.

A "pharmaceutically-acceptable salt" is a cationic salt formed at any acidic (e.g., carboxyl) group, or an anionic salt formed at any basic (e.g., amino) group. Many such salts are known in the art, as described in World Patent Publication 87/05297, Johnston et al., published Sep. 11, 1987 (incorporated by reference herein). Preferred cationic salts include the alkali metal salts (such as sodium and potassium), and alkaline earth metal salts (such as magnesium and calcium). Preferred anionic salts include the halides (such as chloride salts).

A "biohydrolyzable ester" is an ester of a lactam-quinolone that does not essentially interfere with the antimicrobial activity of the compounds, or that are readily metabolized by a human or lower animal subject to yield an antimicrobially-active lactam-quinolone. Such esters include those that do not interfere with the biological activity of quinolone antimicrobials or beta-lactam antimicrobials (cephems, for example). Many such esters are known in the art, as described in World Patent Publication 87/05297, Johnston et al., published Sep. 11, 1987, (incorporated by reference herein). Such esters include lower alkyl esters, lower acyloxy-alkyl esters (such as acetoxymethyl, acetoxyethyl, aminocarbonyloxymethyl, pivaloyloxymethyl and pivaloyloxyethyl esters), lactonyl esters (such as phthalidyl and thiophthalidyl esters), lower alkoxyacyloxyalkyl esters (such as methoxycarbonyloxymethyl, ethoxycarbonyloxyethyl and isopropoxycarbonyloxyethyl esters), alkoxyalkyl esters, choline esters and alkyl acylamino alkyl esters (such as acetamidomethyl esters).

As defined above and as used herein, substituent groups may themselves be substituted. Such substitution may be with one or more substituents. Such substituents include (for example) those listed in C. Hansch and A. Leo, *Substituent Constants for Correlation Analysis in Chemistry and Biology* (1979), incorporated by reference herein. Preferred substituents include (for example) alkyl, alkenyl, alkoxy, hydroxy, oxo, nitro, amino, aminoalkyl (e.g., aminomethyl, etc.), cyano, halo, carboxy, alkoxyaceyl (e.g., carboethoxy, etc.), thiol, aryl, cycloalkyl, heteroaryl, heterocycloalkyl (e.g., piperidinyl, morpholinyl, pyrrolidinyl, etc.), imino, thioxo, hydroxyalkyl, aryloxy, arylalkyl, and combinations thereof.

Also, as used in defining the structure of the compounds of this invention, a particular radical may be defined for use as a substituent in multiple locations. For example, the $R^{8a}$ substituent is defined as a potential substituent of $R^7$, but is also incorporated into the definition of other substituents (such as $R^6$, $R^{12}$, $R^{32}$ and L'). As used herein, such a radical is independently selected each time it is used (e.g., $R^{8a}$ need not be alkyl in all occurrences in defining a given compound of this invention).

Lactam-containing Moiety

Groups $R^{12}$, $R^{13}$, and $R^{14}$, together with bonds "a" and "b" of formula (I), form any of a variety of lactam-containing moieties known in the art to have antimicrobial activity. Such moieties wherein either bond "a" or bond "b" are nil (i.e., do not exist) are mono-cyclic; if both bonds exist, the structures are bi-cyclic. Preferably, bond "a" is a single bond and bond "b" is a double bond.

Preferred lactam moieties include the cephems, oxacephems and carbacephems of the representative formula:

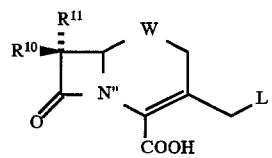

wherein, referring to formula (II), bond "a" is a single bond; bond "b" is a double bond; $R^{12}$ is —$C(R^{8a})$—, where $R^{8a}$ is hydrogen; $R^{13}$ is —$CH(R^{33})$, where $R^{33}$ is COOH; and $R^{14}$ is —W—$C(R^{8a})(R^{38})$—$C'''$—$R^{37}$, where $R^{8a}$ and $R^{38}$ are hydrogen, $R^{37}$ is methylene, and W is S (for cephems), O (for oxacephems) or $C(R^{38})$ (for carbacephems).

Other preferred lactam moieties include the isocephems and iso-oxacephems of the representative formula:

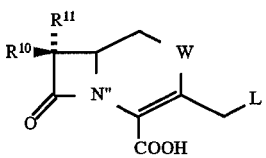

wherein, referring to formula II, bond "a" is a single bond; bond "b" is a double bond; $R^{12}$ is —$C(R^{8a})$ where $R^{8a}$ is hydrogen; $R^{13}$ is —$C(R^{33})$=, where $R^{33}$ is COOH; and $R^{14}$ is —$C(R^{8a})(R^{38})$—W—C'''—$R^{37}$ where $R^{8a}$ and $R^{38}$ are each hydrogen, $R^{37}$ is methylene, and W is S (for isocephems) or O (for iso-oxacephems), Other preferred lactam-containing moieties include the penems, carbapenems and clavems, of the representative formula:

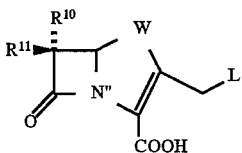

wherein, referring to formula (II), bond "a" is a single bond; bond "b" is a double bond; $R^{12}$ is —$C(R^{8a})$, where $R^{8a}$ is hydrogen; $R^{13}$ is —$C(R^{33})$=, where $R^{33}$ is COOH; and $R^{14}$ is —W—C'''—$R^{37}$, where $R^{37}$ is methylene, and W is S (for penems), $C(R^{38})$ (for carbapenems), or O (for clavems). Such lactam moieties are described in the following articles, all incorporated by reference herein: R. Wise, "In Vitro and Pharmacokinetic Properties of the Carbapenems", 30 *Antimicrobial Agents and Chemotherapy* 343 (1986); and S. McCombie et al., "Synthesis and In Vitro Activity of the Penem Antibiotics", 8 *Medicinal Research Reviews* 393 (1988).

Other preferred lactam-containing moieties of this invention include the penicillins of the representative formula:

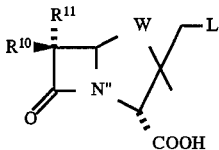

wherein, referring to formula II, bond "a" is a single bond, bond "b" is a single bond; $R^{12}$ is —$C(R^{8a})$—, where $R^{8a}$ is hydrogen; $R^{13}$ is —$CH(R^{33})$— where $R^{33}$ is COOH; and $R^{14}$ is —W—C'''($R^{36}$)—$R^{37}$— where $R^{36}$ is methyl, $R^{37}$ is methylene, and W is S.

Other preferred lactam-containing moieties include the monocyclic beta-lactams, of the representative formula:

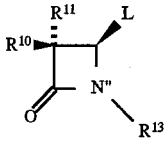

wherein, referring to formula (II), bond "a" is a single bond; bond "b" is nil; $R^{12}$ is —$C(R^{8a})$—, where $R^{8a}$ is hydrogen; $R^{14}$ is nil; and $R^{13}$ is —$SO_3H$ (for a monobactam), —PO($OR^{34}$)OH (for a monophospham); —$C(O)NHSO_2N(R^{34})(R^{35})$ (for a monocarbam), —$OSO_3H$ (for a monosulfactam), —$CH(R^{35})COOH$ (for nocardicins), or —$OCH(R^{34})COOH$. Such lactam moieties are described in C. Cimarusti et al., "Monocyclic 8-lactam Antibiotics", 4 *Medicinal Research Reviews* 1 (1984), incorporated by reference herein.

Other preferred lactam moieties include the monocyclic beta-lactams of the representative formula:

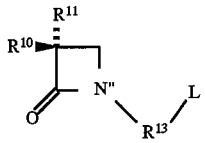

wherein referring to formula II, bond "a" is nil, bond "b" is a single bond; $R^{12}$ is —$C(R^{8a})(R^{29})$— where both $R^{8a}$ and $R^{29}$ are hydrogen; and $R^{14}$ is nil.

Other preferred lactam moieties include the clavams of the representative formula:

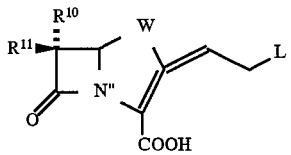

wherein, referring to formula (II), bond "a" is a single bond; bond "b" is a single bond; $R^{12}$ is —$C(R^{8a})$—, where $R^{8a}$ is hydrogen; $R^{13}$ is —$CH(R^{33})$—, where $R^{33}$ is COOH; and $R^{14}$ is W—C'''=C—$(R^{8a})$—$R^{37}$, where $R^{8a}$ is hydrogen and $R^{37}$ is methylene, and W is O.

Other preferred lactam moieties include the 2,3-methylenopenams and -carbapenams of the representative formula:

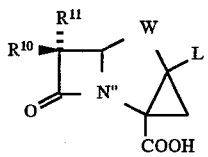

wherein, referring to formula (II), bond "a" is a single bond; bond "b" is a single bond; $R^{12}$ is —$C(R^{8a})$—, where $R^{8a}$ is hydrogen; $R^{13}$ is —$C^*(R^{33})$, where $R^{33}$ is COOH; and $R^{14}$ is W—C'''($R^{36}$)—$R^{37}$, where $R^{37}$ is nil, $R^{36}$ is linked to C* to form a 3-membered carbocyclic ring, and W is $C(R^{38})$ or sulfur.

Lactam moieties of this invention also include the lactivicin analogs of the representative formula:

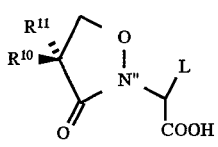

wherein, referring to formula (II), bond "a" is nil; bond "b" is a single bond; $R^{12}$ is —$CH_2$—$R^{32}$, where $R^{32}$ is O; $R^{13}$ is —$CH(R^{33})$—, where $R^{33}$ is COOH; and $R^{14}$ is nil.

Other lactam moieties include the pyrazolidinones of the representative formula:

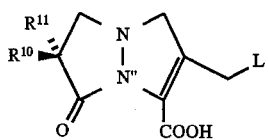

wherein, referring to formula (I), bond "a" is a single bond; bond "b" is a double bond; $R^{12}$ is —$CH_2$—$R^{28}$—, where $R^{28}$ is —N—; $R^{13}$ is —$C(R^{33})$—, where $R^{33}$ is COOH; and $R^{14}$ is W—C'''—$R^{37}$—, where $R^{37}$ is methylene, and W is $C(R^{38})$.

Other lactam moieties include the gamma-lactams of the representative formula:

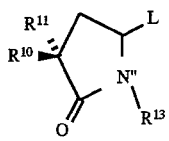

wherein, referring to formula (II), bond "a" is a single bond; bond "b" is nil; $R^{12}$ is —$CH_2$—$R^{28}$—, where $R^{28}$ is —$C(R^{8a})$ and $R^{8a}$ is hydrogen; $R^{13}$ is —$SO_3H$, —$PO(OR^{34})$ OH, —$C(O)NHSO_2N(R^{34})(R^{35})$, —$OSO_3H$, —$CH(R^{35})$ COOH, or —$OCH(R^{34})COOH$; and $R^{14}$ is nil.

Preferred lactam-containing moieties include cephems, isocephems, iso-oxacephems, oxacephems, carbacephems, pentcillins, penems, carbapenems, and monocyclic beta-lactams. Particularly preferred are cephems, penems, carbapenems and monocyclic beta-lactams.

$R^{10}$, in formula (II), is any radical that may be substituted at the active stereoisomeric position of the carbon adjacent to the lactam carbonyl of an antimicrobially-active lactam. (As used herein, the term "antimicrobially-active lactam" refers to a lactam-containing compound, without a quinolonyl substituent moiety, which has antimicrobial activity.) This "active" position is beta (i.e., 7-beta) for cephems, oxacephems and carbacephems (for example). The active position is alpha for penems, carbapenems, clavems and clavams.

Appropriate $R^{10}$ groups will be apparent to one of ordinary skill in the art. Many such $R^{10}$ groups are known in the art, as described in the following documents (all of which are incorporated by reference herein): *Cephalosporins and Penicillins: Chemistry and Biology* (E. Flynn, editor, 1972); *Chemistry and Biology of b-Lactam Antibiotics* (R. Morin et al., editors, 1987); "The Cephalosporin Antibiotics: Seminar-in-Print", 34 Drugs (Supp. 2) 1 (J. Williams, editor, 1987); *New Beta-Lactam Antibiotics: A Review from Chemistry of Clinical Efficacy of the New Cephalosporins* (H. Neu, editor, 1982); M. Sassiver et al., in *Structure Activity Relationships among the Semi-synthetic Antibiotics* (D. Perlman, editor, 1977). W. Durckheimer et al., "Recent Developments in the Field of Beta-Lactam Antibiotics", 24 *Angew. Chem. Int. Ed. Engl.* 180 (1985); G. Rolinson, "Beta-Lactam Antibiotics", 17 *J. Antimicrobial Chemotherapy* 5 (1986); European Patent Publication 187,456, Jung, published Jul. 16, 1986; and World Patent Publication 87/05297, Johnston et al., published Sep. 11, 1987.

For penems, carbapenems, clavems and clavams, $R^{10}$ is preferably lower alkyl, or hydroxy-substituted lower alkyl. Particularly preferred $R^{10}$ groups include hydrogen, hydroxymethyl, ethyl, [1(R)-hydroxyethyl], [1(R)-[(hydroxysulfonyl)oxyethyl]], and [1-methyl-1-hydroxyethyl].

Except for penems, carbapenems, clavems and clavams, preferred $R^{10}$ groups are amides, such as: acetylamino, preferably substituted with aryl, heteroaryl, aryloxy, heteroarylthio and lower alkylthio substituents; arylglycylamino, preferably N-substituted with heteroarylcarbonyl and cycloheteroalkylcarbonyl substituents; arylcarbonylamino; heteroarylcarbonylamino; and lower alkoxyiminoacetylamino, preferably substituted with aryl and heteroaryl substituents. Particularly preferred $R^{10}$ groups include amides of the general formula $R^{18}$—$(CH_2)_m$—$C(=O)NH$— and $R^{18}$ is $R^{17}$. Examples of such preferred $R^{10}$ groups include:

[(2-amino-5-halo-4-thiazolyl)acetyl]amino;

[(4-aminopyridin-2-yl)acetyl]amino;

[[(3,5-dichloro-4-oxo-1(4H)-pyridinyl)acetyl]amino];

[[[2-(aminomethyl)phenyl]acetyl]amino];

[(1H-tetrazol-1-ylacetyl)amino];

[(cyanoacetyl)amino];

[(2-thienylacetyl)amino];

[[(2-amino-4-thiazoyl)acetyl]amino]; and sydnone, 3-[-2-amino]-2-oxoethyl.

The following are other such preferred $R^{10}$ groups.

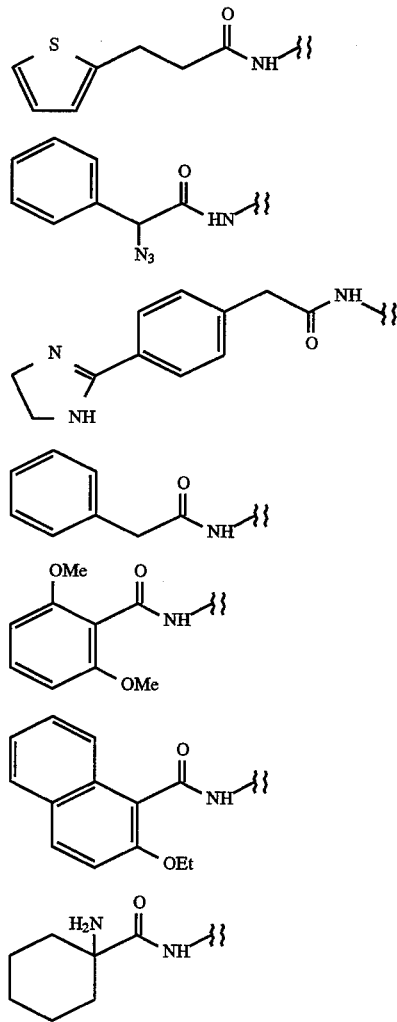

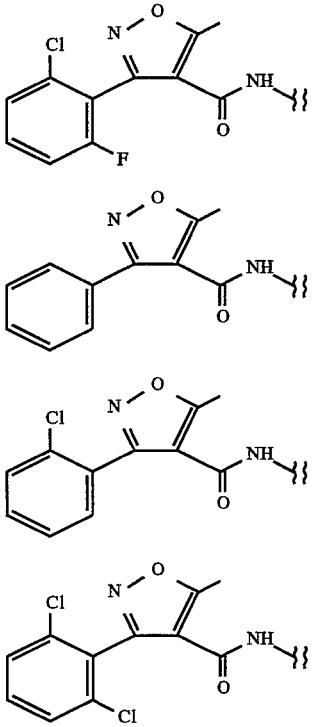

When $R^{10}$ is $R^{18}$—$(CH_2)_m$—$C(=O)NH$—, and $R^{18}$ is —$Y^1$, preferred $R^{10}$ groups include the following:

[sulfamoylphenylacetyl]amino;

[[(4-pyridinylthio)acetyl]amino];

[[[(cyanomethyl)thio]acetyl]amino];

(S)-[[[(2-amino-2-carboxyethyl)thio]acetyl]amino];

[[[(trifluoromethyl)thio]acetyl]amino]; and (E)-[[[(2-aminocarbonyl-2-fluoroethenyl)thio]acetyl] amino].

The following are other such preferred $R^{10}$ groups.

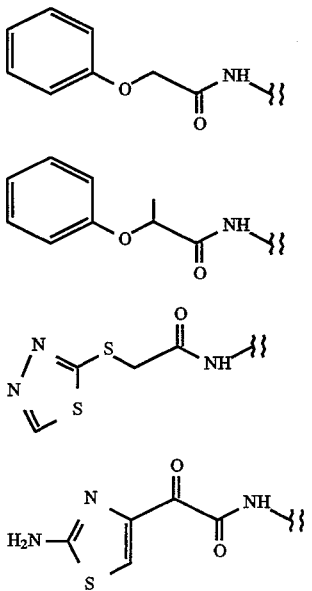

When $R^{10}$ is $R^{18}$—$(CH_2)_m$—$C(=O)NH$—, and $R^{18}$ is —$CH(Y^2)(R^{17})$, preferred $R^{10}$ groups include the following:

[carboxyphenylacetyl]amino;

[(phenoxycarbony)phenylacetyl]amino;

[4-methyl-2,3-dioxo-1-piperazinecarbonyl-D-phenylglycyl]-amino;

[[[3-(2-furylmethyleneamino)-2-oxo-1-imidazolidinyl]-carbonyl]amino]phenyl]acetyl]amino;

(R)-[(aminophenylacetyl)amino];

(R)-[[amino(4-hydroxyphenyl)acetyl]amino];

(R)-[(amino-1,4-cyclohexadien-1-ylacetyl)amino];

[(hydroxyphenylacetyl)amino];

(R)-[[[[(4-ethyl-2,3-dioxo-1-piperazinyl)carbonyl] amino]-(4-hydroxyphenyl)acetyl]amino];

(R)-[[[[(5-carboxy-1H-imidazol-4-yl)carbonyl]amino] phenylacetyl]amino];

(R)-[[[[(4-hydroxy-6-methyl-3-pyridinyl)carbonyl] amino](4-hydroxyphenyl)acetyl]amino];

(R)-[(phenylsulfoacetyl)amino];

(2R,3S)-[[2-[[(4-ethyl-2,3-dioxo-1-piperazinyl)carbonyl] -amino]-3-hydroxy-1-oxobutyl]amino];

[[carboxy(4-hydroxyphenyl)acetyl]amino];

(R)-[[amino[3-[(ethylsulfonyl)amino]phenyl]acetyl] amino];

(R)-[[amino(benzo[b]thien-3-yl)acetyl]amino];

(R)-[[amino(2-naphthyl)acetyl]amino];

(R)-[[amino(2-amino-4-thiazolyl)acetyl]amino];

[[[[(6,7-dihydroxy-4-oxo-4H-1-benzopyran-3-yl) carbonyl]-amino](4-hydroxyphenyl)acetyl]amino];

(R,R)-[[2-[4-[2-amino-2-carboxyethyloxycarbonyl] aminophenyl]-2-hydroxyacetyl]amino]; and (S)-[[(5-hydroxy-4-oxo-1(4H)-pyridin-2-yl) carbonylamino(2-amino-4-thiazolyl)acetyl]amino].

17
The following are other such preferred R[10] groups.
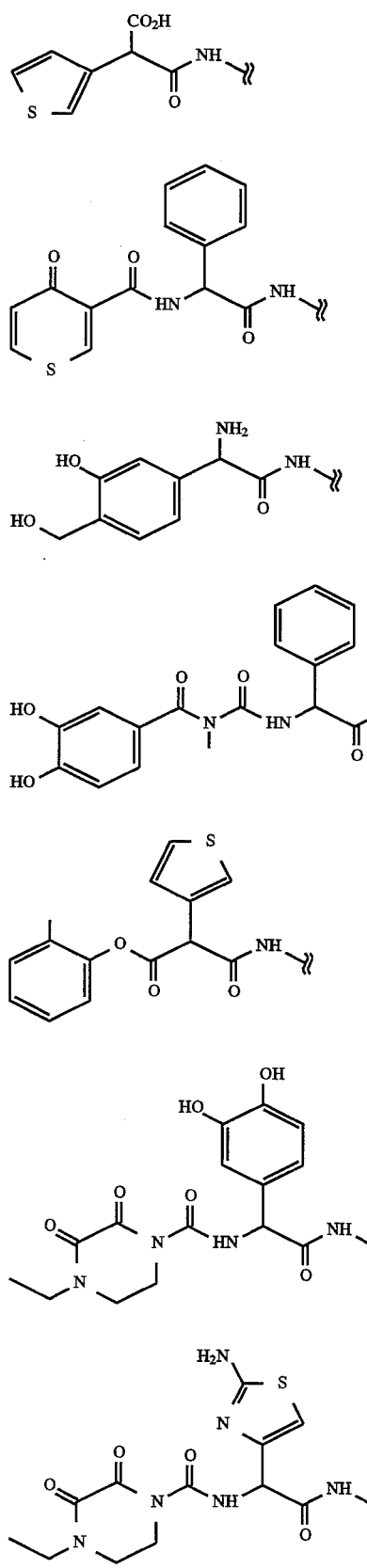
18
-continued
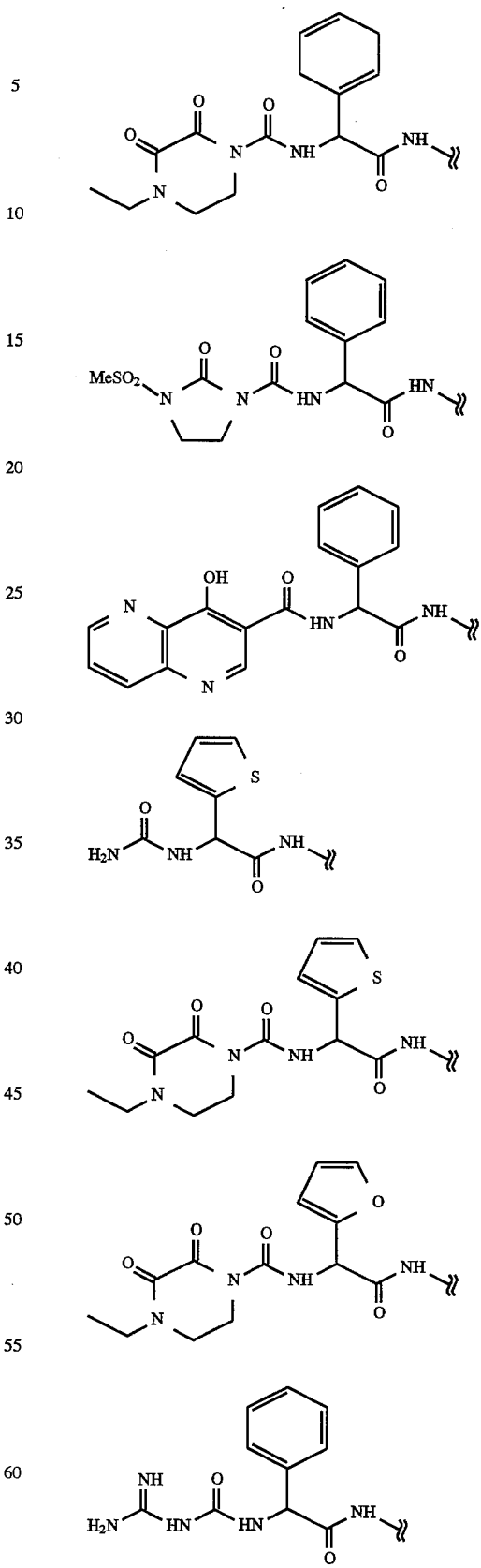

-continued

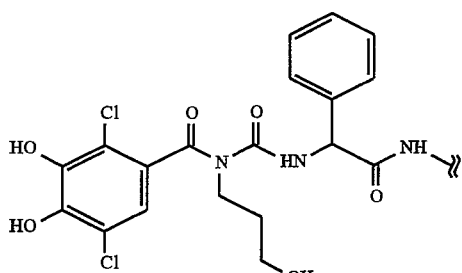

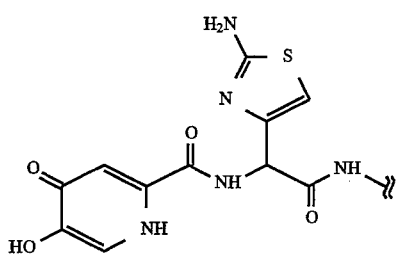

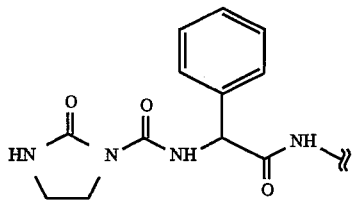

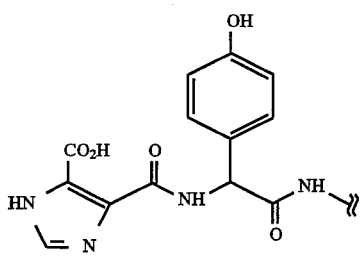

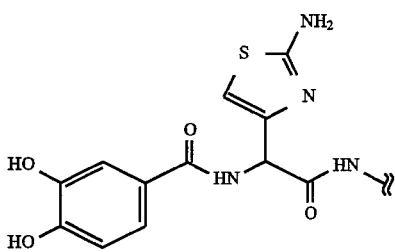

Another preferred R¹⁰ group is R¹⁷—C(=CHR²⁰)—C(=O)NH—. Such groups include (for example) the following structures.

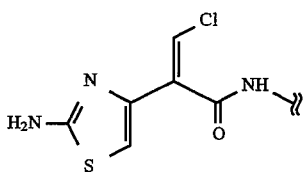

-continued

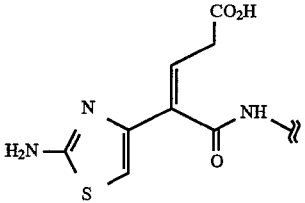

Another class of preferred $R^{10}$ groups (for lactam-containing moieties other than penems, carbapenems, clavems and clavams) include those of the formula:

$$R^{17}—C(=NO—R^{19})—C(=O)NH—.$$

Examples of this preferred class of $R^{10}$ groups include:

2-phenyl-2-hydroxyiminoacetyl;

2-thienyl-2-methoxyiminoacetyl; and

2-[4-(gamma-D-glutamyloxy)phenyl]-2-hydroxyiminoacetyl.

(Z)[[(2-amino-4-thiazolyl)(methoxyimin)acetyl]amino];

[[(2-furanyl(methoxyimino)acetyl]amino];

(Z)-[[(2-amino-4-thiazolyl)[(1-carboxy-1-methyl)ethoxyimino]acetyl]amino];

(Z)-[[(2-amino-4-thiazolyl)(1-carboxymethoxyimino)acetyl]amino];

[[(2-amino-4-thiazolyl)[(1H-imidazol-4-ylmethoxy)imino]acetyl]amino];

(Z)-[[(2-amino-4-thiazolyl-3-oxide)(methoxyimino)acetyl]amino]; and (S,Z)-[[(2-amino-4-thiazolyl)[carboxy(3,4-dihydroxyphenyl)methoxyimino]acetyl]amino].

Other preferred $R^{10}$ groups include the following structures (where "SS" is HCONH—).

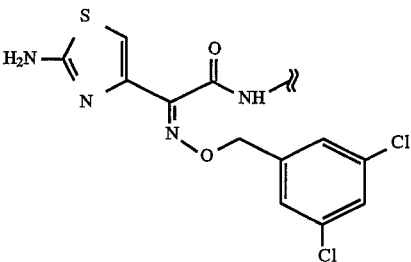

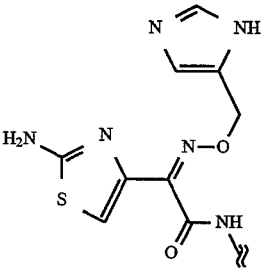

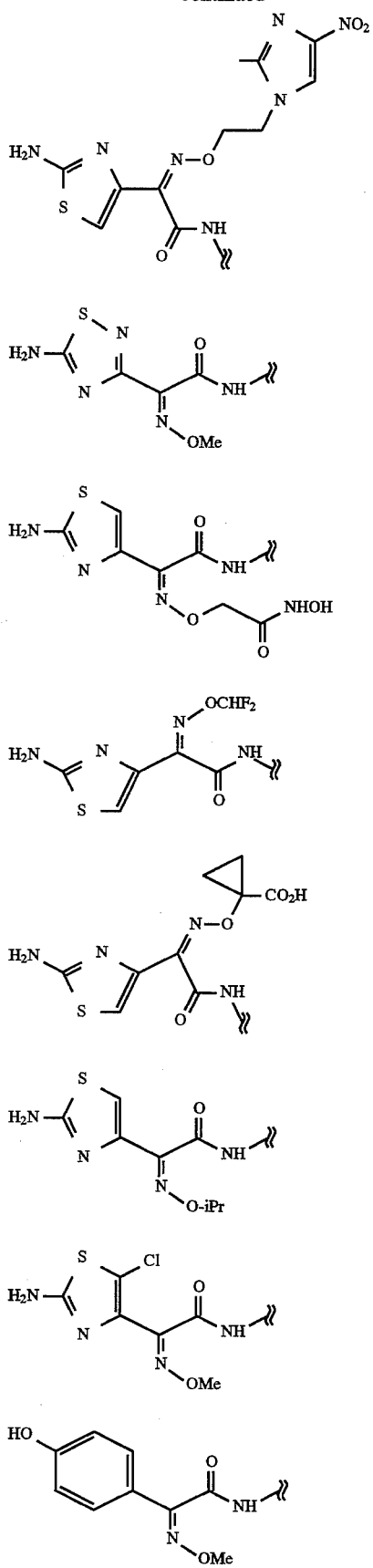
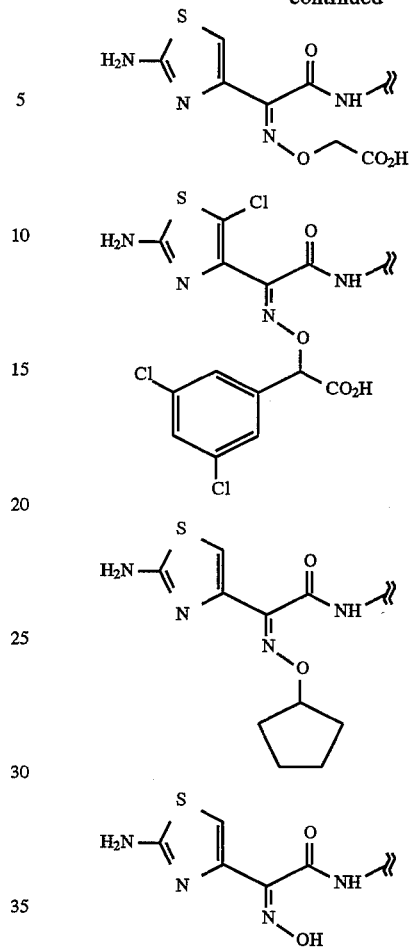

The following are other preferred $R^{10}$ groups.

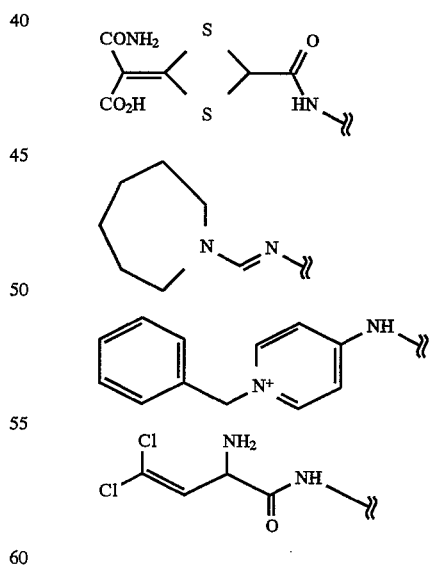

Suitable $R^{11}$ groups are among those well-known in the art, including those defined in the following documents (all incorporated by reference herein). W. Durckheimer et al., "Recent Developments in the Field of Beta-Lactam Antibiotics", 24 *Angew, Chem. Int. Ed, Engl.* 180 (1985); G. Rolinson, "Beta-Lactam Antibiotics", 17 *J. Antimicrobial Chemotherapy* 5 (1986); and European Patent Publication 187,456, Jung, published Jul. 16, 1986. Preferred $R^{11}$ groups include hydrogen, methoxy, ethoxy, propoxy, thiomethyl, halogen, cyano, formyl and formylamino. Particularly preferred $R^{11}$ groups include hydrogen, methoxy, halogen, and formylamino.

Quinolone Moieties

Groups $A^1$, $A^2$, $A^3$, $R^1$, $R^3$, $R^4$ and $R^6$ of formula I form any of a variety of quinolone, naphthyridine or related heterocyclic moieties known in the art to have antimicrobial activity. Such moieties are well known in the art, as described in the following articles, all incorporated by reference herein: J. Wolfson et al., "The Fluoroquinolones: Structures, Mechanisms of Action and Resistance, and Spectra of Activity In Vitro", 28 Antimicrobial Agents and Chemotherapy 581 (1985); and T. Rosen et al., 31 J. Med Chem. 1586 (1988); T. Rosen et al., 31 J. Med. Chem. 1598 (1988); G. Klopman et al., 31 Antimicrob. Agents Chemother. 1831 (1987); 31:1831–1840; J. P. Sanchez et al., 31 J. Med. Chem. 983 (1988); J. M. Domagala et al., 31 J. Med. Chem. 991 (1988); M. P. Wentland et al., in 20 Ann. Rep. Med. Chem. 145 (D. M. Baily, editor, 1986); J. B. Cornett et al., in 21 Ann. Rep. Med. Chem. 139 (D. M. Bailey, editor, 1986); P. B. Fernandes et al., in 22 Ann. Rep. Med. Chem. 117 (D. M. Bailey, editor, 1987); R. Albrecht, 21 Prog. Drug Research 9 (1977); and P. B. Fernandes et al., in 23 Ann. Rep. Med. Chem. (R. C. Allen, editor, 1987).

Preferred quinolone moieties include those where $A^1$ is $C(R^7)$, $A^2$ is $C(R^2)$, and $A^3$ is $C(R^5)$ (i.e., quinolones); $A^1$ is nitrogen, $A^2$ is $C(R^2)$, and $A^3$ is $C(R^5)$ (i.e., naphthyridines); $A^1$ is $C(R^7)$, $A^2$ is $C(R^2)$, and $A^3$ is nitrogen (i.e., cinnoline acid derivatives); and where $A^1$ is nitrogen, $A^2$ is nitrogen, and $A^3$ is $C(R^5)$ (i.e., pyridopyrimidine derivatives). More preferred quinolone moieties are those where $A^1$ is $C(R^7)$, $A^2$ is $C(R^2)$, and $A^3$ is $C(R^5)$ (i.e., quinolones); and where $A^1$ is nitrogen, $A^2$ is $C(R^2)$, and $A^3$ is $C(R^5)$ (i.e., naphthyridines). Particularly preferred quinolone moieties are where $A^1$ is $C(R^7)$, $A^2$ is $C(R^2)$, and $A^3$ is $C(R^5)$ (i.e., quinolones).

$R^1$ is preferably alkyl, aryl, cycloalkyl and alkylamino. More preferably, $R^1$ is ethyl, 2-fluoroethyl, 2-hydroxyethyl, t-butyl, 4-fluorophenyl, 2,4-difluorophenyl, methylamino and cyclopropyl. Cyclopropyl is a particularly preferred $R^1$ group. Preferred quinolone moieties also include those where $A^1$ is $C(R^7)$ and $R^1$ and $R^7$ together comprise a 6-membered heterocyclic ring containing an oxygen or sulfur atom.

$R^2$ is preferably hydrogen or halo. More preferably $R^2$ is chlorine or fluorine. Fluorine is a particularly preferred $R^2$ group.

Preferred $R^3$ groups include nitrogen-containing heterocyclic rings. Particularly preferred are nitrogen-containing heterocyclic rings having from 5 to 8 members. The heterocyclic ring may contain additional heteroatoms, such as oxygen, sulfur, or nitrogen, preferably nitrogen. Such heterocyclic groups are described in U.S. Pat. No. 4,599,334, Petersen et al., issued Jul. 8, 1986; and U.S. Pat. No. 4,670,444, Grohe et al., issued Jun. 2, 1987 (both incorporated by reference herein). Preferred $R^3$ groups include unsubstituted or substituted pyridine, piperidine, morpholine, diazabicyclo[3.1.1]heptane, diazabicyclo[2.2.1]heptane, diazabicyclo[3.2.1]octane, diazabicyclo[2.2.2]octane, thiazolidine, imidazolidine, pyrrole and thiamorpholine, as well as the following particularly preferred $R^3$ groups include piperazine, 3-methylpiperazine, 3-aminopyrrolidine, 3-aminomethylpyrrolidine, N,N-dimethylaminomethylpyrrolidine, N-methylaminomethylpyrrolidine, N-ethylaminomethylpyrrolidine, pyridine, 4-dithiocarbamoylpiperazine, 3-dithiocarbamoylaminopyrrolidine, N-methylpiperazine, 3,5-dimethylpiperazine, and 3-(dithiocarbamoylamino)pyrrolidine.

Preferred lactam-quinolones include those having a 6-fluoroquinolone moiety or an 8-halo-6-fluoroquinolone moiety, of formula:

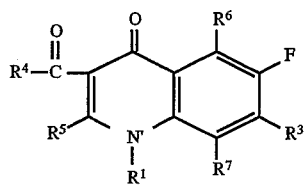

wherein, referring to formula (I), $A^2$ is $C(R^2)$ and $R^2$ is F; $A^3$ is $C(R^5)$; and $A^1$ is $C(R^7)$ where $R^7$ is hydrogen, fluorine or chlorine. Preferred examples of such quinolone moieties include:

1-cyclopropyl-6-fluoro-1,4-dihydro-4-oxo-7-(1-piperazinyl)-3-quinolinecarboxylic acid;

7-(3-aminopyrrolidinyl)-1-cyclopropyl-6-fluoro-1,4-dihydro-4-oxo-3-quinolinecarboxylic acid;

7-[(3-aminomethyl)pyrrolidinyl]-1-cyclopropyl-6-fluoro-1,4-dihydro-4-oxo-3-quinolinecarboxylic acid;

7-(3-aminopyrrolidinyl)-8-chloro-1-cyclopropyl-6-fluoro-1,4-dihydro-4-oxo-3-quinolinecarboxylic acid;

7-(3-aminopyrrolidinyl)-1-cyclopropyl-6,8-difluoro-1,4-dihydro-4-oxo-3-quinolinecarboxylic acid;

7-[(3-aminomethyl)pyrrolidinyl]-1-cyclopropyl-6,8-difluoro-1,4-dihydro-4-oxo-3-quinolinecarboxylic acid;

6,8-difluoro-1-(2-fluoroethyl)-1,4-dihydro-7-(4-methyl-1-piperazinyl)-4-oxo-3-quinolinecarboxylic acid;

1-ethyl-6-fluoro-1,4-dihydro-4-oxo-7-(1-piperazinyl)-3-quinolinecarboxylic acid;

1-ethyl-6-fluoro-1,4-dihydro-7-(4-methyl-1-piperazinyl)-4-oxo-3-quinolinecarboxylic acid;

6-fluoro-1,4-dihydro-1-methylamino-7-(4-methyl-1-piperazinyl)-4-oxo-3-quinolinecarboxylic acid; and 1-cyclopropyl-7-[3-(dimethylamtnomethyl)-1-pyrrolidinyl]-6,8-difluoro-1,4-dihydro-4-oxo-3-quinolinecarboxylic acid;

The following are other examples of such preferred quinolone moieties.

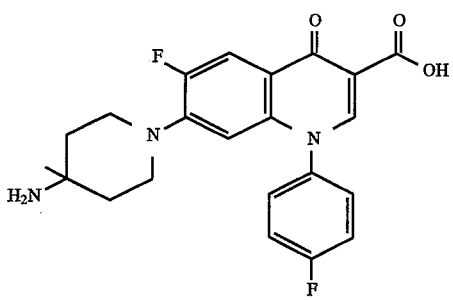

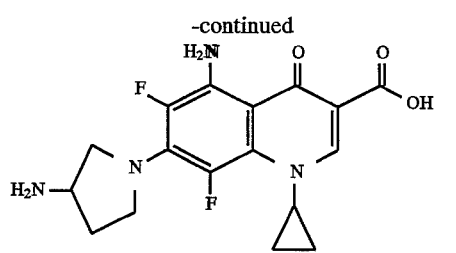
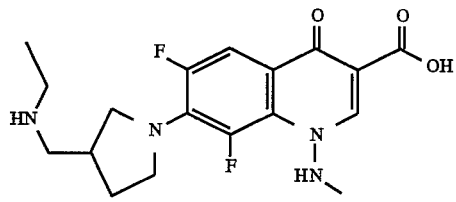
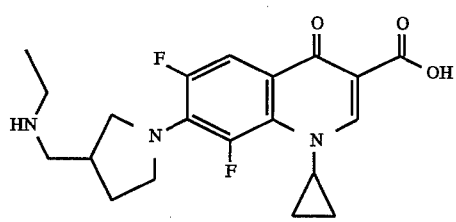
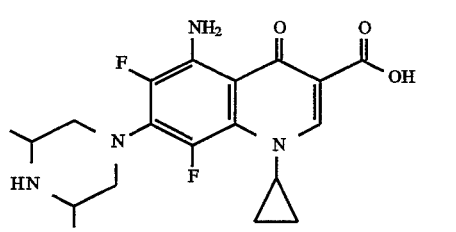
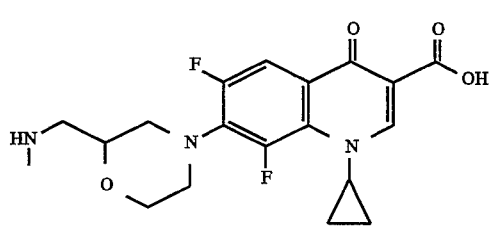
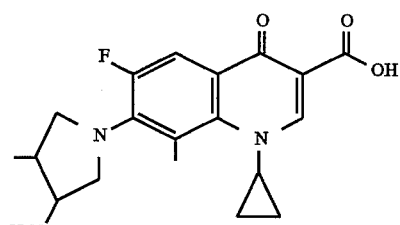
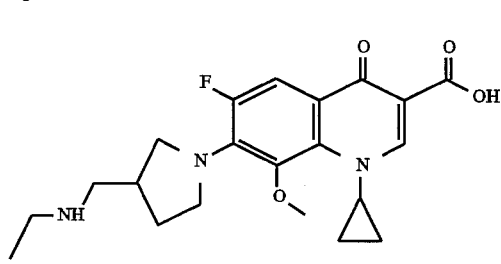
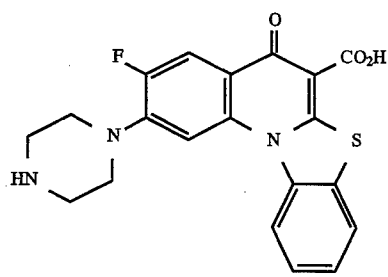
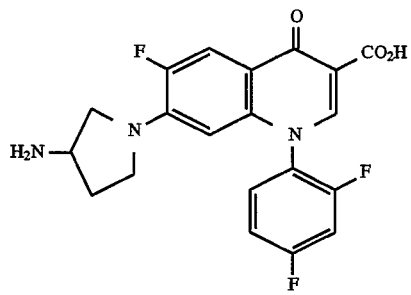
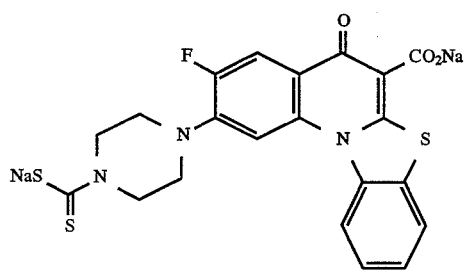
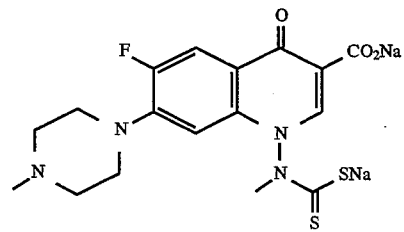
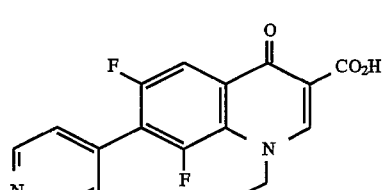

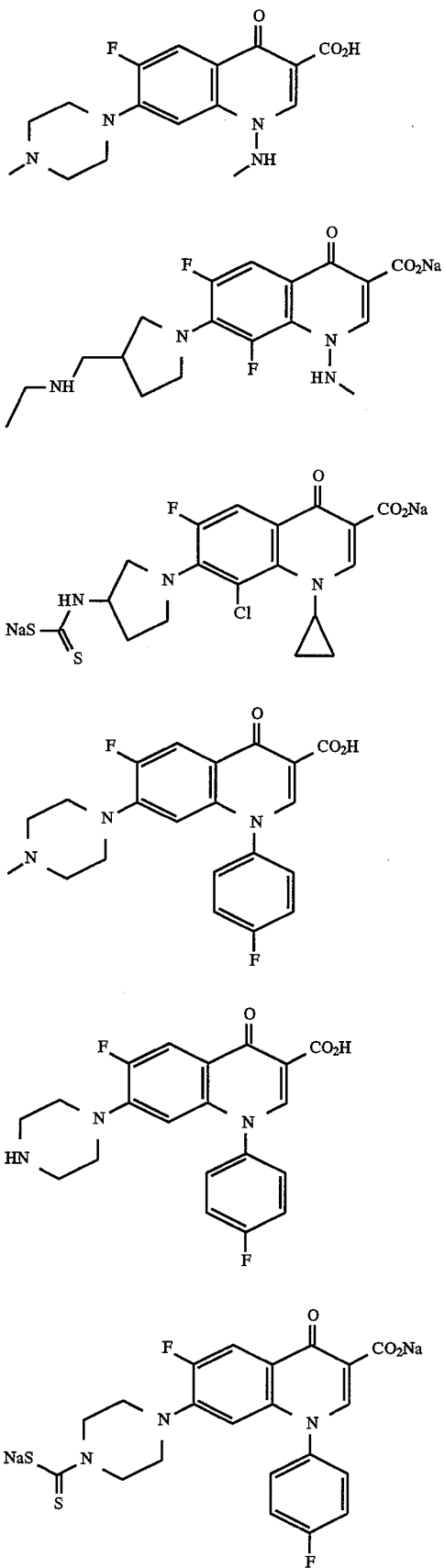

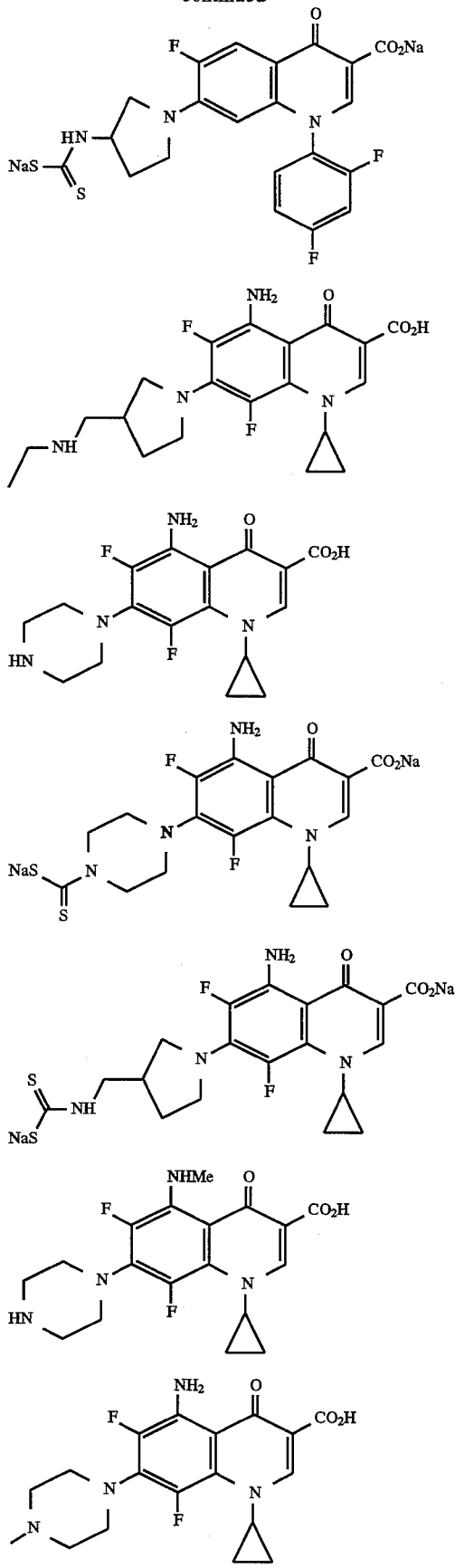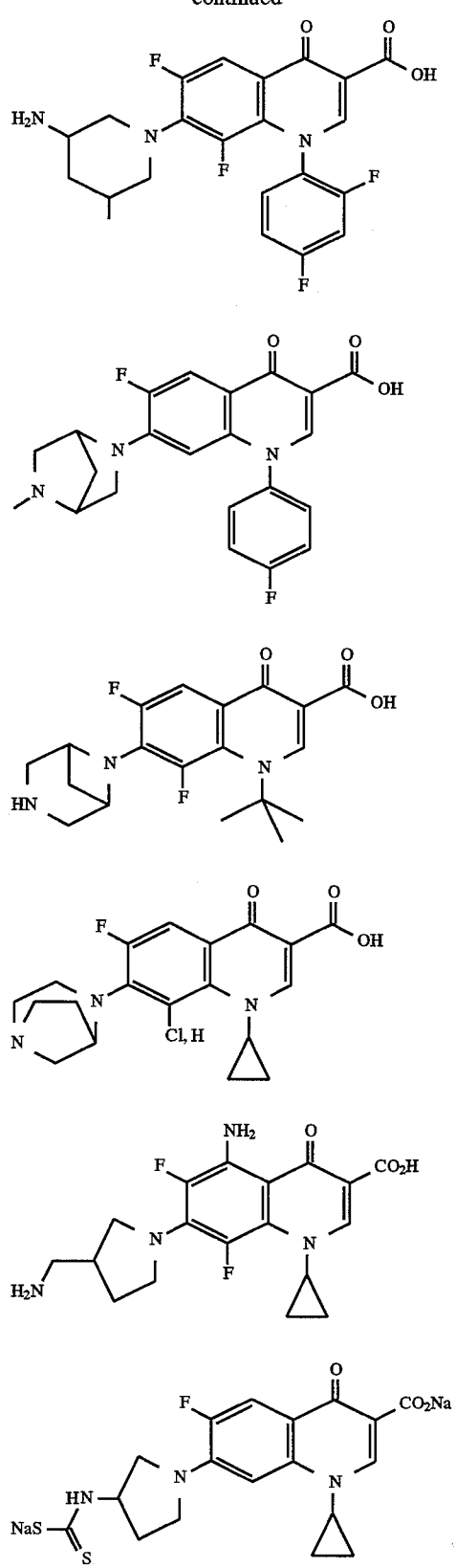
Also preferred are lactam-quinolones having a 1,8-naphthyridine moiety, of formula:

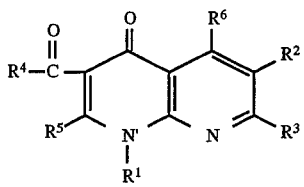

wherein, referring to formula (I), $A^1$ is N; $A^2$ is $C(R^2)$ and $A^3$ is $C(R^5)$. Preferred examples of such quinolone moieties include:

7-(3-aminopyrrolidinyl)-1-(2,4-difluorophenyl)-6-fluoro-1,4-dihydro-4-oxo-1,8-naphthyridine-3-carboxylic acid; and 1-ethyl-6-fluoro-1,4-dihydro-4-oxo-7-(1-piperazinyl)-1,8-naphthyridine-3-carboxylic acid.

The following are other examples of such preferred quinolone moieties.

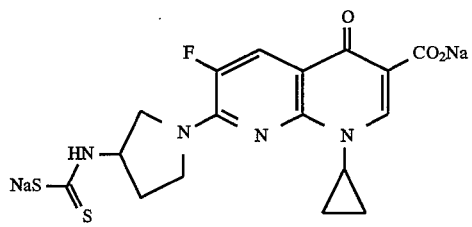

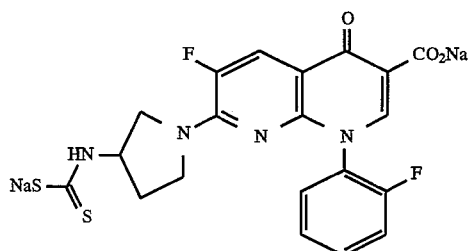

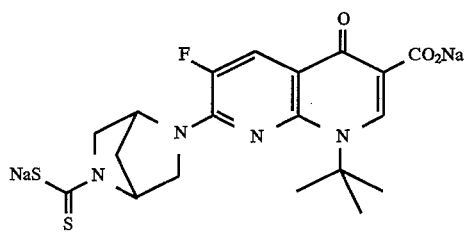

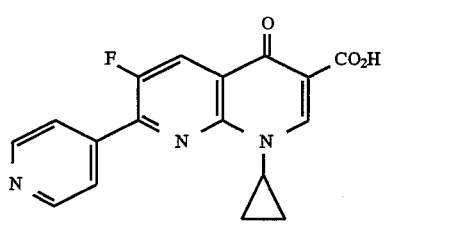

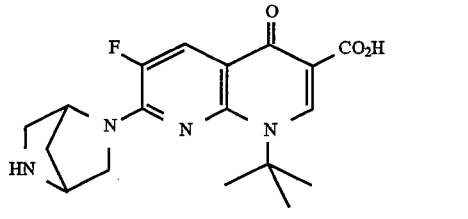

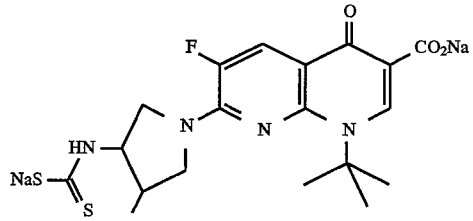

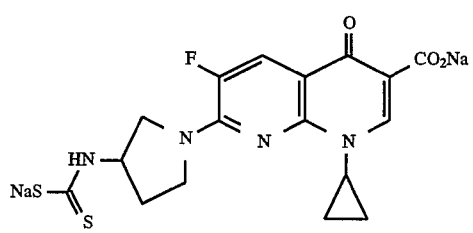

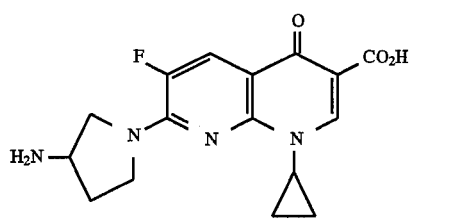

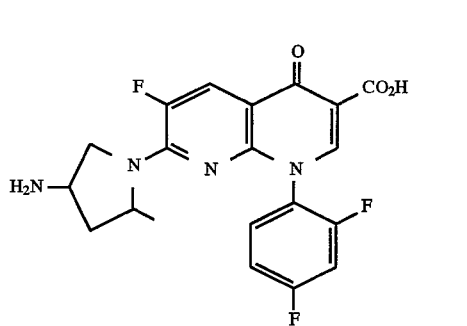

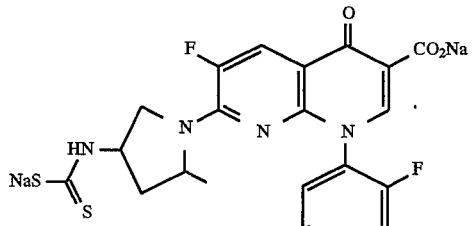

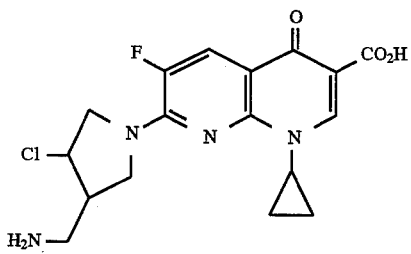

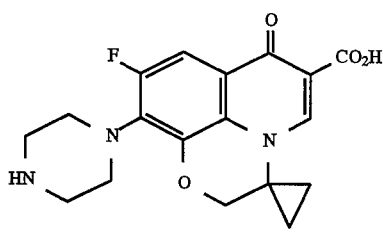

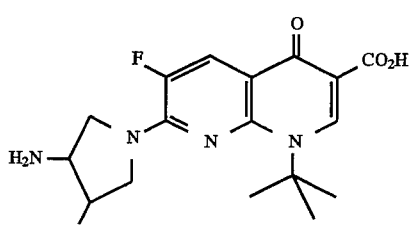

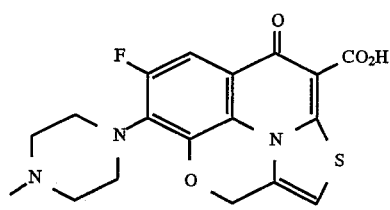

Also preferred are lactam-quinolones having a pyridobenzoxazine or pyridobenzthiazine moiety, of formula:

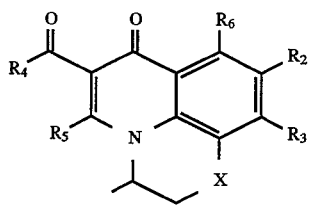

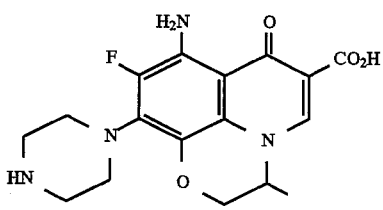

wherein, referring to formula (I), $A^1$ is $C(R^7)$; $A^2$ is $C(R^2)$; $A^3$ is $C(R^5)$; and $R^7$ and $R^1$ together comprise a linking moiety between N' and A to form a 6-membered, oxygen-containing, heterocyclic ring where X (in this formula) is oxygen, sulfur or carbon. Preferred examples of such quinolone moieties include 9-fluoro-4,7-dihydro-3-methyl-10-(4-methyl-1-piperazinyl)-7-oxo-2H-pyrido[1,2,3-de]-1,4-benzoxazine-6-carboxylic acid; and the following structures.

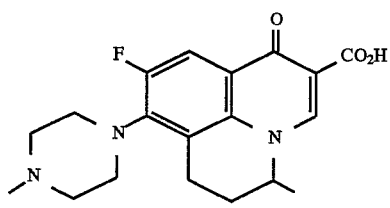

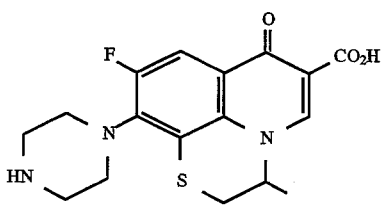

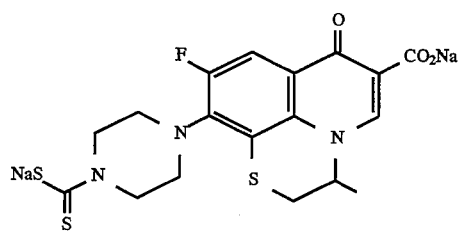

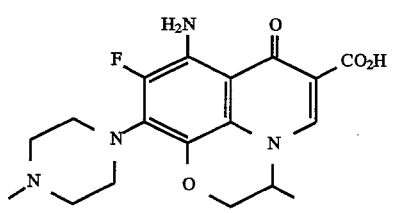

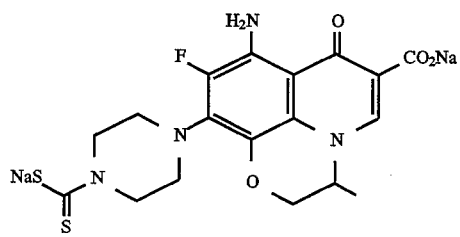

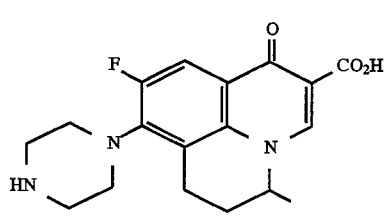

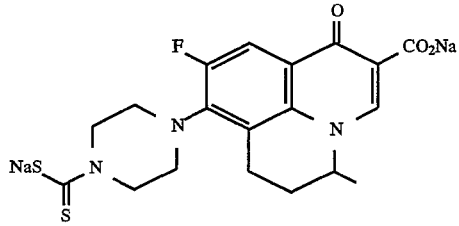

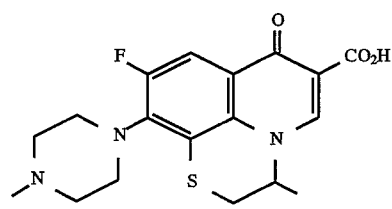

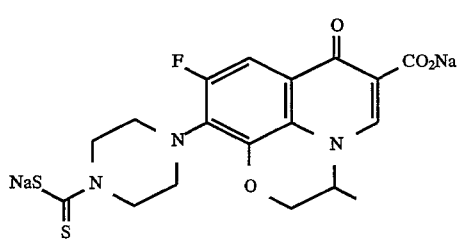

Also preferred are lactam-quinolones having an isothiazoloquinolinedione or isoxazoloquinolinedione moiety, of formula:

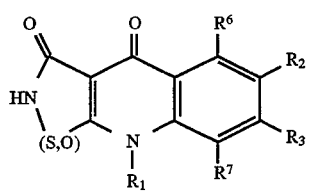

wherein, referring to formula (I), wherein $A^1$ is $C(R^7)$; $A^2$ is $C(R^2)$; $A^3$ is $C(R^5)$; and $R^4$ and $R^5$ together comprise a moiety forming a 5-membered, substituted, heterocyclic ring.

Preferred examples of such quinolone moieties include 9-cyclopropyl-6-fluoro-2,3,4,9-tetrahydro-7-(1-piperazinyl) iso-thiazolo[5,4-b]quinoline-3,4-dione; and:

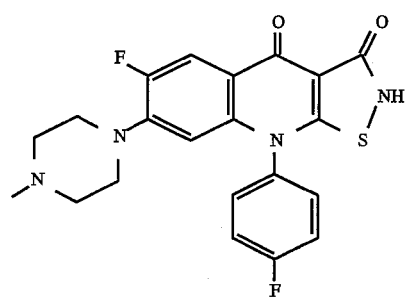

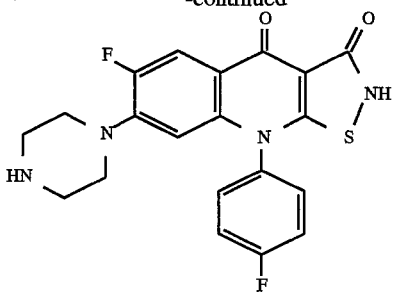

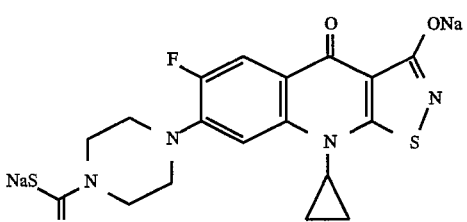

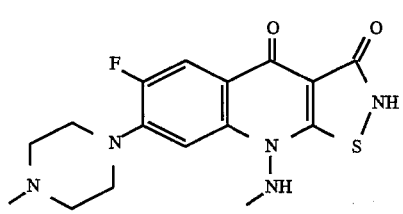

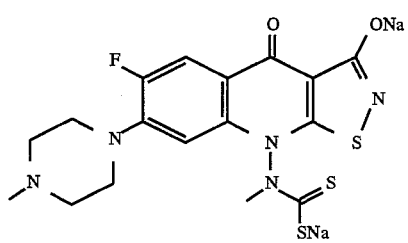

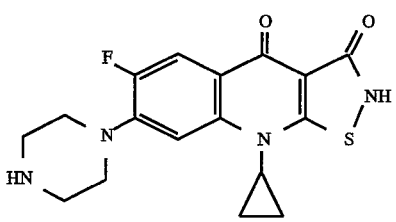

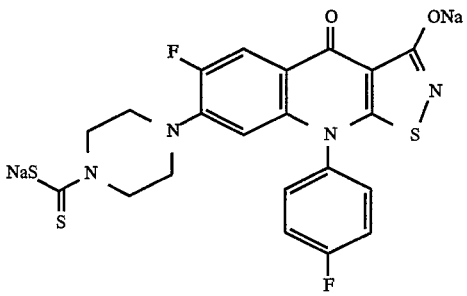

Linking Moieties

Group L, together with the $R^{15}$ or $R^{16}$ substituents of the quinolone moiety, form a variety of linking moieties between the lactam-containing structure (B) and the quinolone structure (Q) of the lactam-quinolones. Representative structures for linking groups are set forth below. (In these structures, $R^{12}$, $R^{13}$, $R^{14}$, and bonds "a" and "b" comprise a cephem structure, for purposes of exemplification only. The linking moieties depicted may be used with any of the lactam-containing moieties of this invention. Also, in these structures, each linking moiety is depicted as a substituent of either $R^1$ or $R^3$, for exemplification purposes only. Each linking moiety may also be substituted at the alternative position.)

Carbamate Linking Moieties

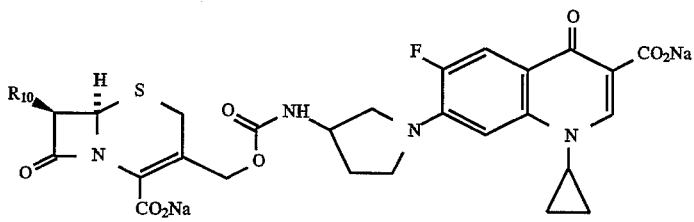

wherein, referring to formulas (I) and (II), L is —$X^4_t$—C(=$Y^2_u$)—Z—Q"; t is 1 and u is 1; $X^4$ is oxygen; $Y^2$ is oxygen; Z is nitrogen; and Q" is Q' which is (for example) a pyrollidinyl $R^{16}$ group.

Another example of a carbamate linking moiety is:

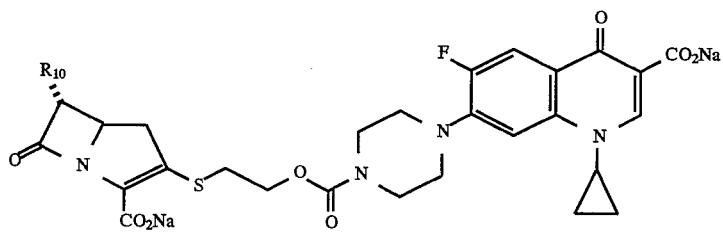

wherein, referring to formulas (I) and (II), L is —$X^2$—$R^{39}$—L'; $X^2$ is —S(O)$_m$ where m is 0; $R^{39}$ is ethyl; and L' is —$X^4_t$—C(=$Y^2_u$)—Z—Q", where t is 1 and u is 1, $X^4$ is oxygen, $Y^2$ is oxygen, Z is nitrogen, and Q" is, together with Z, an $R^{16}$ group which is (for example) a piperazinyl group.

Dithiocarbamate linking moieties:

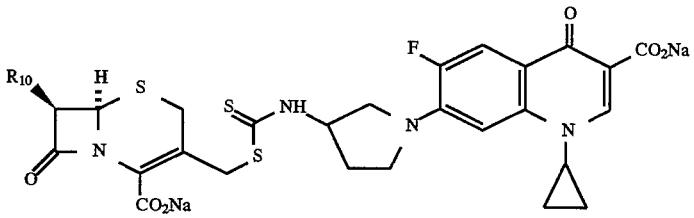

wherein, referring to formulas (I) and (II), L is —$X^4_t$—C(—$Y^2_u$)—Z—Q"; t is 1 and u is 1; $X^4$ is sulfur; $Y^2$ is sulfur; Z is $NR^{41}$, where $R^{41}$ is hydrogen; and Q" is Q' which is (for example) a pyrrolidinyl $R^{16}$ group.

Urea linking moieties:

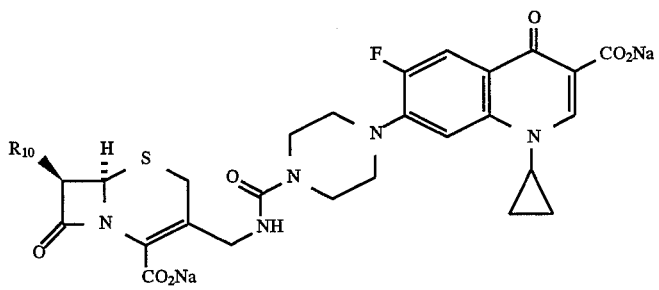

wherein, referring to formulas (I) and (II), L is —$X^4_t$—C(=$Y^2_u$)—Z—Q"; t is 1 and u is 1; $X^4$ is $NR^{40}$, where $R^{40}$ is hydrogen; $Y^2$ is oxygen; Z is nitrogen; and Q" is, together with Z, an $R^{16}$ group which is (for example) a piperazinyl group.

Thiourea linking moieties:

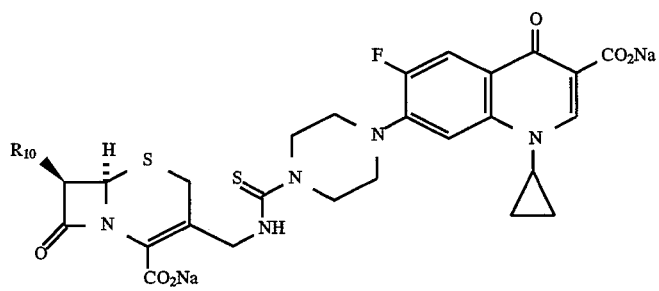

wherein, referring to formulas (I) and (II), L is —$X^4_t$—C(=$Y^2_u$)—Z—Q"; t is 1 and u is 1; $X^4$ is $NR^{40}$, where $R^{40}$ is hydrogen; $Y^2$ is sulfur; Z is nitrogen; and Q" is, together with Z, an $R^{16}$ group which is (for example) a piperazinyl group.

Isouronium linking moieties:

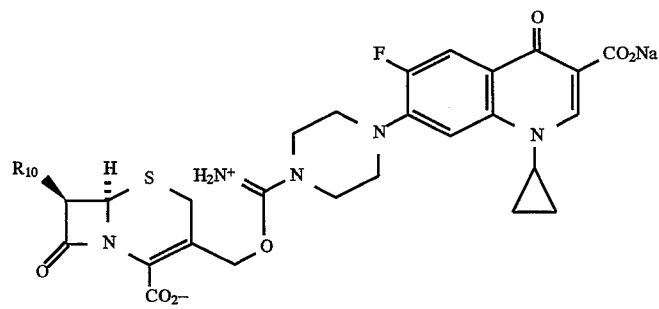

wherein, referring to formulas (I) and (II), L is —$X^4_t$—C(=$Y^2_u$)—Z—Q"; t is 1 and u is 1; $X^4$ is oxygen; $Y^2$ is $N^+(R^{41})(R^{42})$, where $R^{41}$ and $R^{42}$ are hydrogen; Z is nitrogen; and Q" is, together with Z, an $R^{16}$ group which is (for example) a piperazinyl group.

Isothiouronium linking moieties:

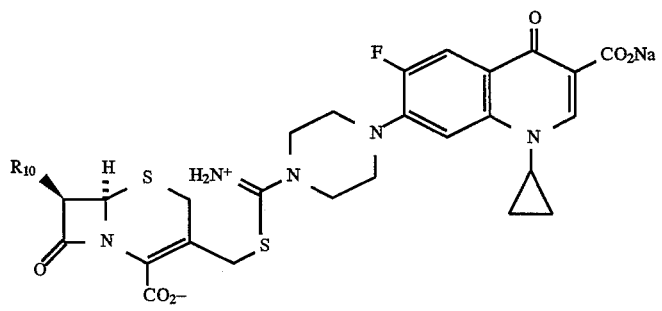

wherein, referring to formulas (I) and (II), L is —$X^4_t$—C(=$Y^2_u$)—Z—Q"; t is 1 and u is 1; $X^4$ is sulfur; $Y^2$ is $N^+(R^{41})(R^{42})$, where $R^{41}$ and $R^{42}$ are hydrogen; Z is nitrogen; and Q" is, together with Z, an $R^{16}$ group which is (for example) a piperazinyl group.

Guanidinium linking moieties:

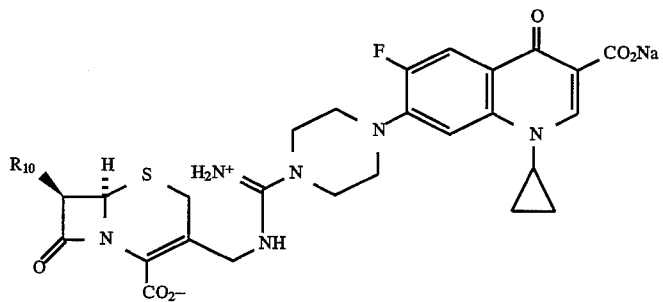

wherein, referring to formulas (I) and (II), L is —$X^4_t$—C(=$Y^2_u$)—Z—Q"; t is 1 and u is 1; $X^4$ is $NR^{40}$, where $R^{40}$ is hydrogen; $Y^2$ is $N^+(R^{41})(R^{42})$, where $R^{41}$ and $R^{42}$ are hydrogen; Z is nitrogen; and Q" is, together with Z, an $R^{16}$ group which is (for example) a piperazinyl group.

Carbonate linking moieties:

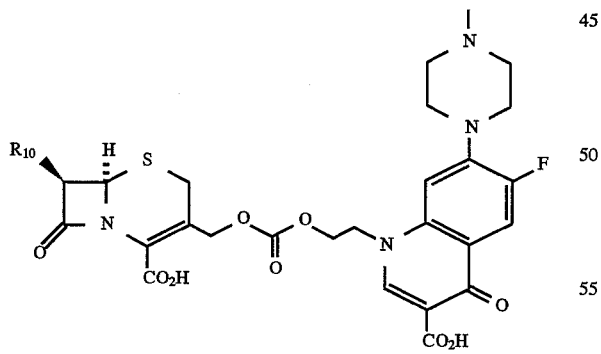

wherein, referring to formulas (I) and (II), L is —$X^4_t$—C(=$Y^2_u$)—Z—Q"; t is 1 and u is 1; $X^4$ is oxygen; $Y^2$ is oxygen; Z is oxygen; and Q" is Q' which is (for example) an ethyl $R^{15}$ group.

Trithiocarbonate linking moieties:

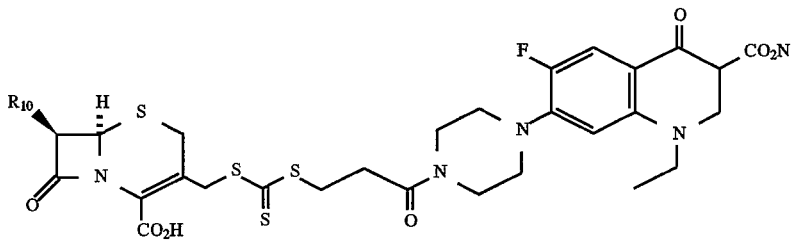

wherein, referring to formulas (I) and (II), L is —$X^4_t$—C(=$Y^2_u$)—Z—Q"; t is 1 and u is 1; $X^4$ is sulfur; $Y^2$ is sulfur; Z is sulfur; and Q" is Q' which is (for example) an N-propionylpyrrolidinyl $R^{16}$ group.

Reversed carbamate linking moieties:

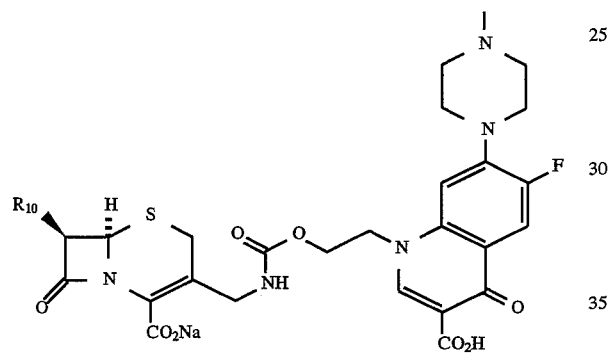

wherein, referring to formulas (I) and (II), L is —$X^4_t$—C(=$Y^2_u$)—Z—Q"; t is 1 and u is 1; $X^4$ is $NR^{40}$, $R^{40}$ is hydrogen; $Y^2$ is oxygen; Z is oxygen; and Q" is Q', which is (for example) an ethyl $R^{15}$ group.

Xanthate linking moieties:

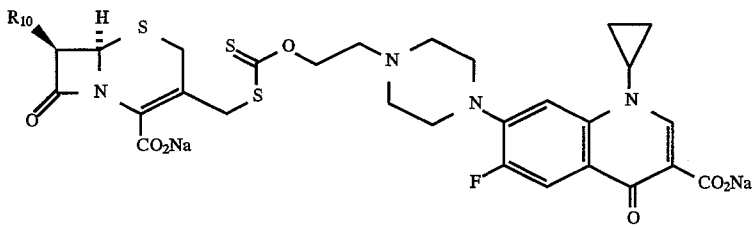

wherein, referring to formulas (I) and (II) L is —$X^4_t$—C(=$Y^2_u$)—Z—Q"; t is 1 and u is 1; $X^4$ is sulfur; $Y^2$ is sulfur; Z is oxygen; and Q" is Q' which is (for example) an N-ethyl piperazinyl $R^{16}$ group.

Reversed isouronium linking moieties:

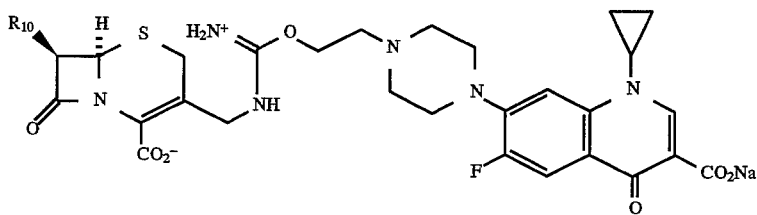

wherein, referring to formulas (I) and (II), L is —$X^4_t$—C(=$Y^2_u$)—Z—Q"; t is 1 and u is 1; $X^4$ is $NR^{40}$, where $R^{40}$ is hydrogen; $Y^2$ is $N^+(R^{41})(R^{42})$, where $R^{42}$ and $R^{42}$ are hydrogen; Z is oxygen; and Q" is Q' which is (for example) an N-ethyl piperazinyl $R^{16}$ group.

Reversed dithiocarbamate linking moieties:

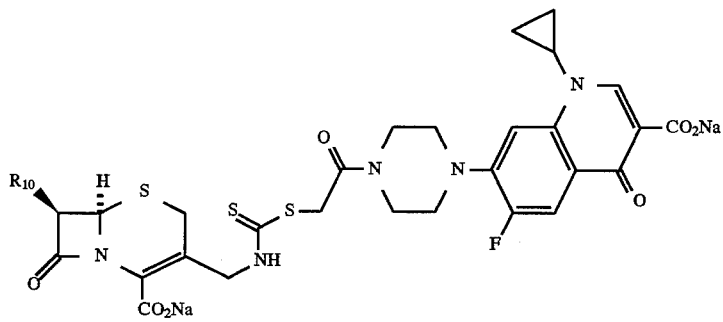

wherein, referring to formulas (I) and (II), L is —$X^4_t$—C(=$Y^2_u$)—Z—Q"; t is 1 and u is 1; $X^4$ is $NR^{40}$, where $R^{40}$ is hydrogen; $Y^2$ is sulfur; Z is sulfur; and Q" is Q' which is (for example) an N-acetylpiperazinyl $R^{16}$ group.

Reversed isothiouronium linking moieties:

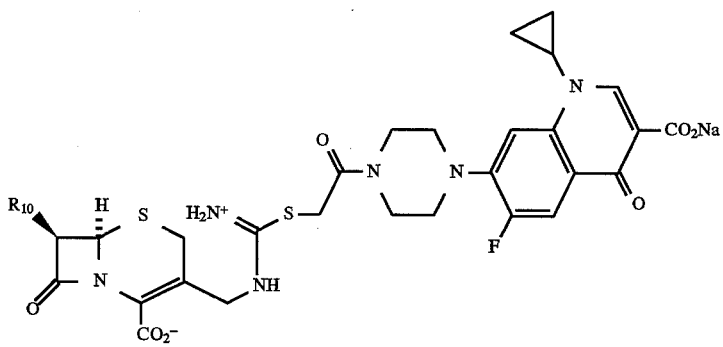

wherein, referring to formulas (I) and (II), L is —$X^4_t$—C(=$Y^2_u$)—Z—Q"; t is 1 and u is 1; $X^4$ is $NR^{40}$, where $R^{40}$ is hydrogen; $Y^2$ is $N^+(R^{41})(R^{42})$, where $R^{41}$ and $R^{42}$ are both hydrogen; Z is sulfur; and Q" is Q' which is (for example) an N-acetylpiperazinyl $R^{16}$ group.

Amine linking moieties:

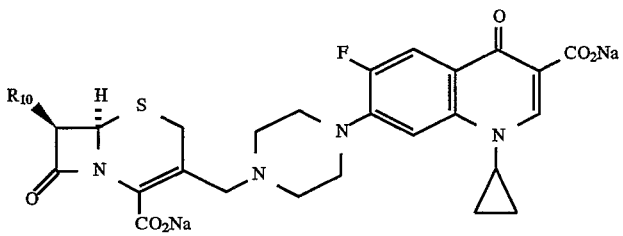

wherein, referring to formulas (I) and (II), L is —X³—Q"; X³ is nitrogen; and Q" is, together with X³, an R¹⁶ group which is (for example) a piperazinyl group.

Imine linking moieties:

wherein L is —X³—Q"; X³ is nitrogen; and Q" is, together with X³, an R¹⁶ group which is (for example) a pyridinium group.

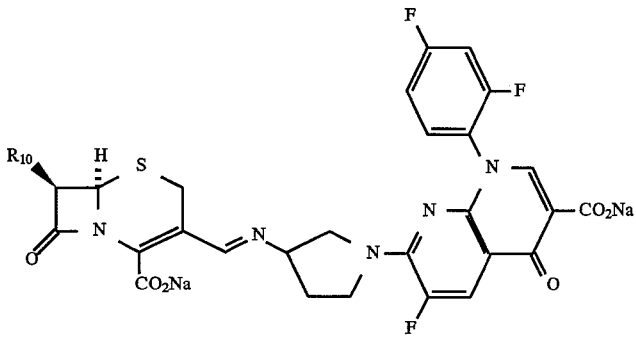

wherein, referring to formulas (I) and (II), L is —X³—Q"; X³ is nitrogen, and is linked to R¹⁴ by a double bond; and Q" is Q' which is (for example) a pyrrolidinyl R¹⁶ group.

Ammonium linking moieties:

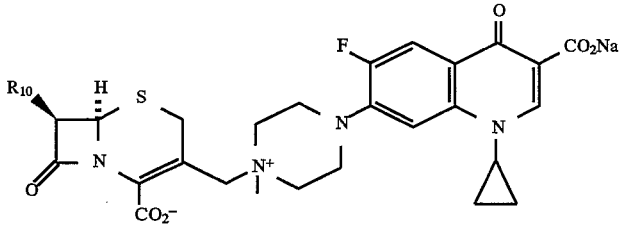

wherein, referring to formulas (I) and (II), L is —X³—Q"; X³ is N⁺(R⁴¹)(R⁴²), R⁴¹ is methyl and R⁴² is part of R¹⁶; and Q" is, together with X³, an R¹⁶ group which is (for example) a piperazinyl group.

Heteroarylium linking moieties:

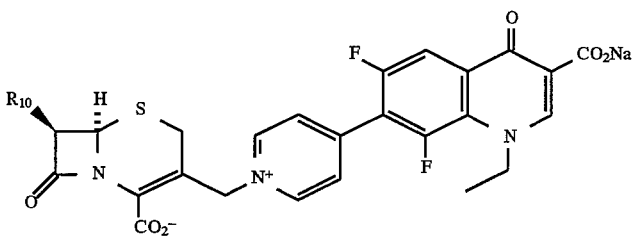

Ether linking moieties:

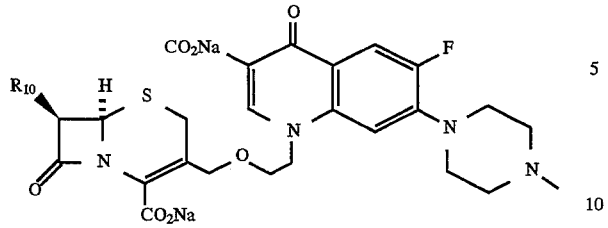

wherein, referring to formulas (I) and (II), L is —X²—Q"; X² is oxygen; and Q" is Q' which is (for example) an ethyl R¹⁵ group.

Thioether, sulfoxide and sulfone linking moieties:

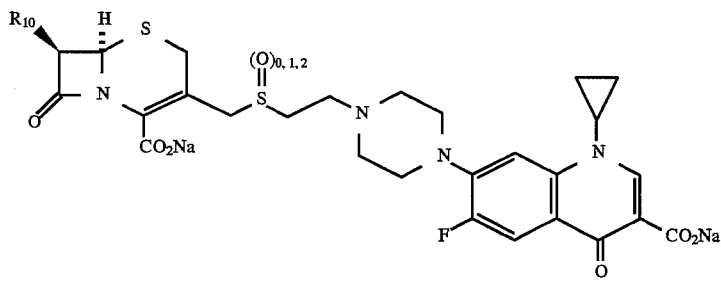

wherein, referring to formulas (I) and (II), L is —X²—Q"; X² is S(O)$_t$, where t=0 (thioether), t=1 (sulfoxide) or t=2 (sulfone); and Q" is Q' which is (for example) an N-ethylpiperazinyl R¹⁶ group.

Phosphono linking moieties:

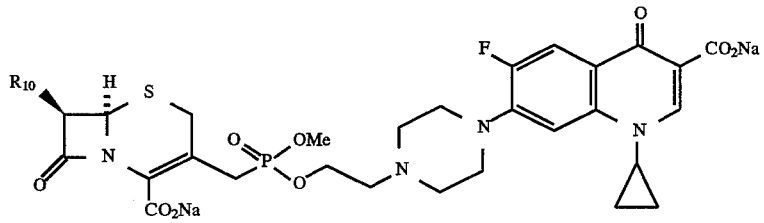

wherein, referring to formulas (I) and (II), L is —X⁵$_t$—PO(Y³$_u$R⁸)—Z—Q"; t is 0 and u is 1 (for example); Y³ is oxygen; R⁸ is methyl; Z' is oxygen; and Q" is Q' which is (for example) an N-ethylpiperazinyl R¹⁶ group.

Phosphoramide linking moieties:

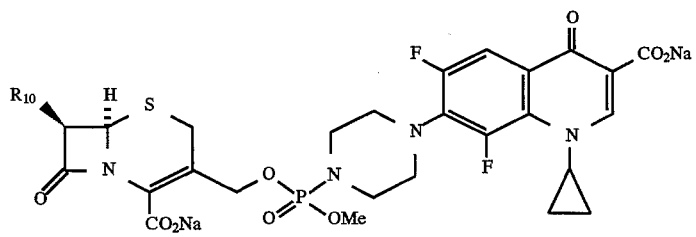

wherein, referring to formulas (I) and (II), L is —X⁵$_t$—PO(Y³$_u$R⁸)—Z—Q"; t is 1 and u is 1; X⁵ is oxygen; Y³ is oxygen; R⁸ is methyl; Z' is nitrogen and Q" is, together with Z, an R¹⁶ group which is (for example) a piperazinyl group.

Phosphate linking moieties:

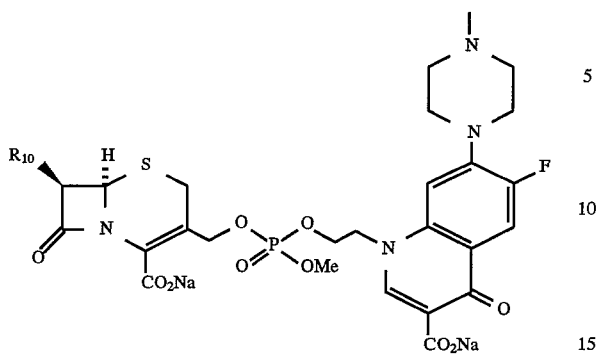

wherein, referring to formulas (I) and (II), L is —$X^5_t$—PO($Y^3_u R^8$)—Z—Q"; t is 1 and u is 1; $X^5$ is oxygen; $Y^3$ is oxygen; $R^8$ is methyl; Z' is oxygen; and Q" is Q' which is (for example) an ethyl $R^{15}$ group.

Other sulfoxide-containing linkages (a sulfonamide, for example):

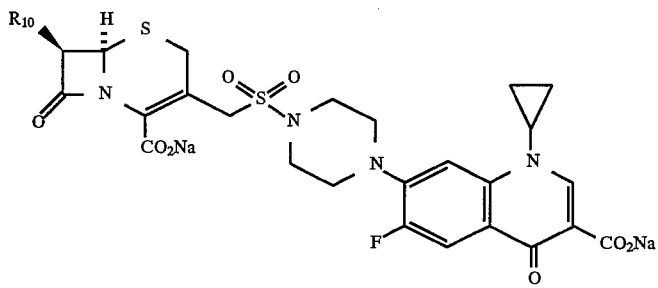

wherein, referring to formulas (I) and (II), L is —$X^5_t$—$SO_2$—Z'—Q"; where t is 0; Z' is nitrogen; and Q" is, together with Z', an $R^{16}$ group which is (for example) a piperazinyl group.

Ester or thioester linking moiety:

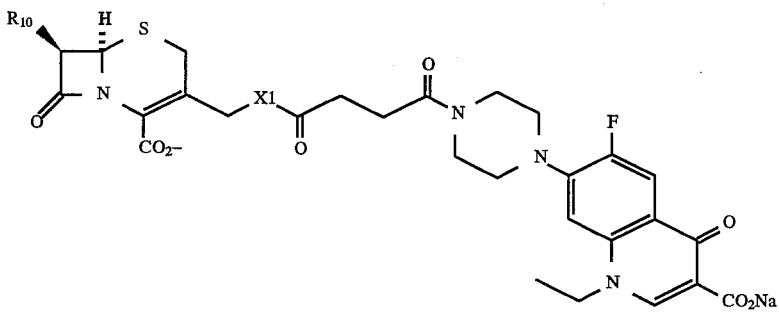

wherein, referring to formulas (I) and (II), L is —$X^4_t$—C(=$Y^2_u$)—Z—Q"; t is 1 and u is 1; $X^4$ is oxygen (for an ester) or sulfur (for a thioester); $Y^2$ is oxygen; Z is nil; and Q" is Q' which is (for example) an N-propionylpiperazinyl $R^{16}$ group.

Amide or hydrazide linking moiety:

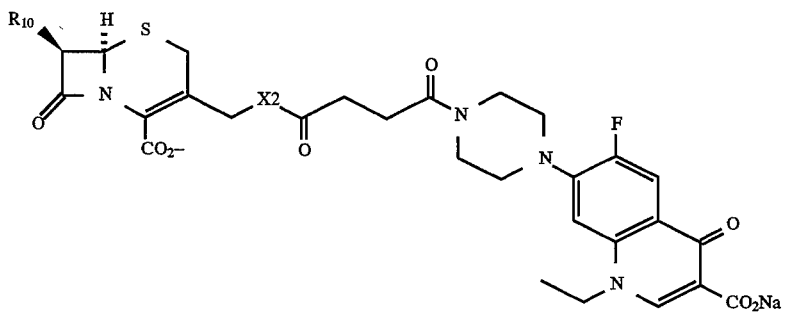

wherein, referring to formulas (I) and (II), —$X^4_t$—$C(=Y_u)$—Z—Q"; t is 1 and u is 1; $X^4$ is $N(R^{40})$, where $R^{40}$ is hydrogen (for an amide), or $X^2$ is $R^{43}$—$NR^{41}$ (for a hydrazide), where $R^{41}$ is hydrogen and $R^{43}$ is $NR^{41}$, and $R^{41}$ is hydrogen; $Y^2$ is oxygen; Z is nil; and Q" is Q' which is (for example) an N-propionylpiperazinyl $R^{16}$ group.

Preferred linking moieties include carbamate, dithiocarbamate, urea, thiourea, isothiouronium, amine, ammonium, and heteroarylium containing moieties. Particularly preferred linking moieties include carbamate and dithiocarbamate linking moieties.

The specific physical, chemical, and pharmacological properties of the lactam-quinolones of this invention may depend upon the particular combination of the integral lactam-containing moiety, quinolone moiety and linking moiety comprising the compound. For example, selection of particular integral moieties may affect the relative susceptibility of the lactam-quinolone to bacterial resistance mechanisms (e.g., beta-lactamase activity).

Preferred lactam-quinolones include compounds having the following specific combinations of lactam-containing moieties, quinolone moieties and linking moieties.

1) Carbamate-linked cephem quinolones, such as compounds of the following classes.

(a) where—the lactam-containing moiety is a cephem, wherein referring to Formula (II), bond "a" is a single bond; bond "b" is a double bond; $R^{12}$ is —CH—; $R^{13}$ is —C(COOH)—; and $R^{14}$ is —S—$CH_2$—C'''—$CH_2$—;

where the quinolone moiety is a structure, wherein referring to Formula (I), $A^2$ is —CF—; $A^3$ is —CH—; $R^4$ is —OH; and $R^3$ is $R^{16}$ and is a substituent moiety of L; and where the linking moiety is a carbamate, where L is —O—C(=O)—Z—Q"; Z is nitrogen and Q", together with Z, is a substituted $R^{16}$ group (b) where—the lactam-containing moiety is a cephem, wherein referring to Formula (II), bond "a" is a single bond; bond "b" is a double bond; $R^{12}$ is —CH—; $R^{13}$ is —C(COOH)—; and $R^{14}$ is —S—$CH_2$—C'''—$CH_2$—;

the quinolone moiety is a structure, wherein referring to Formula (I), $A^2$ is —CF—; $A^3$ is —CH—; $R^4$ is —OH; and $R^3$ is $R^{15}$ and is a substituent moiety of L; and the linking moiety is a carbamate, where L is —O—C(=O)—Z—Q"; Z is nitrogen and Q", together with Z, is a substituted $R^{15}$ group (c) where—the lactam-containing moiety is a cephem, wherein referring to Formula (II), bond "a" is a single bond; bond "b" is a double bond; $R^{12}$ is —CH—; $R^{13}$ is —C(COOH)—; and $R^{14}$ is —S—$CH_2$—C'''—$CH_2$—;

the quinolone moiety is a 6-fluoroquinolone, wherein referring to Formula (I), $A^1$ is —$C(R^7)$—; $A^2$ is —CF—; $A^3$ is —CH—; $R^4$ is —OH; and $R^3$ is $R^{16}$ and is a substituent moiety of L; and the linking moiety is a carbamate, where L is —O—C(=O)—Z—Q"; Z is nitrogen and Q", together with Z, is a substituted $R^{16}$ group (d) where—the lactam-containing moiety is a cephem, wherein referring to Formula (II), bond "a" is a single bond; bond "b" is a double bond; $R^{12}$ is —CH—; $R^{13}$ is —C(COOH)—; and $R^{14}$ is —S—$CH_2$—C'''—$CH_2$—;

the quinolone moiety is a naphthyridinone, wherein referring to Formula (I), $A^1$ is —N—; $A^2$ is —CF—; $A^3$ is —CH—; $R^4$ is —OH; and $R^3$ is $R^{16}$ and is a substituent moiety of L; and the linking moiety is a carbamate, where L is —O—C(=O)—Z—Q"; Z is nitrogen and Q", together with Z, is a substituted $R^{16}$ group (e) where—the lactam-containing moiety is a cephem, wherein referring to Formula (II), bond "a" is a single bond; bond "b" is a double bond; $R^{11}$ is —H or —OMe; $R^{12}$ is —CH—; $R^{13}$ is —C(COOH)—; and $R^{14}$ is —S—$CH_2$—C'''—$CH_2$—; and $R^{10}$ is [[(2-thienyl)acetyl]amino], [[(2-amino-4-thiazolyl)(methoxyimino)acetyl]amino], [[(4-pyridylthio)acetyl]amino], [(phenoxy)acetyl]amino], [[(2-amino-4-thiazolyl)acetyl]amino], or [[(2-amino-4-thiazolyl)[[(3,4-dihydroxyphenyl) carbonyl]amino]acetyl]amino];

the quinolone moiety is a structure, wherein referring to Formula (I), $A^2$ is —CF—; $A^3$ is —CH—; $R^4$ is —OH; $R^6$ is —H; $A^1$ is —CH—, —CF—, —CCl—, or —N—; and $R^3$ is cyclopropyl, ethyl, 2,4-difluorophenyl, 4-fluorophenyl, or t-butyl; and $R^3$ is $R^{16}$, being either a 3-amino-1-pyrrolidinyl group (substituted at the 3-amino position by the L moiety), or a 1-piperazinyl group (substituted at the 4-position by the L moiety); and the linking moiety is a carbamate, where L is —O—C(=O)—Z—Q"; Z is nitrogen and Q", together with Z, is $R^{16}$, either a 3-amino substituted 1-pyrrolidinyl group, or a 4-substituted 1-piperazinyl group Carbamate-linked cephem quinolones of classes (c), (d) and (e) are preferred; compounds of class (e) are particularly preferred.

(2) Carbamate-linked penem quinolones, such as compounds of the following classes.

(a) where—the lactam-containing moiety is a penem, wherein referring to Formula (II), bond "a" is a single bond; bond "b" is a double bond; $R^{12}$ is —CH—; $R^{13}$ is —C(COOH)—; and $R^{14}$ is —S—C'''—$CH_2$—;

the quinolone moiety is a structure, wherein referring to Formula (I), $A^2$ is —CF—; $A^3$ is —CH—; $R^4$ is —OH; and $R^3$ is $R^{16}$ and is a substituent moiety of L; and the linking moiety is a carbamate, where L is —O—C(=O)—Z—Q"; Z is nitrogen and Q", together with Z, is a substituted $R^{16}$ group (b) where—the lactam-containing moiety is a penem, wherein referring to Formula (II), bond "a" is a single bond; bond "b" is a double bond; $R^{12}$ is —CH—; $R^{13}$ is —C(COOH)—; and $R^{14}$ is —S—C'''—$CH_2$—;

the quinolone moiety is a structure, wherein referring to Formula (I), $A^2$ is —CF—; $A^3$ is —CH—; $R^4$ is —OH; and $R^3$ is $R^{15}$ and is a substituent moiety of L; and the linking moiety is a carbamate, where L is —O—C(=O)—Z—Q"; Z is nitrogen and Q", together with Z, is a substituted $R^{15}$ group (c) where—the lactam-containing moiety is a penem, wherein referring to Formula (II), bond "a" is a single bond; bond "b" is a double bond; $R^{10}$ is (1-hydroxyethyl); $R^{11}$ is —H; $R^{12}$ is —CH—; $R^{13}$ is —C(COOH)—; and $R^{14}$ is —S—C'''—$CH_2$—;

the quinolone moiety is a 6-fluoroquinolone, wherein referring to Formula (I), $A^1$ is —C($R^7$)—; $A^2$ is —CF—; $A^3$ is —CH—; $R^4$ is —OH; and $R^3$ is $R^{16}$ and is a substituent moiety of L;

the linking moiety is a carbamate, where L is —O—C(=O)—Z—Q"; Z is nitrogen and Q", together with Z, is a substituted $R^{16}$ group (d) where—the lactam-containing moiety is a penem, wherein referring to Formula (II), bond "a" is a single bond; bond "b" is a double bond; $R^{12}$ is —CH—; $R^{13}$ is —C(COOH)—; and $R^{14}$ is —S—C'''—$CH_2$—;

the quinolone moiety is a naphthyridinone, wherein referring to Formula (I), $A^1$ is —N—; $A^2$ is —CF—; $A^3$ is —CH—; $R^4$ is —OH; and $R^3$ is $R^{16}$ and is a substituent moiety of L; and the linking moiety is a carbamate, where L is —O—C(=O)—Z—Q"; Z is nitrogen and Q", together with Z, is a substituted $R^{16}$ group (e) where—the lactam-containing moiety is a penem, wherein referring to Formula (II), bond "a" is a single bond; bond "b" is a double bond; $R^{12}$ is —CH—; $R^{13}$ is —C(COOH)—; and $R^{14}$ is —S—C'''—$CH_2$—;

the quinolone moiety is a structure, wherein referring to Formula (I), $A^2$ is —CF—; $A^3$ is —CH—; $R^4$ is —OH; $R^6$ is —H; $A^1$ is —CH—, —CF—, —CCl—, or —N—; and $R^3$ is cyclopropyl, ethyl, 2,4-difluorophenyl, 4-fluorophenyl, or t-butyl; and $R^3$ is $R^{16}$, being either a 3-amino-1-pyrrolidinyl group (substituted at the 3-amino position by the L moiety), or a 1-piperazinyl group (substituted at the 4-position by the L moiety); and the linking moiety is a carbamate, where L is —O—C(=O)—Z—Q"; Z is nitrogen and Q", together with Z, is $R^{16,}$ either a 3-amino substituted 1-pyrrolidinyl group, or a 4-substituted 1-piperazinyl group (f) where—the lactam-containing moiety is a penem, wherein referring to Formula (II), bond "a" is a single bond; bond "b" is a double bond; $R^{12}$ is —CH—; $R^{13}$ is —C(COOH)—; and $R^{14}$ is —S—C'''—;

the quinolone moiety is a structure, wherein referring to Formula (I), $A^2$ is —CF—; $A^3$ is —CH—; $R^4$ is —OH; and $R^3$ is $R^{16}$ and is a substituent moiety of L; and the linking moiety is a carbamate, where L is —S—$CH_2CH_2$—O—C(=O)—Z—Q"; Z is nitrogen and Q", together with Z, is a substituted $R^{16}$ group (g) where—the lactam-containing moiety is a penem, wherein referring to Formula (II), bond "a" is a single bond; bond "b" is a double bond; $R^{12}$ is —CH—; $R^{13}$ is —C(COOH)—; and $R^{14}$ is —S—C'''—;

the quinolone moiety is a structure, wherein referring to Formula (I), $A^2$ is —CF—; $A^3$ is —CH—; $R^4$ is —OH; and $R^3$ is $R^{15}$ and is a substituent moiety of L; and the linking moiety is a carbamate, where L is —S—$CH_2CH_2$—O—C(=O)—Z—Q"; Z is nitrogen and Q", together with Z, is a substituted $R^{15}$ group (h) where—the lactam-containing moiety is a penem, wherein referring to Formula (II), bond "a" is a single bond; bond "b" is a double bond; $R^{12}$ is —CH—; $R^{13}$ is —C(COOH)—; and $R^{14}$ is —S—C'''—;

the quinolone moiety is a 6-fluoroquinolone, wherein referring to Formula (I), $A^1$ is —C($R^7$)—; $A^2$ is —CF—; $A^3$ is —CH—; $R^4$ is —OH; and $R^3$ is $R^{16}$ and is a substituent moiety of L;

the linking moiety is a carbamate, where L is —S—$CH_2CH_2$—O—C(=O)—Z—Q"; Z is nitrogen and Q", together with Z, is a substituted $R^{16}$ group (i) where—the lactam-containing moiety is a penem, wherein referring to Formula (II), bond "a" is a single bond; bond "b" is a double bond; $R^{12}$ is —CH—; $R^{13}$ is —C(COOH)—; and $R^{14}$ is —S—C'''—;

the quinolone moiety is a naphthyridinone, wherein referring to Formula (I), $A^1$ is —N—; $A^2$ is —CF—; $A^3$ is —CH—; $R^4$ is —OH; and $R^3$ is $R^{16}$ and is a substituent moiety of L; and the linking moiety is a carbamate, where L is —S—$CH_2CH_2$—O—C(=O)—Z—Q"; Z is nitrogen and Q", together with Z, is a substituted $R^{16}$ group (j) where the lactam-containing moiety is a penem, wherein referring to Formula (II), bond "a" is a single bond; bond "b" is a double bond; $R^{10}$ is (1-hydroxyethyl); $R^{11}$ is —H; $R^{12}$ is —CH—; $R^{13}$ is —C(COOH)—; and $R^{14}$ is —S—C'''—;

the quinolone moiety is a structure, wherein referring to Formula (I), $A^2$ is —CF—; $A^3$ is —CH—; $R^4$ is —OH; $R^6$ is —H; $A^1$ is —CH—, —CF—, —CCl—, or —N—; and $R^3$ is cyclopropyl, ethyl, 2,4-difluorophenyl, 4-fluorophenyl, or t-butyl; and $R^3$ is $R^{16}$, being either a 3-amino-1-pyrrolidinyl group (substituted at the 3-amino position by the L moiety), or a 1-piperazinyl group (substituted at the 4-position by the L moiety); and the linking moiety is a carbamate, where L is —S—$CH_2CH_2$—O—C(=O)—Z—Q"; Z is nitrogen and Q", together with Z, is $R^{16,}$ either a 3-amino substituted 1-pyrrolidinyl group, or a 4-substituted 1-piperazinyl group Carbamate-linked penem quinolones of classes (c), (d), (e), (h), (i) and (j) are preferred; compounds of classes (e) and (j) are more preferred.

3. Carbamate-linked carbacephem quinolones, such as compounds of the following classes.

(a) where—the lactam-containing moiety is a carbapenem, wherein referring to Formula (II), bond "a" is a single bond; bond "b" is a double bond; $R^{12}$ is —CH—; $R^{13}$ is —C(COOH)—; and $R^{14}$ is —CH($R^{37}$)—C'''—$CH_2$—;

the quinolone moiety is a structure, wherein referring to Formula (I), $A^2$ is —CF—; $A^3$ is —CH—; $R^4$ is —OH; and $R^3$ is $R^{16}$ and is a substituent moiety of L; and the linking moiety is a carbamate, where L is —O—C(=O)—Z—Q"; Z is nitrogen and Q", together with Z, is a substituted $R^{16}$ group (b) where—the lactam-containing moiety is a carbapenem, wherein referring to Formula (II), bond "a" is a single bond; bond "b" is a double bond; $R^{12}$ is —CH—; $R^{13}$ is —C(COOH)—; and $R^{14}$ is —CH($R^{37}$)—C'''—CH$_2$—;

the quinolone moiety is a structure, wherein referring to Formula (I), $A^2$ is —CF—; $A^3$ is —CH—; $R^4$ is —OH; and $R^3$ is $R^{15}$ and is a substituent moiety of L; and the linking moiety is a carbamate, where L is —O—C(=O)—Z—Q''; Z is nitrogen and Q'', together with Z, is a substituted $R^{15}$ group (c) where—the lactam-containing moiety is a carbapenem, wherein referring to Formula (II), bond "a" is a single bond; bond "b" is a double bond; $R^{12}$ is —CH—; $R^{13}$ is —C(COOH)—; and $R^{14}$ is —CH($R^{37}$)—C'''—CH$_2$—;

the quinolone moiety is a 6-fluoroquinolone, wherein referring to Formula (I), $A^1$ is —C($R^7$)—; $A^2$ is —CF—; $A^3$ is —CH—; $R^4$ is —OH; and $R^3$ is $R^{16}$ and is a substituent moiety of L; and the linking moiety is a carbamate, where L is —O—C(=O)—Z—Q''; Z is nitrogen and Q'', together with Z, is a substituted $R^{16}$ group (d) where—the lactam-containing moiety is a carbapenem, wherein referring to Formula (II), bond "a" is a single bond; bond "b" is a double bond; $R^{12}$ is —CH—; $R^{13}$ is —C(COOH)—; and $R^{14}$ is —CH($R^{37}$)—C'''—CH$_2$—;

the quinolone moiety is a naphthyridinone, wherein referring to Formula (I), $A^1$ is —N—; $A^2$ is —CF—; $A^3$ is —CH—; $R^4$ is —OH; and $R^3$ is $R^{16}$ and is a substituent moiety of L; and the linking moiety is a carbamate, where L is —O—C(=O)—Z—Q''; Z is nitrogen and Q'', together with Z, is a substituted $R^{16}$ group (e) where the lactam-containing moiety is a carbapenem, wherein referring to Formula (II), bond "a" is a single bond; bond "b" is a double bond; $R^{10}$ is (1-hydroxyethyl); $R^{11}$ is —H; $R^{12}$ is —CH—; $R^{13}$ is —C(COOH)—; and $R^{14}$ is —CH($R^{38}$)—C'''—CH$_2$—; $R^{38}$ is —H or —Me;

the quinolone moiety is a structure, wherein referring to Formula (I), $A^2$ is —CF—; $A^3$ is —CH—; $R^4$ is —OH; $R^6$ is —H; $A^1$ is —CH—, —CF—, —CCl—, or —N—; and $R^3$ is cyclopropyl, ethyl, 2,4-difluorophenyl, 4-fluorophenyl, or t-butyl; and $R^3$ is $R^{16}$, being either a 3-amino-1-pyrrolidinyl group (substituted at the 3-amino position by the L moiety), or a 1-piperazinyl group (substituted at the 4-position by the L moiety); and the linking moiety is a carbamate, where L is —O—C(=O)—Z—Q''; Z is nitrogen and Q'', together with Z, is $R^{16,}$ either a 3-amino substituted 1-pyrrolidinyl group, or a 4-substituted 1-piperazinyl group (f) where—the lactam-containing moiety is a carbapenem, wherein referring to Formula (II), bond "a" is a single bond; bond "b" is a double bond; $R^{12}$ is —CH—; $R^{13}$ is —C(COOH)—; and $R^{14}$ is —CH($R^{38}$)—C'''—;

the quinolone moiety is a structure, wherein referring to Formula (I), $A^2$ is —CF—; $A^3$ is —CH—; $R^4$ is —OH; and $R^3$ is $R^{16}$ and is a substituent moiety of L; and the linking moiety is a carbamate, where L is —S—CH$_2$CH$_2$—O—C(=O)—Z—Q''; Z is nitrogen and Q'', together with Z, is a substituted $R^{16}$ group (g) where—the lactam-containing moiety is a carbapenem, wherein referring to Formula (II), bond "a" is a single bond; bond "b" is a double bond; $R^{12}$ is —CH—; $R^{13}$ is —C(COOH)—; and $R^{14}$ is —CH($R^{38}$)—C'''—;

the quinolone moiety is a structure, wherein referring to Formula (I), $A^2$ is —CF—; $A^3$ is —CH—; $R^4$ is —OH; and $R^3$ is $R^{15}$ and is a substituent moiety of L; and the linking moiety is a carbamate, where L is —S—CH$_2$CH$_2$—O—C(=O)—Z—Q''; Z is nitrogen and Q'', together with Z, is a substituted $R^{15}$ group (h) where—the lactam-containing moiety is a carbapenem, wherein referring to Formula (II), bond "a" is a single bond; bond "b" is a double bond; $R^{12}$ is —CH—; $R^{13}$ is —C(COOH)—; and $R^{14}$ is —CH($R^{38}$)—C'''—;

the quinolone moiety is a 6-fluoroquinolone, wherein referring to Formula (I), $A^1$ is —C($R^7$)—; $A^2$ is —CF—; $A^3$ is —CH—; $R^4$ is —OH; and $R^3$ is $R^{16}$ and is a substituent moiety of L;

the linking moiety is a carbamate, where L is —S—CH$_2$CH$_2$—O—C(=O)—Z—Q''; Z is nitrogen and Q'', together with Z, is a substituted $R^{16}$ group (i) where—the lactam-containing moiety is a carbapenem, wherein referring to Formula (II), bond "a" is a single bond; bond "b" is a double bond; $R^{12}$ is —CH—; $R^{13}$ is —C(COOH)—; and $R^{14}$ is —CH($R^{38}$)—C'''—;

the quinolone moiety is a naphthyridinone, wherein referring to Formula (I), $A^1$ is —N—; $A^2$ is —CF—; $A^3$ is —CH—; $R^4$ is —OH; and $R^3$ is $R^{16}$ and is a substituent moiety of L; and the linking moiety is a carbamate, where L is —S—CH$_2$CH$_2$—O—C(=O)—Z—Q''; Z is nitrogen and Q'', together with Z, is a substituted $R^{16}$ group (j)—where the lactam-containing moiety is a carbapenem, wherein referring to Formula (II), bond "a" is a single bond; bond "b" is a double bond; $R^{10}$ is (1-hydroxyethyl); $R^{11}$ is —H; $R^{12}$ is —CH—; $R^{13}$ is —C(COOH)—; and $R^{14}$ is —CH($R^{38}$)—C'''—; $R^{38}$ is —H or —Me;

the quinolone moiety is a structure, wherein referring to Formula (I), $A^2$ is —CF—; $A^3$ is —CH—; $R^4$ is —OH; $R^6$ is —H; $A^1$ is —CH—, —CF—, —CCl—, or —N—; and $R^3$ is cyclopropyl, ethyl, 2,4-difluorophenyl, 4-fluorophenyl, or t-butyl; and $R^3$ is $R^{16}$, being either a 3-amino-1-pyrrolidinyl group (substituted at the 3-amino position by the L moiety), or a 1-piperazinyl group (substituted at the 4-position by the L moiety); and the linking moiety is a carbamate, where L is —S—CH$_2$CH$_2$—O—C(=O)—Z—Q''; Z is nitrogen and Q'', together with Z, is $R^{16,}$ either a 3-amino substituted 1-pyrrolidinyl group, or a 4-substituted 1-piperazinyl group Carbamate-linked carbacephem quinolones of classes (c), (d), (e), (h), (i), and (j) are preferred; compounds of classes (e) and (j) are more preferred.

4. Carbamate-linked oxacephem quinolones, such as compounds of the class where the lactam-containing moiety is a oxacephem, wherein referring to Formula (II), bond "a" is a single bond; bond "b" is a double bond; $R^{12}$ is —CH—; $R^{13}$ is —C(COOH)—; and $R^{14}$ is —O—CH$_2$—C'''—CH$_2$—;

the quinolone moiety is a structure, wherein referring to Formula (I), $A^2$ is —CF—; $A^3$ is —CH—; $R^4$ is —OH; and $R^3$ is $R^{16}$ and is a substituent moiety of L; and the linking moiety is a carbamate, where L is —O—C(=O)—Z—Q"; Z is nitrogen and Q", together with Z, is a substituted $R^{16}$ group.

5. Carbamate-linked isocephem quinolones, such as compounds of the class where the lactam-containing moiety is a isocephem, wherein referring to Formula (II), bond "a" is a single bond; bond "b" is a double bond; $R^{12}$ is —CH—; $R^{13}$ is —C(COOH)—; and $R^{14}$ is —$CH_2$—S—C'''—$CH_2$—;

the quinolone moiety is a structure, wherein referring to Formula (I), $A^2$ is —CF—; $A^3$ is —CH—; $R^4$ is —OH; and $R^3$ is $R^{16}$ and is a substituent moiety of L; and the linking moiety is a carbamate, where L is —O—C(=O)—Z—Q"; Z is nitrogen and Q", together with Z, is a substituted $R^{16}$ group.

6. Carbamate-linked iso-oxacephem quinolones, such as compounds of the class where the lactam-containing moiety is a iso-oxacephem, wherein referring to Formula (II), bond "a" is a single bond; bond "b" is a double bond; $R^{12}$ is —CH—; $R^{13}$ is —C(COOH)—; and $R^{14}$ is —$CH_2$—O—C'''—$CH_2$—;

the quinolone moiety is a structure, wherein referring to Formula (I), $A^2$ is —CF—; $A^3$ is —CH—; $R^4$ is —OH; and $R^3$ is $R^{16}$ and is a substituent moiety of L; and the linking moiety is a carbamate, where L is —O—C(=O)—Z—Q"; Z is nitrogen and Q", together with Z, is a substituted $R^{16}$ group.

7. Carbamate-linked carbacephem quinolones, such as compounds of the class where the lactam-containing moiety is a carbacephem, wherein referring to Formula (II), bond "a" is a single bond; bond "b" is a double bond; $R^{12}$ is —CH—; $R^{13}$ is —C(COOH)—; and $R^{14}$ is —$CH_2$—CH2—C'''—$CH_2$—;

the quinolone moiety is a structure, wherein referring to Formula (I), $A^2$ is —CF—; $A^3$ is —CH—; $R^4$ is —OH; and $R^3$ is $R^{16}$ and is a substituent moiety of L; and the linking moiety is a carbamate, where L is —O—C(=O)—Z—Q"; Z is nitrogen and Q", together with Z, is a substituted $R^{16}$ group.

8. Carbamate-linked penicillin qutnolones, such as compounds of the class where the lactam-containing moiety is a penicillin, wherein referring to Formula (II), bond "a" is a single bond; bond "b" is a single bond; $R^{12}$ is —CH—; $R^{13}$ is —C(COOH)—; and $R^{14}$ is —S—C'''(Me)—$CH_2$—;

the quinolone moiety is a structure, wherein referring to Formula (I), $A^2$ is —CF—; $A^3$ is —CH—; $R^4$ is —OH; and $R^3$ is $R^{16}$ and is a substituent moiety of L; and the linking moiety is a carbamate, where L is —O—C(=O)—Z—Q"; Z is nitrogen and Q", together with Z, is a substituted $R^{16}$ group.

9. Carbamate-linked monobactam quinolones, such as compounds of the class where the lactam-containing moiety is a monobactam, wherein referring to Formula (II), bond "a" is a single bond; bond "b" is nil; $R^{12}$ is —CH— and is bonded directly to L; and $R^{14}$ is nil;

the quinolone moiety is a structure, wherein referring to Formula (I), $A^2$ is —CF—; $A^3$ is —CH—; $R^4$ is —OH; and $R^3$ is $R^{16}$ and is a substituent moiety of L; and the linking moiety is a carbamate, where L is —$CH_2$—O—C(=O)—Z—Q"; Z is nitrogen and Q", together with Z, is a substituted $R^{16}$ group.

10. Dithiocarbamate-linked cephem quinolones, such as compounds of the following classes.

(a) where—the lactam-containing moiety is a cephem, wherein referring to Formula (II), bond "a" is a single bond; bond "b" is a double bond; $R^{12}$ is —CH—; $R^{13}$ is —C(COOH)—; and $R^{14}$ is —S—$CH_2$—C'''—$CH_2$—;

the quinolone moiety is a structure, wherein referring to Formula (I), $A^2$ is —CF—; $A^3$ is —CH—; $R^4$ is —OH; and $R^3$ is $R^{16}$ and is a substituent moiety of L; and the linking moiety is a dithiocarbamate, where L is —S—C(=S)—Z—Q"; Z is nitrogen and Q", together with Z, is a substituted $R^{16}$ group (b) where—the lactam-containing moiety is a cephem, wherein referring to Formula (II), bond "a" is a single bond; bond "b" is a double bond; $R^{12}$ is —CH—; $R^{13}$ is —C(COOH)—; and $R^{14}$ is —S—$CH_2$—C'''—$CH_2$—;

the quinolone moiety is a structure, wherein referring to Formula (I), $A^2$ is —CF—; $A^3$ is —CH—; $R^4$ is —OH; and $R^3$ is $R^{15}$ and is a substituent moiety of L; and the linking moiety is a dithiocarbamate, where L is —S—C(=S)—Z—Q"; Z is nitrogen and Q", together with Z, is a substituted $R^{15}$ group (c) where—the lactam-containing moiety is a cephem, wherein referring to Formula (II), bond "a" is a single bond; bond "b" is a double bond; $R^{12}$ is —CH—; $R^{13}$ is —C(COOH)—; and $R^{14}$ is —S—$CH_2$—C'''—$CH_2$—;

the quinolone moiety is a 6-fluoroquinolone, wherein referring to Formula (I), $A^1$ is —C($R^7$)—; $A^2$ is —CF—; $A^3$ is —CH—; $R^4$ is —OH; and $R^3$ is $R^{16}$ and is a substituent moiety of L;

the linking moiety is a dithiocarbamate, where L is —S—C(=S)—Z—Q"; Z is nitrogen and Q", together with Z, is a substituted $R^{16}$ group (d) where—the lactam-containing moiety is a cephem, wherein referring to Formula (II), bond "a" is a single bond; bond "b" is a double bond; $R^{12}$ is —CH—; $R^{13}$ is —C(COOH)—; and $R^{14}$ is —S—$CH_2$—C'''—$CH_2$—;

the quinolone moiety is a naphthyridinone, wherein referring to Formula (I), $A^1$ is —N—; $A^2$ is —CF—; $A^3$ is —CH—; $R^4$ is —OH; and $R^3$ is $R^{16}$ and is a substituent moiety of L; and the linking moiety is a dithiocarbamate, where L is —S—C(=S)—Z—Q"; Z is nitrogen and Q", together with Z, is a substituted $R^{16}$ group (e) where—the lactam-containing moiety is a cephem, wherein referring to Formula (II), bond "a" is a single bond; bond "b" is a double bond; $R^{11}$ is —H or —OMe; $R^{12}$ is —CH—; $R^{13}$ is —C(COOH)—; and $R^{14}$ is —S—$CH_2$—C'''—$CH_2$—; and $R^{10}$ is [[(2-thienyl)acetyl]-amino], [[(2-amino-4-thiazolyl)(methoxyimino)-acetyl]amino], [[(4-pyridylthio)acetyl]amino], [(phenoxy)acetyl]amino], [[(2-amino-4-thiazolyl)-acetyl]amino], or [[(2-amino-4-thiazolyl)-[[(3,4-dihydroxyphenyl)carbonyl]amino]acetyl]-amino];

the quinolone moiety is a structure, wherein referring to Formula (I), $A^2$ is —CF—; $A^3$ is —CH—; $R^4$ is —OH; $R^6$ is —H; $A^1$ is —CH—, —CF—, —CCl—, or —N—; and $R^3$ is cyclopropyl, ethyl, 2,4-difluorophenyl, 4-fluorophenyl, or t-butyl; and $R^3$ is $R^{16}$ being either a 3-amino-1-pyrrolidinyl group (substituted at the 3-amino position by the L moiety), or a 1-piperazinyl group (substituted at the 4-position by the L moiety); and the linking moiety is a dithiocarbamate, where L is —S—C(=S)—Z—Q"; Z is nitrogen and Q", together with Z, is $R^{16}$, either a 3-amino substituted 1-pyrrolidinyl group, or a 4-substituted 1-piperazinyl group Dithiocarbamate-linked cephem quinolones of classes (c), (d) and (e) are preferred; compounds of class (e) are more preferred.

11. Dithiocarbamate-linked penem quinolones, such as compounds of the following classes.

(a) where—the lactam-containing moiety is a penem, wherein referring to Formula (II), bond "a" is a single bond; bond "b" is a double bond; $R^{12}$ is —CH—; $R^{13}$ is —C(COOH)—; and $R^{14}$ is —S—C'''—$CH_2$—;

the quinolone moiety is a structure, wherein referring to Formula (I), $A^2$ is —CF—; $A^3$ is —CH—; $R^4$ is —OH; and $R^3$ is $R^{16}$ and is a substituent moiety of L; and the linking moiety is a dithiocarbamate, where L is —S—C(=S)—Z—Q"; Z is nitrogen and Q", together with Z, is a substituted $R^{16}$ group (b) where—the lactam-containing moiety is a penem, wherein referring to Formula (II), bond "a" is a single bond; bond "b" is a double bond; $R^{10}$ is (1-hydroxyethyl); $R^{11}$ is —H; $R^{12}$ is —CH—; $R^{13}$ is —C(COOH)—; and $R^{14}$ is —S—C'''—$CH_2$—;

the quinolone moiety is a structure, wherein referring to Formula (I), $A^2$ is —CF—; $A^3$ is —CH—; $R^4$ is —OH; $R^6$ is —H; $A^1$ is —CH—, —CF—, —CCl—, or —N—; and $R^3$ is cyclopropyl, ethyl, 2,4-difluorophenyl, 4-fluorophenyl, or t-butyl; and $R^3$ is $R^{16}$, being either a 3-amino-1-pyrrolidinyl group (substituted at the 3-amino position by the L moiety), or a 1-piperazinyl group (substituted at the 4-position by the L moiety); and the linking moiety is a dithiocarbamate, where L is —S—C(=S)—Z—Q"; Z is nitrogen and Q", together with Z, is $R^{16}$, either a 3-amino substituted 1-pyrrolidinyl group, or a 4-substituted 1-piperazinyl group (c) where—the lactam-containing moiety is a penem, wherein referring to Formula (II), bond "a" is a single bond; bond "b" is a double bond; $R^{12}$ is —CH—; $R^{13}$ is —C(COOH)—; and $R^{14}$ is —S—C'''—;

the quinolone moiety is a structure, wherein referring to Formula (I), $A^2$ is —CF—; $A^3$ is —CH—; $R^4$ is —OH; and $R^3$ is $R^{16}$ and is a substituent moiety of L; and the linking moiety is a dithiocarbamate, where L is —S—$CH_2CH_2$—S—C(=S)—Z—Q"; Z is nitrogen and together with Z, is a substituted $R^{16}$ group (d) where—the lactam-containing moiety is a penem, wherein referring to Formula (II), bond "a" is a single bond; bond "b" is a double bond; $R^{12}$ is —CH—; $R^{13}$ is —C(COOH)—; and $R^{14}$ is —S—C'''—;

the quinolone moiety is a structure, wherein referring to Formula (I), $A^2$ is —CF—; $A^3$ is —CH—; $R^4$ is —OH; and $R^3$ is $R^{15}$ and is a substituent moiety of L; and the linking moiety is a dithiocarbamate, where L is —S—$CH_2CH_2$—S—C(=S)—Z—Q"; Z is nitrogen and Q", together with Z, is a substituted $R^{15}$ group (e) where—the lactam-containing moiety is a penem, wherein referring to Formula (II), bond "a" is a single bond; bond "b" is a double bond; $R^{12}$ is —CH—; $R^{13}$ is —C(COOH)—; and $R^{14}$ is —S—C'''—;

the quinolone moiety is a 6-fluoroquinolone, wherein referring to Formula (I), $A^1$ is —C($R^7$)—; $A^2$ is —CF—; $A^3$ is —CH—; $R^4$ is —OH; and $R^3$ is $R^{16}$ and is a substituent moiety of L;

the linking moiety is a dithiocarbamate, where L is —S—$CH_2CH_2$—S—C(=S)—Z—Q"; Z is nitrogen and Q", together with Z, is a substituted $R^{16}$ group (f) where—the lactam-containing moiety is a penem, wherein referring to Formula (II), bond "a" is a single bond; bond "b" is a double bond; $R^{12}$ is —CH—; $R^{13}$ is —C(COOH)—; and $R^{14}$ is —S—C'''—;

the quinolone moiety is a naphthyridinone, wherein referring to Formula (I), $A^1$ is —N—; $A^2$ is —CF—; $A^3$ is —CH—; $R^4$ is —OH; and $R^3$ is $R^{16}$ and is a substituent moiety of L; and the linking moiety is a dithiocarbamate, where L is —S—$CH_2CH_2$—S—C(=S)—Z—Q"; Z is nitrogen and Q", together with Z, is a substituted $R^{16}$ group (g) where—the lactam-containing moiety is a penem, wherein referring to Formula (II), bond "a" is a single bond; bond "b" is a double bond; $R^{10}$ is (1-hydroxyethyl); $R^{11}$ is —H; $R^{12}$ is —CH—; $R^{13}$ is —C(COOH)—; and $R^{14}$ is —S—C'''—;

the quinolone moiety is a structure, wherein referring to Formula (I), $A^2$ is —CF—; $A^3$ is —CH—; $R^4$ is —OH; $R^6$ is —H; $A^1$ is —CH—, —CF—, —CCl—, or —N—; and $R^3$ is cyclopropyl, ethyl, 2,4-difluorophenyl, 4-fluorophenyl, or t-butyl; and $R^3$ is $R^{16}$, being either a 3-amino-1-pyrrolidinyl group (substituted at the 3-amino position by the L moiety), or a 1-piperazinyl group (substituted at the 4-position by the L moiety); and the linking moiety is a dithiocarbamate, where L is —S—$CH_2CH_2$—S—C(=S)—Z—Q"; Z is nitrogen and Q", together with Z, is $R^{16}$, either a 3-amino substituted 1-pyrrolidinyl group, or a 4-substituted 1-piperazinyl group Dithiocarbamate-linked penem quinolones of classes (b), (e), (f) and (g) are preferred; compounds of class (g) are more preferred.

12. Dithiocarbamate-linked carbapenem quinolones, such as compounds of the following classes.

(a) where—the lactam-containing moiety is a carbapenem, wherein referring to Formula (II), bond "a" is a single bond; bond "b" is a double bond; $R^{12}$ is —CH—; $R^{13}$ is —C(COOH)—; and $R^{14}$ is —CH($R^{37}$)—C'''—$CH_2$—;

the quinolone moiety is a structure, wherein referring to Formula (I), $A^2$ is —CF—; $A^3$ is —CH—; $R^4$ is —OH; and $R^3$ is $R^{16}$ and is a substituent moiety of L; and the linking moiety is a dithiocarbamate, where L is —S—C(=S)—Z—Q"; Z is nitrogen and Q", together with Z, is a substituted $R^{16}$ group (b) where—the lactam-containing moiety is a carbapenem, wherein referring to Formula (II), bond "a" is a single bond; bond "b" is a double bond; $R^{10}$ is (1-hydroxyethyl); $R^{11}$ is —H; $R^{12}$ is —CH—; $R^{13}$ is —C(COOH)—; and $R^{14}$ is —CH($R^{38}$)—C'''—$CH_2$—; $R^{38}$ is —H or —Me;

the quinolone moiety is a structure, wherein referring to Formula (I), $A^2$ is —CF—; $A^3$ is —CH—; $R^4$ is —OH; $R^6$ is —H; $A^1$ is —CH—, —CF—, —CCl—, or —N—; and $R^3$ is cyclopropyl, ethyl, 2,4-difluorophenyl, 4-fluorophenyl, or t-butyl; and $R^3$ is $R^{16}$, being either a 3-amino-1-pyrrolidinyl group (substituted at the 3-amino position by the L moiety), or a 1-piperazinyl group (substituted at the 4-position by the L moiety); and the linking moiety is a dithiocarbamate, where L is —S—C(=S)—Z—Q"; Z is nitrogen and Q", together with Z, is $R^{16}$, either a 3-amino substituted 1-pyrrolidinyl group, or a 4-substituted 1-piperazinyl group (c) where—the lactam-containing moiety is a carbapenem, wherein referring to Formula (II), bond "a" is a single bond; bond "b" is a double bond; $R^{12}$ is —CH—; $R^{13}$ is —C(COOH)—; and $R^{14}$ is —CH($R^{38}$)—C'''—;

the quinolone moiety is a structure, wherein referring to Formula (I), $A^2$ is —CF—; $A^3$ is —CH—; $R^4$ is —OH; and $R^3$ is $R^{16}$ and is a substituent moiety of L; and the linking moiety is a dithiocarbamate, where L is —S—CH$_2$CH$_2$—S—C(=S)—Z—Q"; Z is nitrogen and Q", together with Z, is a substituted $R^{16}$ group (d) where—the lactam-containing moiety is a carbapenem, wherein referring to Formula (II), bond "a" is a single bond; bond "b" is a double bond; $R^{12}$ is —CH—; $R^{13}$ is —C(COOH)—; and $R^{14}$ is —CH($R^{38}$)—C'''—;

the quinolone moiety is a structure, wherein referring to Formula (I), $A^2$ is —CF—; $A^3$ is —CH—; $R^4$ is —OH; and $R^3$ is $R^{15}$ and is a substituent moiety of L; and the linking moiety is a dithiocarbamate, where L is —S—CH$_2$CH$_2$—S—C(=S)—Z—Q"; Z is nitrogen and Q", together with Z, is a substituted $R^{15}$ group (e) where—the lactam-containing moiety is a carbapenem, wherein referring to Formula (II), bond "a" is a single bond; bond "b" is a double bond; $R^{12}$ is —CH—; $R^{13}$ is —C(COOH)—; and $R^{14}$ is —CH($R^{38}$)—C'''—;

the quinolone moiety is a 6-fluoroquinolone, wherein referring to Formula (I), $A^1$ is —C($R^7$)—; $A^2$ is —CF—; $A^3$ is —CH—; $R^4$ is —OH; and $R^3$ is $R^{16}$ and is a substituent moiety of L; and the linking moiety is a dithiocarbamate, where L is —S—CH$_2$CH$_2$—S—C(=S)—Z—Q"; Z is nitrogen and Q", together with Z, is a substituted $R^{16}$ group (f) where—the lactam-containing moiety is a carbapenem, wherein referring to Formula (II), bond "a" is a single bond; bond "b" is a double bond; $R^{12}$ is —CH—; $R^{13}$ is —C(COOH)—; and $R^{14}$ is —CH($R^{38}$)—C'''—;

the quinolone moiety is a naphthyridinone, wherein referring to Formula (I), $A^1$ is —N—; $A^2$ is —CF—; $A^3$ is —CH—; $R^4$ is —OH; and $R^3$ is $R^{16}$ and is a substituent moiety of L; and the linking moiety is a dithiocarbamate, where L is —S—CH$_2$CH$_2$—S—C(=S)—Z—Q"; Z is nitrogen and Q", together with Z, is a substituted $R^{16}$ group (g) where—the lactam-containing moiety is a carbapenem, wherein referring to Formula (II), bond "a" is a single bond; bond "b" is a double bond; $R^{10}$ is (1-hydroxyethyl); $R^{11}$ is —H; $R^{12}$ is —CH—; $R^{13}$ is —C(COOH)—; and $R^{14}$ is —CH($R^{38}$)—C'''—; $R^{38}$ is —H or —Me;

the quinolone moiety is a structure, wherein referring to Formula (I), $A^2$ is —CF—; $A^3$ is —CH—; $R^4$ is —OH; $R^6$ is —H; $A^1$ is —CH—, —CF—, —CCl—, or —N—; and $R^3$ is cyclopropyl, ethyl, 2,4-difluorophenyl, 4-fluorophenyl, or t-butyl; and $R^3$ is $R^{16}$, being either a 3-amino-1-pyrrolidinyl group (substituted at the 3-amino position by the L moiety), or a 1-piperazinyl group (substituted at the 4-position by the L moiety); and the linking moiety is a dithiocarbamate, where L is —S—CH$_2$CH$_2$—S—C(=S)—Z—Q"; Z is nitrogen and Q", together with Z, is $R^{16}$, either a 3-amino substituted 1-pyrrolidinyl group, or a 4-substituted 1-piperazinyl group Dithiocarbamate-linked carbapenem quinolones of classes (b), (e), (f) and (g) are preferred; compounds of class (g) are more preferred.

13. Dithiocarbamate-linked oxacephem quinolones, such as compounds of the class where the lactam-containing moiety is a oxacephem, wherein referring to Formula (II), bond "a" is a single bond; bond "b" is a double bond; $R^{12}$ is —CH—; $R^{13}$ is —C(COOH)—; and $R^{14}$ is —O—CH$_2$—C'''—CH$_2$—;

the quinolone moiety is a structure, wherein referring to Formula (I), $A^2$ is —CF—; $A^3$ is —CH—; $R^4$ is —OH; and $R^3$ is $R^{16}$ and is a substituent moiety of L; and the linking moiety is a dithiocarbamate, where L is —S—C(=S)—Z—Q"; Z is nitrogen and Q", together with Z, is a substituted $R^{16}$ group.

14. Dithiocarbamate-linked isocephem quinolones, such as compounds of the class where the lactam-containing moiety is a isocephem, wherein referring to Formula (II), bond "a" is a single bond; bond "b" is a double bond; $R^{12}$ is —CH—; $R^{13}$ is —C(COOH)—; and $R^{14}$ is —CH$_2$—S—C'''—CH$_2$—;

the quinolone moiety is a structure, wherein referring to Formula (I), $A^2$ is —CF—; $A^3$ is —CH—; $R^4$ is —OH; and $R^3$ is $R^{16}$ and is a substituent moiety of L; and the linking moiety is a dithiocarbamate, where L is —S—C(=S)—Z—Q"; Z is nitrogen and Q", together with Z, is a substituted $R^{16}$ group.

15. Dithiocarbamate-linked iso-oxacephem quinolones, such as compounds of the class where the lactam-containing moiety is a iso-oxacephem, wherein referring to Formula (II), bond "a" is a single bond; bond "b" is a double bond; $R^{12}$ is —CH—; $R^{13}$ is —C(COOH)—; and $R^{14}$ is —CH$_2$—O—C'''—CH$_2$—;

the quinolone moiety is a structure, wherein referring to Formula (I), $A^2$ is —CF—; $A^3$ is —CH—; $R^4$ is —OH; and $R^3$ is $R^{16}$ and is a substituent moiety of L; and the linking moiety is a dithiocarbamate, where L is —S—C(=S)—Z—Q"; Z is nitrogen and Q", together with Z, is a substituted $R^{16}$ group.

16. Dithiocarbamate-linked carbacephem quinolones, such as compounds of the class where the lactam-containing moiety is a carbacephem, wherein referring to Formula (II), bond "a" is a single bond; bond "b" is a double bond; $R^{12}$ is —CH—; $R^{13}$ is —C(COOH)—; and $R^{14}$ is —CH$_2$—CH2—C'''—CH$_2$—;

the quinolone moiety is a structure, wherein referring to Formula (I), $A^2$ is —CF—; $A^3$ is —CH—; $R^4$ is —OH; and $R^3$ is $R^{16}$ and is a substituent moiety of L; and the linking moiety is a dithiocarbamate, where L is —S—C(=S)—Z—Q"; Z is nitrogen and Q", together with Z, is a substituted $R^{16}$ group.

17. Dithiocarbamate-linked monobactam quinolones, such as compounds of the class where the lactam-containing moiety is a monobactam, wherein referring to Formula (II), bond "a" is a single bond; bond "b" is nil; $R^{12}$ is —CH— and is bonded directly to L; and $R^{14}$ is nil;

the quinolone moiety is a structure, wherein referring to Formula (I), $A^2$ is —CF—; $A^3$ is —CH—; $R^4$ is —OH; and $R^3$ is $R^{16}$ and is a substituent moiety of L; and the linking moiety is a dithiocarbamate, where L is —S—C(=S)—Z—Q"; Z is nitrogen and Q", together with Z, is a substituted $R^{16}$ group.

18. Urea-linked cephem quinolones, such as compounds of the following classes.

(a) where—the lactam-containing moiety is a cephem, wherein referring to Formula (II), bond "a" is a single bond; bond "b" is a double bond; $R^{12}$ is —CH—; $R^{13}$ is —C(COOH)—; and $R^{14}$ is —S—CH$_2$—C'"—CH$_2$—;

the quinolone moiety is a structure, wherein referring to Formula (I), $A^2$ is —CF—; $A^3$ is —CH—; $R^4$ is —OH; and $R^3$ is $R^{16}$ and is a substituent moiety of L; and the linking moiety is a urea, where L is —NH—C(=O)—Z—Q"; Z is nitrogen and Q", together with Z, is a substituted $R^{16}$ group (b) where—the lactam-containing moiety is a cephem, wherein referring to Formula (II), bond "a" is a single bond; bond "b" is a double bond; $R^{11}$ is —H or —OMe; $R^{12}$ is —CH—; $R^{13}$ is —C(COOH)—; $R^{14}$ is —S—CH$_2$—C'"—CH$_2$—; and $R^{10}$ is [[(2-thienyl)acetyl]-amino], [[(2-amino-4-thiazolyl)(methoxyimino)-acetyl]amino], [[(4-pyridylthio)acetyl]amino], [(phenoxy)acetyl]amino], [[(2-amino-4-thiazolyl)-acetyl]amino], or [[(2-amino-4-thiazolyl)-[[(3,4-dihydroxyphenyl)carbonyl]amino]acetyl]-amino];

the quinolone moiety is a structure, wherein referring to Formula (I), $A^2$ is —CF—; $A^3$ is —CH—; $R^4$ is —OH; $R^6$ is —H; $A^1$ is —CH—, —CF—, —CCl—, or —N—; and $R^3$ is cyclopropyl, ethyl, 2,4-difluorophenyl, 4-fluorophenyl, or t-butyl; and $R^3$ is $R^{16}$, being either a 3-amino-1-pyrrolidinyl group (substituted at the 3-amino position by the L moiety), or a 1-piperazinyl group (substituted at the 4-position by the L moiety); and the linking moiety is a urea, where L is —NH—C(=O)—Z—Q"; Z is nitrogen and Q", together with Z, is $R^{16}$, either a 3-amino substituted 1-pyrrolidinyl group, or a 4-substituted 1-piperazinyl group Urea-linked cephem quinolones of class (b) are preferred.

19. Urea-linked penem quinolones, such as compounds of the following classes.

(a) where—the lactam-containing moiety is a penem, wherein referring to Formula (II), bond "a" is a single bond; bond "b" is a double bond; $R^{12}$ is —CH—; $R^{13}$ is —C(COOH)—; and $R^{14}$ is —S—C'"—CH$_2$—;

the quinolone moiety is a structure, wherein referring to Formula (I), $A^2$ is —CF—; $A^3$ is —CH—; $R^4$ is —OH; and $R^3$ is $R^{16}$ and is a substituent moiety of L; and the linking moiety is a urea, where L is —NH—C(=O)—Z—Q"; Z is nitrogen and Q", together with Z, is a substituted $R^{16}$ group (b) where—the lactam-containing moiety is a penem, wherein referring to Formula (II), bond "a" is a single bond; bond "b" is a double bond; $R^{10}$ is (1-hydroxyethyl); $R^{11}$ is —H; $R^{12}$ is —CH—; $R^{13}$ is —C(COOH)—; and $R^{14}$ is —S—C'"—CH$_2$—;

the quinolone moiety is a structure, wherein referring to Formula (I), $A^2$ is —CF—; $A^3$ is —CH—; $R^4$ is —OH;

$R^6$ is —H; $A^1$ is —CH—, —CF—, —CCl—, or —N—; and $R^3$ is cyclopropyl, ethyl, 2,4-difluorophenyl, 4-fluorophenyl, or t-butyl; and $R^3$ is $R^{16}$, being either a 3-amino-1-pyrrolidinyl group (substituted at the 3-amino position by the L moiety), or a 1-piperazinyl group (substituted at the 4-position by the L moiety) ; and the linking moiety is a urea, where L is —NH—C(=O)—Z—Q"; Z is nitrogen and Q", together with Z, is $R^{16}$, either a 3-amino substituted 1-pyrrolidinyl group, or a 4-substituted 1-piperazinyl group (c) where the lactam-containing moiety is a penem, wherein referring to Formula (II), bond "a" is a single bond; bond "b" is a double bond; $R^{12}$ is —CH—; $R^{13}$ is —C(COOH)—; and $R^{14}$ is —S—C'"—;

the quinolone moiety is a structure, wherein referring to Formula (I), $A^2$ is —CF—; $A^3$ is —CH—; $R^4$ is —OH; and $R^3$ is $R^{16}$ and is a substituent moiety of L; and the linking moiety is a urea, where L is —S—CH$_2$CH$_2$—NH—C(=O)—Z—Q"; Z is nitrogen and Q", together with Z, is a substituted $R^{16}$ group (d) where—the lactam-containing moiety is a penem, wherein referring to Formula (II), bond "a" is a single bond; bond "b" is a double bond; $R^{10}$ is (1-hydroxyethyl); $R^{11}$ is —H; $R^{12}$ is —CH—; $R^{13}$ is —C(COOH)—; and $R^{14}$ is —S—C'"—CH$_2$—;

the quinolone moiety is a structure, wherein referring to Formula (I), $A^2$ is —CF—; $A^3$ is —CH—; $R^4$ is —OH; $R^6$ is —H; $A^1$ is —CH—, —CF—, —CCl—, or —N—; and $R^3$ is cyclopropyl, ethyl, 2,4-difluorophenyl, 4-fluorophenyl, or t-butyl; and $R^3$ is $R^{16,}$ being either a 3-amino-1-pyrrolidinyl group (substituted at the 3-amino position by the L moiety), or a 1-piperazinyl group (substituted at the 4-position by the L moiety); and the linking moiety is a urea, where L is —S—CH$_2$CH$_2$—NH—C(=O)—Z—Q"; Z is nitrogen and Q", together with Z, is $R^{16}$, either a 3-amino substituted 1-pyrrolidinyl group, or a 4-substituted 1-piperazinyl group Urea-linked penem quinolones of classes (b) and (d) are preferred.

20. Urea-linked carbapenem quinolones, such as compounds of the following classes.

(a) where—the lactam-containing moiety is a carbapenem, wherein referring to Formula (II), bond "a" is a single bond; bond "b" is a double bond; $R^{12}$ is —CH—; $R^{13}$ is —C(COOH)—; and $R^{14}$ is —CH($R^{37}$)—C'"—CH$_2$—;

the quinolone moiety is a structure, wherein referring to Formula (I), $A^2$ is —CF—; $A^3$ is —CH—; $R^4$ is —OH; and $R^3$ is $R^{16}$ and is a substituent moiety of L; and the linking moiety is a urea, where L is —NH—C(=O)—Z—Q"; Z is nitrogen and Q", together with Z, is a substituted $R^{16}$ group (b) where—the lactam-containing moiety is a carbapenem, wherein referring to Formula (II), bond "a" is a single bond; bond "b" is a double bond; $R^{10}$ is (1-hydroxyethyl); $R^{11}$ is —H; $R^{12}$ is —CH—; $R^{13}$ is —C(COOH)—; and $R^{14}$ is —CH($R^{38}$)—C'"—CH$_2$—; $R^{38}$ is —H or —Me;

the quinolone moiety is a structure, wherein referring to Formula (I), $A^2$ is —CF—; $A^3$ is —CH—; $R^4$ is —OH; $R^6$ is —H; $A^1$ is —CH—, —CF—, —CCl—, or —N—; and $R^3$ is cyclopropyl, ethyl, 2,4- difluorophenyl, 4-fluorophenyl, or t-butyl; and $R^3$ is $R^{16}$, being either a 3-amino-1-pyrrolidinyl group (substituted at the 3-amino position by the L moiety), or a 1-piperazinyl group (substituted at the 4-position by the L moiety); and the linking moiety is a urea, where L is —NH—C(=O)—Z—Q"; Z is nitrogen and Q", together with Z, is $R^{16,}$ either a 3-amino substituted 1-pyrrolidinyl group, or a 4-substituted 1-piperazinyl group (c) where the lactam-containing moiety is a carbapenem, wherein referring to Formula (II), bond "a" is a single bond; bond "b" is a double bond; $R^{12}$ is —CH—; $R^{13}$ is —C(COOH)—; and $R^{14}$ is —CH($R^{38}$)—C'''—;

the quinolone moiety is a structure, wherein referring to Formula (I), $A^2$ is —CF—; $A^3$ is —CH—; $R^4$ is —OH; and $R^3$ is $R^{16}$ and is a substituent moiety of L; and the linking moiety is a urea, where L is —S—CH$_2$CH$_2$—NH—C(=O)—Z—Q"; Z is nitrogen and Q", together with Z, is a substituted $R^{16}$ group (d) where—the lactam-containing moiety is a carbapenem, wherein referring to Formula (II), bond "a" is a single bond; bond "b" is a double bond; $R^{10}$ is (1-hydroxyethyl); $R^{11}$ is —H; $R^{12}$ is —CH—; $R^{13}$ is —C(COOH)—; and $R^{14}$ is —CH($R^{38}$)—C'''—; $R^{38}$ is —H or —Me;

the quinolone moiety is a structure, wherein referring to Formula (I), $A^2$ is —CF—; $A^3$ is —CH—; $R^4$ is —OH; $R^6$ is —H; $A^1$ is —CH—, —CF—, —CCl—, or —N—; and $R^3$ is cyclopropyl, ethyl, 2,4-difluorophenyl, 4-fluorophenyl, or t-butyl; and $R^3$ is $R^{16}$, being either a 3-amino-1-pyrrolidinyl group (substituted at the 3-amino position by the L moiety), or a 1-piperazinyl group (substituted at the 4-position by the L moiety); and the linking moiety is a urea, where L is —S—CH$_2$CH$_2$—NH—C(=O)—Z—Q"; Z is nitrogen and Q", together with Z, is $R^{16}$, either a 3-amino substituted 1-pyrrolidinyl group, or a 4-substituted 1-piperazinyl group Urea-linked carbapenem quinolones of classes (b) and (d) are preferred.

21. Thiourea-linked cephem quinolones, such as compounds of the following classes.

(a) where—the lactam-containing moiety is a cephem, wherein referring to Formula (II), bond "a" is a single bond; bond "b" is a double bond; $R^{12}$ is —CH—; $R^{13}$ is —C(COOH)—; and $R^{14}$ is —S—CH$_2$—C'''—CH$_2$—;

the quinolone moiety is a structure, wherein referring to Formula (I), $A^2$ is —CF—; $A^3$ is —CH—; $R^4$ is —OH; and $R^3$ is $R^{16}$ and is a substituent moiety of L; and the linking moiety is a thiourea, where L is —NH—C(=S)—Z—Q"; Z is nitrogen and Q", together with Z, is a substituted $R^{16}$ group (b) where—the lactam-containing moiety is a cephem, wherein referring to Formula (II), bond "a" is a single bond; bond "b" is a double bond; $R^{11}$ is —H or —OMe; $R^{12}$ is —CH—; $R^{13}$ is —C(COOH)—; and $R^{14}$ is —S—CH$_2$—C'''—CH$_2$—; and $R^{10}$ is [[(2-thienyl)acetyl]-amino], [[(2-amino-4-thiazolyl)(methoxyimino)-acetyl]amino], [[(4-pyridylthio)acetyl]amino], [(phenoxy)acetyl]amino], [[(2-amino-4-thiazolyl)acetyl]amino], or [[(2-amino-4-thiazolyl)-[[(3,4-dihydroxyphenyl)carbonyl]amino]acetyl]-amino];

the quinolone moiety is a structure, wherein referring to Formula (I), $A^2$ is —CF—; $A^3$ is —CH—; $R^4$ is —OH; $R^6$ is —H; $A^1$ is —CH—, —CF—, —CCl—, or —N—; and. $R^3$ is cyclopropyl, ethyl, 2,4-difluorophenyl, 4-fluorophenyl, or t-butyl; and $R^3$ is $R^{16}$, being either a 3-amino-1-pyrrolidinyl group (substituted at the 3-amino position by the L moiety), or a 1-piperazinyl group (substituted at the 4-position by the L moiety); and the linking moiety is a thiourea, where L is —NH—C(=S)—Z—Q"; Z is nitrogen and Q", together with Z, is $R^{16,}$ either a 3-amino substituted 1-pyrrolidinyl group, or a 4-substituted 1-piperazinyl group Thiourea-linked cephem quinolones of class (b) are preferred.

22. Thiourea-linked penem quinolones, such as compounds of the following classes.

(a) where—the lactam-containing moiety is a penem, wherein referring to Formula (II), bond "a" is a single bond; bond "b" is a double bond; $R^{12}$ is —CH—; $R^{13}$ is —C(COOH)—; and $R^{14}$ is —S—C'''—CH$_2$—;

the quinolone moiety is a structure, wherein referring to Formula (I), $A^2$ is —CF—; $A^3$ is —CH—; $R^4$ is —OH; and $R^3$ is $R^{16}$ and is a substituent moiety of L; and the linking moiety is a thiourea, where L is —NH—C(=S)—Z—Q"; Z is nitrogen and Q", together with Z, is a substituted $R^{16}$ group (b) where—the lactam-containing moiety is a penem, wherein referring to Formula (II), bond "a" is a single bond; bond "b" is a double bond; $R^{10}$ is (1-hydroxyethyl); $R^{11}$ is —H; $R^{12}$ is —CH—; $R^{13}$ is —C(COOH)—; and $R^{14}$ is —S—C'''—CH$_2$—;

the quinolone moiety is a structure, wherein referring to Formula (I), $A^2$ is —CF—; $A^3$ is —CH—; $R^4$ is —OH; $R^6$ is —H; $A^1$ is —CH—, —CF—, —CCl—, or —N—; and $R^3$ is cyclopropyl, ethyl, 2,4-difluorophenyl, 4-fluorophenyl, or t-butyl; and $R^3$ is $R^{16}$, being either a 3-amino-1-pyrrolidinyl group (substituted at the 3-amino position by the L moiety), or a 1-piperazinyl group (substituted at the 4-position by the L moiety); and the linking moiety is a thiourea, where L is —NH—C(=S)—Z—Q"; Z is nitrogen and Q", together with Z, is $R^{16}$, either a 3-amino substituted 1-pyrrolidinyl group, or a 4-substituted 1-piperazinyl group (c) where—the lactam-containing moiety is a penem, wherein referring to Formula (II), bond "a" is a single bond; bond "b" is a double bond; $R^{12}$ is —CH—; $R^{13}$ is —C(COOH)—; and $R^{14}$ is —S—C'''—;

the quinolone moiety is a structure, wherein referring to Formula (I), $A^2$ is —CF—; $A^3$ is —CH—; $R^4$ is —OH; and $R^3$ is $R^{16}$ and is a substituent moiety of L; and the linking moiety is a thiourea, where L is —S—CH$_2$CH$_2$—NH—C(=S)—Z—Q"; Z is nitrogen and Q", together with Z, is a substituted $R^{16}$ group (d) where—the lactam-containing moiety is B penem, wherein referring to Formula (II), bond "a" is a single bond; bond "b" is a double bond; $R^{10}$ is (1-hydroxyethyl); $R^{11}$ is —H; $R^{12}$ is —CH—; $R^{13}$ is —C(COOH)—; and $R^{14}$ is —S—C'''—;

the quinolone moiety is a structure, wherein referring to Formula (I), $A^2$ is —CF—; $A^3$ is —CH—; $R^4$ is —OH; $R^6$ is —H; $A^1$ is —CH—, —CF—, —CCl—, or —N—; and $R^3$ is cyclopropyl, ethyl, 2,4-difluorophenyl, 4-fluorophenyl, or t-butyl; and $R^3$ is $R^{16}$, being either a 3-amino-1-pyrrolidinyl group (substituted at the 3-amino position by the L moiety), or a 1-piperazinyl group (substituted at the 4-position by the L moiety); and the linking moiety is a thiourea, where L is —S—$CH_2CH_2$—NH—C(=S)—Z—Q"; Z is nitrogen and Q", together with Z, is $R^{16}$, either a 3-amino substituted 1-pyrrolidinyl group, or a 4-substituted 1-piperazinyl group Thiourea-linked penem quinolones of classes (b) and (d) are preferred.

23. Thiourea-linked carbapenem quinolones, such as compounds of the following classes.

(a) where—the lactam-containing moiety is a carbapenem, wherein referring to Formula (II), bond "a" is a single bond; bond "b" is a double bond; $R^{12}$ is —CH—; $R^{13}$ is —C(COOH)—; and $R^{14}$ is —CH($R^{37}$)—C'"—$CH_2$—;

the quinolone moiety is a structure, wherein referring to Formula (I), $A^2$ is —CF—; $A^3$ is —CH—; $R^4$ is —OH; and $R^3$ is $R^{16}$ and is a substituent moiety of L; and the linking moiety is a thiourea, where L is —NH—C(=S)—Z—Q"; Z is nitrogen and Q", together with Z, is a substituted $R^{16}$ group (b) where—the lactam-containing moiety is a carbapenem, wherein referring to Formula (II), bond "a" is a single bond; bond "b" is a double bond; $R^{10}$ is (1-hydroxyethyl); $R^{11}$ is —H; $R^{12}$ is —CH—; $R^{13}$ is —C(COOH)—; and $R^{14}$ is —CH($R^{38}$)—C'"—$CH_2$—; $R^{38}$ is —H or —Me;

the quinolone moiety is a structure, wherein referring to Formula (I), $A^2$ is —CF—; $A^3$ is —CH—; $R^4$ is —OH; $R^6$ is —H; $A^1$ is —CH—, —CF—, —CCl—, or —N—; and $R^3$ is cyclopropyl, ethyl, 2,4-difluorophenyl, 4-fluorophenyl, or t-butyl; and $R^3$ is $R^{16}$, being either a 3-amino-1-pyrrolidinyl group (substituted at the 3-amino position by the L moiety), or a 1-piperazinyl group (substituted at the 4-position by the L moiety); and the linking moiety is a thiourea, where L is —NH—C(=S)—Z—Q"; Z is nitrogen and Q", together with Z, is $R^{16}$, either a 3-amino substituted 1-pyrrolidinyl group, or a 4-substituted 1-piperazinyl group (c) where—the lactam-containing moiety is a carbapenem, wherein referring to Formula (II), bond "a" is a single bond; bond "b" is a double bond; $R^{12}$ is —CH—; $R^{13}$ is —C(COOH)—; and $R^{14}$ is —CH($R^{38}$)—C'"—;

the quinolone moiety is a structure, wherein referring to Formula (I), $A^2$ is —CF—; $A^3$ is —CH—; $R^4$ is —OH; and $R^3$ is $R^{16}$ and is a substituent moiety of L; and the linking moiety is a thiourea, where L is —S—$CH_2CH_2$—NH—C(=S)—Z—Q"; Z is nitrogen and Q", together with Z, is a substituted $R^{16}$ group (d) where—the lactam-containing moiety is a carbapenem, wherein referring to Formula (II), bond "a" is a single bond; bond "b" is a double bond; $R^{10}$ is (1-hydroxyethyl); $R^{11}$ is —H; $R^{12}$ is —CH—; $R^{13}$ is —C(COOH)—; and $R^{14}$ is —CH($R^{38}$)—C'"—; $R^{38}$ is —H or —Me;

the quinolone moiety is a structure, wherein referring to Formula (I), $A^2$ is —CF—; $A^3$ is —CH—; $R^4$ is —OH; $R^6$ is —H; $A^1$ is —CH—, —CF—, —CCl—, or —N—; and $R^3$ is cyclopropyl, ethyl, 2,4-difluorophenyl, 4-fluorophenyl, or t-butyl; and $R^3$ is $R^{16}$, being either a 3-amino-1-pyrrolidinyl group (substituted at the 3-amino position by the L moiety), or a 1-piperazinyl group (substituted at the 4-position by the L moiety); and the linking moiety is a thiourea, where L is —S—$CH_2CH_2$—NH—C(=S)—Z—Q"; Z is nitrogen and Q", together with Z, is $R^{16}$, either a 3-amino substituted 1-pyrrolidinyl group, or a 4-substituted 1-piperazinyl group Thiourea-linked carbapenem quinolones of classes (b) and (d) are preferred.

24. Isothiouronium-linked cephem quinolones, such as compounds of the following classes.

(a) where—the lactam-containing moiety is a cephem, wherein referring to Formula (II), bond "a" is a single bond; bond "b" is a double bond; $R^{12}$ is —CH—; $R^{13}$ is —C(COOH)—; and $R^{14}$ is —S—$CH_2$—C'"—$CH_2$—;

the quinolone moiety is a structure, wherein referring to Formula (I), $A^2$ is —CF—; $A^3$ is —CH—; $R^4$ is —OH; and $R^3$ is $R^{16}$ and is a substituent moiety of L; and the linking moiety is a isothiouronium, where L is —S—C(=NH2+)—Z—Q"; Z is nitrogen and Q", together with Z, is a substituted $R^{16}$ group (b) where—the lactam-containing moiety is a cephem, wherein referring to Formula (II), bond "a" is a single bond; bond "b" is a double bond; $R^{11}$ is —H or —OMe; $R^{12}$ is —CH—; $R^{13}$ is —C(COOH)—; and $R^{14}$ is —S—$CH_2$—C'"—$CH_2$—; and $R^{10}$ [[(2-thienyl)acetyl] amino], [[(2-amino-4-thiazolyl)-(methoxyimino) acetyl]amino], [[(4-pyridylthio)acetyl]amino], [(phenoxy)acetyl]amino], [[(2-amino-4-thiazolyl) acetyl]amino], or [[(2-amino-4-thiazolyl)[[(3,4-dihydroxyphenyl)carbonyl]amino]acetyl]amino];

the quinolone moiety is a structure, wherein referring to Formula (I), $A^2$ is —CF—; $A^3$ is —CH—; $R^4$ is —OH; $R^6$ is —H; $A^1$ is —CH—, —CF—, —CCl—, or —N—; and $R^3$ is cyclopropyl, ethyl, 2,4-difluorophenyl, 4-fluorophenyl, or t-butyl; and $R^3$ is $R^{16}$, being either a 3-amino-1-pyrrolidinyl group (substituted at the 3-amino position by the L moiety), or a 1-piperazinyl group (substituted at the 4-position by the L moiety); and the linking moiety is a isothiouronium, where L is —S—C(=NH2+)—Z—Q"; Z is nitrogen and Q", together with Z, is $R^{16,}$ either a 3-amino substituted 1-pyrrolidinyl group, or a 4-substituted 1-piperazinyl group Isothiouronium-linked cephem quinolones of class (b) are preferred.

30. Isothiouronium-linked penem quinolones, such as compounds of the following classes.

(a) where—the lactam-containing moiety is a penem, wherein referring to Formula (II), bond "a" is a single bond; bond "b" is a double bond; $R^{12}$ is —CH—; $R^{13}$ is —C(COOH)—; and $R^{14}$ is —S—C'"—$CH_2$—;

the quinolone moiety is a structure, wherein referring to Formula (I), $A^2$ is —CF—; $A^3$ is —CH—; $R^4$ is —OH; and $R^3$ is $R^{16}$ and is a substituent moiety of L; and the linking moiety is a isothiouronium, where L is —S—C(=NH2+)—Z—Q"; Z is nitrogen and Q", together with Z, is a substituted $R^{16}$ group (b) where—the lactam-containing moiety is a penem, wherein referring to Formula (II), bond "a" is a single bond; bond "b" is a double bond; $R^{10}$ is (1-hydroxyethyl); $R^{11}$ is —H; $R^{12}$ is —CH—; $R^{13}$ is —C(COOH)—; and $R^{14}$ is —S—C'"—$CH_2$—;

the quinolone moiety is a structure, wherein referring to Formula (I), $A^2$ is —CF—; $A^3$ is —CH—; $R^4$ is —OH; $R^6$ is —H; $A^1$ is —CH—, —CF—, —CCl—, or —N—; and $R^3$ is cyclopropyl, ethyl, 2,4-difluorophenyl, 4-fluorophenyl, or t-butyl; and $R^3$ is $R^{16}$, being either a 3-amino-1-pyrrolidinyl group (substituted at the 3-amino position by the L moiety), or a 1-piperazinyl group (substituted at the 4-position by the L moiety); and the linking moiety is a isothiouronium, where L is —S—C(=NH2+)—Z—Q"; Z is nitrogen and Q", together with Z, is $R^{16}$, either a 3-amino substituted 1-pyrrolidinyl group, or a 4-substituted 1-piperazinyl group (c) where—the lactam-containing moiety is a penem, wherein referring to Formula (II), bond "a" is a single bond; bond "b" is a double bond; $R^{12}$ is —CH—; $R^{13}$ is —C(COOH)—; and $R^{14}$ is —S—C'"—;

the quinolone moiety is a structure, wherein referring to Formula (I), $A^2$ is —CF—; $A^3$ is —CH—; $R^4$ is —OH; and $R^3$ is $R^{16}$ and is a substituent moiety of L; and the linking moiety is a isothiouronium, where L is —S—CH$_2$CH$_2$—S—C(=NH2+)—Z—Q"; Z is nitrogen and Q", together with Z, is a substituted $R^{16}$ group (d) where the lactam-containing moiety is a penem, wherein referring to Formula (II), bond "a" is a single bond; bond "b" is a double bond; $R^{10}$ is (1-hydroxyethyl); $R^{11}$ is —H; $R^{12}$ is —CH—; $R^{13}$ is —C(COOH)—; and $R^{14}$ is —S—C'"—;

the quinolone moiety is a structure, wherein referring to Formula (I), $A^2$ is —CF—; $A^3$ is —CH—; $R^4$ is —OH; $R^6$ is —H; $A^1$ is —CH—, —CF—, —CCl—, or —N—; and $R^3$ is cyclopropyl, ethyl, 2,4-difluorophenyl, 4-fluorophenyl, or t-butyl; and $R^3$ is $R^{16}$, being either a 3-amino-1-pyrrolidinyl group (substituted at the 3-amino position by the L moiety), or a 1-piperazinyl group (substituted at the 4-position by the L moiety); and the linking moiety is a isothiouronium, where L is —S—CH$_2$CH$_2$—S—C(=NH2+)—Z—Q"; Z is nitrogen and Q", together with Z, is $R^{16}$, either a 3-amino substituted 1-pyrrolidinyl group, or a 4-substituted 1-piperazinyl group Isothiouronium-linked penem quinolones of classes (b) and (d) are preferred.

31. Isothiouronium-linked carbapenem quinolones, such as compounds of the following classes.

(a) where—the lactam-containing moiety is a carbapenem, wherein referring to Formula (II), bond "a" is a single bond; bond "b" is a double bond; $R^{12}$ is —CH—; $R^{13}$ is —C(COOH)—; and $R^{14}$ is —CH($R^{37}$)—C'"—CH$_2$—;

the quinolone moiety is a structure, wherein referring to Formula (I), $A^2$ is —CF—; $A^3$ is —CH—; $R^4$ is —OH; and $R^3$ is $R^{16}$ and is a substituent moiety of L; and the linking moiety is a isothiouronium, where L is —S—C(=NH2+)—Z—Q"; Z is nitrogen and Q", together with Z, is a substituted $R^{16}$ group (b) where—the lactam containing moiety is a carbapenem, wherein referring to Formula (II), bond "a" is a single bond; bond "b" is a double bond; $R^{10}$ is (1-hydroxyethyl); $R^{11}$ is —H; $R^{12}$ is —CH—; $R^{13}$ is —C(COOH)—; and $R^{14}$ is —CH($R^{38}$)—C'"—CH$_2$—; $R^{38}$ is —H or —Me;

the quinolone moiety is a structure, wherein referring to Formula (I), $A^2$ is —CF—; $A^3$ is —CH—; $R^4$ is —OH; $R^6$ is —H; $A^1$ is —CH—, —CF—, —CCl—, or —N—; and $R^3$ is cyclopropyl, ethyl, 2,4-difluorophenyl, 4-fluorophenyl, or t-butyl; and $R^3$ is $R^{16}$, being either a 3-amino-1-pyrrolidinyl group (substituted at the 3-amino position by the L moiety), or a 1-piperazinyl group (substituted at the 4-position by the L moiety); and the linking moiety is a isothiouronium, where L is —S—C(=NH2+)—Z—Q"; Z is nitrogen and Q", together with Z, is $R^{16}$, either a 3-amino substituted 1-pyrrolidinyl group, or a 4-substituted 1-piperazinyl group (c) where—the lactam-containing moiety is a carbapenem, wherein referring to Formula (II), bond "a" is a single bond; bond "b" is a double bond; $R^{12}$ is —CH—; $R^{13}$ is —C(COOH)—; and $R^{14}$ is —CH($R^{38}$)—C'"—;

the quinolone moiety is a structure, wherein referring to Formula (I), $A^2$ is —CF—; $A^3$ is —CH—; $R^4$ is —OH; and $R^3$ is $R^{16}$ and is a substituent moiety of L; and the linking moiety is a isothiouronium, where L is —S—CH$_2$CH$_2$—S—C(=NH2+)—Z—Q"; Z is nitrogen and Q", together with Z, is a substituted $R^{16}$ group (d) where—the lactam-containing moiety is a carbapenem, wherein referring to Formula (II), bond "a" is a single bond; bond "b" is a double bond; $R^{10}$ is (1-hydroxyethyl); $R^{11}$ is —H; $R^{12}$ is —CH—; $R^{13}$ is —C(COOH)—; and $R^{14}$ is —CH($R^{38}$)—C'"—; $R^{38}$ is —H or —Me;

the quinolone moiety is a structure, wherein referring to Formula (I), $A^2$ is —CF—; $A^3$ is —CH—; $R^4$ is —OH; $R^6$ is —H; $A^1$ is —CH—, —CF—, —CCl—, or —N—; and $R^3$ is cyclopropyl, ethyl, 2,4-difluorophenyl, 4-fluorophenyl, or t-butyl; and $R^3$ is $R^{16}$, being either a 3-amino-1-pyrrolidinyl group (substituted at the 3-amino position by the L moiety), or a 1-piperazinyl group (substituted at the 4-position by the L moiety); and the linking moiety is a isothiouronium, where L is S—CH$_2$CH$_2$—S—C(=NH2+)—Z—Q"; Z is nitrogen and Q", together with Z, is $R^{16}$, either a 3-amino substituted 1-pyrrolidinyl group, or a 4-substituted 1-piperazinyl group Isothiouronium-linked carbapenems of classes (b) and (d) are preferred.

32. Quaternary ammonium-1 inked cephem quinolones, such as compounds of the following classes.

(a) where—the lactam-containing moiety is a cephem, wherein referring to Formula (II), bond "a" is a single bond; bond "b" is a double bond; $R^{12}$ is —CH—; $R^{13}$ is —C(COOH)—; and $R^{14}$ is —S—CH$_2$—C'"—CH$_2$—;

the quinolone moiety is a structure, wherein referring to Formula (I), $A^2$ is —CF—; $A^3$ is —CH—; $R^4$ is —OH; and $R^3$ is $R^{16}$ and is a substituent moiety of L; and the linking moiety is a quaternary amine moiety, where L is —$X^3$-Q"; $X^3$ is N+($R^{41}$)($R^{42}$), and Q", together with $X^3$, is a substituted $R^{16}$ group (b) where—the lactam-containing moiety is a cephem, wherein referring to Formula (II), bond "a" is a single bond; bond "b" is a double bond; $R^{11}$ is —H or —OMe; $R^{12}$ is —CH—; $R^{13}$ is —C(COOH)—; and $R^{14}$ is —S—CH$_2$—C'"—CH$_2$—; and $R^{10}$ is [[(2-thienyl)acetyl]-amino], [[(2-amino-4-thiazolyl)(methoxyimino)-acetyl]amino], [[(4-pyridylthio)

acetyl]amino], [(phenoxy) acetyl]amino], [[(2-amino-4-thiazolyl)-acetyl]amino], or [[(2-amino-4-thiazolyl)[[(3,4-dihydroxyphenyl)carbonyl]amino]acetyl]amino];

the quinolone moiety is a structure, wherein referring to Formula (I), $A^2$ is —CF—; $A^3$ is —CH—; $R^4$ is —OH; $R^6$ is —H; $A^1$ is —CH—, —CF—, —CCl—, or —N—; and $R^3$ is cyclopropyl, ethyl, 2,4-difluorophenyl, 4-fluorophenyl, or t-butyl; and $R^3$ is $R^{16}$, being a 1-substituted 1-methyl-piperazinio-4-yl moiety; and the linking moiety is a quaternary amine moiety, where L is —$X^3$—Q"; $X^3$ is N+$(R^{41})(R^{42})$, and Q", together with $X^3$, is $R^{16}$, a 1-substituted 1-methyl-1-piperazinio-4-yl group Quaternary ammmonium-linked cephem quinolones of class (b) are preferred.

33. Quaternary ammonium-linked penem quinolones, such as compounds of the following classes.

(a) where—the lactam-containing moiety is a penem, wherein referring to Formula (II), bond "a" is a single bond; bond "b" is a double bond; $R^{12}$ is —CH—; $R^{13}$ is —C(COOH)—; and $R^{14}$ is —S—C'"—$CH_2$—;

the quinolone moiety is a structure, wherein referring to Formula (I), $A^2$ is —CF—; $A^3$ is —CH—; $R^4$ is —OH; and $R^3$ is $R^{16}$ and is a substituent moiety of L; and the linking moiety is a quaternary amine moiety, where L is —$X^3$—Q"; $X^3$ is N+$(R^{41})(R^{42})$, and Q", together with $X^3$, is a substituted $R^{16}$ group (b) where—the lactam-containing moiety is a penem, wherein rferring to Formula (II), bond "a" is a single bond; bond "b" is a double bond; $R^{12}$ is —CH—; $R^{13}$ is —C(COOH)—; and $R^{14}$ is —S—C'"—;

the quinolone moiety is a structure, wherein referring to Formula (I), $A^2$ is —CF—; $A^3$ is —CH—; $R^4$ is —OH; and $R^3$ is $R^{16}$ and is a substituent moiety of L; and the linking moiety is a quaternary amine moiety, where L is —S—$CH_2CH_2$—$X^3$—Q"; $X^3$ is N+$(R^{41})(R^{42})$, and Q", together with $X^3$, is a substituted $R^{16}$ group (c) where—the lactam-containing moiety is a penem, wherein referring to Formula (II), bond "a" is a single bond; bond "b" is a double bond; $R^{10}$ is (1-hydroxyethyl); $R^{11}$ is —H; $R^{12}$ is —CH—; $R^{13}$ is —C(COOH)—; and $R^{14}$ is —S—C'"—;

the quinolone moiety is a structure, wherein referring to Formula (I), $A^2$ is —CF—; $A^3$ is —CH—; $R^4$ is —OH; $R^6$ is —H; $A^1$ is —CH—, —CF—, —CCl—, or —N—; and $R^3$ is cyclopropyl, ethyl, 2,4-difluorophenyl, 4-fluorophenyl, or t-butyl; and $R^3$ is $R^{16}$, being a 1-substituted 1-methyl-piperazinio-4-yl moiety; and the linking moiety is a quaternary amine moiety, where L is —S—$CH_2CH_2$—$X^3$—Q"; $X^3$ is N+(R41)(R42), and Q", together with $X^3$, is $R^{16}$, a 1-substituted 1-methyl-1-piperazinio-4-yl group Quaternary ammonium-linked penem quinolones of class (c) are preferred.

34. Quaternary ammonium-linked carbapenem quinolones, such as compounds of the following classes.

(a) where the lactam-containing moiety is a carbapenem, wherein referring to Formula (II), bond "a" is a single bond; bond "b" is a double bond; $R^{12}$ is —CH—; $R^{13}$ is —C(COOH)—; and $R^{14}$ is —CH($R^{37}$)—C'"—$CH_2$—;

the quinolone moiety is a structure, wherein referring to Formula (I), $A^2$ is —CF—; $A^3$ is —CH—; $R^4$ is —OH; and $R^3$ is $R^{16}$ and is a substituent moiety of L; and the linking moiety is a quaternary amine moiety, where L is —$X^3$—Q"; $X^3$ is N+(R41)(R42), and Q", together with $X^3$, is a substituted $R^{16}$ group (b) where the lactam-containing moiety is a carbapenem, wherein referring to Formula (II), bond "a" is a single bond; bond "b" is a double bond; $R^{12}$ is —CH—; $R^{13}$ is —C(COOH)—; and $R^{14}$ is —CH($R^{38}$)—C'"—;

the quinolone moiety is a structure, wherein referring to Formula (I), $A^2$ is —CF—; $A^3$ is —CH—; $R^4$ is —OH; and $R^3$ is $R^{16}$ and is a substituent moiety of L; and the linking moiety is a quaternary amine moiety, where L is —S—$CH_2CH_2$—$X^3$—Q"; $X^3$ is N+(R41)(R42), and Q", together with $X^3$, is a substituted $R^{16}$ group c) where the lactam-containing moiety is a carbapenem, wherein referring to Formula (II), bond "a" is a single bond; bond "b" is a double bond; $R^{10}$ is (1-hydroxyethyl); $R^{11}$ is —H; $R^{12}$ is —CH—; $R^{13}$ is —C(COOH)—; and $R^{14}$ is —CH($R^{38}$)—C'"—; $R^{38}$ is —H or —Me;

the quinolone moiety is a structure, wherein referring to Formula (I), $A^2$ is —CF—; $A^3$ is —CH—; $R^4$ is —OH; $R^6$ is —H; $A^1$ is —CH—, —CF—, —CCl—, or —N—; and $R^3$ is cyclopropyl, ethyl, 2,4-difluorophenyl, 4-fluorophenyl, or t-butyl; and $R^3$ is $R^{16}$, being a 1-substituted 1-methyl-piperazinio-4-yl moiety; and the linking moiety is a quaternary amine moiety, where L is —S—$CH_2CH_2$—$X^3$—Q"; $X^3$ is N+(R41)(R42), and Q", together with $X^3$, is $R^{16}$, a 1-substituted 1-methyl-1-piperazinio-4-yl group Quaternary ammonium-linked carbapenem quinolones of class (c) are preferred.

35. Amine-linked cephem quinolones, such as compounds of the following classes.

(a) where the lactam-containing moiety is a cephem, wherein referring to Formula (II), bond "a" is a single bond; bond "b" is a double bond; $R^{12}$ is —CH—; $R^{13}$ is —C(COOH)—; and $R^{14}$ is —S—$CH_2$—C'"—$CH_2$—;

the quinolone moiety is a structure, wherein referring to Formula (I), $A^2$ is —CF—; $A^3$ is —CH—; $R^4$ is —OH; and $R^3$ is $R^{16}$ and is a substituent moiety of L; and the linking moiety is an amine, where L is —$X^3$—Q"; $X^3$ is nitrogen and Q", together with $X^3$, is a substituted $R^{16}$ group (b) where the lactam-containing moiety is a cephem, wherein referring to Formula (II), bond "a" is a single bond; bond "b" is a double bond; $R^{11}$ is —H or —OMe; $R^{12}$ is —CH—; $R^{13}$ is —C(COOH)—; and $R^{14}$ is —S—$CH_2$—C'"—$CH_2$—; and $R^{10}$ [[(2-thienyl)acetyl]amino], [[(2-amino-4-thiazolyl)(methoxyimino)acetyl]amino], [[(4-pyridylthio)acetyl]amino], [(phenoxy)acetyl]amino], [[(2-amino-4-thiazolyl)acetyl]amino], or [[(2-amino-4-thiazolyl)[[(3,4-dihydroxyphenyl)carbonyl]amino]acetyl]amino];

the quinolone moiety is a structure, wherein referring to Formula (I), $A^2$ is —CF—; $A^3$ is —CH—; $R^4$ is —OH; $R^6$ is —H; $A^1$ is —CH—, —CF—, —CCl—, or —N—; and $R^3$ is cyclopropyl, ethyl, 2,4-difluorophenyl, 4-fluorophenyl, or t-butyl; and $R^3$ is $R^{16}$, being either a 3-amino-1-pyrrolidinyl group (substituted at the 3-amino position by the L moiety), or a 1-piperazinyl group (substituted at the 4-position by the L moiety); and the linking moiety is a amine, where L is —$X^3$—$Q'''$; $X^3$ is nitrogen and $Q''$, together with $X^3$, is $R^{16}$, either a 3-amino substituted 1-pyrrolidinyl group, or a 4-substituted 1-piperazinyl group Amine-linked cephem quinolones of class (b) are preferred.

36. Amine-linked penem quinolones, such as compounds of the following classes.

(a) where the lactam-containing moiety is a penem, wherein referring to Formula (II), bond "a" is a single bond; bond "b" is a double bond; $R^{12}$ is —CH—; $R^{13}$ is —C(COOH)—; and $R^{14}$ is —S—$C'''$—$CH_2$—;

the quinolone moiety is a structure, wherein referring to Formula (I), $A^2$ is —CF—; $A^3$ is —CH—; $R^4$ is —OH; and $R^3$ is $R^{16}$ and is a substituent moiety of L; and the linking moiety is an amine, where L is —$X^3$—$Q''$; $X^3$ is nitrogen and $Q''$, together with $X^3$, is a substituted $R^{16}$ group (b) where where the lactam-containing moiety is a penem, wherein referring to Formula (II), bond "a" is a single bond; bond "b" is a double bond; $R^{10}$ is (1-hydroxyethyl); $R^{11}$ is —H; $R^{12}$ is —CH—; $R^{13}$ is —C(COOH)—; and $R^{14}$ is —S—$C'''$—$CH_2$—;

the quinolone moiety is a structure, wherein referring to Formula (I), $A^2$ is —CF—; $A^3$ is —CH—; $R^4$ is —OH; $R^6$ is —H; $A^1$ is —CH—, —CF—, —CCl—, or —N—; and $R^3$ is cyclopropyl, ethyl, 2,4-difluorophenyl, 4-fluorophenyl, or t-butyl; and $R^3$ is $R^{16}$, being either a 3-amino-1-pyrrolidinyl group (substituted at the 3-amino position by the L moiety), or a 1-piperazinyl group (substituted at the 4-position by the L moiety); and the linking moiety is a amine, where L is —$X^3$—$Q''$; $X^3$ is nitrogen and $Q''$, together with $X^3$, is $R^{16}$, either a 3-amino substituted 1-pyrrolidinyl group, or a 4-substituted 1-piperazinyl group (c) where the lactam-containing moiety is a penem, wherein referring to Formula (II), bond "a" is a single bond; bond "b" is a double bond; $R^{12}$ is —CH—; $R^{13}$ is —C(COOH)—; and $R^{14}$ is —S—$C'''$—;

the quinolone moiety is a structure, wherein referring to Formula (I), $A^2$ is —CF—; $A^3$ is —CH—; $R^4$ is —OH; and $R^3$ is $R^{16}$ and is a substituent moiety of L; and the linking moiety is a amine, where L is —S—$CH_2CH_2$—$X^3$—$Q''$; $X^3$ is nitrogen and $Q''$, together with $X^3$, is a substituted $R^{16}$ group (d) where the lactam-containing moiety is a penem, wherein referring to Formula (II), bond "a" is a single bond; bond "b" is a double bond; $R^{10}$ is (1-hydroxyethyl); $R^{11}$ is —H; $R^{12}$ is —CH—; $R^{13}$ is —C(COOH)—; and $R^{14}$ is —S—$C'''$—;

the quinolone moiety is a structure, wherein referring to Formula (I), $A^2$ is —CF—; $A^3$ is —CH—; $R^4$ is —OH; $R^6$ is —H; $A^1$ is —CH—, —CF—, —CCl—, or —N—; and $R^3$ is cyclopropyl, ethyl, 2,4-difluorophenyl, 4-fluorophenyl, or t-butyl; and $R^3$ is $R^{16}$, being either a 3-amino-1-pyrrolidinyl group (substituted at the 3-amino position by the L moiety), or a 1-piperazinyl group (substituted at the 4-position by the L moiety); and the linking moiety is a amine, where L is —S—$CH_2CH_2$—$X^3$—$Q''$; $X^3$ is nitrogen and $Q''$, together with $X^3$, is $R^{16}$, either a 3-amino substituted 1-pyrrolidinyl group, or a 4-substituted 1-piperazinyl group Amine-linked penem quinolones of classes (b) and (d) are preferred.

37. Amine-linked carbapenem quinolones, such as compounds of the following classes.

(a) where the lactam-containing moiety is a carbapenem, werein referring to Formula (II), bond "a" is a single bond; bond "b" is a double bond; $R^{12}$ is —CH—; $R^{13}$ is —C(COOH)—; and $R^{14}$ is —CH($R^{37}$)—$C'''$—$CH_2$—;

and, where the quinolone moiety is a structure, wherein referring to Formula (I), $A^2$ is —CF—; $A^3$ is —CH—; $R^4$ is —OH; and $R^3$ is $R^{16}$ and is a substituent moiety of L; and the linking moiety is an amine, where L is —$X^3$—$Q''$; $X^3$ is nitrogen and $Q''$, together with $X^3$, is a substituted $R^{16}$ group (b) where the lactam-containing moiety is a carbapenem, wherein referring to Formula (II), bond "a" is a single bond; bond "b" is a double bond; $R^{10}$ is (1-hydroxyethyl); $R^{11}$ is —H; $R^{12}$ is —CH—; $R^{13}$ is —C(COOH)—; and $R^{14}$ is —CH($R^{38}$)—$C'''$—$CH_2$—; $R^{38}$ is —H or —Me;

the quinolone moiety is a structure, wherein referring to Formula (I), $A^2$ is —CF—; $A^3$ is —CH—; $R^4$ is —OH; $R^6$ is —H; $A^1$ is —CH—, —CF—, —CCl—, or —N—; and $R^3$ is cyclopropyl, ethyl, 2,4-difluorophenyl, 4-fluorophenyl, or t-butyl; and $R^3$ is $R^{16}$, being either a 3-amino-1-pyrrolidinyl group (substituted at the 3-amino position by the L moiety), or a 1-piperazinyl group (substituted at the 4-position by the L moiety); and the linking moiety is an amine, where L is —$X^3$—$Q''$; $X^3$ is nitrogen and $Q''$, together with $X^3$, is $R^{16}$, either a 3-amino substituted 1-pyrrolidinyl group, or a 4-substituted 1-piperazinyl group (c) where the lactam-containing moiety is a carbapenem, wherein referring to Formula (II), bond "a" is a single bond; bond "b" is a double bond; $R^{12}$ is —CH—; $R^{13}$ is —C(COOH)—; and $R^{14}$ is —CH($R^{38}$)—$C'''$—;

the quinolone moiety is a structure, wherein referring to Formula (I), $A^2$ is —CF—; $A^3$ is —CH—; $R^4$ is —OH; and $R^3$ is $R^{16}$ and is a substituent moiety of L; and the linking moiety is an amine, where L is —S—$CH_2CH_2$—$X^3$—$Q''$; $X^3$ is nitrogen and $Q''$, together with $X^3$, is a substituted $R^{16}$ group (d) where the lactam-containing moiety is a carbapenem, wherein referring to Formula (II), bond "a" is a single bond; bond "b" is a double bond; $R^{10}$ is (1-hydroxyethyl); $R^{11}$ is —H; $R^{12}$ is —CH—; $R^{13}$ is —C(COOH)—; and $R^{14}$ is —CH($R^{38}$)—$C'''$—; $R^{38}$ is —H or —Me;

the quinolone moiety is a structure, wherein referring to Formula (I), $A^2$ is —CF—; $A^3$ is —CH—; $R^4$ is —OH; $R^6$ is —H; $A^1$ is —CH—, —CF—, —CCl—, or —N—; and $R^3$ is cyclopropyl, ethyl, 2,4-difluorophenyl, 4-fluorophenyl, or t-butyl; and $R^3$ is $R^{16}$, being either a 3-amino-1-pyrrolidinyl group (substituted at the 3-amino position by the L moiety), or a 1-piperazinyl group (substituted at the 4-position by the L moiety); and the linking moiety is an amine, where L is —S—$CH_2CH_2$—$X^3$—$Q''$; $X^3$ is nitrogen and $Q''$, together with $X^3$, is $R^{16}$, either a 3-amino substituted 1-pyrrolidinyl group, or a 4-substituted 1-piperazinyl group Amine-linked carbapenem quinolones of classes (b) and (d) are preferred.

38. Pyridinium-linked cephem quinolones, such as compounds of the following classes.

(a) where the lactam-containing moiety is a cephem, wherein referring to Formula (II), bond "a" is a single bond; bond "b" is a double bond; $R^{12}$ is —CH—; $R^{13}$ is —C(COOH)—; and $R^{14}$ is —S—CH$_2$—C'''—CH$_2$—;

the quinolone moiety is a structure, wherein referring to Formula (I), $A^2$ is —CF—; $A^3$ is —CH—; $R^4$ is —OH; and $R^3$ is $R^{16}$ and is a substituent moiety of L; and the linking moiety is a pyridinium moiety, where L is —$X^3$—Q"; $X^3$ is nitrogen, and Q", together with $X^3$, is a substituted $R^{16}$ group (b) where the lactam-containing moiety is a cephem, wherein referring to Formula (II), bond "a" is a single bond; bond "b" is a double bond; $R^{11}$ is —H or —OMe; $R^{12}$ is —CH—; $R^{13}$ is —C(COOH)—; and $R^{14}$ is —S—CH$_2$—C'''—CH$_2$—; and $R^{10}$ [[(2-thienyl)acetyl]amino], [[(2-amino-4-thiazolyl)(methoxyimino)acetyl]amino], [[(4-pyridylthio)acetyl]amino], [(phenoxy)acetyl]amino], [[(2-amino-4-thiazolyl)acetyl]amino], or [[(2-amino-4-thiazolyl)[(3,4-dihydroxyphenyl)carbonyl]amino]acetyl]amino];

the quinolone moiety is a structure, wherein referring to Formula (I), $A^2$ is —CF—; $A^3$ is —CH—; $R^4$ is —OH; $R^6$ is —H; $A^1$ is —CH—, —CF—, —CCl—, or —N—; and $R^3$ is cyclopropyl, ethyl, 2,4-difluorophenyl, 4-fluorophenyl, or t-butyl; and $R^3$ is $R^{16}$, being a 1-substituted pyridinio-4-yl moiety; and the linking moiety is a pyridinium moiety, where L is —$X^3$—Q"; $X^3$ is nitrogen, and Q", together with $X^3$, is $R^{16}$, a 1-substituted pyridinio-4-yl group Pyridinium-linked cephem quinolones of class (b) are preferred.

39. Pyridinium-linked penem quinolones, such as compounds of the following classes.

(a) where the lactam-containing moiety is a penem, wherein referring to Formula (II), bond "a" is a single bond; bond "b" is a double bond; $R^{12}$ is —CH—; $R^{13}$ is —C(COOH)—; and $R^{14}$ is —S—C'''—CH$_2$—;

the quinolone moiety is a structure, wherein referring to Formula (I), $A^2$ is —CF—; $A^3$ is —CH—; $R^4$ is —OH; and $R^3$ is $R^{16}$ and is a substituent moiety of L; and the linking moiety is a pyridinium moiety, where L is —$X^3$—Q"; $X^3$ is nitrogen, and Q", together with $X^3$, is a substituted $R^{16}$ group (b) where the lactam-containing moiety is a penem, wherein referring to Formula (II), bond "a" is a single bond; bond "b" is a double bond; $R^{12}$ is —CH—; $R^{13}$ is —C(COOH)—; and $R^{14}$ is —S—C'''—;

the quinolone moiety is a structure, wherein referring to Formula (I), $A^2$ is —CF—; $A^3$ is —CH—; $R^4$ is —OH; and $R^3$ is $R^{16}$ and is a substituent moiety of L; and the linking moiety is a pyridinium moiety, where L is —S—CH$_2$CH$_2$—$X^3$—Q"; $X^3$ is nitrogen, and Q", together with $X^3$, is a substituted $R^{16}$ group (c) where the lactam-containing moiety is a penem, wherein referring to Formula (II), bond "a" is a single bond; bond "b" is a double bond; $R^{10}$ is (1-hydroxyethyl); $R^{11}$ is —H; $R^{12}$ is —CH—; $R^{13}$ is —C(COOH)—; and $R^{14}$ is —S—C'''—;

the quinolone moiety is a structure, wherein referring to Formula (I), $A^2$ is —CF—; $A^3$ is —CH—; $R^4$ is —OH; $R^6$ is —H; $A^1$ is —CH—, —CF—, —CCl—, or —N—; and $R^3$ is cyclopropyl, ethyl, 2,4-difluorophenyl, 4-fluorophenyl, or t-butyl; and $R^3$ is $R^{16}$, being a 1-substituted pyridinio-4-yl moiety; and the linking moiety is a pyridinium moiety, where L is —S—CH$_2$CH$_2$—$X^3$—Q"; $X^3$ is nitrogen, and Q", together with $X^3$, is $R^{16}$, a 1-substituted pyridinio-4-yl group Pyridinium-linked penem quinolones of class (c) are preferred.

40. Pyridinium-linked carbapenem quinolones, such as compounds of the following classes.

(a) where the lactam-containing moiety is a carbapenem, werein referring to Formula (II), bond "a" is a single bond; bond "b" is a double bond; $R^{12}$ is —CH—; $R^{13}$ is —C(COOH)—; and $R^{14}$ is —CH($R^{37}$)—C'''—CH$_2$—;

the quinolone moiety is a structure, wherein referring to Formula (I), $A^2$ is —CF—; $A^3$ is —CH—; $R^4$ is —OH; and $R^3$ is $R^{16}$ and is a substituent moiety of L; and the linking moiety is a pyridinium moiety, where L is —$X^3$—Q"; $X^3$ is nitrogen, and Q", together with $X^3$, is a substituted $R^{16}$ group (b) where the lactam-containing moiety is a carbapenem, wherein referring to Formula (II), bond "a" is a single bond; bond "b" is a double bond; $R^{12}$ is —CH—; $R^{13}$ is —C(COOH)—; and $R^{14}$ is —CH($R^{38}$)—C'''—;

the quinolone moiety is a structure, wherein referring to Formula (I), $A^2$ is —CF—; $A^3$ is —CH—; $R^4$ is —OH; and $R^3$ is $R^{16}$ and is a substituent moiety of L; and the linking moiety is a pyridinium moiety, where L is —S—CH$_2$CH$_2$—$X^3$—Q"; $X^3$ is nitrogen, and Q", together with $X^3$, is a substituted $R^{16}$ group (c) where the lactam-containing moiety is a carbapenem, wherein referring to Formula (II), bond "a" is a single bond; bond "b" is a double bond; $R^{10}$ is (1-hydroxyethyl); $R^{11}$ is —H; $R^{12}$ is —CH—; $R^{13}$ is —C(COOH)—; and $R^{14}$ is —CH($R^{38}$)—C'''—; $R^{38}$ is —H or —Me;

the quinolone moiety is a structure, wherein referring to Formula (I), $A^2$ is —CF—; $A^3$ is —CH—; $R^4$ is —OH; $R^6$ is —H; $A^1$ is —CH—, —CF—, —CCl—, or —N—; and $R^3$ is cyclopropyl, ethyl, 2,4-difluorophenyl, 4-fluorophenyl, or t-butyl; and $R^3$ is $R^{16}$, being a 1-substituted pyridinio-4-yl moiety; and the linking moiety is a pyridinium moiety, where L is —S—CH$_2$CH$_2$—$X^3$—Q"; $X^3$ is nitrogen, and Q", together with $X^3$, is $R^{16}$, a 1-substituted pyridinio-4-yl group Pyridinium-linked carbapenem quinolones of class (c) are preferred.

Preferred lactam-quinolones also include compounds wherein:

(1) if bond "a" or bond "b" is nil, then $R^{14}$—L is L;

(2) if bond "a" and "b" are single bonds, $R^{14}$—L is —W—C'''=C($R^{8a}$)—$R^{37}$—L, or —W—C'''($R^{36}$)—$R^{37}$—L; or (3) if bond "a" is a single bond and bond "b" is a double bond, $R^{14}$—L is —$C(R^{8a})(R^{38})$—W—C'''—$R^{37}$—L; or (preferably) —W'—$C(R^{8a})(R^{38})$—C'''—$R^{37}$—L, —W—$C(R^{8a})(R^{38})$—C'''—$R^{37}$—L", or —W—C'''—$R^{37}$—L; where (a) W' is O, or $C(R^{38})$; and
(b) L" is Q', —$X^2$—Q", —N—Q", $N(R^{40})$—Q", $R^{43}$—$N(R^{41})$—Q", —$X^4_r$—$C(=Y^3_u)$—Z—Q", —$X^5_r$—$PO(Y^4_u R^{8a})$—Z'—Q", or $X^5_r$—$SO_2$—Z'—Q" (preferably —$X^2$—Q", or —$X^4_r$—$C(=Y^3_u)$—Z—Q").

Preferred lactam-quinolones include (for example) the following compounds.

[5R-[5a,6a]]-3-[[[4-[3-Carboxy-1-(2,4-difluorophenyl)-6-fluoro-1,4-dihydro-4-oxo-1,8-naphthyridin-7-yl]-1-piperazinyl]thioxomethyl]thiomethyl]-6-[(R)-1-hydroxyethyl]-4-methyl-7-oxo-1-azabicyclo[3.2.0]hept-2-ene-2-carboxylic acid disodium salt

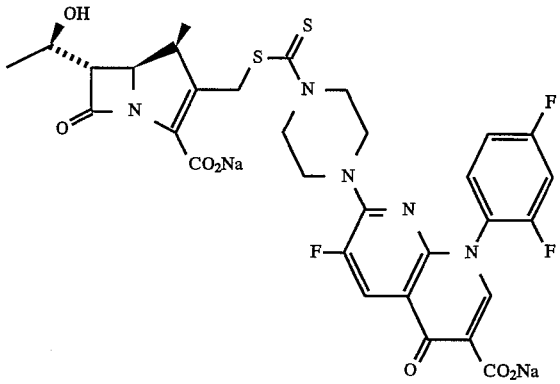

[5R-[5a,6a]]-3-[[[4-(3-Carboxy-1-cyclopropyl-6-fluoro-1,4-dihydro-4-oxo-7-quinolinyl)-1-piperazinyl]thioxomethyl]thiomethyl]-6-[(R)-1-hydroxyethyl]-7-oxo-4-thia-1-azabicyclo[3.2.0]hept-2-ene-2-carboxylic acid disodium salt

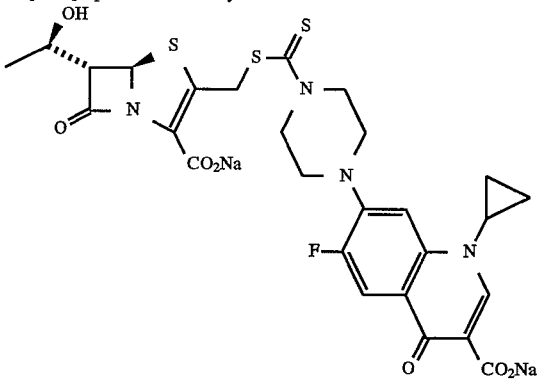

[6R-[6a,7b]]-3-[[[4-[6-Carboxy-8-ethyl-5,8-dihydro-5-oxo-pyrido[2,3-d]pyrimidin-2-yl]-1-piperazinyl]thioxomethyl]thiomethyl]-7-[[[[3-[(3,4-dihydroxyphenyl)methyleneamino]-2-oxo-1-imidazolidinyl]carbonylamino]phenyl]acetyl]amino]-5-thia-1-azabicyclo[4.2.0]oct-2-ene-2-carboxylic acid disodium salt

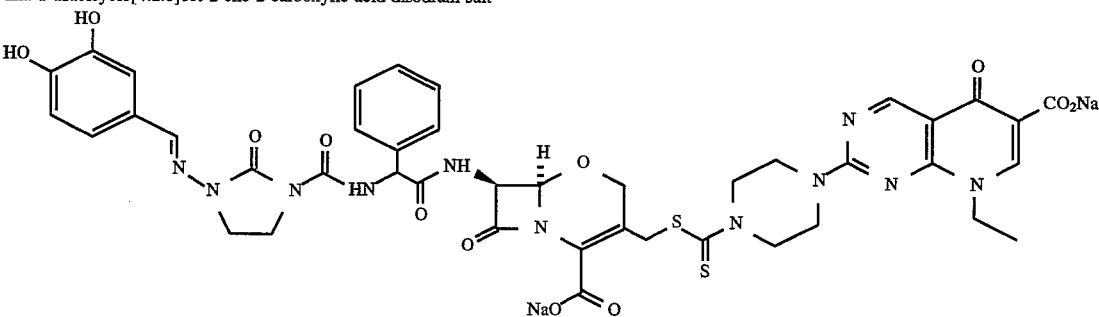

[5R-[5a,6b]]-3-[[[4-[3-Carboxy-1-ethyl-6-fluoro-1,4 dihydro-4-oxo-7-quinolinyl]-1-piperazinyl]carbonyloxy] methyl]-6-[(R)-1-hydroxyethyl]-7-oxo-1-azabicyclo[3.2.0] hept-2-ene-2-carboxylic acid disodium salt

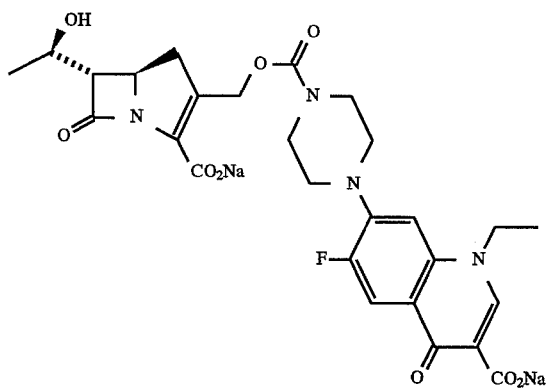

[5R-[5a,6a]]-3-[[[4-[3-Carboxy-cyclopropyl-6-fluoro-1,4-dihydro-4-oxo-7-quinolinyl)-1-piperazinyl]iminomethyl]thiomethyl]-6-[(R)-1-hydroxyethyl]-7-oxo-1-azabicyclo[3.2.0]hept-2-ene-2-carboxylic acid disodium salt

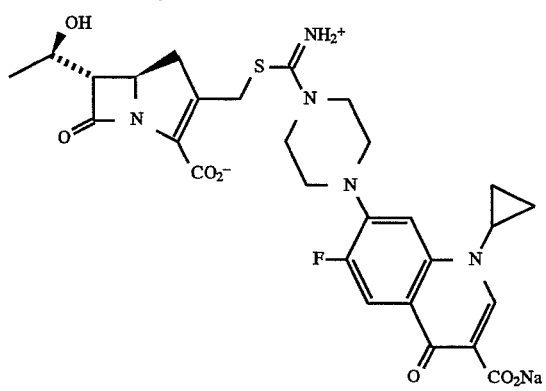

[5R-[5a,6a]]-3-[[[4-[3-Carboxy-1-(2,4-difluorophenyl)-6-fluoro-1,4-dihydro-4-oxo-1,8-naphthyridin-7-yl]-1-piperazinyl]iminomethyl]thiomethyl]-6-[(R)-1-hydroxyethyl]-7-oxo-4-thia-1-azabicyclo[3.2.0]hept-2-ene-2-carboxylic acid-sodium salt

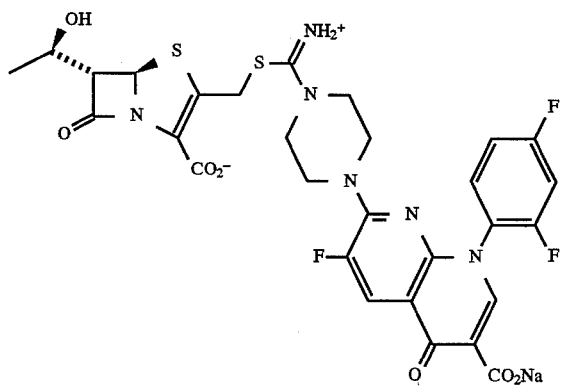

[6R-[6a,7b]]-3-[[[4-(3-Carboxy-1-cyclopropyl-6-fluoro-1,4-dihydro-4-oxo-7-quinolinyl)-1-piperazinyl]iminomethyl]thiomethyl]-8-oxo-7-[(2-thienylacetyl)amino]-5-thia-1-azabicyclo[4.2.0]oct-2-ene-2-carboxylic acid sodium salt

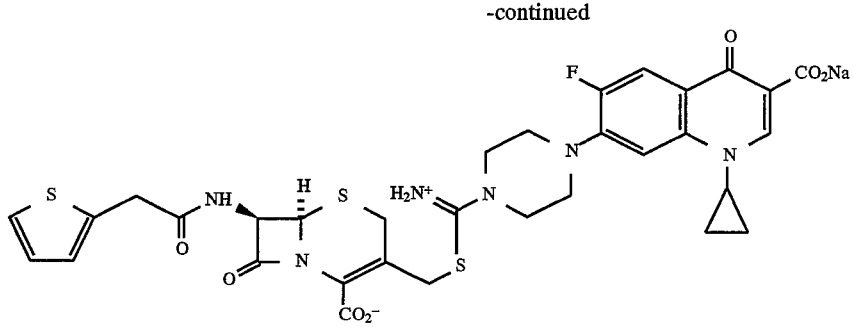

[6R-[6a,7b(Z)]]-7-[[(2-Amino-4-thiazolyl)(methoxyimino)
acetyl]amino]-3-[[[4-[3-carboxy-1-(2,4-difluorophenyl)-6-
fluoro-1,4-dihydro-4-oxo-1,8-naphthyridin-7-yl]-1-pipera-
zinyl]iminomethyl]thiomethyl]-5-thia-1-azabicyclo[4.2.0]
oct-2-ene-2-carboxylic acid sodium salt

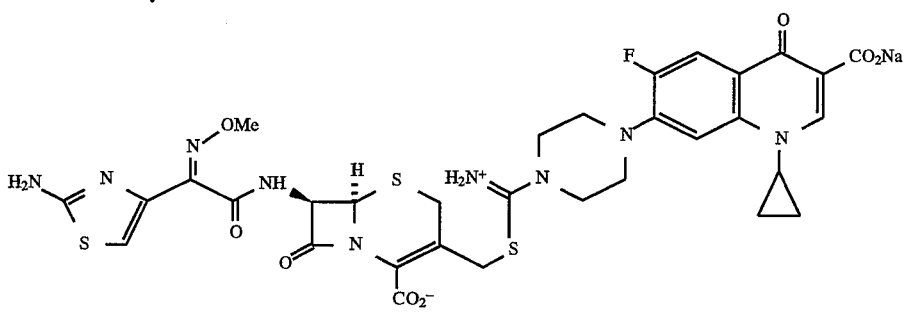

[6R-[6a,7b]]-3-[[[1-(3-Carboxy-8-chloro-1-cyclopropyl-6-
fluoro-4-dihydro-4-oxo-7-quinolinyl)-3-pyrrolidinylamino]
iminomethyl]thiomethyl]-7-[[(R)-hydroxy(phenyl)acetyl]
amino]-7-methoxy-8-oxo-5-thia-1-azabicyclo[4.2.0]oct-2-
ene-2-carboxylic acid sodium salt

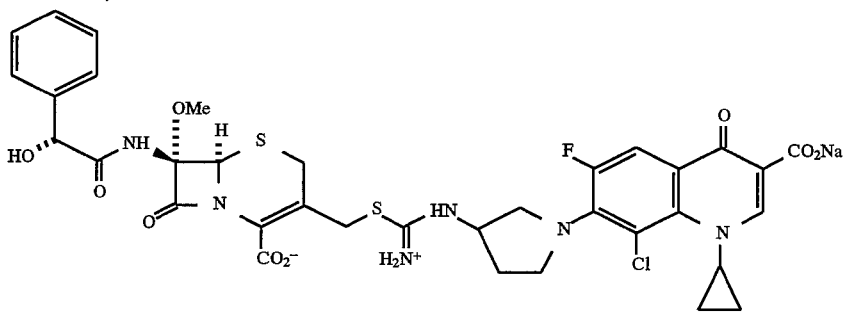

(3S)-2-[[[4-[3-Carboxy-1-cyclopropyl-6-fluoro-1,4-dihydro-4-
oxo-7-quinolinyl]-1-piperazinyl]iminomethyl]thio]-3-[[phen-
oxyacetyl]amino]-4-oxo-1-azetidinesulfonic acid sodium salt

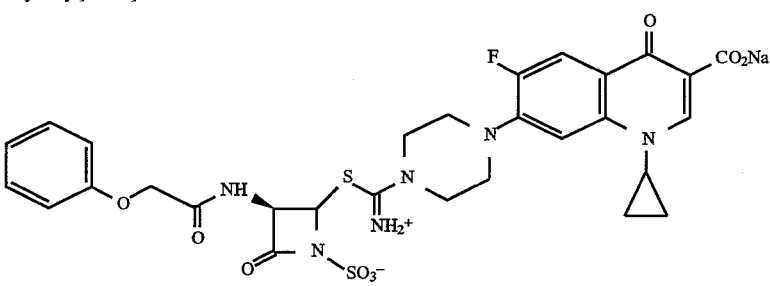

[6R-[6a,7b]]-3-[[[[4-[3-Carboxy-1-cyclopropyl-1,4-dihydro-4-
oxo-7-quinolinyl]-1-piperazinyl]thioxomethyl]amino]methyl]-
7-(2-thienylacetyl)amino]-5-thia-1-azabicyclo[4.2.0]oct-2-
ene-2-carboxylic acid disodium salt

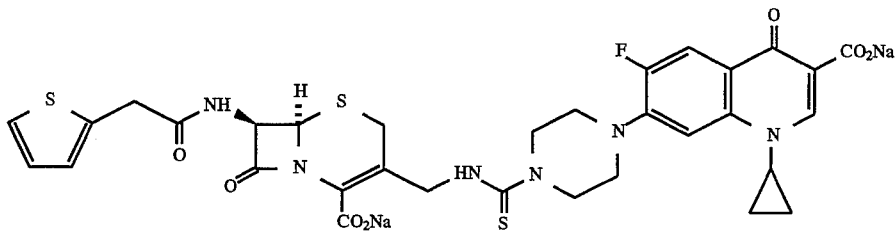

[6R-[6a,7b]]-3-[[[[1-[3-Carboxy-8-chloro-1-cyclopropyl-6-fluoro-1,4-dihydro-4-oxo-7-quinolinyl]-3-pyrrolidinylamino]thioxomethyl]amino]methyl]-7-[(2-thienylacetyl)amino]-5-thia-1-azabicyclo[4.2.0]oct-2-ene-2-carboxylic acid disodium salt

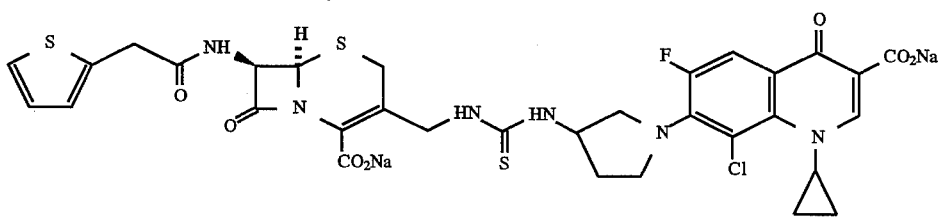

[5R-[4b,5a,6a]]-3-[[[1-[3-Carboxy-1-(2,4-difluorophenyl)-6-fluoro-1,4-dihydro-4-oxo-1,8-naphthyridin-7-yl]-3-pyrrolidinyl]amino]thioxomethylamino]methyl]-6-[(R)-1-hydroxyethyl]-4-methyl-7-oxo-1-azabicyclo[3.2.0]hept-2-ene-2-carboxylic acid disodium salt

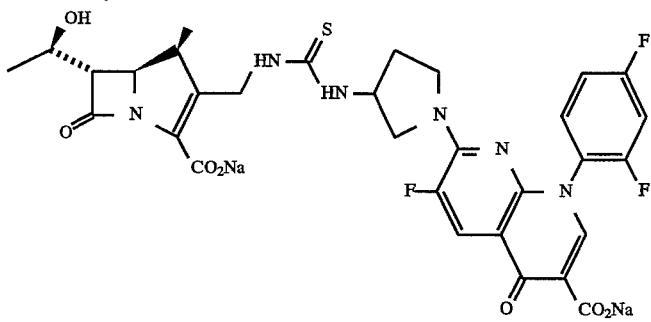

[5R-[5a,6a]]-3-[[[4-(3-Carboxy-1-cyclopropyl-6-fluoro-1,4-dihydro-4-oxo-7-quinolinyl)-1-piperazinyl]thioxomethylamino]methyl]-6-[(R)-1-hydroxyethyl]-7-oxo-4-thia-1-azabicyclo[3.2.0]hept-2-ene-2-carboxylic acid disodium salt

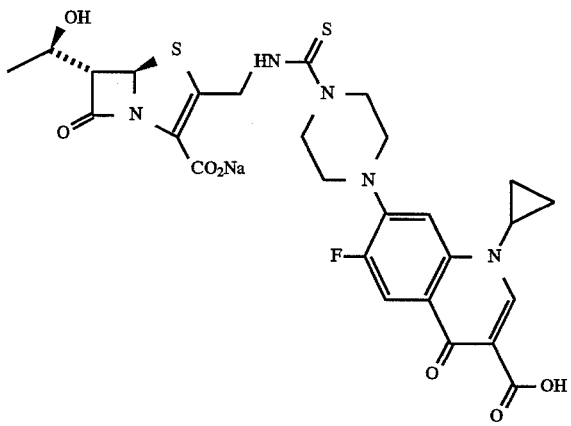

[5R-[5a,6a]]-3-[[[4-(3-Carboxy-1-cyclopropyl-6-fluoro-1,4-dihydro-4-oxo-7-quinolinyl)-1-piperazinyl]carbonylamino]methyl]-6-[(R)-1-hydroxyethyl]-7-oxo-4-thia-1-azabicyclo[3.2.0]hept-2-ene-2-carboxylic acid disodium salt

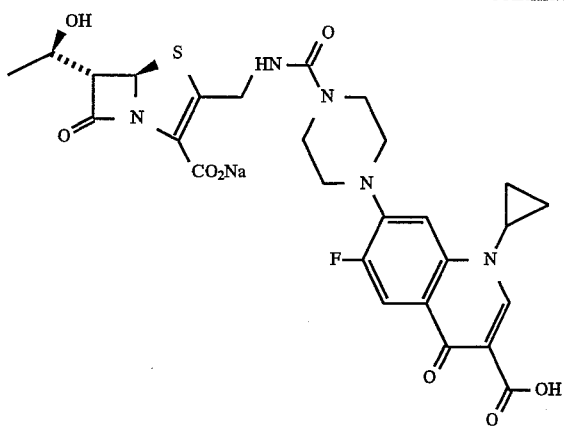

[6R-[6a,7b]]-3-[[[2-[4-(3-Carboxy-1-ethyl-6-fluoro-1,4-dihydro-4-oxo-7-quinolinyl)-1-piperazinyl]ethoxy]thioxomethylthio]methyl]-7-[[carboxy(4-hydroxyphenyl)acetyl]amino]-8-oxo-5-oxa-1-azabicyclo[4.2.0]oct-2-ene-2-carboxylic acid trisodium salt

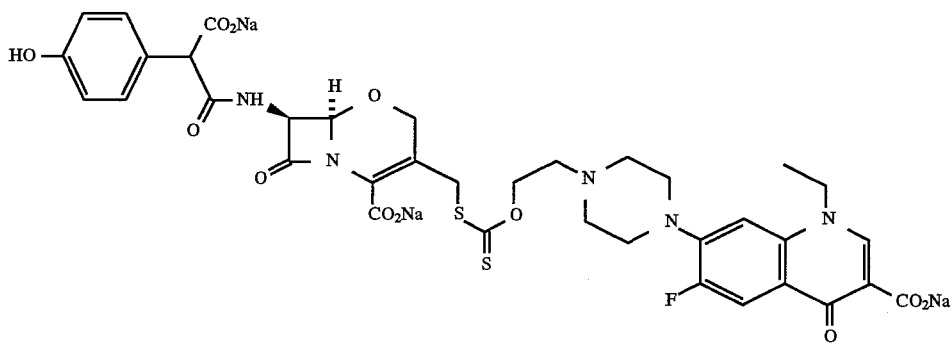

[6R-[6a,7b]]-7-[[(R)-amino(4-hydroxyphenyl)acetyl]amino]-3-[[[2-[4-(3-carboxy-1-cyclopropyl-6-fluoro-1,4-dihydro-4-oxo-7-quinolinyl)-1-piperazinyl]ethylthio]thioxomethylamino]methyl]-8-oxo-5-thia-1-azabicyclo[4.2.0]oct-2-ene-2-carboxylic acid disodium salt

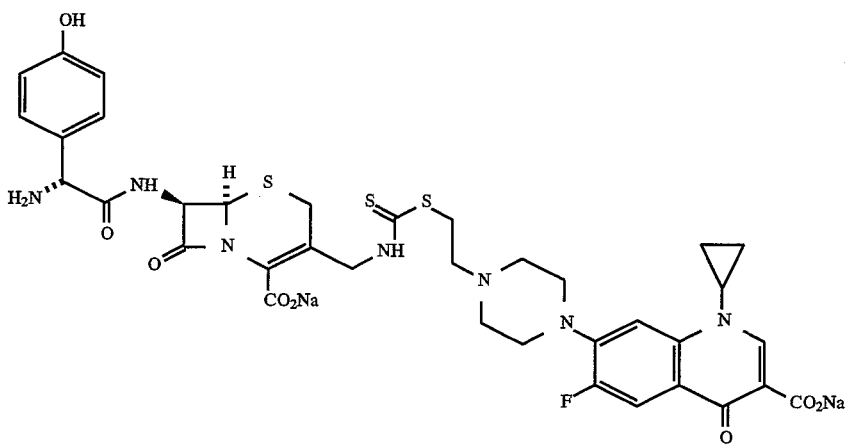

[5b-[5a,6a]]-3-[[[1-(3-Carboxy-8-chloro-6-fluoro-1,4-dihydro-4-oxo-7-quinolinyl)-3-pyrrolidinylamino]carbonyl methylthio]thioxomethylamino]methyl]-6-[(R)-1-hydroxyethyl]-7-oxo-4-thia-1-azabicyclo[3.2.0]hept-2-ene-2-carboxylic acid disodium salt

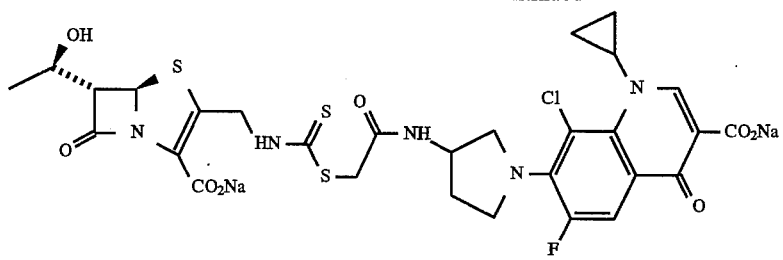

[6R-[6a,7b]]-3-[[[4-(3-carboxy-1-cyclopropyl-6-fluoro-1,4-dihydro-4-oxo-7-quinolinyl)-1-piperazinyl]iminomethyl]aminomethyl]-8-oxo-7-[(2-thienylacetyl)amino]-5-thia-1-azabicyclo[4.2.0]oct-2-ene-2-carboxylic acid sodium salt

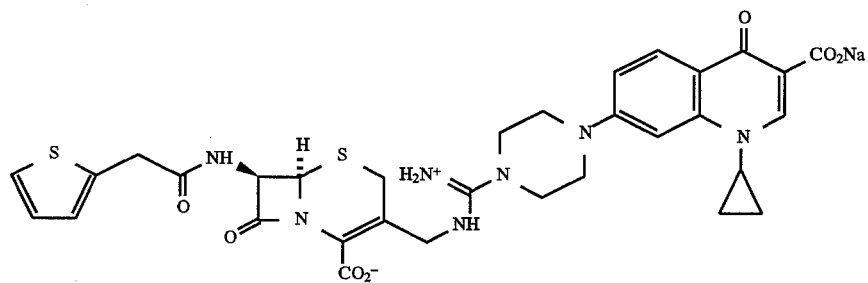

[5R-[5a,6a]]-3-[[[[1-(3-Carboxy-2-cyclopropyl-6,8-difluoro-1,4-dihydro-4-oxo-7-quinolinyl-)-3-pyrrolidinyl]methylamino]-iminomethyl]aminomethyl]-6-[(R)-1-hydroxyethyl]-7-oxo-4-thia-1-azabicyclo[3.2.0]hept-2-ene-2-carboxylic acid sodium salt

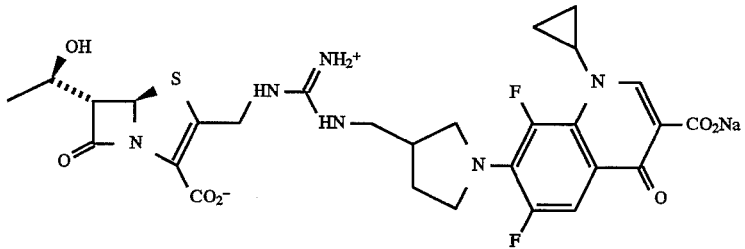

(3)-3-[[(2-Amino-4-thiazoyl)(1-carboxymethoxyimino)-acetyl]amino]-2-[[2-[3-carboxy-6-fluoro-1,4-dihydro-4-oxo-7-(4-methyl-1-piperazinyl)-1-quinolinyl]ethoxy]thioxo methylthio]-4-oxo-1-azetidinesulfonic acid trisodium salt

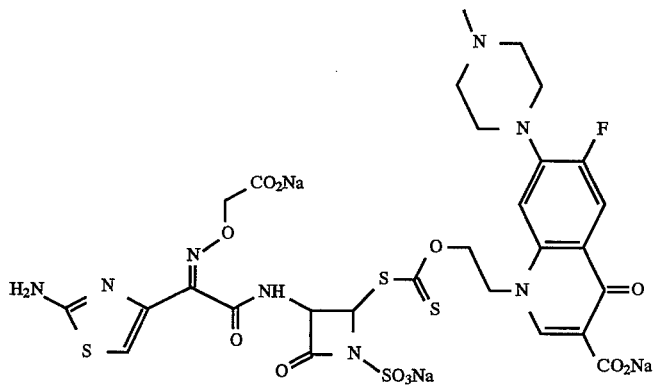

[6R-[6a,7b]]-7-[[(R)-amino(phenyl)acetyl]amino]-3-[[[1-(3-carboxy-8-chloro-1-cyclopropyl-6-fluoro-1,4-dihydro-4-oxo-7-quinolinyl)-3-pyrrolidinylamino]carbonylamino]methyl]-8-oxo-5-thia-1-azabicyclo[4.2.0]oct-2-ene-2-carboxylic acid disodium salt

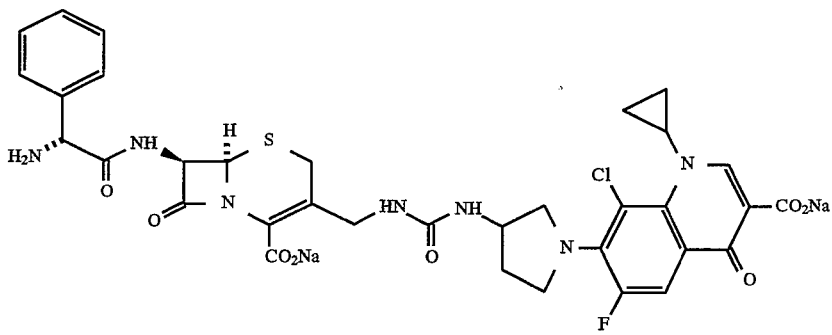

5R-[5a,6a]]-3-[[1-[3-Carboxy-1-(2,4-difluorophenyl)-6-fluoro-1,4-dihydro-4-oxo-1,8-naphthyridin-7-yl]-3-pyrrolidinyl]aminomethylene]-6-[(R)-1-hydroxyethyl]-7-oxo-4-thia-1-azabicyclo[3.2.0]hept-2-ene-2-carboxylic acid sodium salt

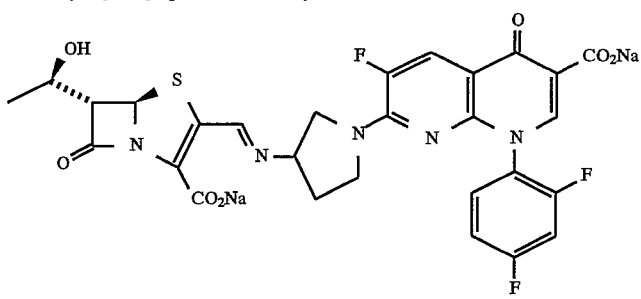

[5R-[5a,6a]]-3-[[[1-[3-Carboxy-1-(2,4-difluorophenyl)-6-fluoro-1,4-dihydro-4-oxo-1,8-naphthyridin-7-yl]-3-pyrrolidinylamino]hydroxyphosphinyl]oxymethyl]-6-[(R)-1-hydroxyethyl]-7-oxo-4-thia-1-azabicyclo[3.2.0]hept-2-ene-2-carboxylic acid trisodium salt

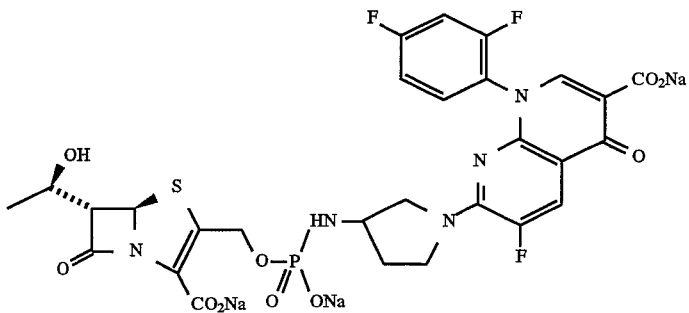

[6R-[6a,7b]]-3-[[[4-(3-Carboxy-1-cyclopropyl-6-fluoro-1,4-dihydro-4-oxo-7-quinolinyl)-1-piperazinyl]hydroxyphosphinyl]oxymethyl]-8-oxo-7-[(2-thienylacetyl)amino]-5-thia-1-azabicyclo[4.2.0]oct-2-ene-2-carboxylic acid trisodium salt

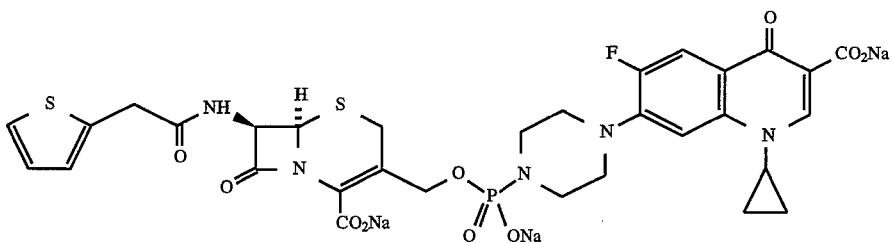

(3S)-2-[2-[3-Carboxy-6-fluoro-1,4-dihydro-7-(4-methyl-1-piperazinyl)-4-oxo-1-quinolinyl]ethyloxy]-4-oxo-3-[phenylacetyl]amino]-1-azetidinesulfonic acid disodium salt

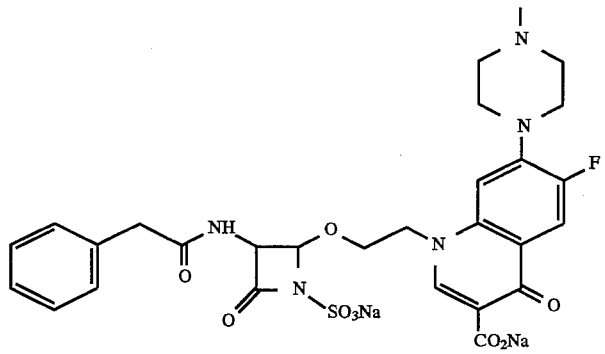

(3S)-2-[4-[1-(3-Carboxy-1-cyclopropyl-6-fluoro-1,4-dihydro-4-oxo-7-quinolinyl]-3-piperazinyl]phenoxy]-3-[[[[(2-oxo-1-imidazolidinyl)carbonyl]amino](phenyl)acetyl]amino]-4-oxo-1-azetidinesulfonic acid sodium salt

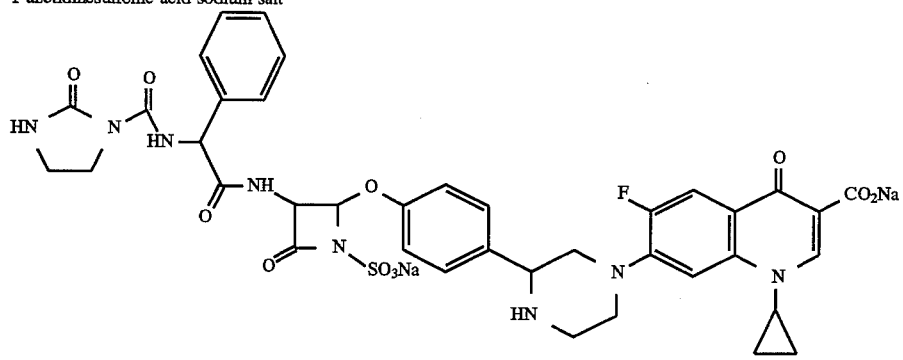

[6R-[6a,7b]]-3-[[2-[4-(3-Carboxy-1-cyclopropyl-6-fluoro-1,4-dihydro-4-oxo-7-quinolinyl)-1-piperazinyl]ethyl]sulfinylmethyl]-8-oxo-7-[(2-thienylacetyl)amino]-5-thia-1-azabicyclo[4.2.0]oct-2-ene-2-carboxylic acid disodium salt

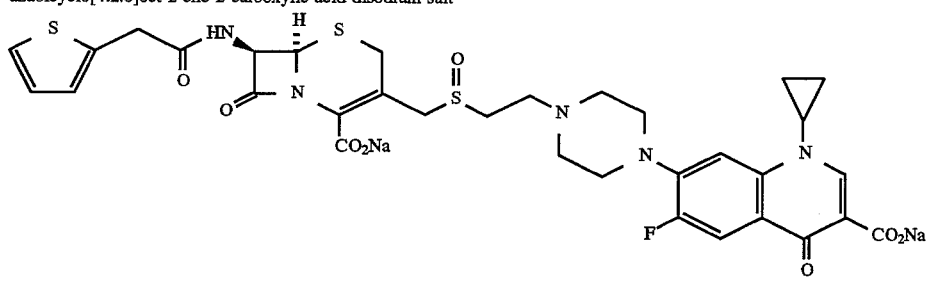

[5R-[5a,6a]]-3-[[[2-[3-carboxy-6-fluoro-1,4-dihydro-4-oxo-7-(4-methyl-1-piperazinyl)-1-quinolinyl]ethoxy]carbonylamino]methyl]-6-[(R)-1-hydroxyethyl]-7-oxo-4-thia-1-azabicyclo[3.2.0]hept-2-ene-2-carboxylic acid disodium salt

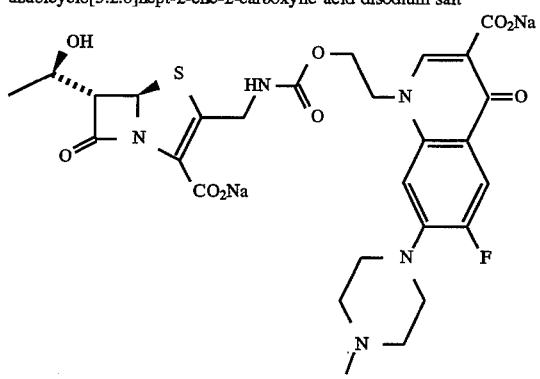

[5R-[4b,5a,6a]]-3-[[[4-(3-Carboxy-1-cyclopropyl-6-fluoro-1,4-dihydro-4-oxo-7-quinolinyl)-1-piperazinyl]methyliminomethyl]methylthio]-6-[(R)-1-hydroxyethyl]-4-methyl-7-oxo-
4-thia-1-azabicyclo[3.2.0]hept-1-ene-2-carboxylic acid
disodium salt

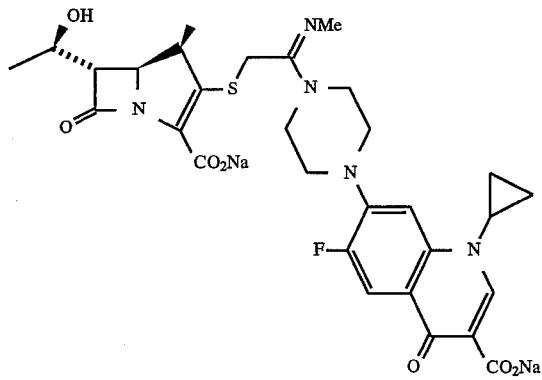

[5R-[5a,6a]]-3-[2-[[1-(3-carboxy-8-chloro-1-cyclopropyl-6-
fluoro-1,4-dihydro-4-oxo-7-quinolinyl)-3-pyrrolidinylamino]
iminomethyl]amino]ethylthio]-6-(R)-1-hydroxyethyl-7-oxo-1-
azabicyclo[3.2.0]hept-2-ene-2-carboxylic acid monosodium salt

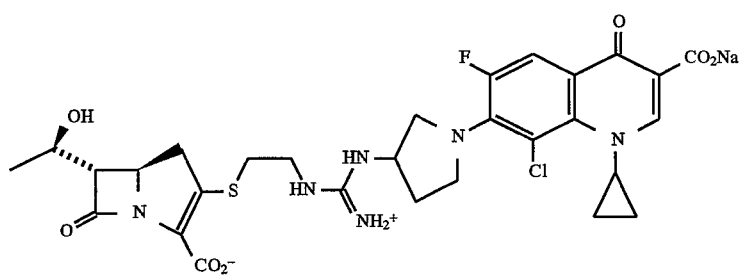

[5R-[4b,5a,6a]]-1-[2-[[2-Carboxy-6-[(R)-1-hydroxyethyl]-4-
methoxy-7-oxo-1-azabicyclo[3.2.0]hept-2-en-3-yl]thio]ethyl]-
4-(3-carboxy-1-ethyl-1,4-dihydro-4-oxo-7-quinolinyl)pyridi-
nium sodium salt

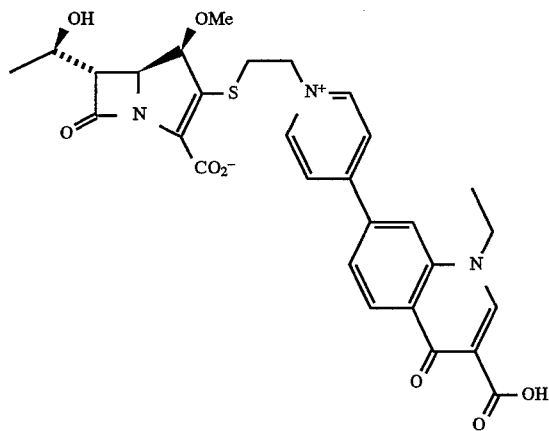

[6R-[6a,7b]]-7-[[(2-Amino-4-thiazolyl)(methoxyimino)]acetyl
amino]-3-[[[4-(3-carboxy-1-cyclopropyl-6-fluoro-1,4-
dihydro-4-oxo-7-quinolinyl)-1-piperazinyl]carbonyloxy]
methyl]-8-oxo-5-thia-1-azabicyclo[4.2.0]oct-2-ene-2-
carboxylic acid disodium salt

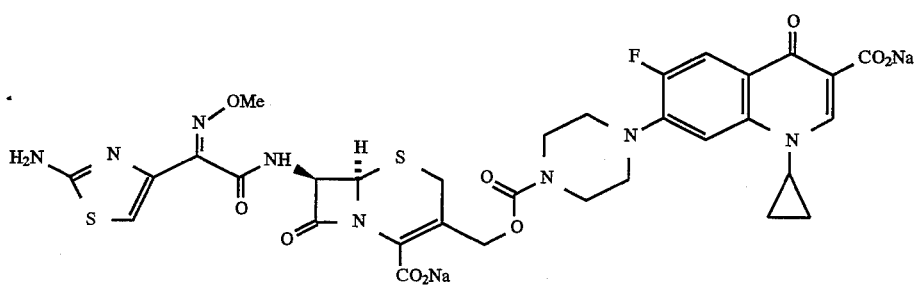

[6R-[6a,7b]]-3-[[[1-(3-Carboxy-8-chloro-1-cyclopropyl-6-
fluoro-1,4-dihydro-4-oxo-7-quinolinyl)-3-pyrrolidinyl-
amino]carbonyloxy]methyl]-8-oxo-7-[2-thienylacetyl)amino]-
5-thia-1-azabicyclo[4.2.0]oct-2-ene-2-carboxylic acid
disodium salt

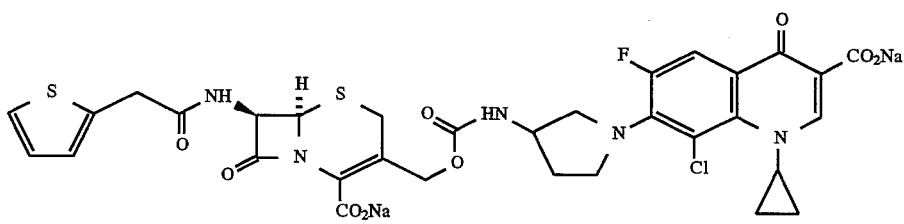

[5R-[5a,6a]]-3-[[[1-[3-Carboxy-1-(2,4-difluorophenyl)-6-
fluoro-1,4-dihydro-4-oxo-1,8-naphthyridin-7-yl]-3-
pyrrolidinylamino]carbonyloxymethyl]-6-[(R)-1-
hydroxymethyl]-7-oxo-4-thia-1-azabicyclo[3.2.0]hept-2-ene-
2-carboxylic acid disodium salt

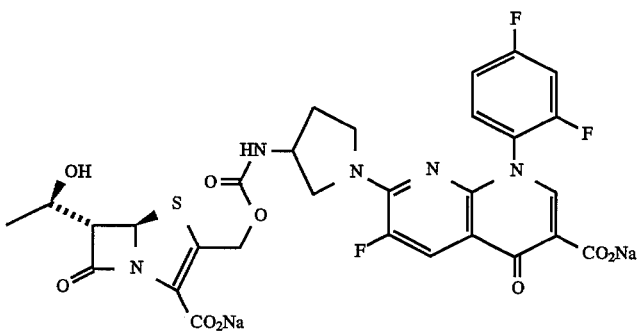

[6R-(6a,7b)]-7-[[[(2-Aminocarbonyl-2-fluoro)ethenyl-
thio]acetyl)amino]-3-[[[1-(3-carboxy-8-chloro-1-
cyclopropyl-6-fluoro-1,4-dihydro-4-oxo-7-quinolinyl)-3-
pyrrolidinylamino]carbonyloxy]methyl]-8-oxo-5-oxa-1-
azabicyclo[4.2.0]oct-2-ene-2-carboxylic acid disodium salt

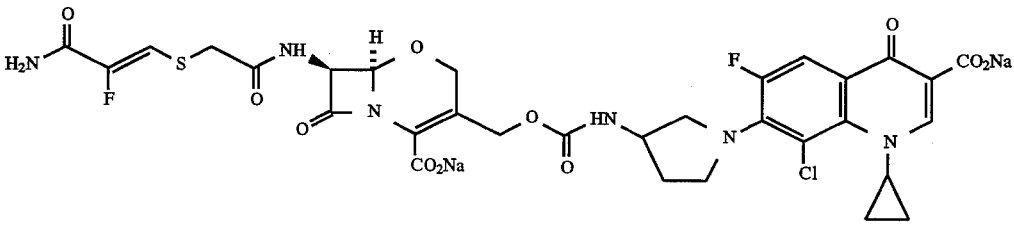

[6R-(6a,7b)]-3-[[[4-(3-carboxy-1-ethyl-6-fluoro-1,4-
dihydro-4-oxo-7-quinolinyl)-1-piperazinyl]carbonyloxy]-
methyl]-7-[[carboxy(phenyl)acetyl]amino]-7-methoxy-8-
oxo-5-oxa-1-azabicyclo[4.2.0]oct-2-ene-2-carboxylic
acid disodium salt

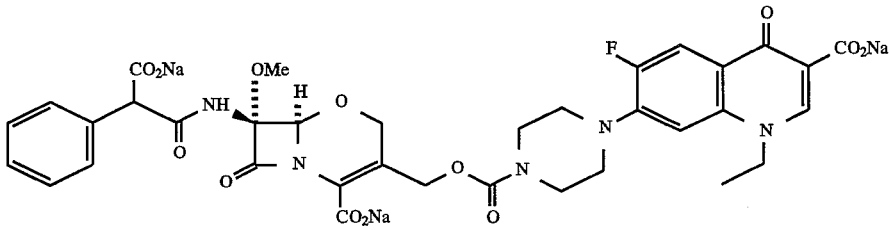

[6R-[6a,7b]]-7-[[(2-amino-4-thiazoyl)(1-carboxyethoxy)imino)acetyl]amino]-3-[[[[4-(3-carboxy-1-cyclopropyl-6,8-difluoro-1,4-dihydro-4-oxo-7-quinolinyl)-1-piperazinyl]carbonyloxy]-methyl]-8-oxo-5-oxa-1-azabicyclo[4.2.0]oct-2-ene-2-carboxylic acid disodium salt

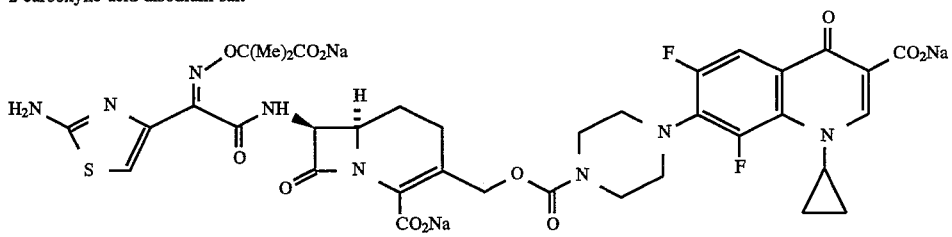

[6R-[6a,7b]]-3-[[[[3-carboxy-6-fluoro-1,4-dihydro-4-oxo-7-(4-methyl-1-piperazinyl)-1-quinolinyl]methyl-amino]carbonyloxy]methyl]-7-[[[(S)(5-hydroxy-4-oxo-1(4H)-pyridin-2-yl)carbonylamino](2-amino-4-thiazoyl)acetyl]-amino]-8-oxo-1-azabicyclo[4.2.0]oct-2-ene-2-carboxylic acid disodium salt

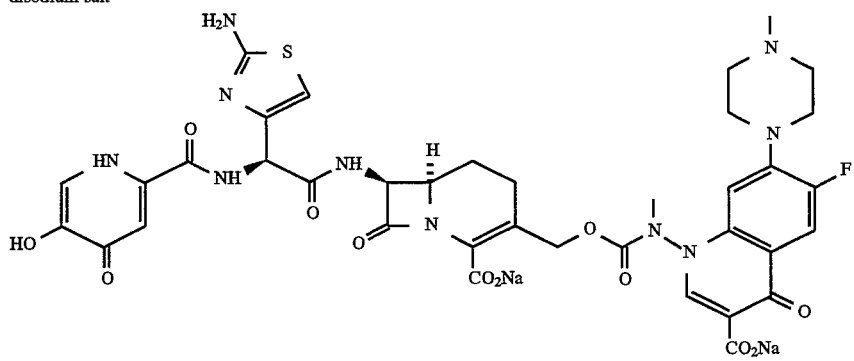

[6R-(6a,7b)]-7-[[[(R)-4-ethyl-2,3-dioxo-1-piperazinyl)carbonyl]amino](hydroxyphenyl)acetyl]-amino]-3-[[[4-[6-carboxy-8-ethyl-5,8-dihydro-5-oxopyrido-[2,3-d]pyrimidin-2-yl]1-piperazinyl]carbonyloxy]-methyl]-8-oxo-5-thia-1-azabicyclo[4.2.0]oct-2-ene-2-carboxylic acid disodium salt

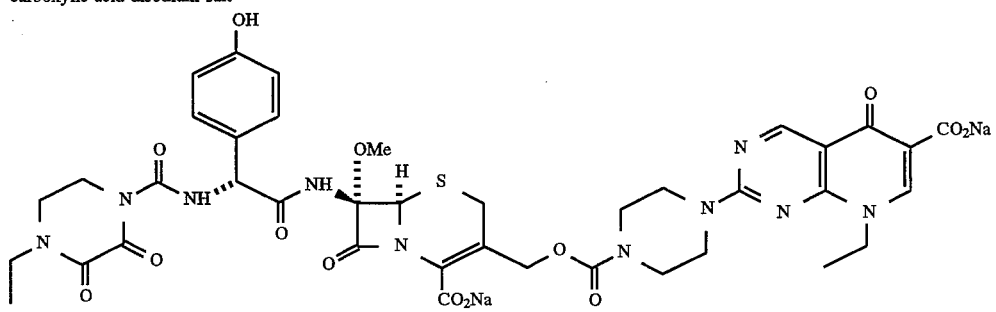

[6R-(6a,7b)]-7-[[(2-Amino-4-thiazoyl)acetyl]amino]-3-[[[1-[3-carboxy-1-(2,4-difluorophenyl)-6-fluoro-1,4-dihydro-4-oxo-1,8-naphthyridin-7-yl]-3-pyrrolidinylamino]-carbonyloxy]methyl]-8-oxo-5-thia-1-azabicyclo[4.2.0]oct-2-ene-2-carboxylic acid disodium salt

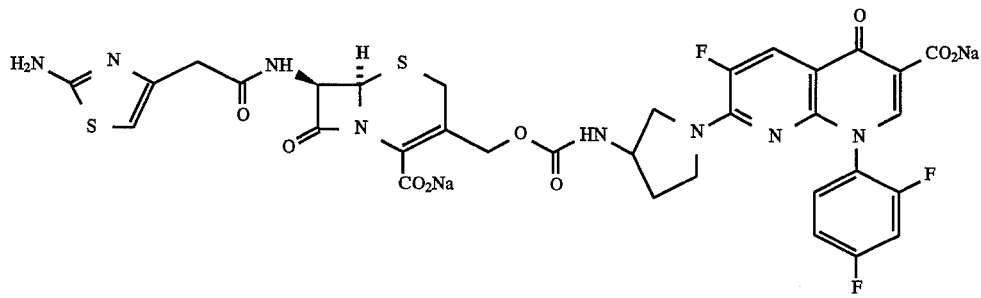

[3S]-3-[[(2-Amino-4-thiazolyl)(methoxyimino)acetyl]amino]-2-[[[1-(3-carboxy-1-cyclopropyl-8-chloro-6-fluoro-1,4-dihydro-4-oxo-7-quinolinyl)-3-pyrrolidinylamino]thioxomethyl]thio]-4-oxo-1-azetidinesulfonic acid disodium salt

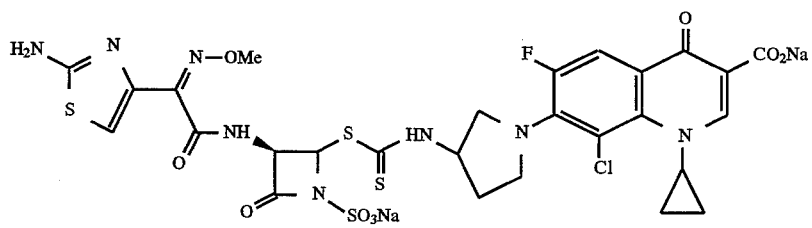

[3S]-2-[[[4-(3-Carboxy-1-cyclopropyl-6-fluoro-1,4-dihydro-4-oxo-7-quinolinyl)-1-piperazinyl]thioxomethyl]-thio]-4-oxo-3-[(phenoxyacetyl)amino]-1-azetidinesulfonic acid disodium salt

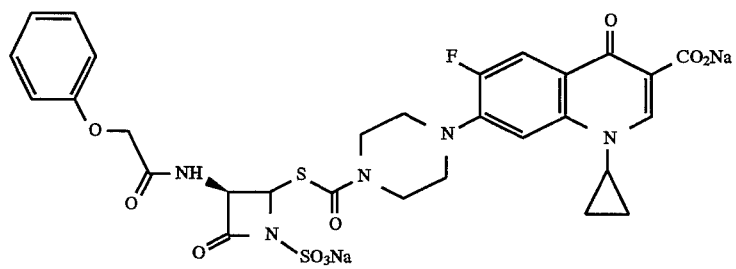

[6R-(6a,7b)]-7-[[(2-Amino-4-thiazolyl)acetyl]amino]-3-[[[[[1-(3-carboxy-1-cyclopropyl-6,8-difluoro-1,4-dihydro-4-oxo-7-quinolinyl)-3-pyrrolidinyl]methyl]methylamino]-thioxomethyl]thiomethyl]-8-oxo-5-thia-1-azabicyclo[4.2.0]oct-2-ene-2-carboxylic acid disodium salt

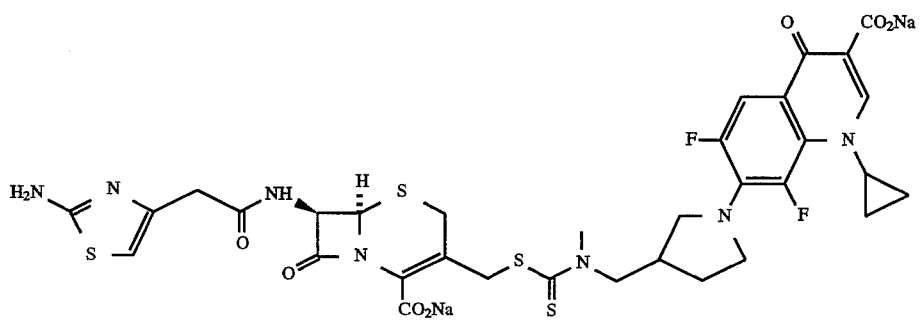

[6R-(6a,7b)]-7-[[[(2-Amino-4-thiazolyl)[(1-carboxy-1-methyl)ethoxyimino]acetyl]-3-[[[4-(3-carboxy-1-cyclopropyl-6-fluoro-1,4-dihydro-4-oxo-7-quinolinyl)-1-piperazinyl]thioxomethyl]thiomethyl]-5,8-dioxo-5-thia-1-azabicyclo[4.2.0]oct-2-ene-2-carboxylic acid disodium salt

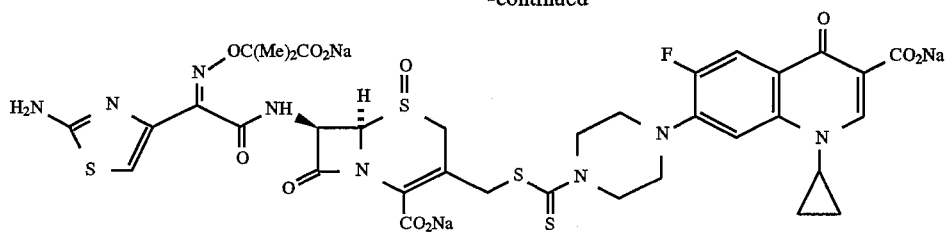

[6R-(6a,7b)]-3-[[[4-(3-Carboxy-1-ethyl-6-fluoro-1,4-
dihydro-4-oxo-7-quinolinyl)-1-piperazinyl]thioxomethyl]-
thiomethyl]-7-[[(2-furanyl(methoxyimino)acetyl]amino]-
8-oxo-5-thia-1-azabicyclo[4.2.0]oct-2-ene-2-carboxylic
acid disodium salt

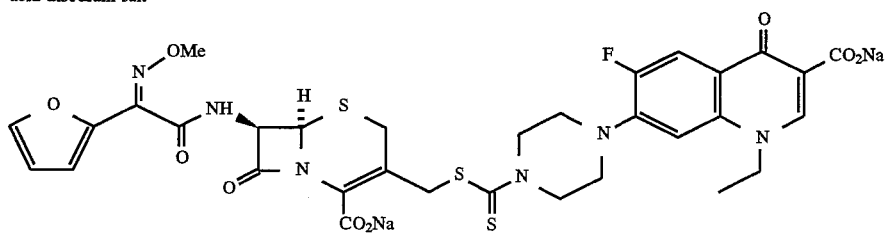

[6R-(6a,7b)]-7-[[Amino[benzo[b]thien-3-yl]acetyl]amino]-
3-[[[4-[3-carboxy-6-fluoro-1-(2,4-difluorophenyl)-
1,4-dihydro-4-oxo-7-(1,8-naphthyridinyl)]-1-piperazinyl]-
thioxomethyl]thiomethyl]-8-oxo-5-thia-1-azabicyclo[4.2.0]
oct-2-ene-2-carboxylic acid disodium salt

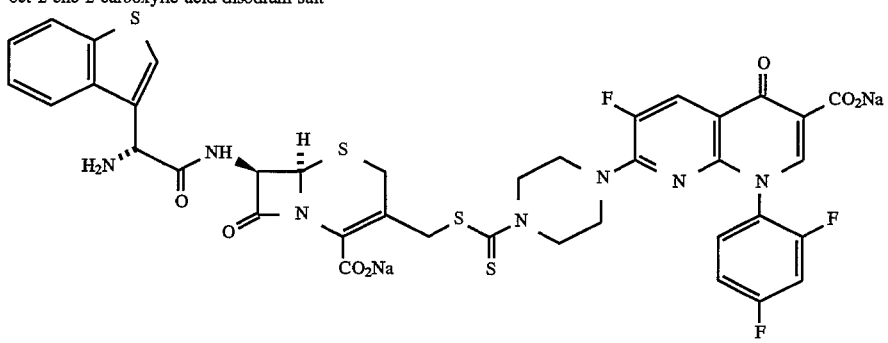

[5R-(5a,6b)]-3-[[1-(3-Carboxy-1-ethyl-6-fluoro-1,4-dihydro-
4-oxo-7-quinolinyl)-3-pyrrolidinylamino]methyl]-6-[(R)-1-
hydroxyethyl]-7-oxo-1-azabicyclo[3.2.0]hept-2-ene-2-carbox-
ylic acid disodium salt

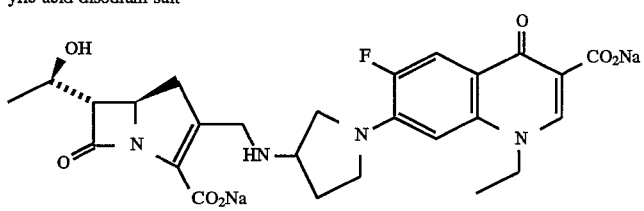

[6R-(6a,7b)]-3-[[4-(3-Carboxy-1-cyclopropyl-6-fluoro-
1,4-dihydro-4-oxo-7-quinolinyl)-1-piperazinyl]methyl]-
8-oxo-7-[(2-thienylacetyl)amino]-5-thia-1-azabicyclo-
[4.2.0]oct-2-ene-2-carboxylic acid disodium salt

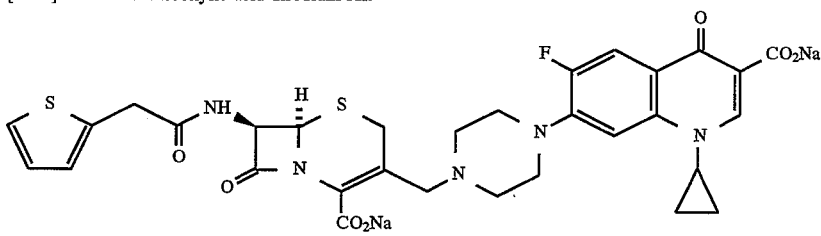

[6R-[6a,7b](Z)]-7-[[(2-Amino-4-thiazolyl)(methoxyimino)-
acetyl]amino]-3-[[[[1-(3-carboxy-8-chloro-1-cyclopropyl-6- fluoro-1,4-dihydro-4-oxo-7-quinolinyl)-3-pyrrolidinyl]
methyl]methylamino]methyl]-8-oxo-5-thia-1-azabicyclo[4.2.0]
oct-2-ene-2-carboxylic acid disodium salt

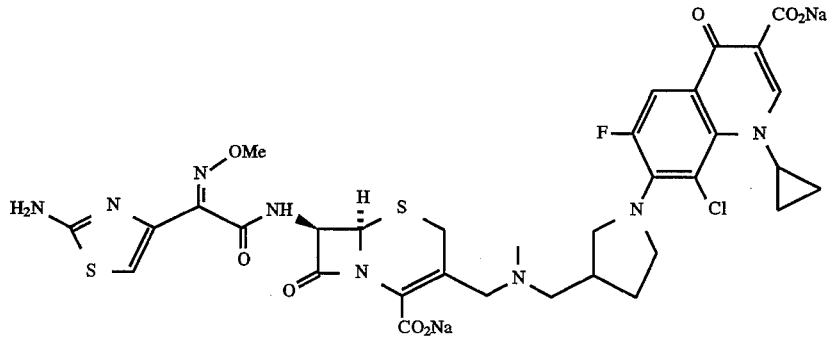

[6R-(6a,7b)]-[7-[[(2-Amino-4-thiazolyl)(methoxyimino)-
acetyl]amino]-2-carboxy-8-oxo-5-thia-1-azabicyclo-
[4.2.0]oct-2-en-3-yl]methyl]-[[1-[3-carboxy-8-chloro-1-
cyclopropyl-6-fluoro-1,4-dihydro-4-oxo-7-quinolinyl]-3-
pyrrolidinyl]methyl]dimethylammonium sodium salt

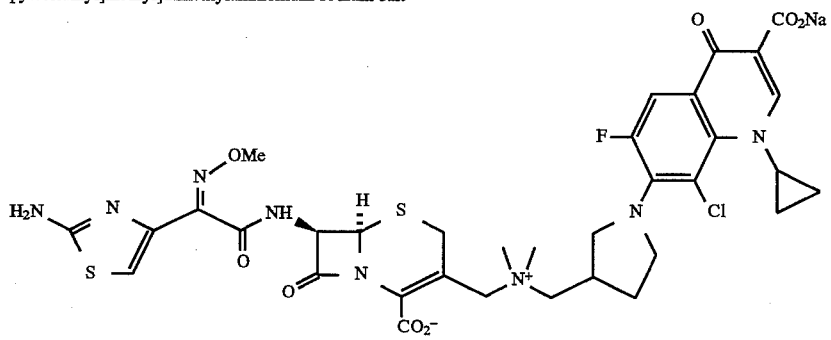

[6R-(6a,7b)]-3-[[4-(3-Carboxy-1-cyclopropyl-6,8-difluoro-
1,4-dihydro-4-oxo-7-quinolinyl)-1-piperazinyl]methyl]-7-
[[2(R)-[[(4-ethyl-2,3-dioxo-1-piperazinyl)carbonyl]amino]-
3(S)-hydroxy-1-oxobutyl]amino]-8-oxo-5-thia-1-azabicyclo
[4.2.0]oct-2-ene-2-carboxylic acid disodium salt

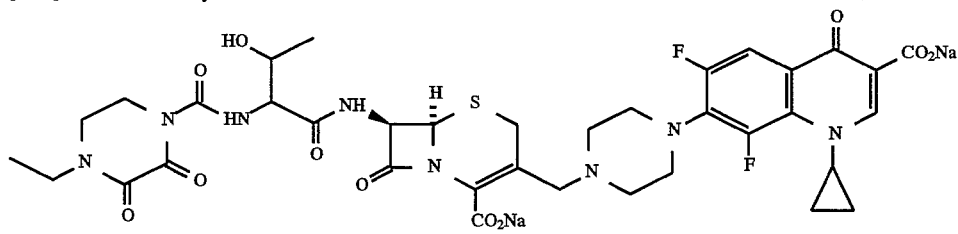

Other preferred lactam-quinolones are exemplified by the following structures.

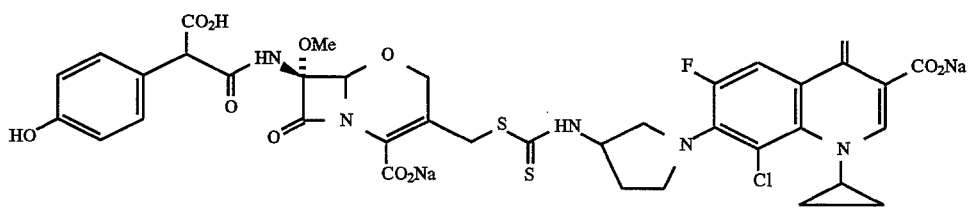

-continued
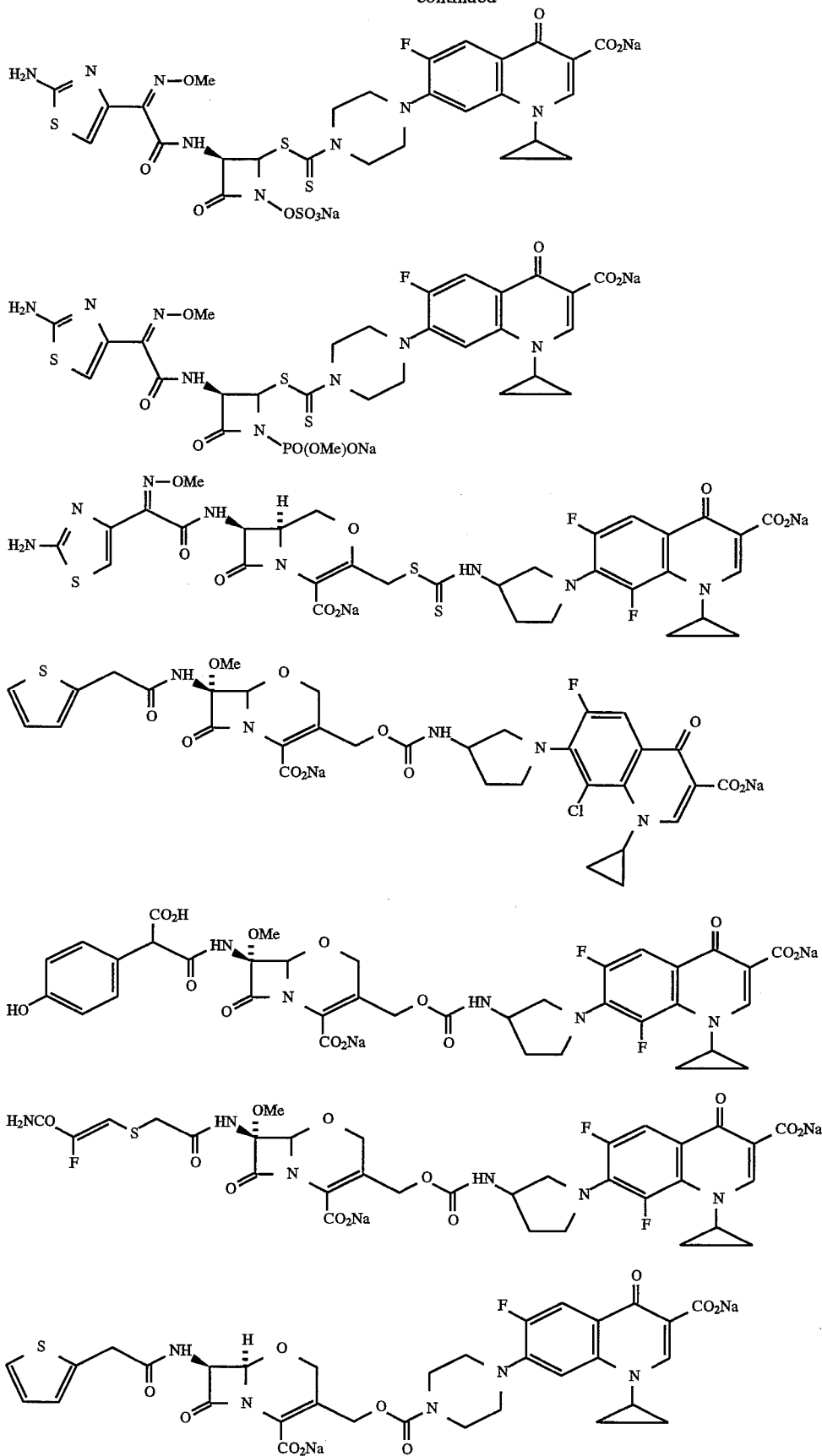

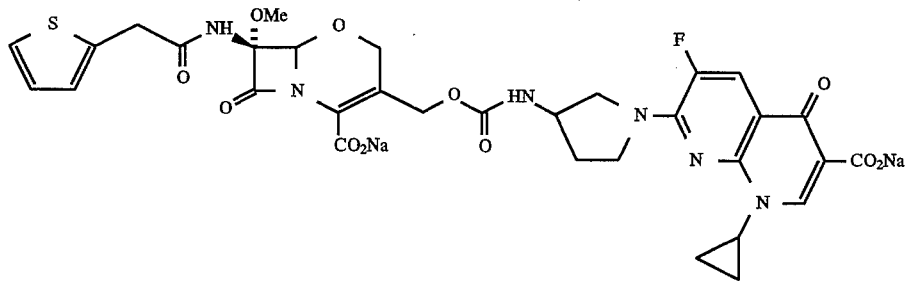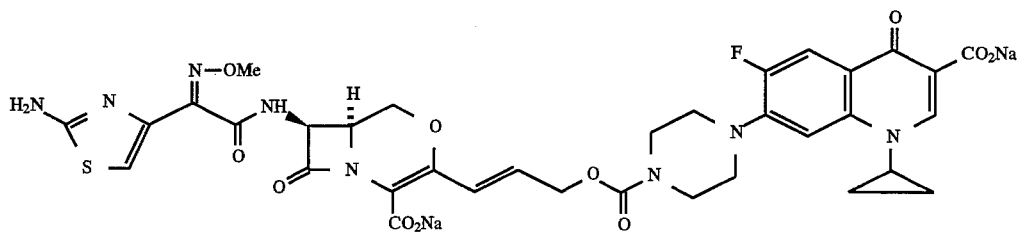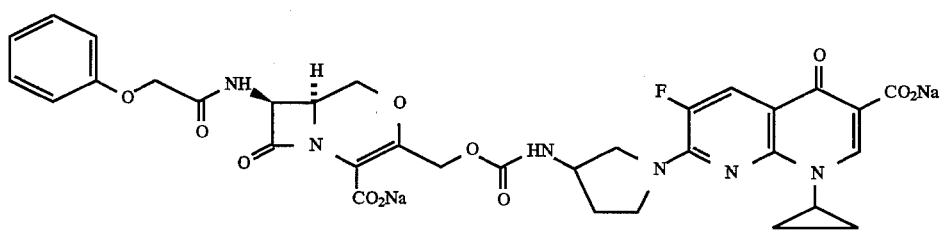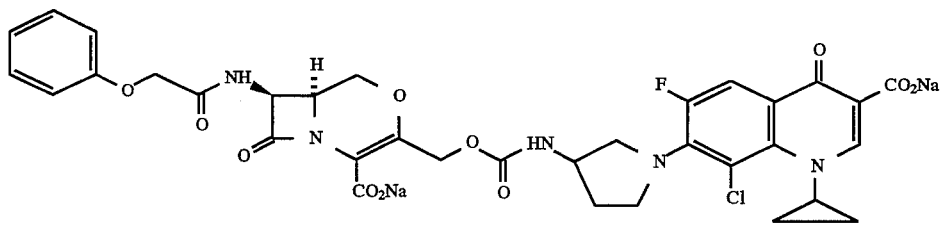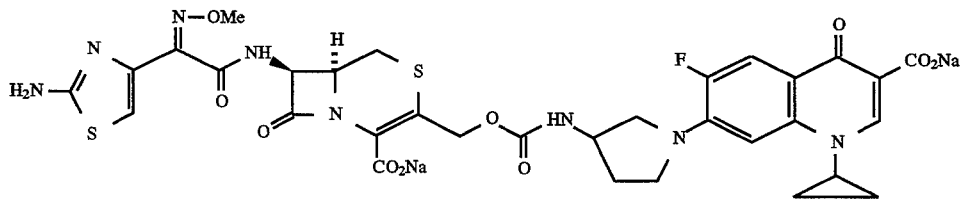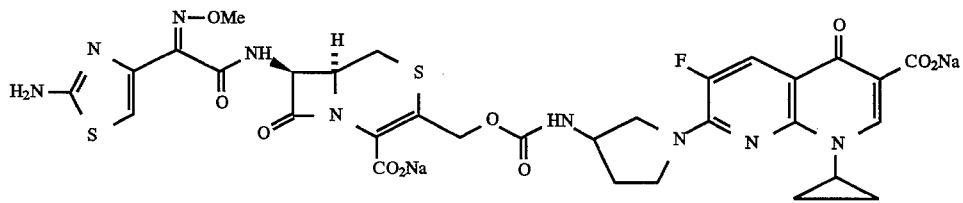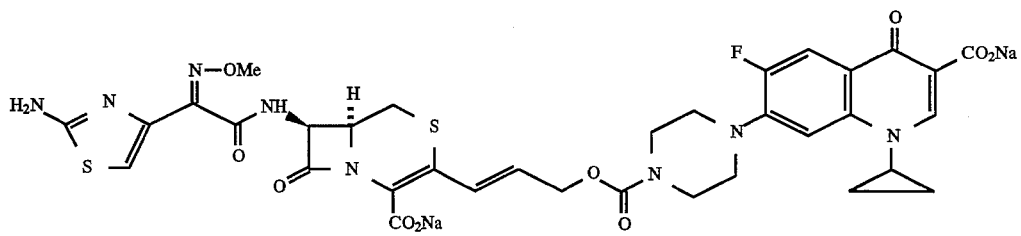

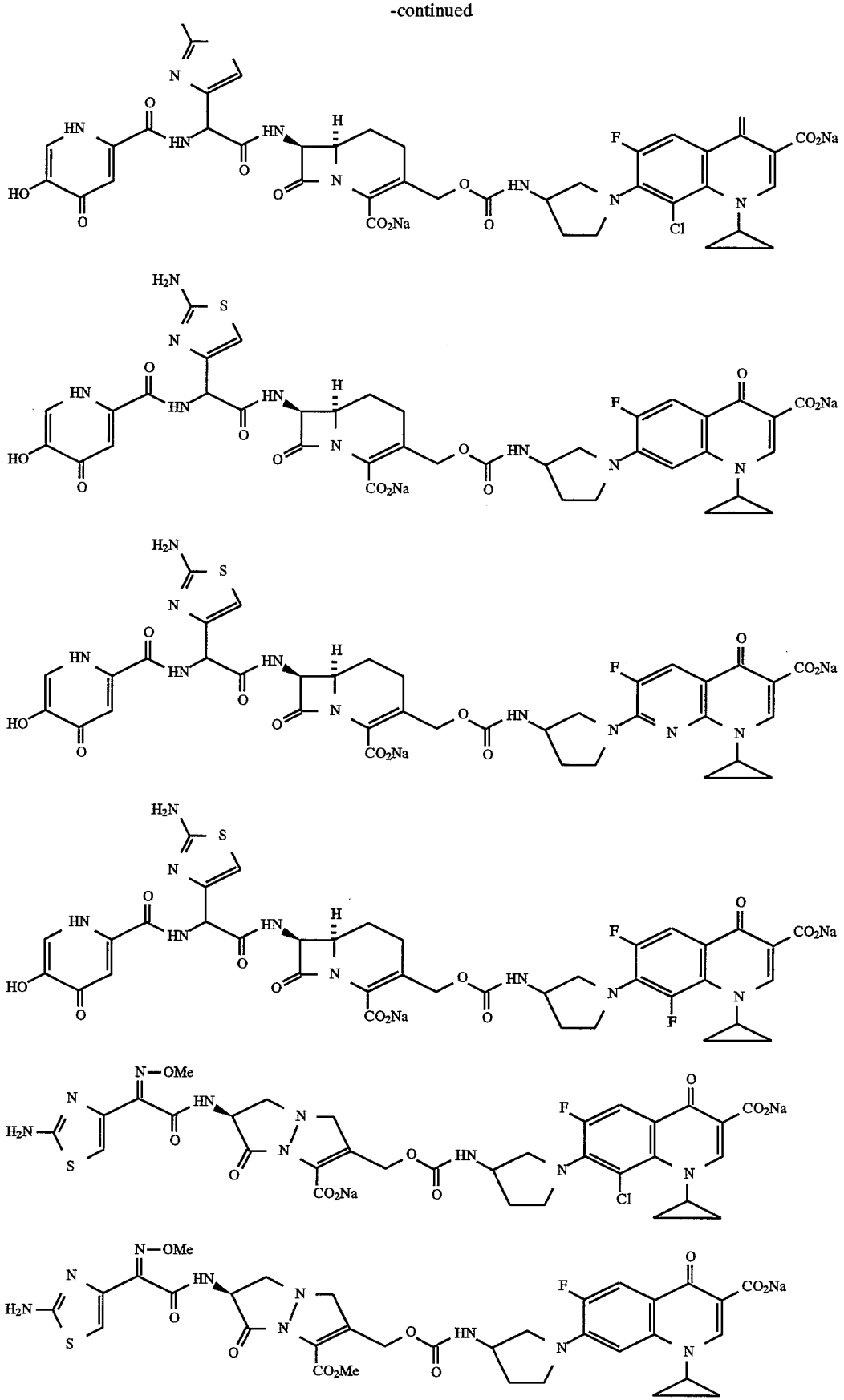

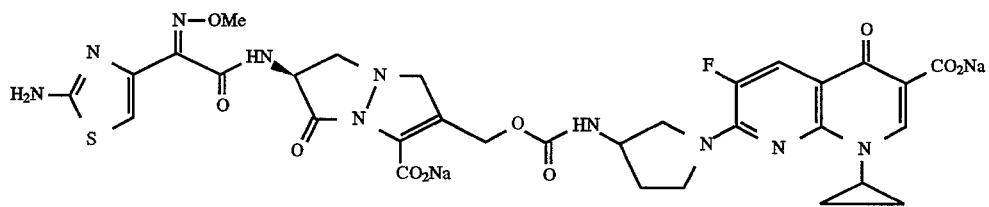
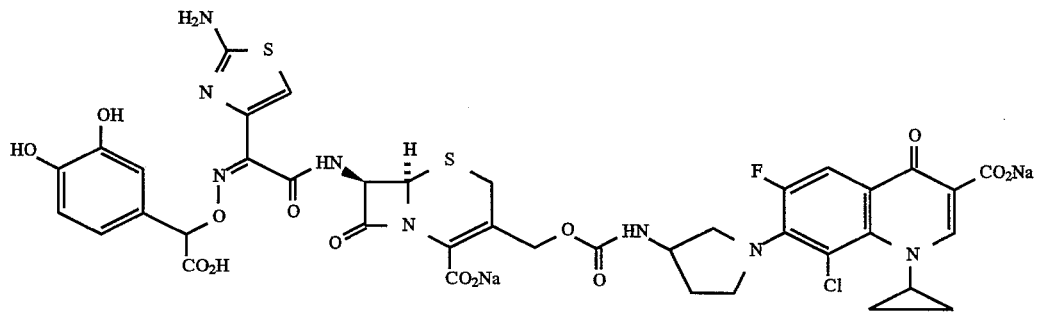
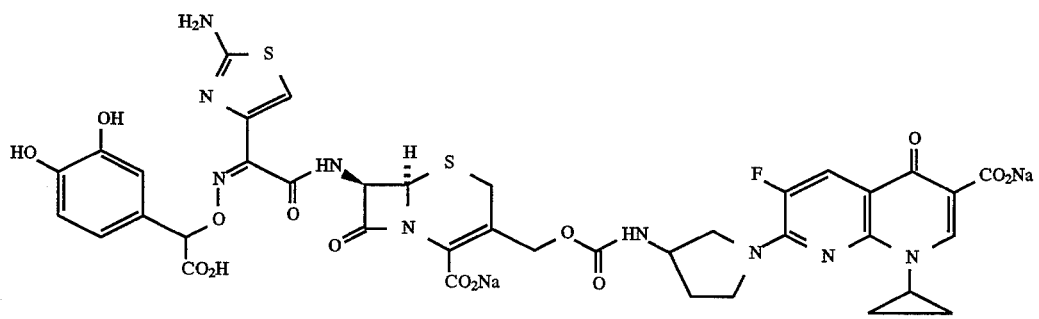
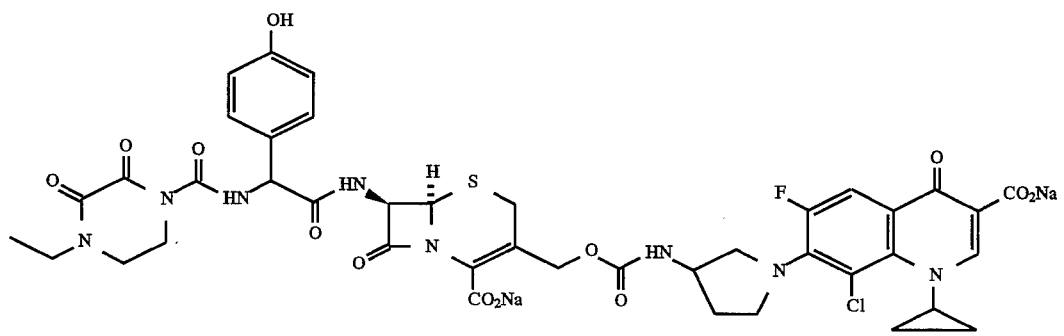
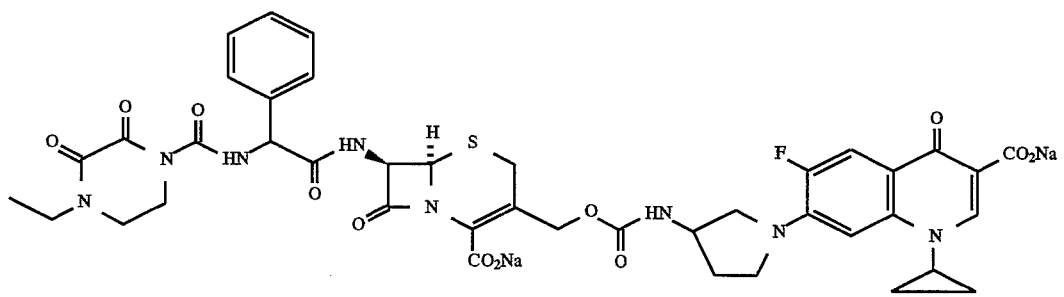

-continued
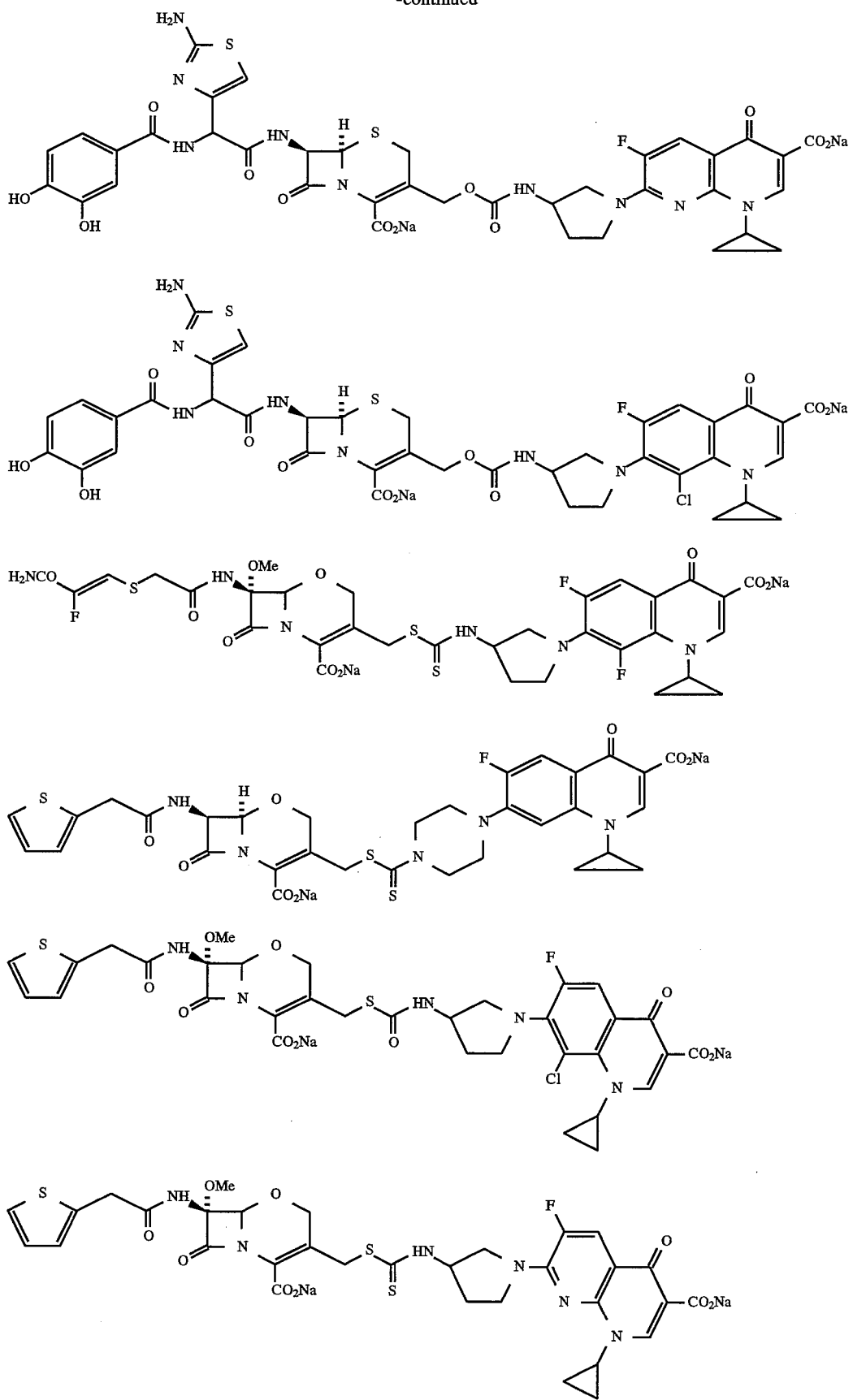

-continued
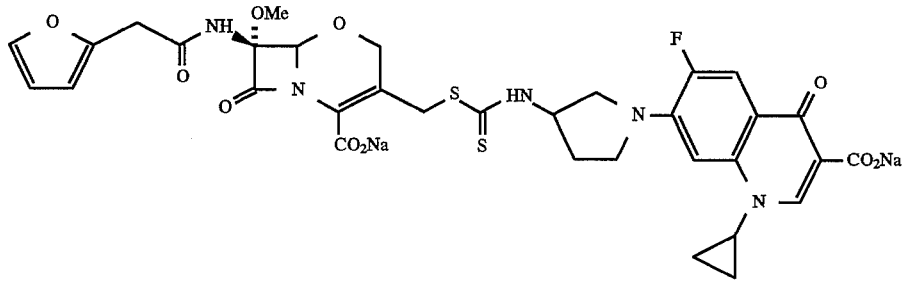
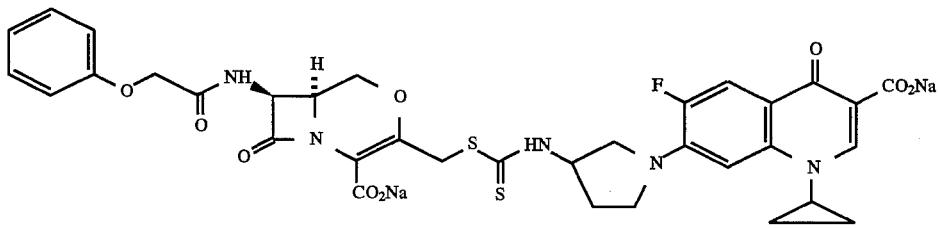
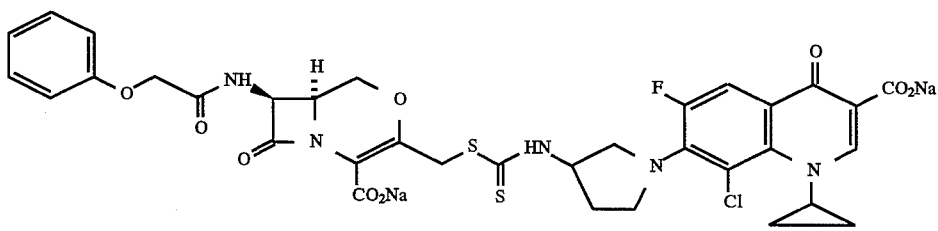
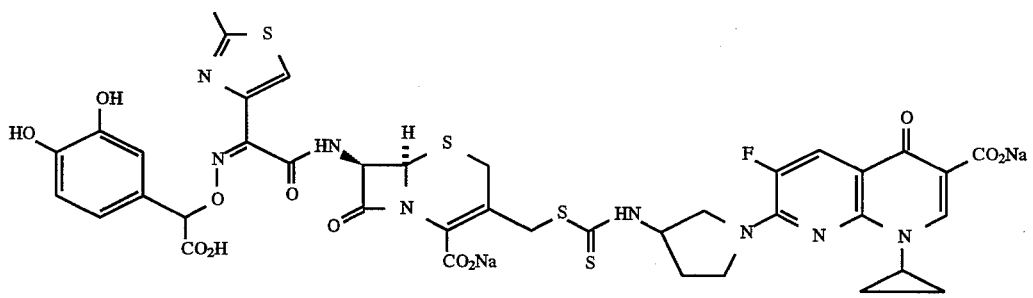
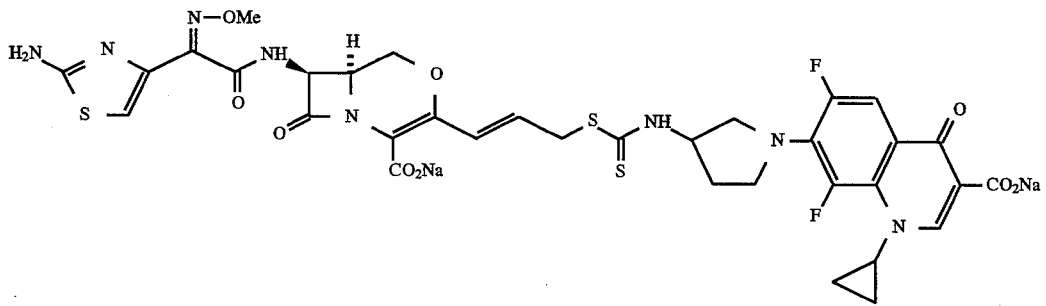
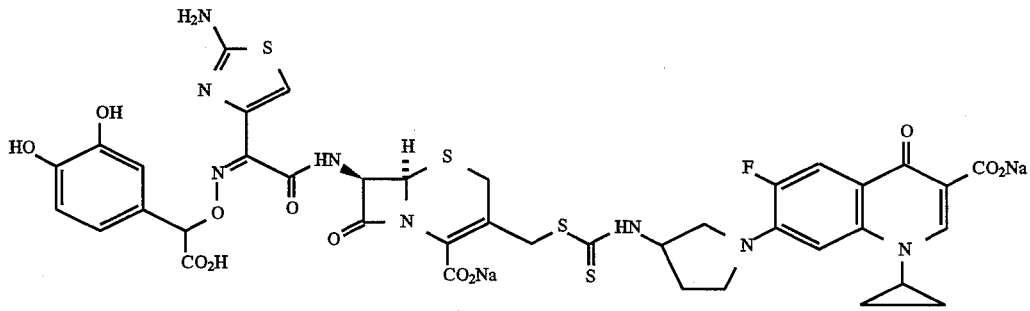

-continued
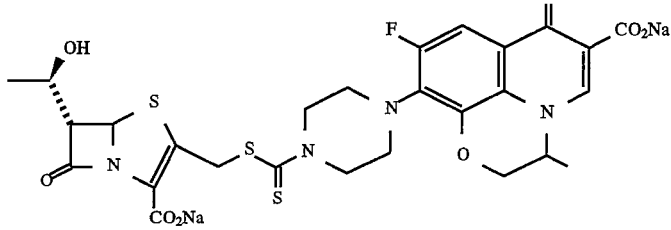
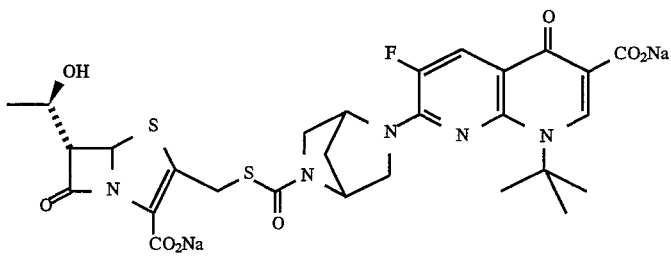
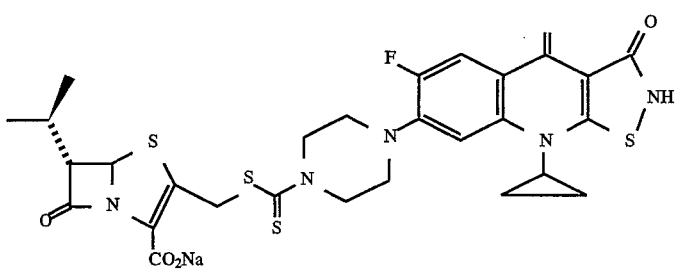
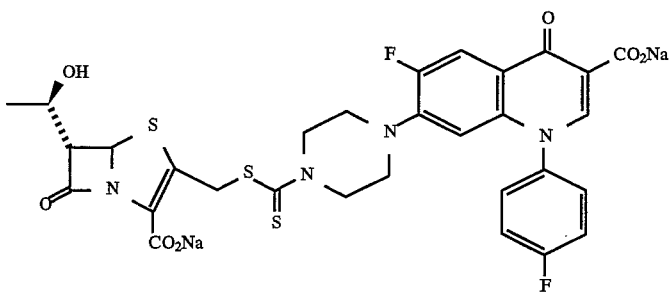
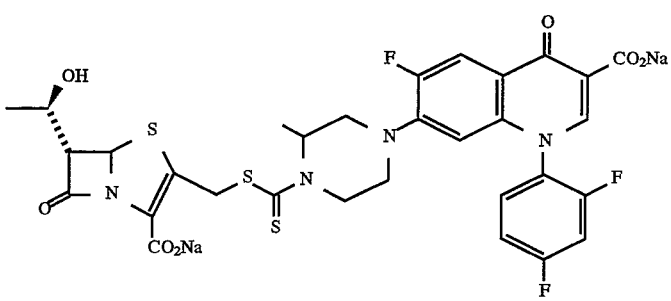
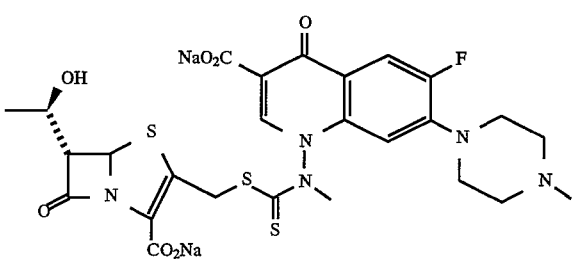

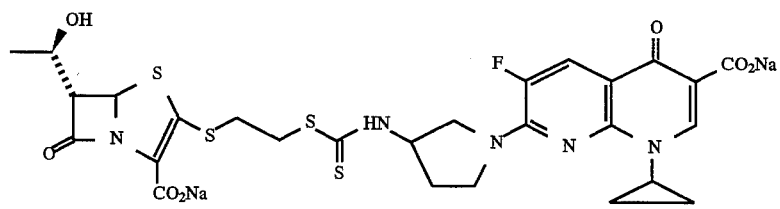
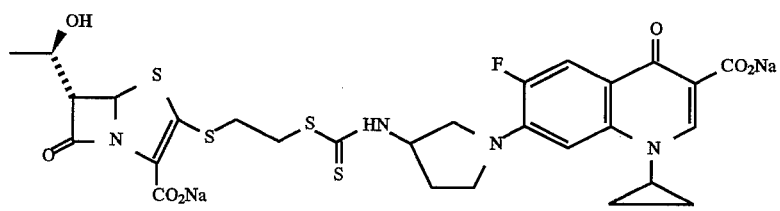
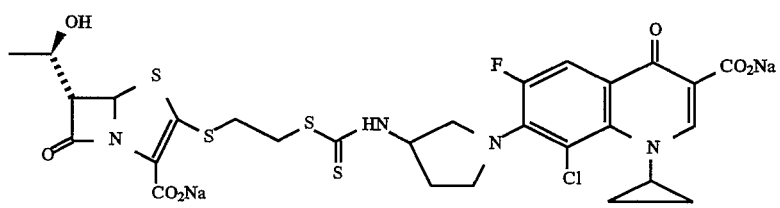
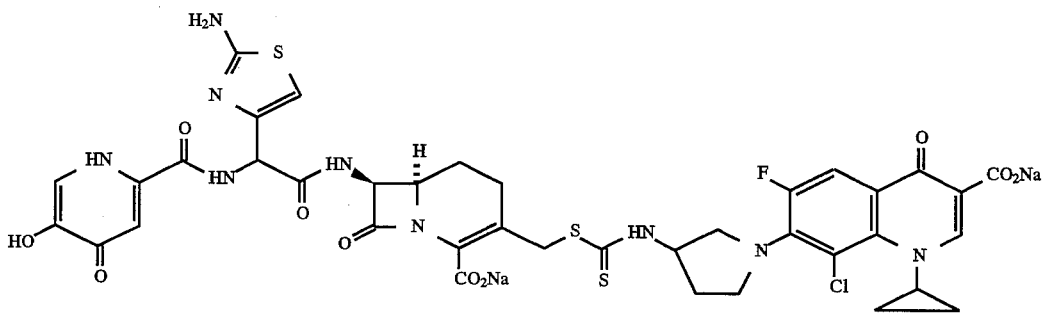
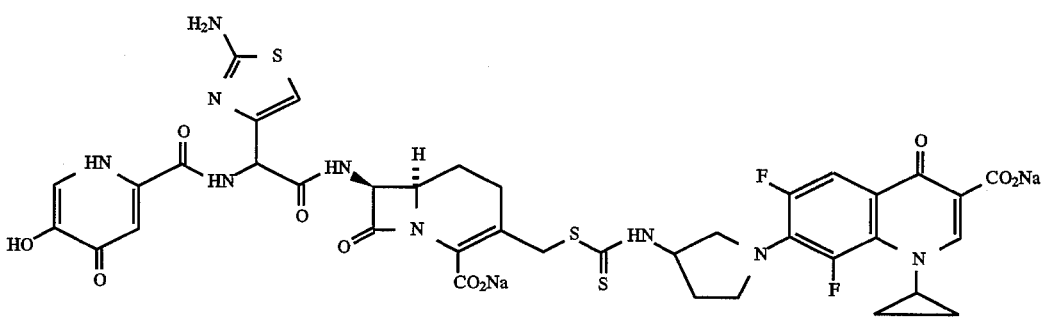
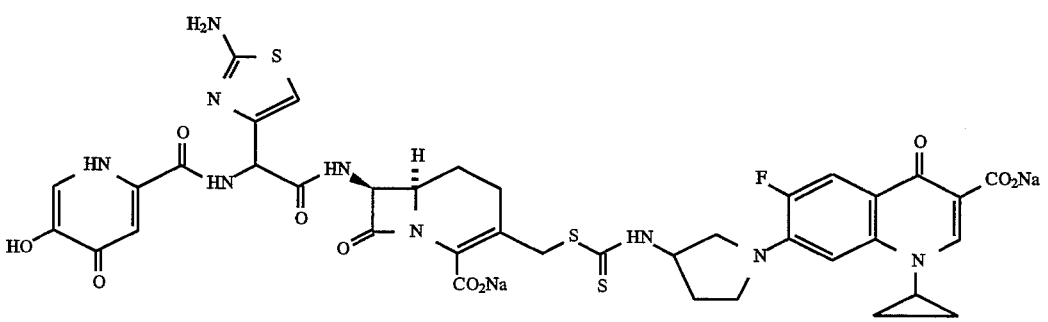

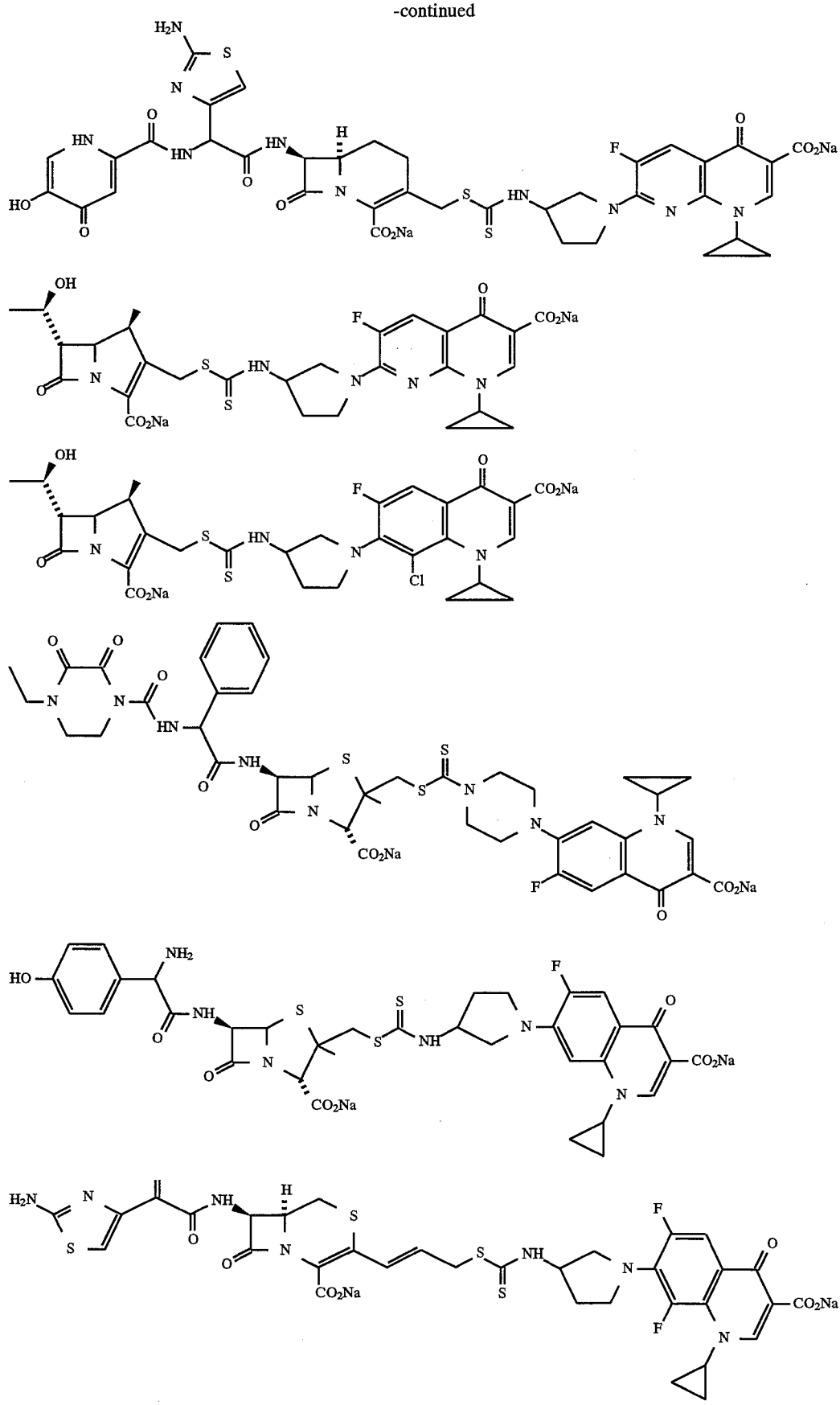

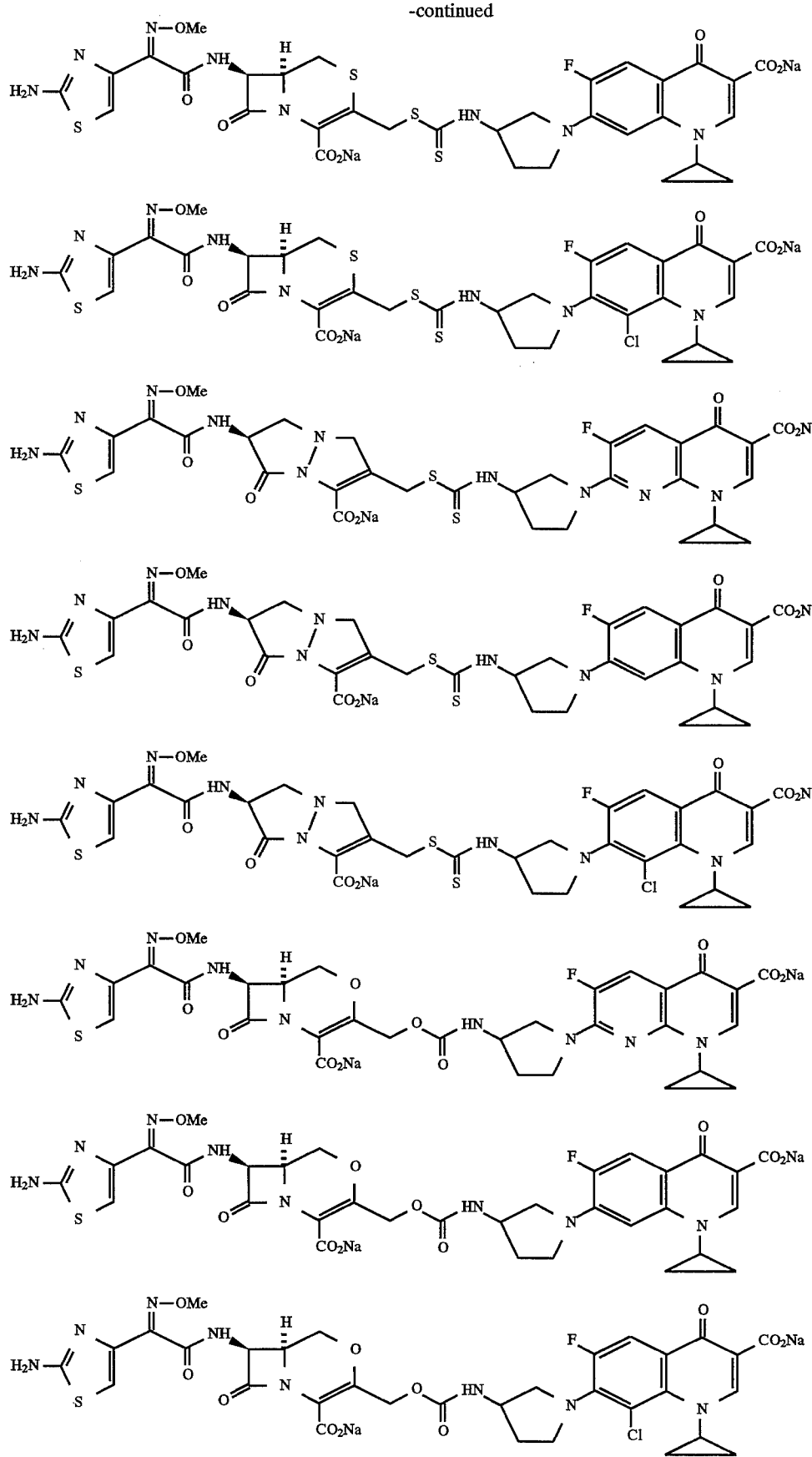

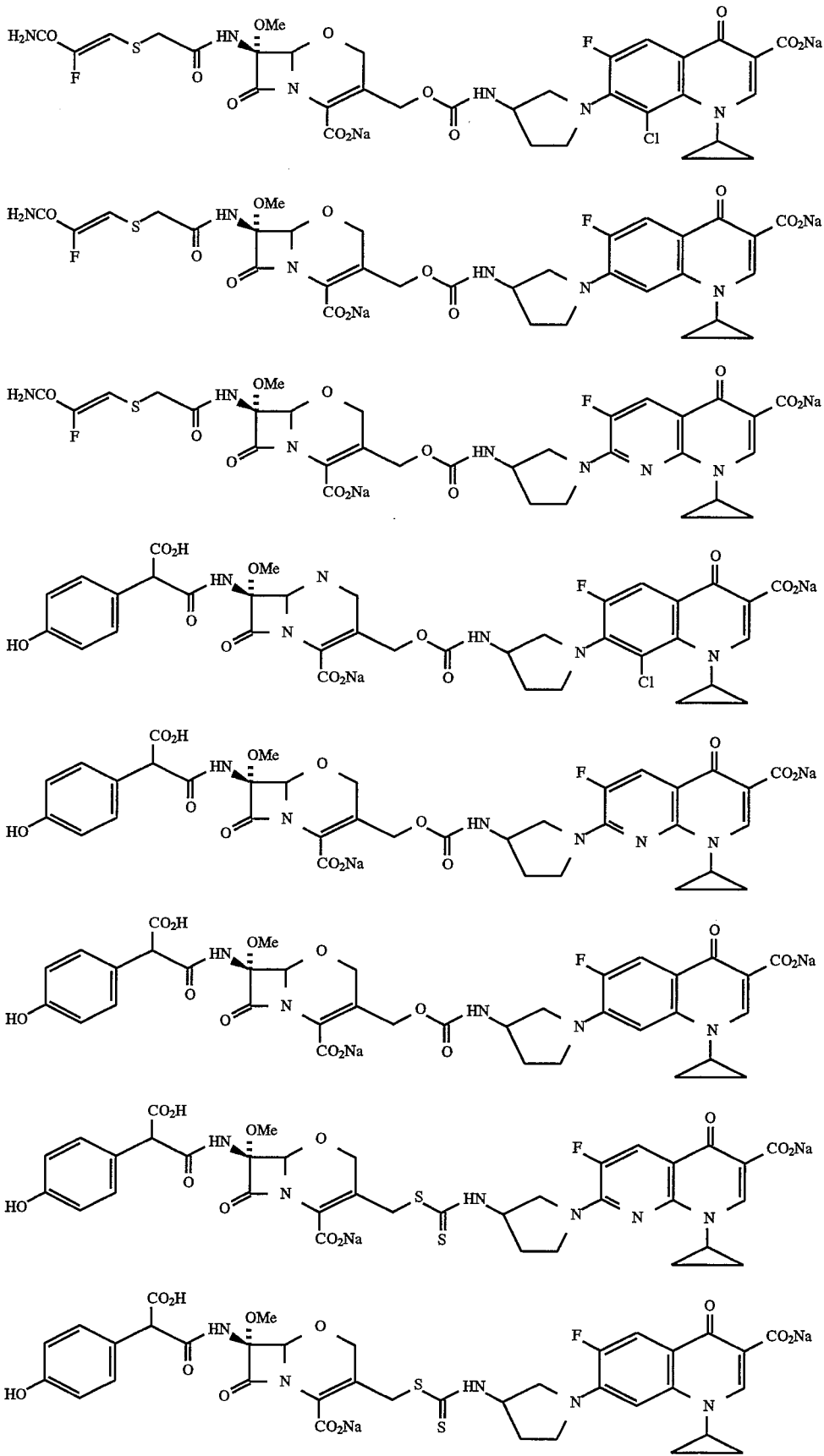

-continued
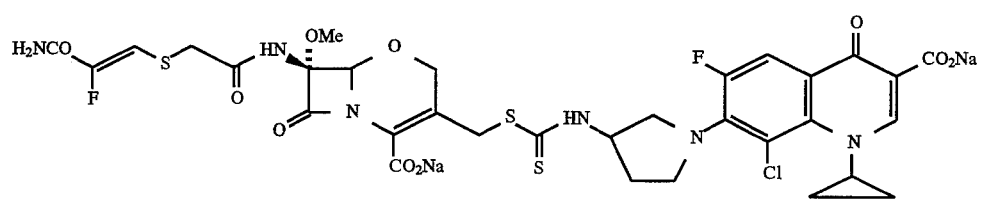
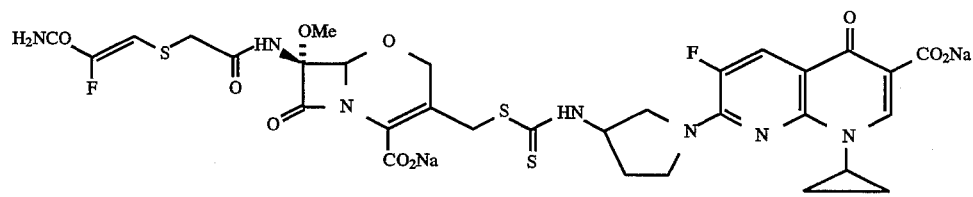
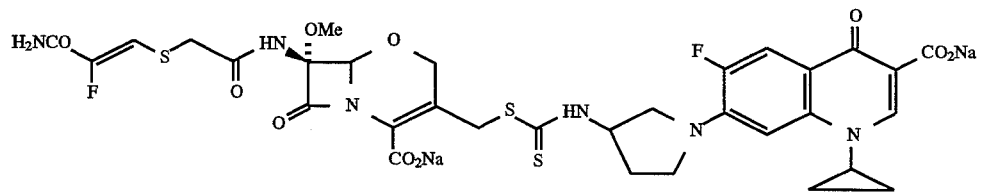
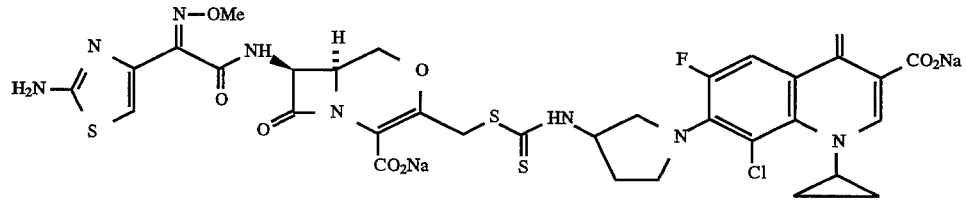
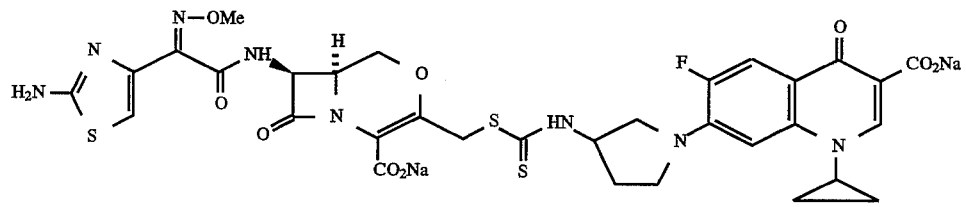
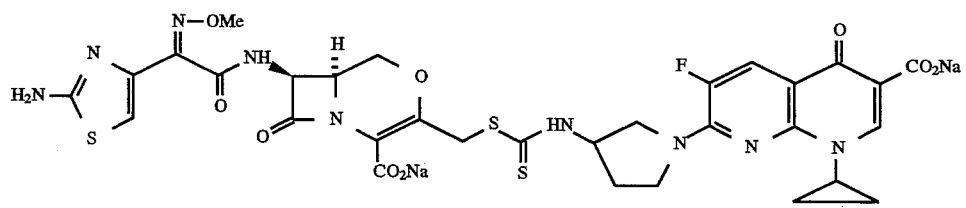
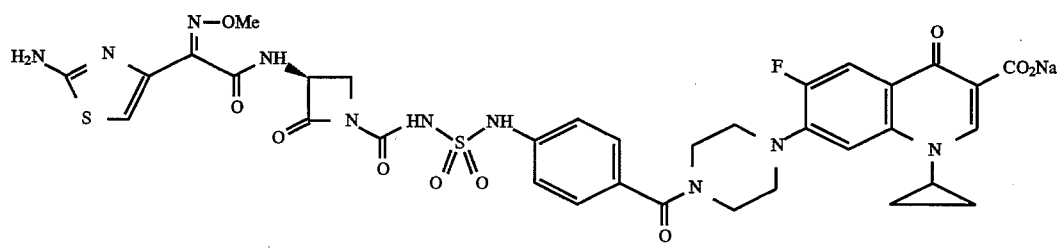

-continued
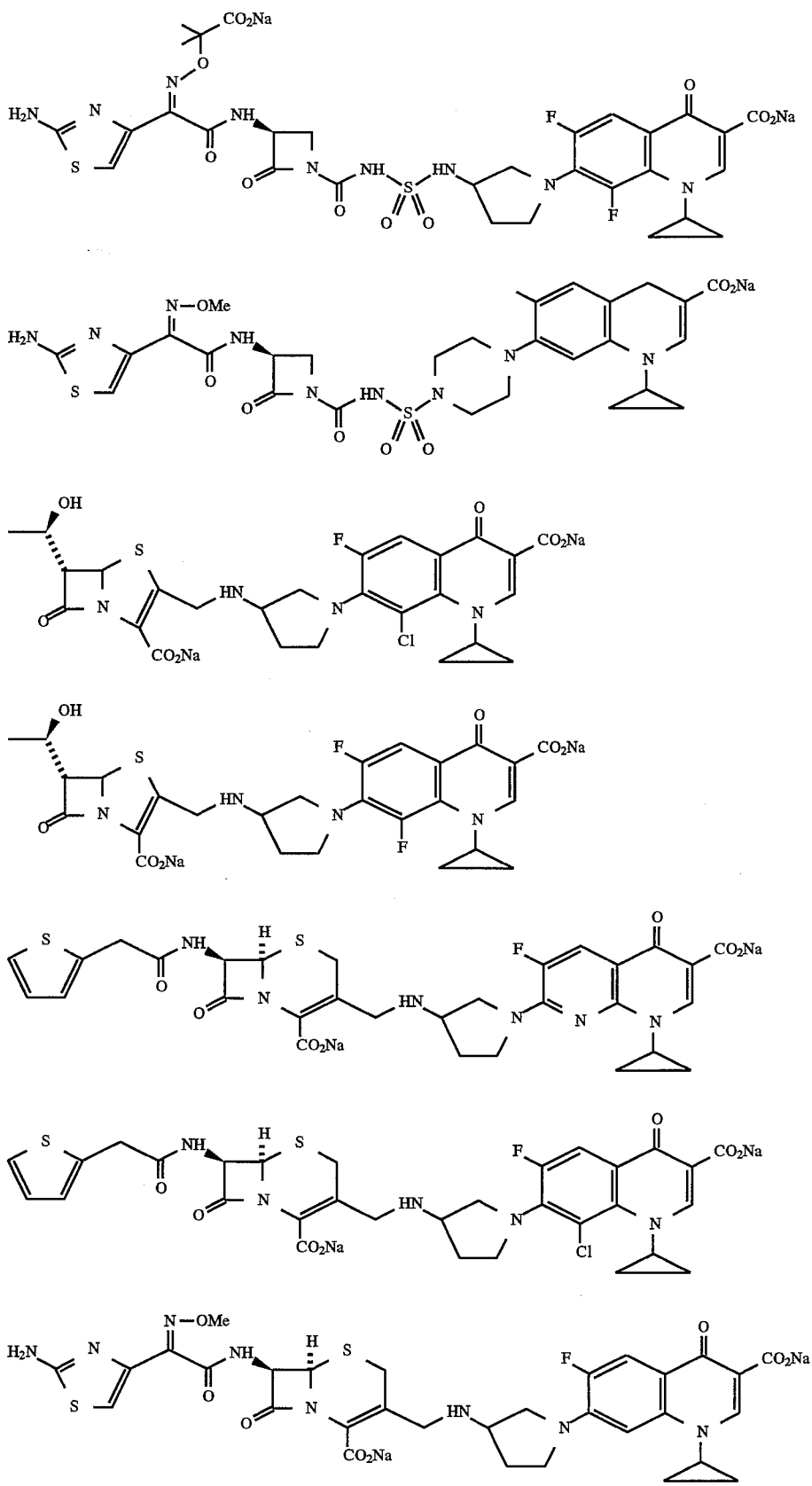

-continued
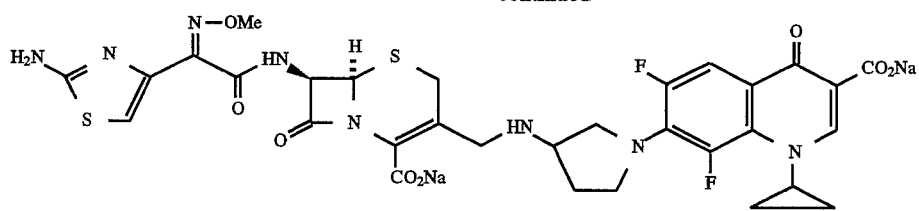
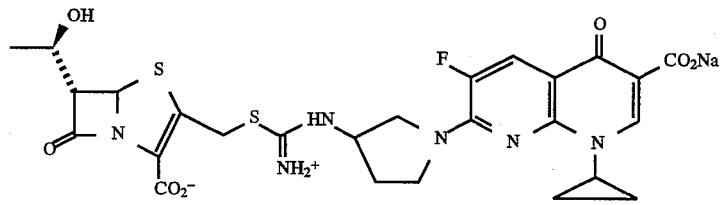
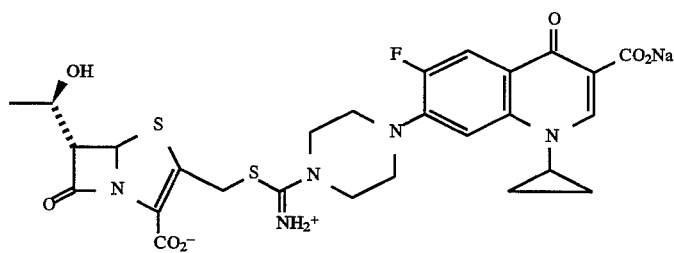
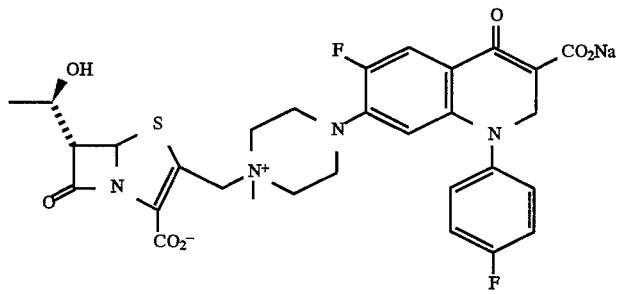
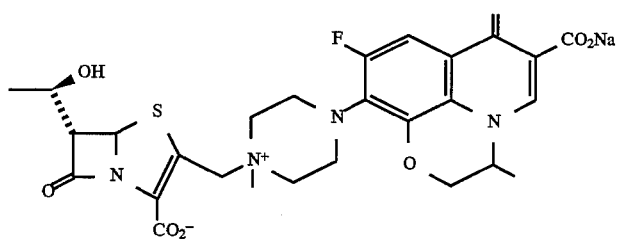
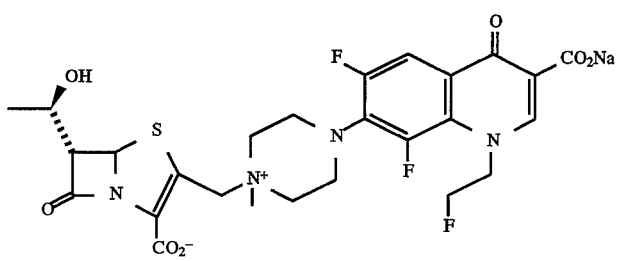

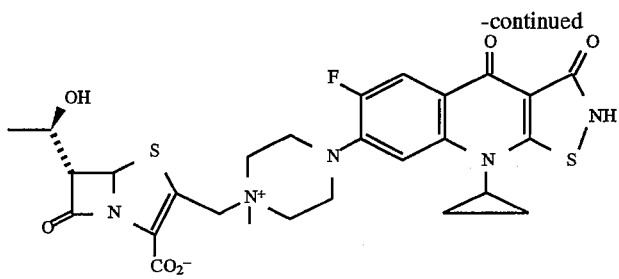

METHODS OF MANUFACTURE

The lactam-quinolones of this invention may be made using any of a variety of synthetic techniques known in the art. Manufacture of lactam-quinolone generally involves the preparation of a lactam-containing moiety, a quinolone moiety and a procedure or set of procedures for linking the lactam-containing and quinolone moieties. Procedures for making a broad variety of lactam-containing moieties and quinolone moieties are well known in the art. For example, procedures for preparing lactam-containing moieties are described in the following references, all incorporated by reference herein (including articles cited within these references): *Cephalosporins and Penicillins: Chemistry and Biology* (E. H. Flynn, ed, 1972) Chapters 2, 3, 4, 5, 6, 7, 15 and Appendix I; *Recent Advances in the Chemistry of β-Lactam Antibiotics* (A. G. Brown and S. M. Roberts, ed., 1985); *Topics in Antibiotic Chemistry*, Vol. 3, (Part B) and Vol. 4, (P. Sommes, ed., 1980); *Recent Advances in the Chemistry of β-lactam Antibiotics* (J. Elks, ed., 1976); *Structure-Activity Relationships Among the Semisynthetic Antibiotics* (D. Perlman, ed, 1977); Chapts. 1, 2, 3, 4; *Antibiotics, Chemotherapeutics and Antibacterial Agents for Disease Control* (M. Grayson, ed, 1982); Chemistry and Biology of β-Lactam Antibiotics, Vols 1–3 (K. B. Morin and M. Gorman, eds, 1982); 4 *Medicinal Research Reviews* 1–24 (1984); 8 *Medicinal Research Review* 393–440 (1988); 24 *Angew. Chem. Int. Ed. Engl.* 180–202 (1985); 40 *J. Antibiotics* 182–189 (1987); European Patent Publication 266,060; 42 *J. Antibiotics* 993 (1989); U.S. Pat. No. 4,742,053; 35 *Chem. Pharm. Bull.* 1903–1909 (1987); 32 *J. Med. Chem.*, 601–604 (1989); U.S. Pat. No. 4,791,106; Japanese Patent Publication 62/158291; 31 *J. Med. Chem.* 1987–1993 (1988); 30 *J. Med. Chem.*, 514–522 (1987); 28 *Tet. Let.* 285–288 (1987); 28 *Tet. Let.* 289–292 (1987); 52 *J. Org. Chem.*, 4007–4013 (1987); 40 *J. Antibiotics*, 370–384 (1987); 40 *J. Antibiotics*, 1636–1639 (1987); 37 *J. Antibiotics*, 685–688 (1984); 23 *Heterocycles*, 2255–2270; 27 *Heterocycles*, 49–55; 33 *Chem. Pharm. Bull.* 4371–4381 (1985); 28 *Tet. Let*, 5103–5106 (1987); 53 *J. Org. Chem.*, 4154–4156 (1988); 39 *J. Antibiotics*, 1351–1355 (1986); 59 *Pure and Appl. Chem.*, 467–474 (1987); 1987 *J.C.S. Chem. Comm.*; 44 *Tetrahedron*, 3231–3240 (1988); 28 *Tet. Let.*, 2883–2886, (1987); 40 *J. Antibiotics*, 1563–1571 (1987); 33 *Chem. Pharm. Bull.*, 4382–4394 (1985); 37 *J. Antibiotics*, 57–62 (1984); U.S. Pat. No. 4,631,150; 34 *Chem. Pharm. Bull.*, 999–1014 (1986); 52 *J. Org. Chem.*, 4401–4403 (1987); 39 *Tetrahedron*, 2505–2513 (1983); 38 *J. Antibiotics*, 1382–1400 (1985); European Patent Application 053,815; 40 *J. Antibiotics*, 1563–1571 (1987); 40 *J. Antibiotics*, 1716–1732 (2987); 47 *J. Org. Chem.*, 5160–5167 (1981); U.S. Pat. Nos. 4,777,252; 4,762,922; European Patent Publication 287,734; U.S. Pat. No. 4,762,827; European Patent Publication 282,895; European Patent Publication 282,365; U.S. Pat. No. 4,777,673;

Also, for example, procedures for preparing quinolones useful in the methods of this invention are described in the following references, all incorporated by reference herein (including articles listed within these references); 21 *Progress in Drug Research*, 9–104 (1977); 31 *J. Med. Chem.*, 503–506 (1988); 32 *J. Med. Chem.*, 1313–1318 (1989); 1987 *Liebigs Ann. Chem.*, 871–879 (1987); 14 *Drugs Exptl. Clin. Res.*, 379–383 (1988); 31 *J. Med. Chem.*, 983–991 (1988); 32 *J. Med. Chem.*, 537–542 (1989); 78 *J. Pharm. Sci.*, 585–588 (1989); 26 *J. Het. Chem.*, (1989); 24 *J. Het. Chem.*, 181–185 (1987); U.S. Pat. No. 4,599,334, 35 *Chem. Pharm. Bull.*, 2281–2285 (1987); 29 *J. Med. Chem.*, 2363–2369 (1986); 31 *J. Med. Chem.*, 991–1001 (1988); 25 *J. Het. Chem.*, 479–485 (1988); European Patent Publication 266,576; European Patent Publication 251,308, 36 *Chem. Pharm. Bull.*, 1223–1228 (1988); European Patent Publication 227,088; European Patent Publication 227,039; European Patent Publication 228,661; 31 *J. Med. Chem.*, 1586–1590 (1988); 31 *J. Med. Chem.*, 1598–1611 (1988); and 23 *J. Med. Chem.*, 1358–1363 (1980);

Procedures for linking the lactam-containing moiety and quinolone moieties may vary according to the type of linking group desired. For example, the lactam-quinolones having a carbamate linking moiety may be made by the following general reaction sequence:

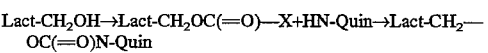

where X is a reactive leaving group (such as alkoxy, halo, or N-heteroaryl), "Lact" represents an appropriately protected lactam-containing structure (such as a penem, carbapenem, cephem, monocyclic beta-lactam, oxacephem, or carbacephem) and "Quin" represents an appropriately protected quinolone. The sequence can be envisioned as formation of the intermediate lactam carbonate derivative, followed by acylation of a quinolone amino functionality to form a carbamate coupled conjugate of the lactam and quinolone.

Alternatively, "reversed" dithiocarbamate conjugates can be prepared by the following sequence.

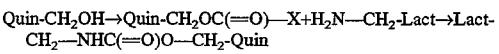

where X is a reactive leaving group (such as alkoxy, halo, or N-heteroaryl), "Lact" represents an appropriately protected lactam-containing structure (such as a penem, carbapenem, cephem, oxacephem, or carbacephem) and "Quin" represents an appropriately protected quinolone. The sequence can be envisioned as formation of the intermediate quinolone carbonate derivative, followed by acylation of a lactam amino functionality to form a carbamate coupled conjugate of the lactam and quinolone.

Lactam-Quinolones having a dithiocarbamate linking moiety may be made by the following general reaction sequence:

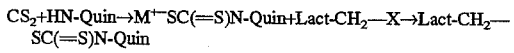

where X is a reactive leaving group (such as halo, a sulfonate ester, acetate, thiobenzoate or other activated hydroxyl functionality), "Lact" represents an appropriately protected lactam-containing structure (such as a penem, carbapenem, cephem, monocyclic beta-lactam, oxacephem, or carbacephem), and "Quin" represents an appropriately protected quinolone. The sequence can be envisioned as formation of the intermediate quinolone dithiocarbamate salt, followed by nucleophilic displacement of the lactam X substituent to form a dithiocarbamate coupled conjugate of the lactam and quinolone.

Alternatively, "reversed" dithiocarbamate conjugates can be prepared by the following sequence.

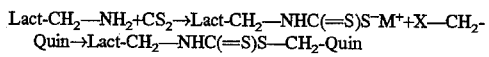

where X is a reactive leaving group (such as halo, a sulfonate ester, or other activated hydroxyl functionality), "Lact" represents an appropriately protected lactam-containing structure (such as a penem, carbapenem, cephem, oxacephem, or carbacephem), and "Quin" represents an appropriately protected quinolone. The sequence can be envisioned as formation of the intermediate lactam dithiocarbamate salt, followed by nucleophilic displacement of the suitable quinolone X substituent to form a "reversed" dithiocarbamate coupled conjugate of the lactam and quinolone.

Lactam-quinolones having a thiourea or urea linking moiety may be made by the following general reaction sequence:

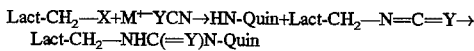

(thiourea: Y is sulfur; urea: Y is oxygen)

where X is a reactive leaving group (such as halo, a sulfonate ester, dichloroacetate, thiobenzoate or other activated hydroxyl functionality), and Y is either O or S. "Lact" represents an appropriately protected lactam-containing structure (such as a penem, carbapenem, cephem, monocyclic beta-lactam, oxacephem, or carbacephem), and "Quin" represents an appropriately protected quinolone. The sequence can be envisioned as formation of the intermediate lactam isothiocyanate (Y=S) or isocyanate (Y=O), followed by reaction with the quinolone amino substituent to form a thiourea (Y=S) or urea (Y=O) coupled conjugate of the lactam and quinolone.

Alternatively, the thiourea or urea conjugates can be prepared by the following sequence.

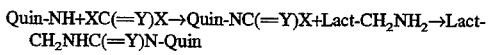

(thiourea: Y is sulfur; urea: Y is oxygen)

where X is a reactive leaving group such as halo, N-heteroaryl or activated hydroxyl functionality, and Y is either S or O. "Lact" represents an appropriately protected lactam-containing structure (such as penem, carbapenem, cephem, monocyclic beta-lactam, oxacephem, or carbacephem), and "Quin" represents an appropriately protected quinolone. The sequence can be envisioned as formation of the intermediate quinolone activated thio carbamate (Y=S) or carbamate (Y=O), followed by reaction with the lactam amino substituent to form a thiourea (Y=S) or urea (Y=O) coupled conjugate of the lactam and quinolone.

Lactam-quinolones having an imine, amine or ammonium linking moiety may be made by the following general reaction sequence:

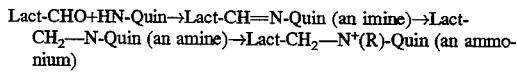

"Lact" represents an appropriately protected lactam-containing structure (such as a penem, carbapenem, cephem, oxacephem, or carbacephem), and "Quin" represents an appropriately protected quinolone. The sequence can be envisioned as the condensation of the quinolone amine with the lactam aldehyde to form the imine coupled lactam-quinolone conjugate. Reduction of the imine yields the corresponding amine coupled lactam-quinolone conjugate. Alkylation yields the corresponding quaternary ammonium-coupled lactam-quinolone conjugate.

Alternatively, the quaternary ammonium and amine (R is H) conjugates can be prepared by the following general sequence.

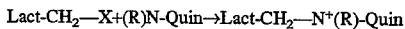

where X is a reactive leaving group (such as halo, a sulfonate ester, or other activated hydroxyl functionality, etc.) This sequence can be envisioned as an alkylation of a quinolone amino group with the lactam starting material to obtain the amine or quaternary ammonium coupled conjugate between the lactam and quinolone.

Lactam-quinolones having an amide linking moiety may be made by the following general reaction sequence:

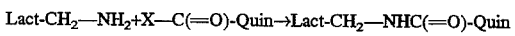

where X is a reactive leaving group (such as halo, an HOBt ester, mixed anhydride or other activated carboxyl functionality), "Lact" represents an appropriately protected lactam-containing structure (such as a penem, carbapenem, cephem, oxacephem, or carbacephem), and "Quin" represents an appropriately protected quinolone. The reaction can be envisioned as an acylation of the lactam amino substituent with the activated quinolone carboxyl group, to form an amide coupled conjugate of the lactam and quinolone.

Alternatively, "reversed" amide conjungates can be prepared by the following sequence.

where X is a reactive leaving group (such as halo, an HOBT ester, mixed anhydride or another activated carboxyl functionality), "Lact" represents an appropriately protected lactam-containing structure (such as a penem, carbapenem, cephem, oxacephem or carbacephem), and "Quin" represents an appropriately protected quinolone. The reaction can be envisioned as an acylation of the quinolone amino substituent with the activated lactam carboxyl group to form a "reversed" amide coupled conjungate of the lactam and quinolone.

Lactam-quinolones having a guanidinium linking moiety may be made by the following general reaction sequence:

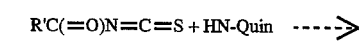

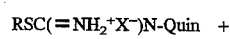

Lact-CH$_2$—NH$_2$ ----▷

Lact-CH$_2$—NHC(=NH$_2{}^+$X$^-$)N-Quin where "Lact" represents an appropriately protected lactam-containing structure (such as penem, carbapenem, cephem, oxacephem, or carbacephem) and "Quin" represents an appropriately protected quinolone. The sequence can be envisioned as formation of the intermediate quinolone isothiouronium salt, followed by reaction with the lactam amino substituent to form a guanidinium coupled conjugate of the lactam and quinolone.

Lactam-quinolones having a heteroarylium linking moiety may be made by the following general reaction sequence:

Lact-CH$_2$—X+N$_{Het}$-Quin→Lact-CH$_2$—N$^+{}_{Het}$-Quin where X is a reactive leaving group (such as halo, a sulfonate ester, acetate, thiobenzoate or other activated hydroxyl functionality), "Lact" represents an appropriately protected lactam-containing structure (such as a penem, carbapenem, cephem, monocyclic beta-lactam, oxacephem, or carbacephem) and "Quin" represents an appropriately protected quinolone that contains a heteroaromatic nitrogen-containing substituent (for example, pyridine). The sequence can be envisioned as an alkylation of the quinolone heteroaromatic nitrogen containing substituent by the lactam to form the pyridinium-type conjugate.

Lactam-quinolones having a xanthate linking moiety may be made by the following general reaction sequence:

CS$_2$+HO-Quin→M$^{+-}$SC(=S)O-Quin+Lact-CH$_2$—X→Lact-CH$_2$—SC(=S)O-Quin where X is a reactive leaving group (such as halo, a sulfonate ester, acetate, thiobenzoate or other activated hydroxyl functionality), "Lact" represents an appropriately protected lactam-containing structure (such as a penem, carbapenem, cephem, monocyclic beta-lactam, oxacephem, or carbacephem), and "Quin" represents an appropriately protected quinolone. The sequence can be envisioned as formation of the intermediate quinolone xanthate salt, followed by nucleophilic displacement of the lactam X substituent to form a xanthate coupled conjugate of the lactam and quinolone.

Lactam-quinolones having a thioether, sulfoxide or sulfone linking moiety may be made by the following general reaction sequence:

Lact-CH$_2$—X + HS-Quin ----▷

Lact-CH$_2$—S-Quin (a thioether) ----▷

Lact-CH$_2$—SO-Quin (a sulfoxide) ----▷

Lact-CH$_2$—SO$_2$-Quin (a sulfone)

where X is a reactive leaving group (such as halo, a sulfonate ester, acetate, thiobenzoate or other activated hydroxyl functionality, etc.). "Lact" represents an appropriately protected lactam-containing structure (such as a penem, carbapenem, cephem, monocyclic beta-lactam, oxacephem, or carbacephem), and "Quin" represents an appropriately protected quinolone. The sequence can be envisioned as nucleophilic displacement of the lactam X group with a thio-containing quinolone to form the thioether coupled conjugate of the lactam and the quinolone. Oxidation of the thioether yields the corresponding sulfoxide conjugate. Further oxidation produces the sulfone lactam-quinolone conjugate.

Lactam-quinolones having a vinyl-thioether linking moiety may be made by the following general reaction sequence:

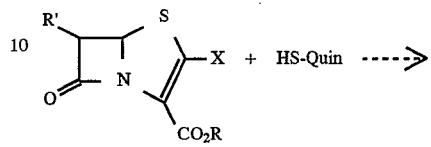

+ HS-Quin ----▷

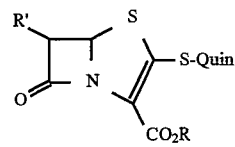

where X is a reactive vinylic leaving group (such as halo, sulfonate ester, phosphate ester or other activated enolic functionality, etc.) The lactam-containing structure may be a penem, as represented above, or more may be another appropriately protected lactam-containing structure (such as carbapenem, cephem, oxacephem, or carbacephem), and "Quin" represents an appropriately protected quinolone possessing a thiol substituent. The sequence can be envisioned as the displacement of the vinylic lactam X substituent to form the corresponding vinyl-thioether coupled conjugate of the lactam and quinolone.

Lactam-quinolones having a phosphonate or phosphonamide linking moiety may be made by the following general reaction sequence:

(RO)$_3$P+Lact-CH$_2$—X→Lact-CH$_2$—PO(OR)$_2$+HY-Quin→Lact-CH$_2$—PO(OR)—Y-Quin (phosphonate: Y is oxygen; phosphonamide: Y is nitrogen)

"Lact" represents an appropriately protected lactam-containing structure (such as a penem, carbapenem, cephem, monocyclic beta-lactam, oxacephem, or carbacephem) as described within this invention, and "Quin" represents an appropriately protected quinolone possessing an amino or hydroxyl substituent. The sequence can be envisioned as Arbusov formation of the intermediate dialkyl quinolone phosphonate followed by an exchange with the quinolone hydroxyl group to form the corresponding phosphonate (Y=O) coupled conjugate, or the quinolone amino group forming the phosphonamide (Y=N) coupled conjugate of the lactam and quinolone.

Lactam-quinolones having a phosphate or phosphoramide linking moiety may be made by the following general reaction sequence:

(RO)$_2$PO—Cl+HY-Quin→(RO)$_2$PO—Y-Quin+Lact-CH$_2$—OH→Lact-CH$_2$—O—PO(OR)—Y-Quin (phosphate: Y is oxygen; phosphoramide: Y is nitrogen)

"Lact" represents an appropriately protected lactam-containing structure (such as a penem, carbapenem, cephem, monocyclic beta-lactam, oxacephem, or carbacephem), and "Quin" represents an appropriately protected quinolone possessing an amino or hydroxyl substituent. The sequence can be envisioned as formation of the intermediate dialkyl quinolone phosphate (Y=O) or phosphoramide (Y=N) followed by an ester exchange with the lactam hydroxyl group to form the corresponding phosphate (Y=O) and phosphoramide (Y=N) coupled conjugates of the lactam and quinolone.

Lactam-quinolones having an isothiouronium linking group may be made by the following general reaction sequence:

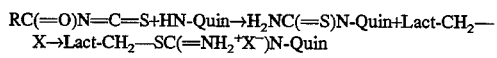

RC(=O)N=C=S+HN-Quin→H₂NC(=S)N-Quin+Lact-CH₂—X→Lact-CH₂—SC(=NH₂⁺X⁻)N-Quin where X is a reactive leaving group (such as halo, a sulfonate ester, acetate, thiobenzoate or other activated hydroxyl functionality), Lact represents an appropriately protected lactam-containing structure (such as a penem, carbapenem, cephem, monocyclic beta-lactam, oxacephem, or carbacephem, and "Quin" represents an appropriately protected quinolone. The sequence can be envisioned as formation of the intermediate quinolone thiourea, followed by nucleophilic displacement of the lactam X substituent to form a isothiouronium coupled conjugate of the lactam and quinolone.

In the reaction sequences described herein, certain functional groups contained in the Lact and Quin structures, (such as carboxyl, hydroxyl, and amino groups) may need to be blocked in order to prevent undesired competing side reactions from occurring with X. Suitable protecting groups for carboxyl substituents include esters. Protecting groups for hydroxyl substituents include ethers, esters, and carbonates; and protecting groups for amino substituents include carbamates, and amides. If various protecting groups are employed, then appropriate deprotecting chemistry, that will not decompose the coupled conjugate, may be required to obtain antibacterially active products.

COMPOSITIONS

The compositions of this invention comprise:

(a) a safe and effective amount of a lactam-quinolone; and (b) a pharmaceutically-acceptable carrier.

A "safe and effective amount" of a lactam-quinolone is an amount that is effective, to inhibit microbial growth at the site of an infection to be treated in a human or lower animal subject, without undue adverse side effects (such as toxicity, irritation, or allergic response), commensurate with a reasonable benefit/risk ratio when used in the manner of this invention. The specific "safe and effective amount" will, obviously, vary with such factors as the particular condition being treated, the physical condition of the patient, the duration of treatment, the nature of concurrent therapy (if any), the specific dosage form to be used, the carrier employed, the solubility of the lactam-quinolone therein, and the dosage regimen desired for the composition.

The compositions of this invention are preferably provided in unit dosage form. As used herein, a "unit dosage form" is a composition of this invention containing an amount of a lactam-quinolone that is suitable for administration to a human or lower animal subject, in a single dose, according to good medical practice. These compositions preferably contain from about 30 mg to about 20,000 mg, more preferably from about 50 mg (milligrams) to about 7000 mg, more preferably from about 500 mg to about 3500 mg, of a lactam-quinolone.

The compositions of this invention may be in any of a variety of forms, suitable (for example) for oral, rectal, topical or parenteral administration. Depending upon the particular route of administration desired, a variety of pharmaceutically-acceptable carriers well-known in the art may be used. These include solid or liquid fillers, diluents, hydrotropes, surface-active agents, and encapsulating substances. Optional pharmaceutically-active materials may be included, which do not substantially interfere with the antimicrobial activity of the lactam-quinolone. The amount of carrier employed in conjunction with the lactam-quinolone is sufficient to provide a practical quantity of material for administration per unit dose of the lactam-quinolone. Techniques and compositions for making dosage forms useful in the methods of this invention are described in the following references, all incorporated by reference herein: 7 *Modern Pharmaceutics*, Chapters 9 and 10 (Banker & Rhodes, editors, 1979); Lieberman et al., *Pharmaceutical Dosage Forms: Tablets* (1981); and Ansel, *Introduction to Pharmaceutical Dosage Forms* 2d Edition (1976).

In particular, pharmaceutically-acceptable carriers for systemic administration include sugars, starches, cellulose and its derivatives, malt, gelatin, talc, calcium sulfate, vegetable oils, synthetic oils, polyols, alginic acid, phosphate buffer solutions, emulsifiers, isotonic saline, and pyrogen-free water. Preferred carriers for parenteral administration include propylene glycol, ethyl oleate, pyrrolidone, ethanol, and sesame oil. Preferably, the pharmaceutically-acceptable carrier, in compositions for parenteral administration, comprises at least about 90% by weight by the total composition.

Various oral dosage forms can be used, including such solid forms as tablets, capsules, granules and bulk powders. These oral forms comprise a safe and effective amount, usually at least about 5%, and preferably from about 25% to about 50%, of the lactam-quinolone. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and flavoring agents. Preferred carriers for oral administration include gelatin, propylene glycol, cottonseed oil and sesame oil.

The compositions of this invention can also be administered topically to a subject, i.e., by the direct laying on or spreading of the composition on the epidermal or epithelial tissue of the subject. Such compositions include, for example, lotions, creams, solutions, gels and solids. These topical compositions preferably comprise a safe and effective amount, usually at least about 0.1%, and preferably from about 1% to about 5%, of the lactam-quinolone. Suitable carriers for topical administration preferably remain in place on the skin as a continuous film, and resist being removed by perspiration or immersion in water. Generally, the carrier is organic in nature and capable of having dispersed or dissolved therein the lactam-quinolone. The carrier may include pharmaceutically-acceptable emolients, emulsifiers, thickening agents, and solvents.

METHODS OF ADMINISTRATION

This invention also provides methods of treating or preventing an infectious disorder in a human or other animal subject, by administering a safe and effective amount of a lactam-quinolone to said subject. As used herein, an "infectious disorder" is any disorder characterized by the presence of a microbial infection. Preferred methods of this invention are for the treatment of bacterial infections. Such infectious disorders include (for example) central nervous system infections, external ear infections, infections of the middle ear (such as acute otitis media), infections of the cranial sinuses, eye infections, infections of the oral cavity (such as infections of the teeth, gums and mucosa), upper respiratory tract infections, lower respiratory tract infections, genitourinary infections, gastrointestinal infections, gynecological infections, septicemia, bone and joint infections, skin and skin structure infections, bacterial endocarditis, burns, antibacterial prophylaxis of surgery, and antibacterial prophylaxis in immunosuppressed patients (such as patients receiving cancer chemotherapy, or organ transplant patients).

The lactam-quinolones and compositions of this invention can be administered topically or systemically. Systemic application includes any method of introducing the lactam-quinolone into the tissues of the body, e.g., intrathecal, epidural, intramuscular, transdermal, intravenous, intraperitoneal, subcutaneous, sublingual, rectal, and oral administration. The specific dosage of antimicrobial to be administered, as well as the duration of treatment, are mutually dependent. The dosage and treatment regimen will also depend upon such factors as the specific lactam-quinolone used, the resistance pattern of the infecting organism to the lactam-quinolone used, the ability of the lactam-quinolone to reach minimum inhibitory concentrations at the site of the infection, the nature and extent of other infections (if any), the personal attributes of the subject (such as weight), compliance with the treatment regimen, and the presence and severity of any side effects of the treatment.

Typically, for a human adult (weighing approximately 70 kilograms), from about 75 mg to about 30,000 mg, more preferably from about 100 mg to about 20,000 mg, more preferably from about 500 mg to about 3500 mg, of lactam-quinolone are administered per day. Treatment regimens preferably extend from about 1 to about 56 days, preferably from about 7 to about 28 days, in duration. Prophylactic regimens (such as avoidance of opportunistic infections in immunocompromised patients) may extend 6 months, or longer, according to good medical practice.

A preferred method of parenteral administration is through intramuscular injection. As is known and practiced in the art, all formulations for parenteral administration must be sterile. For mammals, especially humans, (assuming an approximate body weight of 70 kilograms) individual doses of from about 100 mg to about 7000 mg, preferably from about 500 mg to about 3500 mg, are acceptable.

A preferred method of systemic administration is oral. Individual doses of from about 100 mg to about 2500 mg, preferably from about 250 mg to about 1000 mg are preferred.

Topical administration can be used to deliver the lactam-quinolone systemically, or to treat a local infection. The amounts of lactam-quinolone to be topically administered depends upon such factors as skin sensitivity, type and location of the tissue to be treated, the composition and carrier (if any) to be administered, the particular lactam-quinolone to be administered, as well as the particular disorder to be treated and the extent to which systemic (as distinguished from local) effects are desired.

The following non-limiting examples illustrate the compounds, compositions, processes, and uses of the present invention.

EXAMPLE 1

[6R-[6a,7b]]-[[[4-(3-Carboxy-1-cyclopropyl-6-fluoro-1,4-dihydro-4-oxo-7-quinolinyl)-1-piperazinyl]carbonyloxy]methyl]-8-oxo-7-[(2-thienylacetyl)amino]-5-thia-1-azabicyclo[4.2.0]oct-2-ene-2-carboxylic acid disodium salt, according to this invention, is made by the following general reaction sequence.

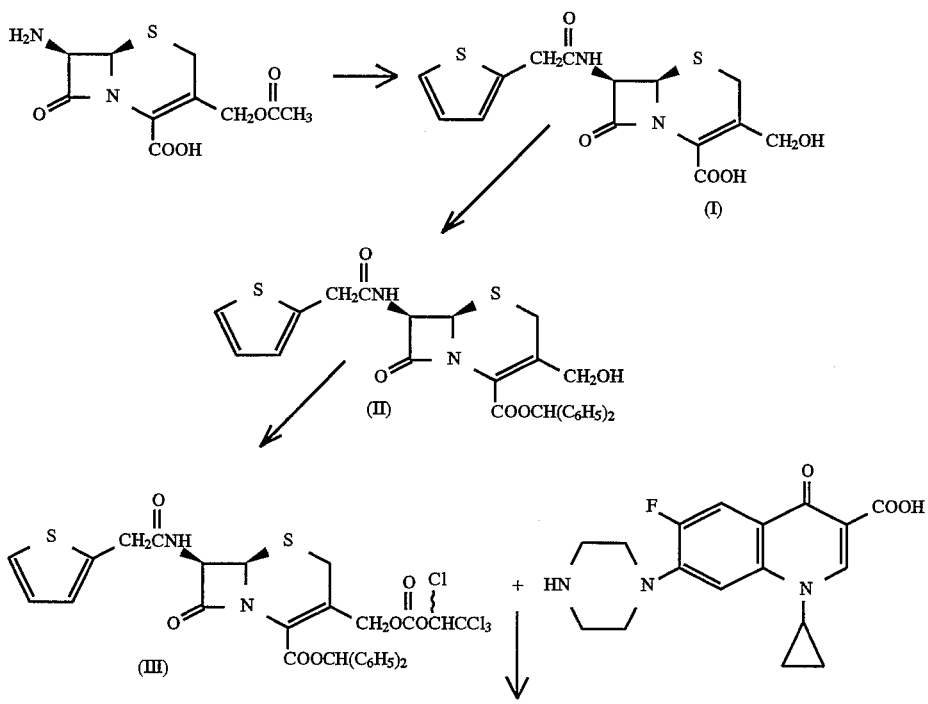

-continued

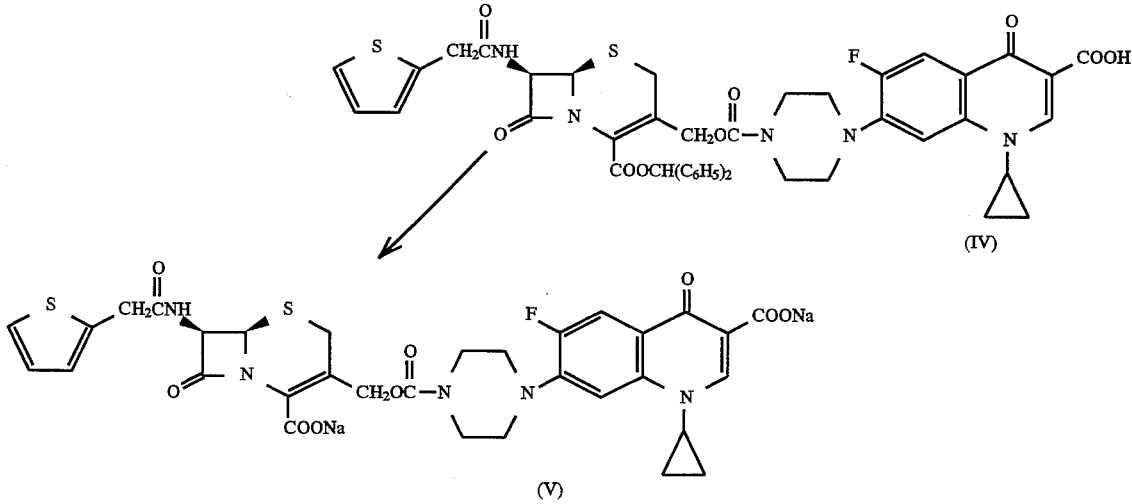

Approximately 28 ml (milliliters) of 1N NaOH is slowly added, with stirring, to a suspension of approximately 7.5 g (grams) of 7-aminocephalosporanic acid in methanol, while maintaining the temperature at approximately −5° C. (23° F.). An additional portion of approximately 28 ml 1N NaOH is added dropwise over 7 minutes at approximately 4° C. (40° F.) and the solution stirred for 30 minutes. Acetone is added to the reaction mixture. Approximately 4.4 g of 2-thiopheneacetyl chloride is then added dropwise over 30 minutes. The reaction mixture is washed with ethyl acetate and the aqueous phase acidified with concentrated HCl. The reaction product is extracted with ethyl acetate, and filtered.

Approximately 0.63 g of this product (I) is dissolved in ethyl acetate and THF (tetrahydrofuran). A solution of approximately 0.38 g of diphenyldiazomethane in ethyl acetate is then added, maintaining the temperature at approximately 5° C. (41° F.). The mixture is stirred for approximately 4 hours. The mixture is then concentrated to dryness, and THF is added, with removal of some insoluble material by filtration. The filtrate is concentrated to a small volume to yield crystals, and ethyl acetate added. The mixture is cooled in an ice bath for approximately 1.5 hours and the product (II) collected by filtration.

A solution of approximately 0.4 g of Product (II), in dichloromethane, is cooled in an ice bath and approximately 0.112 ml 1,2,2,2,-tetrachloroethyl chloroformate is added, followed by the dropwise addition of approximately 0.067 ml pyridine. The reaction is stirred for 35 minutes, then diluted with dichloromethane and washed with ice cold 0.5N HCl and cold water. The organic phase is dried over $Na_2SO_4$, filtered, and concentrated to dryness, yielding product (III).

A mixture of approximately 0.24 g ciprofloxacin (IV) in water and $NaHCO_3$ is heated to approximately 45° C. (113° F.), and stirred for approximately 30 minutes. To this mixture, in a water bath at approximately 19° C. (66° F.), is added a solution of approximately 0.52 g of product (III) in dioxane. The mixture is stirred at approximately 22° C. (44° F.) for approximately 1.5 hours, diluted with ether and water and separated. The aqueous phase is cooled to approximately 5° C. (41° F.), chloroform is added, and the mixture is acidified with HCl. The chloroform extract is washed with 0.5N HCl and water, then dried over $Na_2SO_4$, filtered and concentrated to dryness, yielding product (V).

To a solution of approximately 0.31 g of Product (VI), in anisole, is added approximately 7 ml of trifluoroacetic acid, dropwise at approximately −15° C. (5° F.). The solution is stirred at ambient temperature for approximately 20 minutes, and concentrated to dryness in vacuo. The residue is stirred for approximately 2 hours in ether, and the product is collected by filtration. This free acid is dissolved in water, followed by addition of $NaHCO_3$, with stirring, for approximately 40 minutes. The solution is filtered, and washed with a small amount of DMF to dissolve some solid. The filtrate is then concentrated in vacuo and the solid dissolved in water. The solution is diluted with about 2.5 volumes of acetone and the final product (V) collected by filtration.

Similarly, the following lactam-quinolones are prepared by the general procedure of this Example, with substantially similar results.

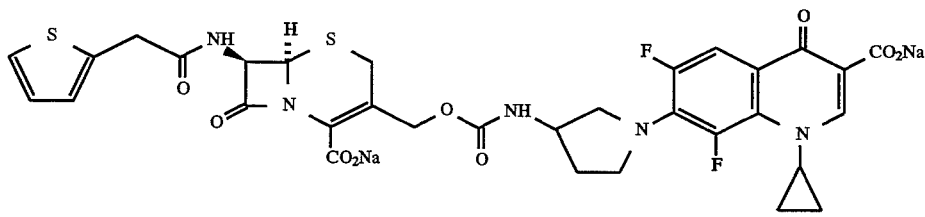

using the quinolone 7-(3-aminopyrrolidinyl)-1-cyclopropyl-6,8-difluoro-1,4-dihydro-4-oxo-3-quinoline carboxylic acid (prepared according to J. P. Sanchez, et al., 31 *J. Med. Chem.* 983 (1988))

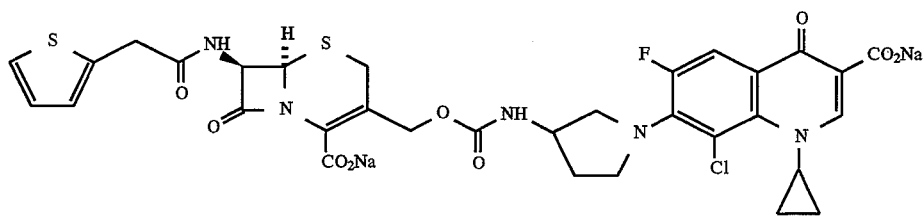

using the quinolone 7-(3-aminopyrrolidinyl)-8-chloro-1-cyclopropyl-6-fluoro-1,4-dihydro-4-oxo-3-quinoline carboxylic acid (prepared according to J. P. Sanchez, et al., 31 *J. Med. Chem.* 983 (1988))

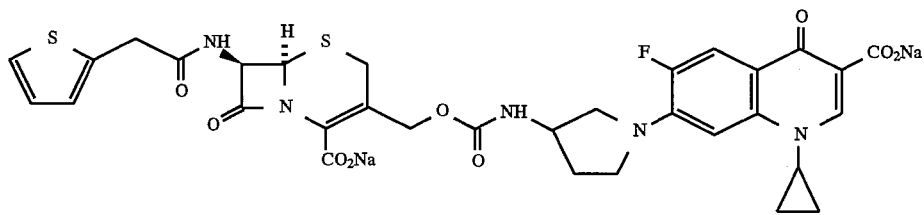

using the quinolone 7-(3-aminopyrrolidinyl)-1-cyclopropyl-6-fluoro-1,4-dihydro-4-oxo-3-quinoline carboxylic acid (prepared according to J. P. Sanchez, et al., 31 *J. Med. Chem.* 983 (1988))

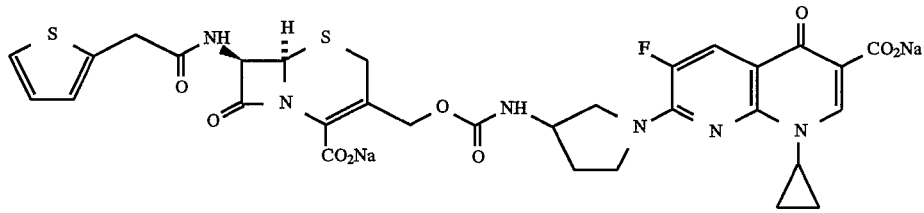

using the naphthyridinone 7-(3-aminopyrrolidinyl)-1-cyclopropyl-6-fluoro-1,4-dihydro-4-oxo-1,8-naphthyridine-3-carboxylic acid (prepared according to J. P. Sanchez, et al., 31 *J. Med. Chem.* 983 (1988))

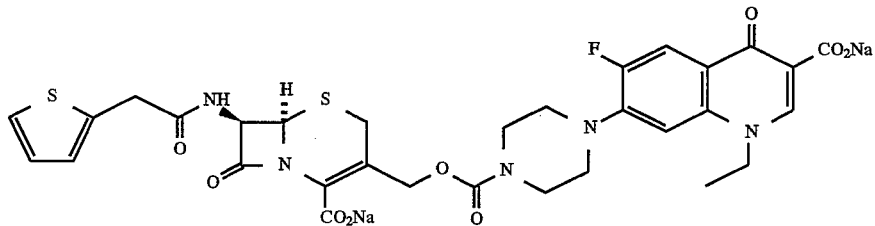

except using the quinolone 1-ethyl-6-fluoro-1,4-dihydro-4-oxo-7-(1-piperazinyl)-3-quinoline carboxylic acid (prepared according to H. Koga, et al., 23 *J. Med. Chem.* 1358 (1980))

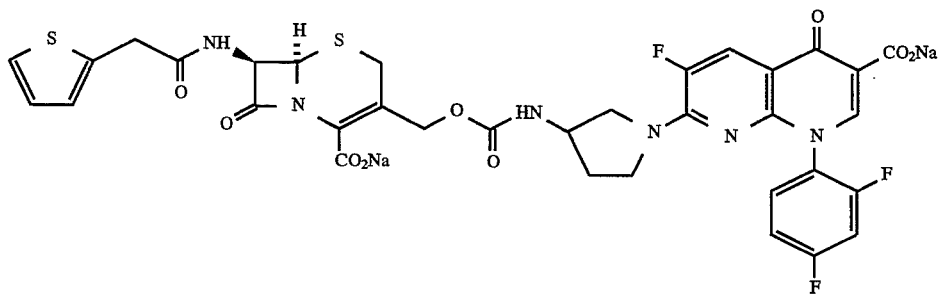

using the naphthyridinone 7-(3-aminopyrrolidinyl)-1-(2,4-difluorophenyl)-6-fluoro-1,4-dihydro-4-oxo-1,8-naphthyridine-3-carboxylic acid (prepared according to D. T. W. Chu, et al., 29 *J. Med. Chem.* 2363 (1986))

using the quinolone 9-fluoro-4,7-dihydro-3-methyl-10-(1-piperazinyl)-7-oxo-2H-pyrido[1,2,3-de]-1,4-benzoxazine-6-carboxylic acid (prepared according to I. Hayakawa, et al., 32 *Chem, Pharm. Bull.* 4907 (1984))

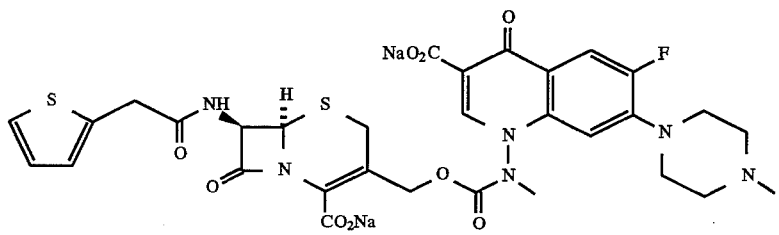

using the quinolone 6-fluoro-1,4-dihydro-1-methylamino-7-(4-methyl-1-piperazinyl)-4-oxo-3-quinoline carboxylic acid (prepared according to M. P. Wentland, et al., 27 *J. Med. Chem.* 1103 (1984))

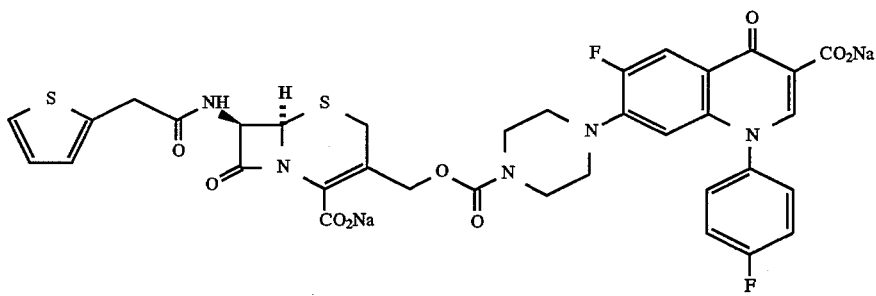

using the quinolone 6-fluoro-1-(4-fluorophenyl)-1,4-dihydro-4-oxo-7-(1-piperazinyl)-3-quinoline carboxylic acid (prepared according to D. T. W. Chu, et al., 28 *J. Med. Chem.* 1558 (1985))

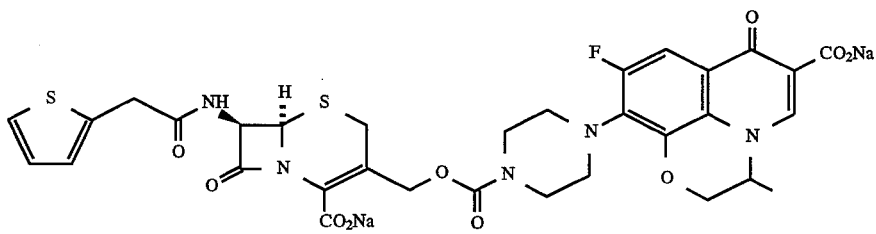

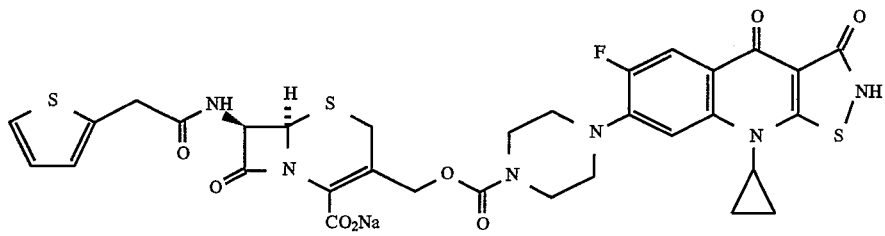

using the quinolone 9-cyclopropyl-6-fluoro-2,3,4,9-tetrahydro-7-(1-piperazinyl)isothiazolo[5,4-b]quinoline-3,4-dione (prepared according to D. T. W. Chu, European Patent Application 227,088)

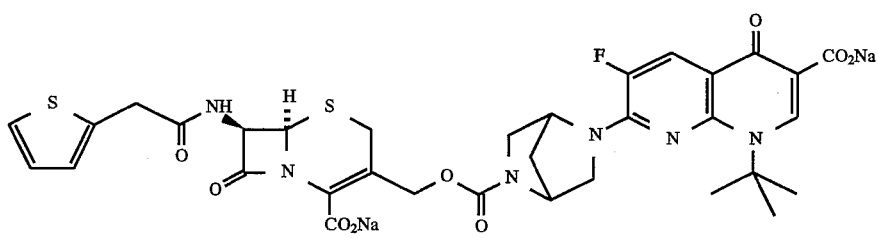

using the naphthyridinone 7-(2,5-diazabicyclo[2.2.1]heptan-2-yl)-1-(1,1-dimethylethyl)-6-fluoro-1,4-dihydro-4-oxo-1,8-naphthyridine-3-carboxylic acid (prepared according to A. Weber, et al., European Patent Application 266576)

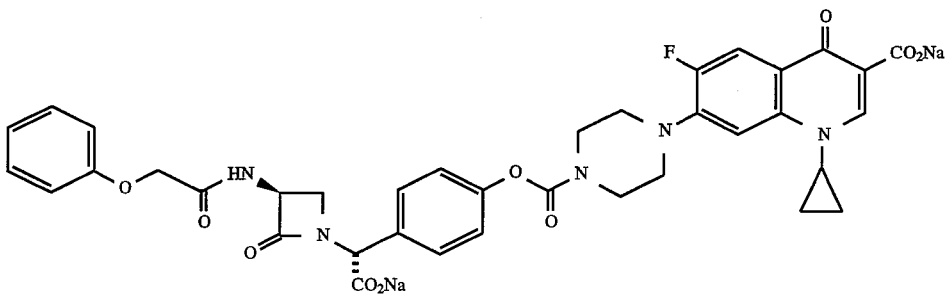

using the beta-lactam alpha-(4-hydroxyphenyl)-2-oxo-3-[(phenoxyacetyl)amino]-1-azetidineacetic acid (prepared according to M. Hashimoto, et al., U.S. Pat. No. 4,207,234)

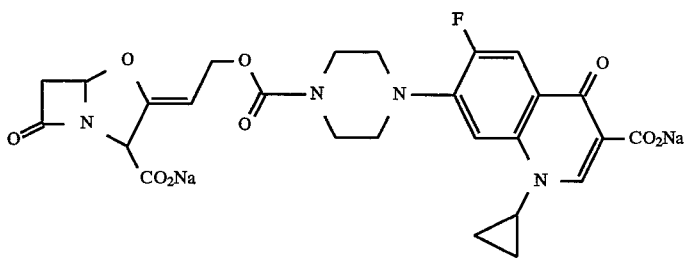

using the beta-lactam 3-(2-hydroxyethylidene)-7-oxo-4-oxa-1-azabicyclo[3.2.0]heptane-2-carboxylic acid (prepared according to P. H. Bentley, et al., Tet. Let. 1889 (1979))

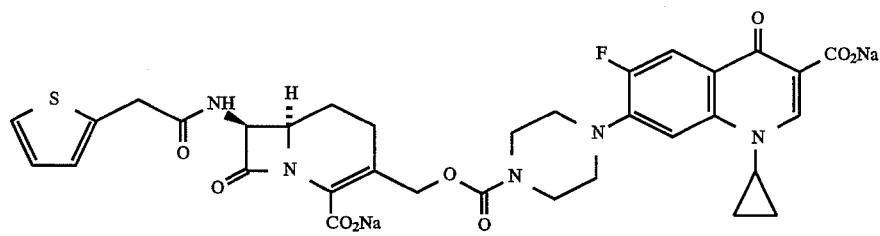

using the beta-lactam 3-(hydroxymethyl)-8-oxo-7-[[(2-thiophene) acetyl]amino)-1-azabicyclo[4.2.0]oct-2-ene-2-carboxylic acid (prepared according to B. G. Christensen, et al., German Offen. 2355209)

methoximino]acetyl]amino]-1-azabicyclo[4.2.0]oct-2-ene-2-carboxylic acid (prepared according to S. Kishimoto, et al., European Patent Application 249,170)

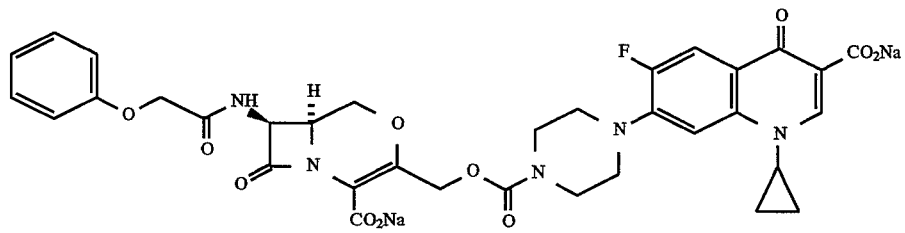

using the beta-lactam 3-(hydroxymethyl)-8-oxo-7-[(phenoxyacetyl) amino]-4-oxa-1-azabicyclo[4.2.0]oct-2-ene-2-carboxylic acid (prepared according to M. Menard, German Offen. 2615693)

The following other lactam-quinolones are made by the general procedure of this Example with substantially similar results.

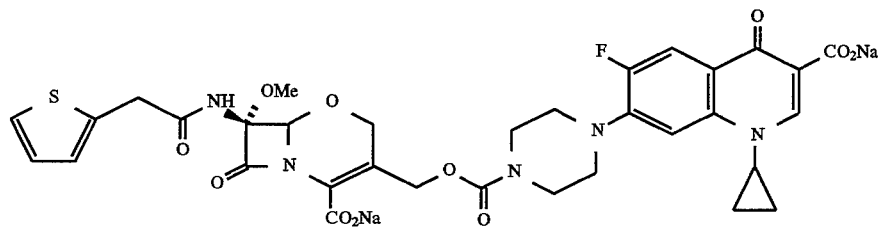

using the beta-lactam 3-(hydroxymethyl)-7-methoxy-8-oxo-7-[[(2-thiophene) acetyl]amino]-5-oxa-1-azabicyclo[4.2.0] oct-2-ene-2-carboxylic acid (prepared according to B. G. Christensen, German Offen. 2355209).

EXAMPLE 2

According to the general procedure of Example 1, the following lactam-quinolone is made:

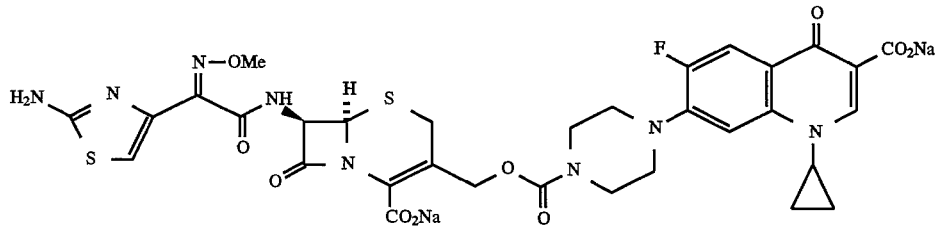

except using the beta-lactam 3-(hydroxymethyl)-8-oxo-5-thia-7-[[[[[(2-triphenylmethyl)amino]-4-thiazolyl]

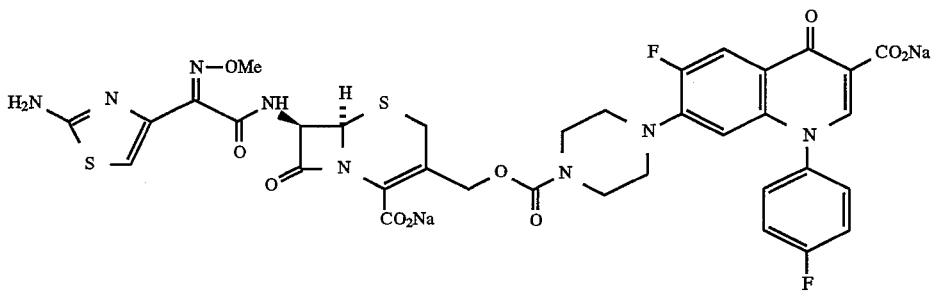

using the quinolone 6-fluoro-1-(4-fluorophenyl)-1,4-dihydro-4-oxo-7-(1-piperazinyl)-3-quinoline carboxylic acid (prepared according to D. T. W. Chu, et al., 28 *J. Med. Chem.* 1558 (1985))

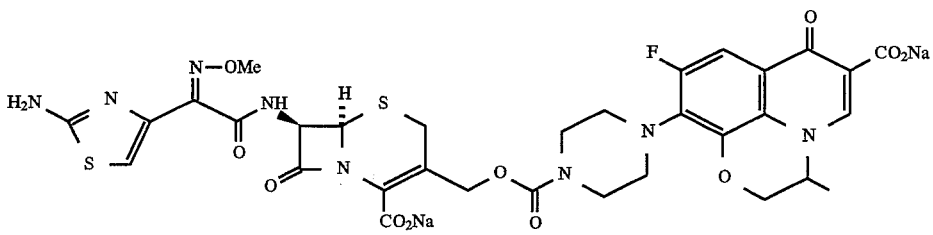

using the quinolone 9-fluoro-4,7-dihydro-3-methyl-10-(1-piperazinyl)-7-oxo-2H-pyrido[1,2,3-de]-1,4-benzoxazine-6-carboxylic acid (prepared according to I. Hayakawa, et al., 32 *Chem. Pharm. Bull.* 4907 (1984))

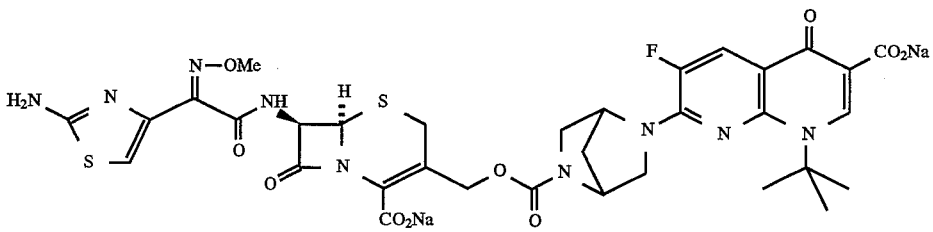

using the naphthyridinone 7-(2,5-diazabicyclo[2.2.1]heptan-2-yl)-1-(1,1-dimethylethyl)-6-fluoro-1,4-dihydro-4-oxo-1,8-naphthyridine-3-carboxylic acid (prepared according to A. Weber, et al., European Patent Application 266576)

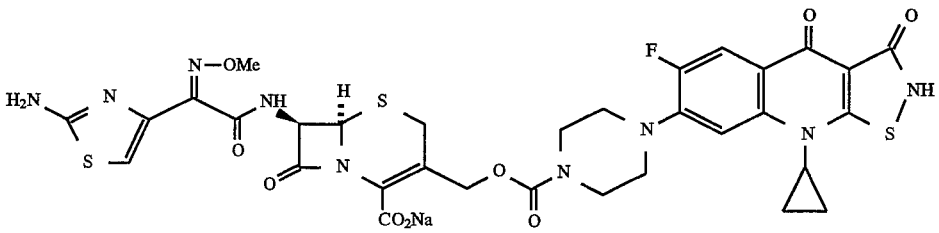

using the quinolone 9-cyclopropyl-6-fluoro-2,3,4,9-tetrahydro-7-(1-piperazinyl)isothiazolo[5,4-b]quinoline-3,4-dione (prepared according to D. T. W. Chu, European Patent Application 227,088)

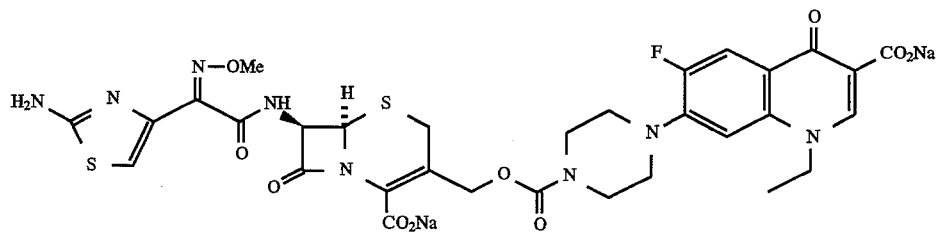

using the quinolone 1-ethyl-6-fluoro-1,4-dihydro-4-oxo-7-(1-piperazinyl)-3-quinoline carboxylic acid (prepared according to H. Koga, et al., 23 *J. Med. Chem.* 1358 (1980))

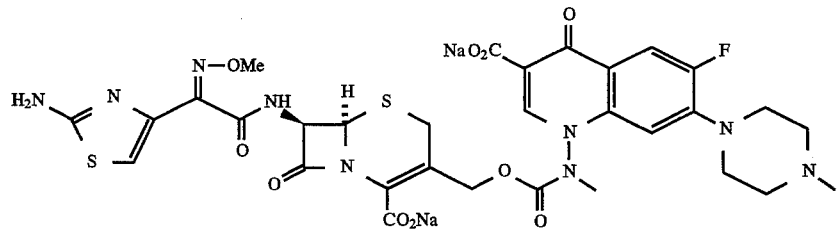

using the quinolone 6-fluoro-1,4-dihydro-1-methylamino-7-(4-methyl-1-piperazinyl)-4-oxo-3-quinoline carboxylic acid (prepared according to M. P. Wentland, et al., 27 *J. Med. Chem.* 1103 (1984))

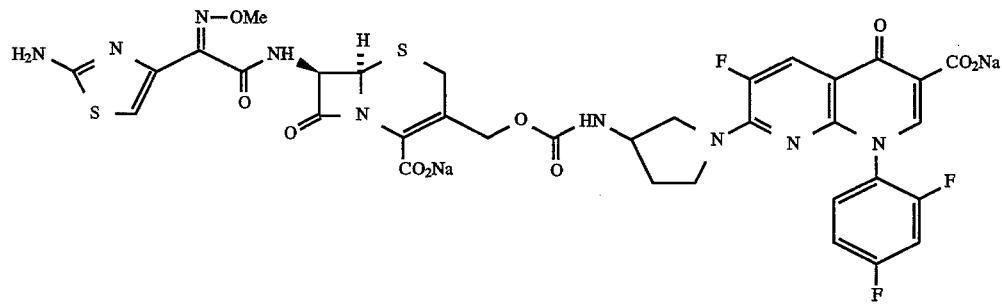

using the naphthyridinone 7-(3-aminopyrrolidinyl)-1-(2,4-difluorophenyl)-6-fluoro-1,4-dihydro-4-oxo-1,8-naphthyridine-3-carboxylic acid (prepared according to D. T. W. Chu, et al., 29 *J. Med. Chem.* 2363 (1986))

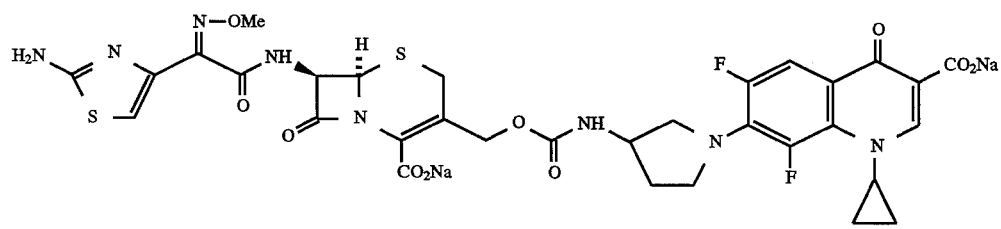

using the quinolone 7-(3-aminopyrrolidinyl)-1-cyclopropyl-6,8-difluoro-1,4-dihydro-4-oxo-3-quinoline carboxylic acid (prepared according to J. P. Sanchez, et al., 31 *J. Med. Chem.* 983 (1988))

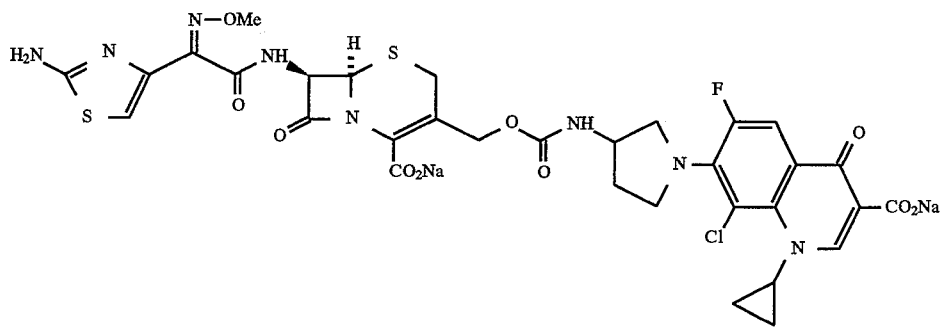

using the quinolone 7-(3-aminopyrrolidinyl)-8-chloro-1-cyclopropyl-6-fluoro-1,4-dihydro-4-oxo-3-quinoline carboxylic acid (prepared according to J. P. Sanchez, et al., 31 *J. Med. Chem.* 983 (1988))

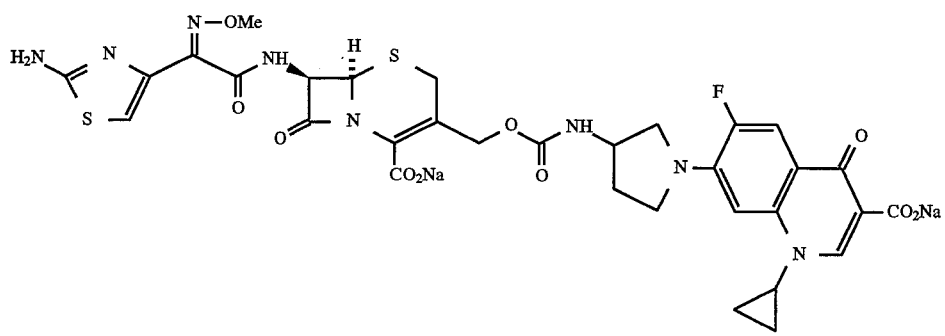

using the quinolone 7-(3-aminopyrrolidinyl)-1-cyclopropyl-6-fluoro-1,4-dihydro-4-oxo-3-quinoline carboxylic acid (prepared according to J. P. Sanchez, et al., 31 *J. Med. Chem.* 983 (1988))

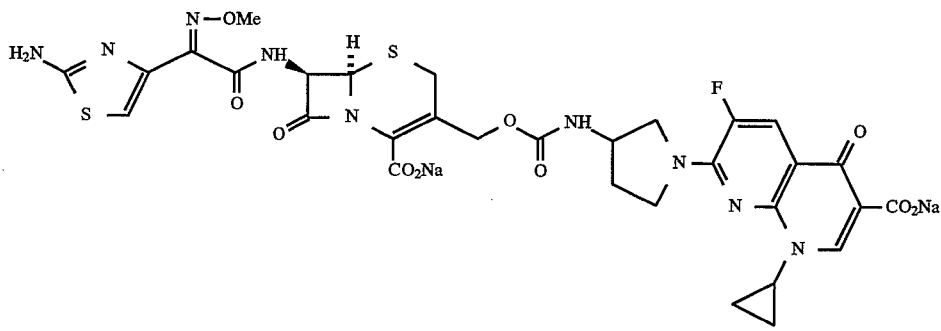

using the naphthyridinone 7-(3-aminopyrrolidinyl)-1-cyclopropyl-6-fluoro-1,4-dihydro-4-oxo-1,8-naphthyridine-3-carboxylic acid (prepared according to J. P. Sanchez, et al., 31 *J. Med. Chem.* 983 (1988))

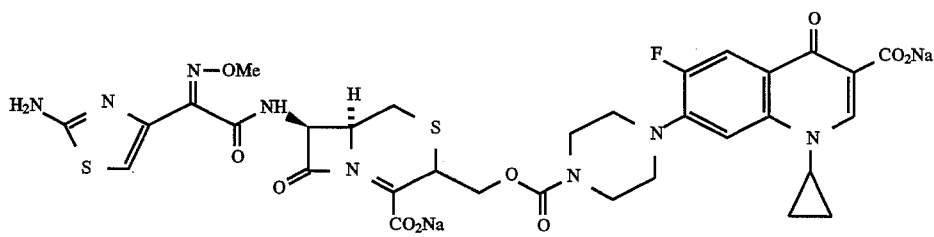

using the beta-lactam t-butyl 3-(hydroxymethyl)-8-oxo-7-[[[[(2-triphenylmethylamino)-4-thiazolyl]methoximino]acetyl]amino]-4-thia-1-azabicyclo[4.2.0]oct-2-ene-2-carboxylate (prepared according to J. G. Teutsch, European Patent Application 153,229)

EXAMPLE 3

According to the general procedure of Example 1, the following lactam-quinolone is made:

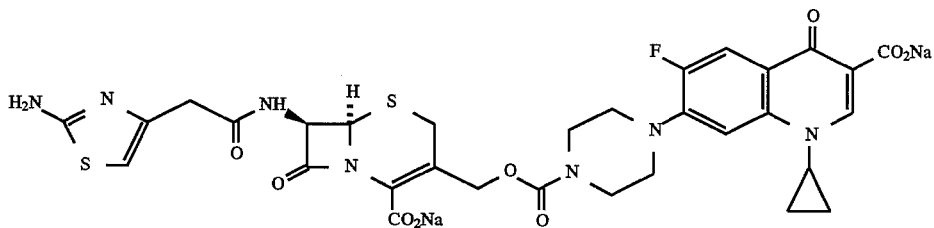

using the beta-lactam 3-(hydroxymethyl)-8-oxo-5-thia-7-[[[(2-triphenylmethylamino)-4-thiazolyl]acetyl]amino]-1-azabicyclo [4.2.0]oct-2-ene-2-carboxylic acid (prepared according to M. Vignau, German Offen. 2704712)

The following other lactam-quinolones are made by the general procedure of this Example, with substantially similar results.

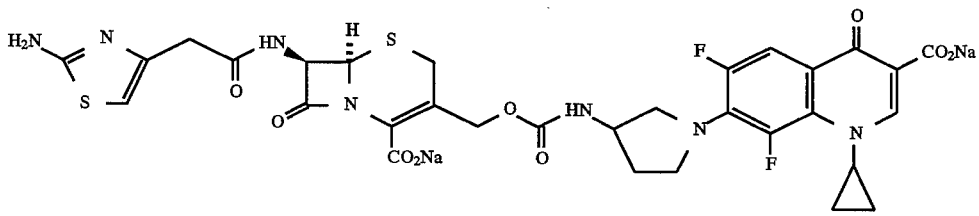

using the quinolone 7-(3-aminopyrrolidinyl)-1-cyclopropyl-6,8-difluoro-1,4-dihydro-4-oxo-3-quinoline carboxylic acid (prepared according to J. P. Sanchez, et al., 31 *J. Med. Chem.* 983 (1988))

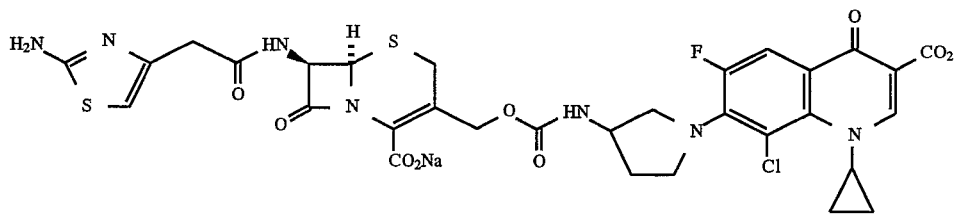

using the quinolone 7-(3-aminopyrrolidinyl)-8-chloro-1-cyclopropyl-6-fluoro-1,4-dihydro-4-oxo-3-quinoline carboxylic acid (prepared according to J. P. Sanchez, et al., 31 *J. Med. Chem.* 983 (1988))

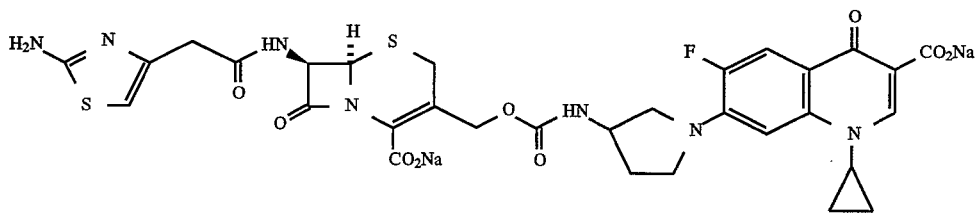

using the quinolone 7-(3-aminopyrrolidinyl)-1-cyclopropyl-6-fluoro-1,4-dihydro-4-oxo-3-quinoline carboxylic acid (prepared according to J. P. Sanchez, et al., 31 *J. Med. Chem.* 983 (1988))

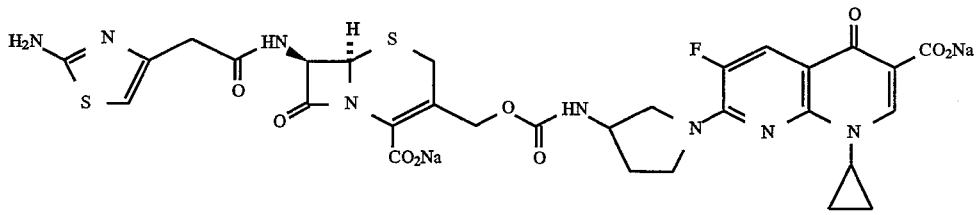

05650517 using the naphthyridinone 7-(3-aminopyrrolidinyl)-1-cyclopropyl-6-fluoro-1,4-dihydro-4-oxo-1,8-naphthyridine-3-carboxylic acid (prepared according to J. P. Sanchez, et al., 31 *J. Med. Chem.* 983 (1988))

except using the beta-lactam 3-(hydroxymethyl)-8-oxo-7-[(phenoxyacetyl)amino]-5-thia-1-azabicyclo[4.2.0]oct-2-ene-2-carboxylic acid (prepared according to K. Fujimoto, et al., 40 *J. Antibiotics* 370 (1987))

EXAMPLE 4

According to the general procedure of Example 1, the following lactam-quinolone is made:

The following other lactam-quinolones are made by the general procedure of this Example, with substantially similar results.

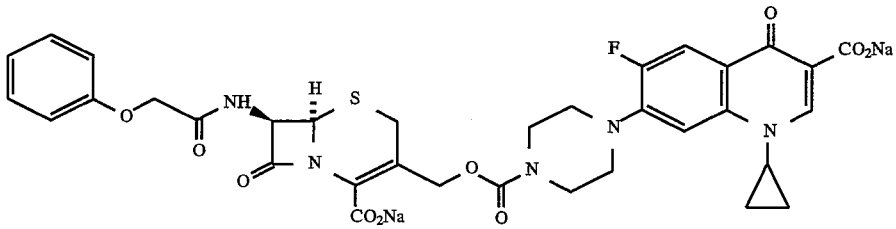

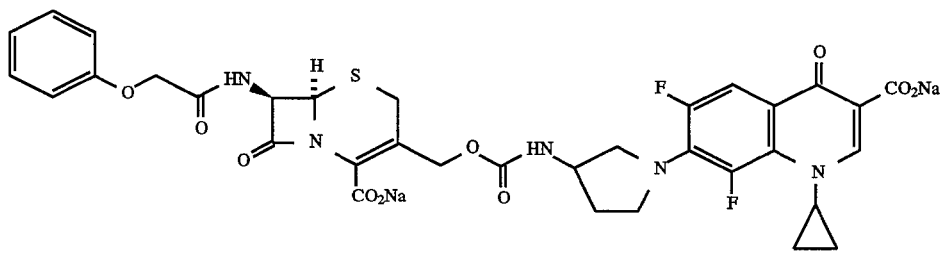

using the quinolone 7-(3-aminopyrrolidinyl)-1-cyclopropyl-6,8-difluoro-1,4-dihydro-4-oxo-3-quinoline carboxylic acid (prepared according to J. P. Sanchez, et al., 31 *J. Med. Chem.* 983 (1988))

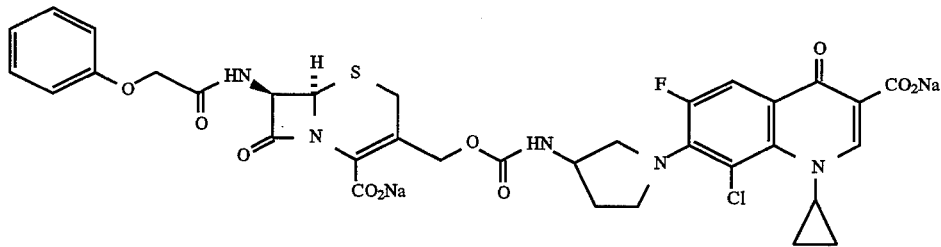

using the quinolone 7-(3-aminopyrrolidinyl)-8-chloro-1-cyclopropyl-6-fluoro-1,4-dihydro-4-oxo-3-quinoline carboxylic acid (prepared according to J. P. Sanchez, et al., 31 *J. Med. Chem.* 983 (1988))

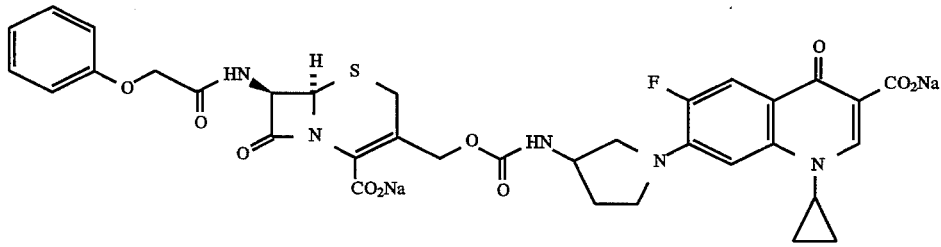

using the quinolone 7-(3-aminopyrrolidinyl)-1-cyclopropyl-6-fluoro-1,4-dihydro-4-oxo-3-quinoline carboxylic acid (prepared according to J. P. Sanchez, et al., 31 *J. Med. Chem.* 983 (1988))

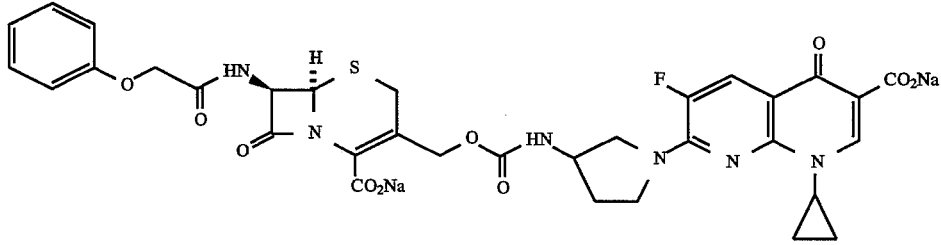

using the naphthyridinone 7-(3-aminopyrrolidinyl)-1-cyclopropyl-6-fluoro-1,4-dihydro-4-oxo-1,8-naphthyridine-3-carboxylic acid (prepared according to J. P. Sanchez, et al., 31 *J. Med. Chem.* 983 (1988))

EXAMPLE 5

According to the general procedure of Example 1, the following lactam-quinolone is made:

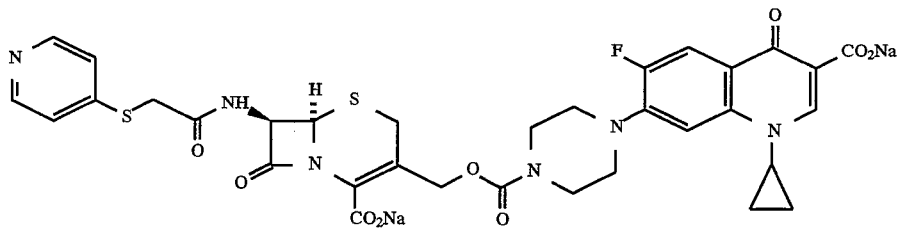

except using the beta-lactam 3-(hydroxymethyl)-8-oxo-7-[(4-pyridylthioacetyl)amino]-5-thia-1-azabicyclo[4.2.0]oct-2-ene-2-carboxylic acid (prepared according to E. J. Richardson, German Offen. 2152820)

The following other lactam-quinolones are made by the general procedure of this Example, with substantially similar results.

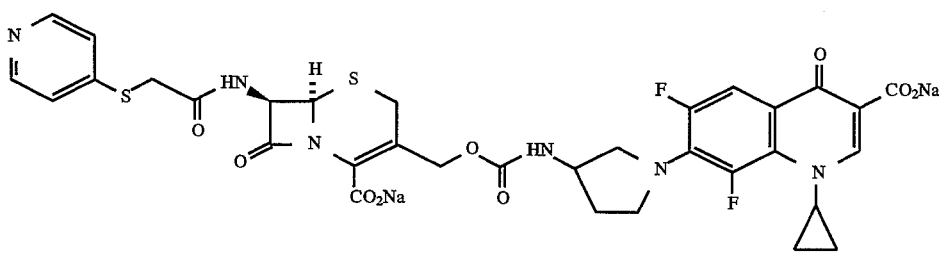

using the quinolone 7-(3-aminopyrrolidinyl)-1-cyclopropyl-6,8-difluoro-1,4-dihydro-4-oxo-3-quinoline carboxylic acid (prepared according to J. P. Sanchez, et al., 31 *J. Med. Chem.* 983 (1988))

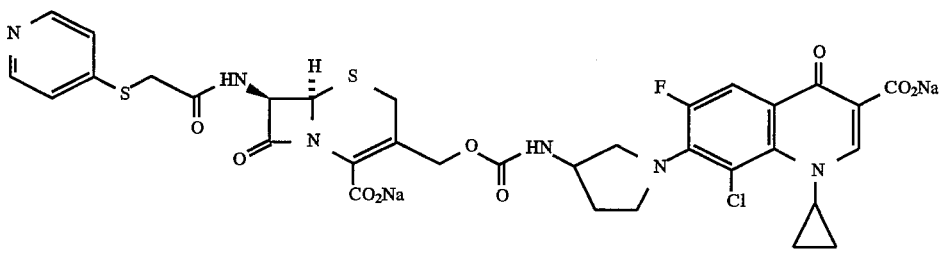

using the quinolone 7-(3-aminopyrrolidinyl)-8-chloro-1-cyclopropyl-6-fluoro-1,4-dihydro-4-oxo-3-quinoline carboxylic acid (prepared according to J. P. Sanchez, et al., 31 *J. Med. Chem.* 983 (1988))

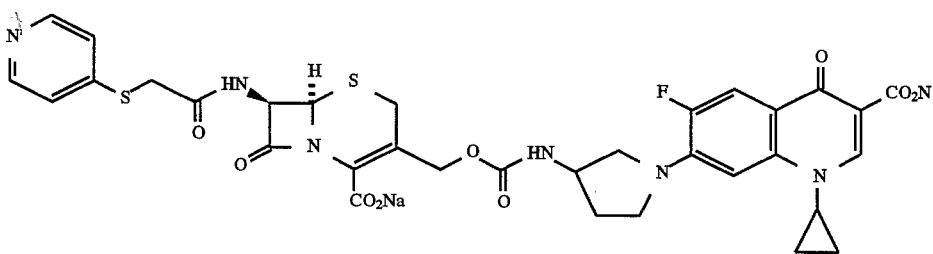

using the quinolone 7-(3-aminopyrrolidinyl)-1-cyclopropyl-6-fluoro-1,4-dihydro-4-oxo-3-quinoline carboxylic acid (prepared according to J. P. Sanchez, et al., 31 *J. Med. Chem.* 983 (1988))

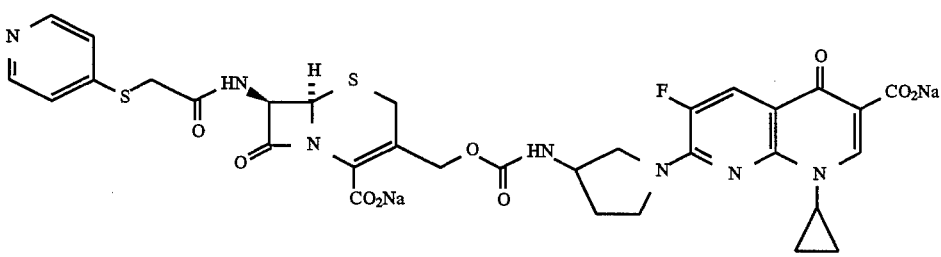

using the naphthyridinone 7-(3-aminopyrrolidinyl)-1-cyclopropyl-6-fluoro-1,4-dihydro-4-oxo-1,8-naphthyridine-3-carboxylic acid (prepared according to J. P. Sanchez, et al., 31 *J. Med. Chem.* 983 (1988))

EXAMPLE 6

According to the general procedure of Example 1, the following lactam-quinolone is made:

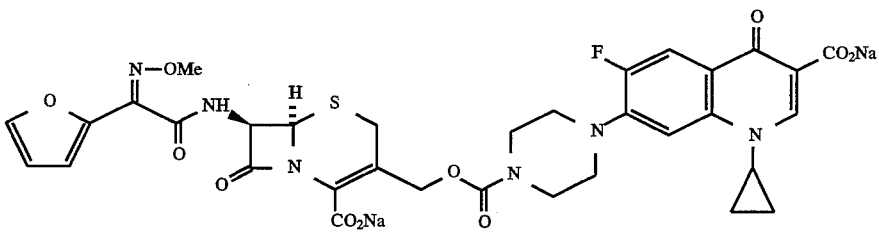

using the beta-lactam 3-(hydroxymethyl)-7-[[2-furanylmethoxy imino)acetyl]amino]-8-oxo-5-thia-1-azabicyclo[4.2.0]oct-2-ene-2-carboxylic acid (prepared according to T. Tsuji, European Patent Application 204,517)

The following other lactam-quinolones are made by the general procedure of this Example, with substantially similar results.

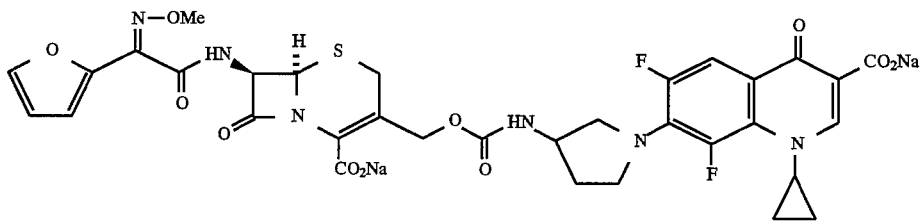

using the quinolone 7-(3-aminopyrrolidinyl)-1-cyclopropyl-6,8-difluoro-1,4-dihydro-4-oxo-3-quinoline carboxylic acid (prepared according to J. P. Sanchez, et al., 31 *J. Med. Chem.* 983 (1988))

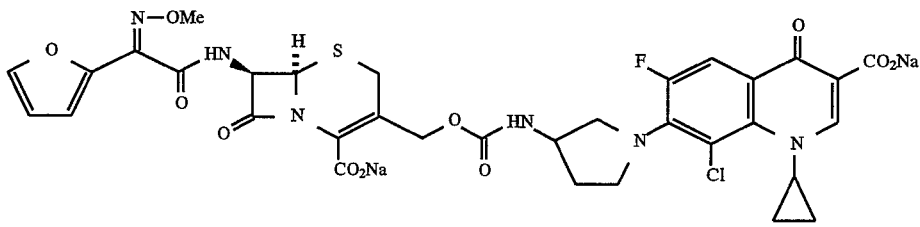

using the quinolone 7-(3-aminopyrrolidinyl)-8-chloro-1-cyclopropyl-6-fluoro-1,4-dihydro-4-oxo-3-quinoline carboxylic acid (prepared according to J. P. Sanchez, et al., 31 *J. Med. Chem.* 983 (1988))

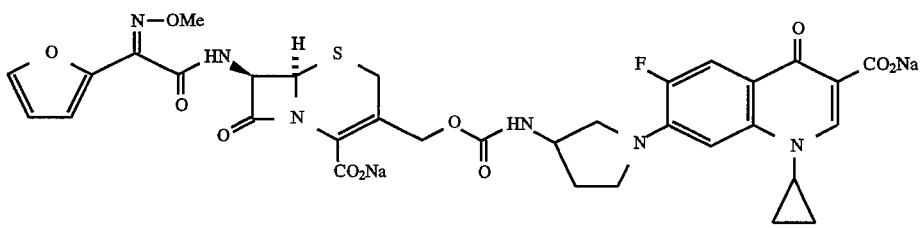

using the quinolone 7-(3-aminopyrrolidinyl)-1-cyclopropyl-6-fluoro-1,4-dihydro-4-oxo-3-quinoline carboxylic acid (prepared according to J. P. Sanchez, et al., 31 *J. Med. Chem.* 983 (1988))

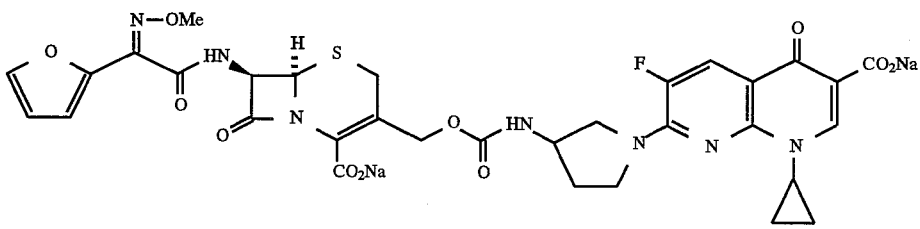

using the naphthyridinone 7-(3-aminopyrrolidinyl)-1-cyclopropyl-6-fluoro-1,4-dihydro-4-oxo-1,8-naphthyridine-3-carboxylic acid (prepared according to J. P. Sanchez, et al., 31 *J. Med. Chem.* 983 (1988))

EXAMPLE 7

According to the general procedure of Example 1, the following lactam-quinolone is made:

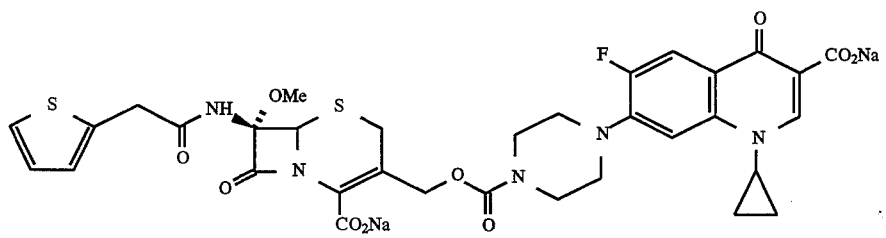

using the beta-lactam 3-(hydroxymethyl)-7-methoxy-8-oxo-5-thia-7-[[(2-thiophene)acetyl]amino]-1-azabicyclo[4.2.0]oct-2-ene-2-carboxylic acid (prepared according to B. G. Christensen, et al., German Offen. 2203653)

The following other lactam-quinolones are made by the general procedure of this Example, with substantially similar results.

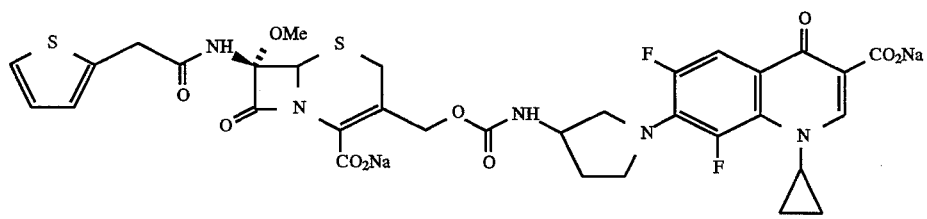

using the quinolone 7-(3-aminopyrrolidinyl)-1-cyclopropyl-6,8-difluoro-1,4-dihydro-4-oxo-3-quinoline carboxylic acid (prepared according to J. P. Sanchez, et al., 31 *J. Med. Chem.* 983 (1988))

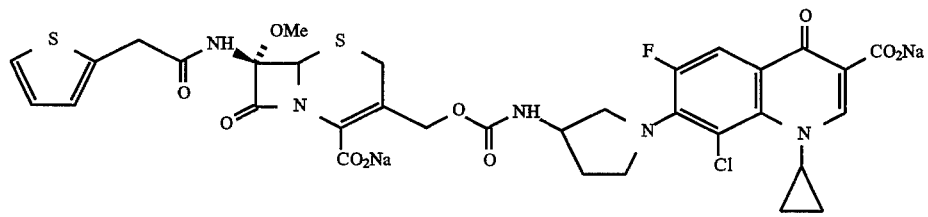

using the quinolone 7-(3-aminopyrrolidinyl)-8-chloro-1-cyclopropyl-6-fluoro-1,4-dihydro-4-oxo-3-quinoline carboxylic acid (prepared according to J. P. Sanchez, et al., 31 *J. Med. Chem.* 983 (1988))

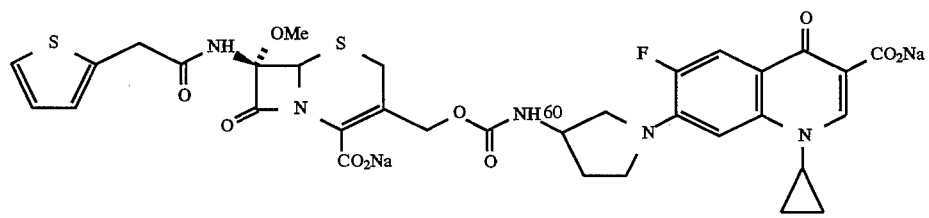

using the quinolone 7-(3-aminopyrrolidinyl-1-cyclopropyl-6-fluoro-1,4-dihydro-4-oxo-3-quinoline carboxylic acid (prepared according to J. P. Sanchez, et al., 31 *J. Med. Chem.* 983 (1988))

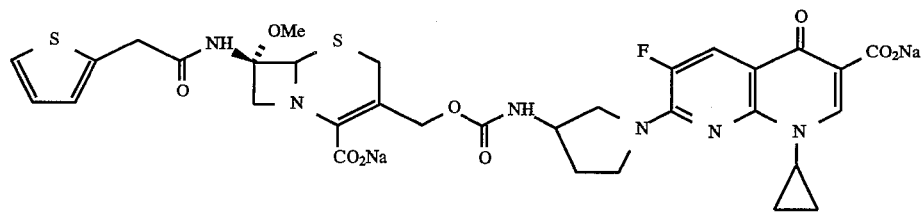

using the naphthyridinone 7-(3-aminopyrrolidinyl)-1-cyclopropyl-6-fluoro-1,4-dihydro-4-oxo-1,8-naphthyridine-3-carboxylic acid (prepared according to J. P. Sanchez, et al., 31 *J. Med. Chem.* 983 (1988))

EXAMPLE 8

[5R-[5α,6α]]-3-[[[4-(3-Carboxy-1-cyclopropyl-6-fluoro-1,4-dihydro-4-oxo-7-quinolinyl)-1-piperazinyl]carbonyloxy]methyl]-6-[(R)-1-hydroxyethyl]-7-oxo-4-thia-1-azabicyclo[3.2.0]hept-2-ene-2-carboxylic Acid Disodium Salt

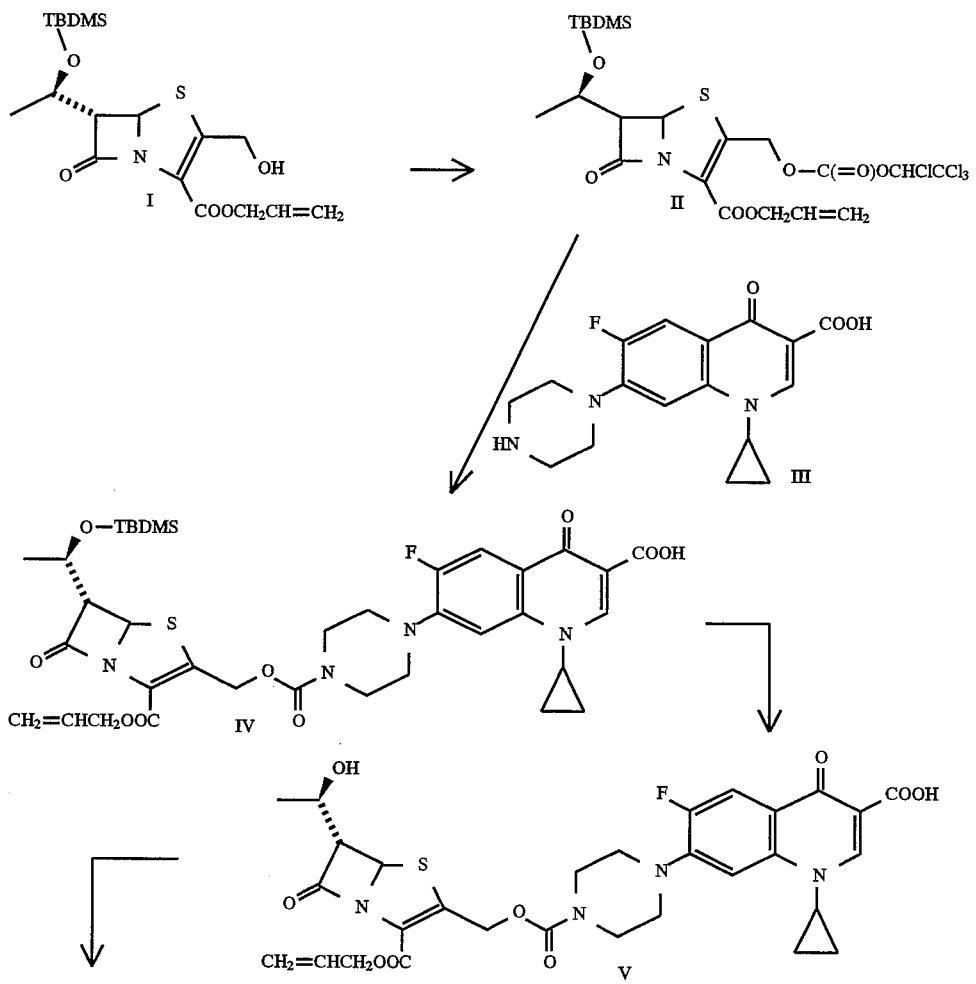

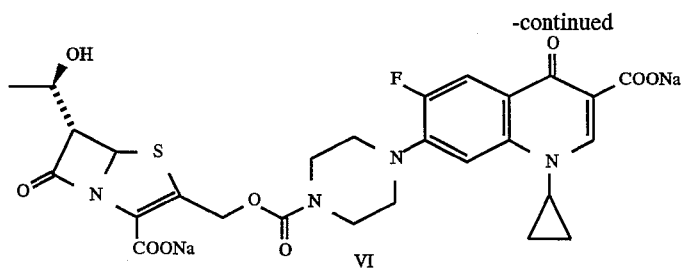

To a solution of [5R-[5α,6α]]-3-(hydroxymethyl)-6-[(R)-1-(t-butyldimethyl-silyloxy)ethyl]-7-oxo-4-thia-1-azabicyclo[3.2.0]-hept-2-ene-2-carboxylic acid allyl ester I (approximately 3.9 g) (prepared according to U.S. Pat. No. 4,631,150) in THF (40 ml) at 0° C. is added approximately 1.5 ml of 1,2,2,2-tetrachloroethyl chloroformate followed by the dropwise addition of pyridine (approximately 0.9 ml). The mixture is stirred for approximately 35 minutes and the tetrachlorocarbonate II is added to a mixture of ciprofloxacin III (approximately 2.9 g) in water (40 ml) and NaHCO₃ (4.4 g) at room temperature. After approximately 40 minutes the reaction is cooled to 2° C. and is diluted with cold 0.1N HCl. The mixture is extracted with chloroform, the organic phase is washed with water and brine, dried over Na₂SO₄, filtered and is concentrated to dryness to give IV. To a mixture of approximately 3.0 g of IV, 26 ml of THF and 2.1 ml of glacial acetic acid at room temperature is added approximately 3.6 g of tetrabutylammonium fluoride trihydrate. The mixture is stirred for approximately 36 hours, concentrated to dryness and the residue is purified by flash chromatography (silica gel) to afford V. To a near solution of V (approximately 1.6 g), THF (70 ml) and triphenylphosphine (approximately 0.08 g) is added sodium 2-ethylhexanoate (approximately 1.1 g). To this clear solution is added tetrakis triphenylphosphine palladium(0) (approximately 0.08 g) and after stirring 30 minutes, the product is collected by filtration and purified by C-18 reverse phase chromatography to give VI.

Similarly, the following lactam-quinolones are prepared by the general procedure of this Example, with substantially similar results.

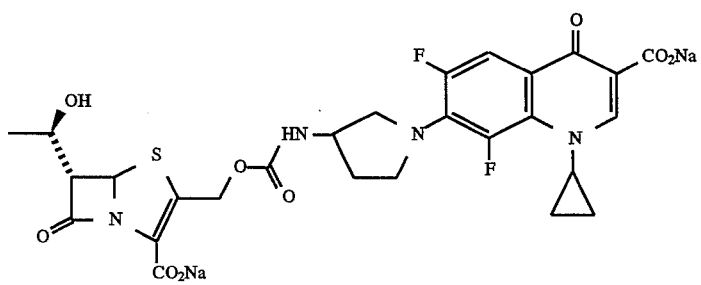

using the quinolone 7-(3-aminopyrrolidinyl)-1-cyclopropyl-6,8-difluoro-1,4-dihydro-4-oxo-3-quinoline carboxylic acid (prepared according to J. P. Sanchez, et al., 31 *J. Med. Chem.* 983 (1988))

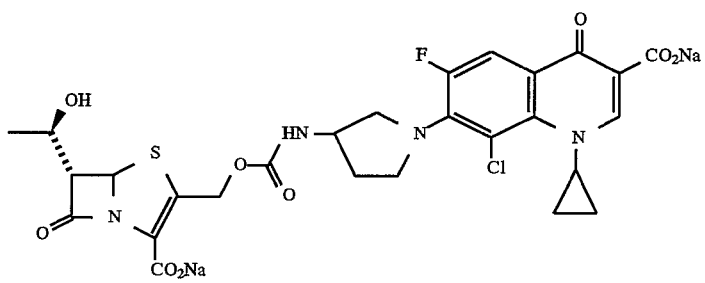

using the quinolone 7-(3-aminopyrrolidinyl)-8-chloro-1-cyclopropyl-6-fluoro-1,4-dihydro-4-oxo-3-quinoline carboxylic acid (prepared according to J. P. Sanchez, et al., 31 *J. Med. Chem.*, 983 (1988))

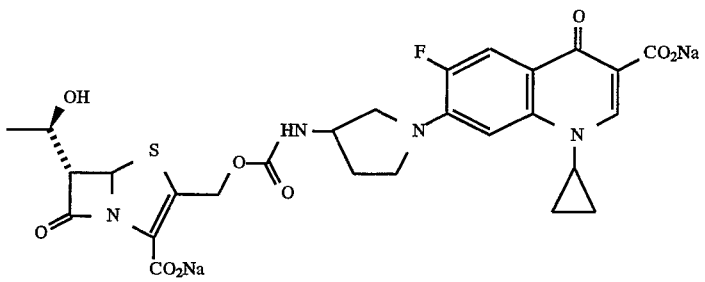

using the quinolone 7-(3-aminopyrrolidinyl)-1-cyclopropyl-6-fluoro-1,4-dihydro-4-oxo-3-quinoline carboxylic acid (prepared according to J. P. Sanchez, et al., 31 *J. Med. Chem.* 983 (1988))

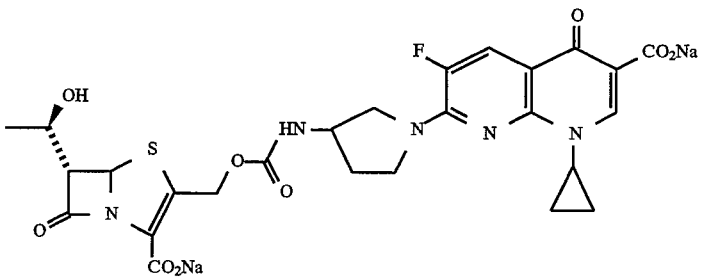

using the naphthyridinone 7-(3-aminopyrrolidinyl)-1-cyclopropyl-6-fluoro-1,4-dihydro-4-oxo-1,8-naphthyridine-3-carboxylic acid (prepared according to J. P. Sanchez, et al., 31 *J. Med. Chem.* 983 (1988))

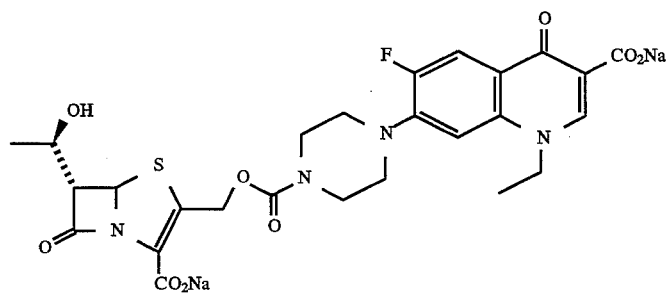

using the quinolone 1-ethyl-6-fluoro-1,4-dihydro-4-oxo-7-(1-piperazinyl)-3-quinoline carboxylic acid (prepared according to H. Koga, et al., 23 *J. Med. Chem.* 1358 (1980))

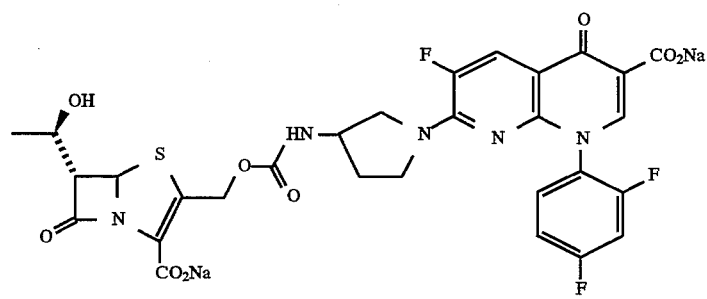

using the naphthyridinone 7-(3-aminopyrrolidinyl)-1-(2,4-difluorophenyl)-6-fluoro-1,4-dihydro-4-oxo-1,8-naphthyridine-3-carboxylic acid (prepared according to D. T. W. Chu, et al., 29 *J. Med. Chem.* 2363 (1986))

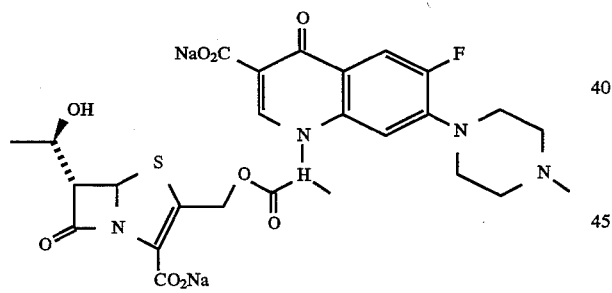

using the quinolone 6-fluoro-1,4-dihydro-1-methylamino-7-(4-methyl-1-piperazinyl)-4-oxo-3-quinoline carboxylic acid (prepared according to M. P. Wentland, et al., 27 *J. Med. Chem.* 1103 (1984))

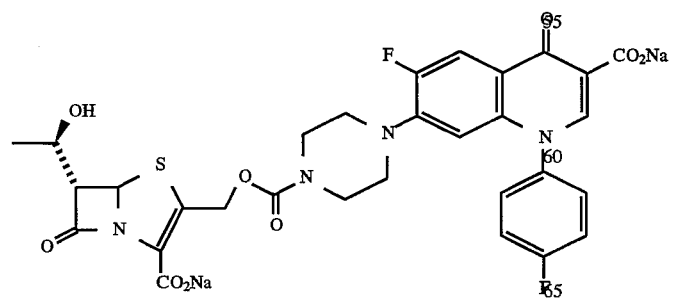

using the quinolone 6-fluoro-1-(4-fluorophenyl)-1,4-dihydro-4-oxo-7-(1-piperazinyl)-3-quinoline carboxylic acid (prepared according to D. T. W. Chu, et al., 28 J. Med. Chem. 1558 (1985))

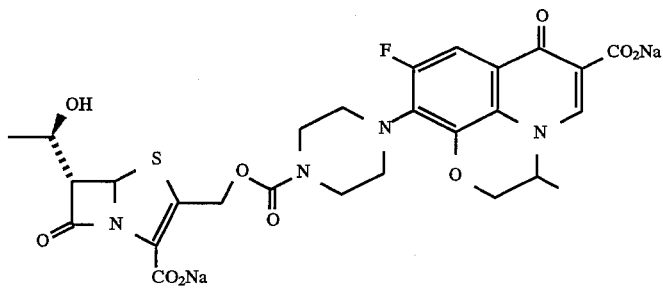

using the quinolone 9-fluoro-4,7-dihydro-3-methyl-10-(1-piperazinyl)-7-oxo-2H-pyrido[1,2,3-de]-1,4-benzoxazine-6-carboxylic acid (prepared according to I. Hayakawa, et al., 32 Chem. Pharm. Bull. 4907 (1984))

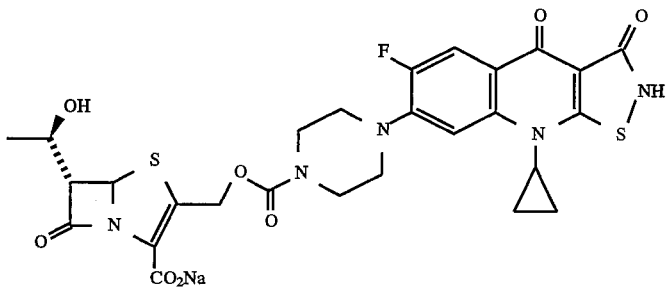

using the quinolone 9-cyclopropyl-6-fluoro-2,3,4,9-tetrahydro-7-(1-piperazinyl)isothiazolo[5,4-b]quinoline-3,4-dione (prepared according to D. T. W. Chu, European Patent Application 227,088)

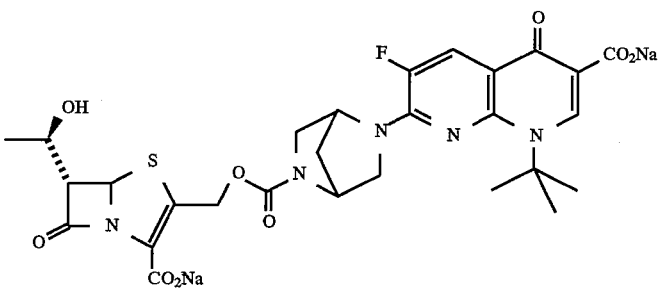

using the naphthyridinone 7-(2,5-diazabicyclo[2.2.1]heptan-2-yl)-1-(1,1-dimethylethyl)-6-fluoro-1,4-dihydro-4-oxo-1,8-naphthyridine-3-carboxylic acid (prepared according to A. Weber, et al., European Patent Application 266576)

EXAMPLE 9

According to the general procedure of Example 8, the following lactam-quinolone is made:

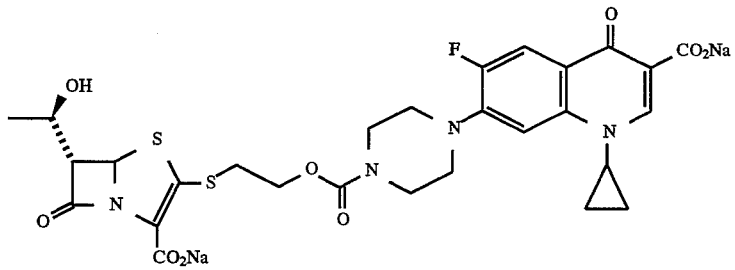

using the beta-lactam allyl 6-[1-[[(1,1-dimethylethyl) dimethyl silyl]oxy]ethyl]-3-[(2-hydroxyethyl)thio]-7-oxo-4-thia-1-azabicyclo[3.2.0]hept-2-ene-2-carboxylate (prepared according to E. Perrone, et al., European Patent Application 199,490)

The following other lactam-quinolones are made by the general procedure of this Example, with substantially similar results.

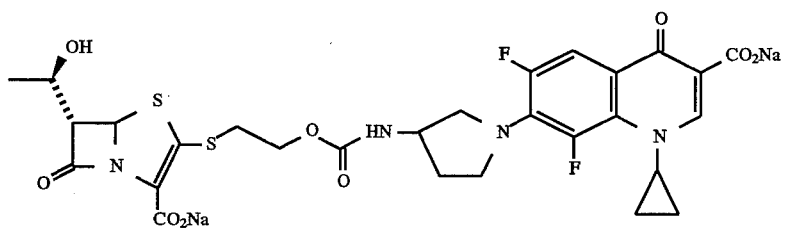

using the quinolone 7-(3-aminopyrrolidinyl)-1-cyclopropyl-6,8-difluoro-1,4-dihydro-4-oxo-3-quinoline carboxylic acid (prepared according to J. P. Sanchez, et al., 31 *J. Med. Chem.* 983 (1988))

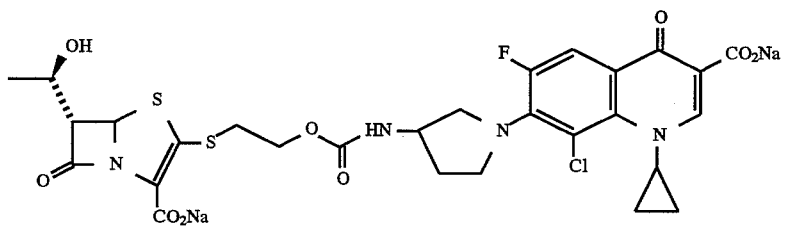

using the quinolone 7-(3-aminopyrrolidinyl)-8-chloro-1-cyclopropyl-6-fluoro-1,4-dihydro-4-oxo-3-quinoline carboxylic acid (prepared according to J. P. Sanchez, et al., 31 *J. Med. Chem.* 983 (1988))

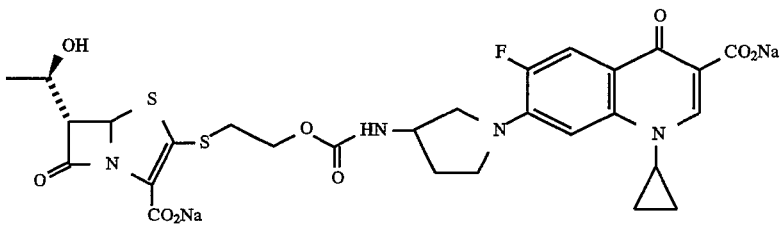

using the quinolone 7-(3-aminopyrrolidinyl-1-cyclopropyl-6-fluoro-1,4-dihydro-4-oxo-3-quinoline carboxylic acid (prepared according to J. P. Sanchez, et al., 31 *J. Med. Chem.* 983 (1988))

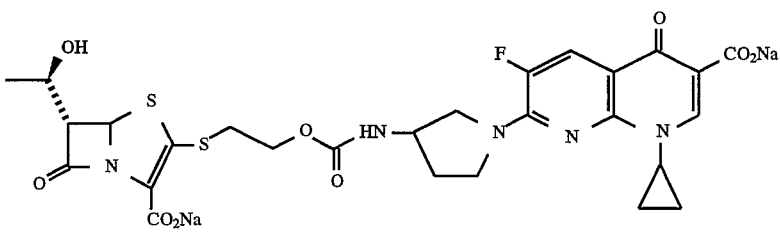

using the naphthyridinone 7-(3-aminopyrrolidinyl)-1-cyclopropyl-6-fluoro-1,4-dihydro-4-oxo-1,8-naphthyridine-3-carboxylic acid (prepared according to J. P. Sanchez, et al., 31 *J. Med. Chem.* 983 (1988))

EXAMPLE 10

According to the general procedure of Example 8, the following lactam-quinolone is made:

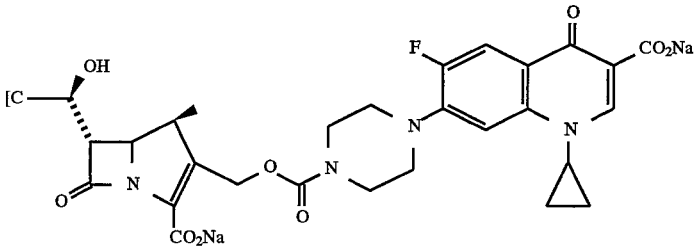

using the beta-lactam allyl 6-[1-[[(1,1-dimethylethyl) dimethyl silyl]oxy]ethyl]-3-(hydroxymethyl)-4-methyl-7-oxo-1-azabicyclo[3.2.0]hept-2-ene-2-carboxylate (prepared according to T. N. Salzmann, et al., European Patent Application 184,844)

The following other lactam-quinolones are made by the general procedure of this Example, with substantially similar results.

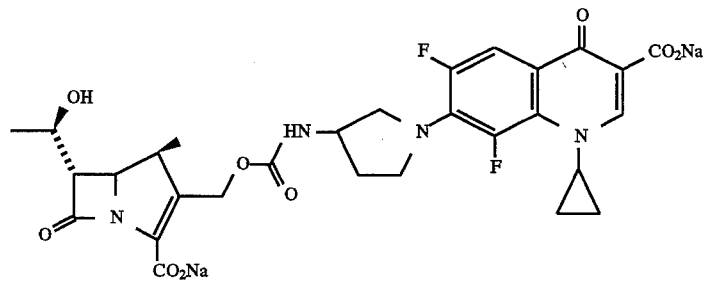

using the quinolone 7-(3-aminopyrrolidinyl)-1-cyclopropyl-6,8-difluoro-1,4-dihydro-4-oxo-3-quinoline carboxylic acid (prepared according to J. P. Sanchez, et al., 31 *J. Med. Chem.* 983 (1988))

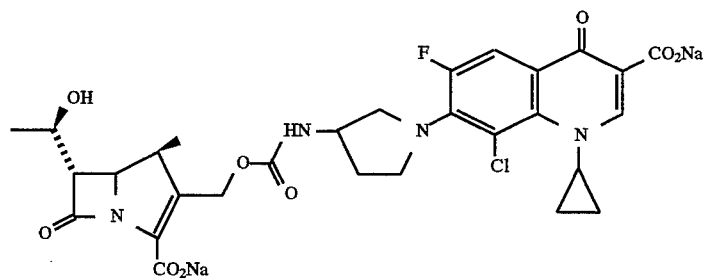

using the quinolone 7-(3-aminopyrrolidinyl)-8-chloro-1-cyclopropyl-6-fluoro-1,4-dihydro-4-oxo-3-quinoline carboxylic acid (prepared according to J. P. Sanchez, et al., 31 *J. Med. Chem.* 983 (1988))

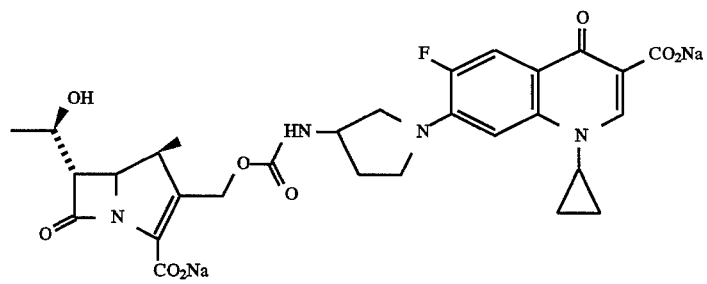

using the quinolone 7-(3-aminopyrrolidinyl-1-cyclopropyl-6-fluoro-1,4-dihydro-4-oxo-3-quinoline carboxylic acid (prepared according to J. P. Sanchez, et al., 31 *J. Med. Chem.* 983 (1988))

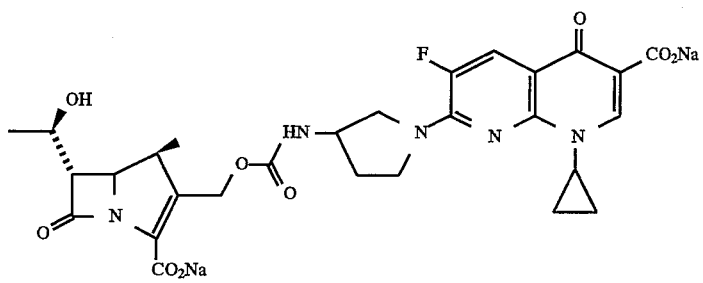

using the naphthyridinone 7-(3-aminopyrrolidinyl)-1-cyclopropyl-6-fluoro-1,4-dihydro-4-oxo-1,8-naphthyridine-3-carboxylic acid (prepared according to J. P. Sanchez, et al., 31 *J. Med. Chem.* 983 (1988))

EXAMPLE 11

[4R,5S,6S]-3-[2-[4-(3-Carboxy-1-cyclopropyl-6-fluoro-1,4-dihydro-4-oxo-7-quinolinyl)-1-piperazinyl]

carbonyloxy]ethyl thio]-6[(R)-1-hydroxyethyl]-4-methyl-7-oxo-1-azabicyclo[3.2.0]hept-2-ene-2-carboxylic acid sodium salts according to this invention, is made according to the following general reaction sequence.

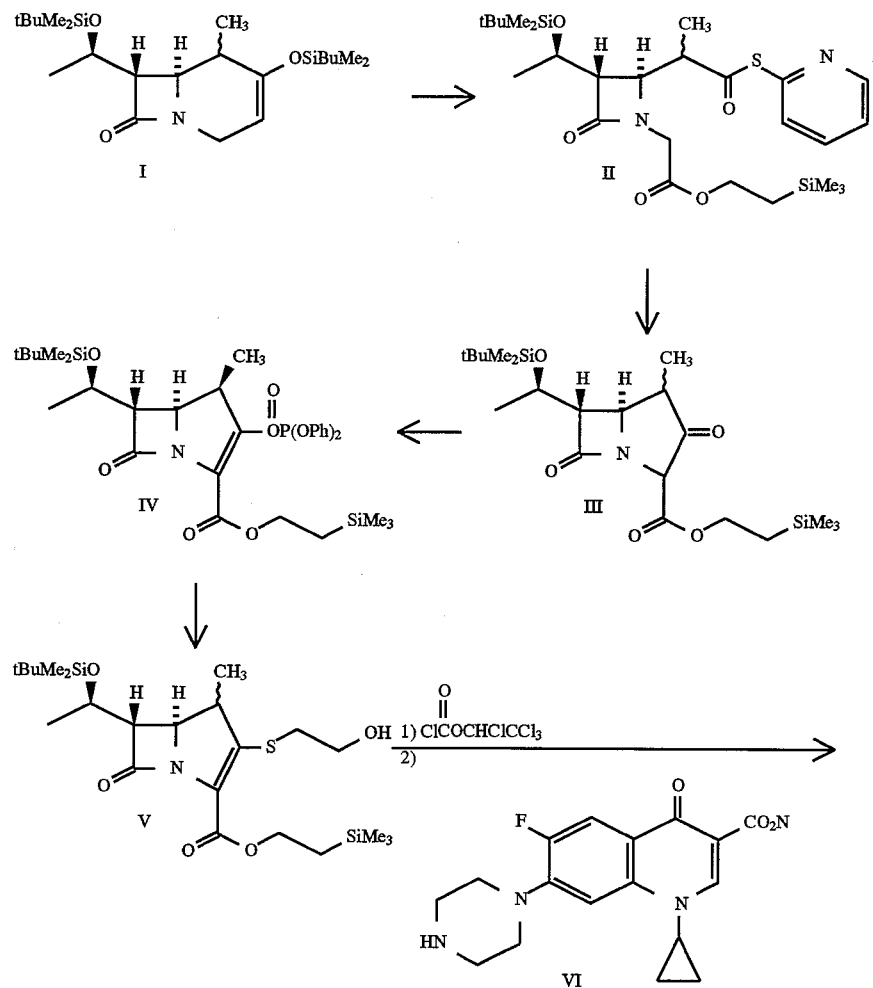

-continued

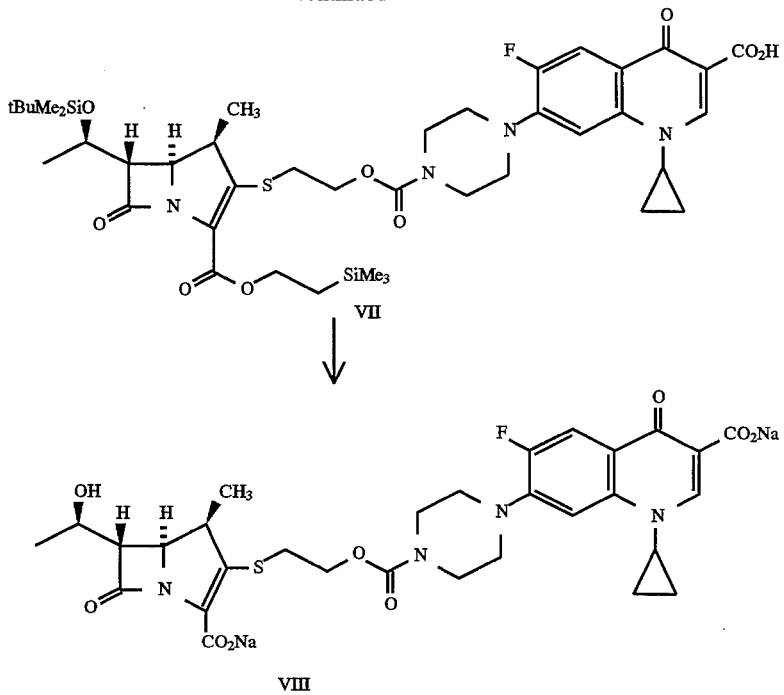

Approximately 7.2 g of 2-(t-butyldimethylsilyloxy)-1-methylcarbaceph-2-em (prepared according to 53 J. Org. Chem., 4154 (1988)), 1.6 g NaHCO₃, 36 ml of 2-(trimethylsilyl)ethanol, and 1 ml of a 0.1% solution of Sudan III in CH₂Cl₂ are combined in approximately 300 ml of CH₂Cl₂. A stream of argon is bubbled through the solution while cooling to approximately −78° C. Ozone is bubbled through the solution until the red color disappears, then argon is bubbled through the solution as it is allowed to warm to room temperature. Approximately 7.1 ml of triethylamine and 9.6 ml of acetic anhydride are added to the solution and it is allowed to stir for approximately 16 hours at room temperature. The mixture is diluted with approximately 400 ml of saturated aqueous ammonium chloride and the aqueous phase is extracted twice with approximately 400 ml of ether. The combined organic layers are washed with approximately 400 ml of saturated aqueous sodium chloride then dried over MgSO₄. After filtration and concentration most of the 2-(trimethylsilyl)ethanol is removed by short path distillation at approximately 60° C./0.1 mmHg. The resulting residue is dissolved in approximately 600 ml of CH₂Cl₂ under an argon atmosphere and approximately 8.2 g of 2,2′-dipyridyl disulfide and 9.8 g of triphenylphosphine are added. After approximately 5 hours at room temperature the solution is concentrated and purified by chromatography on silica gel to give the product II as a mixture of isomers at the position alpha to the thioester carbonyl.

A solution containing approximately 3.0 g of product II in approximately 120 ml of tetrahydrofuran is cooled to approximately −75° C. under an argon atmosphere. Approximately 10.0 ml of a 1.0M solution of sodium bis (trimethylsilyl)amide in tetrahydrofuran is added dropwise over approximately 7 minutes while maintaining the reaction temperature below approximately −70° C. Approximately 3 minutes after completion of the addition approximately 30 ml of 1M HCl is added, the mixture is further diluted with approximately 180 ml of water, and extracted with approximately 40 ml of 1:1 ether:petroleum ether six times. The combined organic layers are washed with approximately 100 ml of water, then approximately 100 ml of saturated aqueous sodium chloride, and dried over MgSO₄. Concentration of the solution provides product III as a mixture of isomers at the 4-position.

Approximately 0.90 ml of diphenyl chlorophosphate and 0.80 ml of N,N-diisopropylethylamine are added simultaneously in a dropwise fashion to a cold solution (ice bath) of approximately 2.8 g of product III dissolved in approximately 30 ml of dry acetonitrile under an argon atmosphere. The ice bath is removed and the mixture is allowed to stir approximately 30 minutes at room temperature before concentrating and purifying by chromatography on silica gel to provide product IV as a single isomer.

A solution containing approximately 1.3 g of product IV in approximately 4.5 ml of dry acetonitrile is cooled in an ice bath under an argon atmosphere. Approximately 0.53 ml of N,N-diisopropylethylamine is added followed by the dropwise addition of approximately 0.20 ml of 2-mercaptoethanol. After stirring for approximately 10 minutes the ice bath is removed and the solution is stirred approximately 3 hours longer at room temperature. Concentration of the solution, followed by chromatography on silica gel, provides product V.

A solution containing approximately 0.15 g of product V in approximately 1.8 ml of dry tetrahydrofuran is cooled in an ice bath under an argon atmosphere. Approximately 0.061 ml of 1,2,2,2-tetrachloroethyl chloroformate is added, followed by the dropwise addition of approximately 0.028 ml of pyridine. After stirring approximately 1 hour the mixture is transferred into a mixture containing approximately 0.126 g of ciprofloxacin (VI) and 0.159 g of NaHCO₃ in approximately 2.5 ml of water which had been stirred approximately 1 hour at room temperature. After stirring approximately 2.5 hours at room temperature the mixture is poured into approximately 15 ml of chloroform and 15 ml of cold 0.1M HCl. The aqueous phase is extracted with chloroform again, and the combined chloroform layers are washed successively with cold 0.1M HCl, water, and saturated aqueous sodium chloride. After drying over Na₂SO₄ and concentrating the resulting residue is treated with approximately 10 ml of ether. The resulting precipitate is washed twice with approximately 5 ml of ether and dried in vacuo to provide product VII.

Approximately 0.11 g of product VIII and 0.41 g tetra-n-butylammonium fluoride trihydrate are stirred together in approximately 0.35 ml of dimethylformamide at room temperature for approximately 16 hours. Approximately 0.20 g of NaHCO₃ is added and the mixture is eluted through a DowexR 50×4 (Na cycle) column with deionized water. The appropriate fractions are partially concentrated in vacuo, then lyophilized to give the final product (VIII).

Similarly, the following lactam-quinolones are prepared by the general procedure of this Example, with substantially similar results.

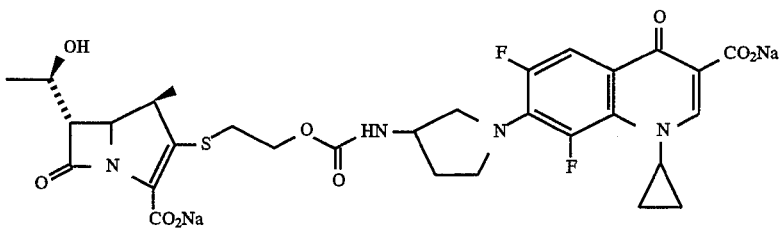

using the quinolone 7-(3-aminopyrrolidinyl)-1-cyclopropyl-6,8-difluoro-1,4-dihydro-4-oxo-3-quinoline carboxylic acid (prepared according to J. P. Sanchez, et al., 31 *J. Med. Chem.* 983 (1988))

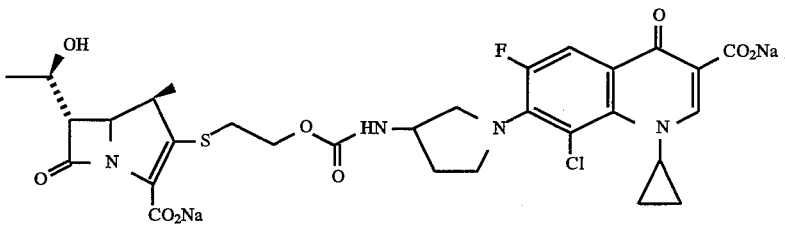

using the quinolone 7-(3-aminopyrrolidinyl)-8-chloro-1-cyclopropyl-6-fluoro-1,4-dihydro-4-oxo-3-quinoline carboxylic acid (prepared according to J. P. Sanchez, et al., 31 *J. Med. Chem.* 983 (1988))

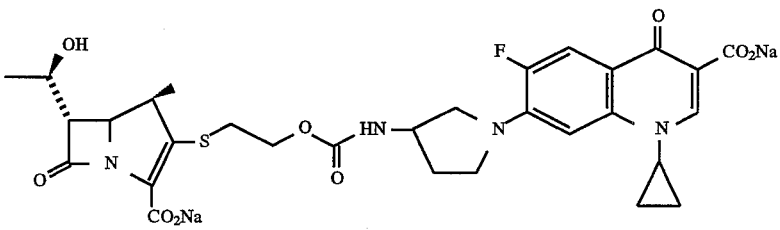

using the quinolone 7-(3-aminopyrrolidinyl)-1-cyclopropyl-6-fluoro-1,4-dihydro-4-oxo-3-quinoline carboxylic acid (prepared according to J. P. Sanchez, et al., 31 *J. Med. Chem.* 983 (1988))

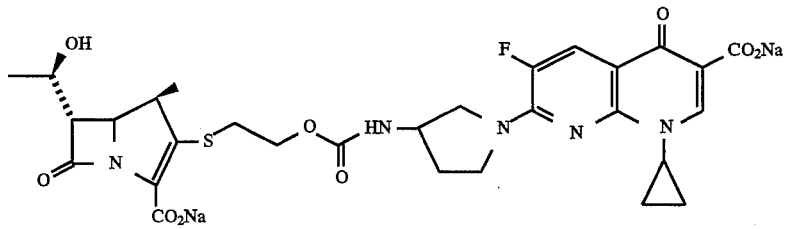

EXAMPLE 12

[2S-(2α,3β,5α,6β)]-3-[[[4-(3-Carboxy-1-cyclopropyl-6-fluoro-1,4-dihydro-4-oxo-7-quinolinyl)-1-piperazinyl]carbonyloxy]methyl]-3-methyl-7-oxo-6-[(phenoxyacetyl)amino]-4-thia-1-azabicyclo [3.2.0]heptane-2-carboxylic Acid Disodium Salt using the naphthyridinone 7-(3-aminopyrrolidinyl)-1-cyclopropyl -6-fluoro-1,4-dihydro-4-oxo-1,8-naphthyridine-3-carboxylic acid (prepared according to J. P. Sanchez, et al., 31 J. Med. Chem. 983 (1988))

dryness to give II. To a mixture of approximately 1.2 g of ciprofloxacin III and 1.8 g of NaHCO₃ in 50 ml of water is added a solution of approximately 2.5 g of II in 75 ml of dioxane. The mixture is stirred at room temperature for approximately 1.5 hours, diluted with ether and water and separated. The aqueous phase is cooled to approximately 5° C., CHCl₃ is added and the mixture is acidified with 1N HCl. The CHCl₃ extract is washed with 0.5N HCl and water, then is dried over Na₂SO₄, filtered and is concentrated to dryness to give IV. A mixture of approximately 2.2 g of IV, 200 ml of 80% THF/H2O and 2.2 g of 10% Pd/C is subjected to hydrogenation for approximately one hour. A solution of approximately 0.51 g of NaHCO₃ in 125 ml of water is

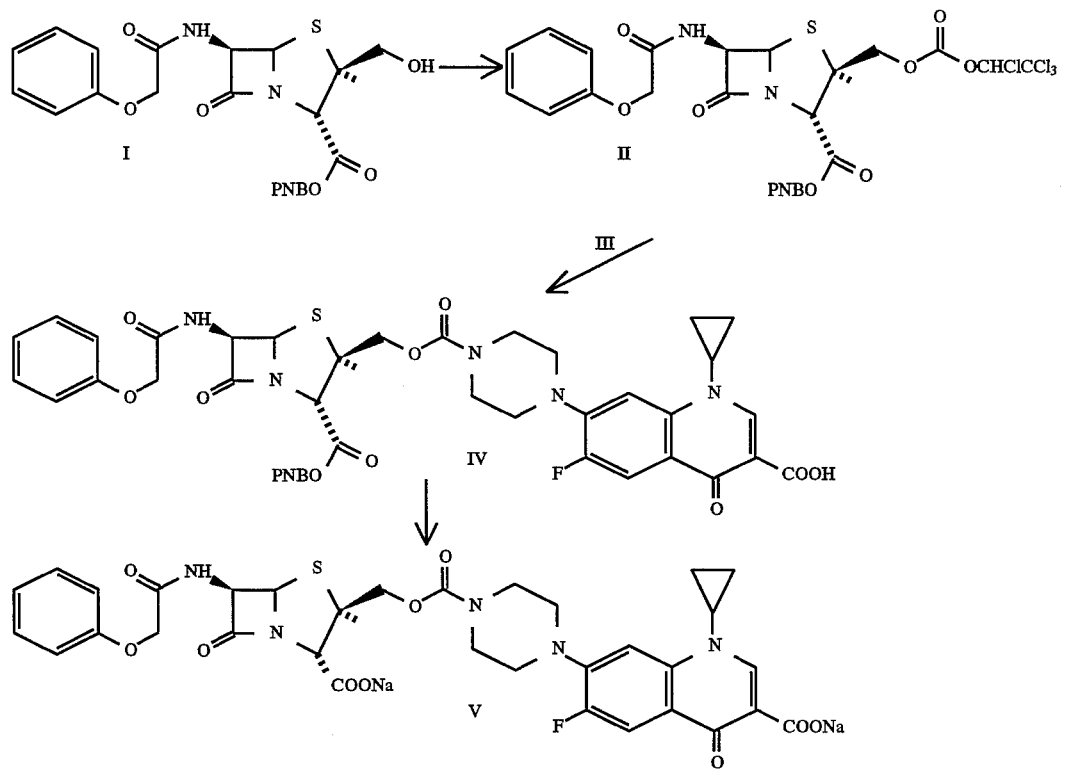

A mixture of approximately 3.8 g of [2S-(2α,3β,5α,6β)]-3-(hydroxymethyl)-3-methyl-7-oxo-6-[(phenoxyacetyl)amino]-4-thia-1-azabicyclo[3.2.0]heptane-2-carboxylic acid 4-nitrobenzyl ester I (prepared according to J. Org. Chem. 1979, 44(17), 3084) and 20 ml of CH₂Cl₂ is cooled in an ice bath and approximately 1.1 ml of 1,2,2,2-tetrachloroethyl chloroformate is added, followed by the dropwise addition of approximately 0.67 ml of pyridine. The reaction is stirred for approximately 40 minutes, then diluted with CH₂Cl₂ and washed with ice cold 0.5N HCl and cold water. The organic phase is dried over Na₂SO₄, filtered and is concentrated to added and the catalyst is removed by filtration. The filtrate is concentrated to dryness and the residue is purified by C-18 reverse phase chromatography to afford the title compound V.

The following other lactam-quinolones are also prepared by the general procedure of this Example and Examples 2–12, with substantially similar results.

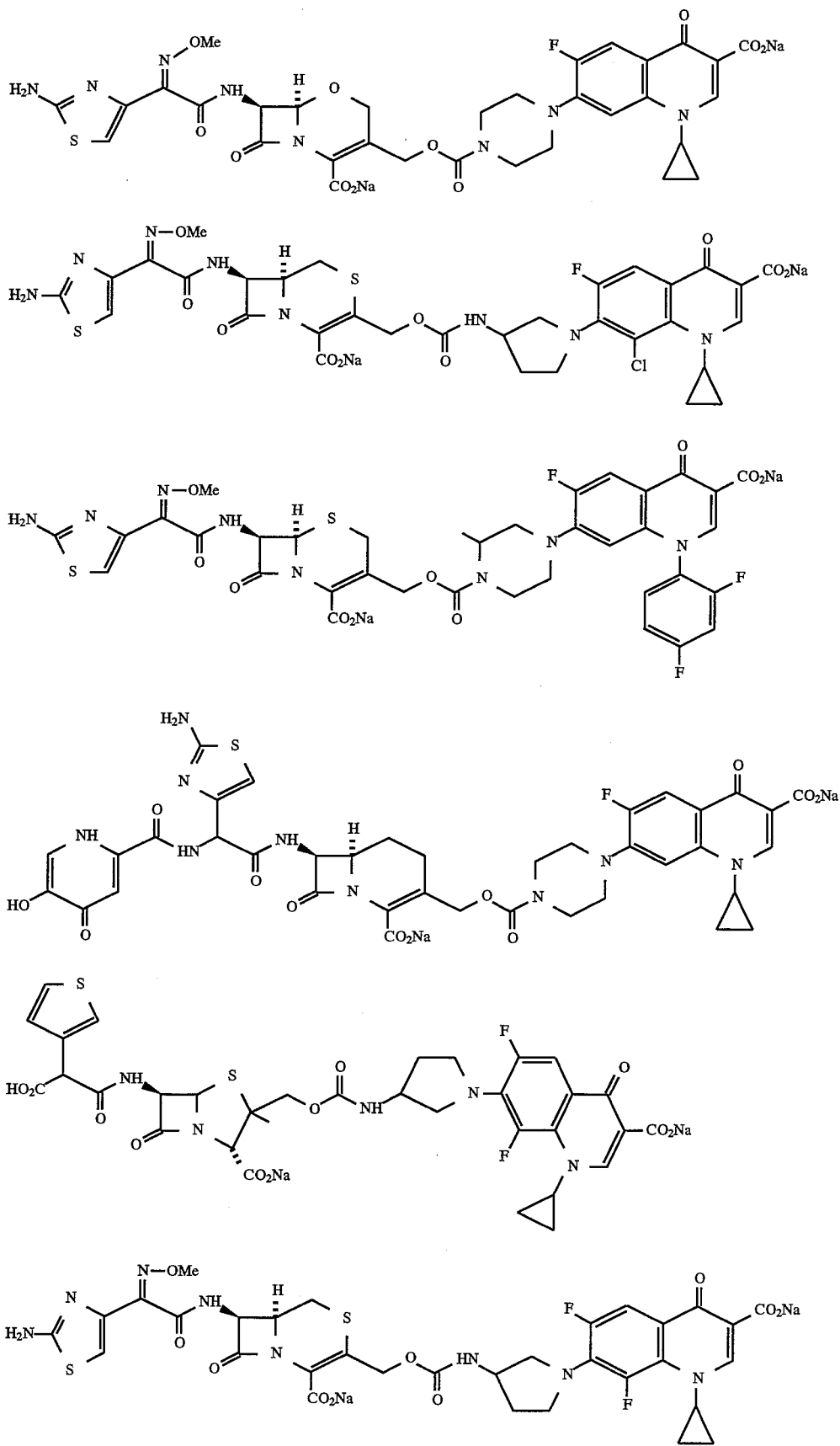

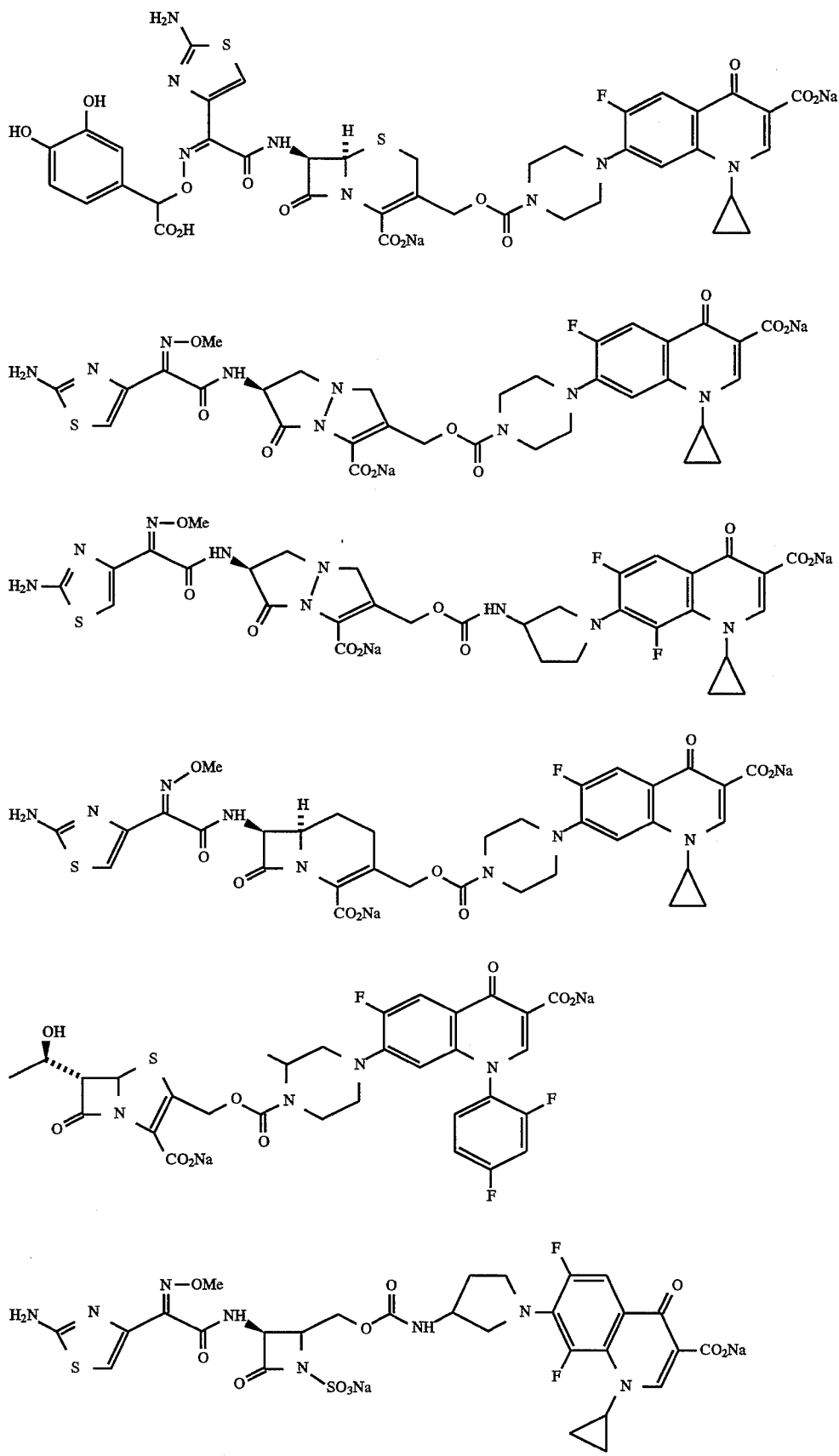
-continued

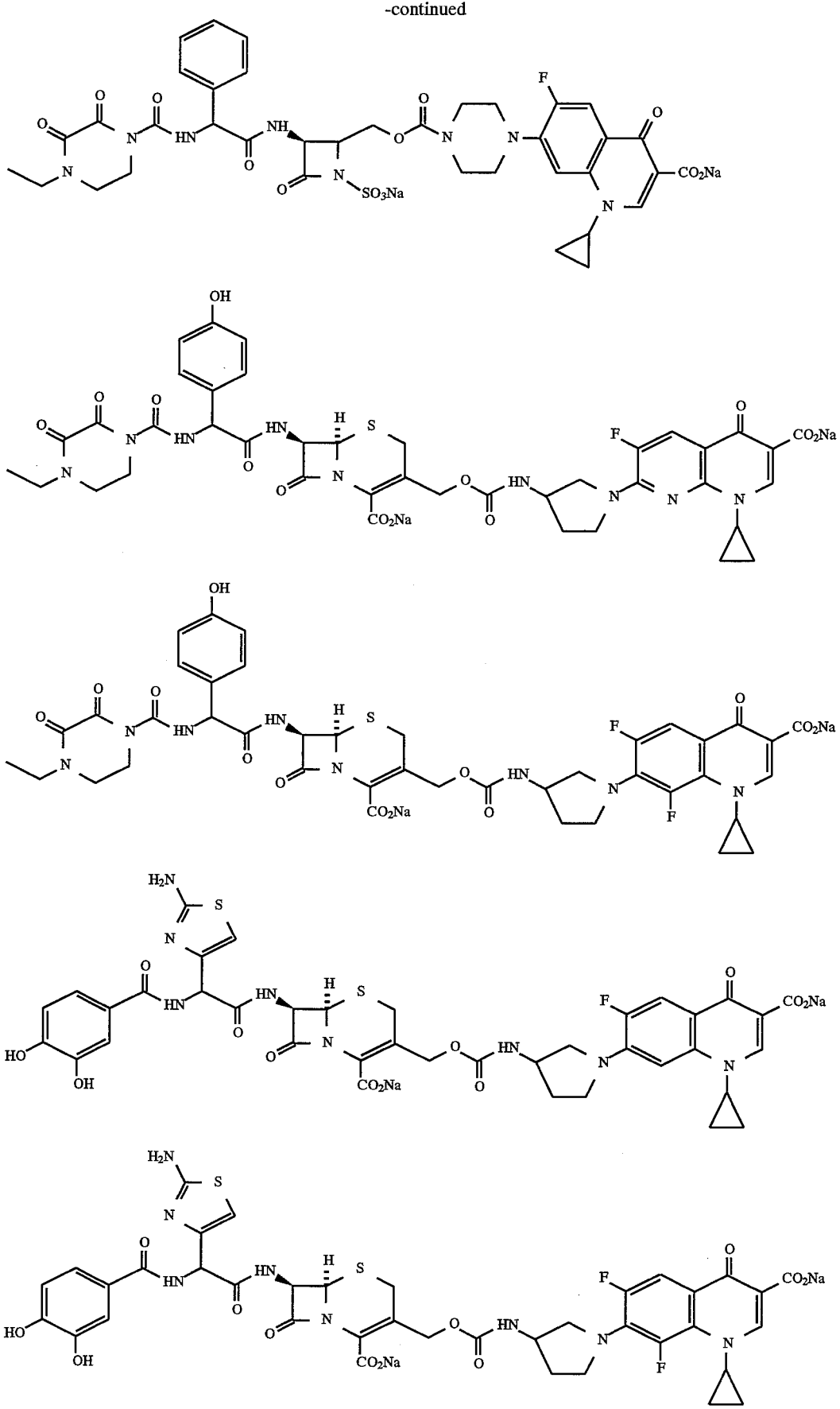

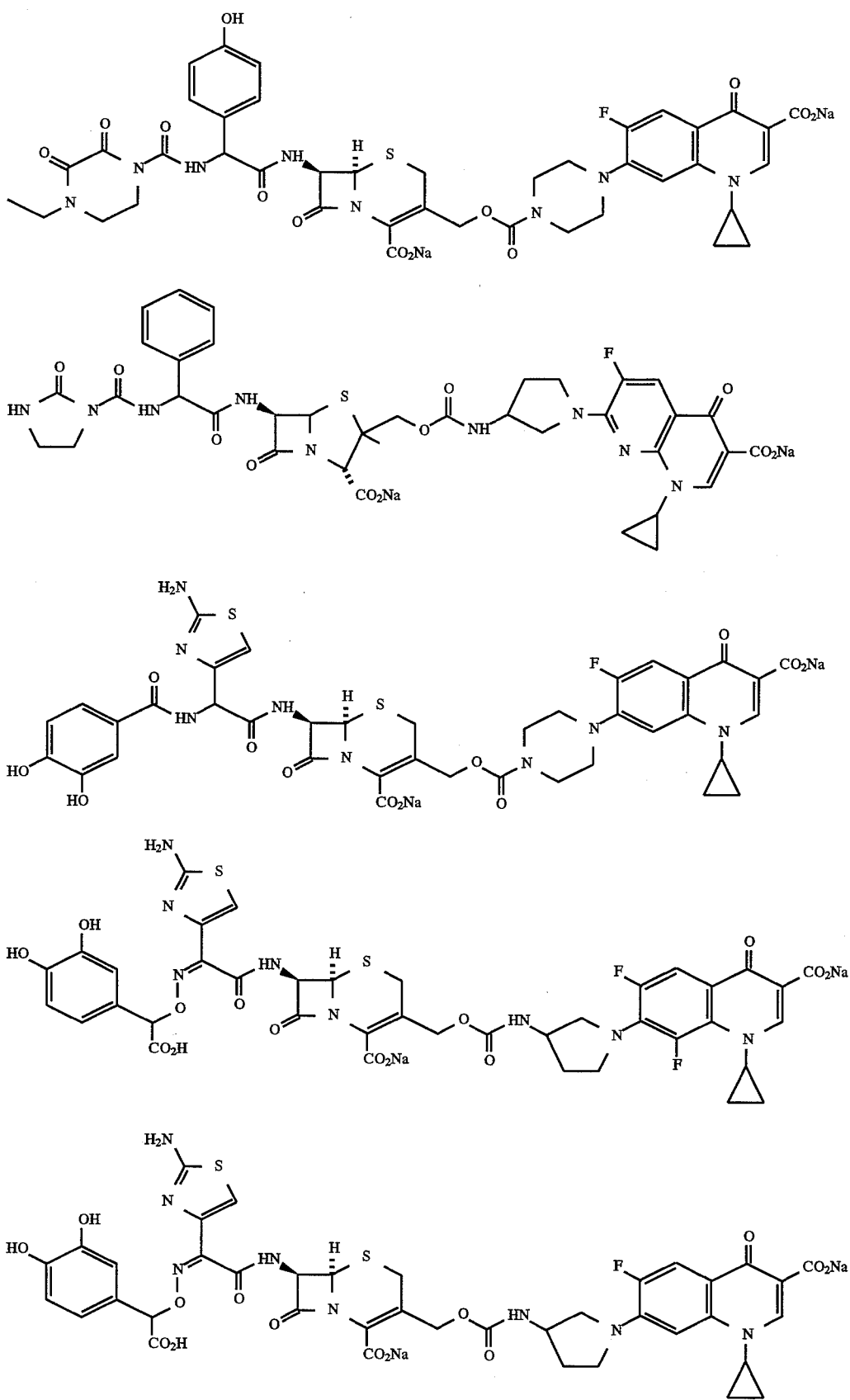

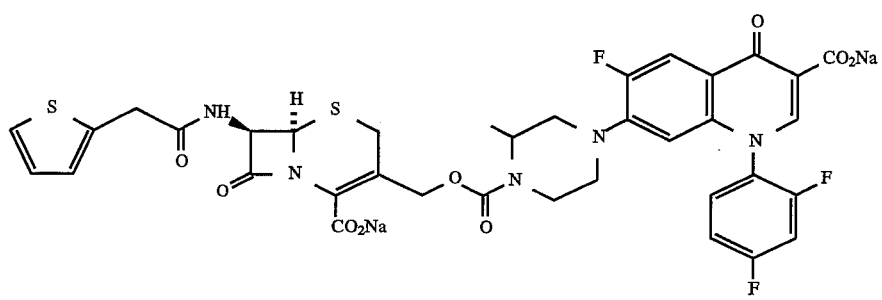
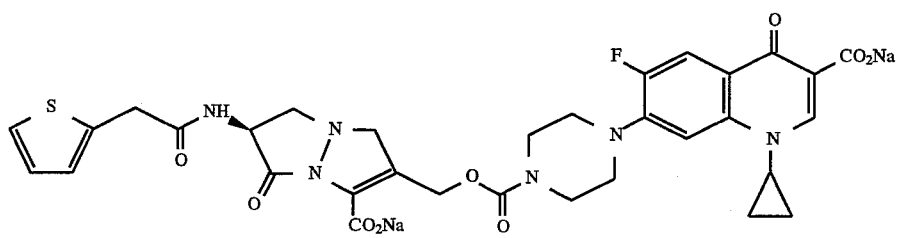
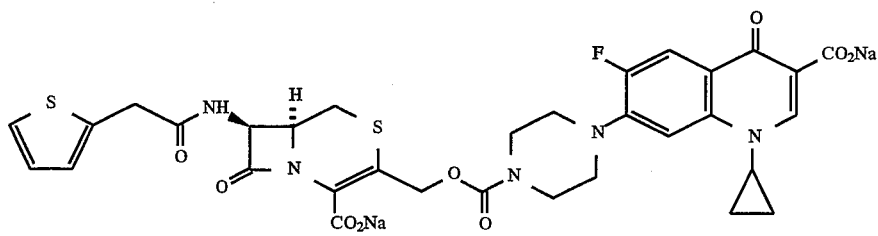
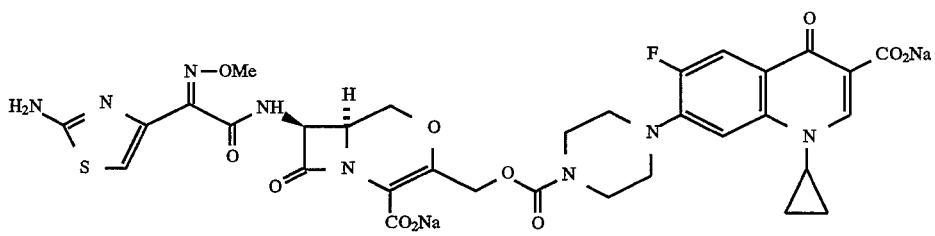
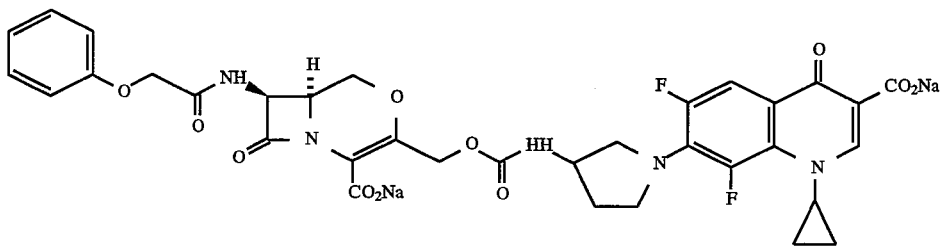
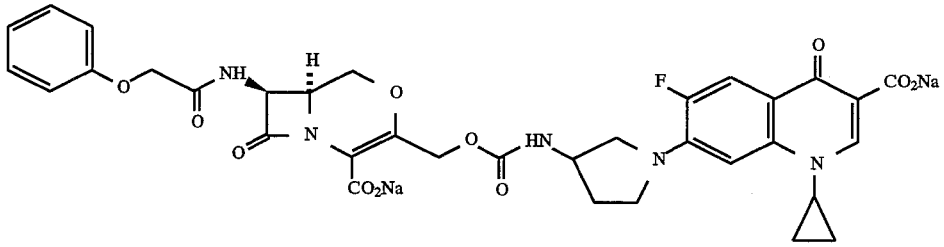

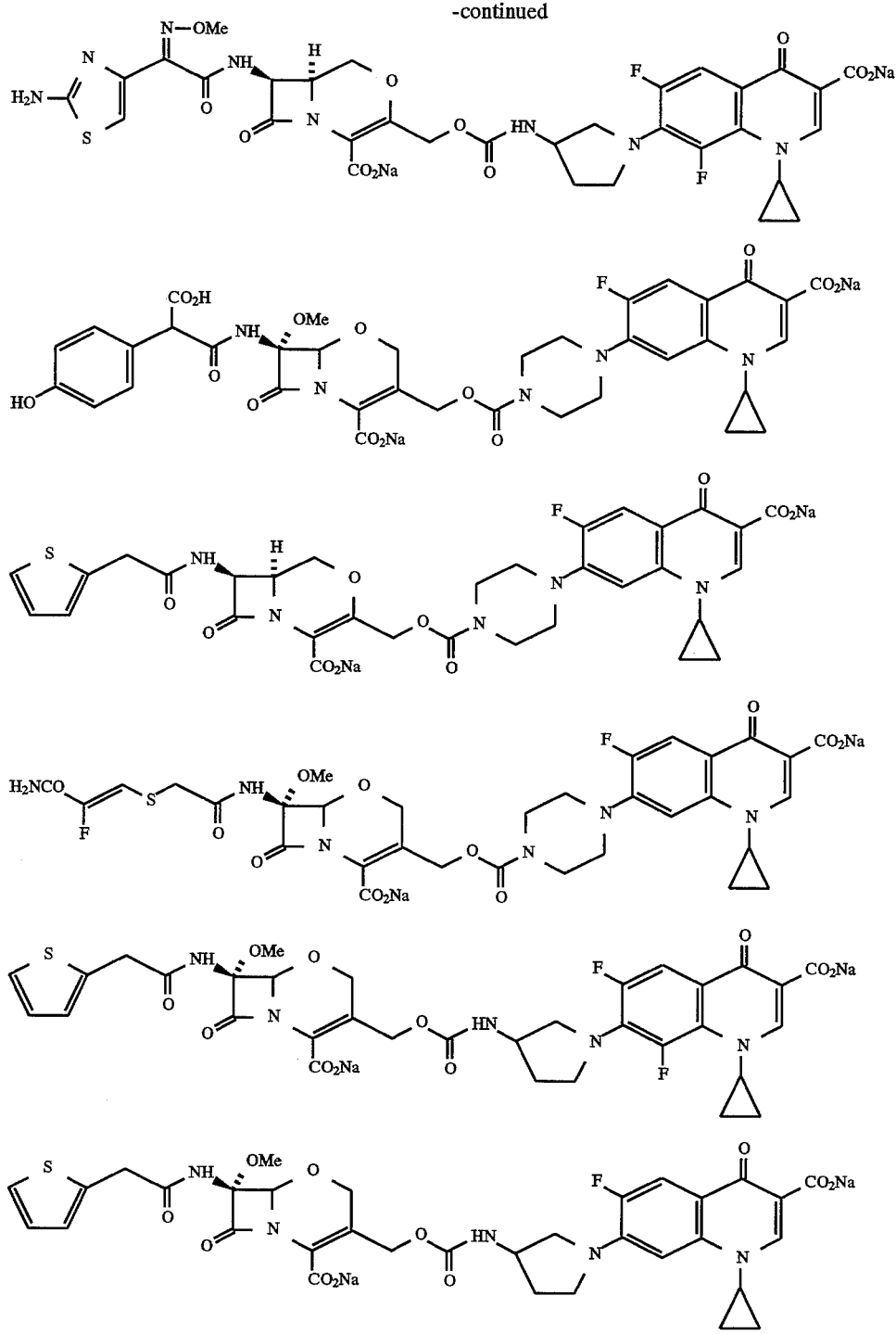
EXAMPLE 13
[6R-[6a,7b]]-3-[[[4-(3-Carboxy-1-cyclopropyl-6-fluoro-1,4-dihydro-4-oxo-7-quinolinyl)-1-piperazinyl]thioxomethylthio]methyl]-8-oxo-7-[(2-thienylacetyl)amino]-5-thia-1-azabicyclo[4.2.0]-oct-2-ene-2-carboxylic acid disodium salt, according to this invention, is made by the following general reaction sequence.

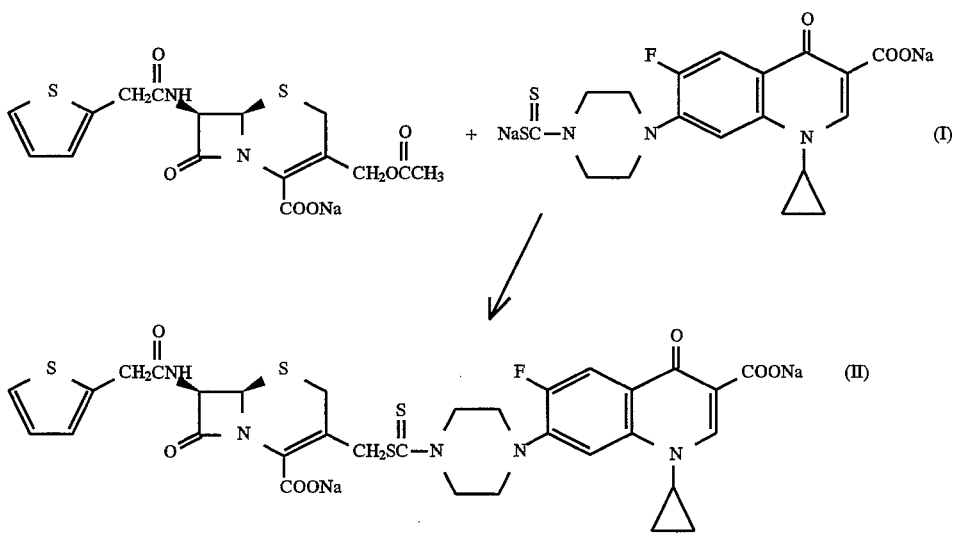

1-Cyclopropyl-6-fluoro-1,4-dihydro-7-[[4-(mercapto) thioxomethyl]-1-piperazinyl]-4-oxo-3-quinoline carboxylic acid disodium salt is first made by suspending approximately 5.0 g of ciprofloxacin in approximately 7.5 ml of 4N sodium hydroxide and water, and cooling to approximately 4° C. (40° F.). Approximately 0.9 ml of carbon disulfide is added dropwise. The reaction is then stirred for approximately 140 minutes. A second equivalent of carbon disulfide (approximately 0.9 ml) is added dropwise. The reaction is then allowed to slowly warm to room temperature (approximately 68° F., 20° C.), as it is stirred for approximately 12 hours. Acetone is added to precipitate a solid product (I), which is collected by filtration, washed with acetone, and dried.

Approximately 1.5 g of this product is then mixed with approximately 1.4 g of cephalothin sodium salt, in water, and stirred at approximately 42° C. (107° F.) for 24 hours. A small volume of acetone is added and the precipitate isolated by filtration. The solid is washed with acetone and air dried, to yield product (II).

Similarly, the following lactam-quinolones are prepared by the general procedure of this Example, with substantially similar results.

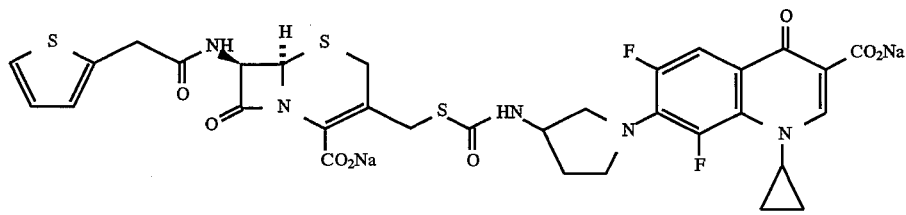

using the quinolone 7-(3-aminopyrrolidinyl)-1-cyclopropyl-6,8-difluoro-1,4-dihydro-4-oxo-3-quinoline carboxylic acid (prepared according to J. P. Sanchez, et. el., J. Med. Chem., 1988, 31, 983)

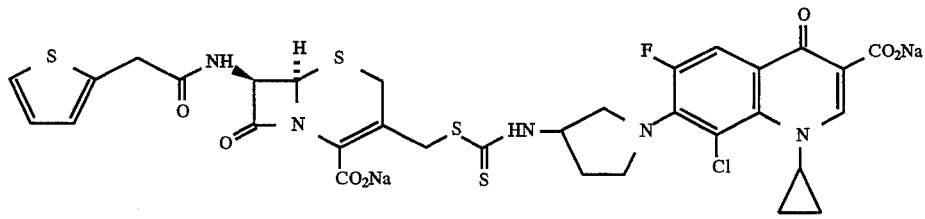

using the quinolone 7-(3-aminopyrrolidinyl)-1-chloro-1-cyclopropyl-6-fluoro-1,4-dihydro-4-oxo-3-quinoline carboxylic acid (prepared according to J. P. Sanchez, et. el., J. Med. Chem., 1988, 31, 983)

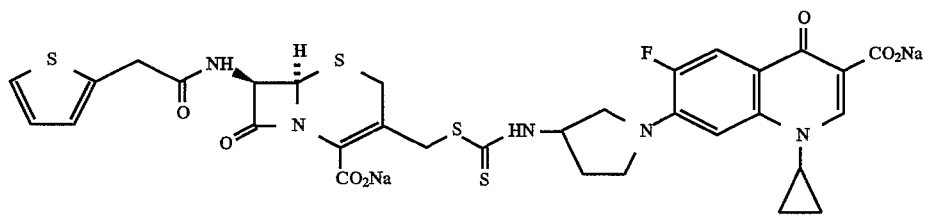

using the quinolone 7-(3-aminopyrrolidinyl)1-cyclopropyl-6-fluoro-1,4-dihydro-4-oxo-3-quinoline carboxylic acid (prepared according to J. P. Sanchez, et. al., J. Med. Chem., 1988, 31, 983)

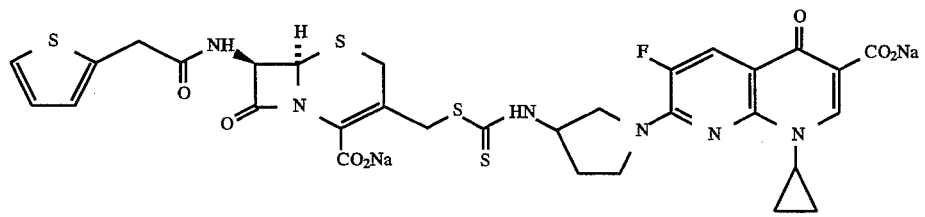

using the naphthyridinone 7-(3-aminopyrrolidinyl)-1-cyclopropyl-6-fluoro-1,4-dihydro-4-oxo-1,8-naphthyridine-3-carboxylic acid (prepared according to J. P. Sanchez, et. al., J. Med. Chem., 1988, 31, 983)

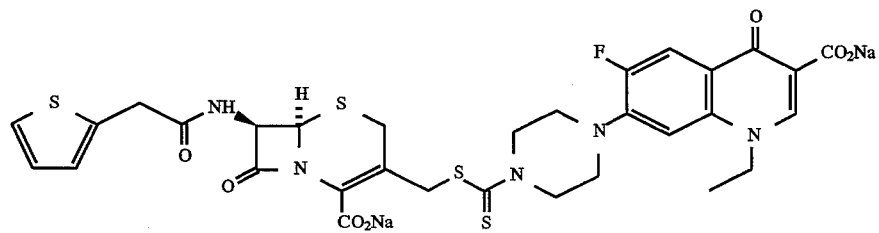

using the quinolone 1-ethyl-6-fluoro-1,4-dihydro-4-oxo-7-(1-piperazinyl)-3- quinoline carboxylic acid (prepared according to H. Koga, et. al., J. Med. Chem., 1980, 23, 1358)

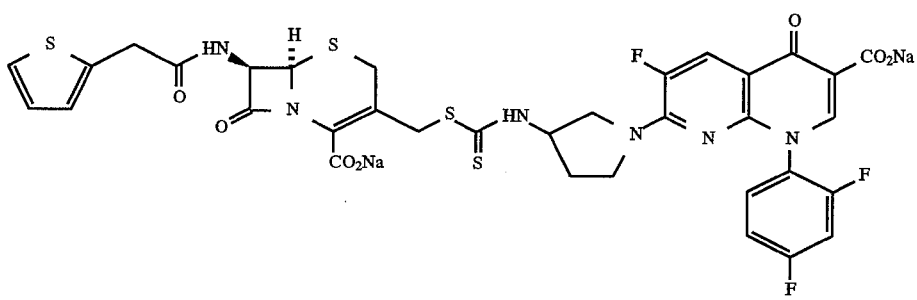

using the naphthyridinone 7-(3-aminopyrrolidinyl)-1-(2,4-difluorophenyl)-6-fluoro-1,4-dihydro-4-oxo-1,8-naphthyridine-3-carboxylic acid (prepared according to D. T. W. Chu, et. al., J. Med. Chem., 1986, 29, 2363)

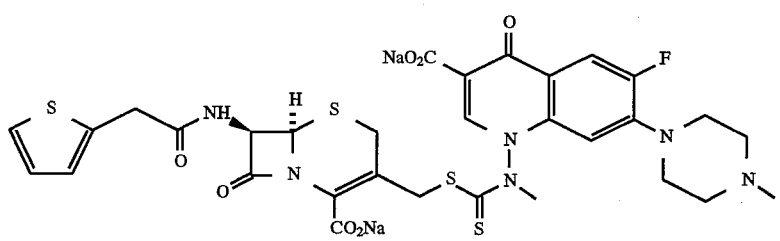

using the quinolone 6-fluoro-1,4-dihydro-1-methylamino-7-(4-methyl-1-piperazinyl)-4-oxo-3-quinoline carboxylic acid (prepared according to M. P. Wentland, et. al., J. Med. Chem., 1984, 27, 1103)

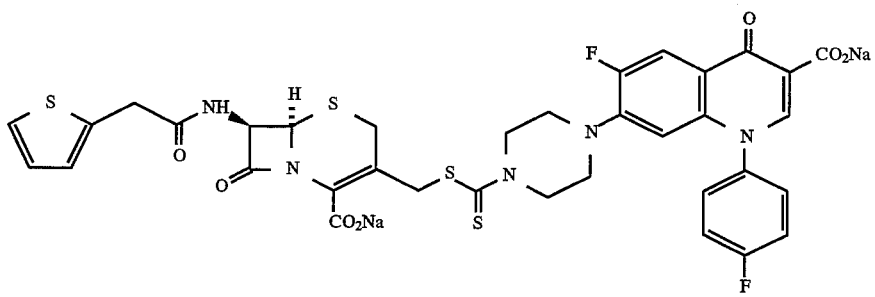

using the quinolone 6-fluoro-1-(1,4-fluorophenyl)-1,4-dihydro-4-oxo-7-(1-piperazinyl)-3-quinoline carboxylic acid (prepared according to D. T. W. Chu, et. al., J. Med. Chem., 1985, 28, 1558)

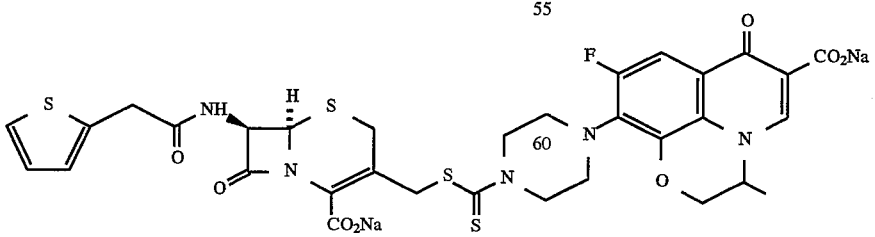

using the quinolone 9-fluoro-4,7-dihydro-3-methyl-10-(1piperazinyl)-7-oxo-2H-pyrido[1,2,3-de]-1,4-benzoxazine-6-carboxylic acid (prepared according to I. Hayakawa, et. al., Chem. Pharm. Bull., 1984, 32, 4907)

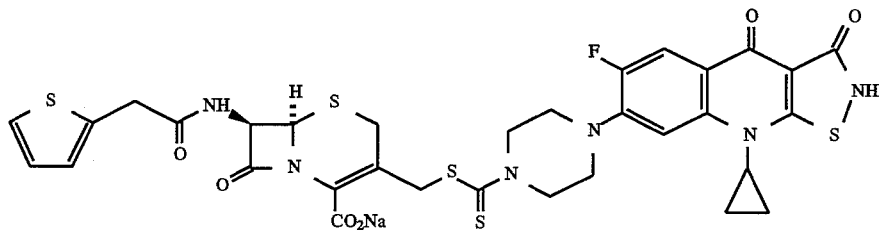

using the quinolone 9-cyclopropyl-6-fluoro-2,3,4,9-tetrahydro-7-(1-piperazinyl)isothiazolo[5,4-b]quinoline-3,4-dione (prepared according to D. T. W. Chu, EP 227,088)

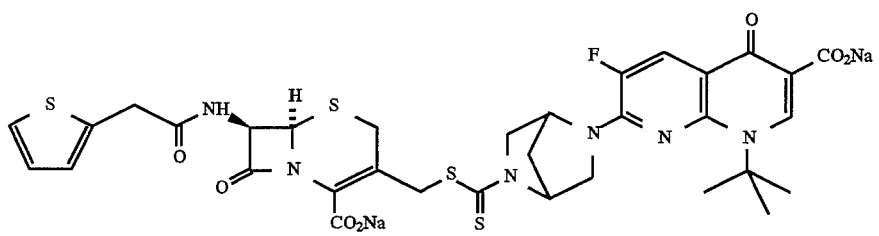

using the naphthyridinone 7-(2,5-diazabicyclo[2.2.1]heptan-2-yl)-1-(1,1-dimethylethyl)-6-fluoro-1,4-dihydro-4-oxo-1,8-naphthyridine-3-carboxylic acid (prepared according to A. Weber, et. al., EP 266576)

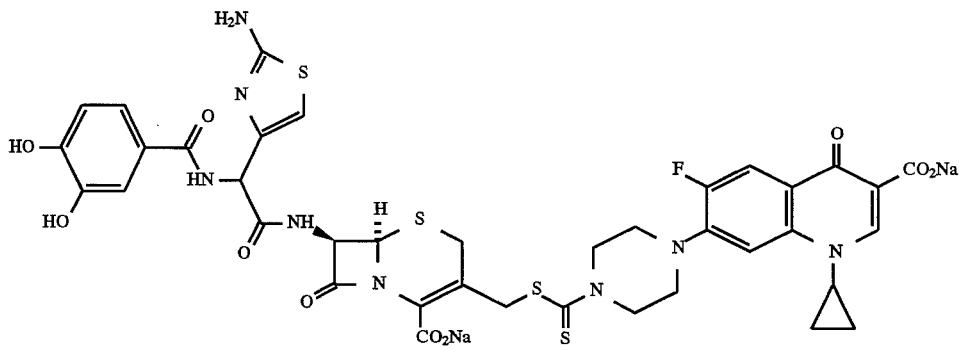

using the beta-lactam 3-(acetyloxymethyl)-7-[[(2-amino-4-thiazolyl)[[(3,4-dihydroxyphenyl)carbonyl]amino]acetyl]amino]-8-oxo-5-thia-1-azabicyclo [4.2.0]oct-2-ene-2-carboxylic acid (prepared according to T. Naito, EP 115,820)

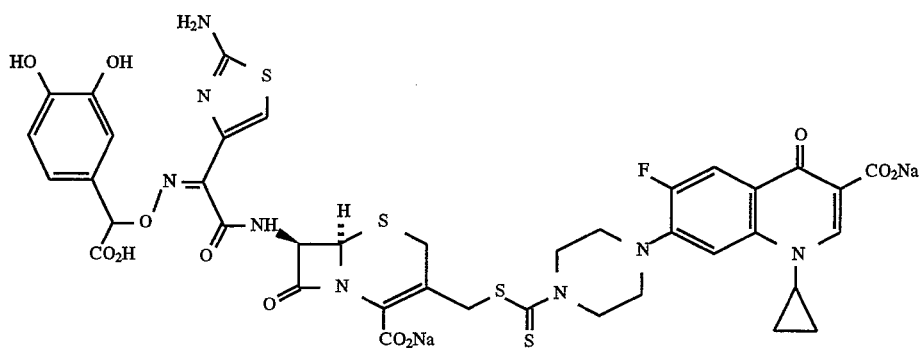

using the beta-lactam 3-(acetyloxymethyl)-7-[[(2-amino-4-thiazolyl)[carboxy (3,4-dihydroxyphenyl)methoxyimino] acetyl]amino]-8-oxo-5-thia-1-azabicyclo[4.2.0]oct-2-ene-2-carboxylic acid (prepared according to H. Ohnishi, et. al., PCT Int. Appl. WO 86/5786)

EXAMPLE 14

According to the general procedure of Example 13, the following lactam-quinolone is made:

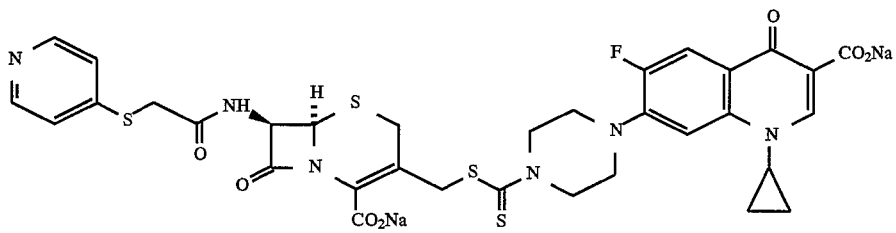

using the beta-lactam 3-(acetyloxymethyl)-8-oxo-7-[(4-pyridylthioacetyl) amino]-5-thia-1-azabicyclo[4.2.0]oct-2-ene-2-carboxylic acid (prepared according to S. Crast, et. al., J. Med. Chem., 1973, 16, 1413).

The following other lactam-quinolones are made by the general procedure of this Example, with substantially similar results.

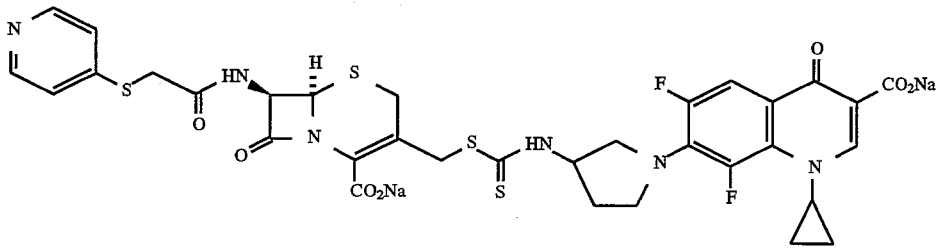

using the quinolone 7-(3-aminopyrrolidinyl)-1-cyclopropyl-6,8-difluoro-1,4-dihydro-4-oxo-3-quinoline carboxylic acid (prepared according to J. P. Sanchez, et. al., J. Med. Chem., 1988, 31, 983)

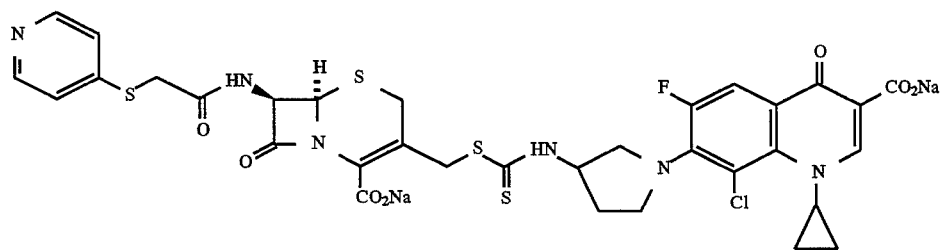

using the quinolone 7-(3-aminopyrrolidinyl)-1-chloro-1-cyclopropyl-6-fluoro-],4-dihydro-4-oxo-3-quinoline carboxylic acid (prepared according to J. P. Sanchez, et. el., J. Med. Chem., 988, 31, 983)

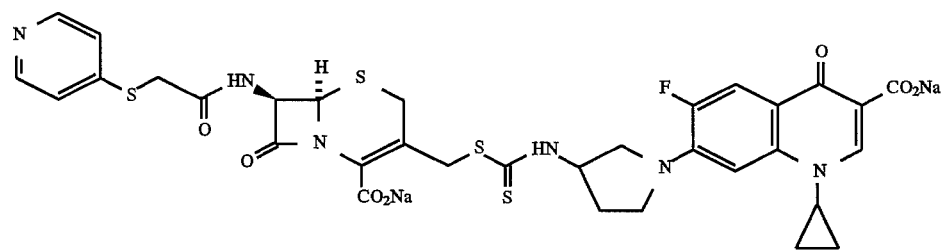

using the quinolone 7-(3-aminopyrrolidinyl)1-cyclopropyl-6-fluoro-1,4-dihydro-4-oxo-3-quinoline carboxylic acid (prepared according to J. P. Sanchez, et. el., J. Med. Chem., 1988, 31, 983)

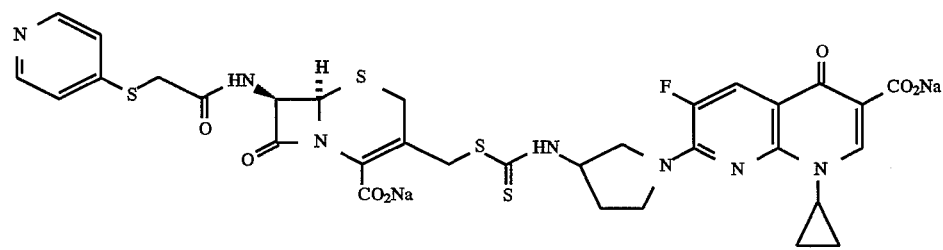

using the naphthyridinone 7-(3-aminopyrrolidinyl)-1-cyclopropyl-6-fluoro-1,4-dihydro-4-oxo-1,8-naphthyridine-3-carboxylic acid (prepared according to J. P. Sanchez, et. al., J. Med. Chem., 1988, 31, 983)

EXAMPLE 15

According to the general procedure of Example 13, the following lactam-quinolone is made:

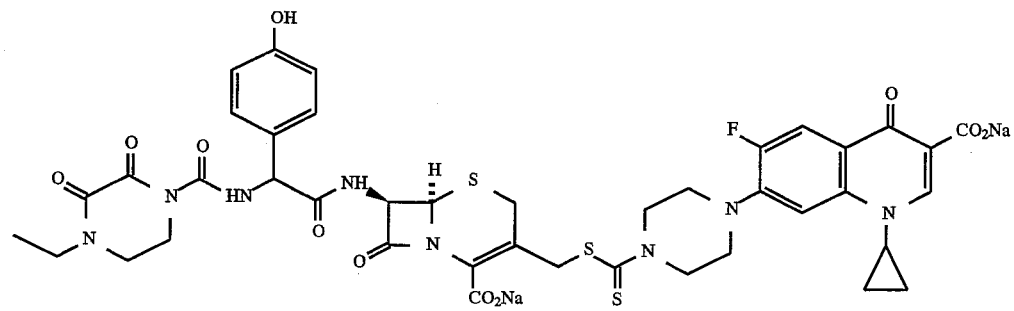

using the beta-lactam 3-(acetyloxymethyl)-7-[[[[[(R)-4-ethyl-2,3-dioxo-1-piperazinyl]carbonyl]amino](4-hydroxyphenyl)acetyl]amino]-8-oxo-5-thia-1-azabicyclo[4.2.0]oct-2-ene-2-carboxylic acid (prepared according to I. Saikawa, et. al., Ger. Offen. DE 2600880)

The following other lactam-quinolones are made by the general procedure of this Example, with substantially similar results.

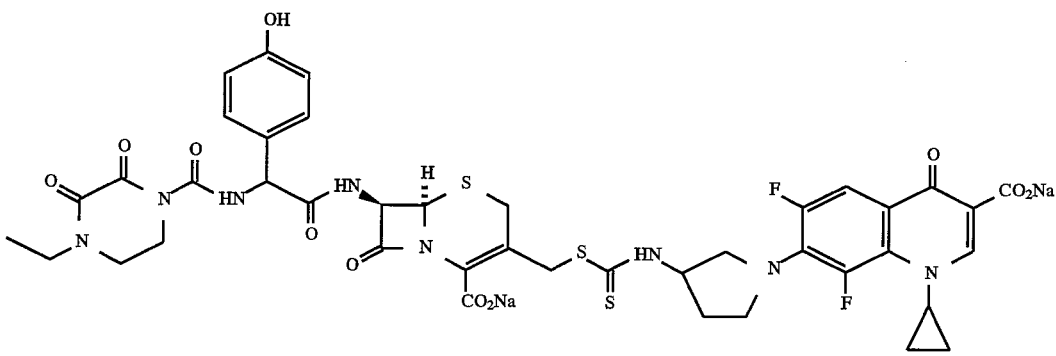

using the quinolone 7-(3-aminopyrrolidinyl)-1-cyclopropyl-6,8-difluoro-1,4-dihydro-4-oxo-3-quinoline carboxylic acid (prepared according to J. P. Sanchez, et. al., J. Med. Chem., 1988, 31, 983)

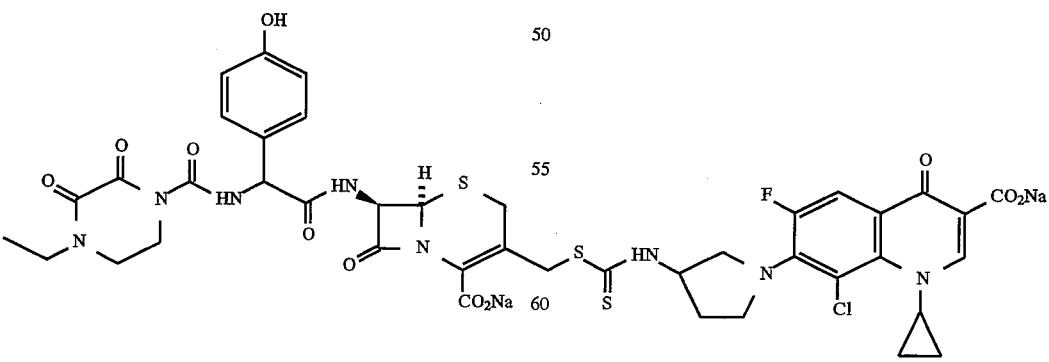

using the quinolone 7-(3-aminopyrrolidinyl)-1-chloro-1-cyclopropyl-6-fluoro-1,4-dihydro-4-oxo-3-quinoline carboxylic acid (prepared according to J. P. Sanchez, et. al., J. Med. Chem., 1988, 31, 983)

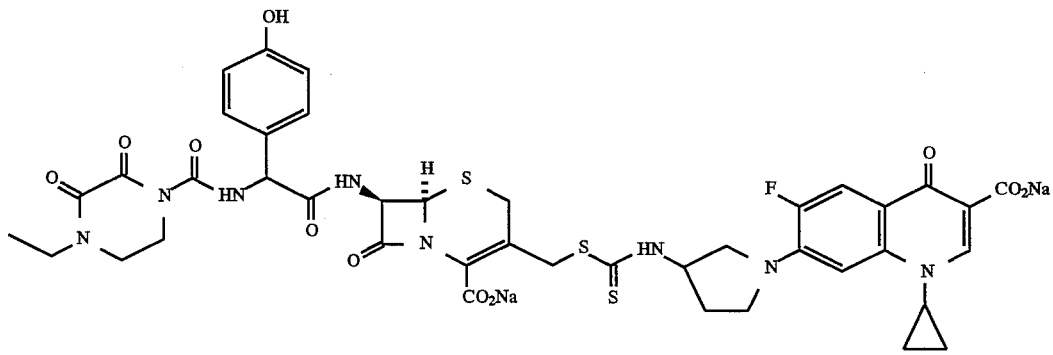

using the quinolone 7-(3-aminopyrrolidinyl)-1-cyclopropyl-6-fluoro-1,4-dihydro-4-oxo-3-quinoline carboxylic acid (prepared according to J. P. Sanchez, et. al., J. Med. Chem., 1988, 31, 983)

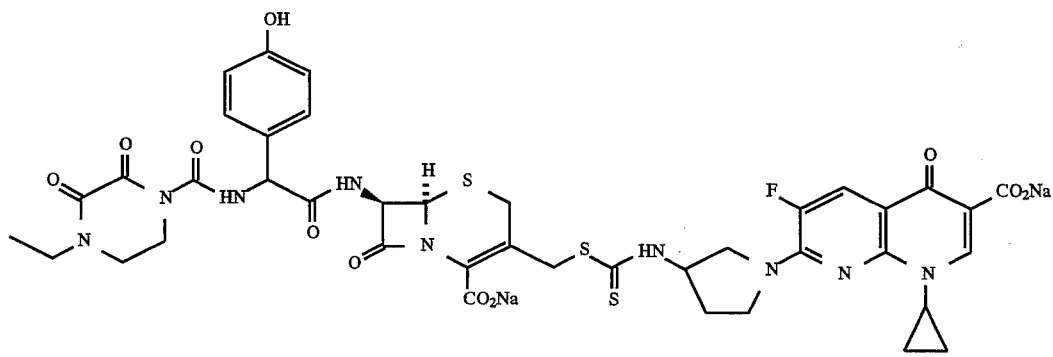

using the naphthyridinone 7-(3-aminopyrrolidinyl)-1-cyclopropyl-6-fluoro-1,4-dihydro-4-oxo-1,8-naphthyridine-3-carboxylic acid (prepared according to J. P. Sanchez, et. al., J. Med. Chem., 1988, 31, 983)

EXAMPLE 16

According to the general procedure of Example 13, the following lactam-quinolone is made:

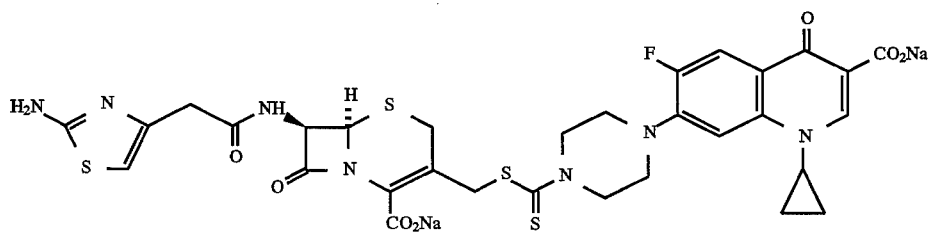

using the beta-lactam 3-(acetyloxymethyl)-7-[[(2-amino-4-thiazolyl)acetyl]amino]-8-oxo-5-thia-1-azabicyclo[4.2.0]oct-2-ene-2-carboxylic acid (prepared according to J. Org. Chem., 1970, 35, 2430)

The following other lactam-quinolones are made by the general procedure of this Example, with substantially similar results.

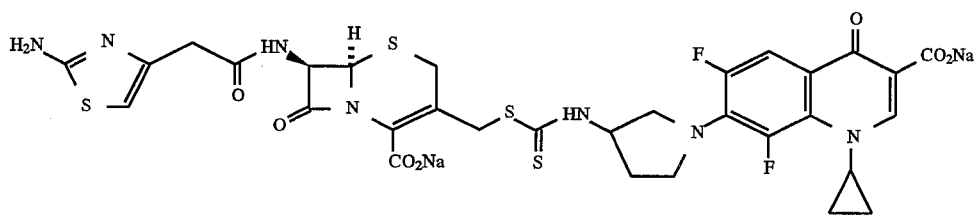

using the quinolone 7-(3-aminopyrrolidinyl)-1-cyclopropyl-6,8-difluoro-1,4-dihydro-4-oxo-3-quinoline carboxylic acid (prepared according to J. P. Sanchez, et. al., J. Med. Chem., 1988, 31, 983)

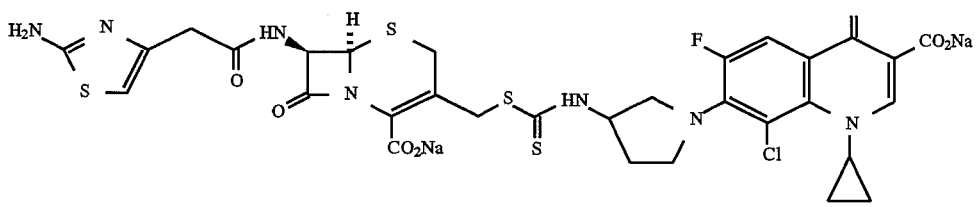

using the quinolone 7-(3-aminopyrrolidinyl)-1-chloro-1-cyclopropyl-6-fluoro-1,4-dihydro-4-oxo-3-quinoline carboxylic acid (prepared according to J. P. Sanchez, et. al., J. Med. Chem., 1988, 31, 983)

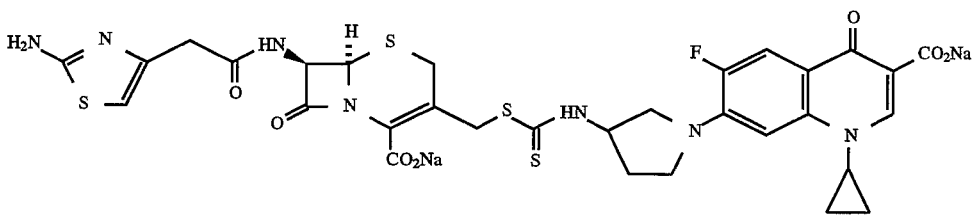

using the quinolone 7-(3-aminopyrrolidinyl)1-cyclopropyl-6-fluoro-1,4-dihydro-4-oxo-3-quinoline carboxylic acid (prepared according to J. P. Sanchez, et. al., J. Med. Chem., 1988, 31, 983)

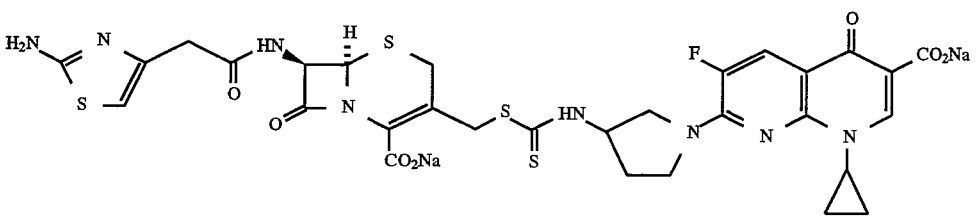

using the naphthyridinone 7-(3-aminopyrrolidinyl)-1-cyclopropyl-6-fluoro-1,4-dihydro-4-oxo-1,8-naphthyridine-3-carboxylic acid (prepared according to J. P. Sanchez, et. al., J. Med. Chem., 1988, 31, 983)

EXAMPLE 17

According to the general procedure of Example 13, the following lactam-quinolone is made:

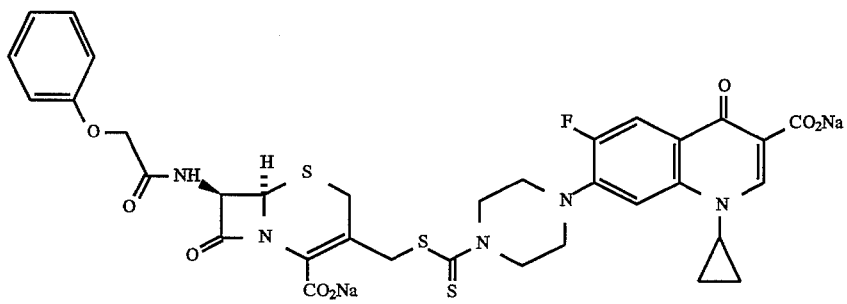

using the beta-lactam 3-(acetyloxymethyl)-8-oxo-7-[(phenoxyacetyl)amino]-5-thia-1-azabicyclo[4.2.0]oct-2-ene-2-carboxylic acid (prepared according to R. B. Morin, et. al., J. Am. Chem. Soc., 1969, 91, 1401)

The following other lactam-quinolones are made by the general procedure of this Example, with substantially similar results.

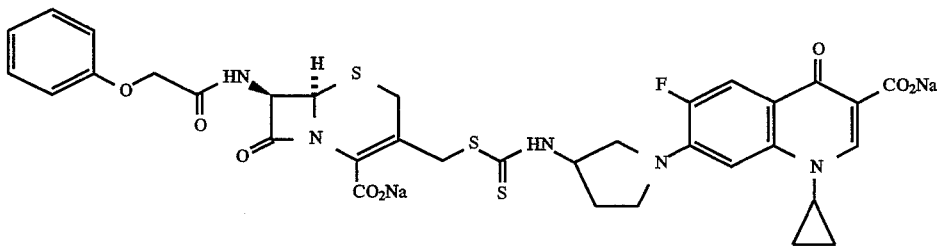

using the quinolone 7-(3-aminopyrrolidinyl)-1-cyclopropyl-6,8-difluoro-1,4-dihydro-4-oxo-3-quinoline carboxylic acid (prepared according to J. P. Sanchez, et. al., J. Med. Chem., 1988, 31, 983)

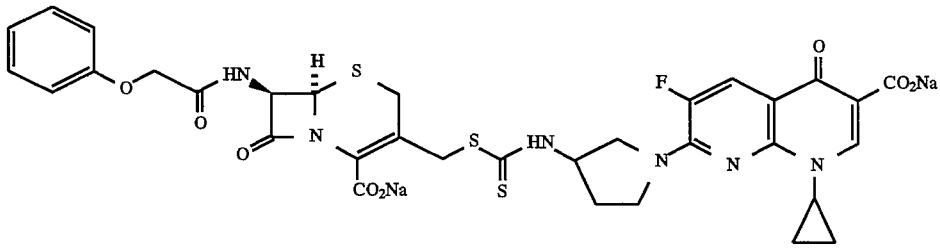

using the quinolone 7-(3-aminopyrrolidinyl)-1-chloro-1-cyclopropyl-6-fluoro-1,4-dihydro-4-oxo-3-quinoline carboxylic acid (prepared according to J. P. Sanchez, et. al., J. Med. Chem., 1988, 31, 983)

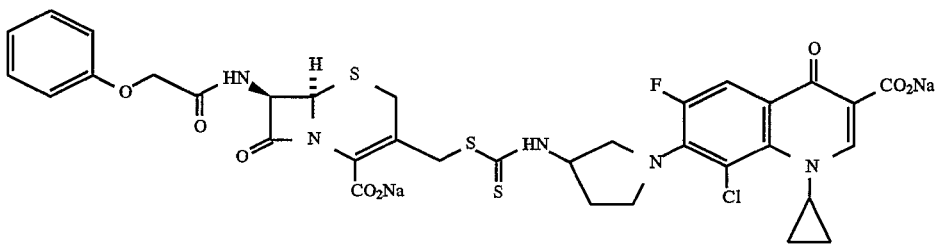

using the quinolone 7-(3-aminopyrrolidinyl)-1-cyclopropyl-6-fluoro-1,4-dihydro-4-oxo-3-quinoline carboxylic acid (prepared according to J. P. Sanchez, et. al., J. Med. Chem., 1988, 31, 983)

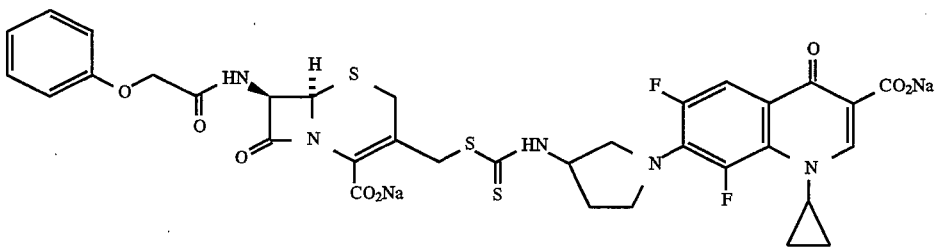

using the naphthyridinone 7-(3-aminopyrrolidinyl)-1-cyclopropyl-6-fluoro-1,4-dihydro-4-oxo-1,8-naphthyridine-3-carboxylic acid (prepared according to J. P. Sanchez, et. al., J. Med. Chem., 1988, 31, 983)

EXAMPLE 18

[6R-[6α, 7β(Z)]]-7-[[[(2-Amino-4-thiazolyl)methoxyimino]acetyl]amino]-3-[[[[4-(3-carboxy-1-cyclopropyl-6-fluoro-1,4-dihydro-4-oxo-7-quinolinyl)-1-piperazinyl]thioxomethyl]thio]methyl]-8-oxo-5-thia-1-azabicyclo[4.2.0]oct-2-ene-2-carboxylic acid disodium salt, according to this invention, is made by the following general reaction sequence.

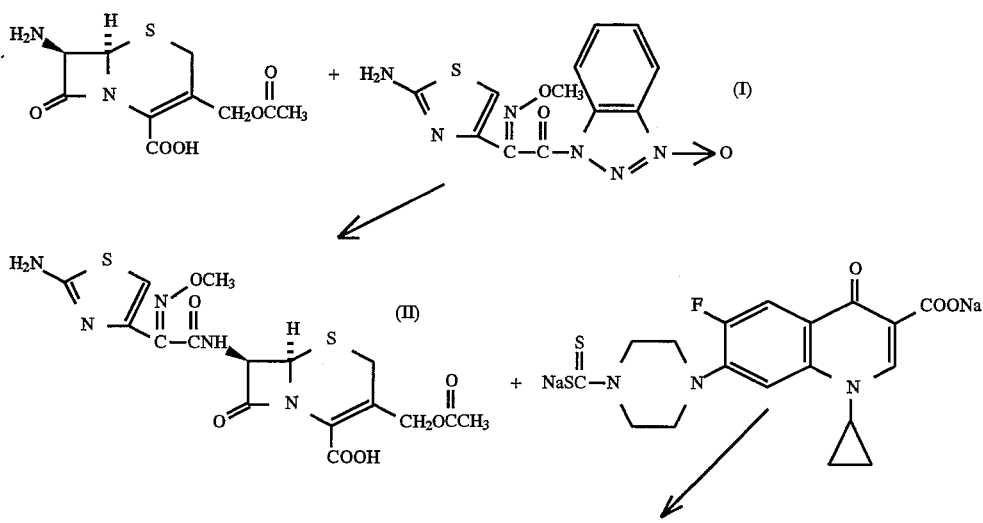

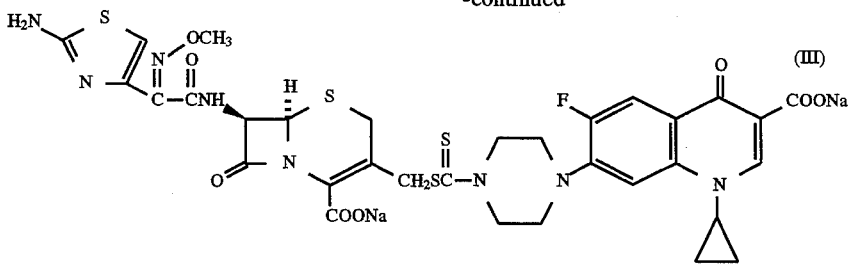

(III)

Approximately 11.4 g of 1-hydroxybenzotriazole hydrate is dissolved in approximately 90 ml of N,N-dimethylacetamide (DMAC). Approximately 12.6 ml of triethylamine is added and the solution cooled in an ice/acetone bath. Approximately 6.3 ml of methanesulfonyl chloride in DMAC is added dropwise at approximately 0° C. (32° F.) over approximately 25 minutes. The reaction is stirred for an additional 90 minutes. Approximately 15 g of 2-amino-2-(methoxyimino)-4-thiazoleacetic acid is then added. After the addition is complete, approximately 11.3 ml of triethylamine is added dropwise, at approximately 5° C. (41° F.) over approximately 30 minutes. The reaction is then stirred for an additional 105 minutes. Water is added dropwise over 20 minutes and the temperature increased to approximately 20° C. (68° F). The suspension is stirred for about 10 minutes, then a precipitate collected by filtration, washed with large volumes of water, and dried to yield product (I).

Approximately 8 g of 7-aminocephalosporanic acid is suspended in 50% aqueous acetone and cooled in an ice bath. Approximately 3.7 ml of triethylamine is added slowly.

(35° F.) approximately 2 hours, and stirred at room temperature for approximately 3 hours. The acetone is removed by evaporation and the aqueous solution cooled in ice. The solution is then layered with ethyl acetate and adjusted to approximately pH 2.3 with concentrated hydrochloric acid. The layers are separated and the aqueous phase extracted with ethyl acetate. The organic extracts are combined and evaporated. The residue is stirred in ether and collected by filtration yielding product (II).

Approximately 1.5 g of product (II) is suspended in water (24 ml), and approximately 0.27 g of sodium bicarbonate is added, followed by approximately 1.2 g of product (I) from Example II. The solution is stirred at approximately 42° C. (107° F.) for 24 hours. The solvent is removed under vacuum, and the residue is stirred in acetone for 20 minutes and collected by filtration, yielding the final product (II).

Similarly, the following lactam-quinolones are prepared by the general procedure of this Example, with substantially similar results.

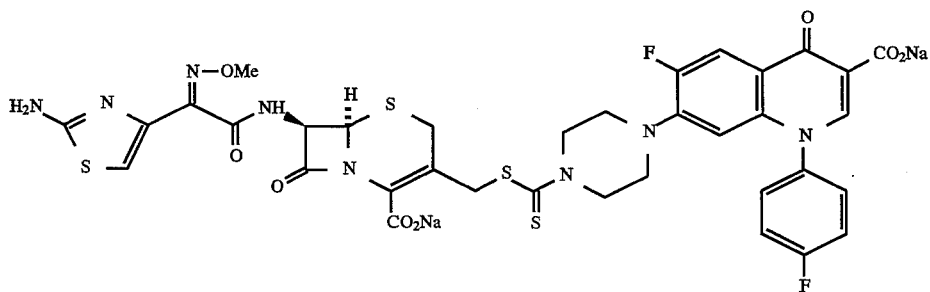

Approximately 11 g of product (I) is added, at approximately 2° C. (35° F.). Solutions of saturated aqueous potassium phosphate monobasic (pH 4.5) and 45% aqueous potassium phosphate dibasic (pH 10) are added as necessary to maintain a pH of approximately 7.5. After the addition of product (I) is complete, the mixture is stirred at approximately 2° C.

using the quinolone 6-fluoro-1-(4-fluorophenyl)-1,4-dihydro-4-oxo-7-(1-piperazinyl)-3-quinoline carboxylic acid (prepared according to D. T. W. Chu, et. al., J. Med. Chem., 1985, 28, 1558)

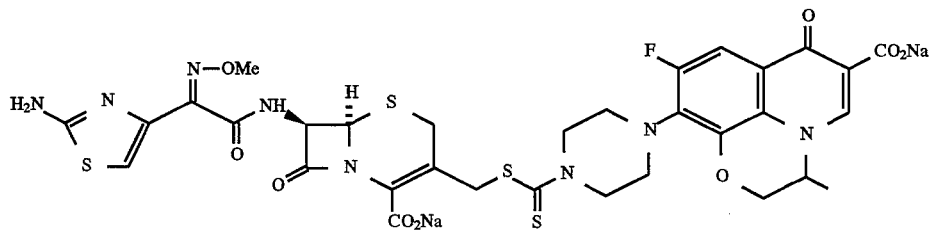

using the quinolone 9-fluoro-4,7-dihydro-3-methyl-10-(1-piperazinyl)-7-oxo-2H-pyrido[1,2,3-de]-1,4-benzoxazine- 6-carboxylic acid (prepared according to I. Hayakawa, et. al., Chem. Pharm. Bull., 1984, 32, 4907)

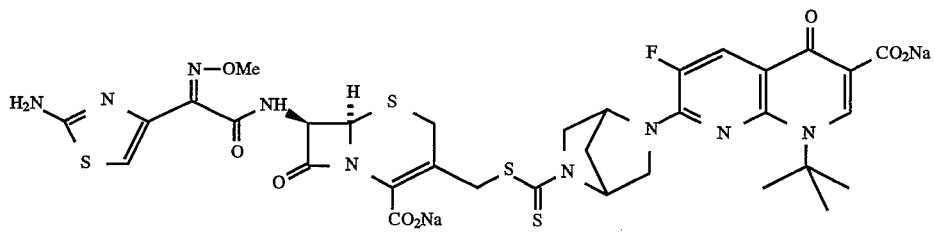

using the naphthyridinone 7-(2,5-diazabicyclo[2.2.1] heptan-2-yl)-1-(1,1-dimethylethyl)-6-fluoro-1,4-dihydro-4-oxo-1,8-naphthyridine-3- carboxylic acid (prepared according to A. Weber, et. al., EP 266576)

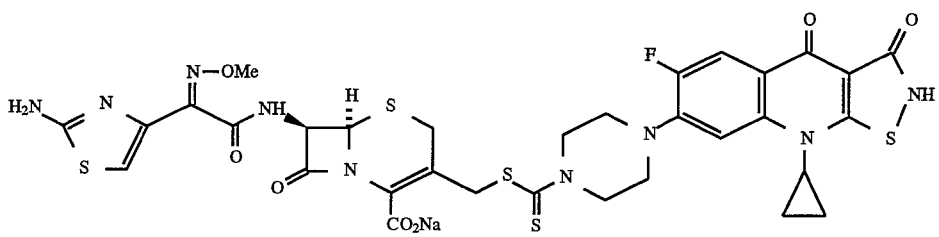

using the quinolone 9-cyclopropyl-6-fluoro-2,3,4,9-tetrahydro-7-(1-piperazinyl)isothiazolo[5,4-b]quinoline-3,4-dione (prepared according to D. T. W. Chu, EP 227,088)

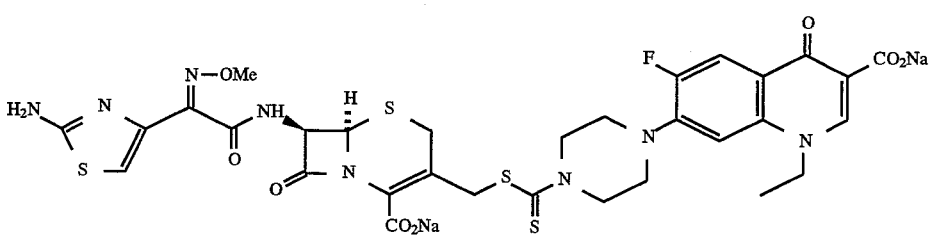

using the quinolone 1-ethyl-6-fluoro-1,4-dihydro-4-oxo-7-(1-piperazinyl)-3-quinoline carboxylic acid (prepared according to H. Koga, et. al., J. Med. Chem., 1980, 23, 1358)

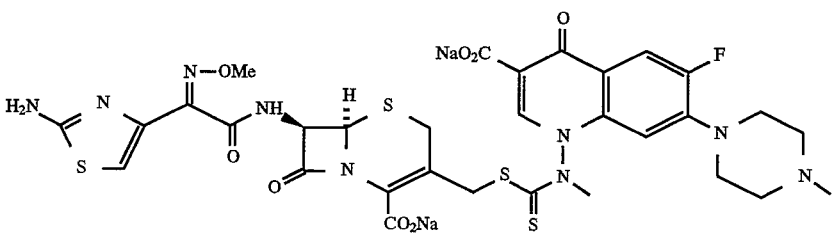

using the quinolone 6-fluoro-1,4-dihydro-1-methylamino-7-(4-methyl-1-piperazinyl)-4-oxo-3-quinoline carboxylic acid (prepared according to M. P. Wentland, et. al., J. Med. Chem., 1984, 27, 1103)

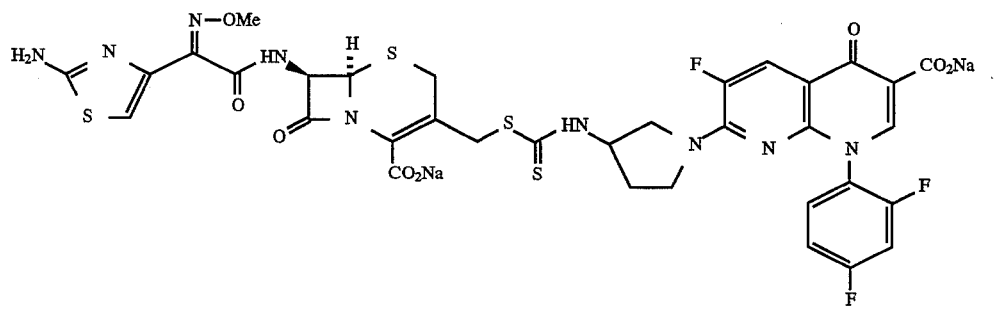

using the naphthyridinone 7-(3-aminopyrrolidinyl)-1-(2,4-difluorophenyl)-6-fluoro-1,4-dihydro-4-oxo-1,8-naphthyridine-3-carboxylic acid (prepared according to D. T. W. Chu, et. al., J. Med. Chem., 1986, 29, 2363)

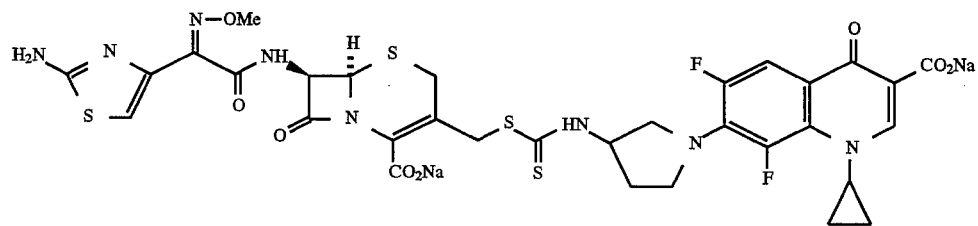

using the quinolone 7-(3-aminopyrrolidinyl)-1-cyclopropyl-6,8-difluoro-1,4-dihydro-4-oxo-3-quinoline carboxylic acid (prepared according to J. P. Sanchez, et. al., J. Med. Chem., 1988, 31, 983)

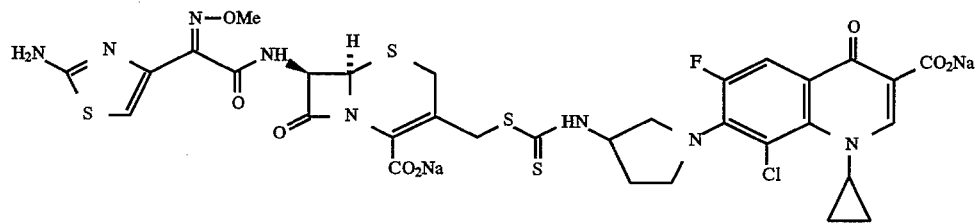

using the quinolone 7-(3-aminopyrrolidinyl)-1-chloro-1-cyclopropyl-6-fluoro-1,4-dihydro-4-oxo-3-quinoline carboxylic acid (prepared according to J. P. Sanchez, et. al., J. Med. Chem., 1988, 31, 983)

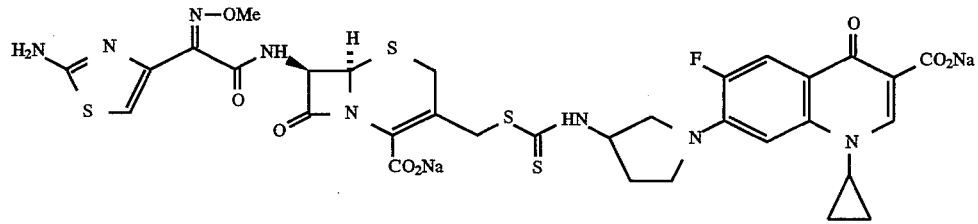

using the quinolone 7-(3-aminopyrrolidinyl)-1-cyclopropyl-6-fluoro-1,4-dihydro-4-oxo-3-quinoline carboxylic acid (prepared according to J. P. Sanchez, et. al., J. Med. Chem., 1988, 31, 983)

239 240

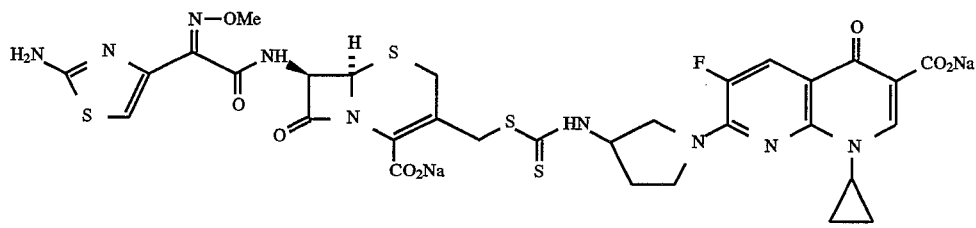

using the naphthyridinone 7-(3-aminopyrrolidinyl)-1-cyclopropyl-6-fluoro-1,4-dihydro-4-oxo-1,8-naphthyridine-3-carboxylic acid (prepared according to J. P. Sanchez, et. al., J. Med. Chem., 1988, 31, 983).

EXAMPLE 19

[6R-[6α, 7β]]-3-[[[[4-(3-Carboxy-1-cyclopropyl-6-fluoro-1,4-dihydro-4-oxo-7-quinolinyl)-1-piperazinyl]thioxomethyl]thio]-methyl]-7-methoxy-8-oxo-7-[(2-thienylacetyl)amino]-S-thia-1-azabicyclo[4.2.0]-oct-2-ene-2-carboxylic Acid, Disodium Salt

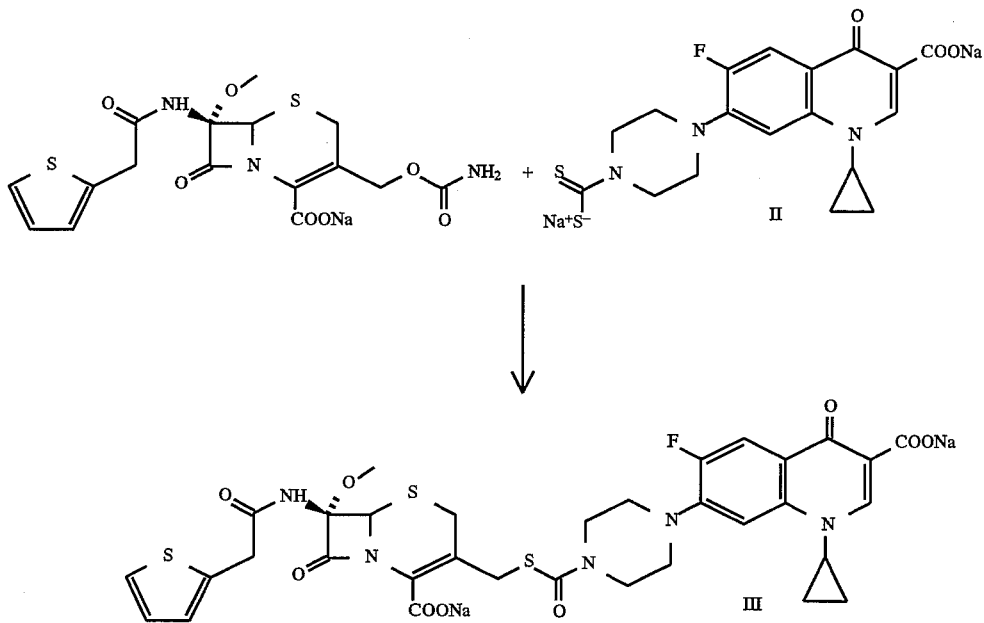

Approximately 5.0 g of cefoxitin sodium salt I (prepared according to U.S. Pat. No. 4,297,488) and II (5.0 g) is stirred in water (50 ml) at 90°–95° (for 45 minutes). The reaction is cooled to room temperature, then refrigerated overnight. Acetone is added and the mixture is stirred for 1 hour. The solid is then collected by filtration and is dried. The crude material was purified by reverse phase chromatography to give III as the disodium salt.

Similarly, the following lactam-quinolones are prepared by the general procedure of this example, with substantially similar results.

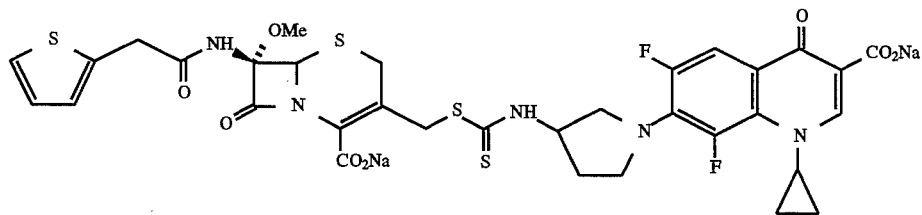

using the quinolone 7-(3-aminopyrrolidinyl)-1-cyclopropyl-6,8-difluoro-1,4-dihydro-4-oxo-3-quinoline carboxylic acid (prepared according to J. P. Sanchez, et. al., J. Med. Chem., 1988, 31, 983)

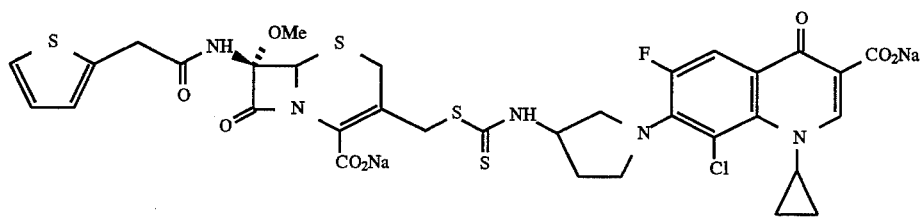

using the quinolone 7-(3-aminopyrrolidinyl)-1-chloro-1-cyclopropyl-6-fluoro-1,4-dihydro-4-oxo-3-quinoline carboxylic acid (prepared according to J. P. Sanchez, et. al., J. Med. Chem., 1988, 31, 983)

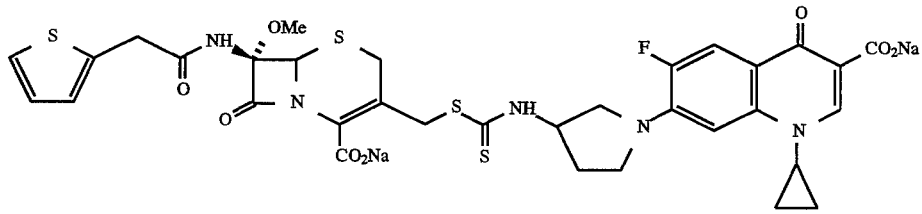

using the quinolone 7-(3-aminopyrrolidinyl)-1-cyclopropyl-6-fluoro-1,4-dihydro-4-oxo-3-quinoline carboxylic acid (prepared according to J. P. Sanchez, et. al., J. Med. Chem., 1988, 31, 983)

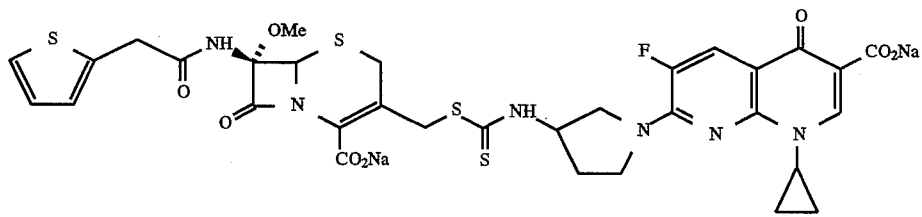

using the naphthyridinone 7-(3-aminopyrrolidinyl)-1-cyclopropyl-6-fluoro-1,4-dihydro-4-oxo-1,8-naphthyridine-3-carboxylic acid (prepared according to J. P. Sanchez, et. al., J. Med. Chem., 1988, 31, 983)

EXAMPLE 20

According to the general procedure of Example 19, the following lactam-quinolone is made:

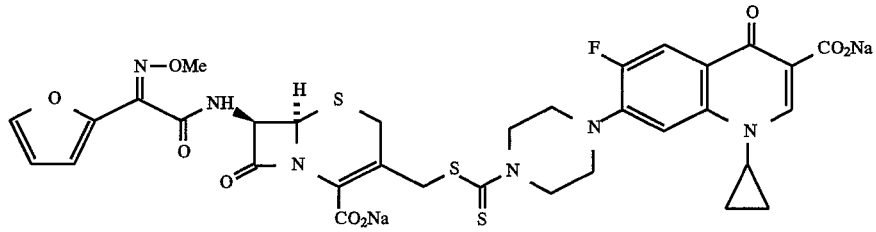

using the beta-lactam 3-[[(aminocarbonyl)oxy]methyl]-7-[[2-furanyl methoxyimino)acetyl]amino]-8-oxo-5-thia-1-azabicyclo [4.2.0]oct-2-ene- carboxylic acid (prepared according to M. C. Cook, et. al., US 3,974,153)

The following other lactam-quinolones are made by the general procedure of this Example, with substantially similar results.

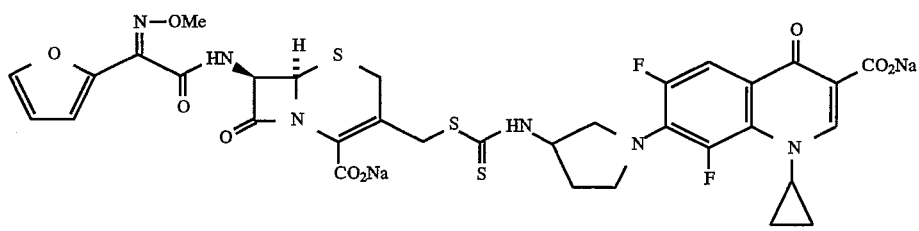

using the quinolone 7-(3-aminopyrrolidinyl)-1-cyclopropyl-6,8-difluoro-1,4-dihydro-4-oxo-3-quinoline carboxylic acid (prepared according to J. P. Sanchez, et. al., J. Med. Chem., 1988, 31, 983)

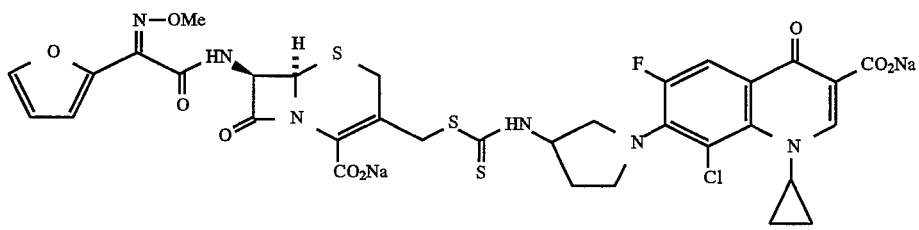

using the quinolone 7-(3-aminopyrrolidinyl)-1-chloro-1-cyclopropyl-6-fluoro-1,4-dihydro-4-oxo-3-quinoline carboxylic acid (prepared according to J. P. Sanchez, et. al., J. Med. Chem., 1988, 31, 983)

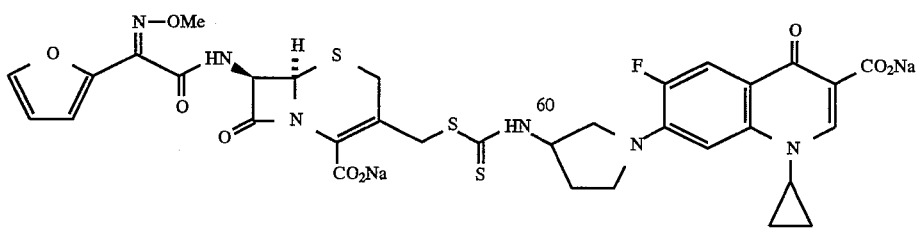

using the quinolone 7-(3-aminopyrrolidinyl)-1-cyclopropyl-6- fluoro-1,4-dihydro-4-oxo-3-quinoline carboxylic acid (prepared according to J. P. Sanchez, et. al., J. Med. Chem., 1988, 31, 983)

mately 1.5 hours, then diluted with water and washed With ether. The aqueous phase is cooled to 5° C., adjusted to pH 2 with 1N HCl and the product is extracted with ethyl acetate. The organic phase is dried over sodium sulfate,

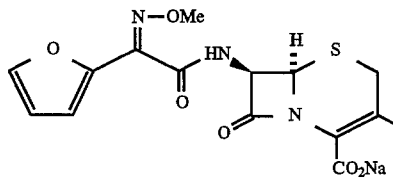
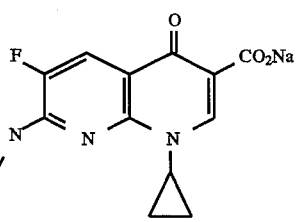

using the naphthyridinone 7-(3-aminopyrrolidinyl)-1-cyclopropyl-6-fluoro-1,4-dihydro4-oxo-1,8-naphthyridine-3-carboxylic acid (prepared according to J. P. Sanchez, et. al., J. Med. Chem., 1988, 31, 983).

EXAMPLE 21

[5R-[5α,6α(R*)]]-3-[[[[4-(3-Carboxy-1-cyclopropyl-6-fluoro-1,4-dihydro-4-oxo-7-quinolinyl)-1-piperazinyl]thioxomethylthio]acetyl]aminomethyl]-7-oxo-4-thia-1-azabicyclo[3.2.0]hept-2-ene-2-carboxylic Acid Disodium Salt filtered and the tiltrate is concentrated to dryness to give II. To a solution of II (0.09 g) in dry DMF (4 ml) at 0° C. is added triethylamine (0.034 ml) followed by III (0.11 g). The mixture is stirred at approximately 2° C. for one hour and at ambient temperature for one hour. The mixture is concentrated to dryness in vacuo. The residue is stirred in water, cooled and adjusted to pH 2 with 1N HCl. The product is collected by filtration and is added to a solution of sodium bicarbonate (0.032 g) in water (5 ml). After the mixture is stirred for one hour and is diluted with acetone, the product IV as the disodium salt is collected by filtration.

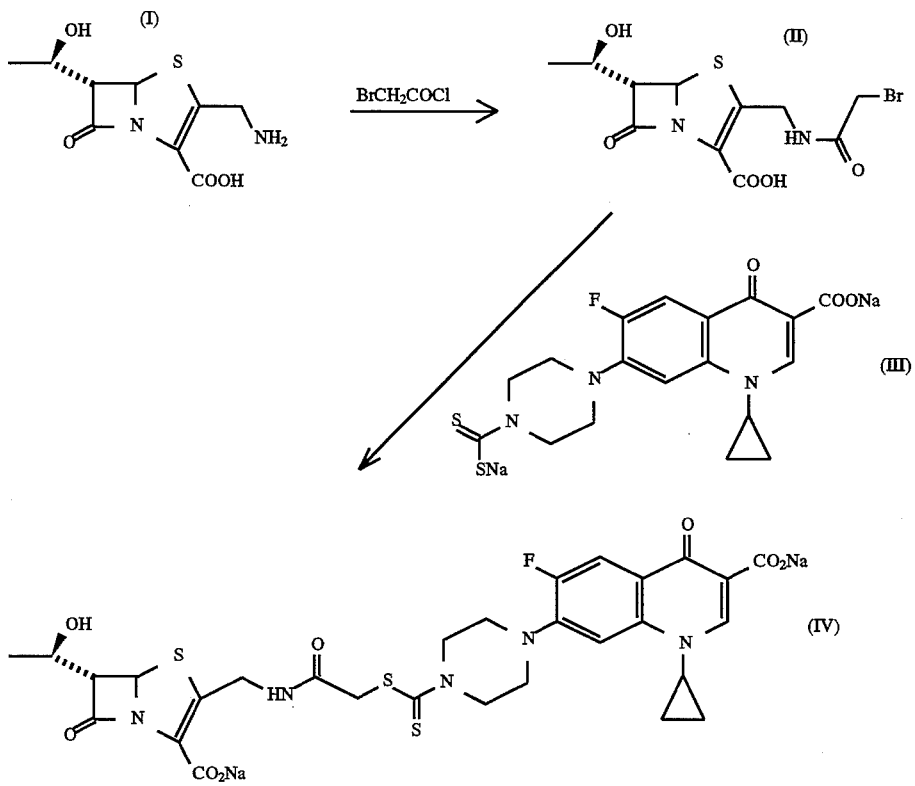

To a solution of sodium bicarbonate (0.086 g) in water (2 ml) at 0° C. is added [5R-[5α,6α]]-3-(aminomethyl)-6-[(R)-1-hydroxyethyl)]-7-oxo-4-thia-1-azabicyclo[3.2.0]hept-2-ene-2-carboxylic acid I (0.1 g) followed by acetone (1.5 ml). To the resulting solution is added bromoacetylchloride (approximately 0.049 ml) in acetone (0.5 ml) dropwise over 7 minutes. The reaction is stirred in the cold for approxi-

EXAMPLE 22

2-(Acetyloxy)-4-oxo-3S-[(phenoxyacetyl)amino]-1-azetidine sulfonic acid sodium is prepared as an intermediate for use in Example 23.

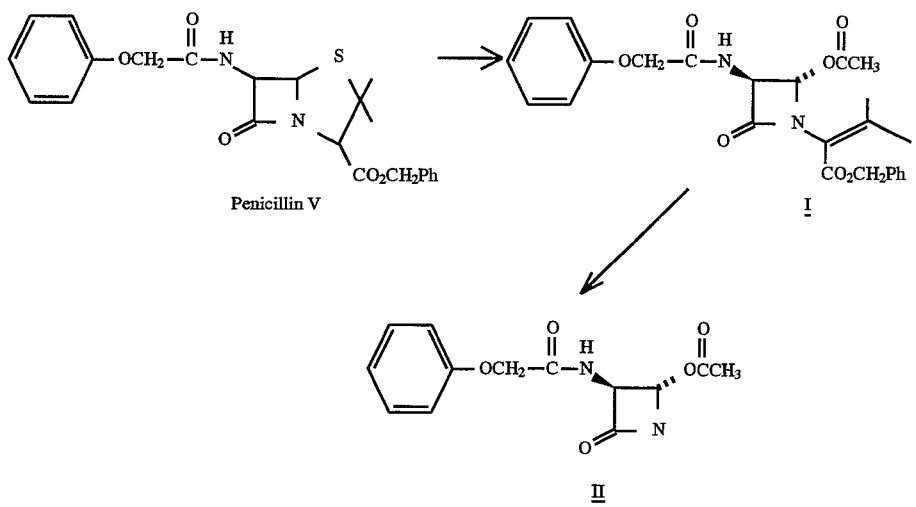

Mercury II acetate (15.9 g, 0.050 mole) is added to a solution of Penicillin V benzyl ester in 35.2 ml of acetic acid and heated to 90° C. for 1.5 hours. The mercury salts are then filtered off over Celite. The liltrate is diluted with water and neutralized with solid sodium carbonate. The layers are separated and the organic layer washed with water, dried over sodium sulfate and concentrated to yield 11.3 g of crude I. This is chromatographed (silcia) to yield 5.6 g of pure I.

I (5.6 g, 0.012 mole) is dissolved in 125 ml of acetone with 2.57 ml of acetic acid and cooled to 0° C. Potassium permanganate (2.47 g, 0.016 mole) is dissolved in 88 ml of water and added dropwise through a dropping funnel keeping the temperature between 0°–5° C. When the addition is complete, the reaction is warmed to room temperature and allowed to stir for 3 hours. The manganese dioxide is filtered off over Celite, washing with methylene chloride. The layers are separated and the organic layer washed with saturated sodium bicarbonate solution and water, dried and concentrated. The oil formed is recrystallized from petroleum ether and ethyl acetate to yield 0.78 g of pure II.

EXAMPLE 23

1-Cyclopropyl-6-fluoro-1,4-dihydro-4-oxo-7-[4-[[[(2S-trans)-3-[(phenoxyacetyl)amino]-2-azetidinyl]thio]thioxomethyl]-1-piperazinyl]-3-quinolinecarboxylic Acid, Sodium Salt

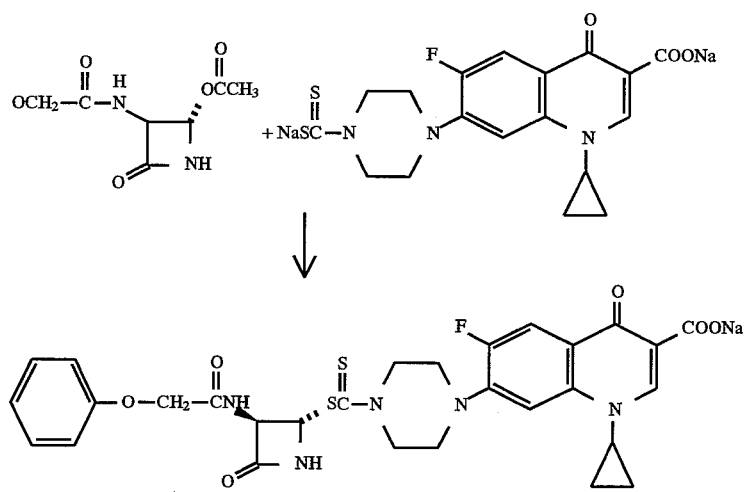

2-(Acetyloxy)-4-oxo-3S-[(phenoxyacetyl)amino]-1-azetidine (I) (2.06 g, 7.4 mmol), as prepared in Example 22, is dissolved in approximately 6 ml of acetone with 2.7 ml of water. A solution of 5.01 g of (II), as prepared in Example 13, in approximately 12.4 ml of water is added to the mixture above and a yellow precipitate forms immediately. The mixture is allowed o to stir for 30 minutes and the precipitate filtered off and washed with water and ether to yield 2 g of III.

EXAMPLE 24

1-Cyclopropyl-6-fluoro-1,4-dihydro-4-oxo-7-[4-[[[(2S-trans)-3-[(phenoxyacetyl)amino]-1-sulfo-2-azetidinyl]thio]thioxomethyl]-1-piperazinyl]-3-quinolinecarboxylic Acid, Disodium Salt

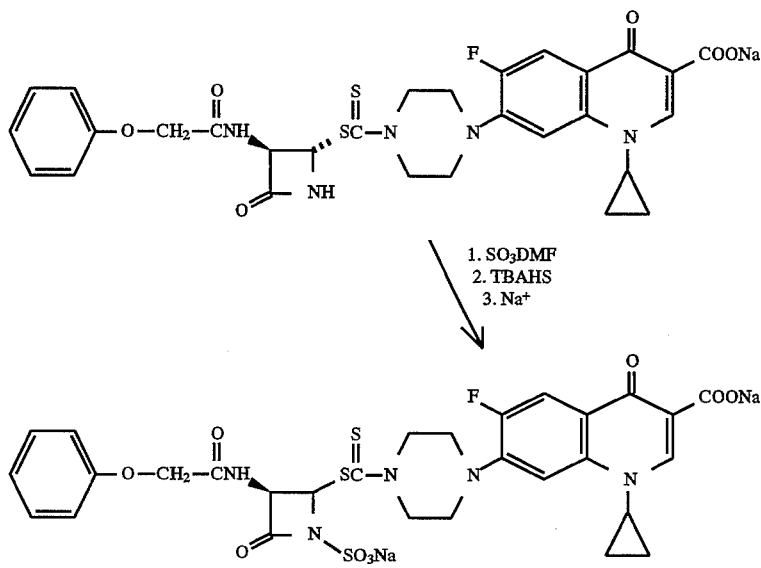

The product of Example 23 (I) (0.5 g, 0.772 mmol) is dissolved in approximately 5 ml of DMF at room temperature under a nitrogen atmosphere. DMF-SO3 complex (1.04 g, 3.86 mmol) was added and, the mixture is allowed to stir overnight. Approximately 70 ml of methylene chloride and 70 ml of 0.5N potassium hydrogen phosphate solution is added and the pH is adjusted to pH=8 with 1N NaOH. Tetrabutylammonium hydrogen sulfate (0.52 g, 1.54 mmol) is added with stirring and the layers separated. The organic layer is washed with water, dried and concentrated. The tetrabutylammonium salt is converted to the sodium salt by dissolving ill in 100-150 ml of 50% ethanol/water and adding excess Dowex 50 W (Na). This is stirred for 1½ hours then the resin is filtered, washed with water and the filtrate concentrated. The residue is first triturated with methylene chloride then with methanol and the product (II) filtered.

Similarly, the following lactam-quinolones are prepared by the general procedure of this Example, with substantially similar results.

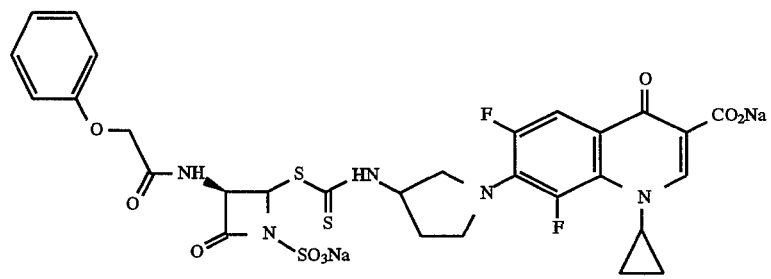

using the quinolone 7-(3-aminopyrrolidinyl)-1-cyclopropyl-6,8-difluoro-1,4-dihydro-4-oxo-3-quinoline carboxylic acid (prepared according to J. P. Sanchez, et. al., J. Med. Chem., 1988, 31, 983)

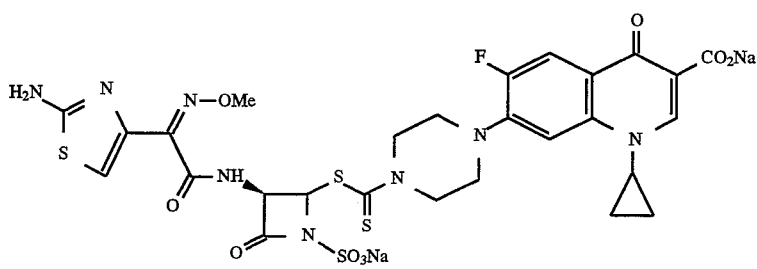

EXAMPLE 25

Product V, according to this invention, is made by the following general sequence.

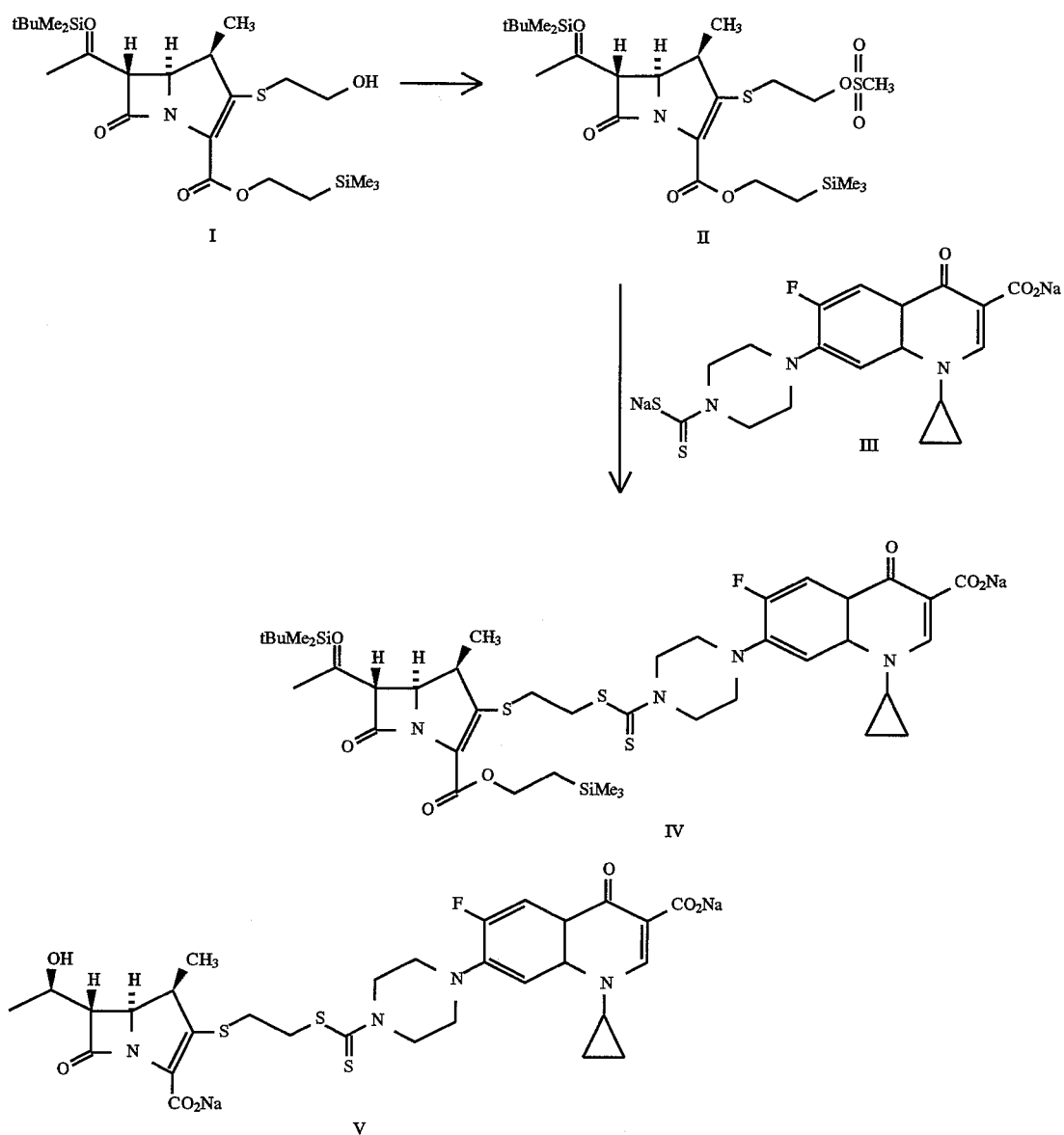

using the beta-lactam N-[2-(acetyloxy)-4-oxo-3-azetidinyl]-2-amino-alpha-(methoxyimino)-4-thiazoleacetamide (prepared according to T. Matsuo, et al., Eur. Pat. Appl. EP 53815)

Approximately 0.20 g of the hydroxyethyl sulfide I (prepared as above) is dissolved in approximately 2 ml of dichloromethane along with approximately 0.084 ml of triethylamine, and the mixture is cooled in an ice bath under an inert atmosphere. Approximately 0.034 ml of methanesulfonyl chloride is added dropwise, and the mixture is stirred approximately 15 minutes longer. The reaction mixture is transferred to a separatory funnel along with approximately 10 ml of dichloromethane used to rinse the reaction flask. The dichloromethane solution is washed sequentially with ice water, cold 10% hydrochloric acid, saturated aqueous sodium bicarbonate, and saturated aqueous sodium chloride. After drying over $Na_2SO_4$ and concentration of the solution product II is obtained.

Approximately 0.2 g of product II is dissolved in approximately 2 ml of dimethylformamide along with approximately 0.16 g of product III (prepared as above). The mixture is heated to approximately 70° C. for approximately 6 hours before cooling to room temperature to provide a. solution containing product IV. The addition of approximately 0.32 g of tetra-n-butylammonium fluoride trihydrate is followed by stirring for approximately 16 hours at room temperature. Approximately 1 ml of saturated aqueous sodium bicarbonate is added and the mixture is eluted through a DowexR 50×4 (Na cycle) column with deionized water. The appropriate fractions are partially concentrated in vacuo, then lyophilized to give the final product V.

Similarly, the following lactam-quinolones are prepared by the general procedure of this Example, with substantially similar results.

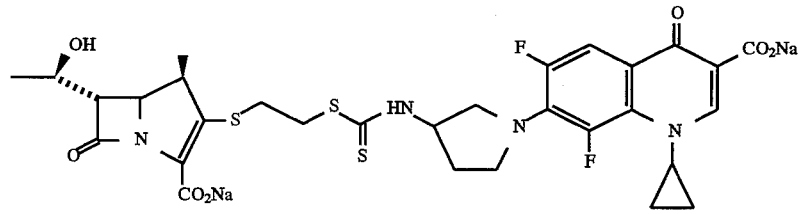

using the quinolone 7-(3-aminopyrrolidinyl)-1-cyclopropyl-6,8-difluoro-1,4-dihydro-4-oxo-3-quinoline carboxylic acid (prepared according to J. P. Sanchez, et. al., J. Med. Chem., 1988, 31, 983)

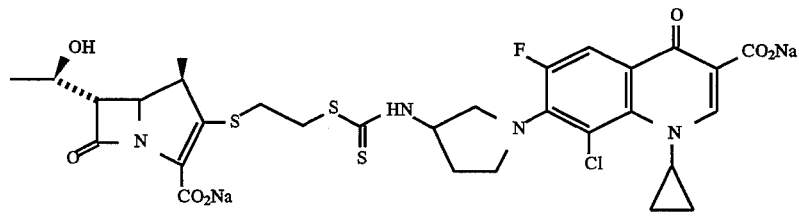

using the quinolone 7-(3-aminopyrrolidinyl)-1-chloro-1-cyclopropyl1-6-fluoro1,4-dihydro-4-oxo-3-quinoline carboxylic acid (prepared according to J. P. Sanchez, et. al., J. Med. Chem., 1988, 31, 983)

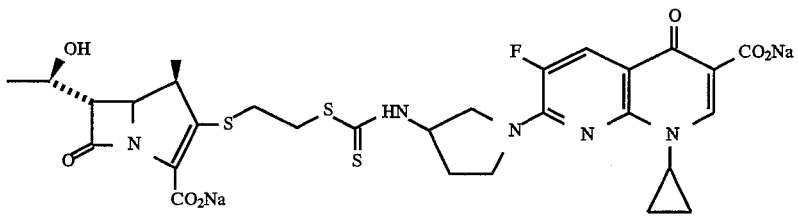

using the quinolone 7-(3-aminopyrrolidinyl)1-cyclopropyl-6-fluoro-1,4-dihydro-4-oxo-3-quinoline carboxylic acid (prepared according to J. P. Sanchez, et. al., J. Med. Chem., 1988, 31, 983)

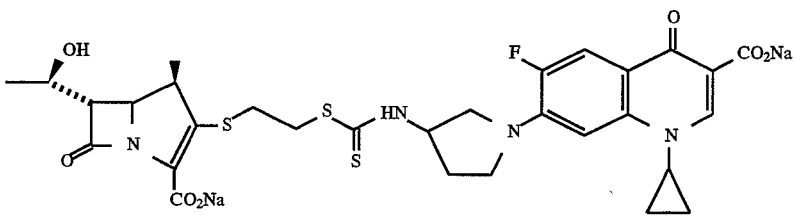

using the naphthyridinone 7-(3-aminopyrrolidinyl)-1-cyclopropyl-6-fluoro-1,4-dihydro-4-oxo-1,8-naphthyridine-3-carboxylic acid (prepared according to J. P. Sanchez, et. al., J. Med. Chem., 1988, 31, 983)

EXAMPLE 26

[5R-[5α,6α]-3-[[[4-(3-Carboxy-1-cyclopropyl-6-fluoro-1,4-dihydro-4-oxo-7-quinolinyl)-1-piperazinyl]thioxomethyl]thio]methyl]-6-[(R)-1-hydroxyethyl]-7-oxo-4-thia-1-azabicyclo[3.2.0]hept-2-ene-2-carboxylic Acid Disodium Salt To a solution of approximately 1.2 g of the penem t-butyldiphenylsilyl ester I (prepared according to M. Alpegiani, Ger. Offen. DE 3312393, 6 Apr. 1983) and 0.27 ml of triethylamine in CH$_2$Cl$_2$/THF at approximately −20° C. is added dropwise a solution of approximately 0.19 ml of methanesulfonyl chloride in THF. After the reaction is stirred for approximately 30 minutes, it is filtered under nitrogen and approximately 1.1 g of II is added and the reaction is stirred at 0°–5° C. for approximately two hours. To the reaction is added approximately 2.2 g of tetrabutylammonium fluoride and stirring is continued for approximately 30 minutes. The reaction is concentrated to dryness and the residue is stirred with acetone and cooled in an ice bath. The mixture is diluted with a solution of water containing approximately 2.1 g of sodium bicarbonate. The solution is extracted with diethylether and the aqueous phase

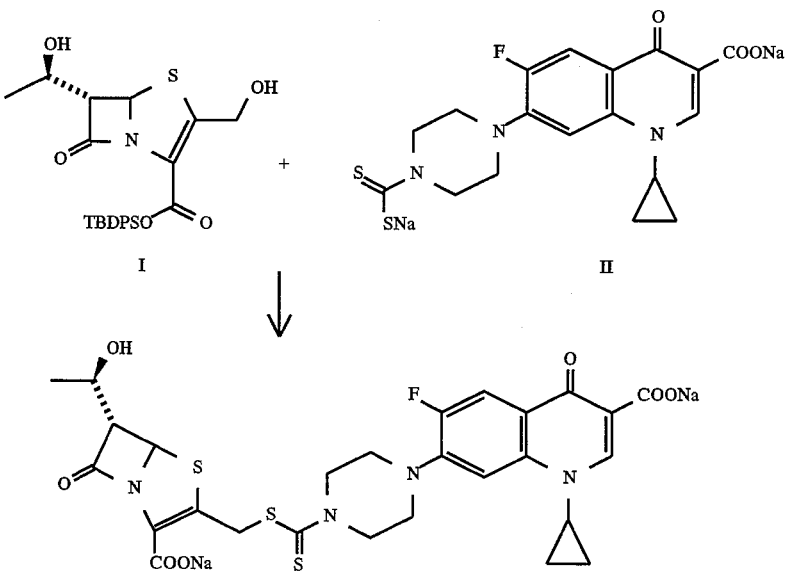

is further diluted with acetone. The product III is collected by filtration and purified by C-18 reverse phase chromatography.

Similarly, the following lactam-quinolones are prepared by the general procedure of this Example, with substantially similar results.

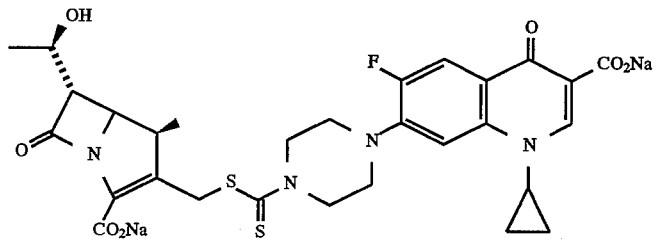

using the beta-lactam 6-(1-hydroxyethyl)-3-(hydroxymethyl)-4-methyl-7-oxo-1-azabicyclo[3.2.0]hept-2-ene-2-carboxylic acid (prepared according to S. M. Schmitt, et al., J. Antibiotics, 1988, 41, 780) which was converted to the t-butyldiphenylsilyl ester as described for Example 6a (M. Alpegiani, Ger. Offen. DE 3312393)

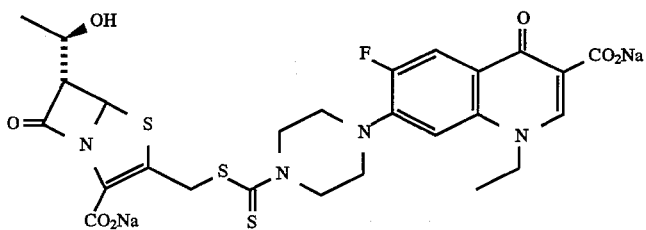

using the quinolone 1-ethyl-6-fluoro-1,4-dihydro-4-oxo-7-(1-piperazinyl)-3-quinoline carboxylic acid (prepared according to H. Koga, et. al., J. Med. Chem., 1980, 23, 1358).

The following other lactam-quinolones are also prepared by the general procedure of this Example and Examples 13–25, with substantially similar results.

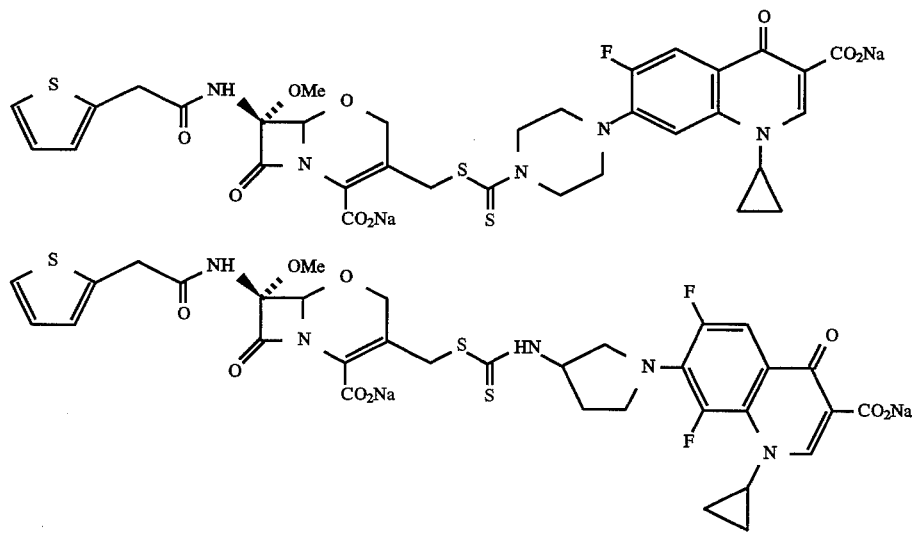

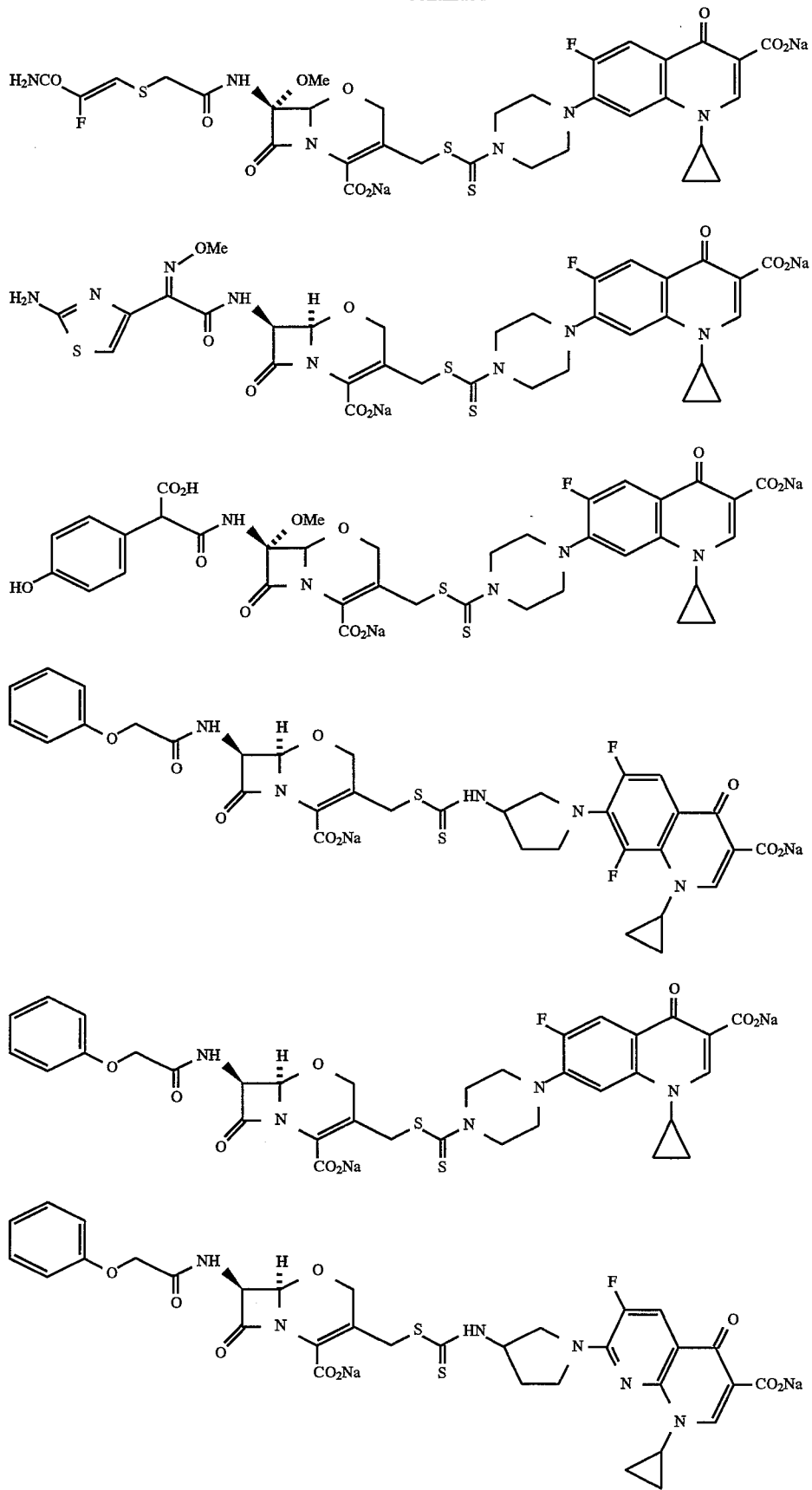

-continued
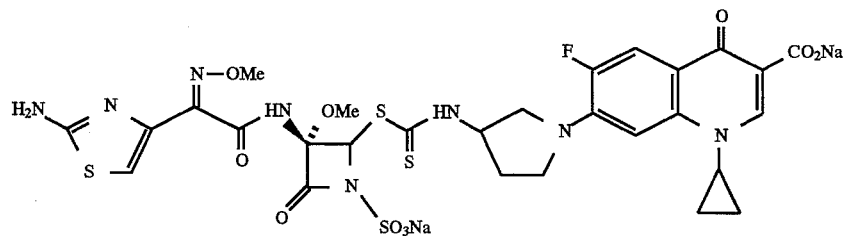
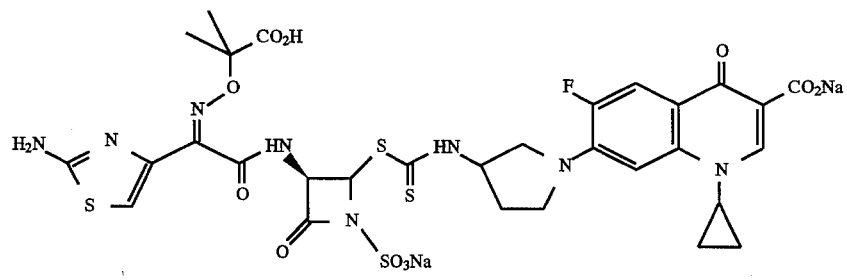
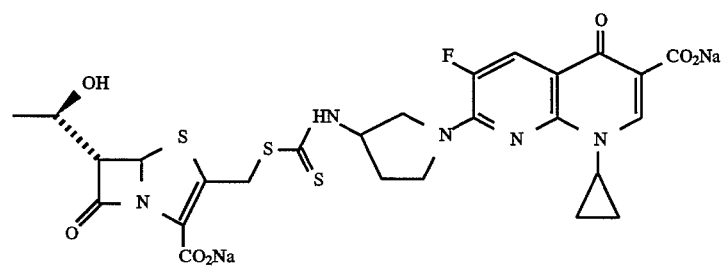
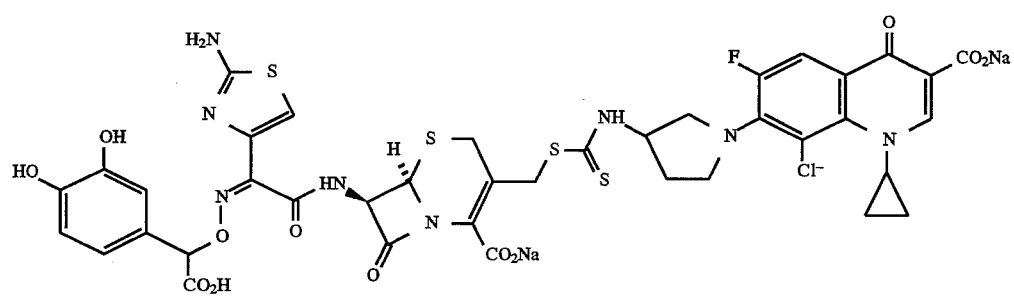
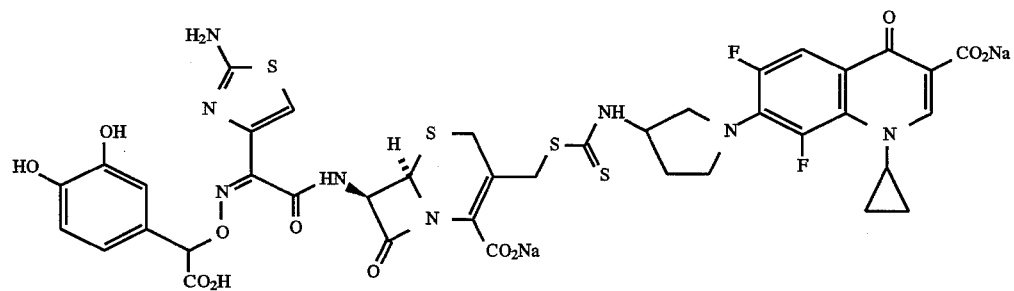
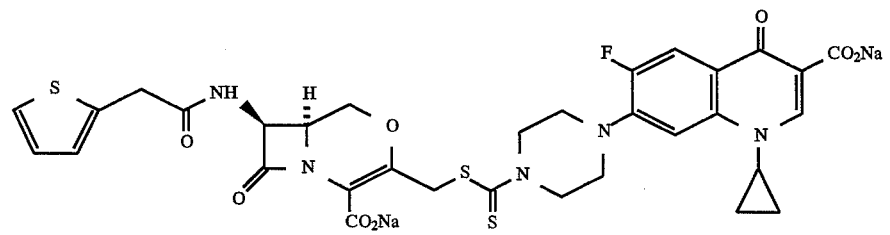

-continued
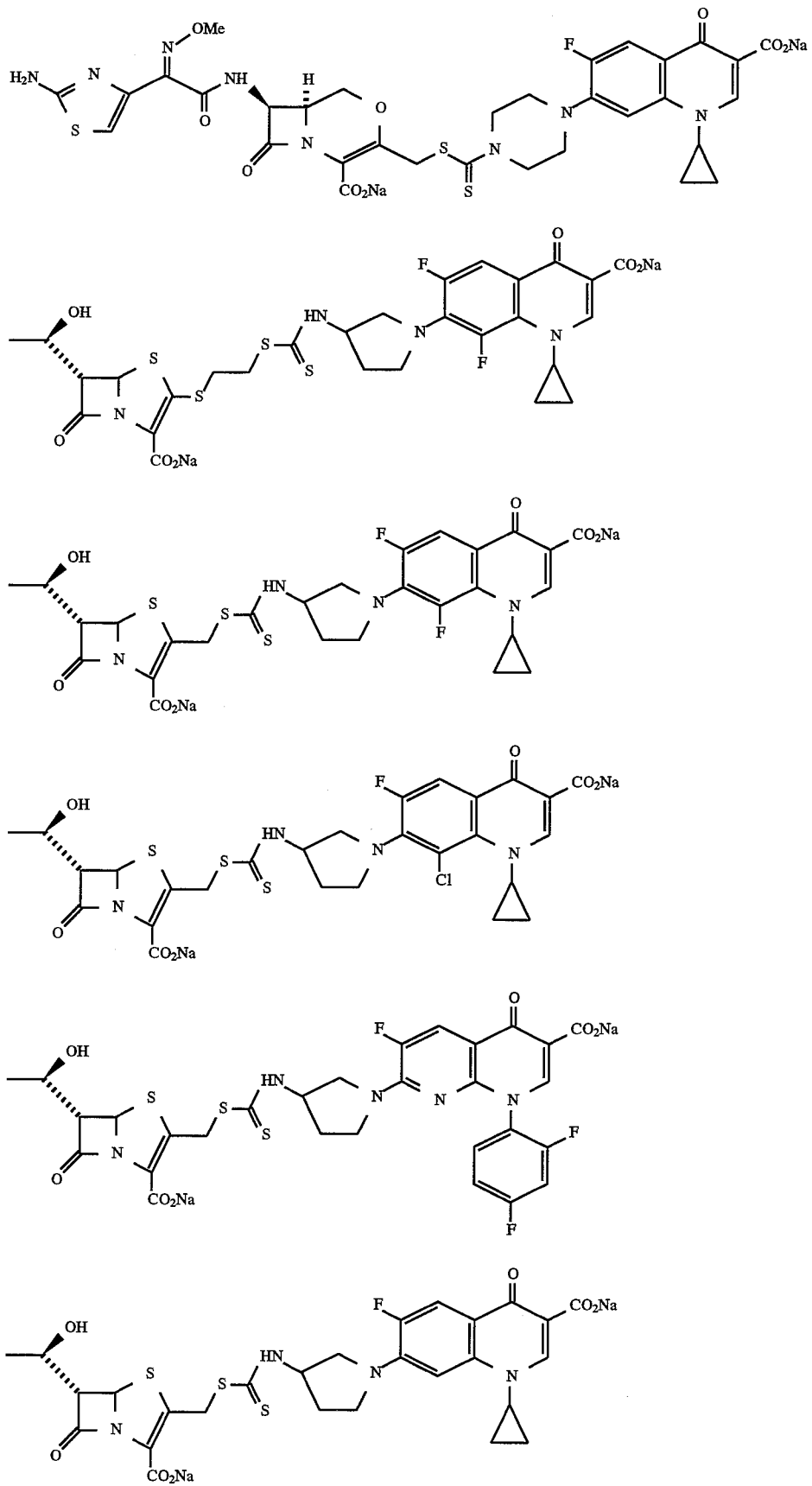

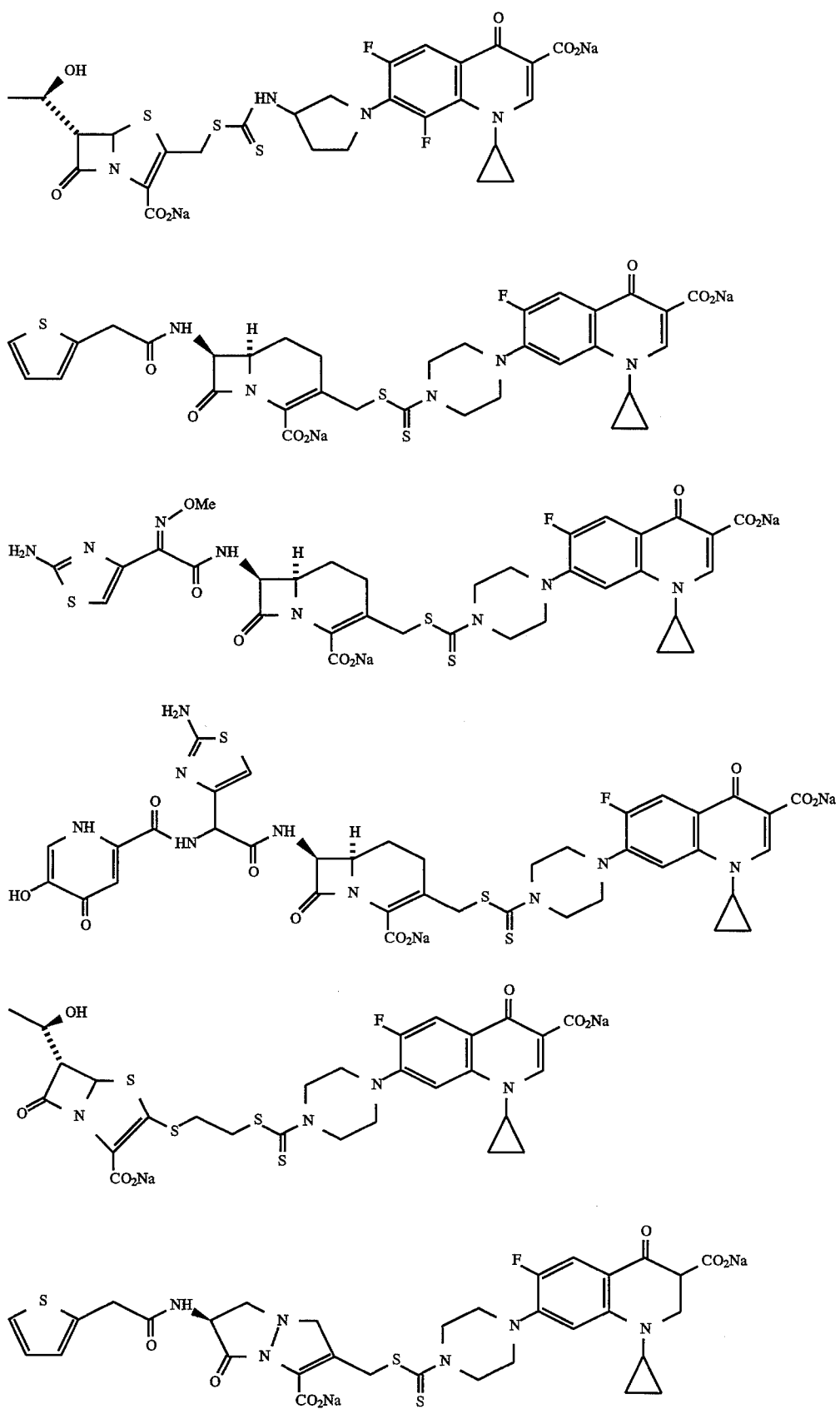

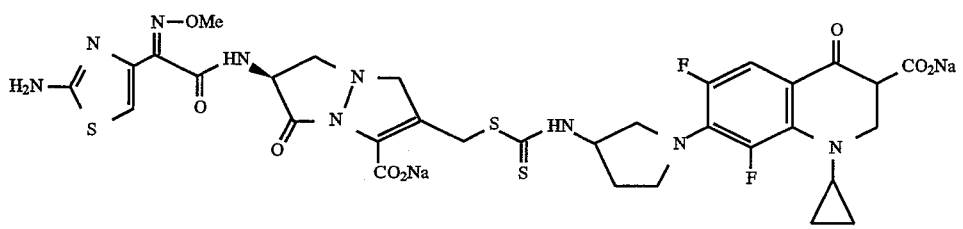
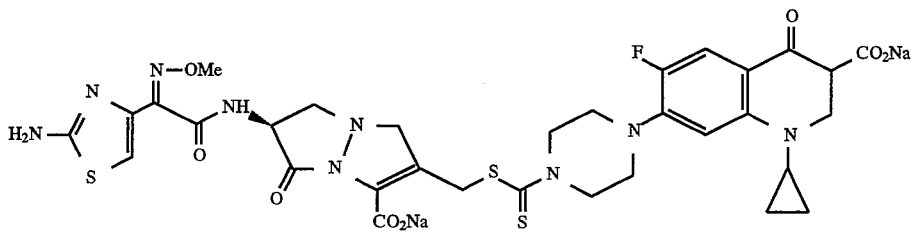
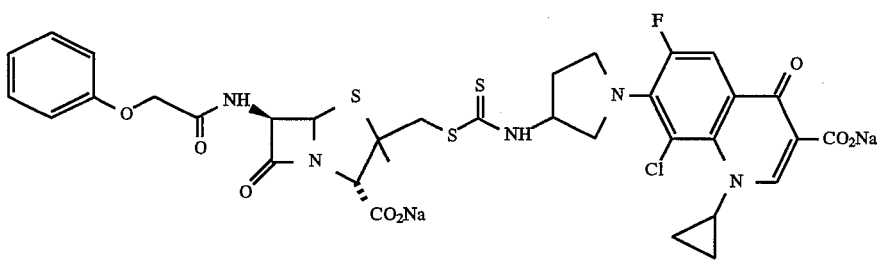
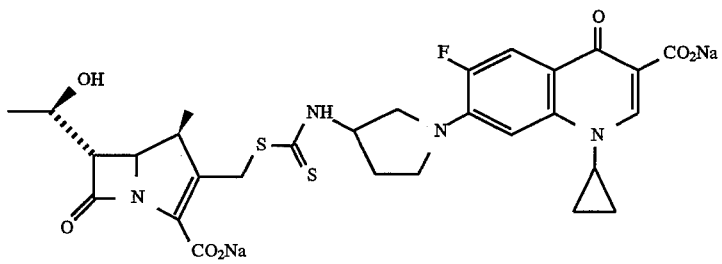
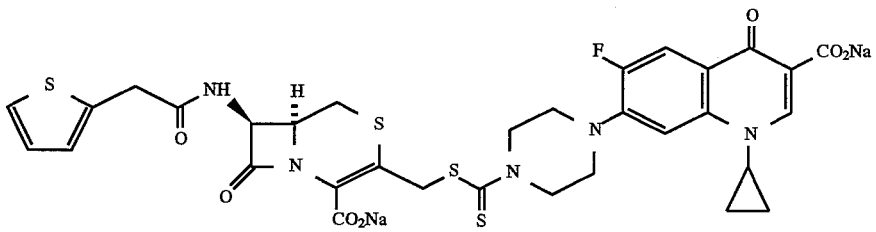
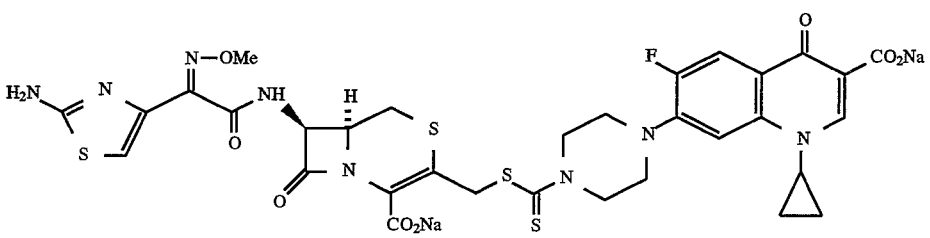

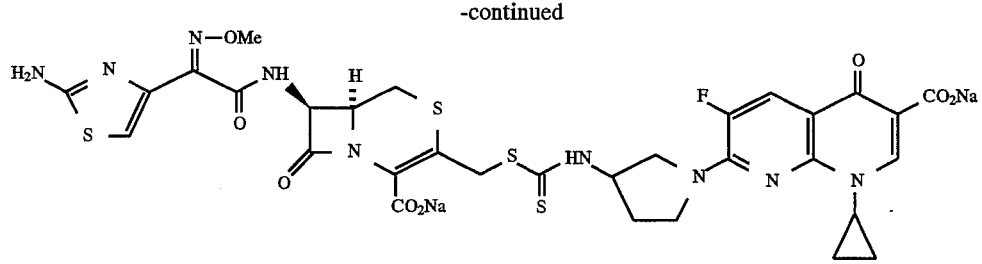
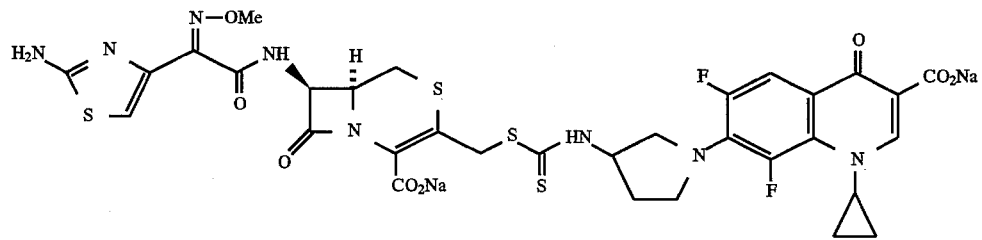
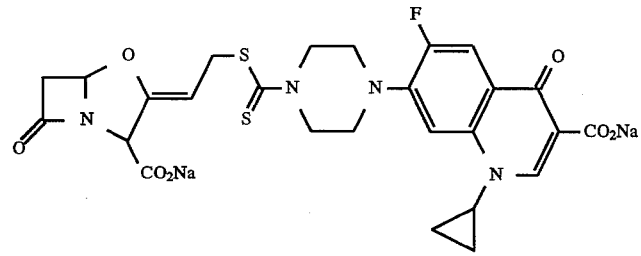
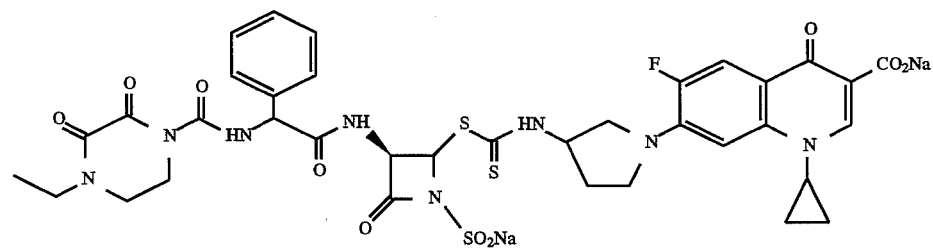
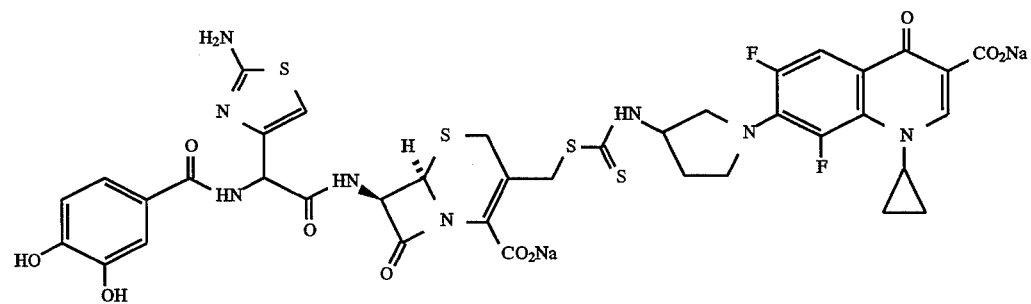
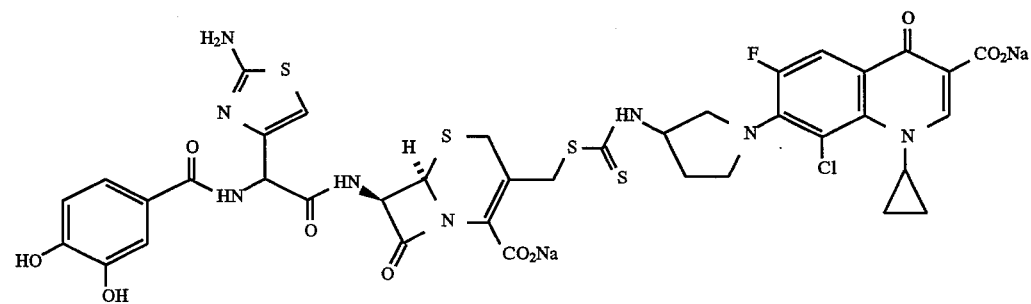

-continued

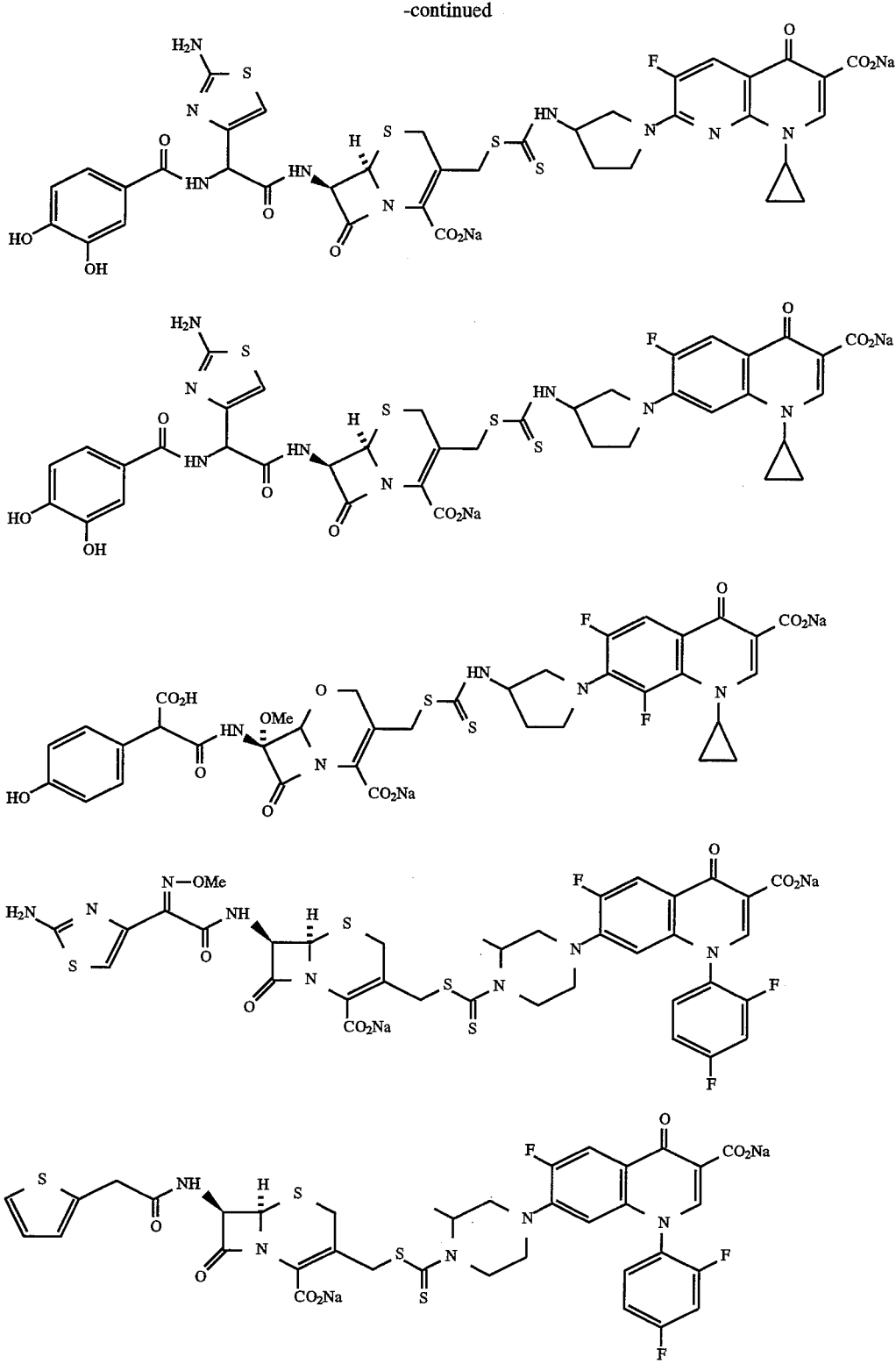

EXAMPLE 27

[5R- [5α,6α]]-3- [[[4-(3-carboxy-1-cyclopropyl-6-fluoro-1,4-dihydro-4-oxo-7-quinolinyl)-1-piperazinyl]-2,2,2-trichloroethoxy]phosphinyl]oxymethyl]-6-[(R)-1-hydroxymethyl]-7-oxo-4-thia-1-azabicyclo[3.2.0]hept-2-ene-2-carboxylic acid; and [5R-[5α,6α]]-3-[[[4-(3-carboxy-1-cyclopropyl-6-fluoro-1,4-dihydro-4-oxo-7-quinolinyl)-1-piperazinyl]hydroxyphosphinyl]oxymethyl]-6-[(R)-1-hydroxymethyl]-7-oxo-4-thia- 1-azabicyclo[3.2.0]hept-2-ene-2-carboxylic acid, according to this invention, are made as follows. First, ciprofloxactn allyl ester is made by the following general reaction sequence.

273

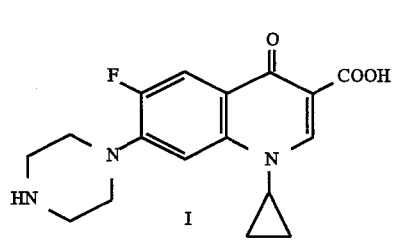

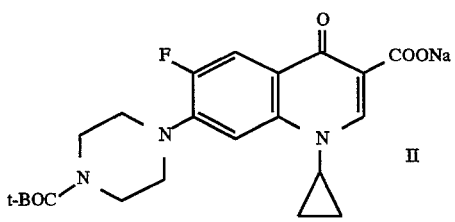

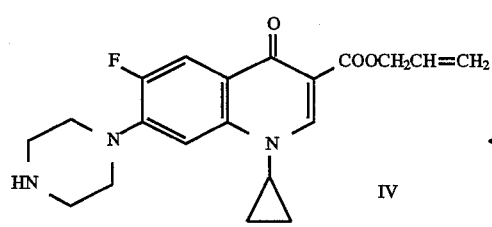

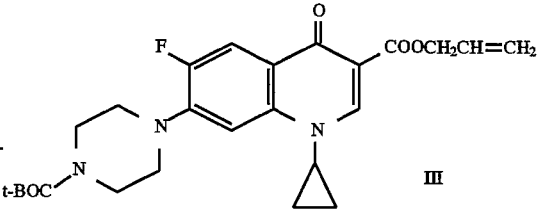

To a solution of approximately 5 g of ciprofloxacin I in approximately 50 ml of water and 15 ml of 1 N NaOH is added approximately 50 ml of dioxane followed by approximately 4.9 g of di-t-butyl dicarbonate. The mixture is stirred at room temperature for approximately 6 hours and is concentrated to approximately 10 ml in vacuo. The mixture is diluted with acetone and t-BOC-ciprofloxacin sodium salt II is collected by filtration. To a mixture of approximately 4.5 g of II in approximately 70 ml of dimethylformamide is added approximately 1.1 ml of allyl iodide at approximately 3°–5° C. The reaction is stirred for approximately 45 hours and is concentrated to dryness in vacuo. The residue is stirred in water and the product is extracted with $CH_2Cl_2$.

274

The extract is dried over $Na_2SO_4$, filtered and the liltrate is concentrated to dryness to give the allyl ester III. A solution of approximately 3.8 g of III in approximately 50 ml of trifluoroacetic acid and 50 ml of $CH_2Cl_2$ is stirred at room temperature for approximately 6 hours and is concentrated to dryness in vacuo. The residue is triturated in anhydrous ether and ciprofloxacin allyl ester IV is collected by filtration.

The product of this invention is then made by the following general reaction sequence.

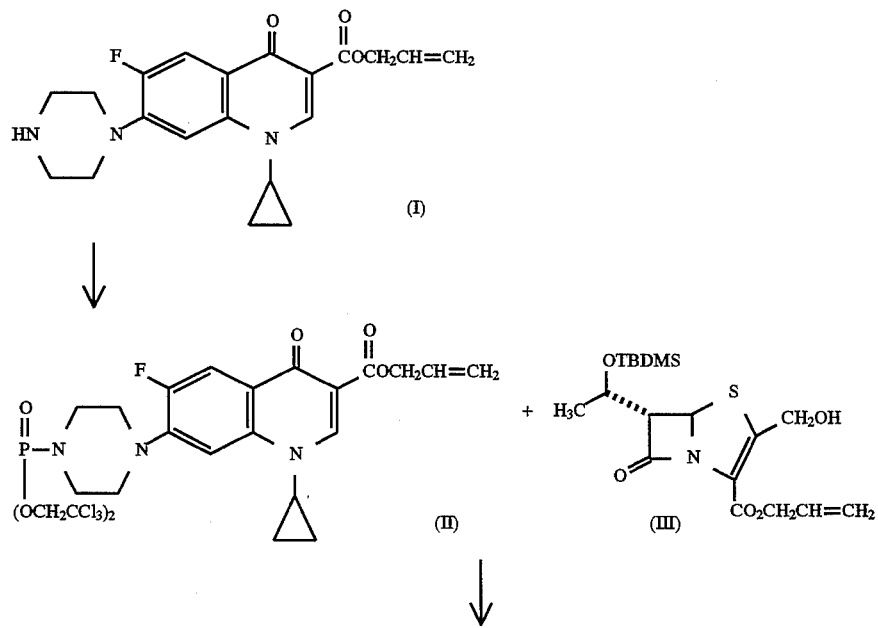

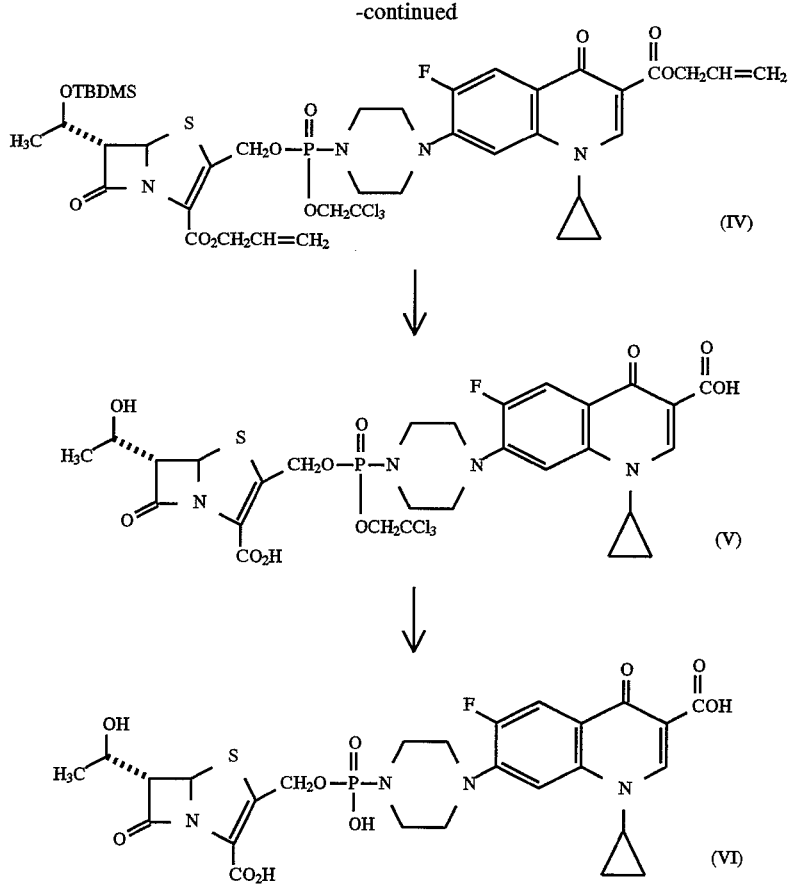

Approximately 4.0 g of bis-2,2,2-trichloroethyl phosphorochloridate, in approximately. 60 ml of pyridine, is stirred under a nitrogen atmosphere and cooled with an ice bath. Ciprofloxacin allyl ester (I) (approximately 4.9 g), in approximately 40 ml of dichloromethane, is slowly added. The reaction is allowed to stir for approximately 12 hours, concentrated, and 1-cyclopropyl-6-fluoro-4-oxo-7-[4-[bis-(2,2,2-trichloroethoxy)phosphonyl]-1-piperazinyl-3-quinolone carboxylic acid allyl ester (II) is isolated by silica gel chromatography.

Approximately 2.0 g of Product (II) is dissolved in approximately 20 ml of t-butyl alcohol containing cesium fluoride (approximately 1.25 g) and approximately 1.3 g of Compound (III), made according to U.S. Pat. No. 4,631,150, Battistini et al., issued Dec. 23, 1986 (incorporated by reference herein). This solution is then stirred for approximately 2 days at room temperature, evaporated and a Product (IV) is obtained after chromatography.

A portion of Product (IV) (approximately 0.5 g) is then taken up in approximately 5 ml of tetrahydrofuran. Acetic acid (approximately 0.25 ml) and approximately 0.35 g (as approximately a 1 M solution in THF) of tetrabutylammonium fluoride is added at room temperature. The reaction mixture is stirred at room temperature for approximately 24 hours under nitrogen. The solvent is removed and the residue dissolved in ethyl acetate, washed with a saturated solution of sodium bicarbonate and dried over sodium sulfate. After evaporation, the crude product is taken up in a mixture of approximately 10 ml of dichloromethane, approximately 60 ml of water and approximately 18 mg of bis(triphenylphosphine)palladium chloride Pd(PPh$_3$)$_2$Cl. The mixture is treated with approximately 700 microliters of tributyltin hydride while maintaining a temperature of approximately 21° C. (70° F.). After rapid stirring for approximately 5 minutes product (IV) is isolated.

Product (IV) is then heated, in the presence of Zn/Cu in DMF (dimethylformamide) at approximately 50° C. (122° F.), according to the procedure of A. Franke et al; 101 Chem. Bet. 944 (1968), to yield product (VI).

EXAMPLE 28

[5R-[5α,6α]]-3-[2-[[4-(3-carboxy-1-cyclopropyl-6-fluoro-1-4-dihydro-4-oxo-7-quinolinyl)-1-piperazinyl] carboxylamino]ethylthio]-6-[(R)-hydroxyethyl]-7-oxo-1-azabicyclo[3.2.0]hept-2-ene-2-carboxylic acid, having the formula

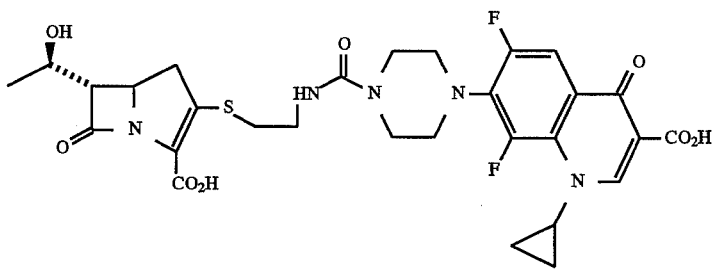

according to this invention, is made by dissolving approximately 0.5 g of 1,1'-carbonyldiimidazole in approximately 10 ml of anhydrous DMF. While stirring under a nitrogen atmosphere, the solution is chilled with an ice bath and approximately 1 g of ciprofloxacin allyl ester (in a small quantity of dried and distilled DMF is then added: Stirring is continued for approximately one hour at this temperature. A solution of thienamycin (made by the procedure of T. Salzmann et al., 102 J. Am. Chem. Soc. 616 (1980)) and an equimolar amount of triethylamine in DMF is then slowly added and the mixture is allowed to slowly warm to room temperature over a period of about 12 hours. The solvent is then removed and the residue is triturated with acetone-water.

Approximately 0.5 g of the above crude product is dissolved in approximately 10 ml of DMF and approximately 60 ml of water is added, followed by 9 mg of bis(triphenylphosphine) palladium chloride. While maintaining this solution at approximately 21° C. (70° F.), approximately 350 microliters of tributyltin hydride is added. After rapid stirring for approximately 5 minutes the final product is isolated.

EXAMPLE 29

According to the general procedure of Example 28, the following lactam-quinolone is made:

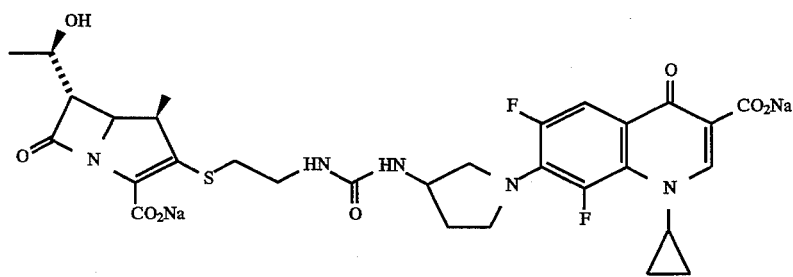

using the beta-lactam 3-[(2-aminoethyl)thio]-6-(1-hydroxyethyl)-4-methyl-7-oxo-1-azabicyclo[3.2.0]hept-2-ene-2-carboxylic acid (prepared according to D. H. Shih, et al., Tet. Lett. 1985, 26, 587).

Similarly, the following lactam-quinolones are prepared by the general procedure of this Example, with substantially similar results.

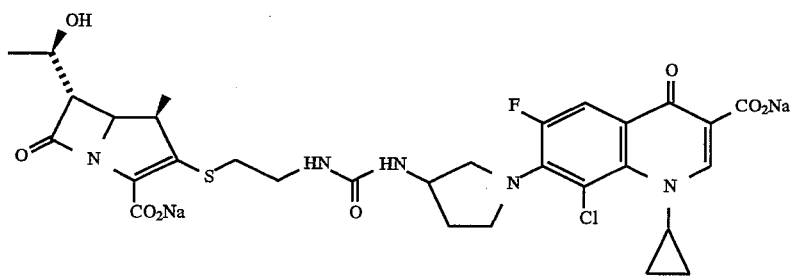

using the quinolone 7-(3-aminopyrrolidinyl)-1-chloro-1-cyclopropyl-6-fluoro-1,4-dihydro-1,4-oxo-3-quinoline carboxylic acid (prepared according to J. P. Sanchez, et. al., J. Med. Chem., 1988, 31, 1983)

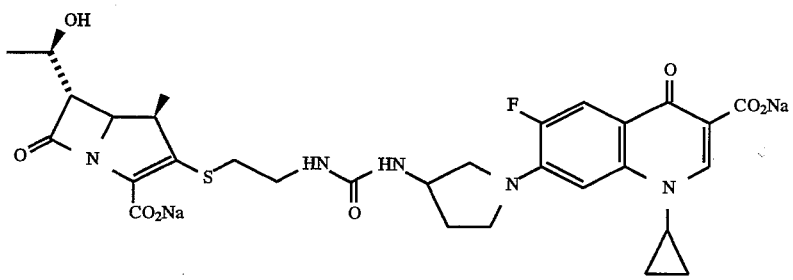

using the quinolone 7-(3-aminopyrrolidinyl)-1-cyclopropyl-6-fluoro-1,4-dihydro-4-oxo-3-quinoline carboxylic acid (prepared according to J. P. Sanchez, et. al., J. Med. Chem., 1988, 31, 983)

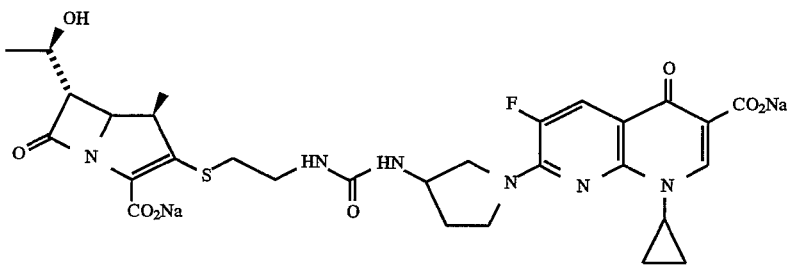

using the naphthyridinone 7-(3-aminopyrrolidinyl)-1-cyclopropyl-6-fluoro-1,4-dihydro-4-oxo-1,8-naphthyridine-3-carboxylic acid (prepared according to J. P. Sanchez, et. al., J. Med. Chem., 1988, 31, 983)

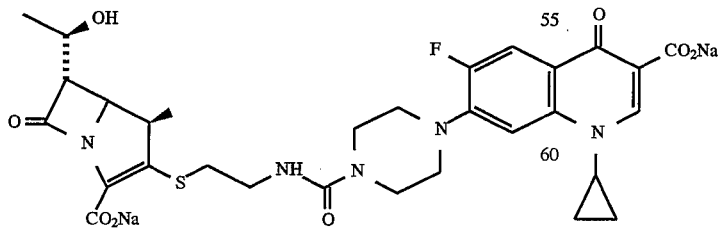

using the quinolone 1-cyclopropyl-6-fluoro-1,4-dihydro-4-oxo-7-(piperazinyl)-3-quinoline carboxylic acid (prepared according to K. Grohe, et al., Ger. Offen. DE 3142854).

EXAMPLE 30

According to the general procedure of Example 28, the following lactam-quinolone is made.

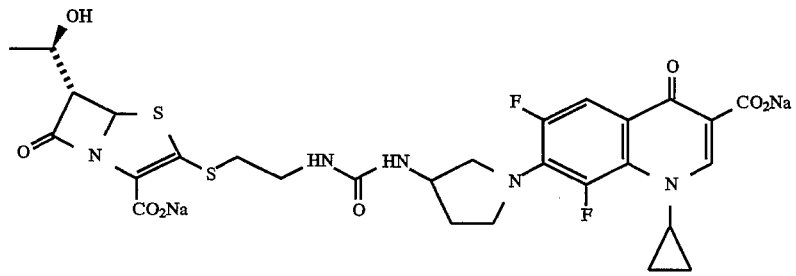

using the beta-lactam 3-[(2-aminoethyl)thio]-6-(1-hydroxyethyl)-7-oxo-4-thia-1-azabicyclo[3.2.0]hept-2-ene-2-carboxylic acid (prepared according to T. Hayashi, et al., Chem. Pharm. Bull., 1981, 29, 3158).

Similarly, the following lactam quinolones are prepared by the general procedure of this Example, with substantially similar results.

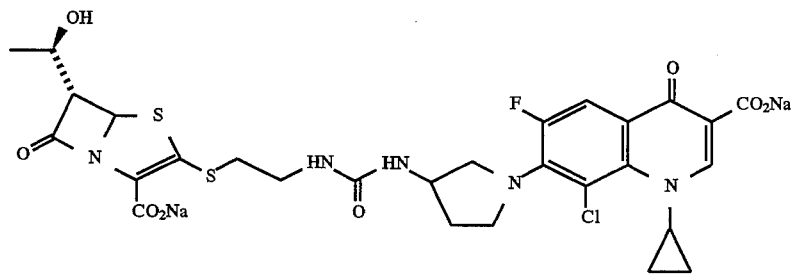

using the quinolone 7-(3-aminopyrrolidinyl)-8-chloro-1-cyclopropyl-6-fluoro-1,4-dihydro-4-oxo-3-quinoline carboxylic acid (prepared according to J. P. Sanchez, et. al., J. Med. Chem., 1988, 31, 983)

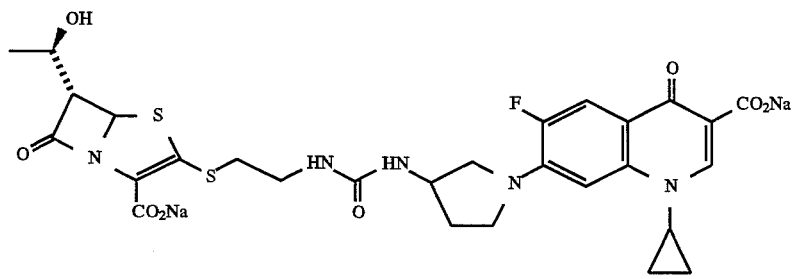

using the quinolone 7-(3-aminopyrrolidinyl)-1-cyclopropyl-6-fluoro-1,4-dihydro-4-oxo-3-quinoline carboxylic acid (prepared according to J. P. Sanchez, et. al., J. Med. Chem., 1988, 31, 983)

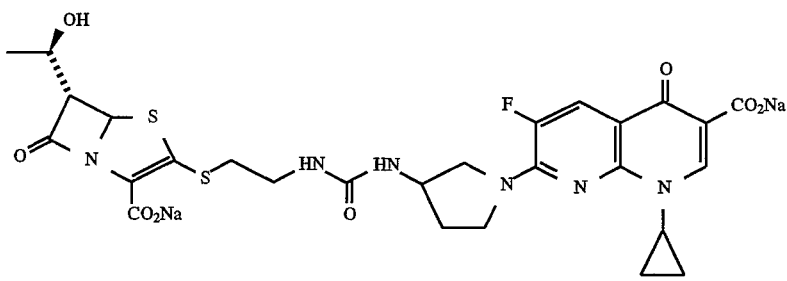

using the naphthyridinone 7-(3-aminopyrrolidinyl)-1-cyclopropyl-6-fluoro-1,4-dihydro-4-oxo-1,8-naphthyridine-3-carboxylic acid (prepared according to J. P. Sanchez, et. al., J. Med. Chem., 1988, 31, 983)

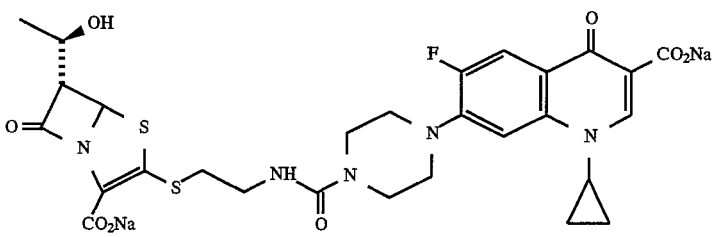

using the quinolone 1-cyclopropyl-6-fluoro-1,4-dihydro-4-oxo-7-(piperazinyl)-3-quinoline carboxylic acid (prepared according to K. Grohe, et al., Ger. Offen. DE 3142854).

EXAMPLE 31

[6R-[6α,7β]]-3-[[[(3-Carboxy-1-cyclopropyl-6-fluoro-1,4-dihydro-4-oxo-7-quinolinyl)-4-piperazinyl]carbonylamino]methyl]-8-oxo-7-[(2-thienylacetyl)amino]-5-thia-1-azabicyclo[4.2.0]oct-2-ene-2-carboxylic Acid Disodium Salt

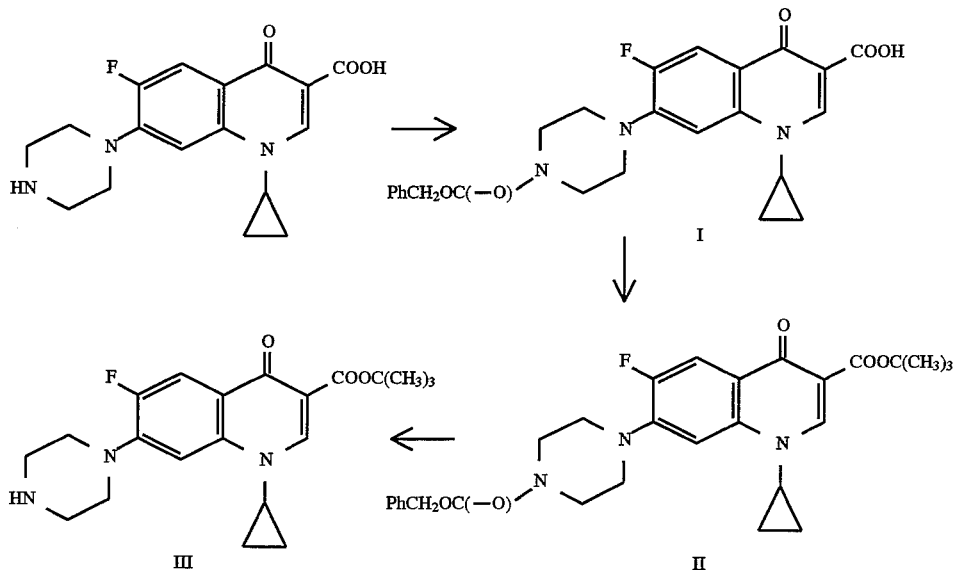

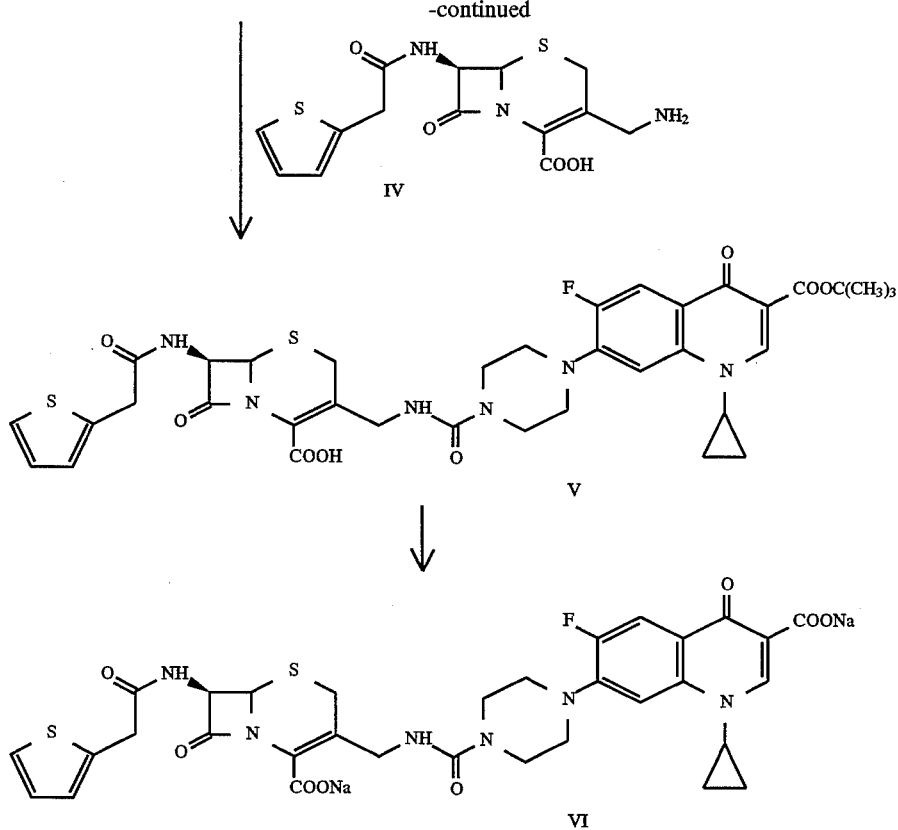

A mixture of approximately 7.2 g of ciprofloxacin, water (100 ml), acetone (70 ml) and 1N NaOH (26 ml) is cooled to approximately 3° C. and a solution of approximately 4.7 ml of benzyl chloroformate in acetone (30 ml) is added dropwise while maintaining the pH at approximately 9–10 by adding additional 1N NaOH. The mixture is stirred at 2°–5° C. for approximately 30 minutes and at room temperature for approximately 2 hours. The mixture is concentrated to approximately 100 ml under reduced pressure, is cooled in an ice bath and is acidified with 2N HCl. The product is collected by filtration, triturated in ethyl acetate and is dried to afford I. A mixture of approximately 5.6 g of I, 120 ml of $CH_2Cl_2$, 6 ml of $H2SO_4$ and 40 ml of isobutylene is shaken in a pressure bottle for approximately 21 hours. The mixture is poured into cold 0.25N NaOH and is stirred rapidly. The organic phase is separated, dried over $Na_2SO_4$, filtered and is concentrated to dryness to give II. A mixture of approximately 4.5 g of II, 75 ml of dimethylformamide and 4 g of 10% Pd/C is subjected to hydrogenation for approximately 16 hours and the catalyst is removed by filtration. The filtrate is concentrated to dryness in vacuo, the residue is triturated in ethyl acetate and the product III is collected by filtration and is dried.

A solution of approximately 2.4 g of III and 0.9 ml of triethylamine in approximately 100 ml of $CH_2Cl_2$ is added dropwise to a solution of excess phosgene in $CH_2Cl_2$ at approximately 2°–5° C. After the reaction is stirred for an additional one hour, the mixture is filtered and the filtrate is concentrated to dryness under reduced pressure. The residue is dissolved in approximately 30 ml of dimethylformamide and is added slowly to a mixture of approximately 2.2 g of [6R-[6α,7β]]-3-aminomethyl-8-oxo-7-[(2-thienylacetyl) amino]-5-thia-1-azabicyclo[4.2.0]oct-2-ene-2-carboxylic acid IV and 1.8 ml of triethylamine in 30 ml of dimethylformamide at approximately 2°–5° C. The reaction is stirred for approximately 4 hours and concentrated to dryness in vacuo. The residue is stirred in water and $CH_2C_2$, then cooled in an ice bath and acidified with 10% citric acid. The organic phase is separated, dried over $Na_2SO_4$, filtered and concentrated to dryness. The residue is purified by silica gel chromatography to give V. To a solution of approximately 0.8 g of V and ]10 ml of anisole ts added approximately 10 ml of trifluoroacetic acid dropwise at approximately −15° C. The solution is stirred at ambient temperature for approximately 20 minutes and then concentrated to dryness in vacuo. The residue is triturated in anhydrous ether and the product is collected by filtration. This free acid of the title compound (approximately 0.47 g) is added to a solution of water and approximately 0.12 g of sodium bicarbonate. Some acetone is added to the stirring mixture to effect solution and then approximately 2.5 volumes of acetone is added to precipitate the product which is collected by filtration to afford VI as the disodium salt.

Similarly, the following lactam-quinolones are prepared by the general procedure of this Example, with substantially similar results.

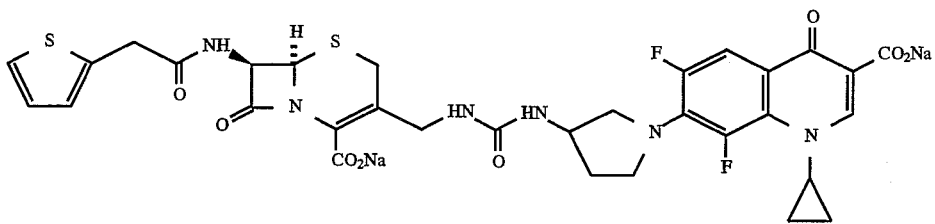

using the quinolone 7-(3-aminopyrrolidinyl)-1-cyclopropyl-6,8-difluoro-1,4-dihydro-4-oxo-3-quinoline carboxylic acid (prepared according to J. P. Sanchez, et. al., J. Med. Chem., 1988, 31, 983)

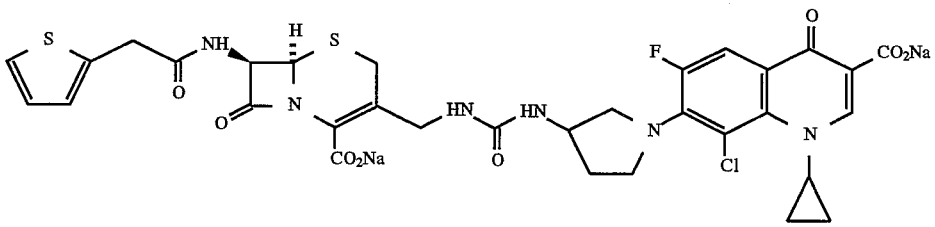

using the quinolone 7-(3-aminopyrrolidinyl)-8-chloro-1-cyclopropyl-6-fluoro-1,4-dihydro-4-oxo-3-quinoline carboxylic acid (prepared according to J. P. Sanchez, et. al., J. Med. Chem., 1988, 31, 983)

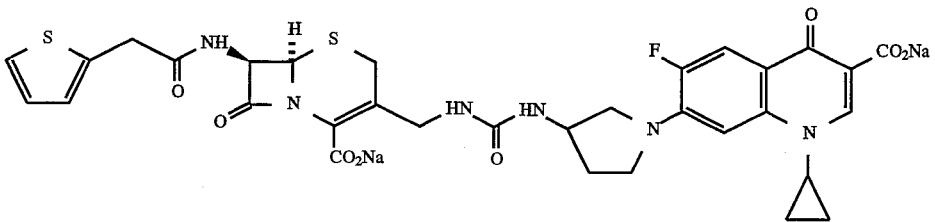

using the quinolone 7-(3-aminopyrrolidinyl)1-cyclopropyl-6-fluoro-1,4-dihydro-4-oxo-3-quinoline carboxylic acid (prepared according to J. P. Sanchez, et. al., J. Med. Chem., 1988, 31, 983)

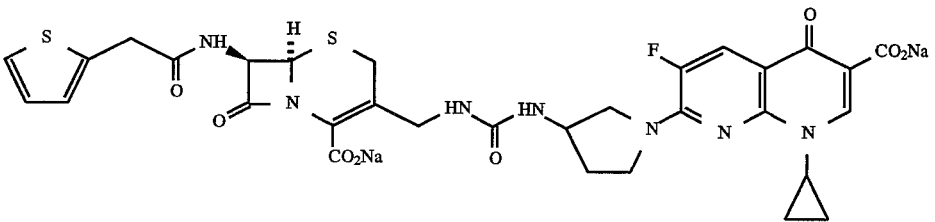

using the naphthyridinone 7-(3-aminopyrrolidinyl)-1-cyclopropyl-6-fluoro-1,4-dihydro-4-oxo-1,8-naphthyridine-3-carboxylic acid (prepared according to J. P. Sanchez, et. al., J. Med. Chem., 1988, 31, 983).

EXAMPLE 32

According to the general procedure of Example 31, the following lactam-quinolone is made.

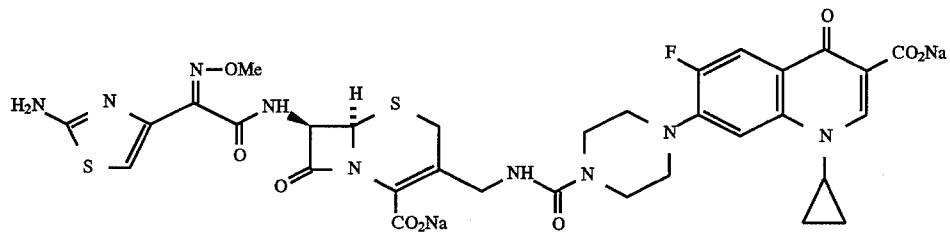

using the beta-lactam 3-(acetyloxymethyl)-7-[[(2-amino-4-thiazolyl) acetyl]amino]-8-oxo-5-thia-1-azabicyclo[4.2.0] oct-2-ene-2-carboxylic acid (prepared as described herein)

Similarly, the following lactam-quinolones are prepared by the general procedure of this Example, with substantially similar results.

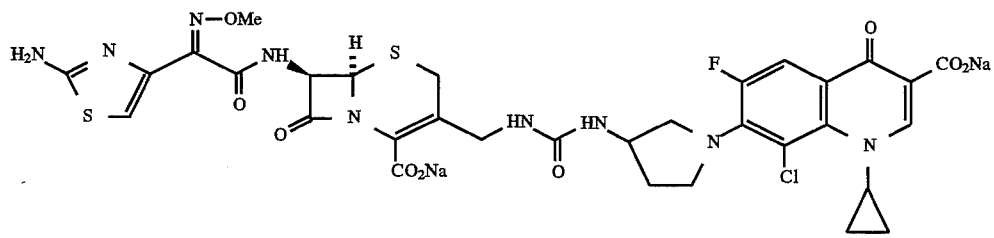

using the quinolone 7-(3-aminopyrrolidinyl)-8-chloro-1-cyclopropyl-6-fluoro-1,4-dihydro-4-oxo-3-quinoline carboxylic acid (prepared according to J. P. Sanchez, et. al., J. Med. Chem., 1988, 31, 983)

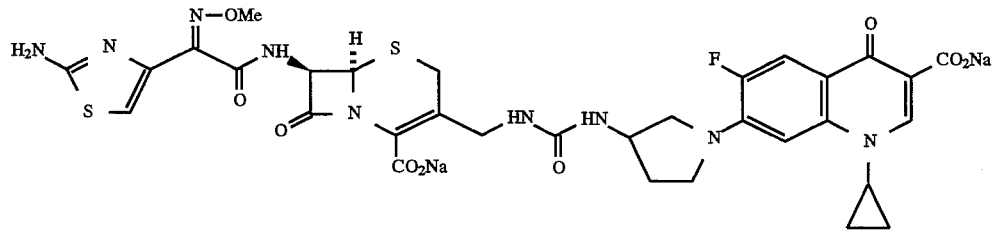

using the quinolone 7-(3-aminopyrrolidinyl-1-cyclopropyl-6-fluoro-1,4-dihydro-4-oxo-3-quinoline carboxylic acid (prepared according to J. P. Sanchez, et. al., J. Med. Chem., 1988, 31, 983)

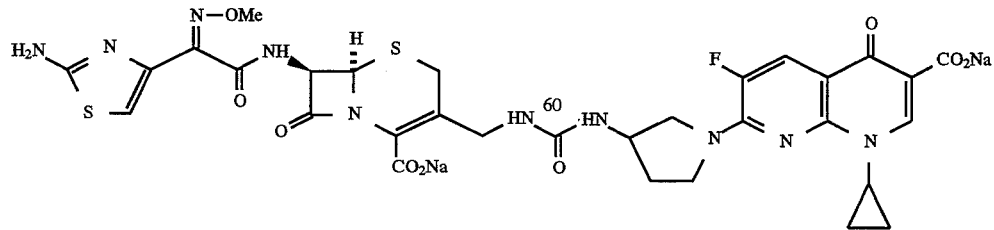

using the naphthyridinone 7-(3-aminopyrrolidinyl)-1-cyclopropyl-6-fluoro-1,4-dihydro-4-oxo-1,8-naphthyridine-3-carboxylic acid (prepared according to J. P. Sanchez, et. al., J. Med. Chem., 988, 31, 983)

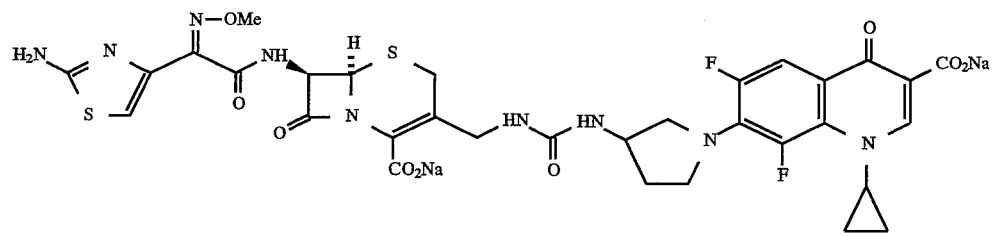

using the quinolone 7-(3-aminopyrrolidinyl)-1-cyclopropyl-6,8-difluoro-1,4-dihydro-4-oxo-3-quinoline carboxylic acid (prepared according to J. P. Sanchez, et. al., J. Med. Chem., 1988, 31, 983).

EXAMPLE 33

According to the general procedure of Example 28, the following lactam-quinolone is made.

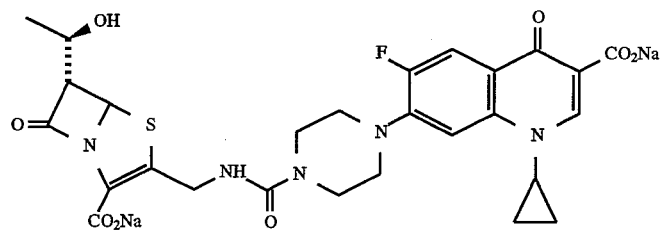

using the beta-lactam 3-(aminomethyl)-6-(1-hydroxyethyl)-7-oxo-4-thia-1-azabicyclo[3.2.0]hept-2-ene-2-carboxylic acid (prepared according to M. Lang, et al., Helv. Chim. Acta, 1986, 69, 1576).

Similarly, the following lactam-quinolones are prepared by the general procedure of this Example, with substantially similar results.

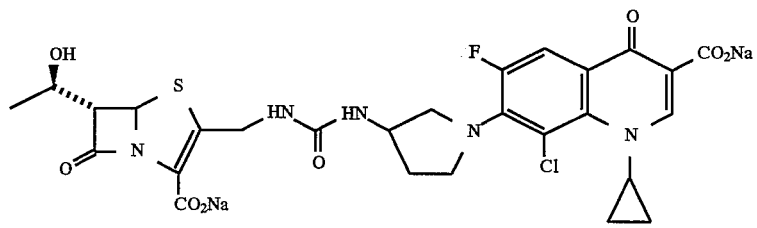

using the quinolone 7-(3-aminopyrrolidinyl)-1-chloro-1-cyclopropyl-6-fluoro-1,4-dihydro-4-oxo-3-quinoline carboxylic acid (prepared according to J. P. Sanchez, et. al., J. Med. Chem., 1988, 31, 983)

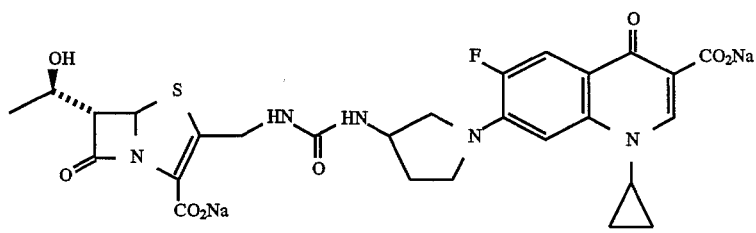

using the quinolone 7-(3-aminopyrrolidinyl1-cyclopropy6-fluoro-1,4-dihydro-4-oxo-3-quinoline carboxylic acid (prepared according to J. P. Sanchez, et. al., J. Med. Chem., 1988, 31, 983)

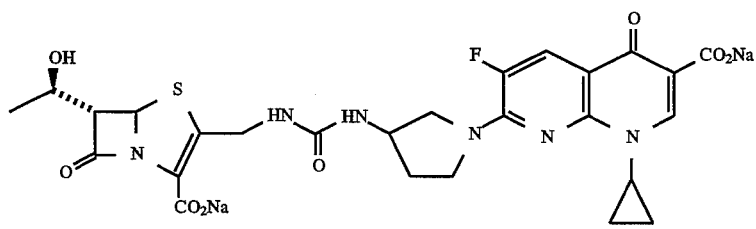

using the naphthyridinone 7-(3-aminopyrrolidinyl)-1-cyclopropyl-6-fluoro-1,4-dihydro-4-oxo-1,8-naphthyridine-3-carboxylic acid (prepared according to J. P. Sanchez, et. al., J. Med. Chem., 1988, 31, 983)

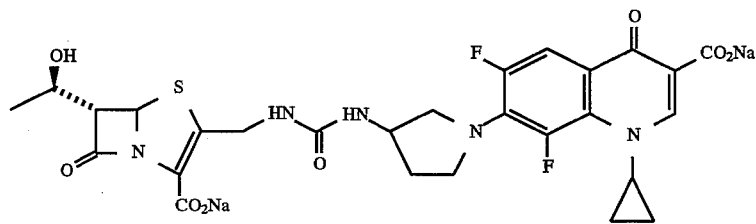

using the quinolone 7-(3-aminopyrrolidinyl)-1-cyclopropyl-6,8-difluoro-1,4-dihydro-4-oxo-3-quinoline carboxylic acid (prepared according to J. P. Sanchez, et. al., J. Med. Chem., 1988, 31, 983).

EXAMPLE 34

3-[[[[(3-Carboxy-8-chloro-1-cyclopropyl-6-fluoro-1,4-dihydro-4-oxo-7-quinolinyl)-3-pyrrolidinylamtnocarbonyl ]methylthio]thioxomethyl]aminomethyl]-8-oxo-7-[(2-thienylacetyl)amino]-5-thia-1-azabicyclo[4.2.0]oct-2-ene-2-carboxylic acid disodium salt, according to this invention, is made by the following general reaction sequence.

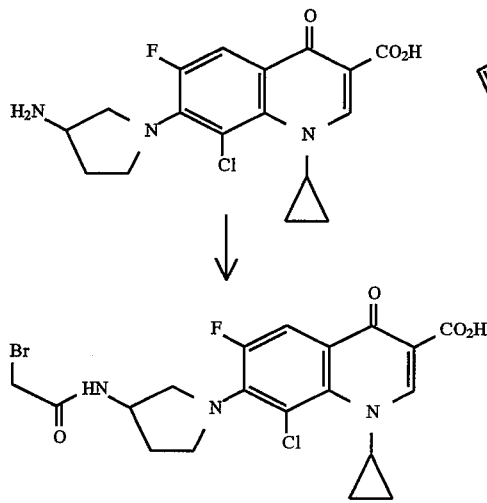
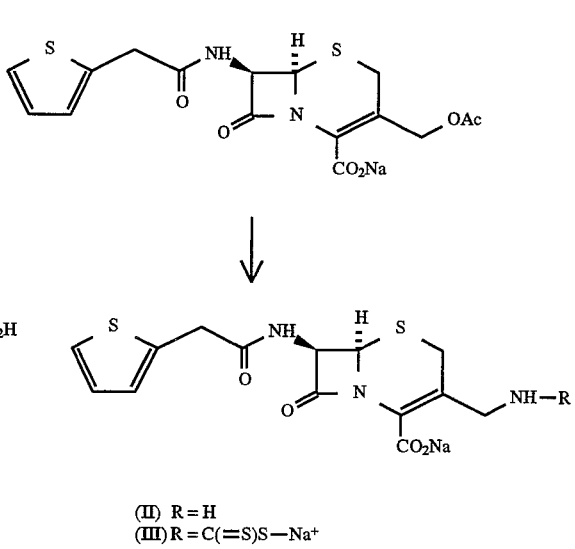

A mixture of 7-(3-amino-1-pyrrolidinyl)-8-chloro-1-cyclo-propyl-6-fluoro-1,4-dihydro-8-oxo-3-quinolinecarboxylic acid (1.5g) (made by procedure of 31 J. Med. Chem. 983 (1988)), and 50% aqueous acetone is adjusted to pH 10 with 1N NaOH. A solution of bromoacetyl chloride (1.3 g) in acetone is added dropwise at approximately 7° C. (45° F.) while maintaining the reaction at pH of from 9 to 11. The mixture is stirred for approximately 2 hours, concentrated to half volume and washed once with ethyl acetate. The aqueous phase is acidified with 1N HCl and the product is collected by filtration. Product (I) is obtained by recrystallization from DMF.

A solution of commercial cephalothin sodium salt (5.0 g), sodium bicarbonate (1.06 g), sodium azide (0.82 g) and water (75 ml) is heated at approximately 50° C. (122° F.) until TLC (thin layer chromatography) shows the starting material is consumed. The reaction is cooled to approximately 3° C. (37° F.), covered with ethyl acetate and acidified with 1N HCl. The ethyl acetate extract is dried over $Na_2SO_4$, filtered and the filtrate is concentrated to dryness to give [6R[6a,7B]]-3-(azidomethyl)-8-oxo-7-](2-thienylacetyl)amino]-5-thia-1-azabicyclo[4.2.0]oct-2-ene-3-carboxylic acid. A mixture of this azido intermediate (1.0 g), 10% Pd/C (1.0 g), $NaHCO_3$ (1.54 g) and 75% methanol/$H_2O$ is subjected to hydrogenation at room temperature until TLC shows the disappearance of starting azide. The catalyst is removed by filtration and the filtrate is concentrated to dryness. The residue is dissolved in water, acidified with 1N HCl and the solution is washed with $CHCl_3$. The aqueous phase is concentrated to dryness and the crude product is purified using 50W-X4 cation exchange resin to give product (II).

To a mixture of approximately 1.0 g of product (II) in 4N NaOH (1.5 ml) is added carbon disulfide (0.13 ml) dropwise and the reaction is stirred for approximately 2 hours at approximately 2° C. (36° F.). More carbon disulfide (approximately 0.13 ml) is added and stirring is continued for another hour. The reaction is stirred for an additional 2 hours at ambient temperature, then cooled to approximately 2° C. and diluted with acetone. Product (III) is collected by filtration.

Approximately 0.2 g of product (III) and 0.19 g of product (I) are dissolved in DMF (25 ml), containing sodium bicarbonate (0.035 g). This mixture is stirred at room temperature for approximately 18 hours and concentrated to dryness in vacuo. The residue is dissolved in water and the final product (IV) is precipitated with acetone.

EXAMPLE 35

(3S)-2-[[[2-[3-Carboxy-6-fluoro-1,4-dihydro-4-oxo-7-(1-piperazinyl)-1-quinolinyl]ethoxy]thioxomethyl]thio]-4-oxo-3-[(phenoxyacetyl)amino]-1-azetidinesulfonic acid disodium salt, according to this invention, is made by the following general reaction sequence.

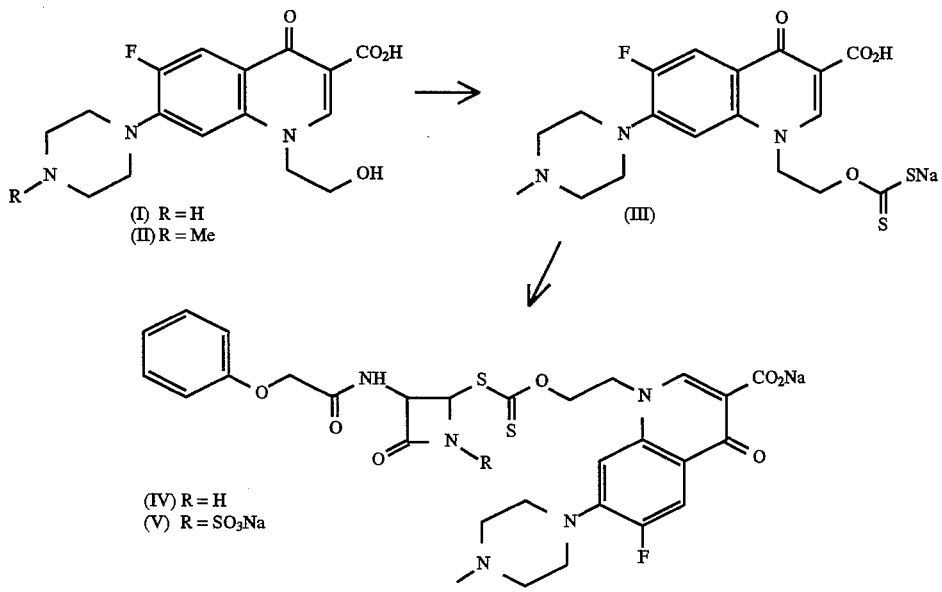

(I) R = H
(II) R = Me (III)

(IV) R = H
(V) R = SO₃Na

A mixture of approximately 3.3 g of 6-fluoro-1,4-dihydro-1-(2-hydroxyethyl)-4-oxo-7-(1-piperazinyl)-quinoline-3-carboxylic acid (I) (prepared according to 23 J. Med. Chem., 1358 (1980)), 1.5 g of triethylamine, 2.8 g of methyl iodide, and 40 ml of DMF is heated at approximately 85° C. (185° F.) with stirring. After approximately 2 hours, the mixture is concentrated to dryness and the residue recrystallized to give product (II).

Approximately 0.55 g of the product (I) is suspended in 0.78 ml of 4N NaOH and 1 ml of water and cooled in an ice bath. 0.093 ml of carbon disulfide is added slowly via syringe. The reaction is stirred in ice for approximately 110 minutes. An additional 0.093 ml of carbon disulfide is added and the solution stirred for 1 hour at approximately 0° C. (32° F.) and then 3 hours at room temperature. A solid is precipitated by the addition of acetone, collected by filtration, and washed with acetone yielding product Approximately 0.26 of product (III) is dissolved in 0.4 ml water and added to a mixture of 0.10 g of 2-(acetyloxy)-4-oxo-3-((phenoxyacetyl)amino)azetidine prepared according to JCS Perkin Trans. I, 447 (1976)) in approximately 0.13 ml of water. This mixture is stirred approximately 30 minutes until the reaction is complete. The product (IV) is isolated by filtration, and recrystallized.

To a solution of 0.1 g of product (IV) in approximately 0.4 ml of dry DMF, is added 0.1 g of DMF·SO₃ complex (prepared according to Synthesis, 699 (1979)). The mixture is stirred for approximately 2 hours at room temperature. The mixture is then diluted with approximately 4 ml of dichloromethane and approximately 4 ml of 0.5N potassium hydrogen phosphate solution. The pH is adjusted to approximately 6 with 1N NaOH. Approximately 0.05 g of tetrabutylammoniumhydrogensulfate is then added, with stirring. The layers are separated and the organic layer is washed with water, dried and concentrated. This residue is taken up in approximately 1ml of water with approximately 0.2 ml of methanol and filtered to yield product (V).

EXAMPLE 36

[3S]-2-[2-[4-(3-Carboxy-1-cyclopropyl-6-fluoro-1,4-dihydro-4-oxo-7-quinolinyl)-1-piperazinyl]ethylthio]-4-oxo-3-[(phenoxy acetyl)amino]-1-azetidinesulfonic acid disodium salt, according to this invention, is made according to the following general synthetic sequence.

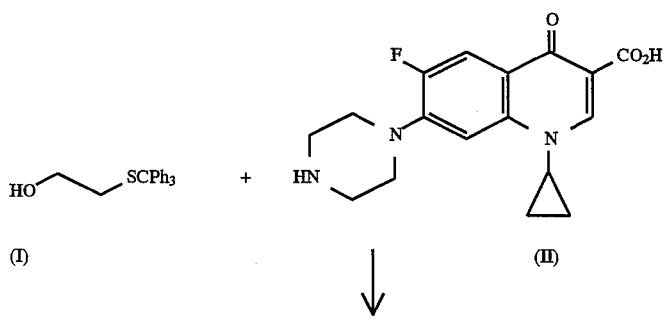

(I)    (II)

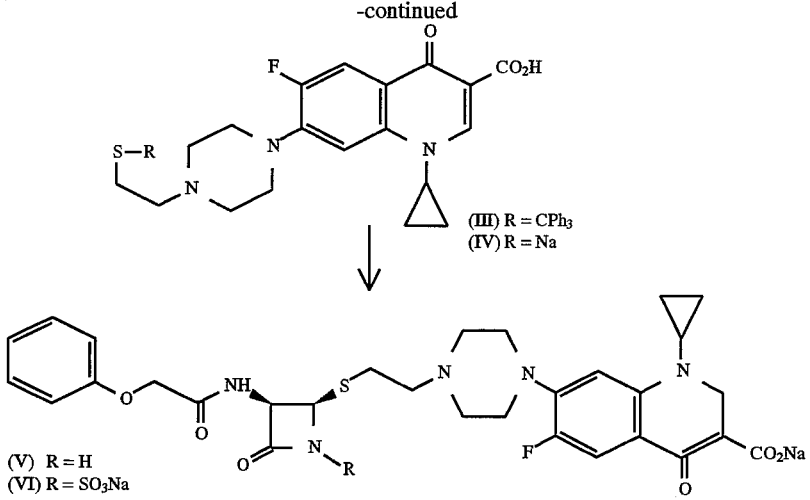

Approximately 22.5 ml of 2-mercaptoethanol and approximately 89.2 g of triphenylmethyl chloride are stirred in 200 ml of DMF at room temperature for approximately 5 hours. The reaction mixture is then poured into a mixture of 1000 ml of water and 500 ml of ethyl acetate. The layers are separated and the aqueous layer is extracted with ethyl acetate. The combined Organic layers are washed with water, dried and evaporated to an oil which solidifies upon standing. This is triturated with hexane and collected by filtration to yield triphenylmethylthioethanol (i).

Approximately 2.0 g of product (I) and 9.6 ml of triethylamine are stirred in 700 ml of dichloromethane and cooled to approximately 14° C. (57° F). A solution of 5.3 ml of methanesulfonyl chloride in 200 ml of dichloromethane is added dropwise, keeping the temperature at approximately 14° C. The icebath is removed and the reaction is stirred at room temperature for approximately 25 minutes. The reaction mixture is then diluted with dichloromethane and washed with water, and 5% sodium bicarbonate solution, then dried and concentrated. The resulting solid is taken up in 100 ml of DMF with 6.9 g of 1-cyclopropyl-6-fluoro-1,4-dihydro-7-(1-piperazinyl)-4-oxo-3-quinolinecarboxylic acid (II) and 4.3 ml of triethylamine and heated at approximately 82° C. (180° F.) for 2.5 hours. The reaction mixture is cooled to room temperature, precipitating a solid product (III).

A solution of 6.0 g of product (III) in 250 ml of glacial acetic acid is treated with 80 ml of 1N HCl solution. The solution is heated for approximately 1.5 hours and the acid evaporated. The residue is triturated with acetone and the product filtered. This is then taken up in 30 ml of 1N NaOH solution which upon evaporation yields product (IV).

Approximately 2.04 g of product (IV) is dissolved in approximately 4 ml water, at 0° C. (32° F.), and then added to a solution of approximately 1.02 g of 2-(acetyloxy)-4-oxo-3-((phenoxy-acetyl)amino)-azetidine, in approximately 28 ml of methanol. After being stirred approximately 1 hour at room temperature, the mixture is concentrated. The resulting product (V) is recrystallized from water and acetone.

To a solution of 1.0 g of product (V) in approximately), 4 ml of dry, DMF, is added 1.0 g of DMF·$SO_3$ complex (prepared according to synthesis, 699 (1979)): The mixture is stirred for approximately 2 hours at room temperature. The mixture is then diluted with approximately) 40 ml of dichloromethane and approximately) 40 ml of 0.5N potassium hydrogen phosphate solution. The pH is adjusted to approximately 6 with 1N NaOH. Approximately 0.49 g of tetrabutylammoniumhydrogensulfate is then added, with stirring. The layers are separated and the organic layer is washed with water, dried and concentrated. This residue is taken up in approximately 10 ml of water with approximately), 2 ml of methanol and filtered to yield product (VI).

Similarly, the following other lactam-quinolones are prepared by the general procedure of this Example, with substantially similar results.

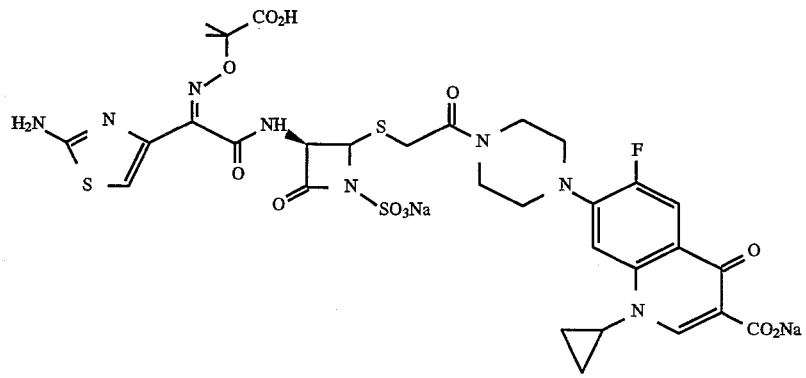

-continued

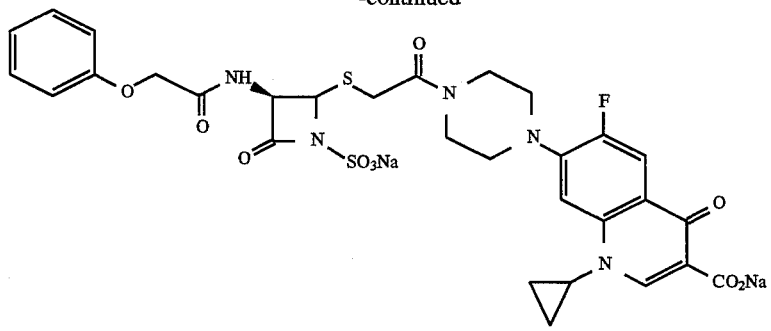

EXAMPLE 37

[6R-(6α,7β)]-3-[[4-(3-Carboxy-1-cyclopropyl-6-fluoro-1,4-dihydro-4-oxo-7-quinolinyl)-1-piperazinyl]methyl]-8-oxo-7-[(2-thienylacetyl)amino]-5-thia-1-azabicyclo[4.2.0]oct-2-ene-2-carboxylic Acid The residue is purified by flash chromatography (silica gel) to give III. To a solution of approximately 1.7 g of III, 20 ml of $CH_2C_{12}$ and 0.03 g of bis(triphenylphosphine)palladium chloride is added approximately 0.2 ml of water and 1.4 ml of tributyltinhydride at approximately 20° C. The mixture is stirred for approximately 15 minutes and then diluted with

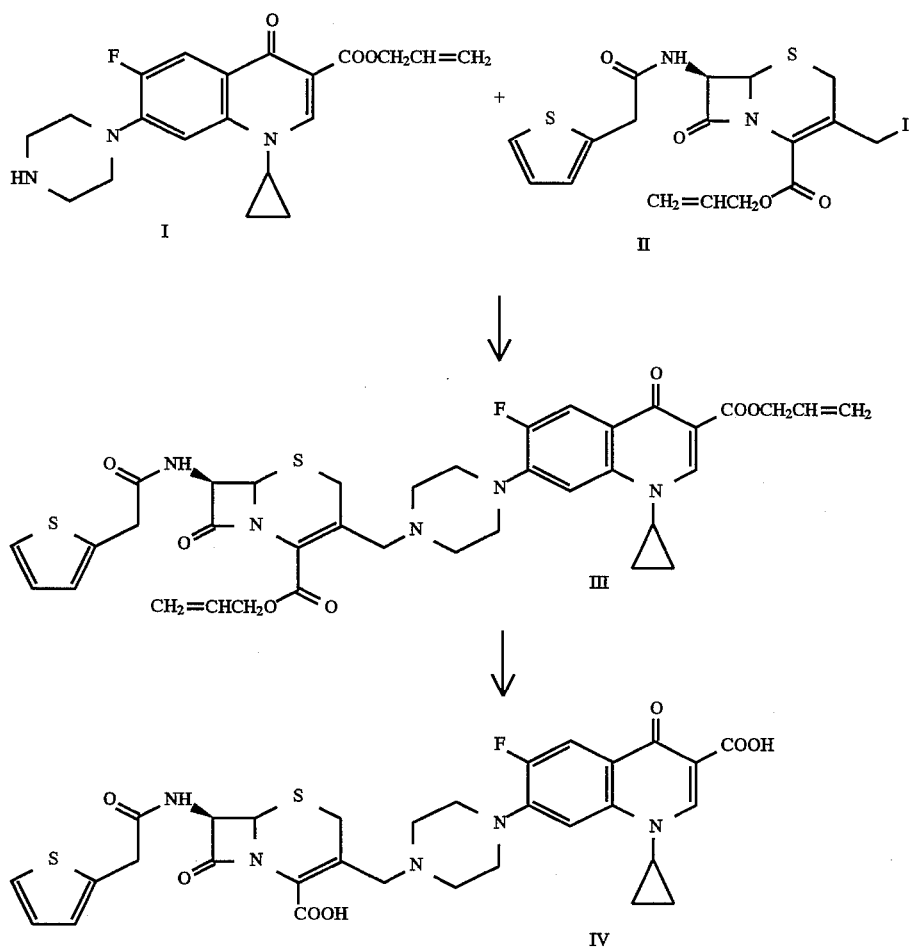

To a mixture of approximately 3.2 g of ciprofloxacin allyl ester I in 30 ml of 50% DMF/dioxane is added approximately 4.3 g of 10-iodo cephem II in portions. The mixture is stirred at room temperature for approximately 2 hours and is concentrated to dryness in vacuo. The residue is added to a mixture of 10% sodium bicarbonate and $CH_2C_{12}$ and is stirred rapidly. The organic phase is separated, dried over $Na_2SO_4$, filtered and the filtrate is concentrated to dryness.

ether and the precipitate is collected by filtration. The solid is triturated with acetone to afford the product IV.

Similarly, the following lactam-quinolone is prepared by the general procedure of this Example, with substantially similar results.

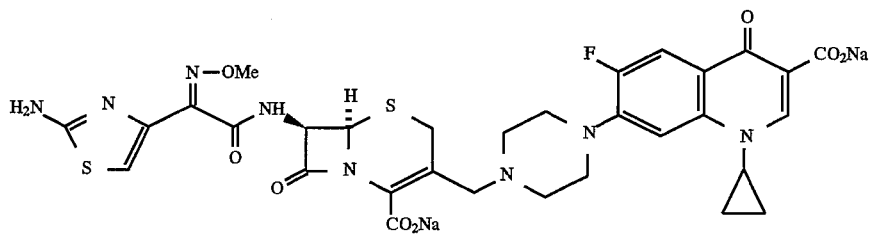

using the beta-lactam [6R-[6a,7b(Z)]]-3-(iodomethyl)-7-[[[2-(trimethylsilylamino)-4-thiazolyl](methoxyimino)acetyl]amino]-8-oxo-5-thia-1-azabicyclo[4.2.0]oct-2-ene-2-carboxylic acid trimethylsilyl ester (prepared according to I. Saito et al., Eur. Pat. Appl. EP 189916 A2, 6 Aug 1986)

The following other lactam-quinolones are also prepared by the general procedure of this Example and Example 37, with substantially similar results.

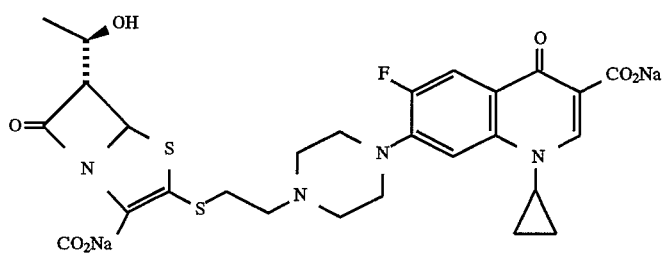

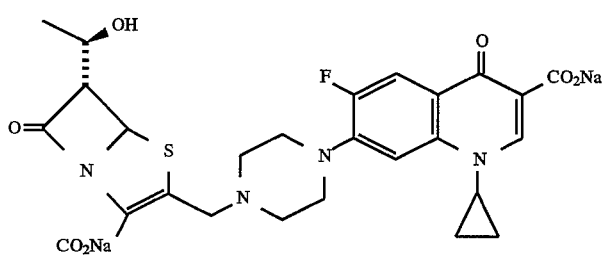

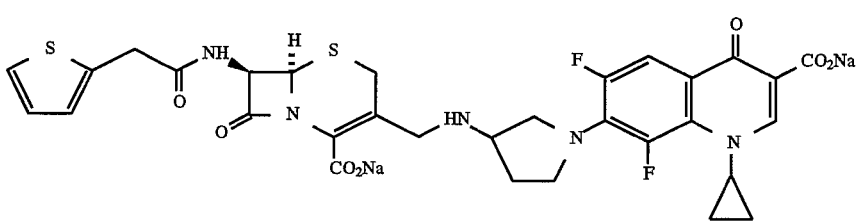

EXAMPLE 38

[6R-[6a,7B]]-4-(3-Carboxy-1-cyclopropyl-6-fluoro-1,4-dihydro-4-oxo-7-quinolinyl)-1-[[2-carboxy-8oxo-7-[(2-thienylacetyl)amino]-5-thia-1-azabicyclo[4.2.0]oct-2-en-3-yl]methyl]-1-methylpiperazinium sodium salt, having the formula

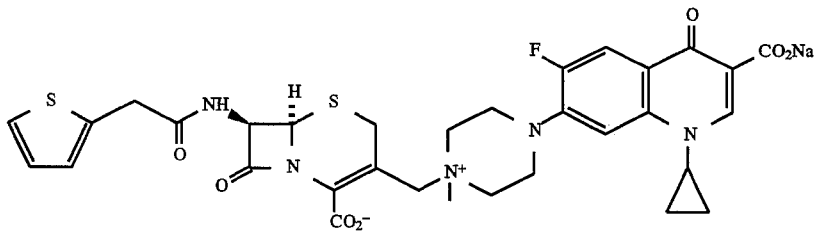

is made by mixing the product of Example 37 and iodomethane (0.020g) in DMF (20 ml). This mixture is stirred at room temperature for approximately 17 hours and concentrated to dryness in vacuo. The residue is repeatedly triturated in aqueous acetone to give the final product.

Similarly, the following lactam-quinolones are prepared by the general procedure of this Example, with substantially similar results.

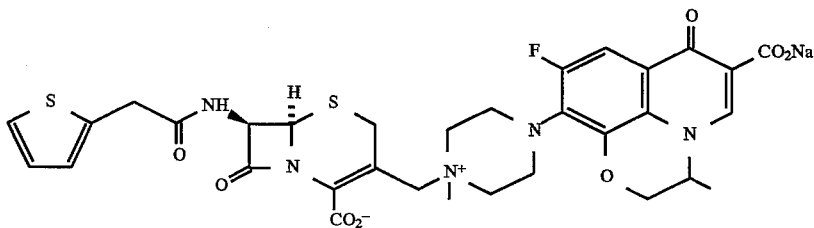

using the quinolone 9-fluoro-4,7-dihydro-3-methyl-10-(1-piperazinyl)-7-oxo-2H-pyrido[1,2,3-de]-1,4-benzoxazine-6-carboxylic acid (prepared according to I. Hayakawa, et. al., Chem. Pharm. Bull., 1984, 32, 4907)

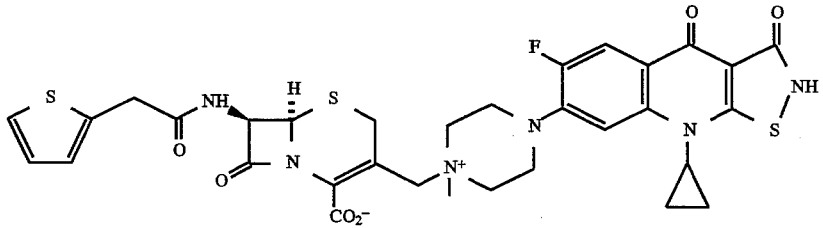

using the quinolone 9-cyclopropyl-6-fluoro-2,3,4,9-tetrahydro-7-(1-piperazinyl)isothiazolo[5,4-b]quinoline-3,4-dione (prepared according to D. T. W. Chu, EP 227,088).

EXAMPLE 39

[6R-[6a,7b]]-4-[3-Carboxy-1-ethyl-6-fluoro-1,4-dihydro-4-oxo-7-quinolinyl]-1-[[2-carboxy-8-oxo-7-(2-thienylacetyl)amino]-5-thia-1-azabicyclo[4.2.0]oct-2-ene-3-yl]-1-methylpiperazinium sodium salt, of the formula

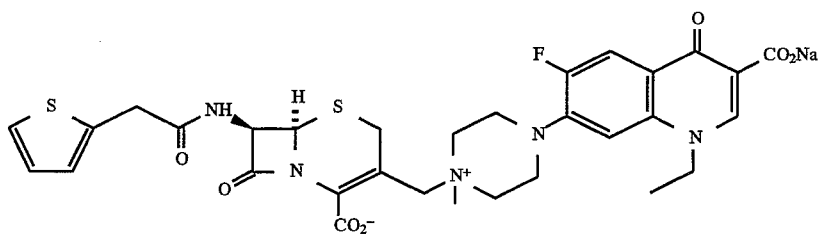

according to this invention, is made as follows.

Approximately 7.9 ml of thionyl chloride is added to a mixture of pefloxacin hydrochloride (2.0 g) (which is made by the procedure of 23 J. Med. Chem. 1358 (1980)) in absolute methanol (54 ml), at approximately 6° C. (43° F.). The mixture is refluxed for 15 hours and concentrated to dryness. Cold aqueous $Na_2CO_3$ is added to the residue, the product is extracted with dichloromethane. The extract is dried over $Na_2SO_4$, filtered and concentrated to dryness. The solid is recrystallized from acetonitrile to give pefloxacin methyl ester.

Approximately 0.23 g of 60% NaH (dispersion in mineral oil) is added to a solution of allyl alcohol (16 ml) in dry THF (160 ml) (0.23 g), followed by 4 Angstrom molecular sieves (92 g) and pefloxacin methyl ester (16 g). The mixture is stirred at room temperature for 2.5 days, cooled, water (1 ml) is added and then filtered. The filtrate is concentrated to dryness, the residue is dissolved in dichloromethane and washed with water. The organic phase is concentrated to dryness and the solid is recrystallized from ethyl acetate to afford pefloxacin allyl ester.

Pefloxacin allyl ester (0.69 g) is added to a solution of [6R-[6a,7b]]3-(iodomethyl)-8-oxo-7-[(2-thienylacetyl) amino]-5-thia-1-azabicyclo[4.2.0]oct-2-ene-2-carboxylic acid allyl ester (1.5 g) in 50% DMF/dioxane (6 ml) and the mixture is stirred for 6 hours at room temperature. The mixture is concentrated to dryness in vacuo and the residue is triturated repeatedly with ethyl acetate and DMF/ethyl acetate to yield [6R-[6a,7b]]-4-[3-[(allyloxy)carbonyl]-1-ethyl-6-fluoro-1,4-dihydro-4-oxo-7-quinolinyl]-1-[2-[(allyloxy)carbonyl]-8-oxo-7-[(2-thienylacetyl)-amino]5-thia-1-azabicyclo[4.2.0]oct-2-en-3-yl]-1-methylpiperazinium iodide.

Approximately 0.20 g of this intermediate is added to a mixture of dichloromethane/DMF (2 ml) and bis(triphenylphosphine)palladium chloride (0.003 g). Water (20 microliters) and tributyltinhydride (0.14 ml) are then added, at approximately 19° C. (66° F.). The mixture is stirred for 20 minutes, diluted with dichloromethane and the precipitate is collected by filtration. This solid is stirred in water and $NaHCO_3$ (0.043 g), diluted with acetone and the product is collected by fillration. Repeated trituration with aqueous acetone yields the final product.

Similarly, the following other lactam-quinolones are prepared by the general procedure of this Example, with substantially similar results.

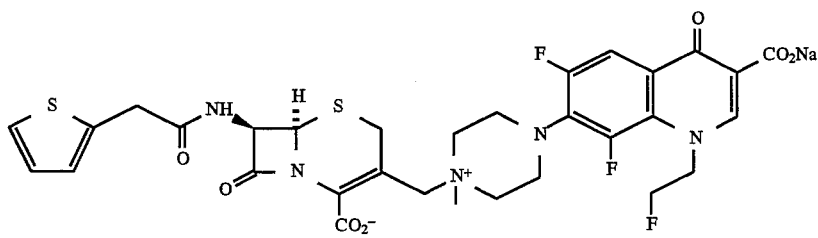

using the quinolone 6,8-difluoro-1-(2-fluoroethyl)-1,4-dihydro-4-oxo-7-(4-methyl-1-piperazinyl)-3-quinoline carboxylic acid (prepared according to T. Irikura, Aust. Pat. Specif. AU 537813)

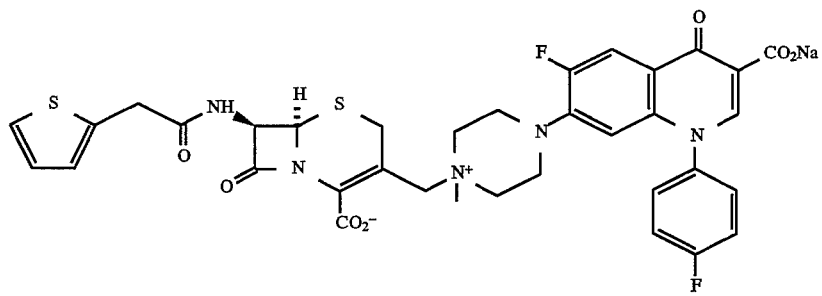

using the quinolone 6-fluoro-1-(4-fluorophenyl)-1,4-dihydro-4-oxo-7(4-methyl-1-piperazinyl)3-quinoline carboxylic acid (prepared according to D. T. W. Chu, et al., J. Med. Chem., 1985, 28, 1558).

EXAMPLE 40

Product III, according to this invention, is made by the following general sequence.

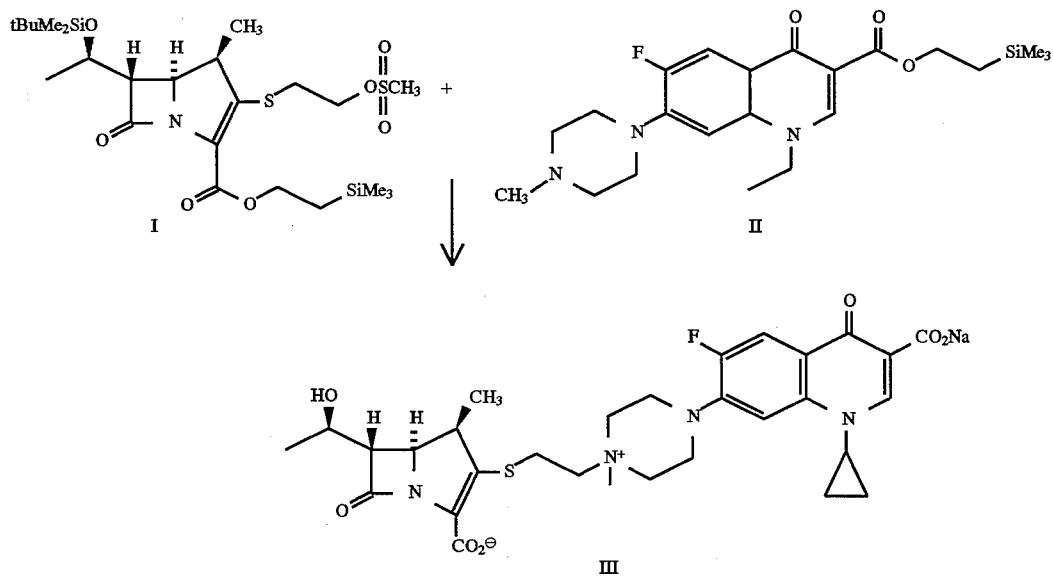

Approximately 7.9 g ml of thionyl chloride is added to a mixture containing approximately 2.0 g of pefloxacin hydrochloride (which is made by the procedure of 23 J. Med. Chem. 1358 (1980)), and 10 g of 2-(trimethylsilyl)ethanol in approximately 150 ml of dichloromethane. The mixture is refluxed approximately 24 hours, cooled to room temperature, and extracted with saturated aqueous sodium bicarbonate. The dichloromethane solution is dried over $Na_2SO_4$, filtered, and concentrated to dryness. The residue is recrystallized from ethyl acetate to afford pefloxacin 2-(trimethylsilyl)ethyl ester II.

Approximately 0.16 g of ester II and 0.20 g of mesylate I (prepared as above) are dissolved in approximately 2 ml of dimethylformamide. After the mixture is stirred approximately 24 hours at room temperature approximately 0. 50 g of tetra-n-butylammonium fluoride is added. The mixture is stirred approximately 8 hours longer at room temperature. Approximately 1 ml of saturated aqueous sodium bicarbonate is added and the mixture is eluted through a DowexR 50×4 (Na cycle) column with deionized water. The appropriate fractions are concentrated in vacuo, then lyophilized to give the final product III.

The following other lactam-quinolones are made by the general procedures of this Example and Examples 38 and 39, with substantially similar results.

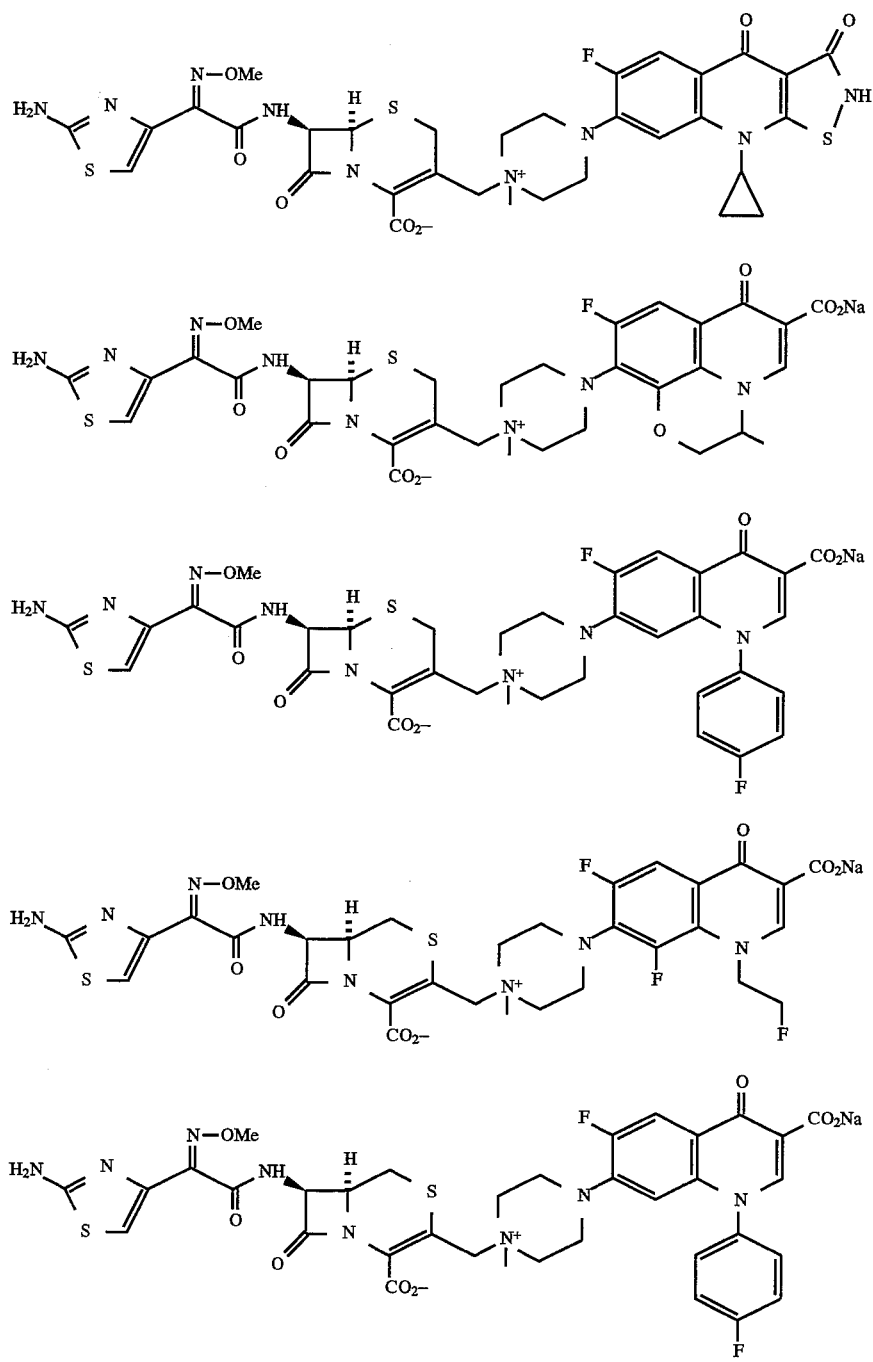

-continued
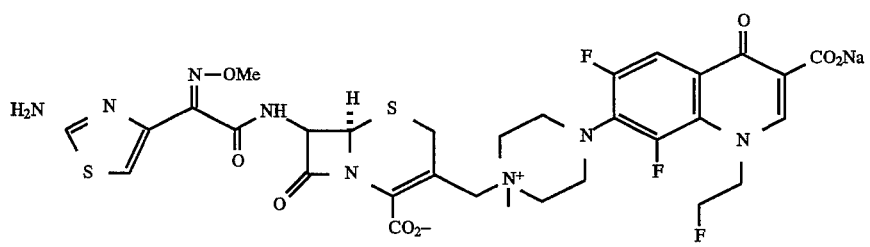
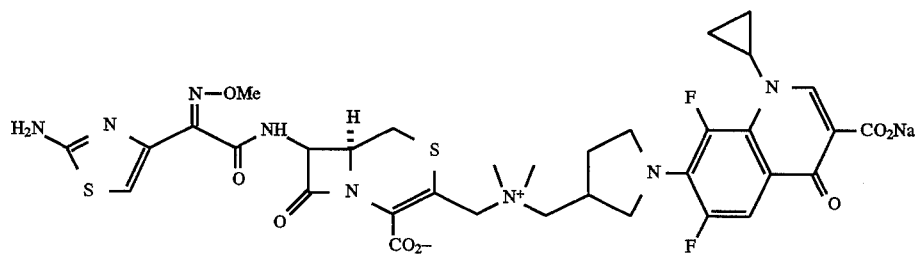
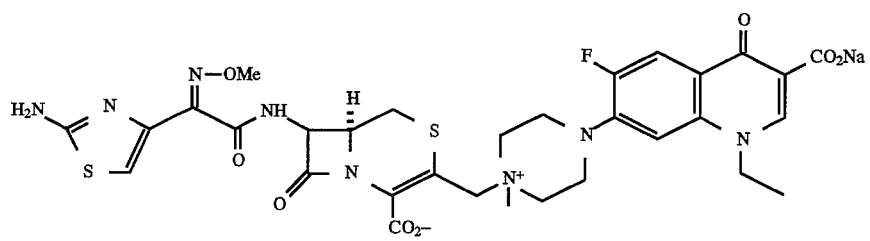
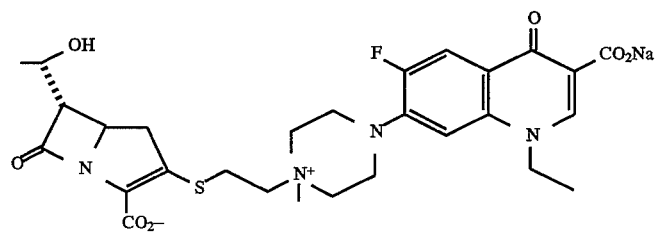
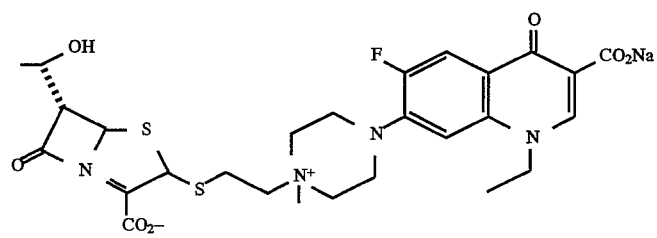
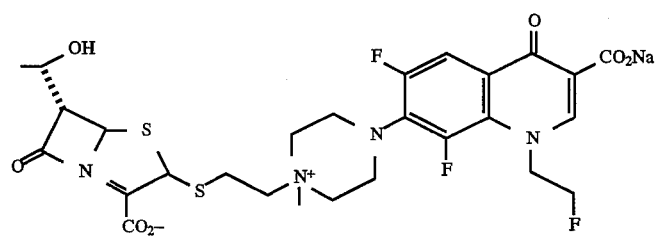

-continued

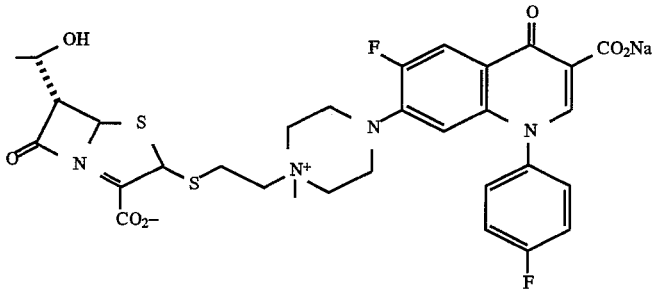

EXAMPLE 41

[6R-[6a,7b]]-3-[[[(3-Carboxy-1-cyclopropyl-6-fluoro-1,4-dihydro-4-oxo-7-quinolinyl)-4-piperazinyl]thioxomethyl]aminomethyl]-8-oxo-7-[(2-thienylacetyl)amino]-5-thia-1-azabicyclo[4.2.0]oct-2-ene-2-carboxylic acid disodium salt, of the following formula

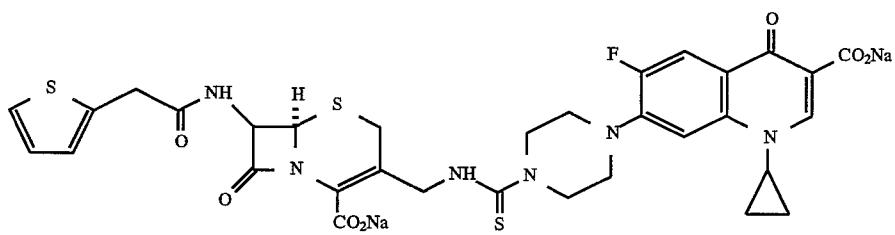

according to this invention, is made as follows. A mixture of approximately 0.80 g of [6R-[6a,7b]]-3-(isothiocyanatomethyl)-8-oxo-7-[(2-thienylacetyl)amino]-5-thia-1-azabicyclo[4.2.0]oct-2-ene-2-carboxylic acid (made by the process of Belgium Patent 719,711), $NaHCO_3$ (0.35 g) and ciprofloxacin (0.69 g) in DMF (50 ml) is heated at approximately 40° C. (104° F.) for 24 hours and concentrated to dryness in vacuo. The residue is recrystallized from aqueous acetone to afford the final product.

Similarly, the following lactam-quinolones are made according to the general procedure of this Example, with substantially similar results.

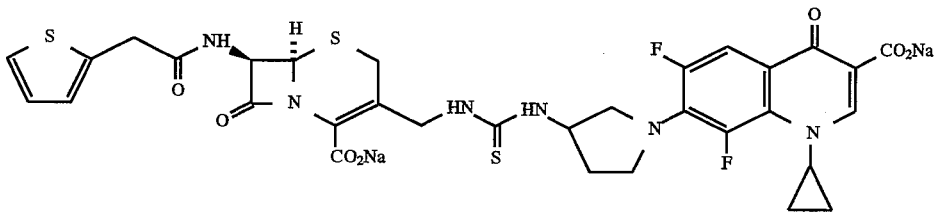

using the quinolone 7-(3-aminopyrrolidinyl)-1-cyclopropyl-6,8-difluoro-1,4-dihydro-4-oxo-3-quinolinecarboxylic acid (prepared according to J. P. Sanchez, et al., J. Med. Chem., 1988, 31, 983)

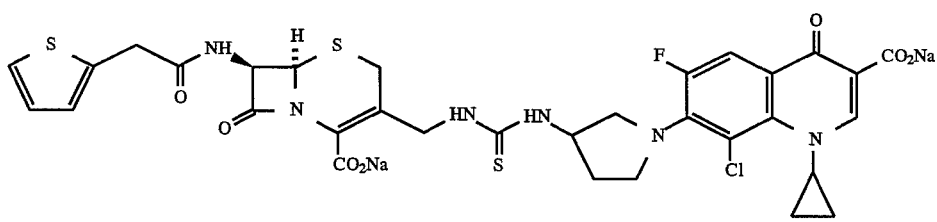

using the quinolone 7-(3-aminopyrrolidinyl)-8-chloro-1-cyclopropyl-6-fluoro-1,4-dihydro-4-oxo-3-quinolinecarboxylic acid (prepared according to J. P. Sanchez, et al., J. Med. Chem., 1988, 31, 983)

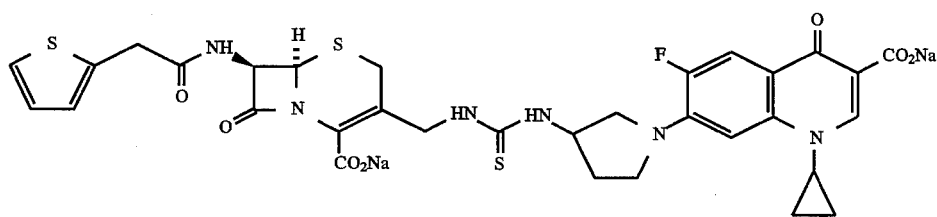

using the quinolone 7-(3-aminopyrrolidinyl)-1-cyclopropyl-6-fluoro-1,4-dihydro-4-oxo-3-quinolinecarboxylic acid (prepared according to J. P. Sanchez, et al., J. Med. Chem., 1988, 31, 983)

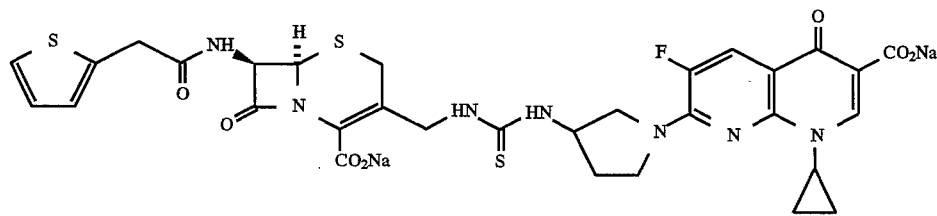

using the naphthyridinone 7-(3-aminopyrrolidinyl)-1-cyclopropyl-6-fluoro-1,4-dihydro-4-oxo-1,8-naphthyridine-3-carboxylic acid (prepared according to J. P. Sanchez, et al., J. Med. Chem., 1988, 31, 983).

EXAMPLE 42

[5R-[5a,6a]]-3-[[[(3-Carboxy-1-cyclopropyl-6-fluoro-1,4-dihydro-4-oxo-7-quinolinyl)-4-piperazinyl]thioxomethyl]aminomethyl]-6[(R)-1-hydroxyethyl]-7-oxo-4-thia-1-azabicyclo[3.2.0]-hept-2-ene-2-carboxylic Acid Disodium Salt

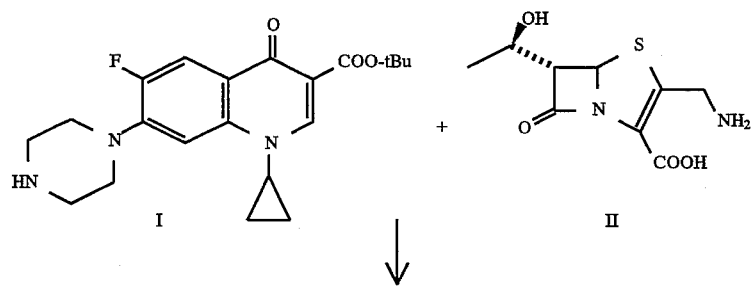

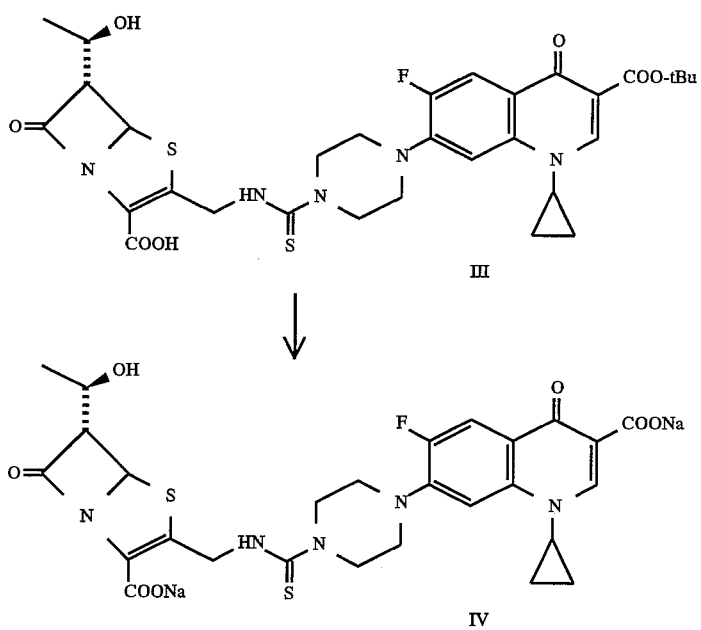

To a solution of approximately 2.2 ml of thiophosgene in 10 ml of $CH_2Cl_2$ is added dropwise a solution of approximately 2.2 g of ciprofloxacin t-butyl ester I and 0.8 g of triethylamine in approximately 30 ml of $CH_2Cl_2$ at approximately 2°–5° C. The mixture is stirred for approximately one hour in the cold, then is filtered and the filtrate is concentrated to dryness. The residue is stirred with acetone and is added slowly to a solution of approximately 1.4 g of II and 2.9 g of sodium bicarbonate in 20 ml of water at approximately 2°–5° C. The reaction is stirred at ambient temperature for approximately 2 hours, is diluted with water and is cooled in an ice bath. The mixture is acidified with 10% citric acid and the product is extracted with $CH_2Cl_2$. The extract is dried over $Na_2SO_4$, filtered and the filtrate is concentrated to dryness. The residue is purified by flash chromatography (silica gel) to give III. To a solution of approximately 1.0 g of III in 20 ml of anisole is added approximately 20 ml of trifluoroacetic acid dropwise at approximately −10° C. The solution is stirred at ambient temperature for approximately 50 minutes and is concentrated to dryness in vacuo. The residue is triturated in diethyl ether and the solid is collected by filtration and suspended in water. To this mixture is added approximately 0.22 g of sodium bicarbonate and acetone is added to effect dissolution. The solution is concentrated to dryness and the residue is purified by C-18 reverse phase chromatography to afford the title compound IV as the disodium salt.

Similarly, the following lactam-quinolones are made according to the general procedure of this Example, with substantially similar results.

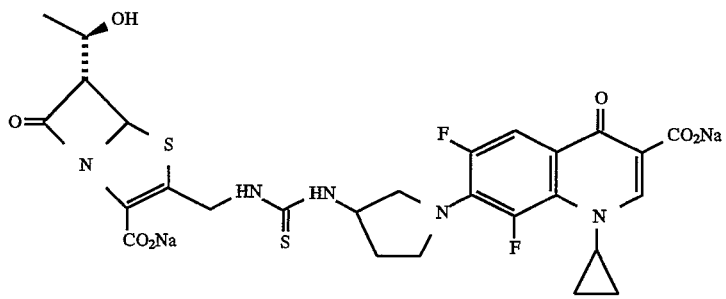

using the quinolone 7-(3-aminopyrrolidinyl)-1-cyclopropyl-6,8-difluoro-1,4-dihydro-4-oxo-3-quinolinecarboxylic acid (prepared according to J. P. Sanchez, et al., J. Med. Chem., 1988, 31, 983)

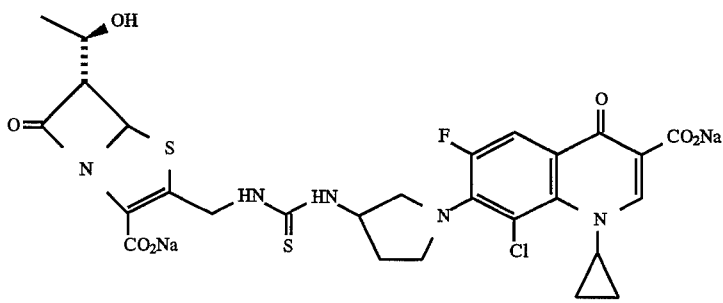

using the quinolone 7-(3-aminopyrrolidinyl)-8-chloro-1-cyclopropyl-6-fluoro-1,4-dihydro-4-oxo-3-quinolinecarboxylic acid (prepared according to J. P. Sanchez, et al., J. Med. Chem., 1988, 31, 983)

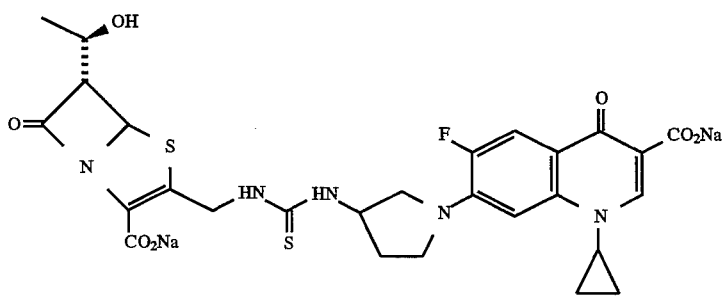

using the quinolone 7-(3-aminopyrrolidinyl)-1-cyclopropyl-6-fluoro-1,4-dihydro-4-oxo-3-quinolinecarboxylic acid (prepared according to J. P. Sanchez, et al., J. Med. Chem., 1988, 31, 983)

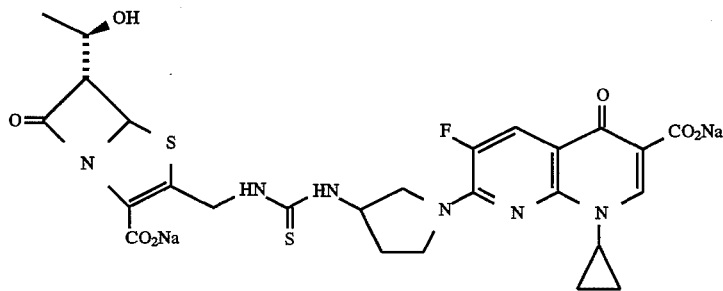

using the naphthyridinone 7-(3-aminopyrrolidinyl)-1-cyclopropyl-6-fluoro-1,4-dihydro-4-oxo-1,8-naphthyridine-3-carboxylic acid (prepared according to J. P. Sanchez, et al., J. Med. Chem., 1988, 31, 983)

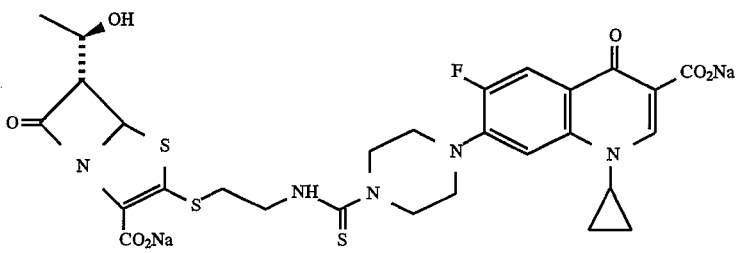

using the beta-lactam 3-[(2-aminoethyl)thio]-6-(1-hydroxyethyl)-7-oxo-4-thia-1-azabicyclo[3.2.0]hept-2-ene-2-carboxylic acid (prepared according to T. Hayashi, et al., Chem. Pharm. Bull., 1981, 29, 3158)

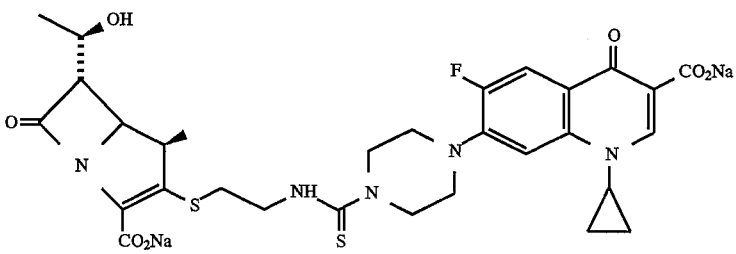

using the beta-lactam 3-[(2-aminoethyl)thio]-6-(1-hydroxyethyl)-4-methyl-7-oxo-1-azabicyclo[3.2.0]hept-2-ene-2-carboxylic acid (prepared according to D. H. Shih, et al., Tet. Lett. 1985, 26, 587)

EXAMPLE 43

According to the general procedure of Example 42, the following lactam-quinolone is made:

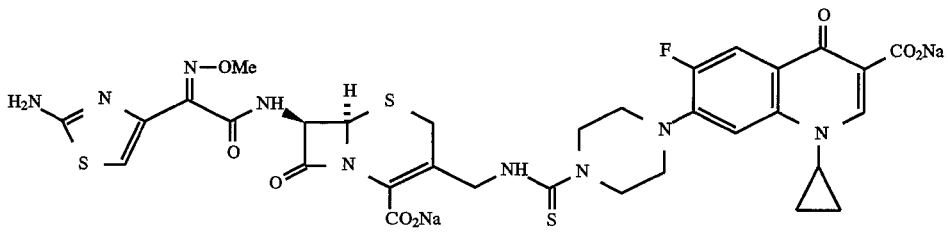

using the beta-lactam [6R-[6a,7b(Z)]]-3-(aminomethyl)-7-[[(2-amino-4-thiazolyl)(methoxyimino)acetyl]amino]-8-oxo-5-thia-1-azabicyclo[4.2.0]oct-2-ene-2-carboxylic acid (prepared according to F. H. Jung, Eur. Pat. Appl. EP 182633 A2, 28 May 1986)

Similarly, the following lactam quinolones are made according to the general procedure of this Example, with substantially similar results.

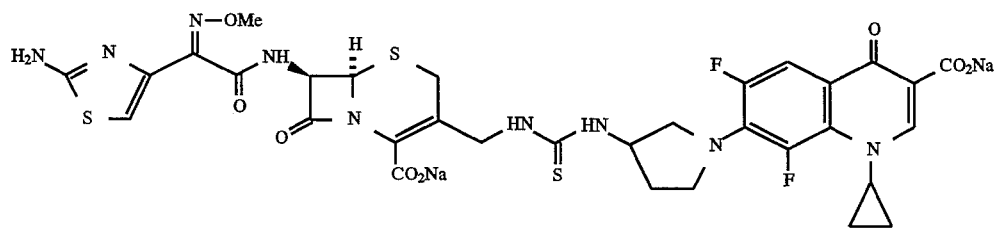

using the quinolone 7-(3-aminopyrrolidinyl)-1-cyclopropyl-6,8-difluoro-1,4-dihydro-4-oxo-3-quinolinecarboxylic acid (prepared according to J. P. Sanchez, et al., J. Med. Chem., 1988, 31, 983)

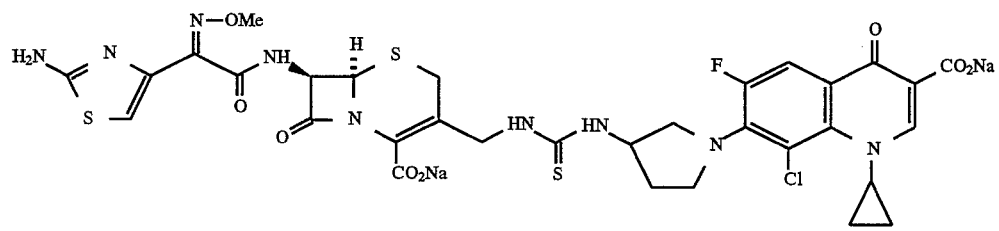

using the quinolone 7-(3-aminopyrrolidinyl)-8-chloro-1-cyclopropyl-6-fluoro-1,4-dihydro-4-oxo-3-quinolinecarboxylic acid (prepared according to J. P. Sanchez, et al., J. Med. Chem., 1988, 31, 983)

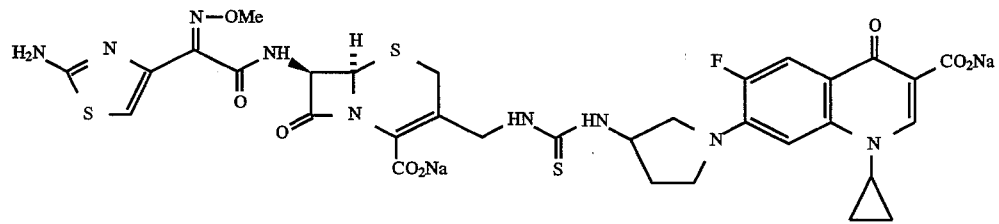

using the naphthyridinone 7-(3-aminopyrrolidinyl)-1-cyclopropyl-6-fluoro-1,4-dihydro-4-oxo-1,8-naphthyridine-3-carboxylic acid (prepared according to J. P. Sanchez, et al., J. Med. Chem., 1988, 31, 983)

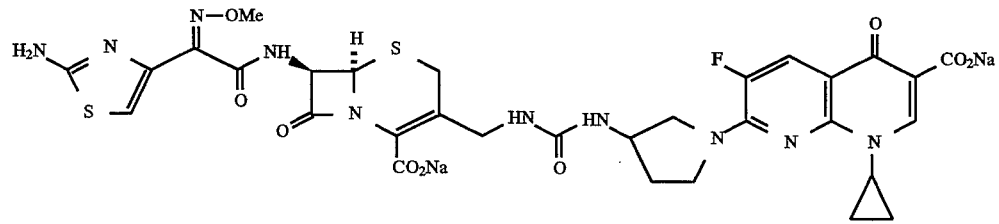

using the naphthyridinone 7-(3-aminopyrrolidinyl)-1-cyclopropyl-6-fluoro-1,4-dihydro-4-oxo-1,8-naphthyridine-3-carboxylic acid (prepared according to J. P. Sanchez, et al., J. Med. Chem., 1988, 31, 983)

The following other lactam-quinolones are also made by the 15 general procedure of this Example and Examples 41 and 42, with substantially similar results.
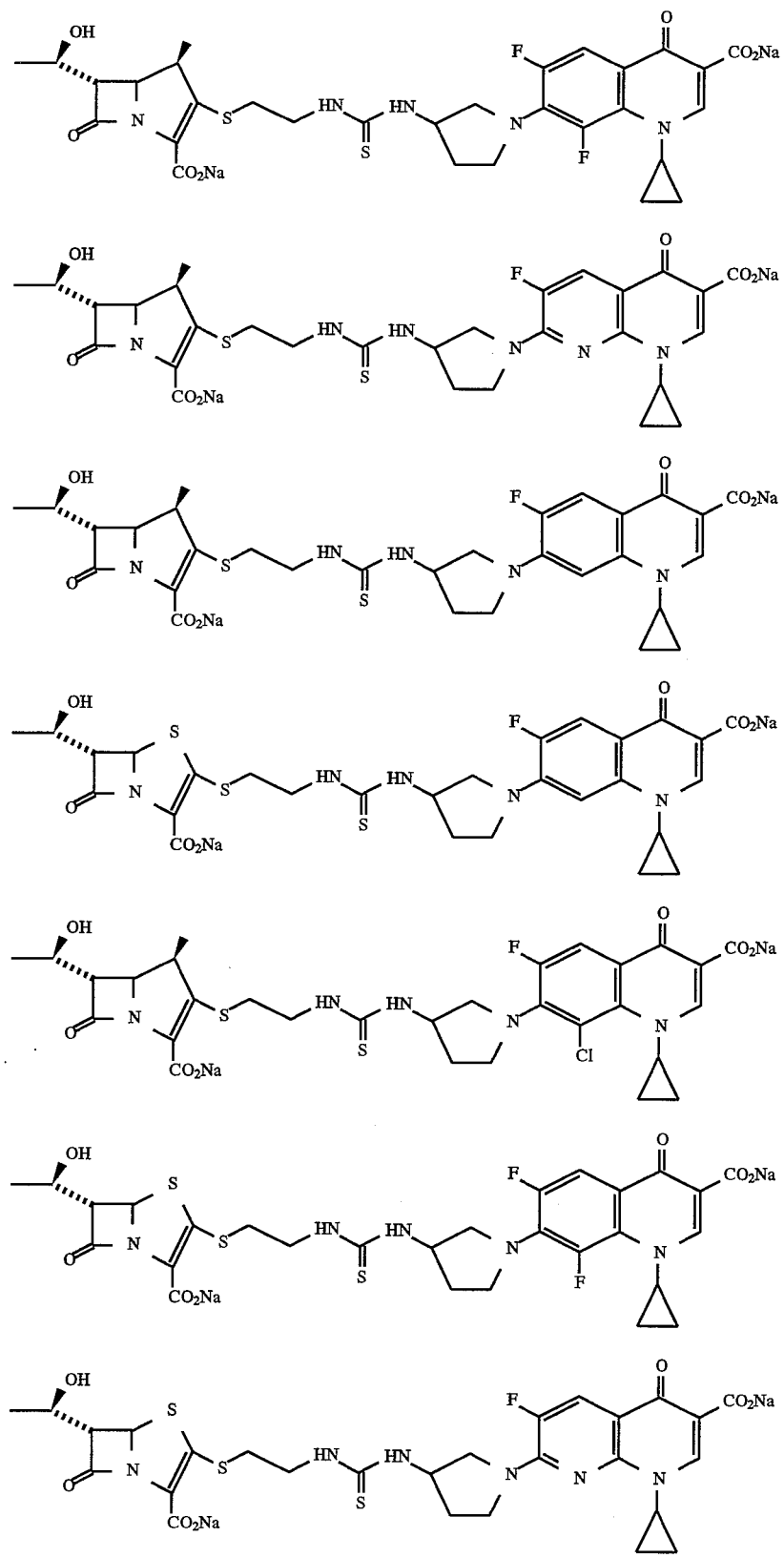

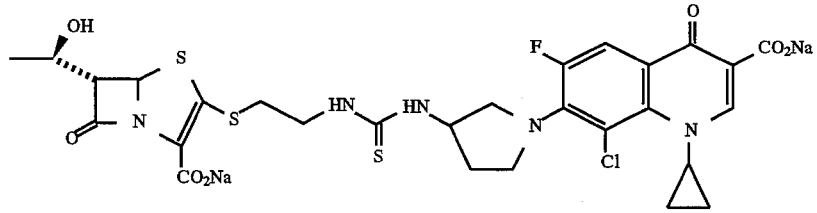

EXAMPLE 44

[6R-[6a,7b]]-3-[[[(3-Carboxy-1-cyclopropyl-6-fluoro-1, 4-dihydro-4-oxo-7-quinolinyl)-4-piperazinyl]iminomethyl] thio methyl]-8-oxo-7-[(2-thienylacetyl)amino]-5-thia-1-azabicyclo [4.2.0]oct-2-ene-2-carboxylic acid sodium salt, of the following formula

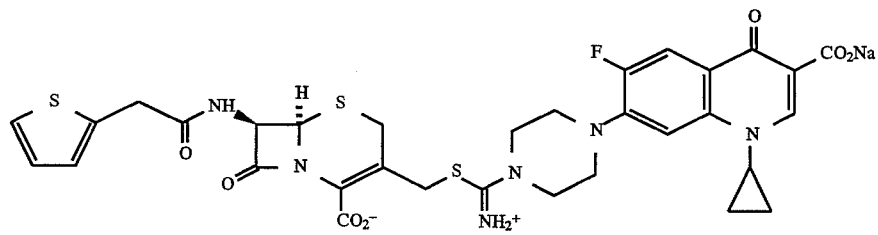

according to this invention, is made as follows. A solution of benzoyl isothiocyanate (0.92 g) in THF (20 ml) is added to a mixture of ciprofloxacin sodium salt (2.0 9) in THF (300 ml), and the reaction is stirred for 20 hours. The reaction is concentrated to dryness and the residue is triturated with acetone. The resultant benzoylurea is added to a preheated at approximately 80° C. (176° F.) solution of 5% aqueous NaOH and the reaction is stirred for 30 minutes. The mixture is cooled to approximately 5° C. (41° F.) and acidified with 1N HCl. The solid is collected by filtration and recrystallized from DMF to yield 7-[4-(aminothioxomethyl)-1-piperazinyl]-1-cyclopropyl -6-fluoro-1,4-dihydro-4-oxo-3-quinolinecarboxylic acid.

A solution of this intermediate (approximately 0.40 g), $NaHCO_3$ (0.17 g) and cephalothin (0.40 g) in $H_2O$ (10 ml) is heated at approximately 55° C. (131° F.) for 20 hours and diluted with saturated aqueous NaCl. The mixture is centrifuged, the aqueous layer is decanted and the residue is purified by recrystallization from methanol/water to give the final product.

Similarly, the following lactam-quinolone is made according to the general procedure of this Example, with substantially similar results.

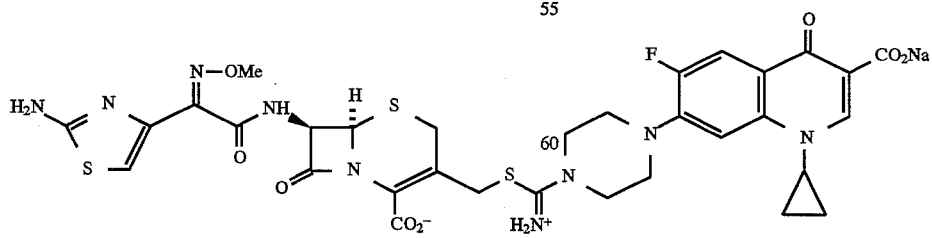

using the beta-lactam [6R-[6a,7b(Z)]]-3-[(acetyloxy)methyl]-7-[[(2-amino-4-thiazolyl)(methoxyimino)acetyl]amino]-8-oxo-5-thia-1-azabicyclo[4.2.0]oct-2-ene-2-carboxylic acid (preparation described herein).

EXAMPLE 45

According to the general procedure of Example 44, the following lactam-quinolone is made:

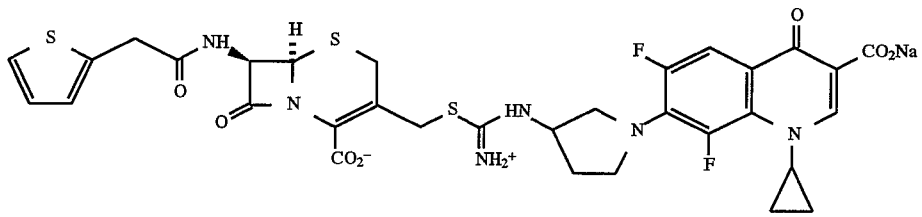

using the quinolone 7-(3-aminopyrrolidinyl)-1-cyclopropyl-6,8-difluoro-1,4-dihydro-4-oxo-3-quinolinecarboxylic acid (prepared according to J. P. Sanchez, et al., J. Med. Chem., 1988, 31, 983)

Similarly, the following lactam-quinolone is made by the general procedure of this Example with substantially similar results.

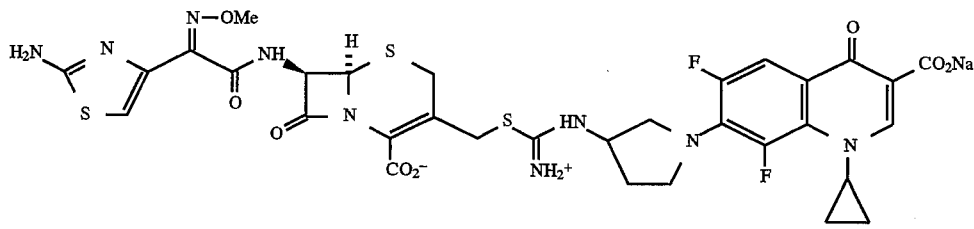

using the beta-lactam [6R-[6a,7b(Z)]]-3-[(acetyloxy)methyl]-7-(2-amino-4-thiazolyl)(methoxyimino)acetyl]amino]-8-oxo-5-thia-1-azabicyclo[4.2.0]oct-2-ene-2-carboxylic acid (preparation described herein).

EXAMPLE 46

According to the general procedure of Example 44, the following lactamoquinolone is made:

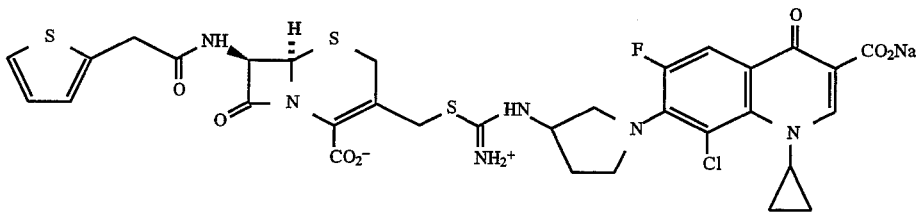

using the quinolone 7-(3-aminopyrrolidinyl)-8-chloro-1-cyclopropyl-6-fluoro-1,4-dihydro-4-oxo-3-quinolinecarboxylic acid (prepared according to J. P. Sanchez, et al., J. Med. Chem., 1988, 31, 983).

Similarly, the following lactam-quinolone is made by the general procedure of this Example with substantially similar results.

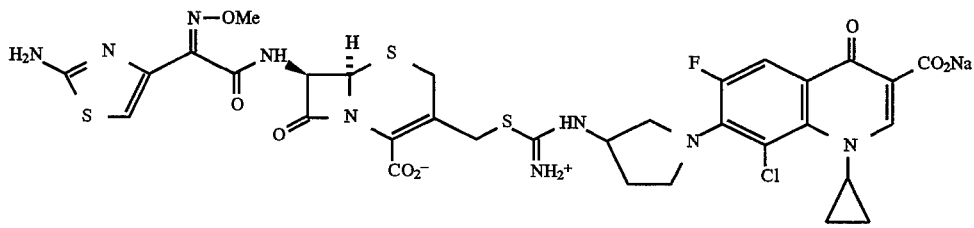

using the beta-lactam [6R-[6a,7b(Z)]]-3-[(acetyloxy) methyl]-7-[[(2-amino-4-thiazolyl)(methoxyimino)acetyl] amino]-8-oxo-5-thia-1-azabicyclo[4.2.0]oct-2-ene-2-carboxylic acid (preparation described herein).

EXAMPLE 47

According to the general procedure of Example 44, the following lactam-quinolone is made:

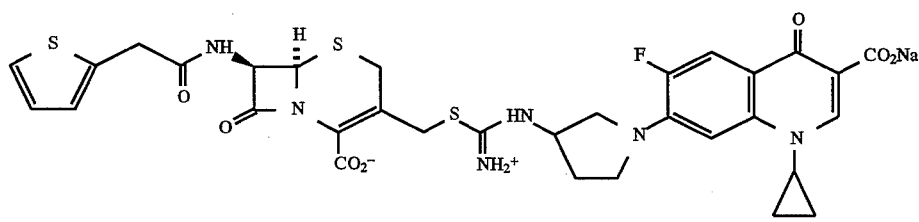

using the quinolone 7-(3-aminopyrrolidinyl)-1-cyclopropyl-6-fluoro-1,4-dihydro-4-oxo-3-quinolinecarboxylic acid (prepared according to J. P. Sanchez, et al., J. Med. Chem., 1988, 31, 983).

Similarly, the following lactam-quinolone is made by the general procedure of this Example with substantially similar results.

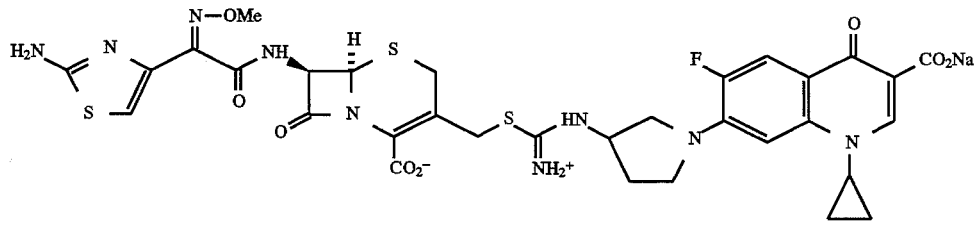

using the beta-lactam [6R-[6a,7b(Z)]]-3-[(acetyloxy) methyl]-7-[[(2-amino-4-thiazolyl) (methoxyimino)acetyl] amino]-8-oxo-5-thia-1-azabicyclo[4.2.0]oct-2-ene-2-carboxylic acid (preparation described herein).

EXAMPLE 48

According to the general procedure of Example 44, the following lactam quinolone is made:

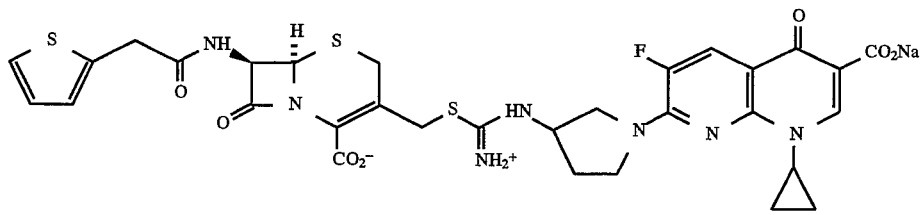

using the naphthyridinone 7-(3-aminopyrrolidinyl)-1-cyclopropyl-6-fluoro-1,4-dihydro-4-oxo-1,8-naphthyridine-3-carboxylic acid (prepared according to J. P. Sanchez, et al., J. Med. Chem., 1988, 31, 983).

Similarly, the following lactam-quinolone is made by the general procedure of this Example with substantially similar results.

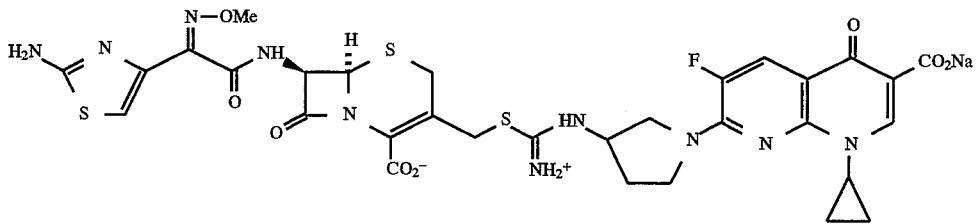

using the beta-lactam [6R-[6a,7b(Z)]]-3-[(acetyloxy) methyl]-7-[[(2-amino-4-thiazolyl) (methoxyimino)acetyl] amino]-8-oxo-5-thia-1-azabicyclo[4.2.0]oct-2-ene-2-carboxylic acid (preparation described herein).

EXAMPLE 49

[5R-[4β,5α,6α]]-3-[2-[[[4-(3-carboxy-1-cyclopropyl-6-fluoro-1,4-dihydro-4-oxo-7-quinolinyl)-1-piperizinyl] iminomethyl]thio]ethylthio]-6-[(R)-1-hydroxyethyl]-4-methyl-7-oxo-1-azabicyclo[3.2.0]hept-2-ene-2-carboxylic acid monosodium salt

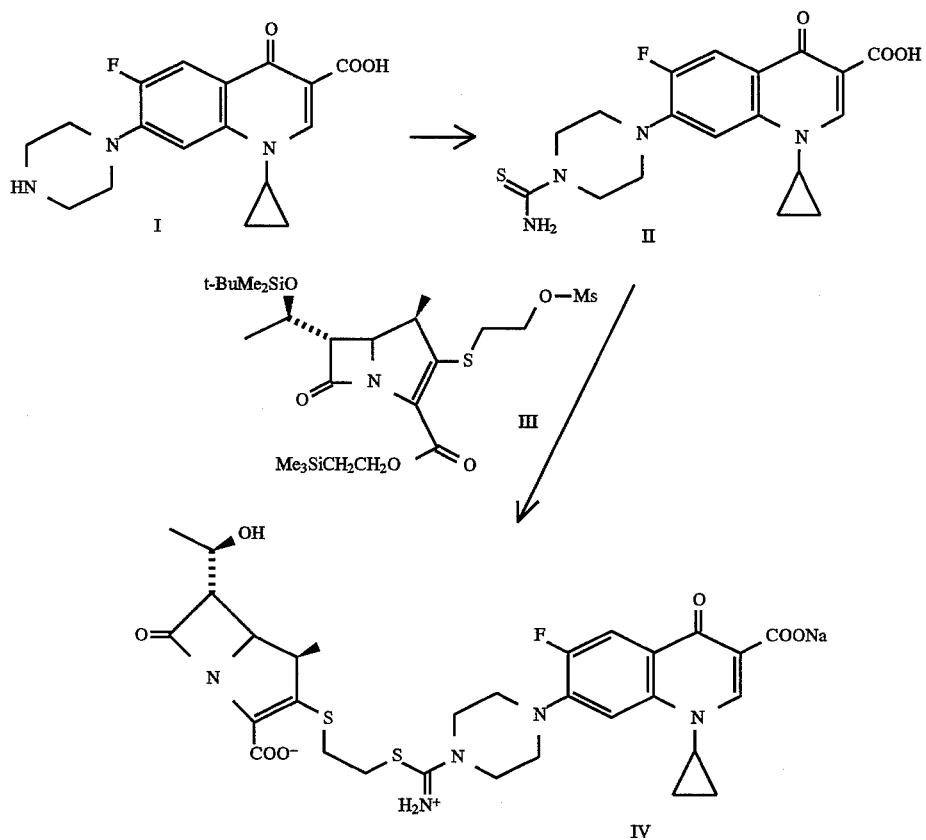

To a mixture of approximately 2.0 g of ciprofloxacin I in 70 ml of DMF at 0° C. is added a solution of approximately 1.2 g of thiocarbonyldiimidazole in 10 ml of DMF and the reaction is stirred cold for approximately one hour. To the reaction is added an excess of saturated NH3/MeOH and the mixture is stirred cold for one hour and overnight at room temperature. The solution is concentrated to dryness in vacuo and the residue is dissolved in a small amount of water containing approximately 5.1 ml of 1N NaOH. The solution is concentrated to dryness and the residue is purified by C-18 reverse phase chromatography. The quinolone sodium salt is stirred in a mixture of Bio-RadR AG 50W-X4 (hydrogen form) in aqueous DMF, filtered, and the filtrate is concentrated in vacuo to give II.

A mixture of approximately 0.8 g of mesylate III and 0.5 g of II in approximately 8 ml of DMF is stirred approximately 20 hours at room temperature. To the reaction is added approximately 2.1 g of tetra-n-butylammonium fluoride and stirring is continued for approximately eight hours. Approximately 4 ml of saturated aqueous sodium bicarbonate is added and the mixture is eluted through a DowexR 50×4 (Na cycle) column with deionized water. The appropriate fractions are concentrated in vacuo and then lyophilized to give the title compound IV.

Similarly, the following lactam-quinolones are made by the general procedure of this Example, with substantially similar results.

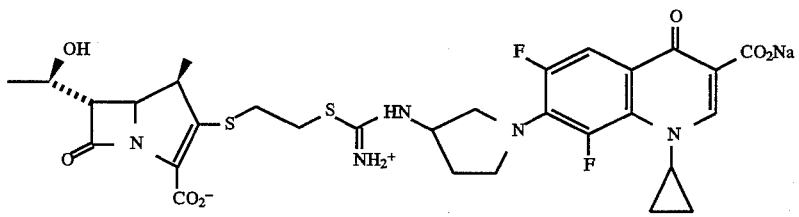

using the quinolone 7-(3-aminopyrrolidinyl)-1-cyclopropyl-6,8-difluoro-1,4-dihydro-4-oxo-3-quinolinecarboxylic acid (prepared according to J. P. Sanchez, et al., J. Med. Chem., 1988, 31, 983)

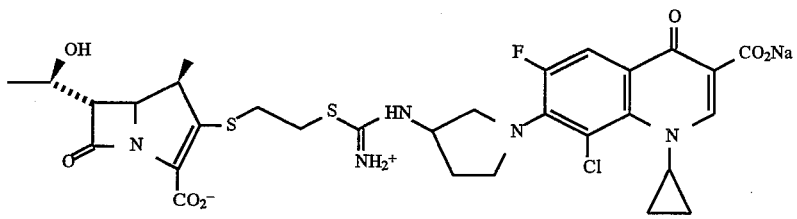

using the quinolone 7-(3-aminopyrrolidinyl)-8-chloro-1-cyclopropyl-6-fluoro-1,4-dihydro-4-oxo-3-quinolinecarboxylic acid (prepared according to J. P. Sanchez, et al., J. Med. Chem., 1988, 31, 983)

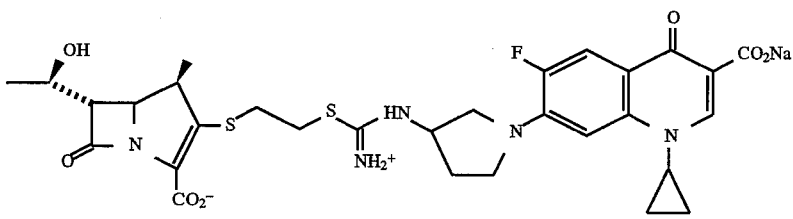

using the quinolone 7-(3-aminopyrrolidinyl)-1-cyclopropyl-6-fluoro-1,4-dihydro-4-oxo-3-quinolinecarboxylic acid (prepared according to J. P. Sanchez, et al., J. Med. Chem., 1988, 31, 983)

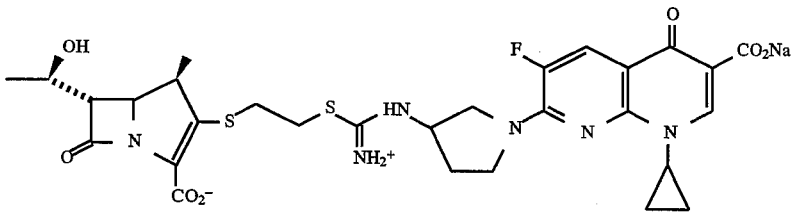

using the naphthyridinone 7-(3-aminopyrrolidinyl)-1-cyclopropyl-6-fluoro-1,4-dihydro-4-oxo-1,8-naphthyridine-3carboxylic acid (prepared according to J. P. Sanchez, et al., J. Med. Chem., 1988, 31, 983).

The following other lactam-quinolones are also made by the general procedure of this Example and Examples 44–48, with substantially similar results.

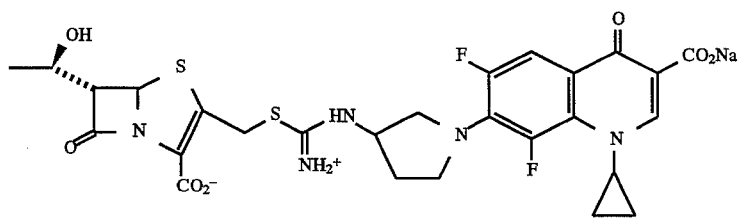
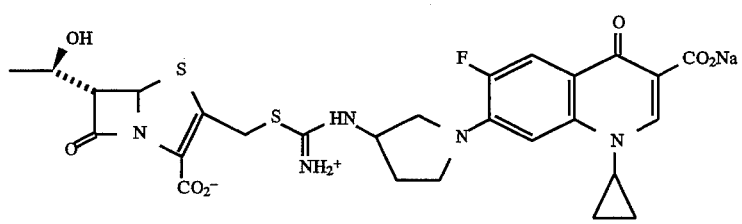
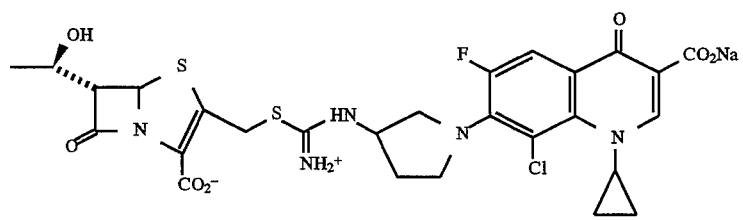
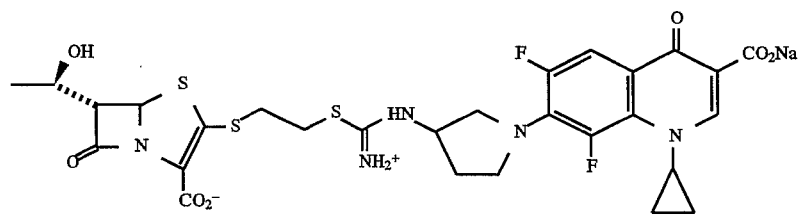
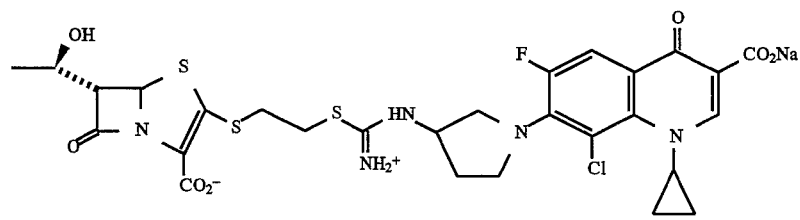
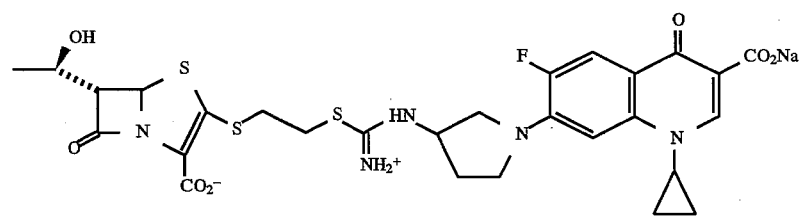
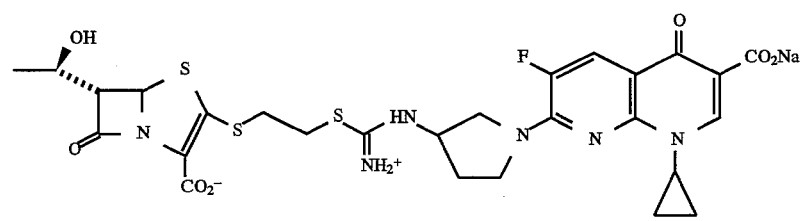

-continued

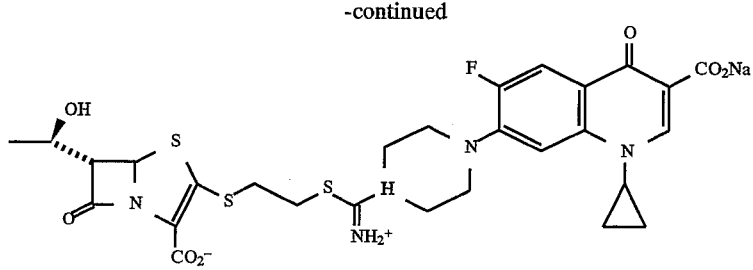

EXAMPLE 50

[5R-[5a,6a]]-3-[[[(3-Carboxy-1-cyclopropyl-7-fluoro-1,4-dihydro-4-oxo-7-quinolinyl)-4-piperazinyl]iminomethyl]amino methyl]-6-[(R)-1-hydroxyethyl)7-oxo-4-thia-1-azabicyclo[3.2.0]hept-2-ene-2-carboxylic acid hydroiodide, of the following formula

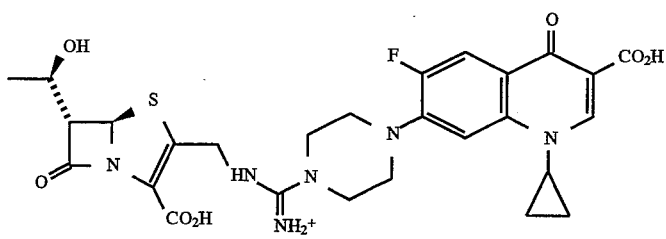

is made as follows. A mixture of 7-[4-(aminothioxomethyl)piperazinyl]1-cyclopropyl-7-fluoro-1,4-dihydro-4-oxo-3-quinolinecarboxylic acid (1.0 g) and iodomethane (0.36 g) in DMF (50 ml) is stirred for 18 hours .and concentrated to dryness in vacuo. The residue is recrystallized from DMF to yield the isothiouronium compound. This quinolone (0.5 g) is refluxed with [5R-[5a,6a]]-3-(aminomethyl)-6-[(R)-1-hydroxyethyl)]-7-oxo-4-thia-1-azabicyclo[3.2.0]hept-2-ene-2-carboxylic acid (0.63 g), triethylamine (0.52 g) and a small amount of t-butanol in acetonitrile/DMF for 24 hours. The reaction is concentrated to dryness, stirred in water and the mixture is acidified with aqueous hydrogen iodide. The solid is collected by filtration and recrystallized from aqueous methanol to give the final product.

EXAMPLE 51

[6R-[6a,7b]]-4-(3-Carboxy-1-ethyl-1,4-dihydro-4-oxo-7-quinolinyl)-1-[[2-carboxy-8-oxo-7-[(2-thienylacetyl)amino]-5-thia-1-azabicyclo[4.2.0]oct-2-en-3-yl]methyl]pyridinium sodium salt, of the formula

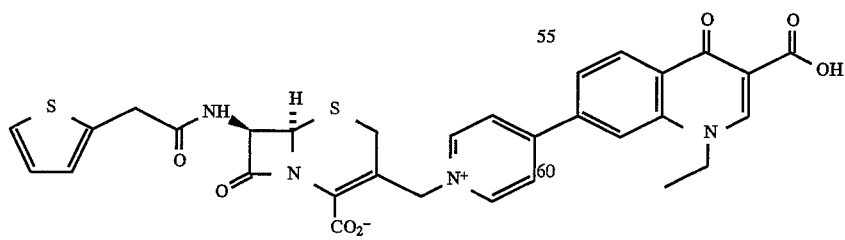

according to this invention, is made as follows. A solution of cephalothin sodium salt (1.0 g), rosoxacin (0.70 g) (made according to U.S. Pat. No. 3,907,808, 1975), NaHCO₃ (0.20 g) and H₂O (25 ml) is heated at approximately 45° C. (113° F.) for 18 hours and diluted with saturated aqueous NaCl. The mixture is centrifuged and the aqueous layer is decanted. The solid is triturated with aqueous acetone to yield the final compound.

The following lactam-quinolone is made according to the general procedure of this Example, with substantially similar results.

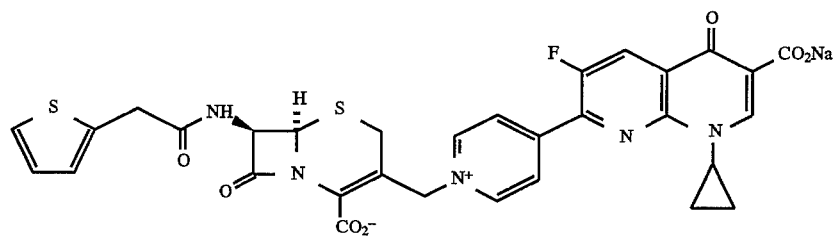

using the quinolone 1-cyclopropyl-6-fluoro-1,4-dihydro-4-oxo-7-(4-pyridyl)-3-quinoline carboxylic acid (prepared according to Y. Nishimura, et al., J. Med. Chem., 1987, 30, 1622).

EXAMPLE 52

According to the general procedure of Example 51, the following lactam-quinolone is made:

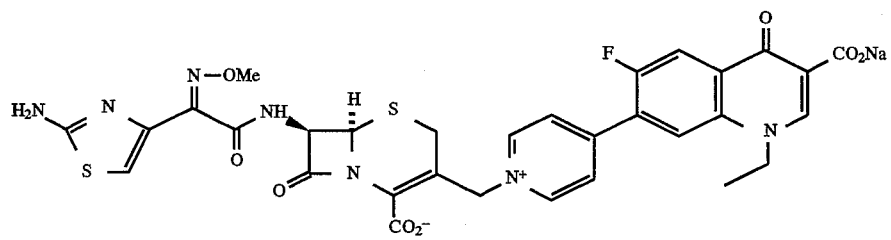

using the beta-lactam 3-(acetyloxymethyl)-7-[[(2 amino-4-thiazolyl)acetyl]amino]-8-oxo-5-thia-1-azabicyclo[4.2.0]oct-2-ene-2-carboxylic acid (prepared as described herein).

Similarly, the following lactam-quinolone is made according to the general procedure of this Example, with substantially similar results.

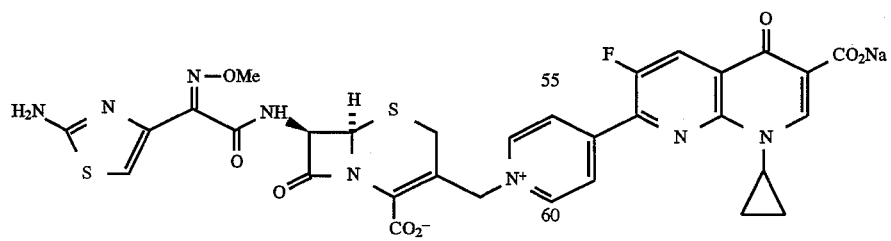

using the quinolone 1-cyclopropyl-6-fluoro-1,4-dihydro-4-oxo-7-(4-pyridyl)-3-quinoline carboxylic acid (prepared according to Y. Nishimura, et al., J. Med. Chem., 1987, 30, 1622).

The following other lactam-quinolones are also made according to the general procedures of this Example and Example 51, with substantially similar results.

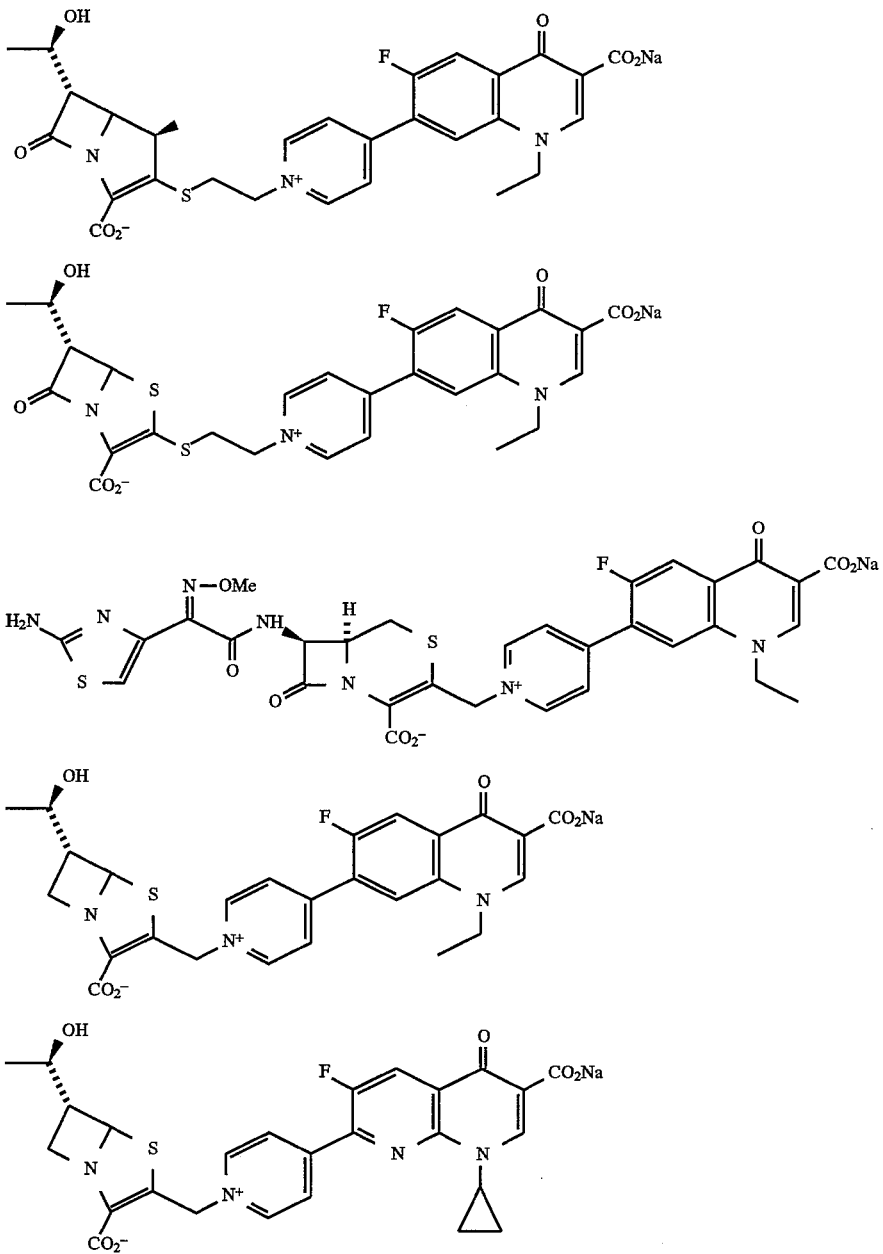

EXAMPLE 53

[6R-(6α,7β)]-3-[[4-(3-Carboxy-1-cyclopropyl-6-fluoro-1,4-dihydro-4-oxo-7-quinolinyl)-1-piperazinyl]carbonyl]-8-oxo-7-[(2-thienylacetyl)amino]-5-thia-1-azabicyclo[4.2.0]oct-2-ene-2-carboxylic Acid Disodium Salt

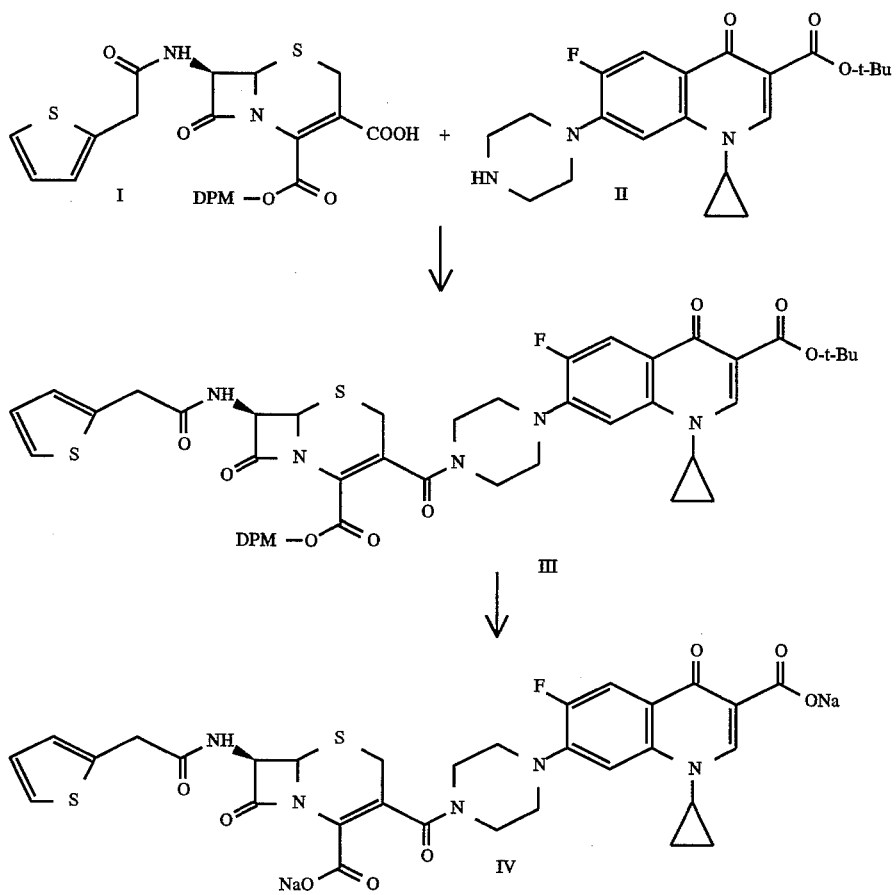

A mixture of approximately 4.6 g of [6R-(6α,7β)]-3-carboxy-8-oxo-7-[(2-thienylacetyl)amino]-5-thia-1-azabicyclo[4.2.0oct-2- ene-2-carboxylic acid diphenylmethyl ester I (prepared according to Helv. Chim. Acta 1975, 58, 2450) and 1.1 ml of 2,6-lutidine in 75 ml of $CH_2C_2$ is cooled in an ice bath and approximately 0.79 ml of oxalyl chloride is added slowly at 0°–5° C. After the mixture is stirred in the cold for approximately 2 hours, a solution of approximately 3.3 g of ciprofloxacin t-butyl ester II and 1.1 ml of 2,6-lutidine in approximately 100 ml of $CH_2Cl_2$ is added slowly at 0°–5° C. The mixture is stirred in the cold for approximately four hours and then is washed with dilute HCl, 10% $NaHCO_3$ and water. The organic phase is dried over $Na_2SO_4$, filtered and the filtrate is concentrated to dryness. The product III is isolated by silica gel chromatography. To a solution of approximately 1.4 g of III in 30 ml of anisole is added approximately 30 ml of trifluoroacetic acid dropwise at approximately −15° C. The solution is stirred at ambient temperature for approximately 20 minutes and is concentrated to dryness in vacuo. The product is triturated in diethyl ether, collected by filtration and the solid is suspended in water. To this mixture is added approximately 0.26 g of $NaHCO_3$ and acetone is added to attain a solution. The solution is concentrated to dryness. and the residue is purified by C-18 reverse phase chromatography to afford the title compound IV.

Similarly, the following lactam-quinolone is made according to the general procedure of this Example, with substantially similar results.

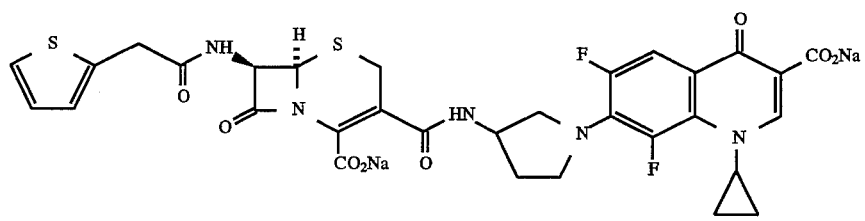

using the quinolone 7-(3-aminopyrrolidinyl)-1-cyclopropyl-6,8-difluoro-1,4-dihydro-4-oxo-3-quinoline carboxylic acid (prepared according to J. P. Sanchez, et. al., J. Med. Chem., 1988, 31, 83).

The following other lactam-quinolones are also made according to the procedure of this Example, with substantially similar results.

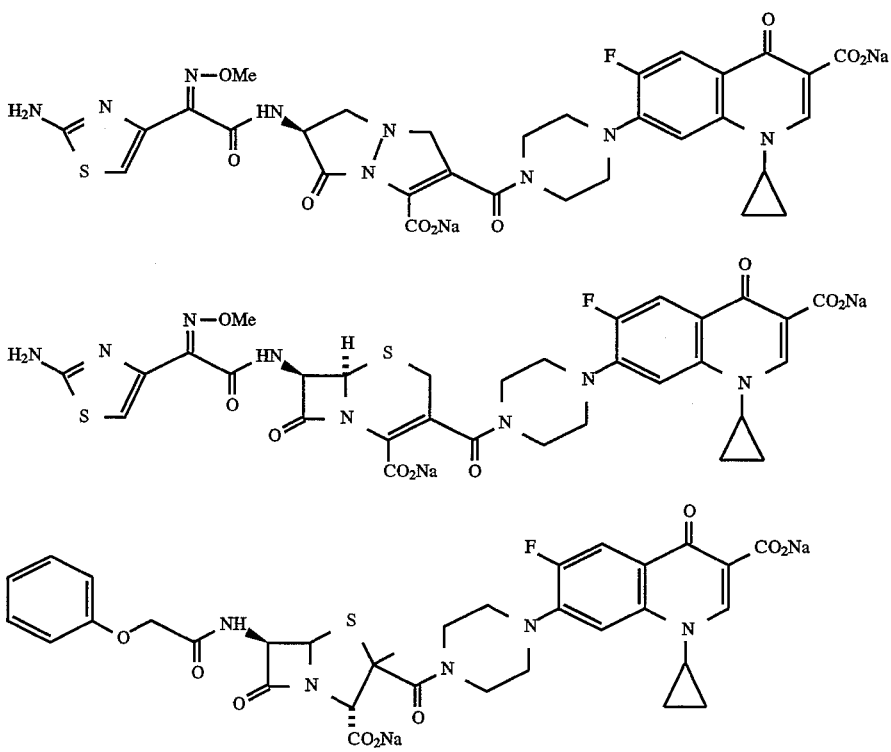

EXAMPLE 54

An antimicrobial composition for parenteral administration, according to this invention, is made comprising:

| Component | Amount |
|---|---|
| [6R-[6a,7b]]-[[[4-(3-Carboxy-1-cyclopropyl-6-fluoro-1,4-dihydro-4-oxo-7-quinolinyl)-1-piperazinyl]carbonyloxy]methyl]-8-oxo-7-[(2-thienylacetyl)amino]-5-thia-1-azabicyclo[4.2.0]oct-2-ene-2-carboxylic acid disodium salt[1] | 100 mg/ml carrier |
| Carrier: sodium citrate buffer with (percent by weight of carrier): | |
| lecithin | 0.48% |
| carboxymethylcellulose | 0.53 |
| povidone | 0.50 |
| methyl paraben | 0.11 |
| propyl paraben | 0.011 |

[1] a lactam-quinolone, made according to Example 1

The above ingredients are mixed, forming a suspension. Approximately 2.0 ml of the suspension is systemically administered, via intramuscular injection, to a human subject suffering from a lower respiratory tract infection, with Streptococcus pneumoniae present. This dosage is repeated twice daily, for approximately 14 days. After 4 days, symptoms of the disease subside, indicating that the pathogen has been substantially eradicated.

EXAMPLE 55

An enteric coated antimicrobial composition for oral administration, according to this invention, is made comprising the following core tablet:

| Component | Amount (mg) |
|---|---|
| [6R-[6a,7b]]-[[[4-(3-Carboxy-1-cyclopropyl-6-fluoro-1,4-dihydro-4-oxo-7-quinolinyl)-1-piperazinyl]carbonyloxy]methyl]-8-oxo-7-[(2-thienylacetyl)amino]-5-thia-1-azabicyclo[4.2.0]oct-2-ene-2-carboxylic acid disodium salt[1] | 350.0 |
| starch | 30.0 |
| magnesium stearate | 5.0 |
| microcrystalline cellulose | 100.0 |
| colloidal silicon dioxide | 2.5 |
| povidone | 12.5 |

[1] a lactam-quinolone, made according to Example 1

The components are admixed into a bulk mixture. Compressed tablets are formed, using tabletting methods known in the art. The tablet is then coated with a suspension of methacrylic acid/methacrylic acid ester polymer in isopropanol/acetone. A human subject, having a urinary tract infection with *Escherichia coli* present, is orally administered two of the tablets, every 8 hours, for 14 days. Symptoms of the disease then subside, indicating substantial eradication of the pathogen.

What is claimed is:
1. A compound having the structure:

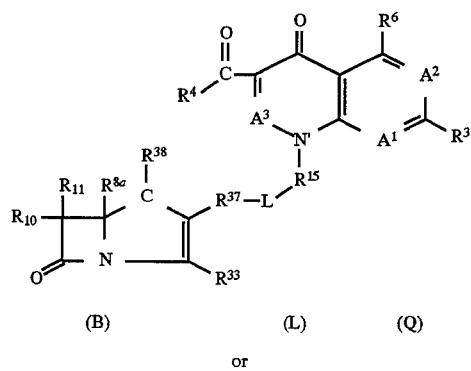

(B)　　　(L)　　　(Q)

or

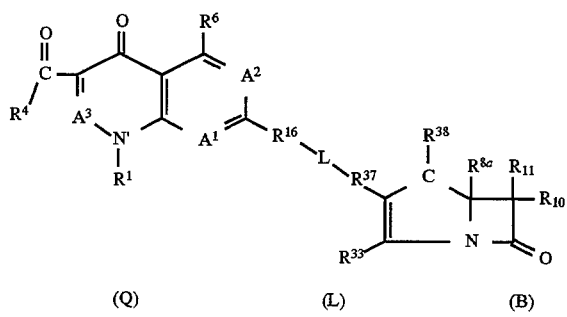

(Q)　　　(L)　　　(B)

wherein
(A) Q is of structure

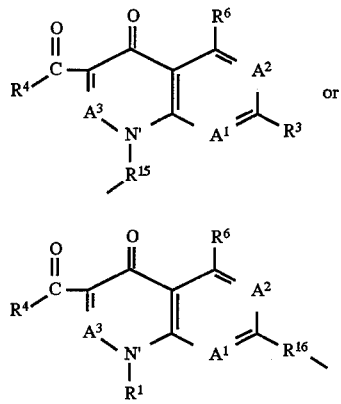

(1) $A^1$ is N or $C(R^7)$; where
  (i) $R^7$ is hydrogen, hydroxy, alkoxy, nitro, cyano, halogen, $C_1$–$C_8$ alkyl, or $N(R^8)(R^9)$, and
  (ii) $R^8$ and $R^9$ are, independently, $R^{8a}$ where $R^{8a}$ is hydrogen; $C_1$–$C_8$ alkyl; $C_2$–$C_8$ alkenyl; a 3–9 atom monocyclic or 7–17 atom polycyclic carbocycle; or a 3–9 atom monocyclic or 7–17 atom polycyclic heterocycle; or $R^8$ and $R^9$ together form a 3–9 atom monocyclic or 7–17 atom polycyclic heterocycle including the nitrogen to which they are bonded; and wherein said heterocycles have one or more heteroatoms selected from O, N, or S;

(2) $A^2$ is N or $C(R^2)$; where $R^2$ is hydrogen or halogen;
(3) $A^3$ is N or $C(R^5)$; where $R^5$ is hydrogen or $R^5$ forms a ring with $R^1$ or $R^4$;
(4) $A^1$ is hydrogen, $R^{15}$, or when $A^3$ is $C(R^5)$, $R^1$ and $R^5$ may form a ring;
(5) $R^3$ is hydrogen, halogen or $R^{16}$;

(6) $R^{15}$ is a $C_1$–$C_8$ alkyl; a 3–9 atom monocyclic or 7–17 atom polycyclic carbocycle; a 3–9 atom monocyclic or 7–17 atom polycyclic heterocycle; alkoxy; hydroxy; $C_2$–$C_8$ alkenyl; arylalkyl; or $N(R^8)(R^9)$; and wherein said arylalkyl is a $C_1$–$C_8$ alkyl substituted with an aryl group; wherein said heterocycles have one or more heteroatoms selected from O, N, or S;

(7) $R^{16}$ is a $C_1$–$C_8$ alkyl; a 3–9 atom monocyclic or 7–17 atom polycyclic carbocycle; or a 3–9 atom monocyclic or 7–17 atom polycyclic heterocycle; wherein said heterocycles have one or more heteroatoms selected from O, N, or S;

(8) $R^4$ is hydroxy or when $A^3$ is $C(R^5)$, $R^4$ and $R^5$ may form a ring; and (9) $R^6$ is hydrogen, halogen, nitro, or $N(R^8)(R^9)$;

(B) wherein:
(1) when $A^1$ is $C(R^7)$, $R^1$ and $R^7$ may together form a 3–9 atom monocyclic or 7–17 atom polycyclic heterocycle including N' and $A^1$; wherein said heterocycles have one or more heteroatoms selected from O, N, or S;

(2) when $A^2$ is $C(R^2)$, $R^2$ and $R^3$ may together form —O—$(CH_2)_n$—O—, where n is an integer from 1 to 4;

(3) when $A^3$ is $C(R^5)$, $R^4$ and $R^5$ may together form a 3–9 atom monocyclic or 7–17 atom polycyclic heterocycle including the carbon atoms to which $R^4$ and $R^5$ are bonded and the carbon atom to which said carbon atoms are bonded; and wherein said heterocycles have one or more heteroatoms selected from O, N, or S; and (4) when $A^3$ is $C(R^5)$, $R^1$ and $R^5$ may together form a 3–9 atom monocyclic or 7–17 atom polycyclic heterocycle including N' and the adjacent carbon to which $R^5$ is bonded; and wherein said heterocycles have one or more heteroatoms selected from O, N, or S;

(C) B is of structure

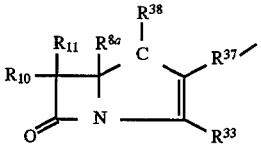

and $R^{10}$ is hydrogen; halogen; $C_1$–$C_8$ alkyl; $C_2$–$C_8$ alkenyl; a 3–8 atom heteroalkyl having 1 or 2 heteroatoms selected from O, N, or S; a 3–9 atom monocyclic or 7–17 atom polycyclic carbocycle; a 3–9 atom monocyclic or 7–17 atom polycyclic heterocycle; $R^{8a}$—O—; $R^{8a}$CH=N–; $(R^8)(R^9)$N—; $R^{17}$—C(=CHR$^{20}$)—C(=O)NH—; $R^{17}$—C(=NO—R$^{19}$)—C(=O)NH—; or $R^{18}$—$(CH_2)_m$—C(=O)NH—; and wherein said heterocycles have one or more heteroatoms selected from O, N, or S; and where (1) m is an integer from 0 to 9;
$R^{17}$ is hydrogen; C1–$C_8$ alkyl; $C_2$–$C_8$ alkenyl; a 3–8 atom heteroalkyl having 1 or 2 heteroatoms selected from O, N, or S; a 3–8 atom heteroalkenyl having 1 or 2 heteroatoms selected from O, N, or S; a 3–9 atom monocyclic or 7–17 atom polycyclic carbocycle; or a 3–9 atom monocyclic or 7–17 atom polycyclic heterocycle; wherein said heterocycles have one or more heteroatoms selected from O, N, or S;

(3) $R^{18}$ is $R^{17}$, —$Y^1$, or —$CH(Y^2)(R^{17})$;
(4) $R^{19}$ is $R^{17}$; arylalkyl; heteroarylalkyl; —$C(R^{22})(R^{23})$COOH; —C(=O)O—$R^{17}$; or —C(=O)NH—$R^{17}$; wherein said arylalkyl is a $C_1$–$C_8$ alkyl substituted with an aryl group and wherein said heteroarylalkyl is a $C_1$–$C_8$ alkyl substituted with an aryl group having one or more heteroatoms selected from O, N, or S; and where $R^{22}$ and $R^{23}$ are, independently, $R^{17}$ or together form a 3–9 atom monocyclic or 7–17 atom polycyclic carbocycle or a 3–9 atom monocyclic or 7–17 atom polycyclic heterocycle, including the carbon atom to which $R^{22}$ and $R^{23}$ are bonded; and wherein said heterocycles have one or more heteroatoms selected from O, N, or S;

(5) $R^{20}$ is $R^{19}$, halogen, —$Y^1$, or —CH($Y^2$)($R^{17}$);

(6) $Y^1$ is —C(=O)O$R^{21}$, —C(=O)$R^{21}$ —N($R^{24}$)$R^{21}$, —S(O)$_p R^{29}$, or —O$R^{29}$; and $Y^2$ is $Y^1$ or —OH, —SH, or —SO$_3$H;

(a) p is an integer from 0 to 2;

(b) $R^{24}$ is hydrogen; $C_1$–$C_8$ alkyl; $C_2$–$C_8$ alkenyl; a 3–8 atom heteroalkyl having 1 or 2 heteroatoms selected from O, N, or S; a 3–8 atom heteroalkenyl comprised of 1 or 2 heteroatoms selected from O, N, or S; a 3–9 atom monocyclic or 7–17 atom polycyclic carbocycle; a 3–9 atom monocyclic or 7–17 atom polycyclic heterocycle; —SO$_3$H; —C(=O)$R^{25}$; or, when $R^{18}$ is —CH(N($R^{24}$)$R^{21}$)(Rp$^{17}$), $R^{24}$ and $R^{21}$ may together form a 3–9 atom monocyclic or 7–17 atom polycyclic heterocycle; wherein said heterocycles consists of one or more heteroatoms selected from O, N, or S; and (c) $R^{25}$ is $R^{17}$; NH($R^{17}$); N($R^{17}$)($R^{26}$); O($R^{26}$); or S($R^{26}$); where $R^{26}$ is $C_1$–$C_8$ alkyl; $C_2$–$C_8$ alkenyl; a 3–9 atom monocyclic or 7–17 atom polycyclic carbocycle; a 3–9 atom monocyclic or a 7–17 atom polycyclic heterocycle; or when $R^{25}$ is N($R^{17}$)($R^{26}$), $R^{26}$ and $R^{17}$ may together form a 3–9 atom monocyclic or a 7–17 atom polycyclic heterocycle; wherein said heterocycles have one or more heteroatoms selected from O, N, or S; and (7) $R^{21}$ is $R^{29}$ or hydrogen; where $R^{29}$ is $C_1$–$C_8$ alkyl; $C_2$–$C_8$ alkenyl; arylalkyl, consisting of a $C_1$–$C_8$ alkyl substituted with an aryl group; a 3–8 atom heteroalkyl, having 1 or 2 heteroatoms selected from O, N, or S; a 3–8 atom heteroalkenyl, having 1 or 2 heteroatoms selected from O, N, or S; heteroarylalkyl, consisting of a $C_1$–$C_8$ alkyl substituted with an aryl group substituted with a heteroatom; a 3–9 atom monocyclic or a 7–17 atom polycyclic carbocycle; a 3–9 atom monocyclic or a 7–17 atom polycyclic heterocycle; or, when $Y^1$ is N($R^{24}$)$R^{21}$ and $R^{21}$ is $R^{29}$, $R^{21}$ and $R^{24}$ may together form a 3–9 atom monocyclic or a 7–17 atom polycyclic heterocycle including the nitrogen atom to which $R^{24}$ is bonded; wherein said heterocycles have one or more heteroatoms selected from O, N, or S;

(D) $R^{11}$ is hydrogen, halogen, alkoxy, or $R^{27}$C(=O)NH—, where $R^{27}$ is hydrogen or $C_1$–C8 alkyl;

(E) $R^{33}$ is H or COOH;

(F) $R^{38}$ is hydrogen, $C_1$–$C_8$ alkyl or alkoxy;

(G) $R^{37}$ is nil; $C_1$–$C_8$ alkyl; $C_2$–$C_8$ alkenyl; a 3–9 atom monocyclic or a 7–17 atom polycyclic carbocycle; or a 3–9 atom monocyclic or a 7–17 atom polycyclic heterocycle; wherein said heterocycles have one or more heteroatoms selected from O, N, or S; and (H) L links Q to B and is L', —$X^2$—$R^{39}$—L', or $X^3$—$R^{39}$—L', where L' is Q', —$X^2$—Q", —$X^3$—Q", —$X^4_t$—C(=$Y^3_u$)—z—Q", —$X^5_t$—PO($Y^4_u R^{8a}$)—Z'—Q", or $X^5_t$—SO$_2$—Z'—Q", —$X^3$—Q" and —O—C(=O)—Z—Q", where (1) t and u are, independently, 0 or 1;

(2) $R^{39}$ is $C_1$–$C_8$ alkyl; $C_2$–$C_8$ alkenyl; a 3–8 atom heteroalkyl having 1 or 2 heteroatoms selected from O, N, or S; a 3–8 atom heteroalkenyl having 1 or 2 heteroatoms selected from O, N, or S; a 3–9 atom monocyclic or a 7–17 atom polycyclic carbocycle; or a 3–9 atom monocyclic or a 7–17 atom polycyclic heterocycle, wherein said heterocycles have one or more heteroatoms selected from O, N, or S;

(3) $X^2$ is oxygen, or S(O)$_v$, where v is an integer from 0 to 2;

(4) $X^3$ is nitrogen; N($R^{40}$); N$^+$($R^{41}$)($R^{42}$); or $R^{43}$—N($R^{41}$); and is linked to $R^{37}$ by a single or double bond; where (a) $R^{40}$ is $R^{8a}$; —O$R^{8a}$; or —C(=O)$R^{8a}$;

(b) $R^{41}$ and $R^{42}$ are, independently, hydrogen; $C_1$–$C_8$ alkyl; $C_2$–$C_8$alkenyl; a 3–9 atom monocyclic or a 7–17 atom polycyclic carbocycle; a 3–9 atom monocyclic or a 7–17 atom polycyclic heterocycle; or, together with Q", form a 3–9 atom monocyclic or a 7–17 atom polycyclic heterocycle as $R^{15}$ or $R^{16}$; wherein said heterocycles have one or more heteroatoms selected from O, N, or S;

(c) $R^{43}$ is N($R^{41}$), oxygen or sulfur;

(5) $X^4$ is oxygen, sulfur, N$R^{40}$, or $R^{43}$ —N$R^{41}$;

(6) $X^5$ is oxygen or N$R^{41}$;

(7) $Y^3$ is oxygen, sulfur, N$R^{40}$ or N+($R^{41}$)(R42);

(8) $Y^4$ is oxygen or N$R^{41}$;

(9) Z is nil, oxygen, sulfur, nitrogen, N$R^{40}$, or N(R41)—$R^{43}$;

(10) Z' is nil, oxygen, nitrogen, or N$R^{41}$;

(11) Q' is $R^{15}$ or $R^{16}$; and

(12) Q" is Q'; or together with $X^2$, $X^3$, Z or Z', is an $R^{15}$ or $R^{16}$ group; and pharmaceutically-acceptable salts and biohydrolyzable esters thereof, and hydrates thereof.

2. A compound according to claim 1 having either the structure:

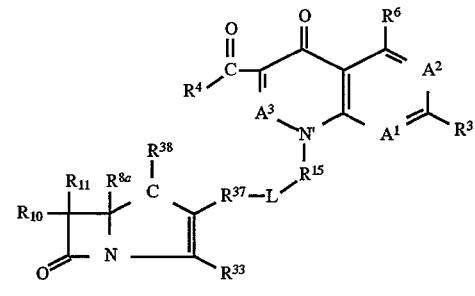

or the structure:

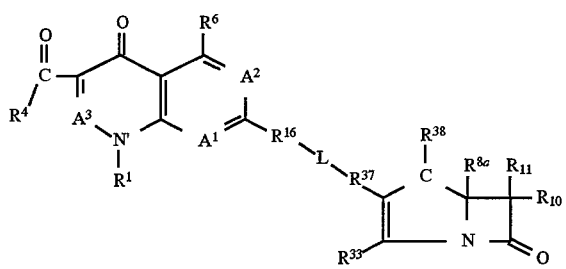

wherein
(A)
$A^1$ is N or C($R^7$); where
(i) $R^7$ is hydrogen; hydroxy; alkoxy; nitro; cyano; halogen; $C_1$–$C_8$ alkyl; or N($R^8$)($R^9$); and (ii) $R^8$ and $R^9$ are, independently, $R^{8a}$ where $R^{8a}$ is hydrogen; $C_1$–$C_8$ alkyl; $C_2$–$C_8$ alkenyl; a 3–9 atom monocyclic or 7–17 atom polycyclic carbocycle; or a 3–9 atom monocyclic or 7–17 atom polycyclic heterocycle; or $R^8$ and $R^9$ together form a 3–9 atom monocyclic or 7–17 atom polycyclic heterocycle including the nitrogen to which they are bonded; wherein said heterocycles have one or more heteroatoms selected from O, N, or S;

(2) $A^2$ is N or $C(R^2)$; where $R^2$ is hydrogen or halogen;

(3) $A^3$ is N or $C(R^5)$; where $R^5$ is hydrogen or $R^5$ forms a ring with R1 or R4;

(4) $R^1$ is hydrogen, $R^{15}$, or when $A^3$ is $C(R^5)$, $R^1$ and $R^5$ may form a ring;

(5) $R^3$ is hydrogen, halogen, or $R^{16}$;

(6) $R^{15}$ is a $C_1$–$C_8$ alkyl; a 3–9 atom monocyclic or a 7–17 atom polycyclic carbocycle; a 3–9 atom monocyclic or a 7–17 atom polycyclic heterocycle; alkoxy; hydroxy; $C_2$–$C_8$ alkenyl; arylalkyl; or $N(R^8)(R^9)$; wherein said arylalkyl is a $C_1$–$C_8$ alkyl substituted with an aryl and wherein said heterocycles have one or more heteroatoms selected from O, N, or S;

(7) $R^{16}$ is a $C_1$–$C_8$ alkyl; a 3–9 atom monocyclic or a 7–17 atom polycyclic carbocycle; or a 3–9 atom monocyclic or a 7–17 atom polycyclic heterocycle; wherein said heterocycles have one or more heteroatoms selected from O, N, or S;

(8) $R^4$ is hydroxy or when $A^3$ is $C(R^5)$, $R^4$ and $R^5$ may form a ring; and (9) $R^6$ is hydrogen, halogen, nitro, or $N(R^8)(R^9)$;

(B) wherein:

(1) when $A^1$ is $C(R^7)$, $R^1$ and $R^7$ may together form a 3–9 atom monocyclic or a 7–17 atom polycyclic heterocycle including N' and $A^1$;

(2) when $A^2$ is $C(R^2)$, $R^2$ and $R^3$ may together form —O—$(CH_2)_n$—O—, where n is an integer from 1 to 4;

(3) when $A^3$ is $C(R^5)$, $R^4$ and $R^5$ may together form a 3–9 atom monocyclic or a 7–17 atom polycyclic heterocycle including the carbon atoms to which $R^4$ and $R^5$ are bonded and the carbon atom to which said carbon atoms are bonded; wherein said heterocycles have one or more heteroatoms selected from O, N, or S;

(4) when $A^3$ is $C(R^5)$, $R^1$ and $R^5$ may together form a 3–9 atom monocyclic or a 7–17 atom polycyclic heterocycle including N' and the adjacent carbon to which $R^5$ is bonded; wherein said heterocycles have one or more heteroatoms selected from O, N, or S;

(C) $R^{10}$ is hydrogen; halogen; $C_1$–$C_8$ alkyl; $C_2$–$C_8$ alkenyl; a 3–8 atom heteroalkyl having 1 or 2 heteroatoms selected from O, N, or S; a 3–9 atom monocyclic or a 7–17 atom polycyclic carbocycle; a 3–9 atom monocyclic and a 7–17 atom polycyclic heterocycle; $R^{8a}$—O—; $R^{8a}CH=N$—; $(R^8)(R^9)N$—; $R^{17}$—C(=CHR$^{20}$)—C(=O)NH—; $R^{17}$—C(=NO—$R^{19}$)—C(=O)NH—; or $R^{18}$—$(CH_2)_m$—C(=O)NH—; wherein said heterocycles have one or more heteroatoms selected from O, N, or S; and where (1) m is an integer from 0 to 9;

(2) $R^{17}$ is hydrogen; $C_1$–$C_8$ alkyl; $C_2$–$C_8$ alkenyl; a 3–8 atom heteroalkyl having 1 or 2 heteroatoms selected from O, N, or S; a 3–8 atom heteroalkenyl having 1 or 2 heteroatoms selected from O, N, or S; a 3–9 atom monocyclic or a 7–17 atom polycyclic carbocycle; or a 3–9 atom monocycle or a 7–17 atom polycycle heterocycle; wherein said heterocycles have one or more heteroatoms selected from O, N, or S;

(3) $R^{18}$ is $R^{17}$, —$Y^1$, or —$CH(Y^2)(R^{17})$;

(4) $R^{19}$ is $R^{17}$; arylalkyl; heteroarylalkyl; —$C(R^{22})(R^{23})$COOH; —C(=O)O—$R^{17}$; or —C(=O)NH—$R^{17}$; wherein said arylalkyl is a $C_1$–$C_8$ alkyl substituted with an aryl group substituted with one or more heteroatoms selected from O, N, S; and wherein said heteroarylalkyl is a $C_1$–$C_8$ alkyl substituted with an aryl group having one or more heteroatoms selected from O, N, or S; and where $R^{22}$ and $R^{23}$ are, independently, $R^{17}$ or together form a 3–9 atom monocyclic or a 7–17 atom polycyclic carbocycle or a 3–9 atom monocyclic or a 7–17 atom polycyclic heterocycle including the carbon atom to which $R^{22}$ and $R^{23}$ are bonded; wherein said heterocycles have one or more heteroatoms selected from the group consisting of O, N, or S;

(5) $R^{20}$ is $R^{19}$, halogen, —$Y^1$, or —$CH(Y^2)(R^{17})$;

(6) $Y^1$ is —C(=O)O$R^{21}$, —C(=O)$R^{21}$, —$N(R^{24})R^{21}$, —$S(O)_pR^{29}$, or —O$R^{29}$; and $Y^2$ is $Y^1$ or —OH, —SH, or —SO$_3$H;

(a) p is an integer from 0 to 2;

(b) $R^{24}$ is hydrogen; $C_1$–$C_8$ alkyl; $C_2$–$C_8$ alkenyl; a 3–8 atom heteroalkyl having 1 or 2 heteroatoms selected from O, N, or S; a 3–8 atom heteroalkenyl having 1 or 2 heteroatoms selected from O, N, or S; a 3–9 atom monocyclic or a 7–17 atom polycyclic carbocycle; a 3–9 atom monocyclic or a 7–17 atom polycyclic heterocycle; —SO$_3$H; —C(=O)$R^{25}$; or, when $R^{18}$ is —$CH(N(R^{24})R^{21})(R^{17})$, $R^{24}$ and $R^{21}$ may together form a 3–9 atom monocyclic or a 7–17 atom polycyclic heterocycle; wherein said heterocycles have one or more heteroatoms selected from O, N, or S; and (c) $R^{25}$ is $R^{17}$, $NH(R^{17})$, $N(R^{17})(R^{26})$, $O(R^{26})$, or $S(R^{26})$; where $R^{26}$ is $C_1$–$C_8$ alkyl; $C_2$–$C_8$ alkenyl; a 3–9 atom monocyclic or a 7–17 atom polycyclic carbocycle; a 3–9 atom monocyclic or a 7–17 atom polycyclic heterocycle; or when $R^{25}$ is $N(R^{17})(R^{26})$, $R^{26}$ and $R^{17}$ may together form a 3–9 atom monocyclic or a 7–17 atom polycyclic hetercycle; and wherein said heterocycles have one or more heteroatoms selected from O, N, or S; and (7) $R^{21}$ is $R^{29}$ or hydrogen; where $R^{29}$ is $C_1$–$C_8$ alkyl; $C_2$–$C_8$ alkenyl; arylalkyl, wherein said arylalkyl consists of a $C_1$–$C_8$ alkyl substituted with an aryl group; heteroalkyl, wherein said heteroalkyl is a $C_1$–$C_8$ alkyl having 1 or 2 heteroatoms selected from O, N, or S; heteroalkenyl, wherein said heteroalkenyl consists of a $C_2$–$C_8$ alkenyl having 1 or 2 heteroatoms selected from O, N, or S; heteroarylalkyl, wherein said heteroarylalkyl is a $C_1$–$C_8$ alkyl substituted with an aryl group having 1 or 2 heteroatoms selected from O, N, or S; a 3–9 atom monocyclic or a 7–17 atom polycyclic carbocycle; a 3–9 atom monocyclic or a 7–17 atom polycyclic heterocycle; or, when Y is $N(R^{24})R^{21}$ and $R^{21}$ is $R^{29}$, $R^{21}$ and $R^{24}$ may together form a 3–9 atom monocyclic or a 7–17 atom polycyclic heterocycle including the nitrogen atom to which $R^{24}$ is bonded; and wherein said heterocycles consist of one or more heteroatoms selected from O, N, or S;

(D) $R^{11}$ is hydrogen, halogen, alkoxy, or $R^{27}C(=O)NH$—, where $R^{27}$ is hydrogen or $C_1$–$C_8$ alkyl; and (E) L is L', —$X^2$—$R^{39}$—L', or —$X^3$—$R^{39}$—L', where L' is Q', —$X^2$—Q", —$X^3$—Q", —$X^4$—C(=$Y^3_u$)—Z—Q", —$X^5$—PO($Y^4_uR^{8a}$)—Z'—Q", or $X^5$—SO$_2$—Z'—Q", —$X^3$—Q" and —O—C(=O)—Z—Q", where (1) t and u are, independently, 0 or 1;

(2) $R^{39}$ is $C_1$-$C_8$ alkyl; $C_2$-$C_8$ alkenyl; a 3-8 atom heteroalkyl having 1 or 2 heteroatoms selected from O, N, or S; a 3-8 atom heteroalkenyl having 1 or 2 heteroatoms selected from O, N or S; a 3-9 atom monocyclic or a 7-17 atom polycyclic carbocycle; or a 3-9 atom monocyclic or a 7-17 atom polycyclic heterocycle; wherein said heterocycles have one or more heteroatoms selected from O, N, or S;

(3) $X^2$ is oxygen, or $S(O)_v$, where v is an integer from 0 to 2;

(4) $X^3$ is nitrogen; $N(R^{40})$; $N^+(R^{41})(R^{42})$; or $R^{43}$—N($R^{41}$); where (a) $R^{40}$ is $R^{8a}$; —$OR^{8a}$; or —$C(=O)R^{8a}$;

(b) $R^{41}$ and $R^{42}$ are, independently, hydrogen; $C_1$-$C_8$ alkyl; $C_2$-$C_8$ alkenyl; 3–9 atom monocyclic or a 7–17 atom polycyclic carbocycles; 3–9 atom monocyclic or a 7–17 atom polycyclic heterocycles; or, together with Q", form a 3–9 atom monocyclic or a 7–17 atom polycyclic heterocycle as $R^{15}$ or $R^{16}$; wherein said heterocycles have one or more heteroatoms selected from O, N, or S;

(c) $R^{43}$ is $N(R^{41})$, oxygen or sulfur;

(5) $X^4$ is oxygen, sulfur, $NR^{40}$, or $R^{43}$—$NR^{41}$;

(6) $X^5$ is oxygen or $NR^{41}$;

(7) $Y^3$ is oxygen, sulfur, $NR^{40}$ or $N^{+(R41)}(R^{42})$;

(8) $Y^4$ is oxygen or $NR^{41}$;

(9) Z is nil, oxygen, sulfur, nitrogen, $NR^{40}$, or $N(R^{41})$—$R^{43}$;

(10) Z' is nil, oxygen, nitrogen, or $NR^{41}$;

(11) Q' is $R^{15}$ or $R^{16}$; and

(12) Q" is Q'; or together with $X^2$, $X^3$, Z or Z', is an $R^{15}$ or $R^{16}$ group; and pharmaceutically-acceptable salts and biohydrolyzable esters thereof, and hydrates thereof.

3. A compound, according to claim 2, wherein $R^{10}$ is $R^{18}$—$(CH_2)_m$—$C(=O)NH$.

4. A compound, according to claim 3, wherein $R^{18}$ is $R^{17}$ or —$Y^1$.

5. A compound, according to claim 1, wherein $R^{18}$ is —$CH(Y^2)(R^{17})$.

6. A compound, according to claim 1, wherein $R^{10}$ is $R^{17}$—$C(=CHR^{20})$—$C(=O)NH$—.

7. A compound, according to claim 1, wherein $R^{11}$ is hydrogen or alkoxy.

8. A compound according to claim 1, wherein: $A^1$ is $C(R^7)$, $A^2$ is $C(R^2)$, and $A^3$ is $C(R^5)$; or $A^1$ is nitrogen, $A^2$ is $C(R^2)$, and $A^3$ is $C(R^5)$.

9. A compound according to claim 1, wherein $A^1$ is $C(R^7)$, $A^2$ is $C(R^2)$, and $A^3$ is $C(R^5)$.

10. A compound, according to claim 9, wherein Q is a 6-fluoroquinolone moiety, a 8-halo-6-fluoroquinolone moiety, a pyridobenzoxazine moiety, a pyridobenthiazine moiety, a isothiazoloquinolinedione, or isoxazoloquinolinedione moiety.

11. A compound, according to claim 9, wherein $R^1$ is alkyl, aryl, cycloalkyl or alkylamino.

12. A compound, according to claim 11, wherein $R^1$ is ethyl, 2-fluoroethyl, 2-hydroxyethyl, t-butyl, 4-fluorophenyl, 2,4-difluorophenyl, methylamino or cylcopropyl.

13. A compound, according to claim 11, wherein $R^2$ is hydrogen or halo.

14. A compound, according to claim 13, wherein $R^2$ is chlorine or fluorine.

15. A compound, according to claim 13, wherein $R^3$ is a nitrogen-containing heterocyclic ring.

16. A compound, according to claim 15, wherein $R^3$ is piperazine, 3-methylpiperazine, 3-aminopyrrolidine, 3-aminomethylpyrrolidine, N,N-methylpyrrolidine, N-methylarninomethylpyrrolidine, N-ethylaminomethylpyrrolidine, pyridine, 4-dithiocarbarmoylpiperazine, 3-(dithiocarbamoylaminomethyl)pyrrolidine, N-methylpiperazine, 3,5-dimethylpiperazine, or 3-(dithiocarbamoylamino)pyrrolidine.

17. A compound, according to claim 16, wherein R$^1$ is cyclopropyl, and $R^2$ is fluorine.

18. A compound, according to claim 17, wherein $R^3$ is piperazine.

19. A compound, according to claim 1, wherein L comprises a linking moiety selected from the group consisting of carbamate, dithiocarbamate, urea, thiourea, isouronium, isothiouronium, guanidine, carbonate, trithiocarbonate, reversed carbamate, xanthate, reversed isouronium, reversed dithiocarbamate, reversed isothiouronium, amine, imine, ammonium, heteroarylium, ether, thioether, phosphono, phosphoramide, phosphate, sulfonamide, ester, thioester, amide and hydrazide groups.

20. A compound, according to claim 19, wherein L is L', and L' is —$X^2$—Q", —$X^3$—Q", or $X^4_t$—$C(=Y^3_u)$—Z—Q".

21. A compound, according to claim 20, wherein Q" is $R^{16}$, or together with $X^2$, $X^3$, Z or Z', is $R^{16}$.

22. A compound, according to claim 21, wherein L' is $X^4_t$—$C(=Y^3_u)$—Z—Q".

23. A compound, according to claim 22, wherein t is 1, u is 1, and $X^4$ is oxygen, sulfur or $NR^{40}$.

24. A compound, according to claim 20, wherein said linking moiety is selected from the group consisting of carbamate, dithicarbamate, urea, thiourea, isothiouronium, amine, ammonium, and heteroarylium groups.

25. A compound, according to claim 24, wherein said linking moiety is a carbamate or dithiocarbamate group.

26. A compound, according to claim 1, wherein $R^3$ is $R^{16}$ and is a substituent moiety of L.

27. A compound, according to claim 26, wherein L' is $X^4_t$—$C(=Y^3_u)$—Z—Q".

28. A compound selected from the group consisting of:

[5R-[5a,6a]]-3-[[[4-(3-Carboxy-cyclopropyl-6-fluoro-1,4-dihydro-4-oxo-7-quinolinyl)-1-piperazinyl] iminomethyl]thiomethyl]-6-[(R)-1-hydroxyethyl]-7-oxo-1-azabicyclo[3.2.0]hept-2-ene-2-carboxylic acid disodium salt;

[5R-[5a,6a]]-3-[2-[[1-(3-Carboxy-8-chloro-1-cyclopropyl-6-fluoro-1,4-dihydro-4-oxo-7-quinolinyl)-3-pyrrolidinylamino]iminomethyl]amino]ethylthio]-6-(R)-1-hydroxyethyl-7-oxo-1-azabicyclo[3.2.0]hept-2-ene-2-carboxylic acid monosodium salt;

[5R[4b,5a,6a]]-3-[[[4-(3-Carboxy-1-cyclopropyl-6-fluoro-1,4-dihydro-4-oxo-7-quinolinyl)-1-piperazinyl] carbonyloxy]methyl]-6-[(R)-1-hydroxyethyl]-4-methyl-7-oxo-1-azabicylo[3.2.0]hept-2-ene-2-carboxylic acid disodium salt;

[5R-[5a,6a]]-3-[[[1-(3-Carboxy-1-cyclopropyl-6-fluoro-1,4-dihydro-4-oxo-7-quinolinyl)-3-pyrrolidinylamino] carbonyloxy]methyl]-6-[(R)-1-hydroxyethyl]-4-methyl-7-oxo-1-azabicylo[3.2.0]hept-2-ene-2-carboxylic acid disodium salt;

[5R-[5a,6a]]-3-[[[1-(3-Carboxy-1-cyclopropyl-6,8-difluoro-1,4-dihydro-4-oxo-7-quinolinyl)-3-pyrrolidinylarnino]carbonyloxy]methyl]-6-[(R)-1- hydroxyethyl]-4-methyl-7-oxo-1-azabicylo[3.2.0]hept-2-ene-2-carboxylic acid disodium salt;

[5R-[5a,6a]]-3-[[[1-(3-Carboxy-8-chloro-1-cyclopropyl-6-fluoro-1,4-dihydro-4-oxo-7-quinolinyl)-3-pyrrolidinylamino]carbonyloxy]methyl]-6-[(R)-1-hydroxyethyl]-4-methyl-7-oxo-1-azabicylo[3.2.0]hept-2-ene-2-carboxylic acid disodium salt;

[5R-[5a,6a]]-3-[[[1-(3-Carboxy-1-cyclopropyl-6-fluoro-1,4-dihydro-4-oxo-1,8-napththyridin-7-yl)-3-pyrrolidinylamino]carbonyloxy]methyl]-6-[(R)-1-hydroxyethyl]-4-methyl-7-oxo-1-azabicylo[3.2.0]hept-2-ene-2-carboxylic acid disodium salt;

[5R-[5a,6a]]-3-[2-[[4-(3-Carboxy-1-cyclopropyl-6-fluoro-1,4-dihydro-4-oxo-7-quinolinyl)-1-piperazinyl]carbonyloxy]ethylthio]-6-[(R)-1-hydroxyethyl]-4-methyl-7-oxo-1-azabicylo[3.2.0]hept-2-ene-2-carboxylic acid disodium salt;

[5R-[5a,6a]]-3-[2-[[1-(3-Carboxy-1-cyclopropyl-6-fluoro-1,4-dihydro-4-oxo-7-quinolinyl)-3-pyrrolidinylamino]carbonyloxy]ethylthio]-6-[(R)-1-hydroxyethyl]-4-methyl-7-oxo-1-azabicylo[3.2.0]hept-2-ene-2-carboxylic acid disodium salt;

[5R-[5a,6a]]-3-[2-[[1-(3-Carboxy-1-cyclopropyl-6,8-difluoro-1,4-dihydro-4-oxo-7-quinolinyl)-3-pyrrolidinylamino]carbonyloxy]ethylthio]-6-[(R)-1-hydroxyethyl]-4-methyl-7-oxo-1-azabicylo[3.2.0]hept-2-ene-2-carboxylic acid disodium salt;

[5R-[5a,6a]]-3-[2-[[1-(3-Carboxy-8-chloro-1-cyclopropyl-6-fluoro-1,4-dihydro-4-oxo-7-quinolinyl)-3-pyrrolidinylamino]carbonyloxy]ethylthio]-6-[(R)-1-hydroxyethyl]-4-methyl-7-oxo-1-azabicylo[3.2.0]hept-2-ene-2-carboxylic acid disodium salt;

[5R-[5a,6a]]-3-[2-[[1-(3-Carboxy-1-cyclopropyl-6-fluoro-1,4-dihydro-4-oxo-1,8-napththyridin-7-yl)-3-pyrrolidinylamino]carbonyloxy]ethylthio]-6-[(R)-1-hydroxyethyl]-4-methyl-7-oxo-1-azabicylo[3.2.0]hept-2-ene-2-carboxylic acid disodium salt;

[5R-[5a,6a]]-3-[[[[1-(3-Carboxy-1-cyclopropyl-6,8-difluoro-1,4-dihydro-4-oxo-7-quinolinyl)-3-pyrrolidinylamino]thioxomethyl]thio]methyl]6-[(R)-1-hydroxyethyl]-4-methyl-7-oxo-1-azabicylo[3.2.0]hept-2-ene-2-carboxylic acid disodium salt;

[5R-[5a,6a]]-3-[2-[[[4-(3-Carboxy-1-cyclopropyl-6-fluoro-1,4-dihydro-4-oxo-7-quinolinyl)-1-piperazinyl]thioxomethyl]thio]ethylthio]6-[(R)-1-hydroxyethyl]-4-methyl-7-oxo-1-azabicylo[3.2.0]hept-2-ene-2-carboxylic acid disodium salt;

[5R-[5a,6a]]-3-[2-[[[1-(3-Carboxy-1-cyclopropyl-6,8-difluoro-1,4-dihydro-4-oxo-7-quinolinyl)-3-pyrrolidinylamino]thioxomethyl]thio]ethylthio]-6-[(R)-1-hydroxyethyl]-4-methyl-7-oxo-1-azabicylo[3.2.0]hept-2-ene-2-carboxylic acid disodium salt;

[5R-[5a,6a]]-3-[2-[[[1-(3-Carboxy-8-chloro-1-cyclopropyl-6-fluoro-1,4-dihydro-4-oxo-7-quinolinyl)-3-pyrrolidinylamino]thioxomethyl]thio]ethylthio]-6-[(R)-1-hydroxyethyl]-4-methyl-7-oxo-1-azabicylo[3.2.0]hept-2-ene-2-carboxylic acid disodium salt;

[5R-[5a,6a]]-3-[2-[[[4-(3-Carboxy-1-cyclopropyl-6-fluoro-1,4-dihydro-4-oxo-7-quinolinyl)-1-piperazinyl]iminomethyl]thio]ethylthio]-6-[(R)-1-hydroxyethyl]-4-methyl-7-oxo-1-azabicylo[3.2.0]hept-2-ene-2-carboxylic acid disodium salt;

[5R-[5a,6a]]-3-[2-[[[4-(3-Carboxy-1-cyclopropyl-6-fluoro-1,4-dihydro-4-oxo-7-quinolinyl)-3-piperazinyl]thioxomethyl]amino]ethylthio]6-[(R)-1-hydroxyethyl]-4-methyl-7-oxo-1-azabicylo[3.2.0]hept-2-ene-2-carboxylic acid disodium salt.

29. A compound, according to claim 28, which is:

[5R-[5a,6a]]-3-[2-[[4-(3-Carboxy-1-cyclopropyl-6-fluoro-1,4-dihydro-4-oxo-7-quinolinyl)-1-piperazinyl]carbonyloxy]ethylthio]-6-[(R)-1-hydroxyethyl]-4-methyl-7-oxo-1-azabicylo[3.2.0]hept-2-ene-2-carboxylic acid disodium salt.

30. A composition for treating or preventing an infectious disorder in a human or other arereal subject, comprising:

(1) a safe and effective amount of a compound of claim 1; and (2) a pharmaceutically-acceptable carrier.

31. A composition for treating or preventing an infectious disorder in a human or other arereal subject, comprising:

(1) a safe and effective amount of a compound of claim 8; and (2) a pharmaceutically-acceptable carrier.

32). A composition for treating or preventing an infectious disorder in a human or other arereal subject, comprising:

(1) a safe and effective amount of a compound of claim 9; and (2) a pharmaceutically-acceptable carrier.

33. A composition for treating or preventing an infectious disorder in a human or other animal subject, comprising:

(1) a safe and effective amount of a compound of claim 15; and (2) a pharmaceutically-acceptable carrier.

34. A composition for treating or preventing an infectious disorder in a human or other animal subject, comprising:

(1) a safe and effective amount of a compound of claim 16; and (2) a pharmaceutically-acceptable carrier.

35. A composition for treating or preventing an infectious disorder in a human or other ammal subject, comprising:

(1) a safe and effective amount of a compound of claim 20; and (2) a pharmaceutically-acceptable carrier.

36. A composition for treating or preventing an infectious disorder in a human or other animal subject, comprising:

(1) a safe and effective amount of a compound of claim 25; and (2) a pharmaceutically-acceptable carrier.

37. A composition for treating or preventing an infectious disorder in a human or other animal subject, comprising:

(1) a safe and effective amount of a compound of claim 28; and (2) a pharmaceutically-acceptable carrier.

38. A composition for treating or preventing an infectious disorder in a human or other animal subject, according to claim 30, wherein said composition is suitable for parenteral administration.

39. A composition for treating or preventing an infectious disorder in a human or other animal subject, according to claim 30, wherein said composition is suitable for oral administration.

40. A method for preventing or treating an infectious disorder in a human or other animal subject, by administering to said subject a safe and effective amount of a compound of claim 1.

41. A method for preventing or treating an infectious disorder in a human or other animal subject, by administering to said subject a safe and effective amount of a compound of claim 15.

42. A method for preventing or treating an infectious disorder in a human or other animal subject, by administering to said subject a safe and effective amount of a compound of claim 18.

43. A method for preventing or treating an infectious disorder in a human or other animal subject, by administering to said subject a safe and effective amount of a compound of claim 20.

44. A method for preventing or treating an infectious disorder in a human or other animal subject, by administering to said subject a safe and effective amount of a compound of claim 25.

45. A method for preventing or treating an infectious disorder in a human or other animal subject, by administering to said subject a safe and effective amount of a compound of claim 28.

* * * * *